(12) United States Patent
Semko et al.

(10) Patent No.: US 11,685,749 B2
(45) Date of Patent: Jun. 27, 2023

(54) C26-LINKED RAPAMYCIN ANALOGS AS MTOR INHIBITORS

(71) Applicant: Revolution Medicines, Inc., Redwood City, CA (US)

(72) Inventors: Christopher Michael Semko, Redwood City, CA (US); Gang Wang, Redwood City, CA (US); G. Leslie Burnett, Redwood City, CA (US); James Bradley Aggen, Redwood City, CA (US); Gert Kiss, Redwood City, CA (US); James Joseph Cregg, Redwood City, CA (US); Micah James Evans Gliedt, Redwood City, CA (US); Jennifer Pitzen, Redwood City, CA (US); Julie Chu-Li Lee, Redwood City, CA (US); Walter Won, Redwood City, CA (US); Arun P. Thottumkara, Redwood City, CA (US); Adrian Liam Gill, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 0 days.

(21) Appl. No.: 17/086,169

(22) Filed: Oct. 30, 2020

(65) Prior Publication Data
US 2022/0340596 A1 Oct. 27, 2022

Related U.S. Application Data

(63) Continuation of application No. PCT/US2019/029738, filed on Apr. 29, 2019.

(60) Provisional application No. 62/836,040, filed on Apr. 18, 2019, provisional application No. 62/752,881, filed on Oct. 30, 2018, provisional application No. 62/665,426, filed on May 1, 2018.

(51) Int. Cl.
*C07D 519/00* (2006.01)

(52) U.S. Cl.
CPC .................................. *C07D 519/00* (2013.01)

(58) Field of Classification Search
CPC ................................................... C07D 519/00
USPC ...................................................... 514/262.1
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |
| 4,861,760 A | 8/1989 | Mazuel et al. |
| 4,911,920 A | 3/1990 | Jani et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,726 A | 6/1992 | Failli et al. |
| 5,120,842 A | 6/1992 | Failli et al. |
| 5,130,307 A | 7/1992 | Failli et al. |
| 5,151,413 A | 9/1992 | Caufield et al. |
| 5,162,333 A | 11/1992 | Failli et al. |
| 5,177,203 A | 1/1993 | Failli et al. |
| 5,212,162 A | 5/1993 | Missel et al. |
| 5,221,670 A | 6/1993 | Caufield |
| 5,233,036 A | 8/1993 | Hughes |
| 5,252,579 A | 10/1993 | Skotnicki et al. |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,262,564 A | 11/1993 | Kun et al. |
| 5,302,584 A | 4/1994 | Kao et al. |
| 5,344,833 A | 9/1994 | Hughes |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,403,841 A | 4/1995 | Lang et al. |
| 5,411,967 A | 5/1995 | Kao et al. |
| 5,463,048 A | 10/1995 | Skotnicki et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |

(Continued)

FOREIGN PATENT DOCUMENTS

| | | |
|---|---|---|
| EP | 0088593 A2 | 9/1983 |
| EP | 0467606 A1 | 1/1992 |

(Continued)

OTHER PUBLICATIONS

Al-Muhammed et al., "In-vivo studies on dexamethasone sodium phosphate liposomes," J Microencapsul. May-Jun. 1996;13(3):293-306.

Apsel, B. et al. (Nov. 2008, e-published Oct. 12, 2008). "Targeted polypharmacology: discovery of dual inhibitors of tyrosine and phosphoinositide kinases," Nature Chemical Biology 4(11):691-699.

Ayral-Kaloustian, S. et al. (Jan. 2010). "Hybrid inhibitors of phosphatidylinositol 3-kinase (PI3K) and the mammalian target of rapamycin (mTOR): design, synthesis, and superior antitumor activity of novel wortmannin-rapamycin conjugates," J Med Chem 53(1):452-459.

(Continued)

Primary Examiner — Kahsay Habte
(74) Attorney, Agent, or Firm — Cooley LLP

(57) ABSTRACT

The present disclosure relates to mTOR inhibitors. Specifically, the embodiments are directed to compounds and compositions inhibiting mTOR, methods of treating diseases mediated by mTOR, and methods of synthesizing these compounds.

8 Claims, No Drawings

Specification includes a Sequence Listing.

(56) References Cited

U.S. PATENT DOCUMENTS

| | | |
|---|---|---|
| 5,527,907 A | 6/1996 | Or et al. |
| 5,563,145 A | 10/1996 | Failli et al. |
| 5,665,772 A | 9/1997 | Cottens et al. |
| 5,741,677 A | 4/1998 | Kozlowski et al. |
| 5,780,462 A | 7/1998 | Lee et al. |
| 6,277,983 B1 | 8/2001 | Shaw et al. |
| 6,323,201 B1 | 11/2001 | Carson et al. |
| 6,342,507 B1 | 1/2002 | Naicker et al. |
| 6,358,969 B1 | 3/2002 | Shelley et al. |
| 6,562,819 B2 | 5/2003 | Carson et al. |
| 6,720,344 B2 | 4/2004 | Kerwin et al. |
| 7,160,867 B2 | 1/2007 | Abel et al. |
| 7,241,771 B2 | 7/2007 | Zhu |
| 7,429,596 B2 | 9/2008 | Tanaka et al. |
| 7,585,868 B2 | 9/2009 | Knight et al. |
| 8,101,602 B2 | 1/2012 | Menear et al. |
| 8,410,131 B2 | 4/2013 | Lane et al. |
| 8,492,405 B2 | 7/2013 | Tsuneo et al. |
| 8,604,032 B2 | 12/2013 | Ren et al. |
| 8,642,604 B2 | 2/2014 | Knight et al. |
| 8,697,709 B2 | 4/2014 | Dar et al. |
| 8,785,454 B2 | 7/2014 | Ren et al. |
| 8,980,899 B2 | 3/2015 | Korennykh et al. |
| 9,321,772 B2 | 4/2016 | Dar et al. |
| 9,358,229 B2 | 6/2016 | Vannucchi et al. |
| 9,493,467 B2 | 11/2016 | Knight et al. |
| 9,512,125 B2 | 12/2016 | Shokat et al. |
| 9,603,891 B2 | 3/2017 | Bae et al. |
| 9,629,843 B2 | 4/2017 | Shokat et al. |
| 10,117,945 B2 | 11/2018 | Shokat et al. |
| 10,160,767 B2 | 12/2018 | Zhong |
| 10,980,889 B1 | 4/2021 | Pitzen et al. |
| 11,364,300 B2 | 6/2022 | Pitzen et al. |
| 2005/0085472 A1 | 4/2005 | Tanaka et al. |
| 2005/0101624 A1 | 5/2005 | Betts et al. |
| 2005/0192311 A1 | 9/2005 | Isozaki et al. |
| 2008/0249123 A1 | 10/2008 | Gu et al. |
| 2009/0074831 A1 | 3/2009 | Falotico et al. |
| 2009/0124638 A1 | 5/2009 | Shokat et al. |
| 2009/0181988 A1 | 7/2009 | Tanaka et al. |
| 2009/0131631 A1 | 10/2009 | Krafft et al. |
| 2009/0270426 A1 | 10/2009 | Knight et al. |
| 2009/0274739 A1 | 11/2009 | Marks et al. |
| 2009/0292118 A1 | 11/2009 | Lee et al. |
| 2009/0312319 A1 | 12/2009 | Ren et al. |
| 2010/0009963 A1 | 1/2010 | Knight et al. |
| 2010/0190749 A1 | 7/2010 | Ren et al. |
| 2010/0190980 A1 | 7/2010 | Umemiya et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |
| 2012/0065426 A1 | 3/2012 | Watanabe et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |
| 2013/0289271 A1 | 10/2013 | Perrin-Ninkovic et al. |
| 2014/0066462 A1 | 3/2014 | Pearce et al. |
| 2014/0288096 A1 | 9/2014 | Knight et al. |
| 2015/0031881 A1 | 1/2015 | Tanaka et al. |
| 2015/0368297 A1 | 12/2015 | Bae et al. |
| 2016/0000789 A1 | 1/2016 | Shokat et al. |
| 2016/0168151 A1 | 6/2016 | Tanaka et al. |
| 2016/0279108 A1 | 9/2016 | Forrest et al. |
| 2016/0354377 A1 | 12/2016 | Dar et al. |
| 2017/0246305 A1 | 8/2017 | Shokat et al. |
| 2019/0284146 A1 | 9/2019 | Yan et al. |
| 2019/0336609 A1 | 11/2019 | Pitzen et al. |
| 2021/0094975 A1 | 4/2021 | Aggen et al. |
| 2021/0338824 A1 | 11/2021 | Pitzen et al. |

FOREIGN PATENT DOCUMENTS

| | | | |
|---|---|---|---|
| EP | 1 916 006 | 4/2008 | |
| GB | 1459571 A | 12/1976 | |
| JP | H0249775 A | 2/1990 | |
| JP | H04112877 A | 4/1992 | |
| JP | H 04230389 | 8/1992 | |
| JP | 2004-161716 A | 6/2004 | |
| JP | 2008-273976 A | 11/2008 | |
| JP | 2009513222 A | 4/2009 | |
| JP | 2012528165 A | 11/2012 | |
| JP | 2016500112 A | 1/2016 | |
| RU | 2152946 C1 | 7/2000 | |
| RU | 2 322 981 C2 | 4/2008 | |
| RU | 2487711 C2 | 7/2013 | |
| WO | WO-92/05179 A1 | 4/1992 | |
| WO | WO-93/11130 A1 | 6/1993 | |
| WO | WO-94/02136 A1 | 2/1994 | |
| WO | WO-94/02485 A1 | 2/1994 | |
| WO | WO-1994004540 A1 | 3/1994 | |
| WO | WO-94/09010 A1 | 4/1994 | |
| WO | WO-94/11380 A1 | 5/1994 | |
| WO | WO-94/25072 A1 | 11/1994 | |
| WO | WO-95/04738 A1 | 2/1995 | |
| WO | WO-95/14023 A1 | 5/1995 | |
| WO | WO-95/16691 A1 | 6/1995 | |
| WO | WO-96/041807 A1 | 12/1996 | |
| WO | WO-99/36553 A2 | 7/1999 | |
| WO | WO-01/014387 A1 | 3/2001 | |
| WO | WO-2004024719 A1 | 3/2004 | |
| WO | WO-2004/101583 A1 | 11/2004 | |
| WO | WO-2005/007085 A2 | 1/2005 | |
| WO | WO-2005/007085 A3 | 1/2005 | |
| WO | WO-2005/105760 A1 | 11/2005 | |
| WO | WO-2006/009518 A1 | 1/2006 | |
| WO | WO-2006/068760 A2 | 6/2006 | |
| WO | WO-2006/068760 A3 | 6/2006 | |
| WO | WO-2006/116727 A2 | 11/2006 | |
| WO | WO-2006/116727 A2 * | 11/2006 | ......... A61K 47/4823 |
| WO | WO 2007/061737 A2 | 5/2007 | |
| WO | WO-2007/057457 A2 | 5/2007 | |
| WO | WO-2007/068462 A2 | 6/2007 | |
| WO | WO-2007/114926 A2 | 10/2007 | |
| WO | WO-2007/114926 A3 | 10/2007 | |
| WO | WO-2007/121453 A2 | 10/2007 | |
| WO | WO-2007/121453 A3 | 10/2007 | |
| WO | WO 2008/046641 A2 | 4/2008 | |
| WO | WO 2008/046641 A3 | 4/2008 | |
| WO | WO-2008/047821 A1 | 4/2008 | |
| WO | WO-2008/065887 A1 | 6/2008 | |
| WO | WO-2008/115974 A2 | 9/2008 | |
| WO | WO-2008/127226 A2 | 10/2008 | |
| WO | WO-2008/127226 A3 | 10/2008 | |
| WO | WO-2009/046436 A1 | 4/2009 | |
| WO | WO-2009/088986 A1 | 7/2009 | |
| WO | WO-2009/088990 A1 | 7/2009 | |
| WO | WO-2009/089262 A1 | 7/2009 | |
| WO | WO-2009/122176 A2 | 10/2009 | |
| WO | WO-2009/131631 A1 | 10/2009 | |
| WO | WO-2010/006072 A2 | 1/2010 | |
| WO | WO-2010/006072 A3 | 1/2010 | |
| WO | WO-2010/006086 A2 | 1/2010 | |
| WO | WO-2010/006086 A3 | 1/2010 | |
| WO | WO-2010/025406 A1 | 3/2010 | |
| WO | WO-2010/036380 A1 | 4/2010 | |
| WO | WO-2010/044885 A2 | 4/2010 | |
| WO | WO-2010/051042 A1 | 5/2010 | |
| WO | WO-2010/051043 A1 | 5/2010 | |
| WO | WO 2010/138487 A1 | 12/2010 | |
| WO | WO-2011/022439 A1 | 2/2011 | |
| WO | WO-2011022440 A2 | 2/2011 | |
| WO | WO-2011/047384 A2 | 4/2011 | |
| WO | WO-2011/047384 A9 | 4/2011 | |
| WO | WO-2012/017449 A1 | 2/2012 | |
| WO | WO-2012/066502 A1 | 5/2012 | |
| WO | WO-2012/103959 A1 | 8/2012 | |
| WO | WO-2012/103960 A1 | 8/2012 | |
| WO | WO-2012/151562 A1 | 11/2012 | |
| WO | WO-2012/154695 A2 | 11/2012 | |

(56) References Cited

FOREIGN PATENT DOCUMENTS

| | | |
|---|---|---|
| WO | WO-2012/154695 A3 | 11/2012 |
| WO | WO-2013/077921 A2 | 5/2013 |
| WO | WO-2013/077921 A3 | 5/2013 |
| WO | WO-2013/077921 A9 | 5/2013 |
| WO | WO-2014/082286 A1 | 6/2014 |
| WO | WO2015066371 A1 | 5/2015 |
| WO | WO 2015/095755 A1 | 6/2015 |
| WO | WO 2015/184983 A1 | 12/2015 |
| WO | WO-2016/040806 A1 | 3/2016 |
| WO | WO-2016/100116 A1 | 6/2016 |
| WO | WO-2017/044720 A1 | 3/2017 |
| WO | WO-2017/121444 A1 | 7/2017 |
| WO | WO-2018/204416 A1 | 11/2018 |
| WO | WO-2019/064182 A1 | 4/2019 |
| WO | WO-2019/212990 A1 | 11/2019 |
| WO | WO-2019/212991 A1 | 11/2019 |
| WO | WO-2020160711 A1 | 8/2020 |

OTHER PUBLICATIONS

Banerjee, S.S. et al. (2012, e-published May 7, 2012). "Poly(ethylene glycol)-Prodrug Conjugates: Concept, Design, and Applications," J Drug Deliv 2012:103973, 17 pages.

CAS Registry No. 53123-88-9, accessed Feb. 27, 2018, 2 pages.

Choi, J. et al. (Jul. 1996). "Structure of the FKBP12-rapamycin complex interacting with the binding domain of human FRAP," Science 273(5272):239-242.

Chonn et al., "Recent advances in liposomal drug-delivery systems," Curr Opin Biotechnol. Dec. 1995;6(6):698-708.

Dowling, R.J. et al. (May 28, 2010). "mTORC1-mediated cell proliferation, but not cell growth, controlled by the 4E-BPs," Science 328(5982):1172-1176.

Drachman, J.G. et al. (2013). "Antibody-drug conjugates: the chemistry behind empowering antibodies to fight cancer," Hematology Am Soc Hematol Educ Program 2013:306-310.

Eyles et al., "Oral delivery and fate of poly(lactic acid) microsphere-encapsulated interferon in rats," J Pharm Pharmacol. Jul. 1997;49(7):669-74.

Feldman, M.E. et al. (Feb. 10, 2009). "Active-site inhibitors of mTOR target rapamycin-resistant outputs of mTORCI and mTORC2," PLoS Biol 7(2):e38.

Flygare. J.A. et al. (Jan. 2013). "Antibody-drug conjugates for the treatment of cancer," Chem Biol Drug Des 81(1):113-121.

Galat, "Functional diversity and pharmacological profiles of the FKBPs and their complexes with small natural ligands," Cell Mol Life Sci. Sep. 2013;70(18):3243-75.

Gao et al., "Controlled release of a contraceptive steroid from biodegradable and injectable gel formulations: in vitro evaluation," Pharm Res. Jun. 1995;12(6):857-63.

Hackam et al., "Translation of Research Evidence From Animals to Humans," JAMA, Oct. 11, 2006, vol. 296, No. 14, pp. 1731-1732.

Hara, K. et al. (Jul. 26, 2002). "Raptor, a binding partner of target of rapamycin (TOR), mediates TOR action," Cell 110(2):177-189.

Hsieh, A.C. et al. (Mar. 16, 2010). "Genetic dissection of the oncogenic mTOR pathway reveals druggable addiction to translational control via 4EBP-el F4E," Cancer Cell 17(3):249-261.

Hsieh, A.C. et al. (Feb. 22, 2012). "The translational landscape of mTOR signalling steers cancer initiation and metastasis," Nature 485(7396):55-61.

Hughes et al., "The isolation, synthesis and characterization of an isomeric form of rapamycin," Tetrahedron Letters, vol. 33, Issue 33, Aug. 11, 1992, pp. 4739-4742.

Infante, J. R. et al. (2013). Abstract C252: A phase 1, dose-escalation study of MLN0128, an investigational oral mammalian target of rapamycin complex 1/2 (mTORC1/2) catalytic inhibitor, in patients (pts) with advanced non-hematologic malignancies. Mol. Cancer Ther. 12; C252.

Jacinto, E. et al. (Nov. 2004, e-published Oct. 3, 2004). "Mammalian TOR complex 2 controls the actin cytoskeleton and is rapamycin insensitive," Nat Cell Biol 6(11):1122-1128.

Jordan, "Tamoxifen: A Most Unlikely Pioneering Medicine," Nature Reviews: Drug Discovery, vol. 2, Mar. 2003, 205-213.

Kallen et al., "X-ray Crystal Structure of 28-O-Methylrapamycin complexed with FKBP12: Is the Cyclohexyl Moiety Part of the Effector Domain of Rapamycin," J. Am. Chem. Soc. 1996, 118, 5857-5861.

Kim, D.H. et al. (Jul. 26, 2002). "mTOR interacts with raptor to form a nutrient-sensitive complex that signals to the cell growth machinery," Cell 110(2):163-175.

Kolb, H.C. et al (Jun. 1, 2001). "Click Chemistry: Diverse Chemical Function from a Few Good Reactions," Angewandte Chemie International Edition 40(11):2004-2021.

Lamming, D.W. et al. (Mar. 30, 2012). "Rapamycin-induced insulin resistance is mediated by mTORC2 loss and uncoupled from longevity," Science 335(6076):1638-1643.

Liu et al., "Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer," J Med Chem. Oct. 14, 2010;53(19):7146-55.

Luengo et al., "Manipulation of the Rapamycin Effector Domain. Selective Nucleophilic Substitution of the C7 Methoxy Group," Org. Chem. 1994, 59, 22, 6512-6513.

McCormick, M.A. et al. (Jan. 12, 2011). "TOR and ageing: a complex pathway for a complex process," Philas Trans R Soc Land B Biol Sci 366(1561):17-27.

Moni et al., "Synthesis of rapamycin glycoconjugates via a CuAAC-based approach," Tetrahedron Letters, vol. 54, Issue 51, Dec. 18, 2013, pp. 6999-7003.

Naing, A. et al. (Sep. 25, 2012, e-published Aug. 30, 2012). "Safety, tolerability, pharmacokinetics and pharmacodynamics of AZD8055 in advanced solid tumours and lymphoma," Br J Cancer 107(7):1093-1099.

Neasta, J. et al. (Jul. 2014, e-published Apr. 19, 2014). "mTOR complex 1: a key player in neuroadaptations induced by drugs of abuse," J Neurochem 130(2):172-184.

Nelson et al., "Manipulation of the C(22)-C(27) Region of Rapamycin: Stability Issues and Biological Implications," Bioorganic & Medicinal Chemistry Letters, vol. 9, No. 2, 1999, pp. 295-300.

Nowak et al., "Discovery of potent and selective inhibitors of the mammalian target of rapamycin (mTOR) kinase," J Med Chem. Nov. 26, 2009;52(22):7081-9.

O'Donnell, A. et al. (Apr. 1, 2008, e-published Mar. 10, 2008). "Phase I pharmacokinetic and pharmacodynamic study of the oral mammalian target of rapamycin inhibitor everolimus in patients with advanced solid tumors," J Clin Onco/ 26(10):1588-1595.

O'Reilly, K.E. et al. (Feb. 1, 2006). "mTOR inhibition induces upstream receptor tyrosine kinase signaling and activates Akt," Cancer Res 66(3):1500-1508.

Ostro et al., "Use of liposomes as injectable-drug delivery systems," Am J Hosp Pharm. Aug. 1989; 46(8):1576-87.

Rao, "Recent developments of collagen-based materials for medical applications and drug delivery systems," J Biomater Sci Polym Ed. 1995;7(7):623-45.

Rhodes, N. et al. (Apr. 1, 2008). "Characterization of an Akt kinase inhibitor with potent pharmacodynamic and antitumor activity," Cancer Res 68(7):2366-2374.

Rodrik-Outmezguine, V.S. et al. (Aug. 2011, e-published Jun. 17, 2011). "mTOR kinase inhibition causes feedback-dependent biphasic regulation of AKT signaling," Cancer Discov 1(3):248-259.

Rodrik-Outmezguine, V.S. et al. "Overcoming mTOR resistance mutations with a new-generation mTOR inhibitor," Nature. Jun. 9, 2016;534(7606):272-6.

Ruggero, D. et al. (May 2004, e-published Apr. 18, 2004). "The translation factor elF-4E promotes tumor formation and cooperates with c-Myc in lymphomagenesis," Nat Med 10(5):484-486.

Sarbassov, D.D. et al. (Jul. 27, 2004). "Rictor, a novel binding partner of mTOR, defines a rapamycin-insensitive and raptor-independent pathway that regulates the cytoskeleton," Curr Biol 14(14):1296-1302.

Sarbassov, D.D. et al. (Apr. 21, 2006). "Prolonged rapamycin treatment inhibits mTORC2 assembly and Akt/PKB," Mol Cell 22(2):159-168.

(56) References Cited

OTHER PUBLICATIONS

Shu et al., "Synthesis of I-125 labeled photoaffinity rapamycin analogs," Journal of Labelled Compounds and Radiopharmaceuticals, vol. 38, No. 3, 1996, pp. 227-237.
Strom et al., "Structural identification of SAR-943 metabolites generated by human liver microsomes in vitro using mass spectrometry in combination with analysis of fragmentation patterns," J. Mass. Spectrom. 2011, 46, 615-624.
Su, K. Y. et al. (Feb. 1, 2012). "Pretreatment epidermal growth factor receptor (EGFR) T790M mutation predicts shorter EGFR tyrosine kinase inhibitor response duration in patients with non-small-cell lung cancer," J Clin Oncol 30(4):433-440.
Thoreen, C.C. et al. (Mar. 20, 2009, e-published Jan. 15, 2009). "An ATP-competitive mammalian target of rapamycin inhibitor reveals rapamycin-resistant functions of mTORC1," J Biol Chem 281(12):8023-8032.
Umeda, N. et al. (Jan. 12, 2011, e-published Dec. 13, 2010). "A photocleavable rapamycin conjugate for spatiotemporal control of small GTPase activity," J Am Chem Soc 133(1):12-14.
Wood, E.R. et al. (Sep. 15, 2004). "A unique structure for epidermal growth factor receptor bound to GW572016 (Lapatinib): relationships among protein conformation, inhibitor off-rate, and receptor activity in tumor cells," Cancer Res 64(18):6652-6659.
Xie et al., "Design, Synthesis and Biological Evaluation of Novel Rapamycin Benzothiazole Hybrids as mTOR Targeted Anti-cancer Agents," Chem Pharm Bull (Tokyo). 2016;64(4):346-55.
Xie et al., "Synthesis of Rapamycin Derivatives Containing the Triazole Moiety Used as Potential mTOR-Targeted Anticancer Agents," Arch Pharm (Weinheim). Jun. 2016;349(6):428-41.
Xu, C.X. et al. (2011, e-published Jun. 14, 2011). "The combination of RAD001 and NVP-BEZ235 exerts synergistic anticancer activity against non-small cell lung cancer in vitro and in vivo," PLoS One 6(6):e20899.
Yang, H. et al. (May 9, 2013, e-published May 1, 2013). "mTOR kinase structure, mechanism and regulation," Nature 497(7448):217-223.
Zeng, H. et al. (Jul. 25, 2013, e-published Jun. 30, 2013). "mTORC1 couples immune signals and metabolic programming to establish T(reg)-cell function," Nature (7459):485-490.
International Search Report dated Dec. 14, 2015, for PCT Application No. PCT/US2015/049693, filed on Sep. 11, 2015, 3 pages.
Written Opinion dated Dec. 14, 2015, or PCT Application No. PCT/US2015/049693, filed on Sep. 11, 2015, 7 pages.
International Search Report dated Aug. 28, 2018, for PCT Application No. PCT/US2018/030531, filed on May 1, 2018, 16 pages.
International Search Report dated Sep. 23, 2019, for PCT Application No. PCT/US2019/029737, filed on Apr. 29, 2019, 12 pages.
International Search Report dated Jun. 26, 2019, for PCT Application No. PCT/US2019/029738, filed on Apr. 29, 2019, 4 pages.
Masuda H. et al., "Synthesis of Alkoxy-, (Alkylthio)-, Phenoxy-, and (Phenylthio)pyrazines and their Olfactive Properties," J. Agric. Food Chem., 1986, 34(2), pp. 377-381.
Yamanishi Y. et al., "Syntheses of trimethylpyrazines and their antibacterial properties," Yakugaku Zasshi, 1967, 87(1), pp. 105-107.
Chou, Ting-Chao, "Drug Combination Studies and Their Synergy Quantification Using the Chou-Talalay Method." Cancer Research (2010); vol. 70(2), pp. 440-446.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/M_mater/docs/osnovi_med_pomoshi.pdf?ysclid=l5wi7xgplo450927514. (Machine Translation).
Kümmerer, K., et al., "Pharmaceuticals in the Environment," Annual Review of Environment and Resources (2010); vol. 35, pp. 57-75.
Mashkovsky, M.D., "Medicaments," 14th edition, vol. 1, Moscow., 2001, 6 pages (with English translation).

\* cited by examiner

SEQUENCE LISTING

<160> NUMBER OF SEQ ID NOS: 5

<210> SEQ ID NO 1
<211> LENGTH: 2549
<212> TYPE: PRT
<213> ORGANISM: Homo sapiens

<400> SEQUENCE: 1

```
Met Leu Gly Thr Gly Pro Ala Ala Thr Ala Thr Thr Ser
1               5                   10              15

Ser Asn Val Ser Val Leu Gln Gln Phe Ala Ser Gly Leu Lys Ser Arg
            20                  25                  30

Asn Glu Glu Thr Arg Ala Lys Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
                100                 105                 110

Asn Leu Leu Pro Ser Asn Asp Pro Val Val Met Glu Met Ala Ser Lys
            115                 120                 125

Ala Ile Gly Arg Leu Ala Met Ala Gly Asp Thr Phe Thr Ala Glu Tyr
            130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
            195                 200                 205

Ala Val Ala Ala Leu Arg Ala Cys Leu Ile Leu Thr Thr Gln Arg Glu
210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
                275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415
```

```
Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
            435                 440                 445

Lys Val Tyr Leu Pro Arg Val Leu Asp Ile Ile Arg Ala Ala Leu Pro
            450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
            530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
            595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
            755                 760                 765

Arg Pro Tyr Met Glu Pro Ile Leu Lys Ala Leu Ile Leu Lys Leu Lys
            770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
```

-continued

Ala Ser Thr Gly Tyr Val Val Glu Pro Tyr Arg Lys Tyr Pro Thr Leu
        835                 840                 845
                850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
        930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
            995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Glu Asp Pro Leu Ile Tyr Gln
    1220                1225                1230

His Arg Met Leu Arg Ser Gly Gln Gly Asp Ala Leu Ala Ser Gly
    1235                1240                1245

```
Pro Val Glu Thr Gly Pro Met Lys Lys Leu His Val Ser Thr Ile
1250                1255                1260

Asn Leu Gln Lys Ala Trp Gly Ala Ala Arg Arg Val Ser Lys Asp
1265                1270                1275

Asp Trp Leu Glu Trp Leu Arg Arg Leu Ser Leu Glu Leu Leu Lys
1280                1285                1290

Asp Ser Ser Ser Pro Ser Leu Arg Ser Cys Trp Ala Leu Ala Gln
1295                1300                1305

Ala Tyr Asn Pro Met Ala Arg Asp Leu Phe Asn Ala Ala Phe Val
1310                1315                1320

Ser Cys Trp Ser Glu Leu Asn Glu Asp Gln Gln Asp Glu Leu Ile
1325                1330                1335

Arg Ser Ile Glu Leu Ala Leu Thr Ser Gln Asp Ile Ala Glu Val
1340                1345                1350

Thr Gln Thr Leu Leu Asn Leu Ala Glu Phe Met Glu His Ser Asp
1355                1360                1365

Lys Gly Pro Leu Pro Leu Arg Asp Asp Asn Gly Ile Val Leu Leu
1370                1375                1380

Gly Glu Arg Ala Ala Lys Cys Arg Ala Tyr Ala Lys Ala Leu His
1385                1390                1395

Tyr Lys Glu Leu Glu Phe Gln Lys Gly Pro Thr Pro Ala Ile Leu
1400                1405                1410

Glu Ser Leu Ile Ser Ile Asn Asn Lys Leu Gln Gln Pro Glu Ala
1415                1420                1425

Ala Ala Gly Val Leu Glu Tyr Ala Met Lys His Phe Gly Glu Leu
1430                1435                1440

Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Asp Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635
```

-continued

Val Arg Ser Leu Val Val Ser Pro His Glu Asp Met Arg Thr Trp
1640                    1645                1650

Leu Lys Tyr Ala Ser Leu Cys Gly Lys Ser Gly Arg Leu Ala Leu
1655                    1660                1665

Ala His Lys Thr Leu Val Leu Leu Leu Gly Val Asp Pro Ser Arg
1670                    1675                1680

Gln Leu Asp His Pro Leu Pro Thr Val His Pro Gln Val Thr Tyr
1685                    1690                1695

Ala Tyr Met Lys Asn Met Trp Lys Ser Ala Arg Lys Ile Asp Ala
1700                    1705                1710

Phe Gln His Met Gln His Phe Val Gln Thr Met Gln Gln Gln Ala
1715                    1720                1725

Gln His Ala Ile Ala Thr Glu Asp Gln Gln His Lys Gln Glu Leu
1730                    1735                1740

His Lys Leu Met Ala Arg Cys Phe Leu Lys Leu Gly Glu Trp Gln
1745                    1750                1755

Leu Asn Leu Gln Gly Ile Asn Glu Ser Thr Ile Pro Lys Val Leu
1760                    1765                1770

Gln Tyr Tyr Ser Ala Ala Thr Glu His Asp Arg Ser Trp Tyr Lys
1775                    1780                1785

Ala Trp His Ala Trp Ala Val Met Asn Phe Glu Ala Val Leu His
1790                    1795                1800

Tyr Lys His Gln Asn Gln Ala Arg Asp Glu Lys Lys Lys Leu Arg
1805                    1810                1815

His Ala Ser Gly Ala Asn Ile Thr Asn Ala Thr Thr Ala Ala Thr
1820                    1825                1830

Thr Ala Ala Thr Ala Thr Thr Thr Ala Ser Thr Glu Gly Ser Asn
1835                    1840                1845

Ser Glu Ser Glu Ala Glu Ser Thr Glu Asn Ser Pro Thr Pro Ser
1850                    1855                1860

Pro Leu Gln Lys Lys Val Thr Glu Asp Leu Ser Lys Thr Leu Leu
1865                    1870                1875

Met Tyr Thr Val Pro Ala Val Gln Gly Phe Phe Arg Ser Ile Ser
1880                    1885                1890

Leu Ser Arg Gly Asn Asn Leu Gln Asp Thr Leu Arg Val Leu Thr
1895                    1900                1905

Leu Trp Phe Asp Tyr Gly His Trp Pro Asp Val Asn Glu Ala Leu
1910                    1915                1920

Val Glu Gly Val Lys Ala Ile Gln Ile Asp Thr Trp Leu Gln Val
1925                    1930                1935

Ile Pro Gln Leu Ile Ala Arg Ile Asp Thr Pro Arg Pro Leu Val
1940                    1945                1950

Gly Arg Leu Ile His Gln Leu Leu Thr Asp Ile Gly Arg Tyr His
1955                    1960                1965

Pro Gln Ala Leu Ile Tyr Pro Leu Thr Val Ala Ser Lys Ser Thr
1970                    1975                1980

Thr Thr Ala Arg His Asn Ala Ala Asn Lys Ile Leu Lys Asn Met
1985                    1990                1995

Cys Glu His Ser Asn Thr Leu Val Gln Gln Ala Met Met Val Ser
2000                    2005                2010

Glu Glu Leu Ile Arg Val Ala Ile Leu Trp His Glu Met Trp His
2015                    2020                2025

Glu Gly Leu Glu Glu Ala Ser Arg Leu Tyr Phe Gly Glu Arg Asn

-continued

Val Lys Gly Met Phe Glu Val Leu Glu Pro Leu His Ala Met Met
2045                2050                2055

Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Ile Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

```
Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 2
<211> LENGTH: 8733
<212> TYPE: DNA
<213> ORGANISM: Homo sapiens

<400> SEQUENCE: 2
gctcccggct tagaggacag cggggaaggc gggcggtggg gcaggggcc tgaagcggcg      60 gtaccggtgc tggcggcggc agctgaggcc ttggccgaag ccgcgcgaac ctcagggcaa    120
gatgcttgga accggacctg ccgccgccac caccgctgcc accacatcta gcaatgtgag    180
cgtcctgcag cagtttgcca gtggcctaaa gagccggaat gaggaaacca gggccaaagc    240
cgccaaggag ctccagcact atgtcaccat ggaactccga gagatgagtc aagaggagtc    300
tactcgcttc tatgaccaac tgaaccatca cattttttga ttggtttcca gctcagatgc    360
caatgagagg aaaggtggca tcttggccat agctagcctc ataggagtgg aaggtgggaa    420
tgccacccga attggcagat tgccaactac tcttcggaac ctcctcccct ccaatgaccc    480
agttgtcatg gaaatggcat ccaaggccat tggccgtctt gccatggcag ggacacttt     540 taccgctgag tacgtggaat ttgaggtgaa gcgagccctg gaatggctgg gtgctgaccg    600
caatgagggc cggagacatg cagctgtcct ggttctccgt gagctggcca tcagcgtccc    660
taccttcttc ttccagcaag tgcaacccct tctttgacaac attttttgtgg ccgtgtggga    720 cccccaaacag gccatccgtg agggagctgt agccgccctt cgtgcctgtc tgattctcac    780
aacccagcgt gagccgaagg agatgcagaa gcctcagtgg tacaggcaca catttgaaga    840
agcagagaag ggatttgatg agaccttggc caaagagaag gcatgaatc gggatgatcg     900 gatccatgga gccttgttga tccttaacga gctggtccga atcagcagca tggagggaga    960
gcgtctgaga gaagaaatgg aagaaatcac acagcagcag ctggtacacg acaagtactg   1020
caaagatctc atgggcttcg gaacaaaacc tcgtcacatt ccccccttca ccagtttcca   1080
ggctgtacag ccccagcagt caaatgcctt ggtggggctg ctggggtaca gctctcacca   1140
aggcctcatg ggatttggga cctcccccag tccagctaag tccaccctgg tggagagcca   1200
gtgttgcaga gacttgatgg aggagaaatt tgatcaggtg tgccagtggg tgctgaaatg   1260
caggaatagc aagaactcgc tgatccaaat gacaatcctt aatttgttgc cccgcttggc   1320
tgcattccga ccttctgcct tcacagatac ccagtatctc aagatacca tgaaccatgt   1380
```

```
cctaagctgt gtcaagaagg agaaggaacg tacagcggcc ttccaagccc tggggctact    1440
ttctgtggct gtgaggtctg agtttaaggt ctatttgcct cgcgtgctgg acatcatccg    1500
agcggccctg cccccaaagg acttcgccca taagaggcag aaggcaatgc aggtggatgc    1560
cacagtcttc acttgcatca gcatgctggc tcgagcaatg gggccaggca tccagcagga    1620
tatcaaggag ctgctggagc ccatgctggc agtgggacta agccctgccc tcactgcagt    1680
gctctacgac ctgagccgtc agattccaca gctaaagaag gacattcaag atgggctact    1740
gaaaatgctg tccctggtcc ttatgcacaa accccttcgc cacccaggca tgcccaaggg    1800
cctggcccat cagctggcct ctcctggcct cacgaccctc cctgaggcca gcgatgtggg    1860
cagcatcact cttgccctcc gaacgcttgg cagctttgaa tttgaaggcc actctctgac    1920
ccaatttgtt cgccactgtg cggatcattt cctgaacagt gagcacaagg agatccgcat    1980
ggaggctgcc cgcacctgct cccgcctgct cacaccctcc atccacctca tcagtggcca    2040
tgctcatgtg gttagccaga ccgcagtgca agtggtggca gatgtgctta gcaaactgct    2100
cgtagttggg ataacagatc ctgaccctga cattcgctac tgtgtcttgg cgtccctgga    2160
cgagcgcttt gatgcacacc tggcccaggc ggagaacttg caggccttgt tgtggctct    2220 gaatgaccag gtgtttgaga tccggggagct ggccatctgc actgtgggcc gactcagtag    2280
catgaaccct gcctttgtca tgcctttcct gcgcaagatg ctcatccaga ttttgacaga    2340
gttggagcac agtgggattg gaagaatcaa agagcagagt gccgcatgc tggggcacct    2400 ggtctccaat gcccccgac tcatccgccc ctacatggag cctattctga aggcattaat    2460
tttgaaactg aaagatccag accctgatcc aaacccaggt gtgatcaata atgtcctggc    2520 aacaataga gaattggcac aggttagtgg cctggaaatg aggaaatggg ttgatgaact    2580
ttttattatc atcatggaca tgctccagga ttcctctttg ttggccaaaa ggcaggtggc    2640
tctgtggacc ctgggacagt tggtggccag cactggctat gtagtagagc cctacaggaa    2700
gtaccctact ttgcttgagg tgctactgaa ttttctgaag actgagcaga accagggtac    2760
acgcagagag gccatccgtg tgttagggct tttaggggct ttggatcctt acaagcacaa    2820
agtgaacatt ggcatgatag accagtcccg ggatgcctct gctgtcagcc tgtcagaatc    2880
caagtcaagt caggattcct ctgactatag cactagtgaa atgctggtca catgggaaa    2940 cttgcctctg gatgagttct acccagctgt gtccatggtg gccctgatgc ggatcttccg    3000
agaccagtca ctctctcatc atcacaccat ggttgtccag gccatcacct tcatcttcaa    3060
gtccctggga ctcaaatgtg tgcagttcct gccccaggtc atgcccacgt tccttaacgt    3120
cattcgagtc tgtgatgggg ccatccggga attttgttc cagcagctgg gaatgttggt    3180
gtcctttgtg aagagccaca tcagaccttta tatggatgaa atagtcaccc tcatgagaga    3240
attctgggtc atgaacacct caattcagag cacgatcatt cttctcattg agcaaattgt    3300
ggtagctctt gggggtgaat ttaagctcta cctgccccag ctgatcccac acatgctgcg    3360
tgtcttcatg catgacaaca gcccaggccg cattgtctct atcaagttac tggctgcaat    3420
ccagctgttt ggcgccaacc tggatgacta cctgcattta ctgctgcctc ctattgttaa    3480
gttgtttgat gcccctgaag ctccactgcc atctcgaaag gcagcgctag agactgtgga    3540
ccgcctgacg gagtccctgg atttcactga ctatgcctcc cggatcattc accctattgt    3600
tcgaacactg gaccagagcc agaactgcg ctccacagcc atggacacgc tgtcttcact    3660
tgtttttcag ctggggaaga agtaccaaat tttcattcca atggtgaata agttctgggt    3720
gcgacaccga atcaatcatc agcgctatga tgtgctcatc tgcagaattg tcaagggata    3780
```

```
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca aagatgactg    3960
gctggaatgg ctgagacggc tgagcctgga gctgctgaag gactcatcat cgccctccct    4020
gcgctcctgc tgggccctgg cacaggccta aacccgatg gccagggatc tcttcaatgc     4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtg ccagcatat gccaaagcac tacactacaa     4320
agaactggag ttccagaaag gccccacccc tgccattcta gaatctctca tcagcattaa    4380
taataagcta cagcagccgg aggcagcggc cggagtgtta aatatgcca tgaaacactt     4440 tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tgggggaatg gggtcaactc caccagcagt gctgtgaaaa    4620
gtggaccctg gttaatgatg agacccaagc caagatggcc cggatggctg ctgcagctgc    4680
atggggttta ggtcagtggg acagcatgga agaatacacc tgtatgatcc ctcgggacac    4740
ccatgatggg gcatttata gagctgtgct ggcactgcat caggacctct tctccttggc     4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaactta gtgttgctcc tgggagttga     5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgag aagaagaaac tgcgtcatgc    5580
cagcggggcc aacatcacca acgccaccac tgccgccacc acggccgcca ctgccaccac    5640
cactgccagc accgagggca gcaacagtga gagcgaggcc gagagcaccg agaacagccc    5700 cacccccatcg ccgctgcaga agaaggtcac tgaggatctg tccaaaaccc tcctgatgta   5760
cacggtgcct gccgtccagg gcttcttccg ttccatctcc ttgtcacgag caacaacct     5820 ccaggataca ctcagagttc tcaccttatg gtttgattat ggtcactggc cagatgtcaa    5880
tgaggcctta gtggagggg tgaaagccat ccagattgat acctggctac aggttatacc     5940
tcagctcatt gcaagaattg atacgcccag acccttggtg ggacgtctca ttcaccagct    6000
tctcacagac attggtcggt accacccca ggccctcatc tacccactga cagtggcttc     6060
taagtctacc acgacagccc ggcacaatgc agccaacaag attctgaaga acatgtgtga    6120
```

-continued

```
gcacagcaac accctggtcc agcaggccat gatggtgagc gaggagctga tccgagtggc    6180
catcctctgg catgagatgt ggcatgaagg cctggaagag gcatctcgtt tgtactttgg    6240
ggaaaggaac gtgaaaggca tgtttgaggt gctggagccc ttgcatgcta tgatggaacg    6300
gggcccccag actctgaagg aaacatcctt taatcaggcc tatggtcgag atttaatgga    6360
ggcccaagag tggtgcagga agtacatgaa atcagggaat gtcaaggacc tcacccaagc    6420
ctgggacctc tattatcatg tgttccgacg aatctcaaag cagctgcctc agctcacatc    6480
cttagagctg caatatgttt ccccaaaact tctgatgtgc cgggaccttg aattggctgt    6540
gccaggaaca tatgacccca accagccaat cattcgcatt cagtccatag caccgtcttt    6600
gcaagtcatc acatccaagc agaggccccg gaaattgaca cttatgggca gcaacggaca    6660
tgagtttgtt ttccttctaa aaggccatga agatctgcgc caggatgagc gtgtgatgca    6720
gctcttcggc ctggttaaca cccttctggc caatgaccca acatctcttc ggaaaaacct    6780
cagcatccag agatacgctg tcatcccttt atcgaccaac tcgggcctca ttggctgggt    6840
tccccactgt gacacactgc acgccctcat ccgggactac agggagaaga agaagatcct    6900
tctcaacatc gagcatcgca tcatgttgcg gatggctccg gactatgacc acttgactct    6960
gatgcagaag gtggaggtgt ttgagcatgc cgtcaataat acagctgggg acgacctggc    7020
caagctgctg tggctgaaaa gccccagctc cgaggtgtgg tttgaccgaa gaaccaatta    7080
tacccgttct ttagcggtca tgtcaatggt tgggtatatt ttaggcctgg gagatagaca    7140
cccatccaac ctgatgctgg accgtctgag tgggaagatc ctgcacattg actttgggga    7200
ctgctttgag gttgctatga cccgagagaa gtttccagag aagattccat ttagactaac    7260
aagaatgttg accaatgcta tggaggttac aggcctggat ggcaactaca gaatcacatg    7320
ccacacagtg atggaggtgc tgcgagagca caaggacagt gtcatggccg tgctggaagc    7380 cttttgtctat gaccccttgc tgaactggag gctgatggac acaaatacca aaggcaacaa    7440
gcgatcccga acgaggacgg attcctactc tgctggccag tcagtcgaaa ttttggacgg    7500
tgtggaactt ggagagccag cccataagaa aacggggacc acagtgccag aatctattca    7560
ttctttcatt ggagacggtt tggtgaaacc agaggcccta aataagaaag ctatccagat    7620
tattaacagg gttcgagata agctcactgg tcgggacttc tctcatgatg acactttgga    7680
tgttccaacg caagttgagc tgctcatcaa acaagcgaca tcccatgaaa acctctgcca    7740
gtgctatatt ggctggtgcc cttttctggta actggaggcc cagatgtgcc catcacgttt    7800
tttctgaggc ttttgtactt tagtaaatgc ttccactaaa ctgaaaccat ggtgagaaag    7860
tttgactttg ttaaatattt tgaaatgtaa atgaaaagaa ctactgtata ttaaaagttg    7920
gtttgaacca actttctagc tgctgttgaa gaatatattg tcagaaacac aaggcttgat    7980
ttggttccca ggacagtgaa acatagtaat accacgtaaa tcaagccatt cattttgggg    8040
aacagaagat cctaaacttt agaaatacgg gttttgactt aactcacaag gaactcatc     8100 ataagtactt gctgatggaa gaatgaccta gttgctcctc tcaacatggg tacagcaaac    8160
tcagcacagc caagaagcct caggtcgtgg agaacatgga ttaggatcct agactgtaaa    8220
gacacagaag atgctgacct caccctgcc acctatccca agacctcact ggtctgtgga     8280
cagcagcaga aatgtttgca agataggcca aaatgagtac aaaaggtctg tcttccatca    8340
gacccagtga tgctgcgact cacacgcttc aattcaagac ctgaccgcta gtaggaggt     8400 ttattcagat cgctggcagc ctcggctgag cagatgcaca gaggggatca ctgtgcagtg    8460
ggaccaccct cactggcctt ctgcagcagg gttctgggat gttttcagtg gtcaaaatac    8520
```

```
tctgtttaga gcaagggctc agaaaacaga aatactgtca tggaggtgct gaacacaggg    8580
aaggtctggt acatattgga aattatgagc agaacaaata ctcaactaaa tgcacaaagt    8640
ataaagtgta gccatgtcta gacaccatgt tgtatcagaa taatttttgt gccaataaat    8700
gacatcagaa ttttaaacat atgtaaaaaa aaa                                 8733
```

```
<210> SEQ ID NO 3
<211> LENGTH: 108
<212> TYPE: PRT
<213> ORGANISM: Homo sapiens

<400> SEQUENCE: 3

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105
```

```
<210> SEQ ID NO 4
<211> LENGTH: 118
<212> TYPE: PRT
<213> ORGANISM: Homo sapiens

<400> SEQUENCE: 4

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
            20                  25                  30

Asp Tyr Ser Thr Thr Pro Gly Gly Thr Leu Phe Ser Thr Thr Pro Gly
        35                  40                  45

Gly Thr Arg Ile Ile Tyr Asp Arg Lys Phe Leu Met Glu Cys Arg Asn
    50                  55                  60

Ser Pro Val Thr Lys Thr Pro Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
            100                 105                 110

Gln Phe Glu Met Asp Ile
        115
```

```
<210> SEQ ID NO 5
<211> LENGTH: 480
<212> TYPE: PRT
<213> ORGANISM: Homo sapiens

<400> SEQUENCE: 5

Met Ser Asp Val Ala Ile Val Lys Glu Gly Trp Leu His Lys Arg Gly
```

-continued

```
 1               5                  10                 15
Glu Tyr Ile Lys Thr Trp Arg Pro Arg Tyr Phe Leu Leu Lys Asn Asp
             20                 25                 30
Gly Thr Phe Ile Gly Tyr Lys Glu Arg Pro Gln Asp Val Asp Gln Arg
             35                 40                 45
Glu Ala Pro Leu Asn Asn Phe Ser Val Ala Gln Cys Gln Leu Met Lys
 50                 55                 60
Thr Glu Arg Pro Arg Pro Asn Thr Phe Ile Ile Arg Cys Leu Gln Trp
 65                 70                 75                 80
Thr Thr Val Ile Glu Arg Thr Phe His Val Glu Thr Pro Glu Glu Arg
             85                 90                 95
Glu Glu Trp Thr Thr Ala Ile Gln Thr Val Ala Asp Gly Leu Lys Lys
             100                105                110
Gln Glu Glu Glu Met Asp Phe Arg Ser Gly Ser Pro Ser Asp Asn
             115                120                125
Ser Gly Ala Glu Glu Met Glu Val Ser Leu Ala Lys Pro Lys His Arg
 130                135                140
Val Thr Met Asn Glu Phe Glu Tyr Leu Lys Leu Leu Gly Lys Gly Thr
 145                150                155                160
Phe Gly Lys Val Ile Leu Val Lys Glu Lys Ala Thr Gly Arg Tyr Tyr
             165                170                175
Ala Met Lys Ile Leu Lys Lys Glu Val Ile Val Ala Lys Asp Glu Val
             180                185                190
Ala His Thr Leu Thr Glu Asn Arg Val Leu Gln Asn Ser Arg His Pro
             195                200                205
Phe Leu Thr Ala Leu Lys Tyr Ser Phe Gln Thr His Asp Arg Leu Cys
 210                215                220
Phe Val Met Glu Tyr Ala Asn Gly Gly Glu Leu Phe Phe His Leu Ser
 225                230                235                240
Arg Glu Arg Val Phe Ser Glu Asp Arg Ala Arg Phe Tyr Gly Ala Glu
             245                250                255
Ile Val Ser Ala Leu Asp Tyr Leu His Ser Glu Lys Asn Val Val Tyr
             260                265                270
Arg Asp Leu Lys Leu Glu Asn Leu Met Leu Asp Lys Asp Gly His Ile
             275                280                285
Lys Ile Thr Asp Phe Gly Leu Cys Lys Glu Gly Ile Lys Asp Gly Ala
 290                295                300
Thr Met Lys Thr Phe Cys Gly Thr Pro Glu Tyr Leu Ala Pro Glu Val
 305                310                315                320
Leu Glu Asp Asn Asp Tyr Gly Arg Ala Val Asp Trp Trp Gly Leu Gly
             325                330                335
Val Val Met Tyr Glu Met Met Cys Gly Arg Leu Pro Phe Tyr Asn Gln
             340                345                350
Asp His Glu Lys Leu Phe Glu Leu Ile Leu Met Glu Glu Ile Arg Phe
             355                360                365
Pro Arg Thr Leu Gly Pro Glu Ala Lys Ser Leu Leu Ser Gly Leu Leu
             370                375                380
Lys Lys Asp Pro Lys Gln Arg Leu Gly Gly Ser Glu Asp Ala Lys
 385                390                395                400
Glu Ile Met Gln His Arg Phe Phe Ala Gly Ile Val Trp Gln His Val
             405                410                415
Tyr Glu Lys Lys Leu Ser Pro Pro Phe Lys Pro Gln Val Thr Ser Glu
             420                425                430
```

```
Thr Asp Thr Arg Tyr Phe Asp Glu Glu Phe Thr Ala Gln Met Ile Thr
        435                 440                 445

Ile Thr Pro Pro Asp Gln Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

C26-LINKED RAPAMYCIN ANALOGS AS MTOR INHIBITORS

CROSS REFERENCE TO RELATED APPLICATIONS

This application is a continuation of International Patent Application No. PCT/US2019/029738, filed Apr. 29, 2019, which claims the benefit of U.S. Provisional Application No. 62/665,426, filed May 1, 2018 and U.S. Provisional Application No. 62/752,881, filed Oct. 30, 2018, and U.S. Provisional Application No. 62/836,040, filed Apr. 18, 2019, the contents of each of which are incorporated herein by reference in their entireties.

REFERENCE TO A SEQUENCE LISTING

The Sequence Listing associated with this application is provided in text format in lieu of a paper copy, and is hereby incorporated by reference into the specification. The name of the text file containing the Sequence Listing is REME_009_01WO_SeqList_ST25.txt. The text file is about 43 Kilo Bytes, was created on Apr. 26, 2019, and is being submitted electronically via EFS-Web.

FIELD OF THE DISCLOSURE

The present disclosure relates to mTOR inhibitors. Specifically, the embodiments are directed to compounds and compositions inhibiting mTOR, methods of treating diseases mediated by mTOR, and methods of synthesizing these compounds.

BACKGROUND OF THE DISCLOSURE

The mammalian target of rapamycin (mTOR) is a serine-threonine kinase related to the lipid kinases of the phosphoinositide 3-kinase (PI3K) family. mTOR exists in two complexes, mTORC1 and mTORC2, which are differentially regulated, have distinct substrate specificities, and are differentially sensitive to rapamycin. mTORC1 integrates signals from growth factor receptors with cellular nutritional status and controls the level of cap-dependent mRNA translation by modulating the activity of key translational components such as the cap-binding protein and oncogene eIF4E.

mTOR signaling has been deciphered in increasing detail. The differing pharmacology of inhibitors of mTOR has been particularly informative. The first reported inhibitor of mTOR, Rapamycin is now understood to be an incomplete inhibitor of mTORC1. Rapamycin is a selective mTORC1 inhibitor through the binding to the FK506 Rapamycin Binding (FRB) domain of mTOR kinase with the aid of FK506 binding protein 12 (FKBP12). The FRB domain of mTOR is accessible in the mTORC1 complex, but less so in the mTORC2 complex. Interestingly, the potency of inhibitory activities against downstream substrates of mTORC1 by the treatment of Rapamycin is known to be diverse among the mTORC1 substrates. For example, Rapamycin strongly inhibits phosphorylation of the mTORC1 substrate S6K and, indirectly, phosphorylation of the downstream ribosomal protein S6 which control ribosomal biogenesis. On the other hand, Rapamycin shows only partial inhibitory activity against phosphorylation of 4E-BP1, a major regulator of eIF4E which controls the initiation of CAP-dependent translation. As a result, more complete inhibitors of mTORC1 signaling are of interest.

A second class of "ATP-site" inhibitors of mTOR kinase were reported. This class of mTOR inhibitors will be referred to as TORi (ATP site TOR inhibitor). The molecules compete with ATP, the substrate for the kinase reaction, in the active site of the mTOR kinase (and are therefore also mTOR active site inhibitors). As a result, these molecules inhibit downstream phosphorylation of a broader range of substrates.

Although mTOR inhibition may have the effect of blocking 4E-BP1 phosphorylation, these agents may also inhibit mTORC2, which leads to a block of Akt activation due to inhibition of phosphorylation of Akt S473.

Disclosed herein, inter alia, are mTOR inhibitors. In some embodiments, compounds disclosed herein are more selective inhibitors of mTORC1 versus mTORC2. In some embodiments, compounds disclosed herein are more selective inhibitors of mTORC2 versus mTORC1. In some embodiments, compounds disclosed herein exhibit no selectivity difference between mTORC1 and mTORC2.

SUMMARY OF THE DISCLOSURE

The present disclosure relates to compounds capable of inhibiting the activity of mTOR. The present disclosure further provides a process for the preparation of compounds of the present disclosure, pharmaceutical preparations comprising such compounds and methods of using such compounds and compositions in the management of diseases or disorders mediated by mTOR.

The present disclosure provides compounds of Formula Ia:

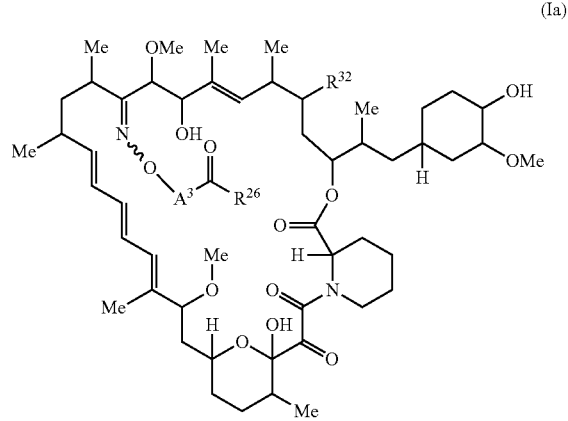

(Ia)

or a pharmaceutically acceptable salt or tautomer thereof, wherein:

$R^{32}$ is H, =O, —$OR^3$, or —$N_3$;

$A^3$ is —[C($R^3$)$_2$]$_n$—, ($C_6$-$C_{10}$)arylene, cycloalkylene, heteroarylene, or heterocyclylene;

$R^{26}$ is -$A^1$-$L^1$-$A^2$-B; -$A^1$-$A^2$-B; -$L^2$-$A^1$-$L^1$-$A^2$-$L^3$-B; or —OH;
$A^1$ and $A^2$ are independently absent or are independently selected from
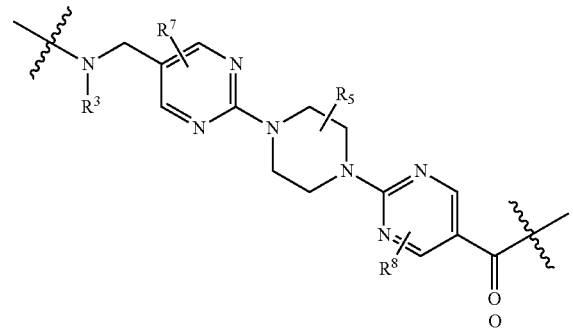
,
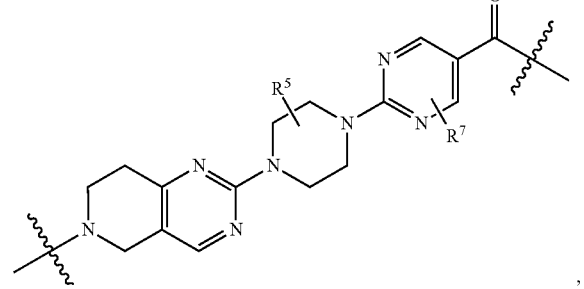
,
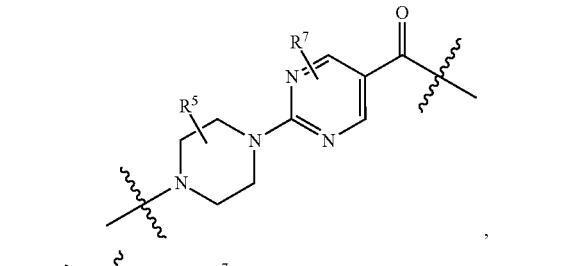
,
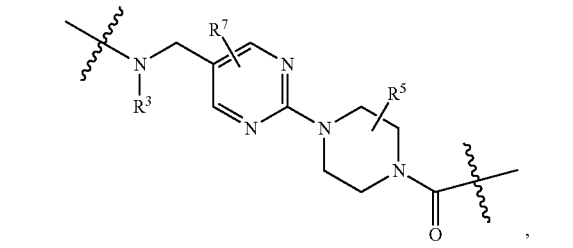
,
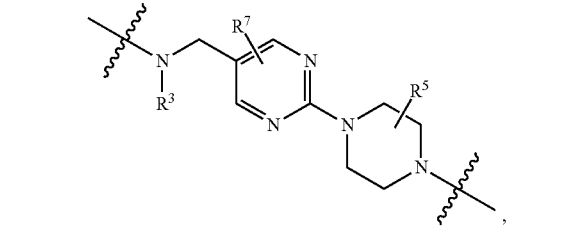
,
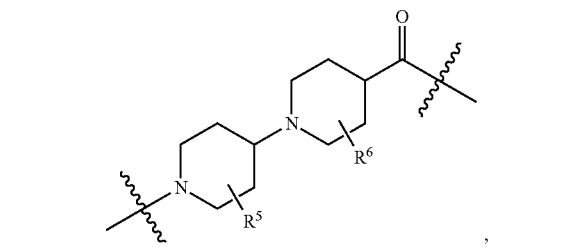
,
-continued
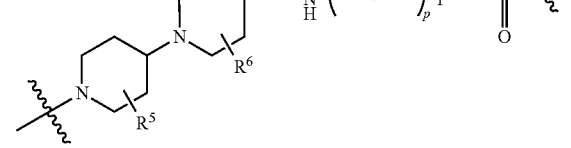
,
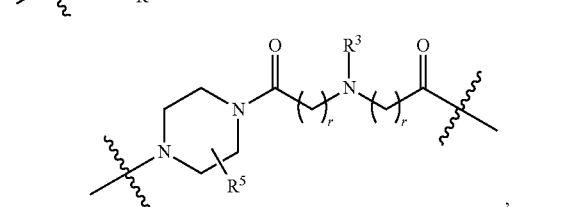
,
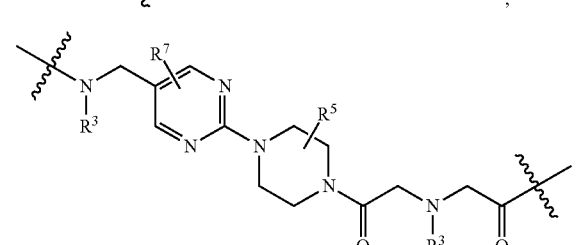
,
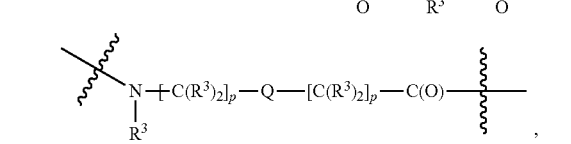
,
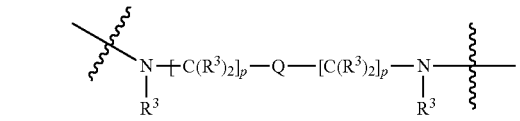
,
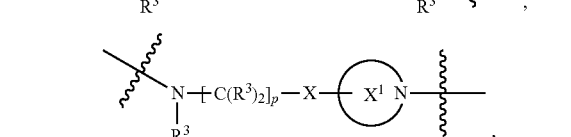
,
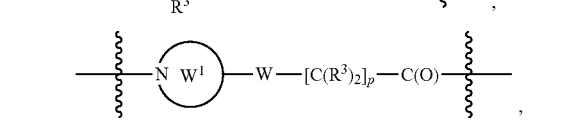
,
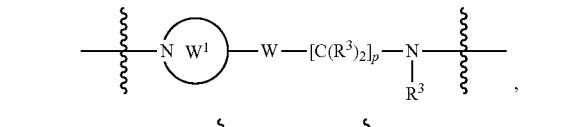
,
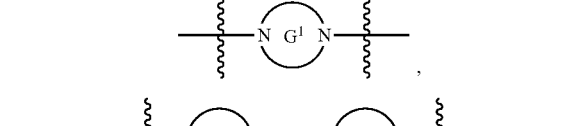
,
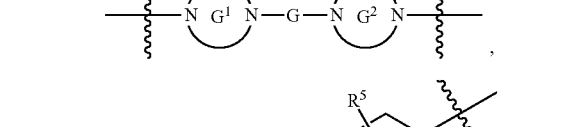
,
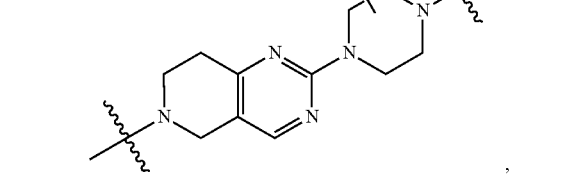
, -continued

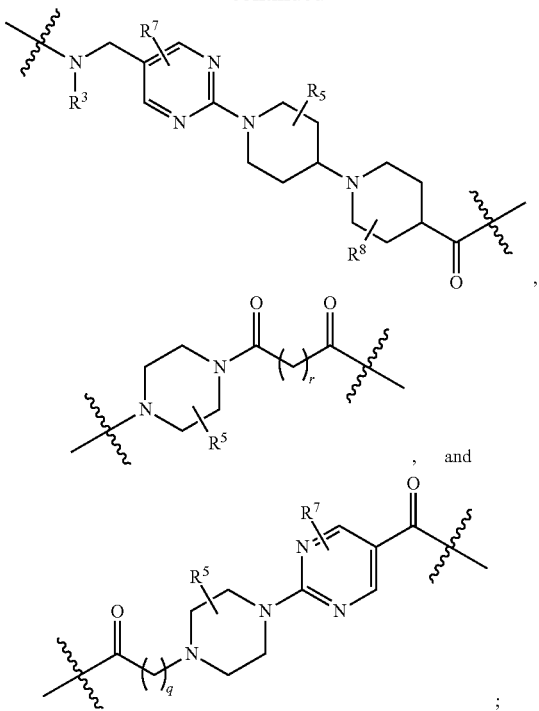

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

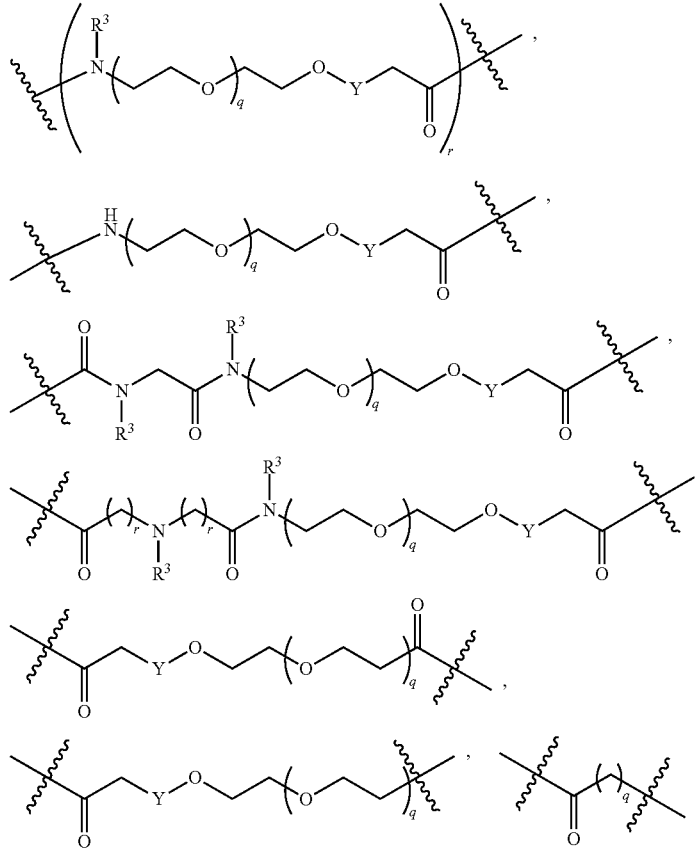

-continued
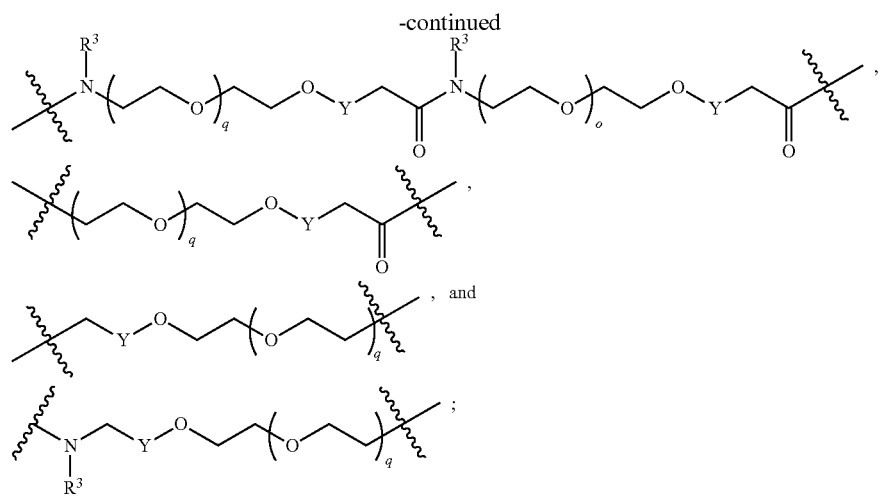
L² and L³ are independently absent or are independently selected from
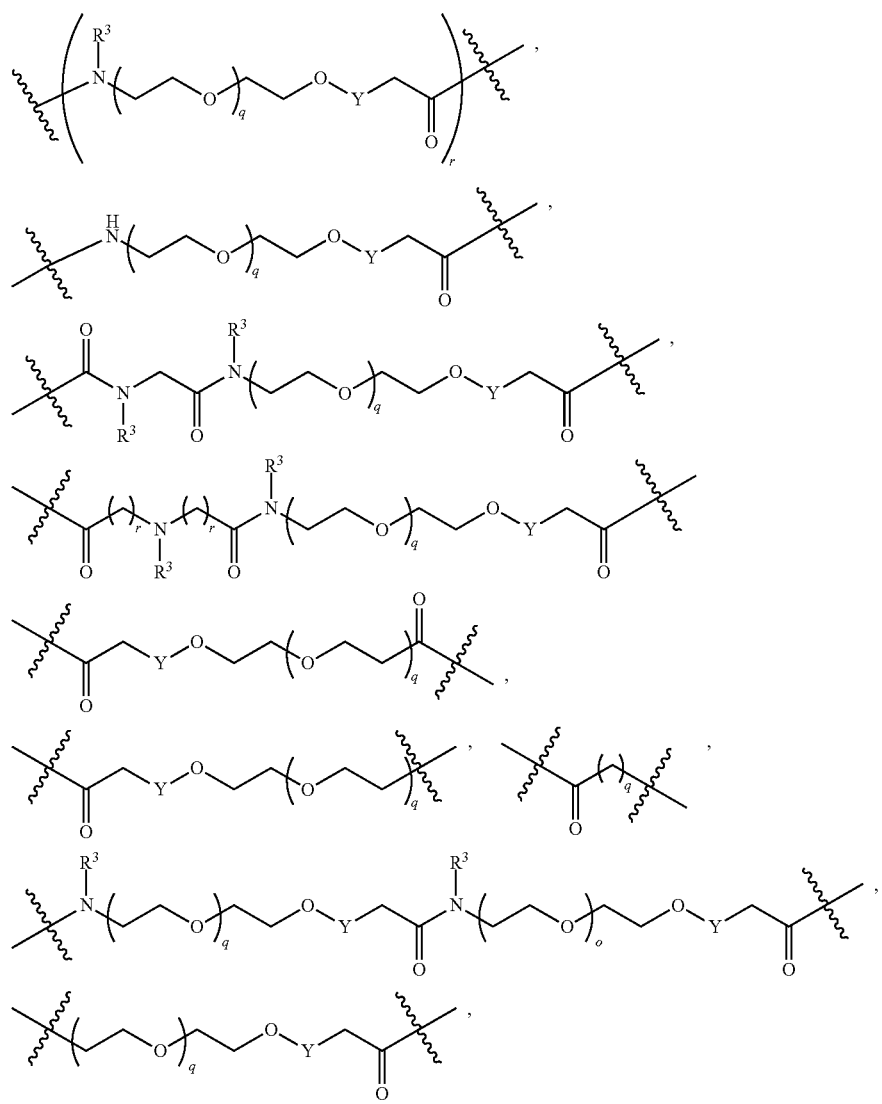

-continued
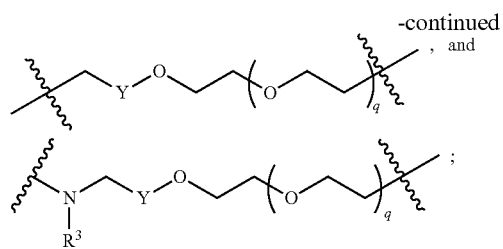, and
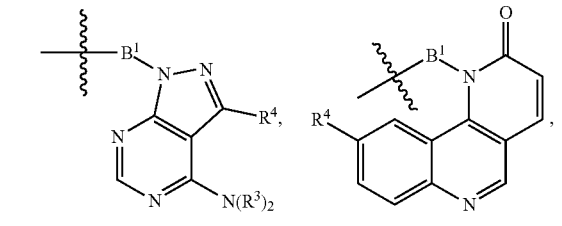;
each B is independently selected from
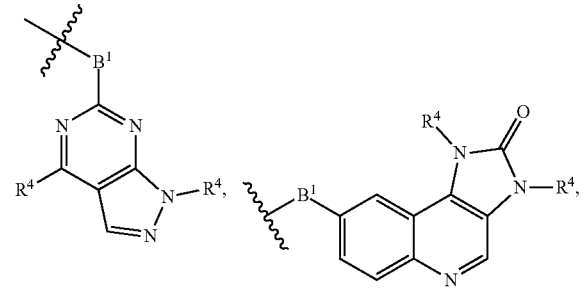
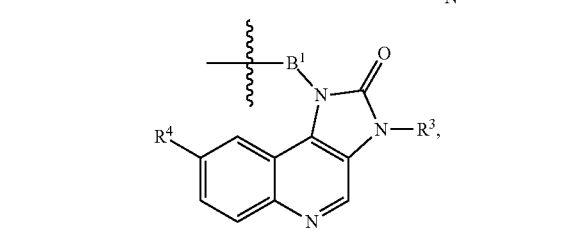
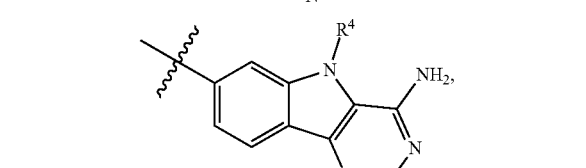
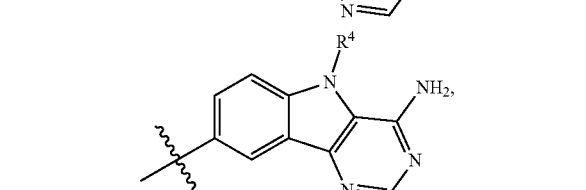
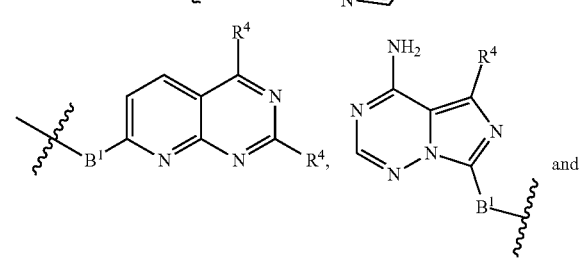
and
-continued
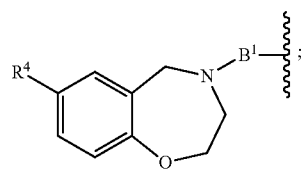;
each $B^1$ is independently selected from
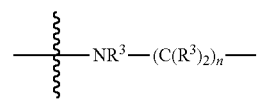,
,
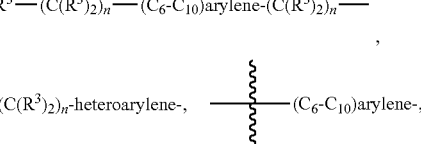,
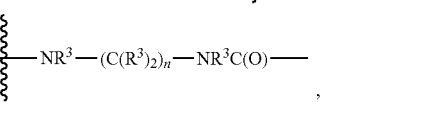,
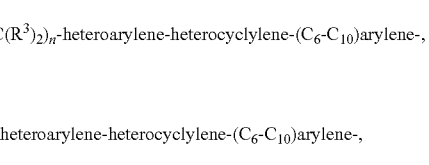,
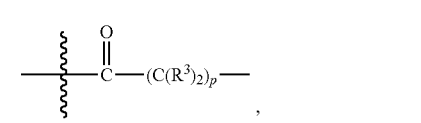,
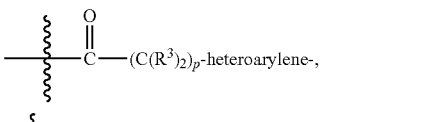,
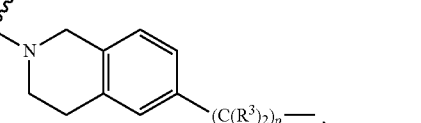,
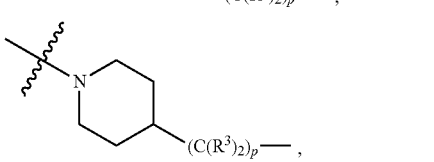, -continued

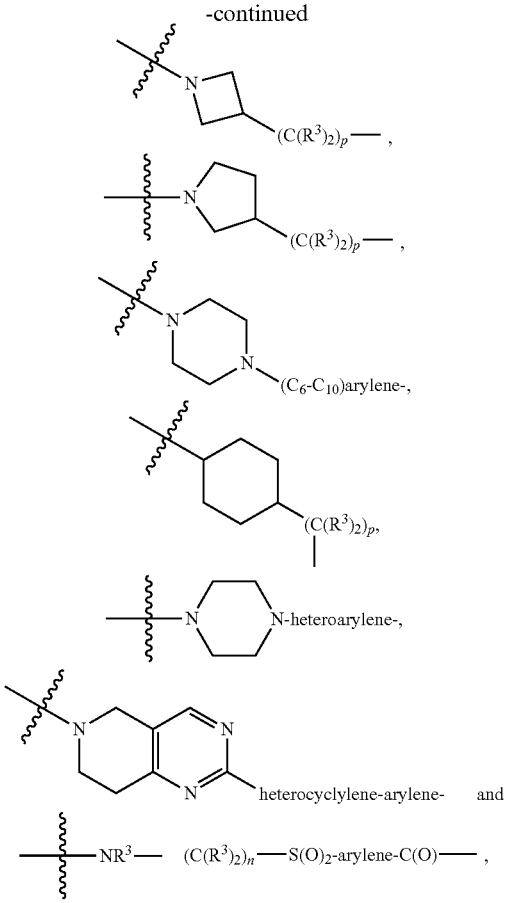

wherein the

bond on the left side of $B^1$, as drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with $-N(R^3)_2$, $-OR^3$, halogen, $(C_1\text{-}C_6)$alkyl, $-(C_1\text{-}C_6)$alkylene-heteroaryl, $-(C_1\text{-}C_6)$alkylene-CN, $-C(O)NR^3$-heteroaryl, or $-C(O)NR^3$-heterocyclyl;

each $R^5$ is independently H, $(C_1\text{-}C_6)$alkyl, $-C(O)OR^3$, or $-N(R^3)_2$, wherein the alkyl of $(C_1\text{-}C_6)$alkyl is optionally substituted with $-N(R^3)_2$ or $-OR^3$;

each $R^6$ is independently H, $(C_1\text{-}C_6)$alkyl, $-C(O)OR^3$, or $-N(R^3)_2$, wherein the alkyl of $(C_1\text{-}C_6)$alkyl is optionally substituted with $-N(R^3)_2$ or $-OR^3$;

each $R^7$ is independently H, $(C_1\text{-}C_6)$alkyl, $-C(O)OR^3$, or $-N(R^3)_2$, wherein the alkyl of $(C_1\text{-}C_6)$alkyl is optionally substituted with $-N(R^3)_2$ or $-OR^3$;

each $R^8$ is independently H, $(C_1\text{-}C_6)$alkyl, $-C(O)OR^3$, or $-N(R^3)_2$, wherein the alkyl of $(C_1\text{-}C_6)$alkyl is optionally substituted with $-N(R^3)_2$ or $-OR^3$;

each Y is independently $C(R^3)_2$ or a bond;

each n is independently an integer from one to 12;

each o is independently an integer from zero to 30;

each p is independently an integer from zero to 12;

each q is independently an integer from zero to 30; and each r is independently an integer from one to 6.

The present disclosure provides compounds of Formula I:

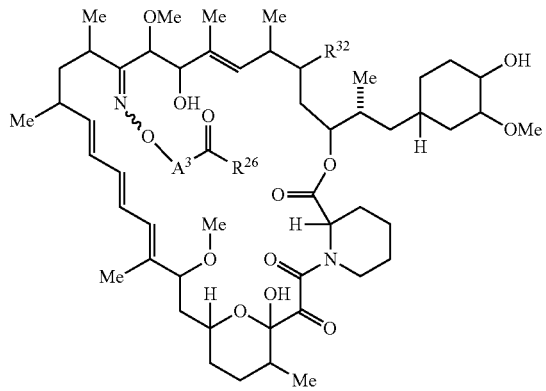

(I)

or a pharmaceutically acceptable salt or tautomer thereof, wherein:

$R^{32}$ is H, =O, or $-OR^3$;

$A^3$ is $-[C(R^3)_2]_n-$, $(C_6\text{-}C_{10})$arylene, cycloalkylene, heteroarylene, or heterocyclylene;

$R^{26}$ is $-A^1\text{-}L^1\text{-}A^2\text{-}B$; $-A^1\text{-}A^2\text{-}B$; $-L^2\text{-}A^1\text{-}L^1\text{-}A^2\text{-}L^3\text{-}B$; or $-OH$;

$A^1$ and $A^2$ are independently absent or are independently selected from

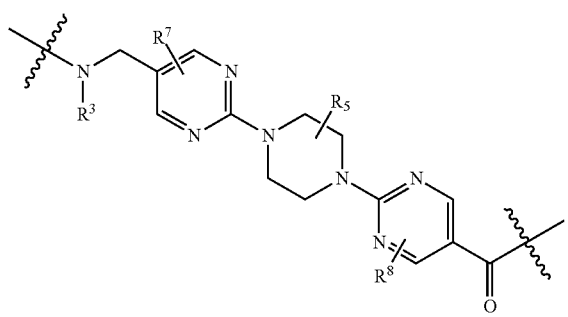

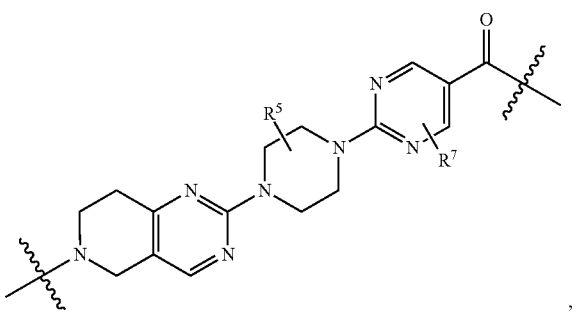

-continued
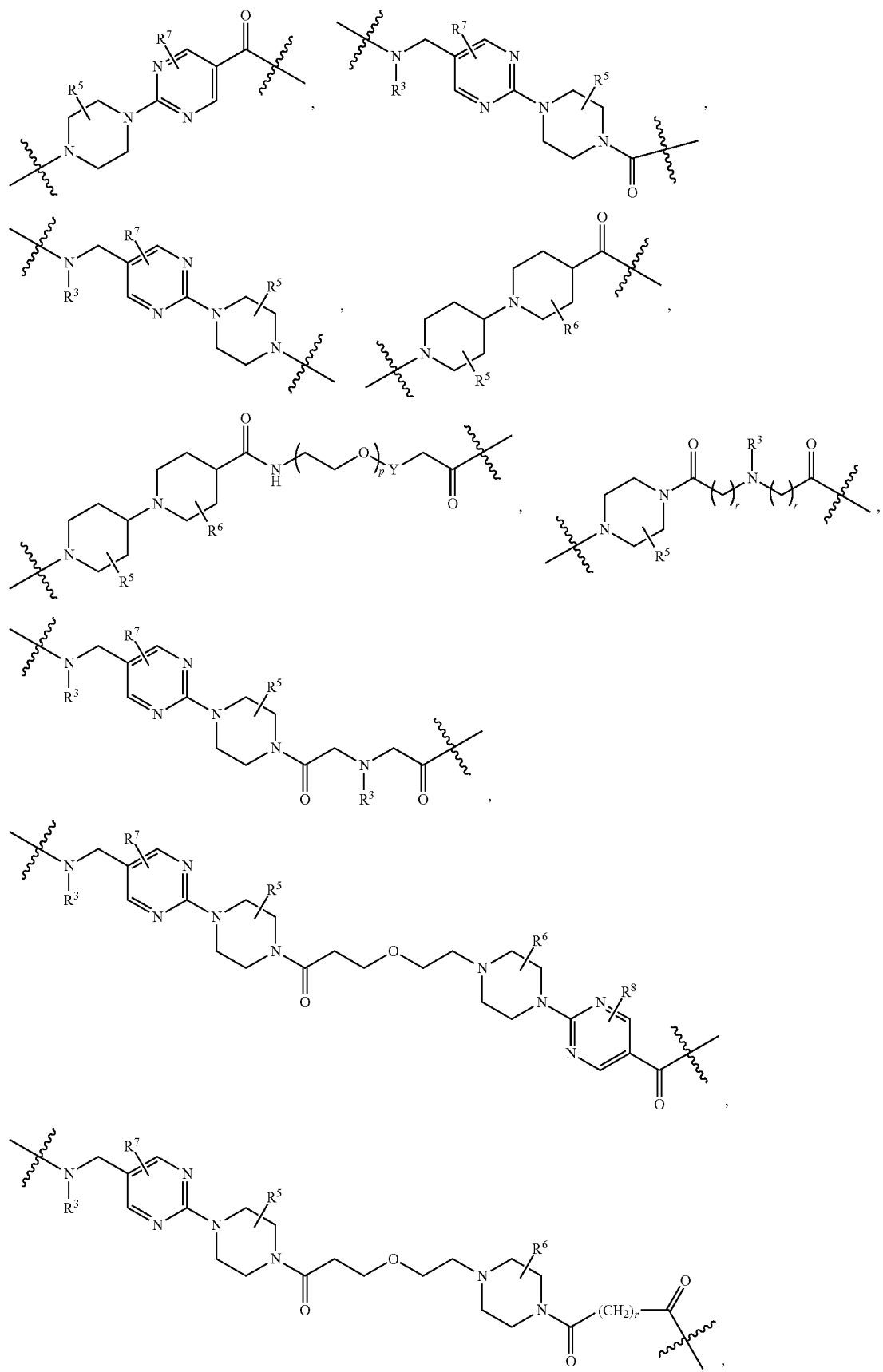

-continued

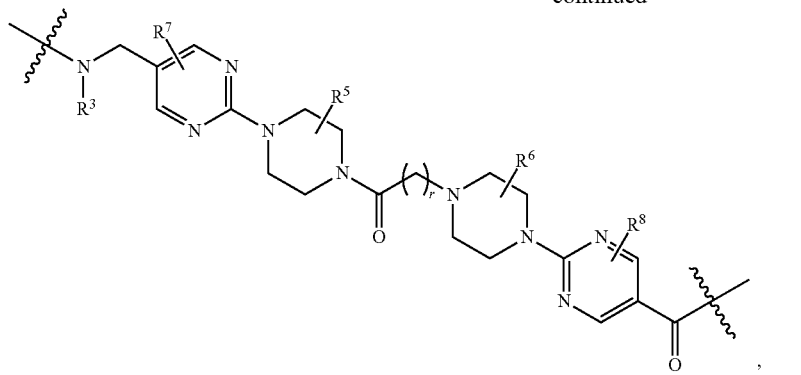

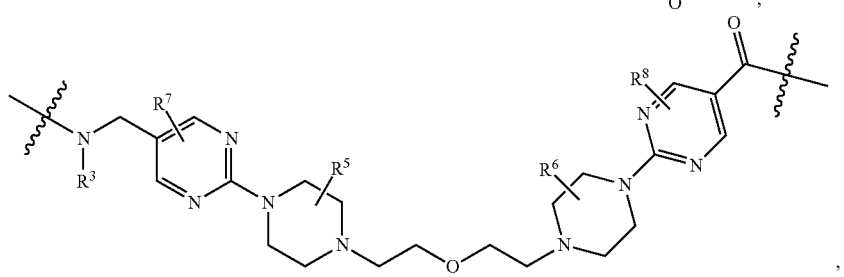

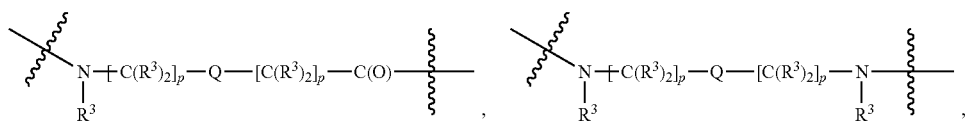

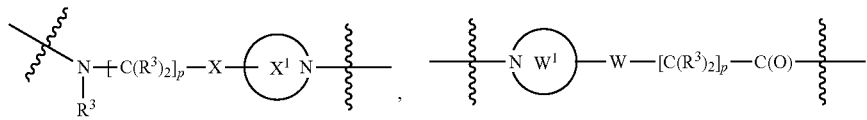

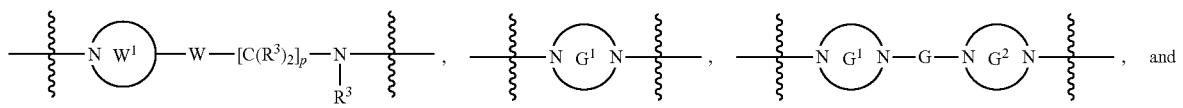

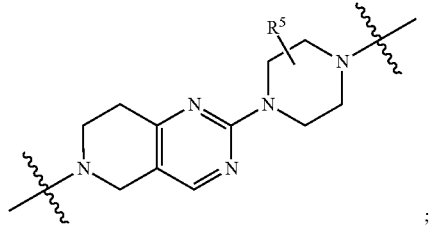

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each W' is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

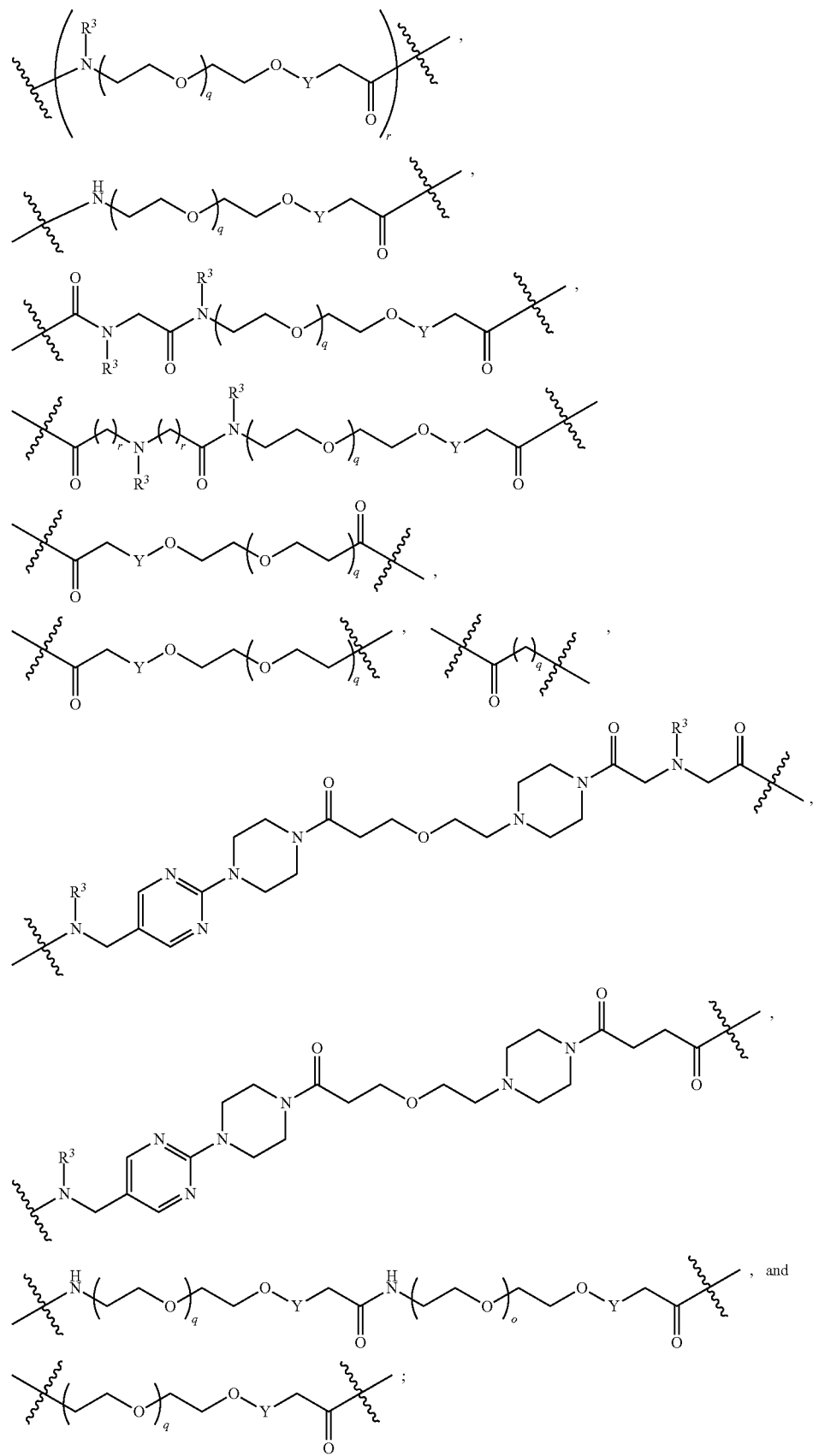

$L^2$ and $L^3$ are independently absent or are independently selected from
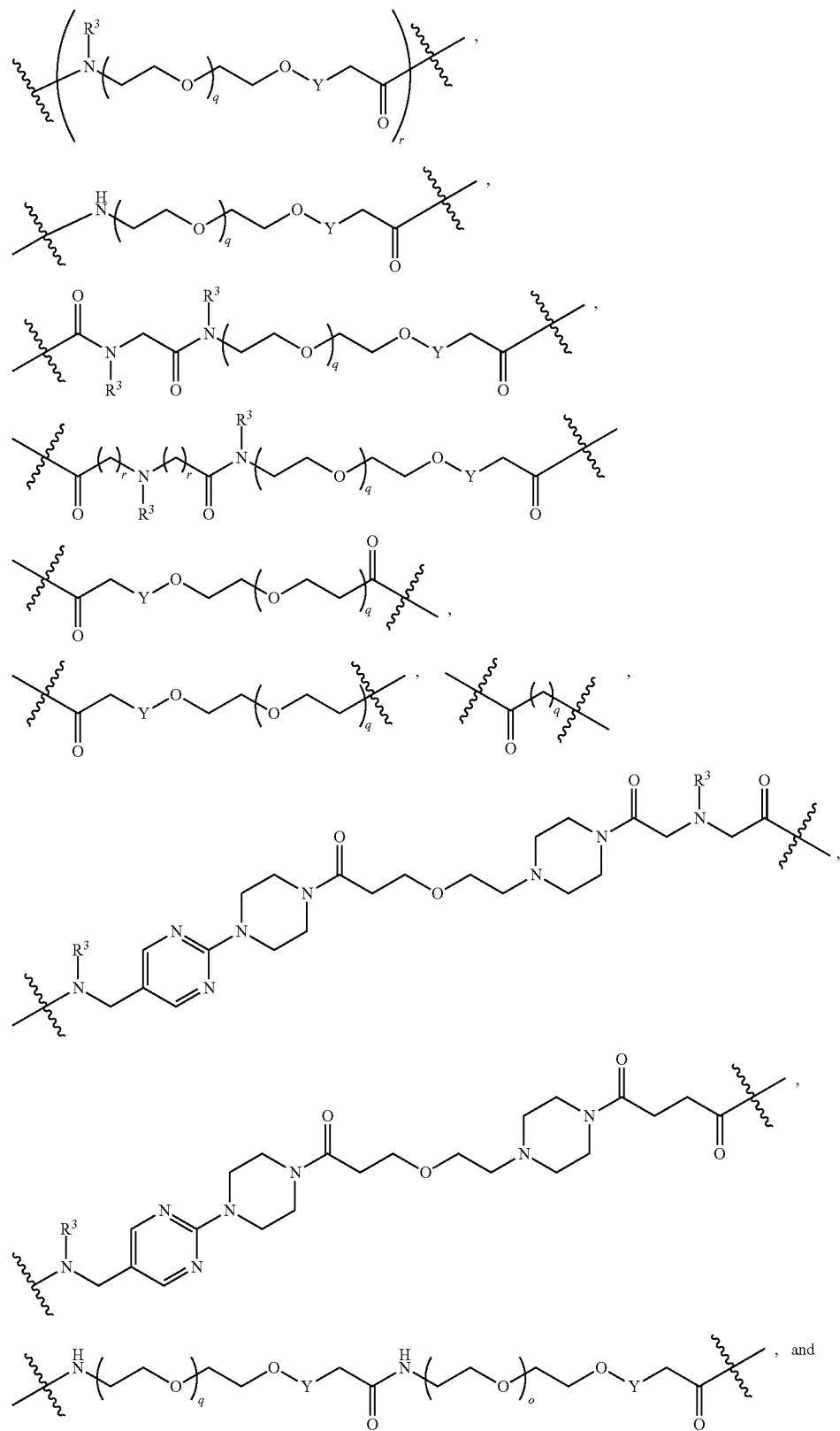

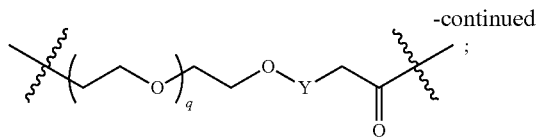
each B is independently selected from
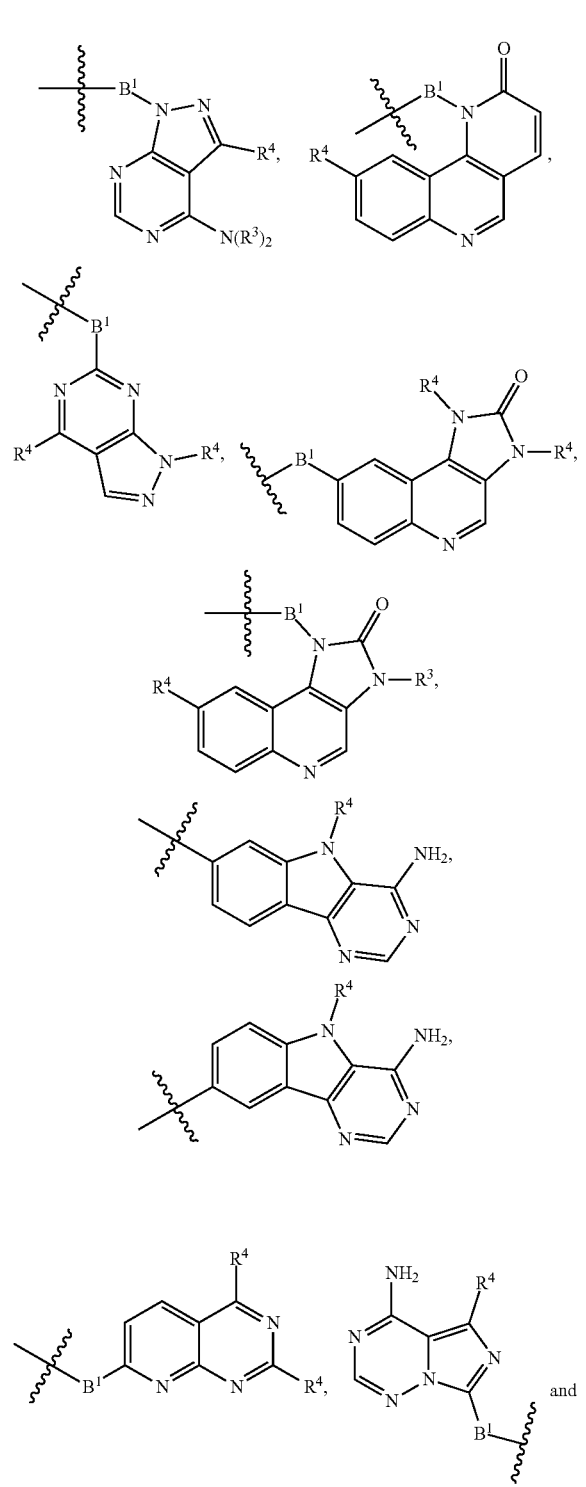
and
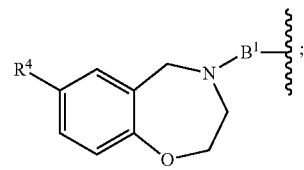
each B¹ is independently selected from
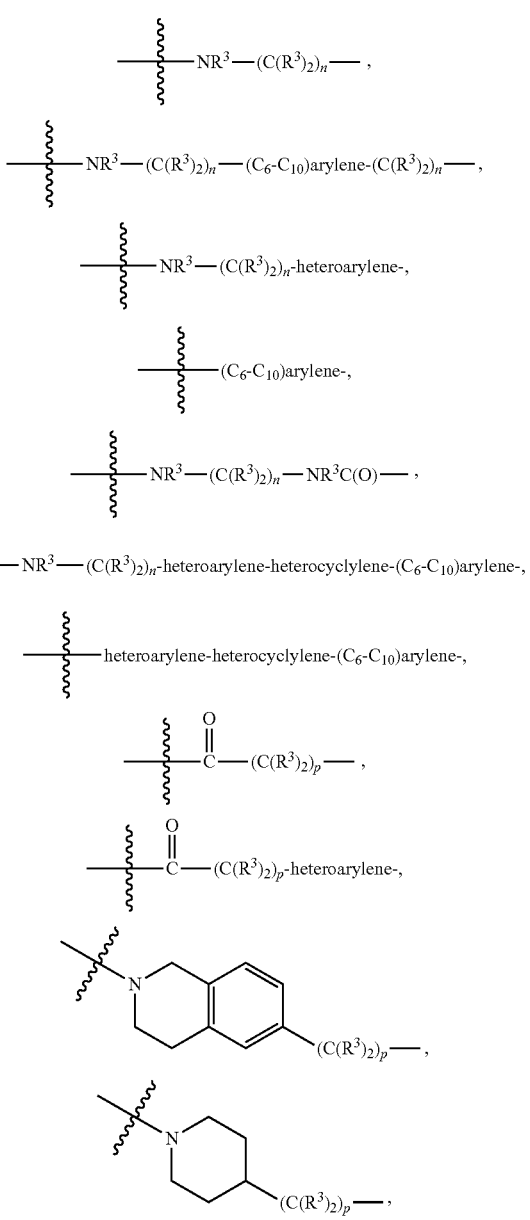

-continued

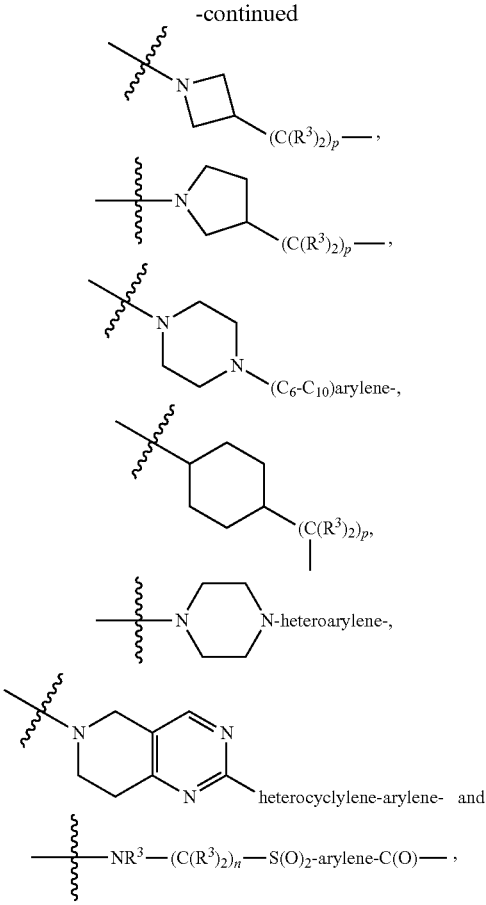

wherein the

bond on the left side of $B^1$, drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1-C_6)$alkyl;

each $R^4$ is independently H, $(C_1-C_6)$alkyl, halogen, 5-12 membered heterocyclyl, 5-12 membered heteroaryl, $(C_6-C_{10})$aryl, wherein the heteroaryl, heterocyclyl, and aryl are each independently optionally substituted with —$N(R^3)_2$, —$OR^3$, halogen, $(C_1-C_6)$alkyl, —$(C_1-C_6)$alkylene-heteroaryl, —$(C_1-C_6)$alkylene-CN, —$C(O)NR^3$-heteroaryl, or —$C(O)NR^3$-heterocyclyl;

each $R^5$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^6$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^7$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^8$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each Y is independently $C(R^3)_2$ or a bond;
each n is independently an integer from one to 12;
each o is independently an integer from zero to 30;
each p is independently an integer from zero to 12;
each q is independently an integer from zero to 30; and
each r is independently an integer from one to 6.

The present disclosure provides a method of treating a disease or disorder mediated by mTOR comprising administering to the subject suffering from or susceptible to developing a disease or disorder mediated by mTOR a therapeutically effective amount of one or more disclosed compounds. The present disclosure provides a method of preventing a disease or disorder mediated by mTOR comprising administering to the subject suffering from or susceptible to developing a disease or disorder mediated by mTOR a therapeutically effective amount of one or more disclosed compounds. The present disclosure provides a method of reducing the risk of a disease or disorder mediated by mTOR comprising administering to the subject suffering from or susceptible to developing a disease or disorder mediated by mTOR a therapeutically effective amount of one or more disclosed compounds.

Another aspect of the present disclosure is directed to a pharmaceutical composition comprising a compound of Formula I, Ia, or Ib, or a pharmaceutically acceptable salt or tautomer of any of the foregoing, and a pharmaceutically acceptable carrier. The pharmaceutically acceptable carrier can further comprise an excipient, diluent, or surfactant. The pharmaceutical composition can be effective for treating, preventing, or reducing the risk of a disease or disorder mediated by mTOR a disease mediated by mTOR in a subject in need thereof.

Another aspect of the present disclosure relates to a compound of Formula I, Ia, or Ib, or a pharmaceutically acceptable salt or tautomer of any of the foregoing, for use in treating, preventing, or reducing the risk of a disease or disorder mediated by mTOR in a subject in need thereof.

Another aspect of the present disclosure relates to the use of a compound of Formula I, Ia, or Ib, or a pharmaceutically acceptable salt or tautomer of any of the foregoing, in the manufacture of a medicament for treating, preventing, or reducing the risk of a disease or disorder mediated by mTOR in a subject in need thereof.

The present disclosure also provides compounds that are useful in inhibiting mTOR.

DETAILED DESCRIPTION OF THE DISCLOSURE

The present disclosure relates to mTOR inhibitors. Specifically, the embodiments are directed to compounds and compositions inhibiting mTOR, methods of treating diseases mediated by mTOR, and methods of synthesizing these compounds.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also may include the plural unless the context clearly dictates otherwise. Unless defined otherwise, all technical and scientific terms used herein have the same meaning as commonly understood by one of ordinary skill in the art to which this Terms The articles "a" and "an" are used in this disclosure and refers to one or more than one (i.e., to at least one) of the grammatical object of the article, unless indicated otherwise. By way of example, "an element" may mean one element or more than one element, unless indicated otherwise.

The term "or" means "and/or" unless indicated otherwise. The term "and/or" means either "and" or "or", or both, unless indicated otherwise.

The term "optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene," by itself or as part of another substituent, means, unless otherwise stated, a divalent radical derived from an alkyl. Typically, an alkyl (or alkylene) group will have from 1 to 24 carbon atoms, such as those groups having 10 or fewer carbon atoms.

The term "alkenyl" means an aliphatic hydrocarbon group containing a carbon-carbon double bond and which may be straight or branched having about 2 to about 6 carbon atoms in the chain. Certain alkenyl groups have 2 to about 4 carbon atoms in the chain. Branched may mean that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkenylene," by itself or as part of another substituent, means, unless otherwise stated, a divalent radical derived from an alkene.

The term "alkynyl" means an aliphatic hydrocarbon group containing a carbon-carbon triple bond and which may be straight or branched having about 2 to about 6 carbon atoms in the chain. Certain alkynyl groups have 2 to about 4 carbon atoms in the chain. Branched may mean that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "alkynylene," by itself or as part of another substituent, means, unless otherwise stated, a divalent radical derived from an alkyne.

The term "cycloalkyl" means a monocyclic or polycyclic saturated or partially unsaturated carbon ring containing 3-18 carbon atoms. Examples of cycloalkyl groups include, without limitation, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

A "cycloalkylene," alone or as part of another substituent, means a divalent radical derived from a cycloalkyl.

The terms "heterocyclyl" or "heterocycloalkyl" or "heterocycle" refers to a monocyclic or polycyclic 3 to 24-membered ring containing carbon and at least one heteroatom selected from oxygen, phosphorous nitrogen, and sulfur and wherein there is not delocalized π electrons (aromaticity) shared among the ring carbon or heteroatom(s). Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

A "heterocyclylene" or "heterocycloalkylene," alone or as part of another substituent, means a divalent radical derived from a "heterocyclyl" or "heterocycloalkyl" or "heterocycle."

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl may refer to multiple rings fused together wherein at least one of the fused rings is an aryl ring.

An "arylene," alone or as part of another substituent, means a divalent radical derived from an aryl.

The term "heteroaryl" refers to an aryl group (or rings) that contain at least one heteroatom such as N, O, or S, wherein the nitrogen and sulfur atom(s) are optionally oxidized, and the nitrogen atom(s) is optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described herein.

The term "heteroaryl" may also include multiple condensed ring systems that have at least one such aromatic ring, which multiple condensed ring systems are further described below. The term may also include multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1, 2, 3, 4-tetrahydro-1,8-naphthyridinyl), carbocycles (to form for example 5,6,7,8-tetrahydroquinolyl) and aryls (to form for example indazolyl) to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen).

A "heteroarylene," alone or as part of another substituent, means a divalent radical derived from a heteroaryl.

Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

The terms "halo" or "halogen," by themselves or as part of another substituent, means, unless otherwise stated, a fluorine, chlorine, bromine, or iodine atom. Additionally, terms such as "haloalkyl" may include monohaloalkyl and polyhaloalkyl. For example, the term "halo($C_1$-$C_4$)alkyl" may include, but is not limited to, fluoromethyl, difluoromethyl, trifluoromethyl, 2,2,2-trifluoroethyl, 4-chlorobutyl, 3-bromopropyl, 1-fluoro-2-bromoethyl, and the like.

The term "hydroxyl," as used herein, means —OH.

The term "hydroxyalkyl" as used herein, means an alkyl moiety as defined herein, substituted with one or more, such as one, two or three, hydroxy groups. In certain instances, the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

The term "oxo," as used herein, means an oxygen that is double bonded to a carbon atom.

A substituent group, as used herein, may be a group selected from the following moieties:

(A) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$OCH_2F$, unsubstituted alkyl, unsubstituted cycloalkyl, unsubstituted heterocycloalkyl, unsubstituted aryl, unsubstituted heteroaryl, and (B) alkyl, cycloalkyl, heterocyclyl, aryl, heteroaryl, substituted with at least one substituent selected from:

(i) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$OCH_3$, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

An "effective amount" when used in connection with a compound is an amount effective for treating or preventing a disease in a subject as described herein.

The term "carrier", as used in this disclosure, encompasses carriers, excipients, and diluents and may mean a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating may include curing, improving, or at least partially ameliorating the disorder.

The term "prevent" or "preventing" with regard to a subject refers to keeping a disease or disorder from afflicting the subject. Preventing may include prophylactic treatment. For instance, preventing can include administering to the subject a compound disclosed herein before a subject is afflicted with a disease and the administration will keep the subject from being afflicted with the disease.

The term "disorder" is used in this disclosure and means, and is used interchangeably with, the terms disease, condition, or illness, unless otherwise indicated.

The term "administer", "administering", or "administration" as used in this disclosure refers to either directly administering a disclosed compound or pharmaceutically acceptable salt or tautomer of the disclosed compound or a composition to a subject, or administering a prodrug derivative or analog of the compound or pharmaceutically acceptable salt or tautomer of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds

The present disclosure provides a compound having the structure of Formula (Ia),

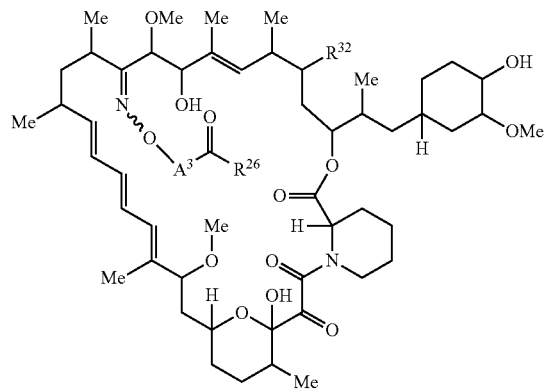

(Ia)

or a pharmaceutically acceptable saltor tautomer thereof, wherein $R^{32}$, $A^3$, and $R^{26}$ are described as above.

The present disclosure provides a compound having the structure of Formula (I),

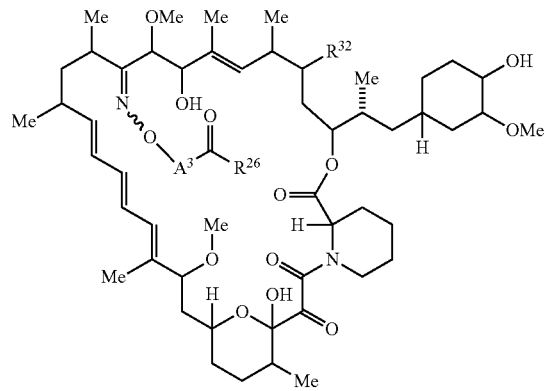

(I)

or a pharmaceutically acceptable salt or tautomer thereof, wherein $R^{32}$, $A^3$, and $R^{26}$ are described as above.

The present disclosure provides a compound having the structure of Formula Ib:

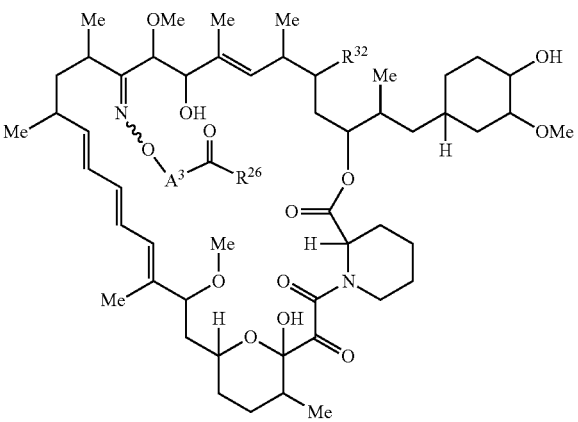

(Ib)

or a pharmaceutically acceptable saltor tautomer thereof, wherein $R^{32}$, $A^3$, and $R^{26}$ are described as above for Formula I.

In certain embodiments, a compound has the following formula:

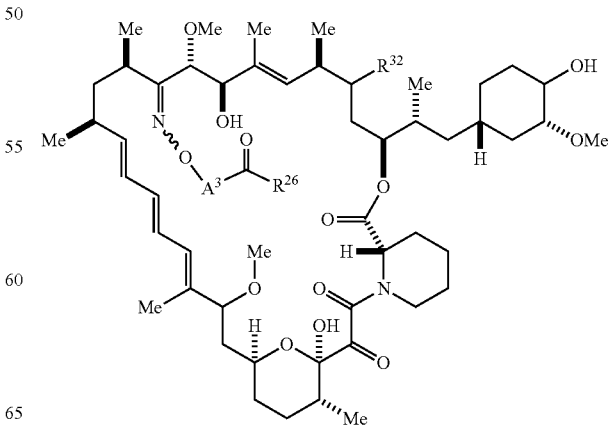

or a pharmaceutically acceptable salt or tautomer thereof.

In certain embodiments, $R^{32}$ is =O. In certain embodiments, $R^{32}$ is —$OR^3$. In certain embodiments, $R^{32}$ is H. In certain embodiments, $R^{32}$ is —$N_3$.

In certain embodiments, $A^3$ is —$[C(R^3)_2]_n$—. In certain embodiments, $A^3$ is $CH_2$. In certain embodiments, $A^3$ is ($C_6$-$C_{10}$)arylene. In certain embodiments, $A^3$ is cycloalkylene. In certain embodiments, $A^3$ is heteroarylene. In certain embodiments, $A^3$ is heterocyclylene.

In certain embodiments, $R^{26}$ is —OH.

In certain embodiments, $R^{26}$ is -$A^1$-$L^1$-$A^2$-B. In certain embodiments, $R^{26}$ is -$A^1$-$A^2$-B. In certain embodiments, $R^{26}$ is -$L^2$-$A^1$-$L_1$-$A^2$-$L^3$-B.

In certain embodiments, $R^{26}$ is -$A^1$-$L^1$-$A^2$-B. In certain embodiments, $R^{26}$ is -$A^1$-$L^1$-$A^2$-B, wherein $A^1$ and $A^2$ are absent. In certain embodiments, $R^{26}$ is -$A^1$-$L^1$-$A^2$-B, wherein $A^2$ is absent. In certain embodiments, $R^{26}$ is -$A^1$-$L^1$-$A^2$-B, wherein $A^1$ is absent.

In certain embodiments, $R^{26}$ is -$A^1$-$A^2$-B. In certain embodiments, $R^{26}$ is -$L^2$-$A^1$-$L^1$-$A^2$-$L^3$-B, wherein $L^2$ and $A^1$ are absent. In certain embodiments, $R^{26}$ is -$L^2$-$A^1$-$L^1$-$A^2$-$L^3$-B, wherein $L^2$ is absent. In certain embodiments, $R^{26}$ is -$L^2$-$A^1$-$L^1$-$A^2$-$L^3$-B, wherein $L^3$ is absent.

As described above, each $L^1$ is independently selected from

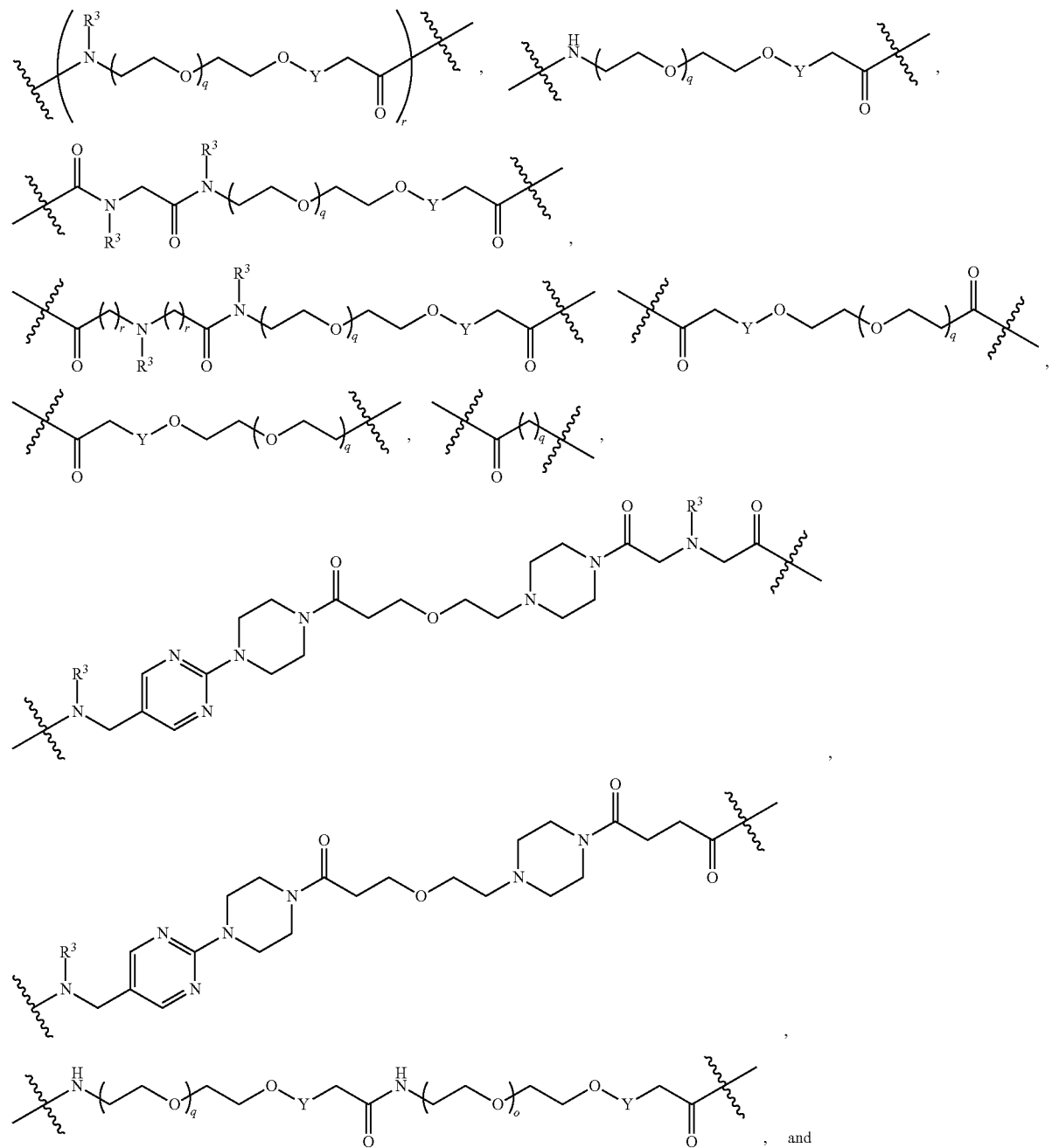

, and

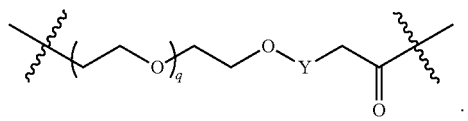
As described above for Formula Ia, each $L^1$ is independently selected from
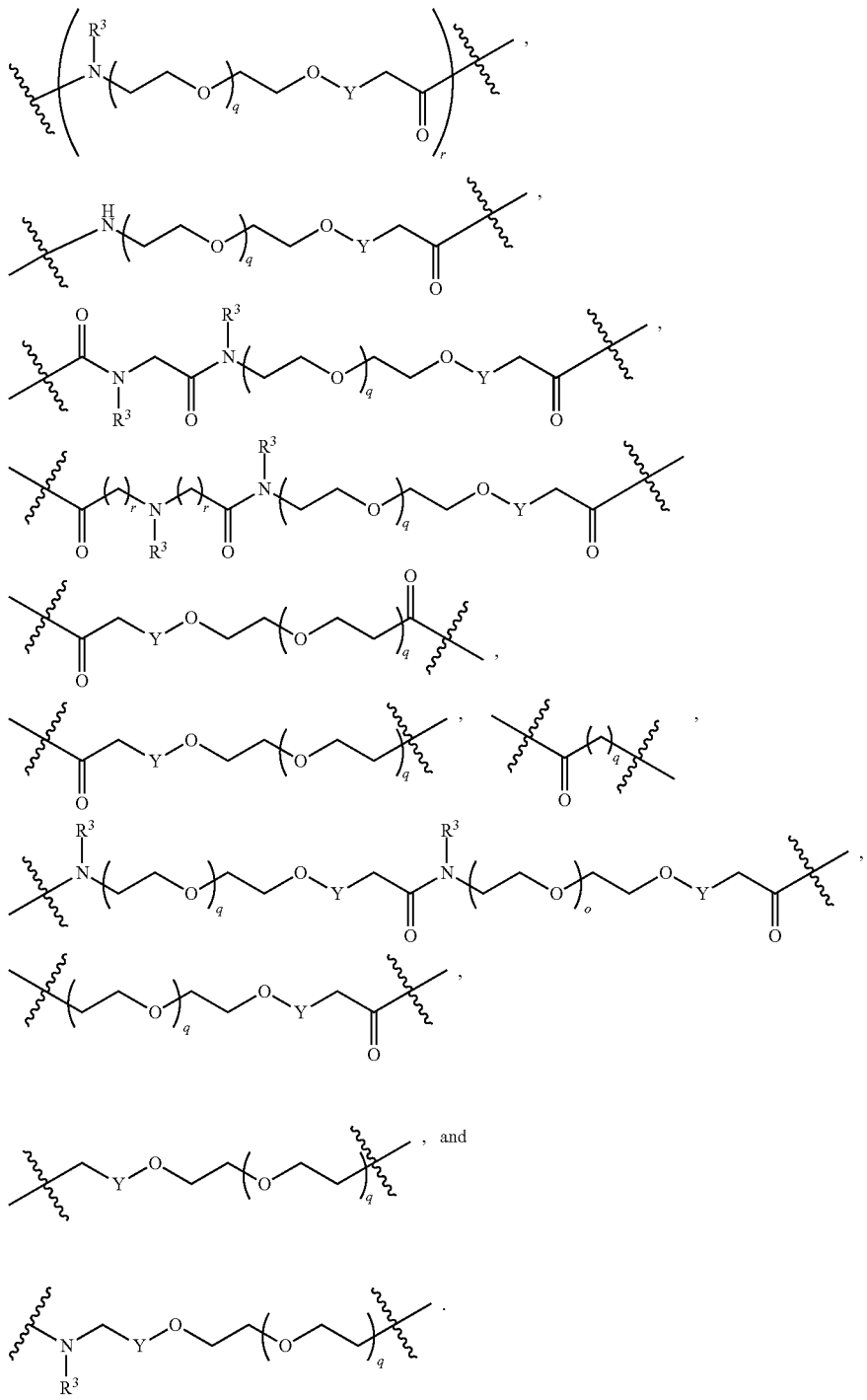

In certain embodiments, L¹ is
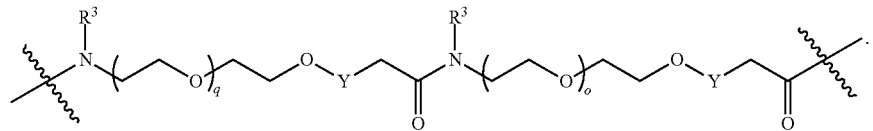
In certain embodiments, L¹ is
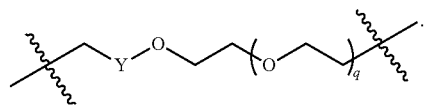
In certain embodiments, L¹ is
In certain embodiments, L¹ is
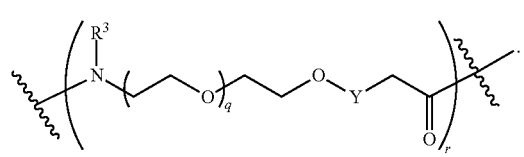
In certain embodiments, L¹ is
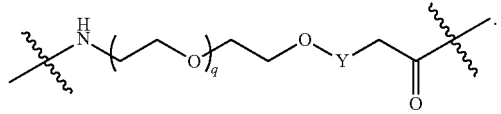
In certain embodiments, L¹ is
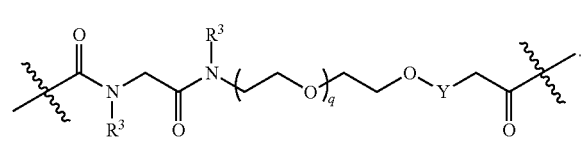
In certain embodiments, L¹ is
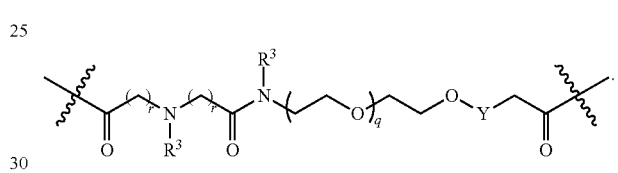
In certain embodiments, L¹ is
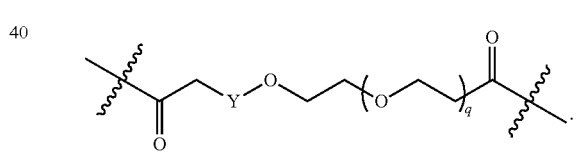
In certain embodiments, L¹ is
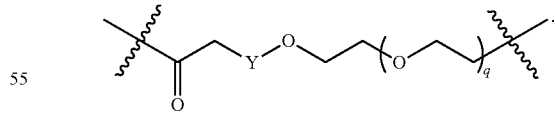
In certain embodiments, L¹ is
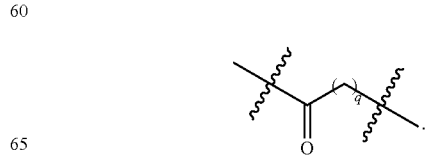

In certain embodiments, $L^1$ is
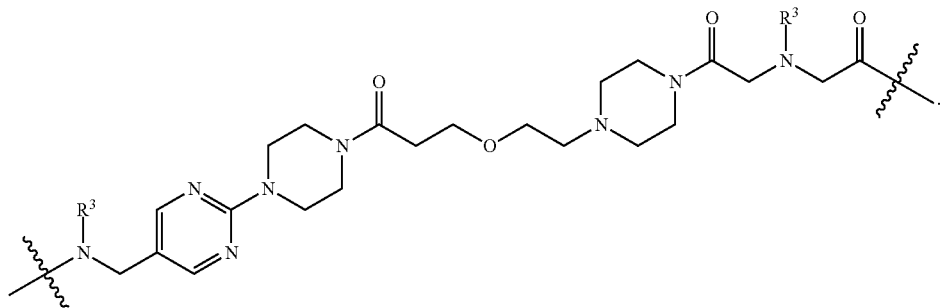
In certain embodiments, $L^1$ is
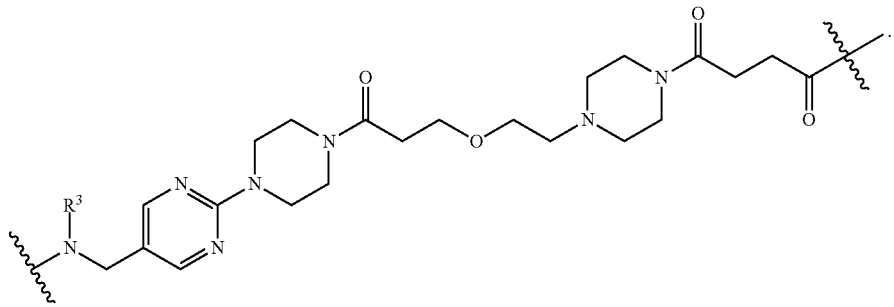
In certain embodiments, $L^1$ is
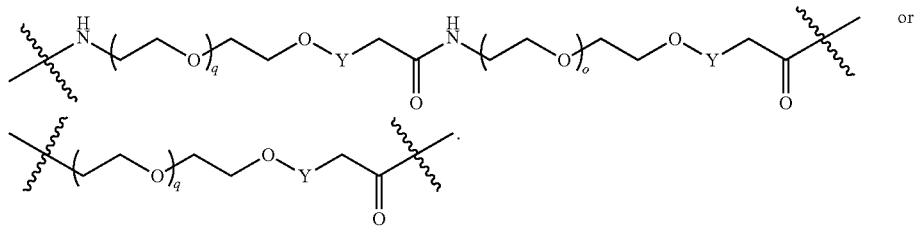 or
As described above, $L^2$ and $L^3$ are independently absent or are independently selected from
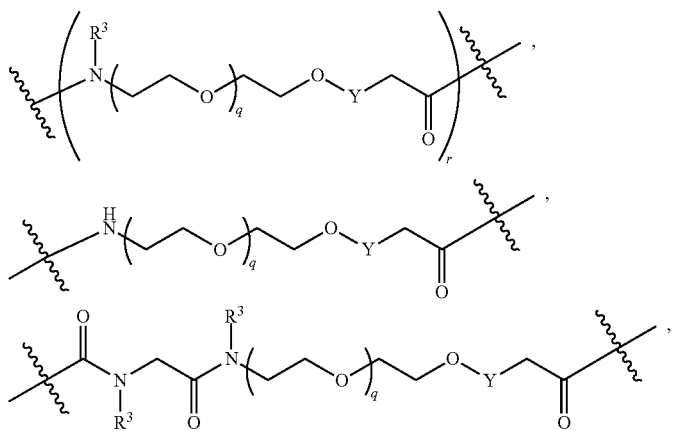

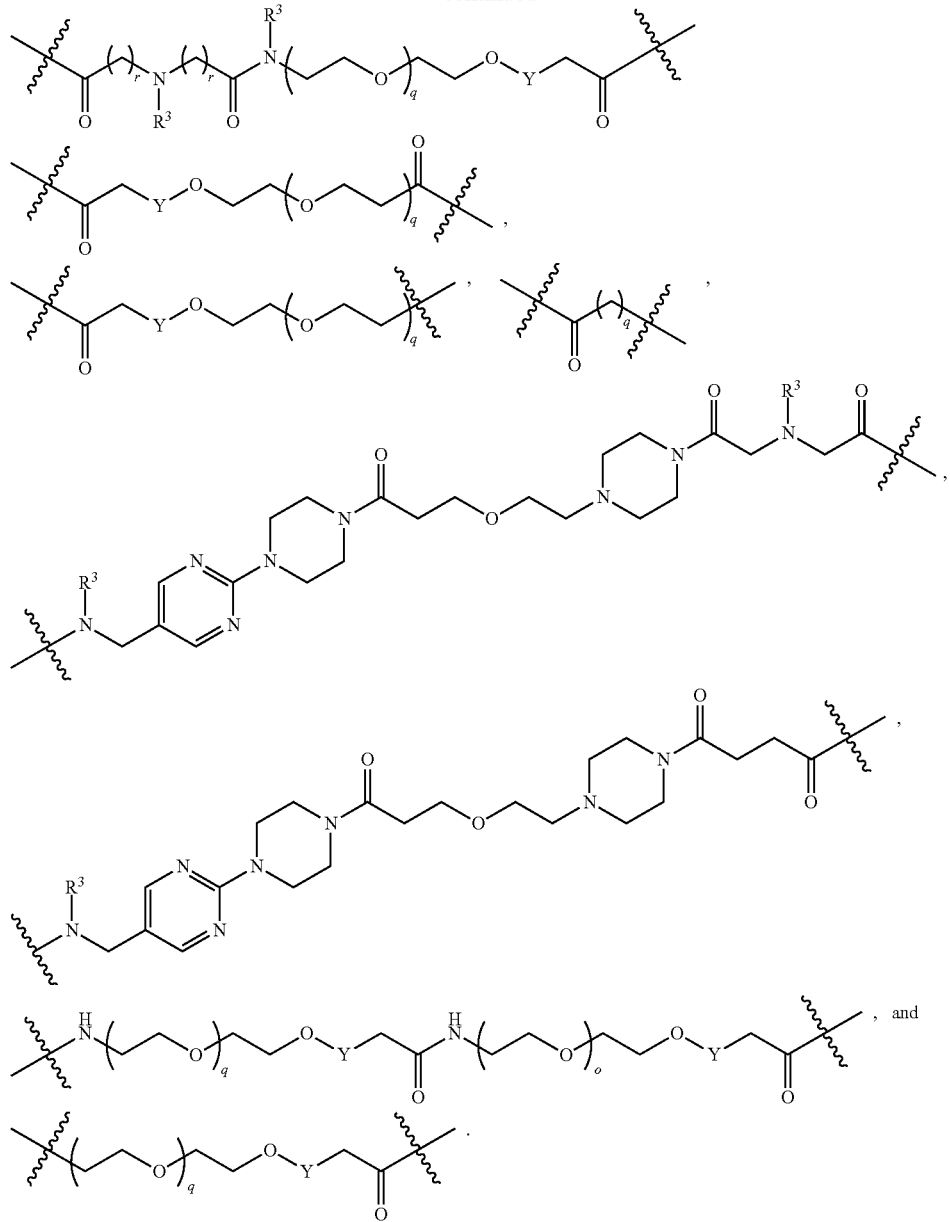
As described above for Formula Ia, $L^2$ and $L^3$ are independently absent or are independently selected from
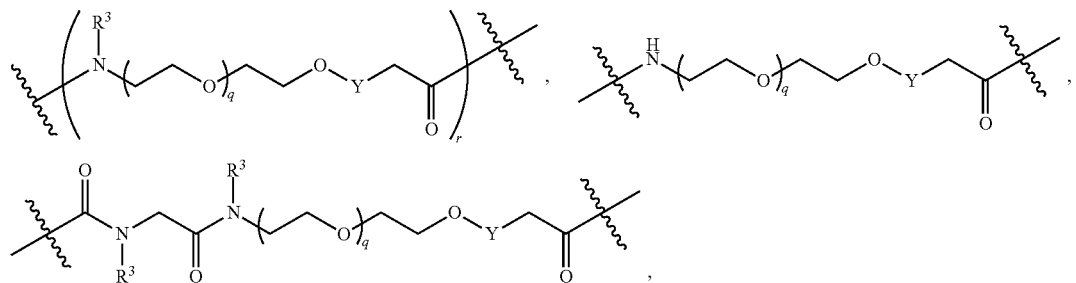

-continued
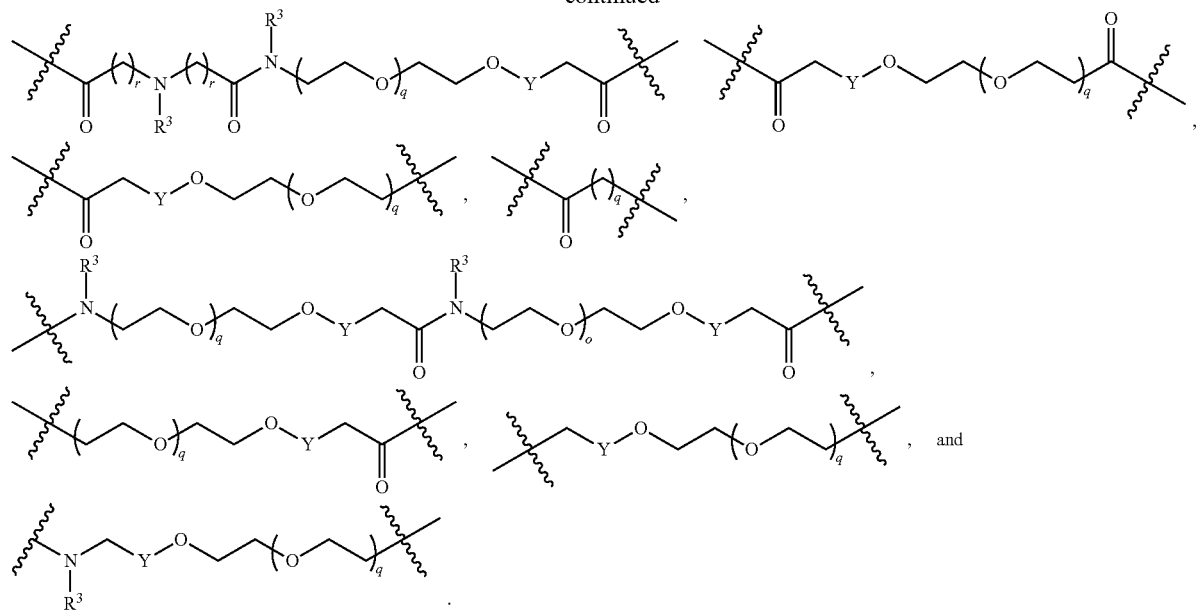
In certain embodiments, $L^2$ is absent.
In certain embodiments, $L^2$ is
In certain embodiments, $L^2$ is
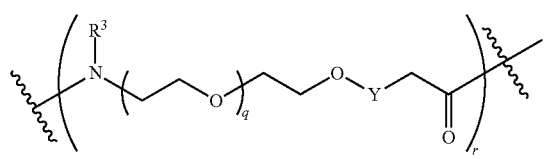
In certain embodiments, $L^2$ is
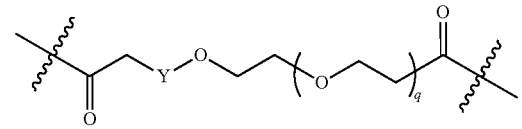
In certain embodiments, $L^2$ is
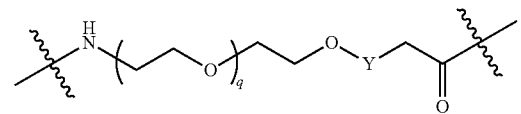
In certain embodiments, $L^2$ is
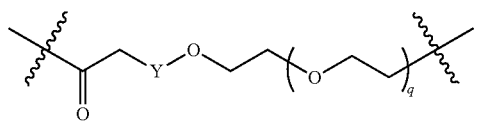
In certain embodiments, $L^2$ is
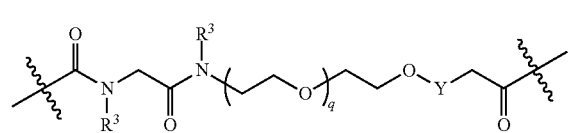
In certain embodiments, $L^2$ is
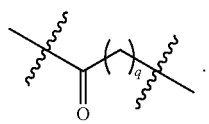

In certain embodiments, L² is
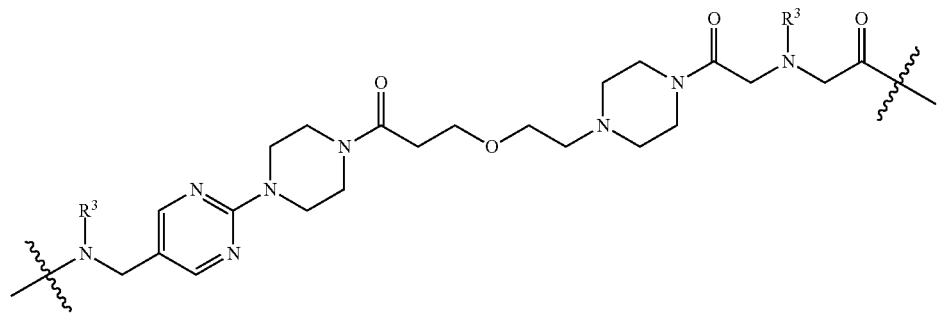
In certain embodiments, L² is
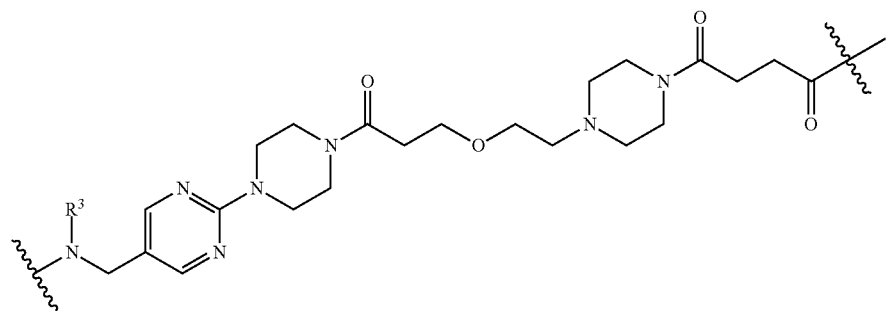
In certain embodiments, L² is
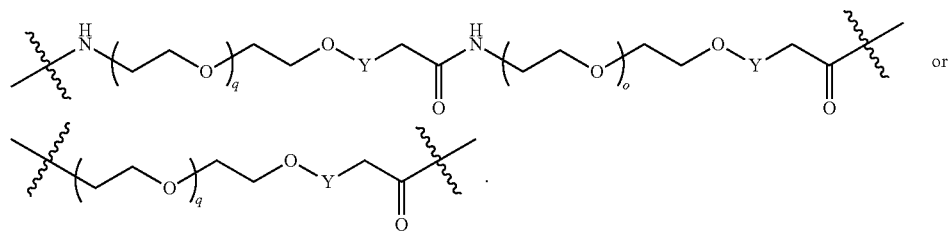 or
In certain embodiments, L² is
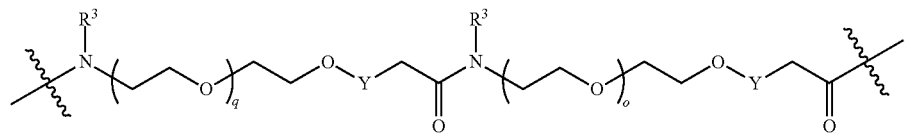
In certain embodiments, L² is
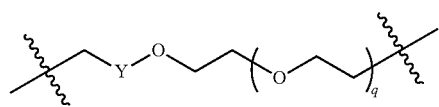
In certain embodiments, L² is
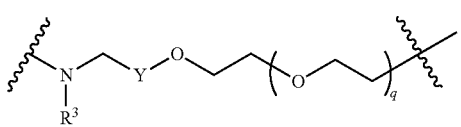
In certain embodiments, L³ is absent.

In certain embodiments, L³ is
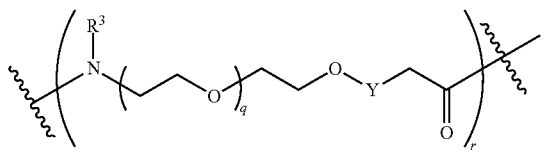
In certain embodiments, L³ is
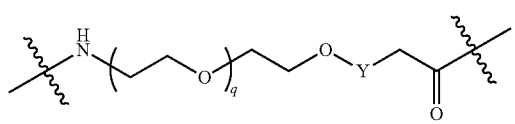
In certain embodiments, L³ is
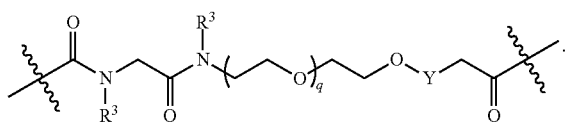
In certain embodiments, L³ is
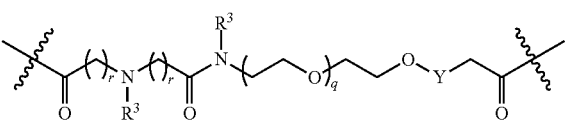
In certain embodiments, L³ is
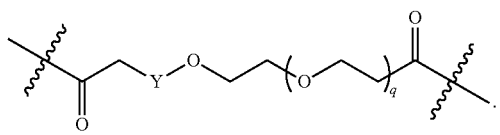
In certain embodiments, L³ is
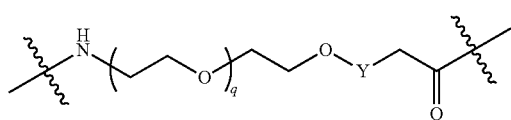
In certain embodiments, L³ is
In certain embodiments, L³ is
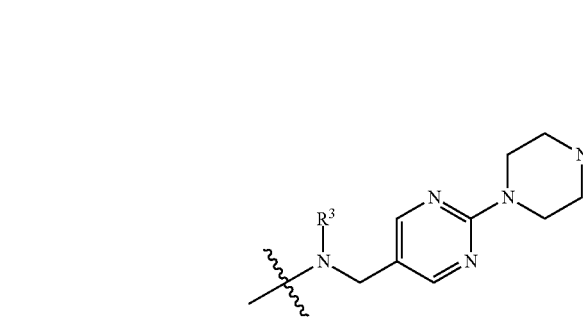
In certain embodiments, L³ is
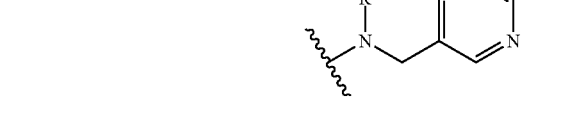

In certain embodiments, L³ is
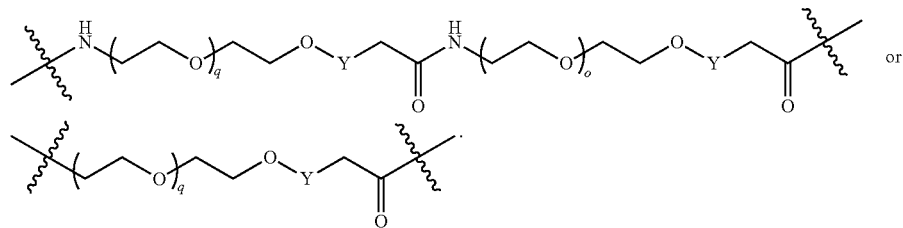 or
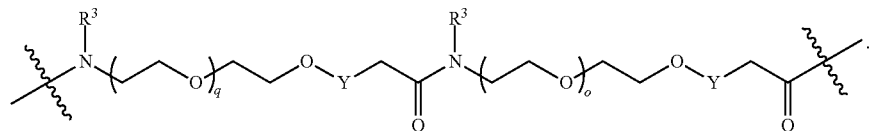.
In certain embodiments, L³ is
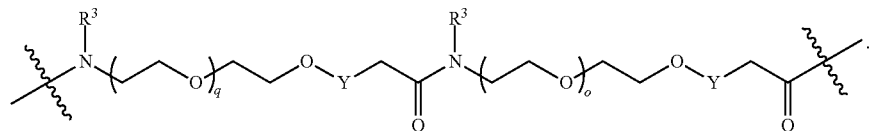.
In certain embodiments, L³ is
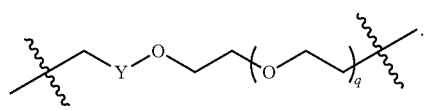.
In certain embodiments, L³ is
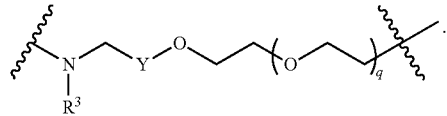.
As described above, A¹ and A² are independently absent or are independently selected from:
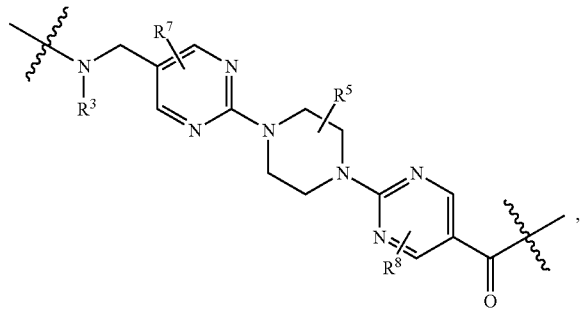,
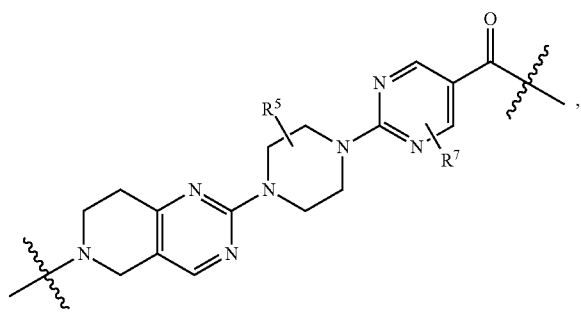,

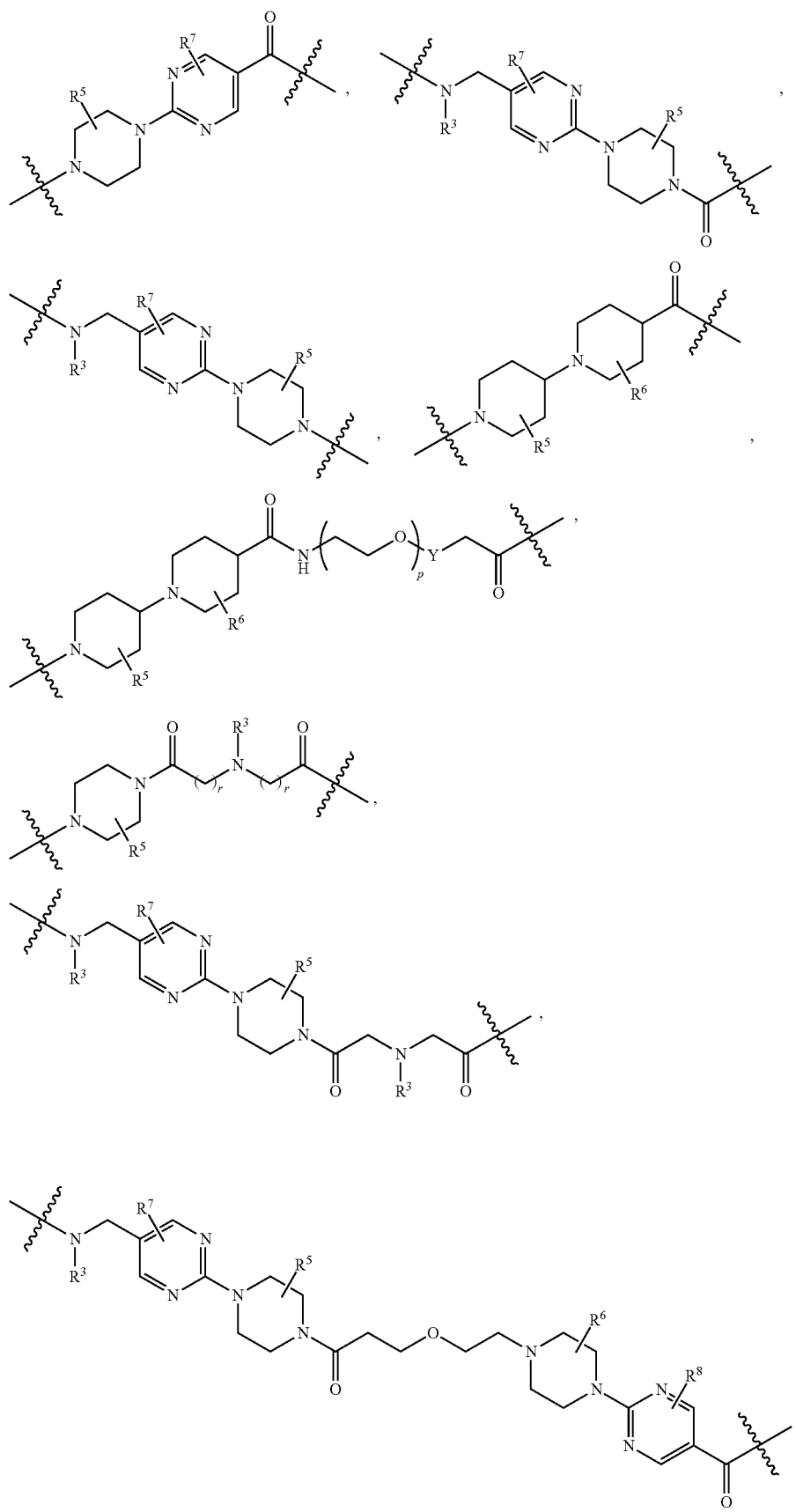

-continued
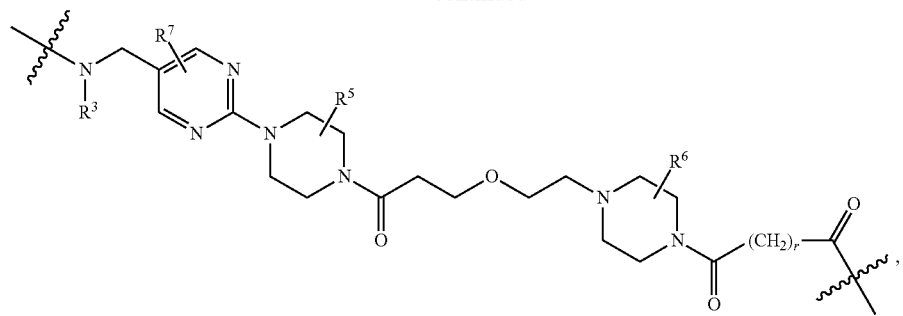
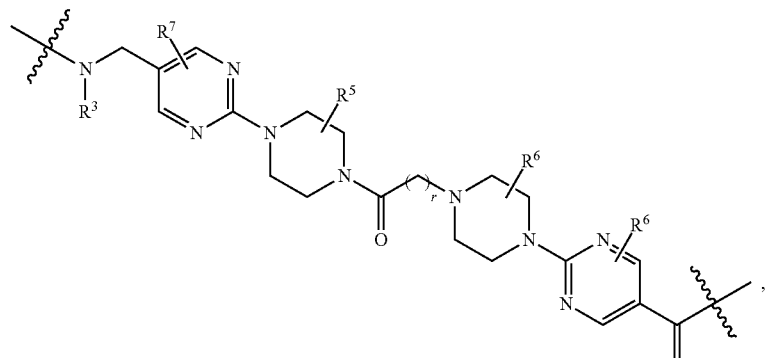
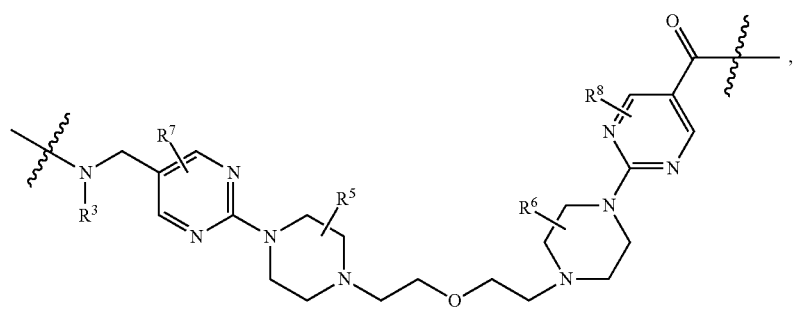
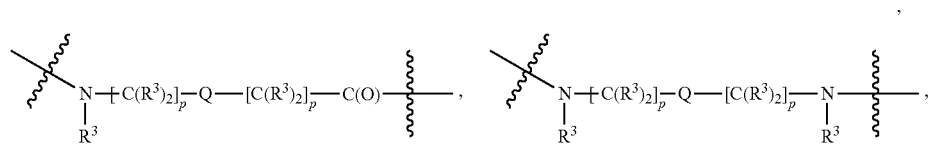
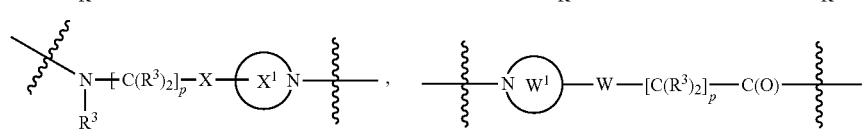
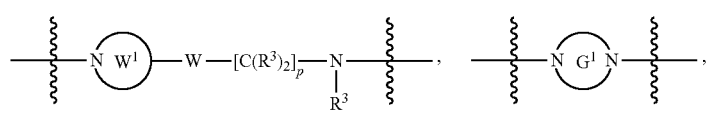
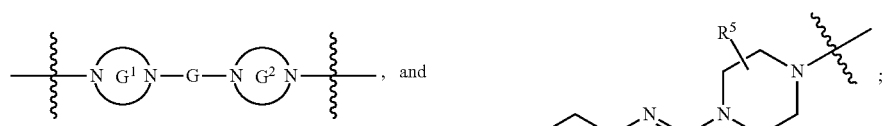
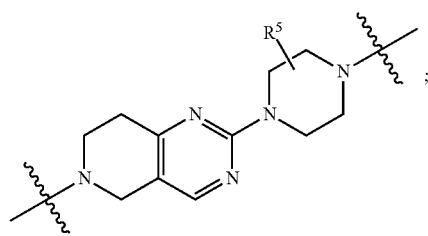

wherein the bond on the left side of A¹, as drawn, is bound to —C(=O)— or L²; and wherein the bond on the right side of the A² moiety, as drawn, is bound to B or L³;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each X¹ is independently a heteroarylene or heterocyclylene ring;

each W is independently absent or 1 to 2 rings selected from arylene, cycloalkylene, heteroarylene, and heterocyclylene;

each W¹ is independently a heteroarylene or heterocyclylene ring;

each G is independently absent or a ring selected from arylene, cycloalkylene, heteroarylene, and heterocyclylene;

each G¹ and G² are independently heteroarylene or heterocyclylene ring.

As described above for Formula Ia, A¹ and A² are independently absent or are independently selected from

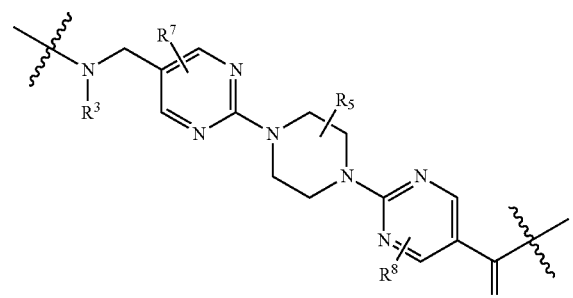

,

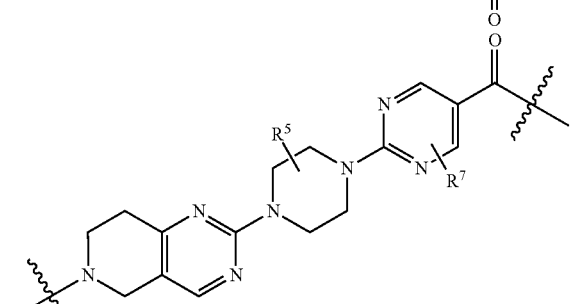

,

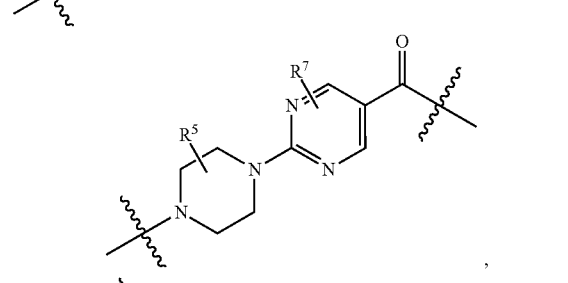

,

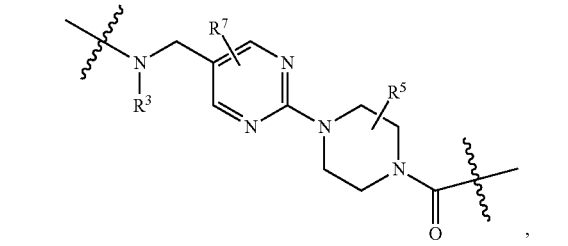

,

-continued

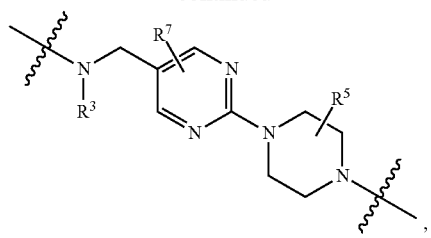

,

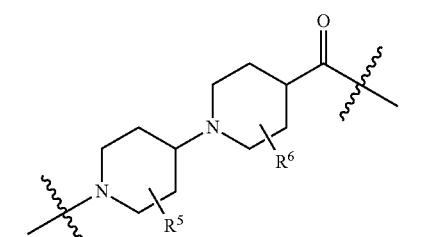

,

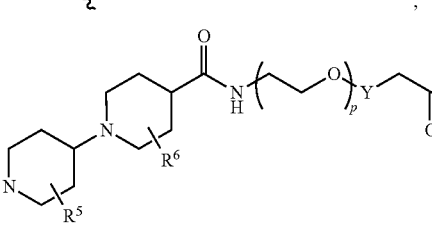

,

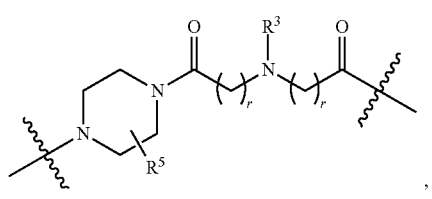

,

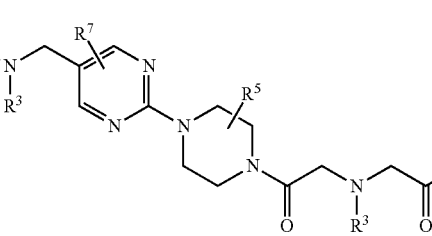

,

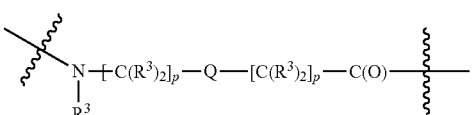

,

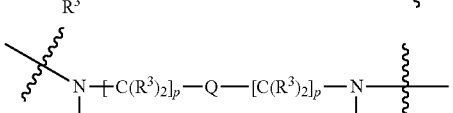

,

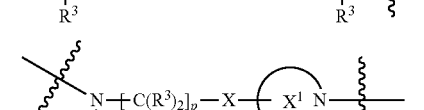

,

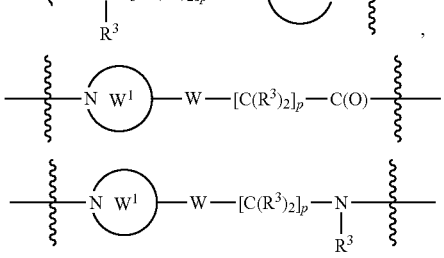

,

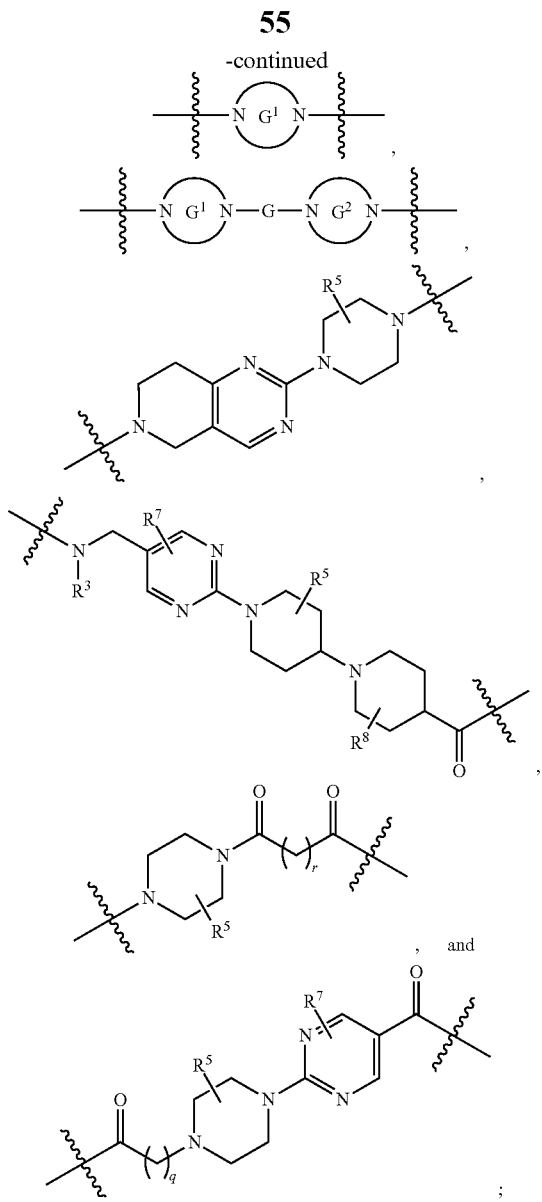

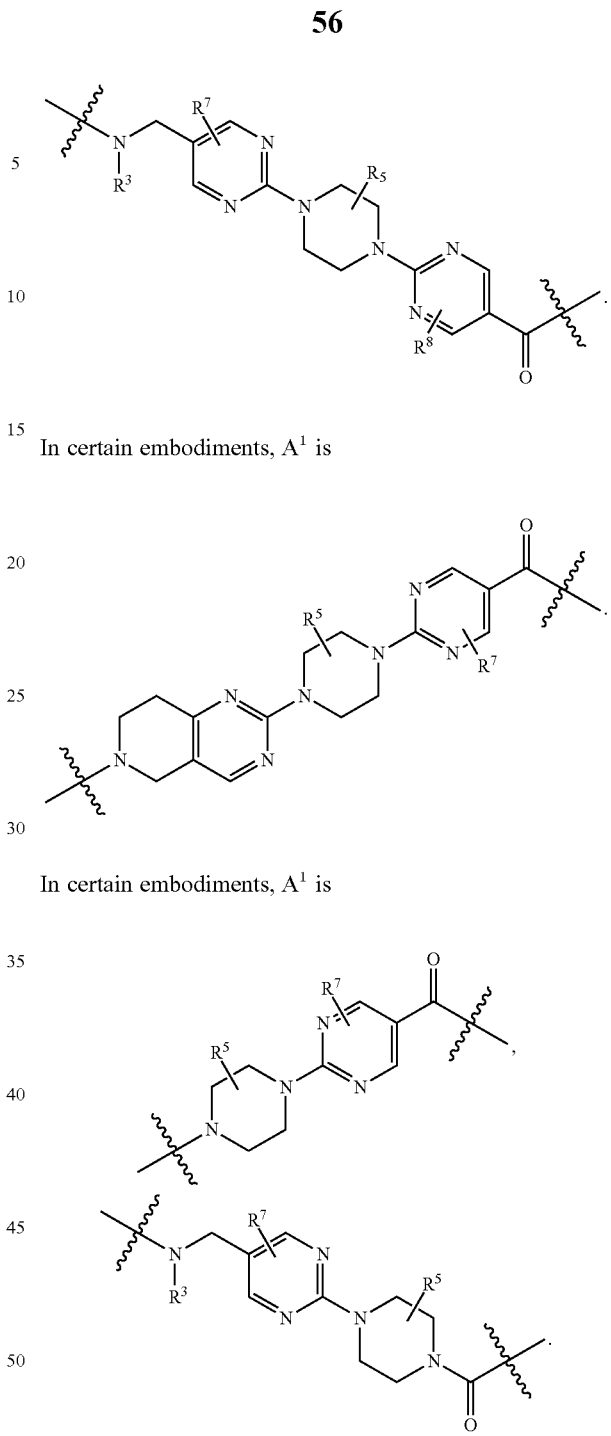

In certain embodiments, $A^1$ is

In certain embodiments, $A^1$ is

In certain embodiments, $A^1$ is

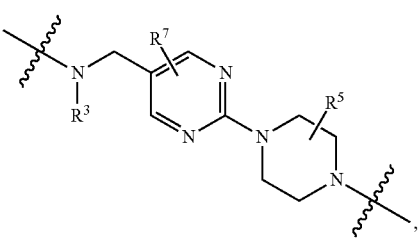

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

In certain embodiments, $A^1$ is absent. In certain embodiments, $A^1$ is

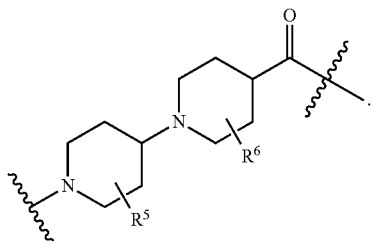
In certain embodiments, A¹ is
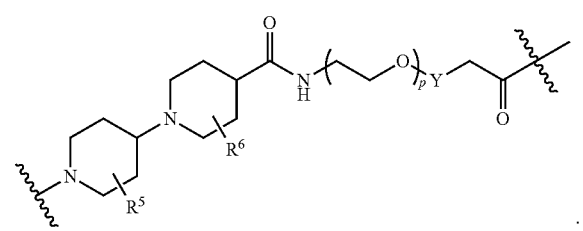
In certain embodiments, A¹ is
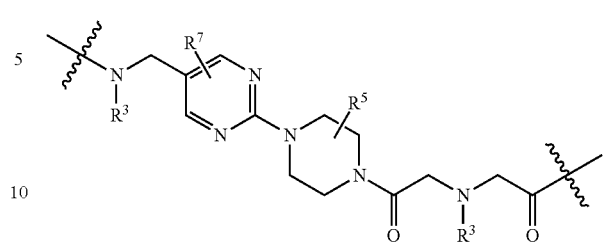
In certain embodiments, A¹ is
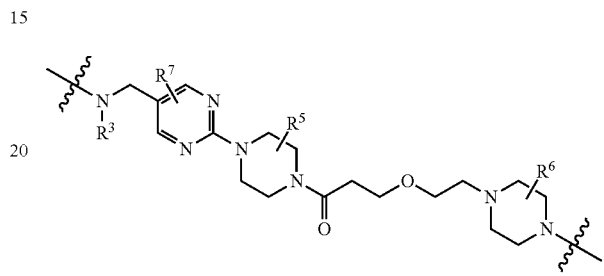
In certain embodiments, A¹ is
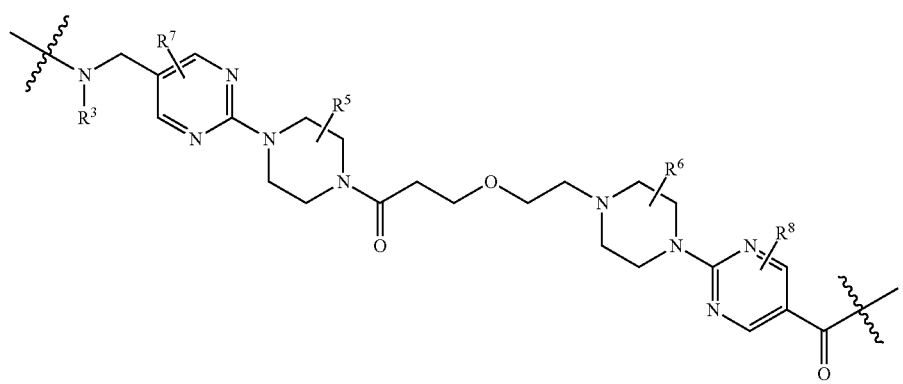
In certain embodiments, A¹ is
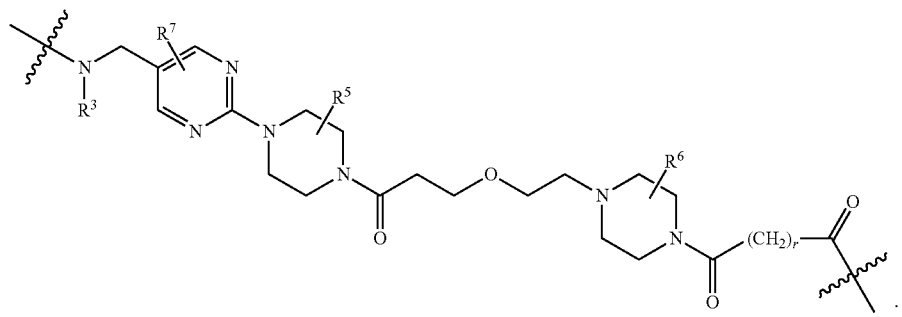

In certain embodiments, $A^1$ is

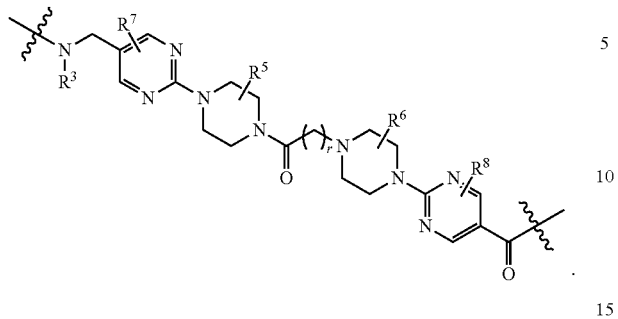

In certain embodiments, $A^1$ is

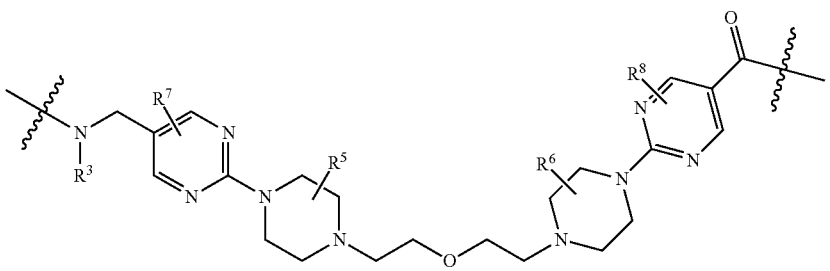

In certain embodiments, $A^1$ is

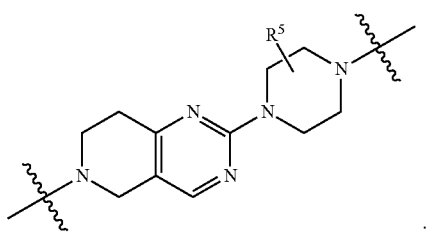

In certain embodiments, $A^1$ is

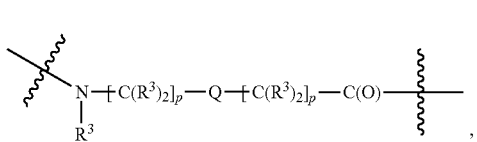

wherein each Q is independently 1 to 3 rings selected from arylene, cycloalkylene, heteroarylene, and heterocyclylene.

In certain embodiments, $A^1$ is

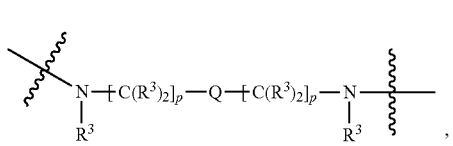

wherein each Q is independently 1 to 3 rings selected from arylene, cycloalkylene, heteroarylene, and heterocyclylene.

In certain embodiments, $A^1$

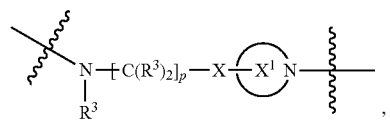

is wherein each X is independently absent or 1 to 2 rings selected from arylene, cycloalkylene, heteroarylene, and heterocyclylene; and each $X^1$ is a heteroarylene or heterocyclylene ring.

In certain embodiments, $A^1$ is

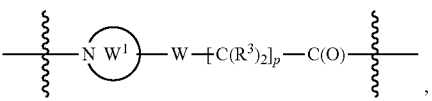

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^1$ is

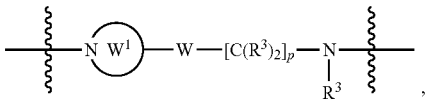

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^1$ is

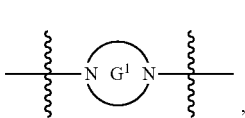

wherein each G is independently absent or a ring selected from arylene, cycloalkylene, heteroarylene, and heterocyclylene.

In certain embodiments, $A^1$ is

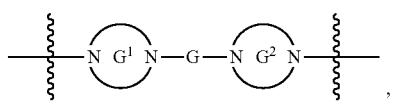

wherein each G is independently absent or a ring selected from arylene, cycloalkylene, heteroarylene, and heterocyclylene; and each $G^1$ and $G^2$ are independently heteroarylene or heterocyclylene ring.

In certain embodiments, $A^1$ is

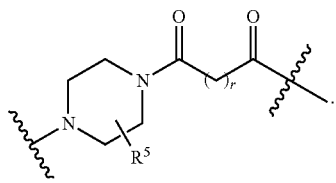

In certain embodiments, $A^1$ is

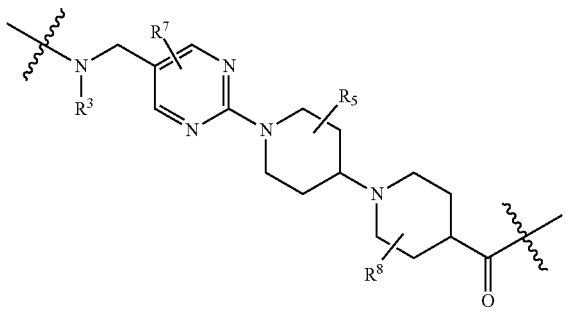

In certain embodiments, $A^1$ is

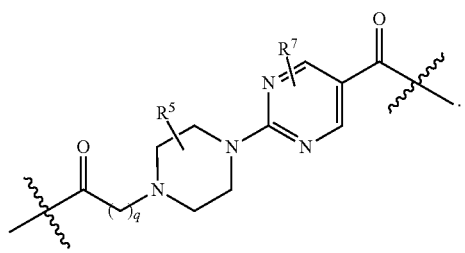

In certain embodiments, $A^2$ is absent. In certain embodiments, $A^2$ is

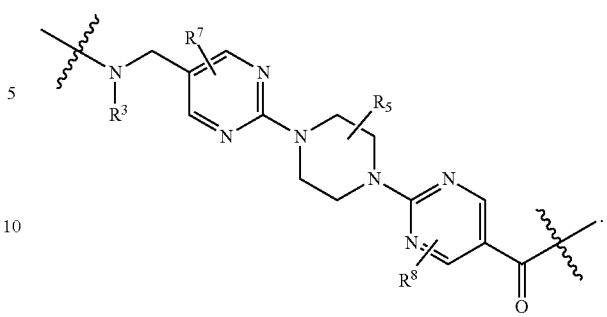

In certain embodiments, $A^2$ is

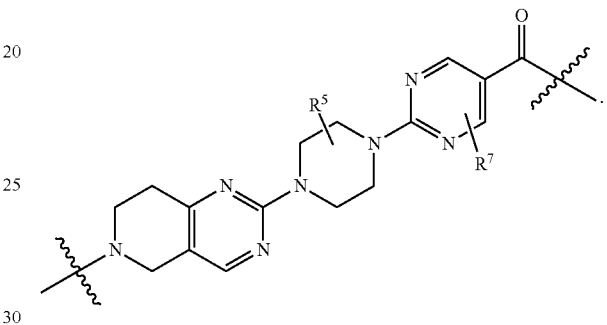

In certain embodiments, $A^2$ is

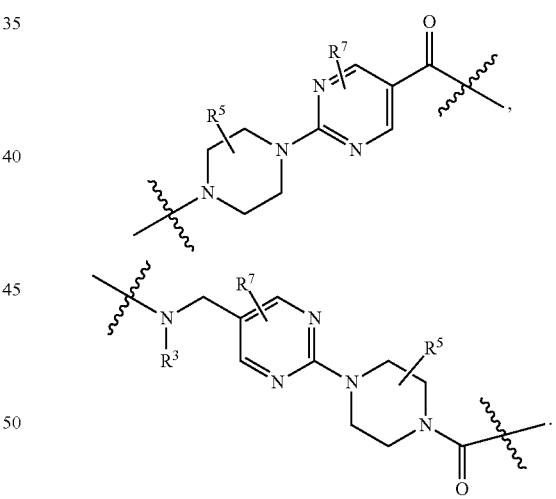

In certain embodiments, $A^2$ is

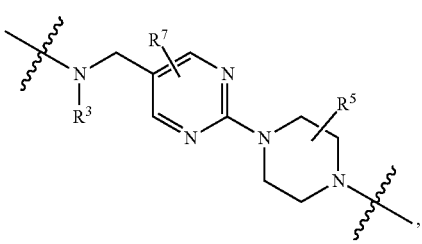

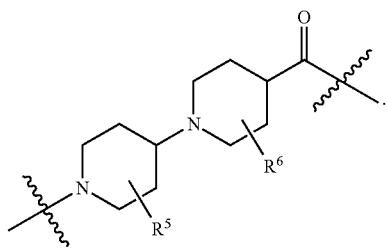
In certain embodiments, $A^2$ is
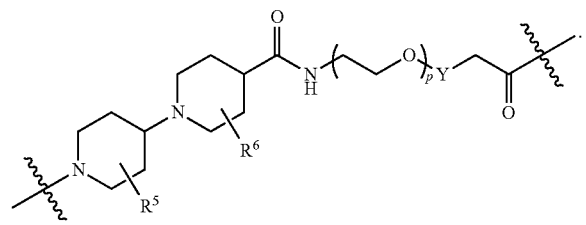
In certain embodiments, $A^2$ is
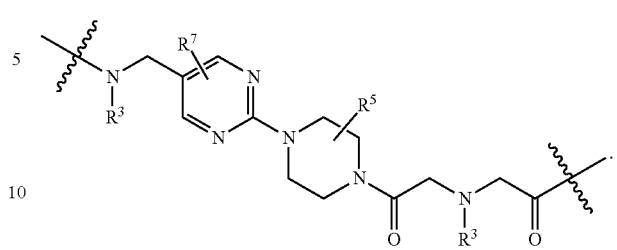
In certain embodiments, $A^2$ is
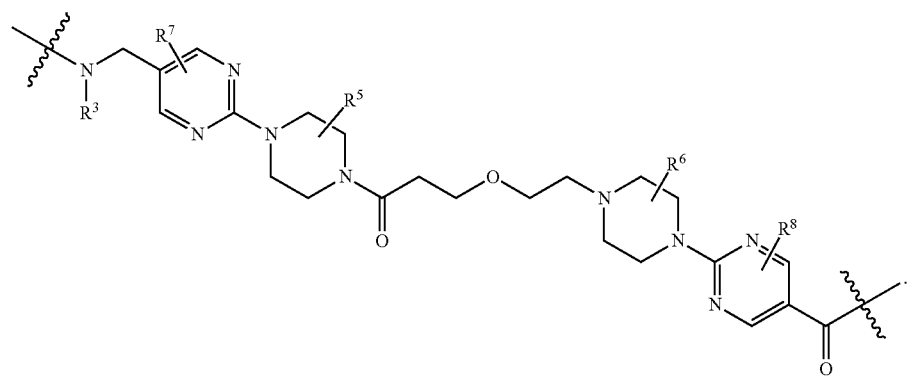
In certain embodiments, $A^2$ is
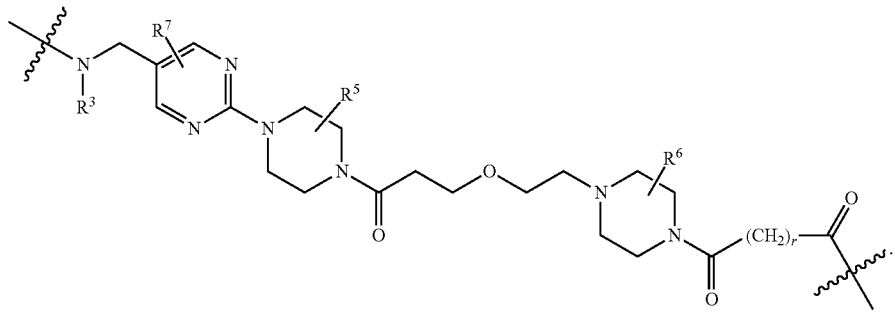
In certain embodiments, $A^2$ is In certain embodiments, $A^2$ is

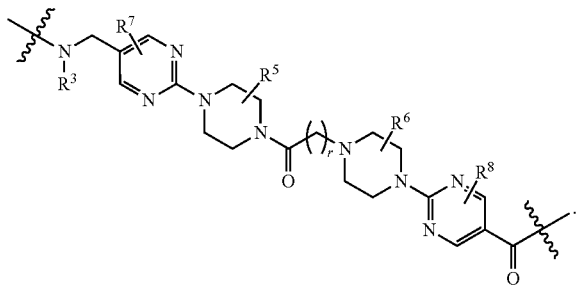

In certain embodiments, $A^2$ is

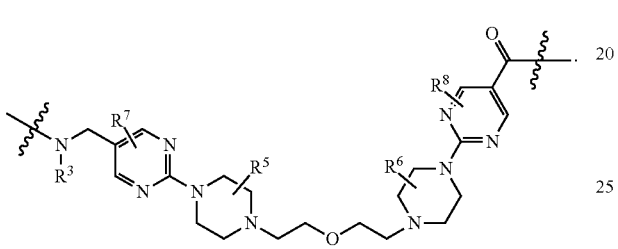

In certain embodiments, $A^2$ is

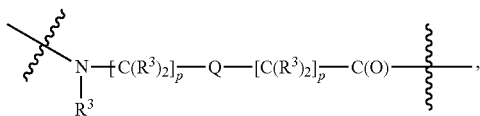

wherein each Q is independently 1 to 3 rings selected from arylene, cycloalkylene, heteroarylene, and heterocyclylene.

In certain embodiments, $A^2$ is

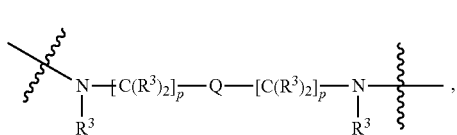

wherein each Q is independently 1 to 3 rings selected from arylene, cycloalkylene, heteroarylene, and heterocyclylene.

In certain embodiments, $A^2$ is

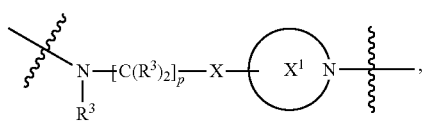

wherein each X is independently absent or 1 to 2 rings selected from arylene, cycloalkylene, heteroarylene, and heterocyclylene; and each $X^1$ is a heteroarylene or heterocyclylene ring.

In certain embodiments, $A^2$ is

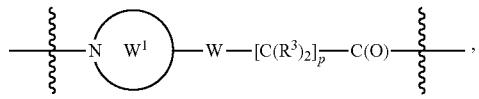

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^2$ is

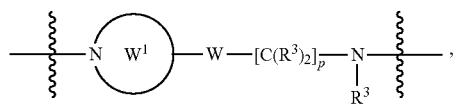

wherein each W is independently absent or 1 to 2 rings selected from arylene, cycloalkylene, heteroarylene, and heterocyclylene; and each $W^1$ is a heteroarylene or heterocyclylene ring.

In certain embodiments, $A^2$ is

wherein each G is independently absent or a ring selected from arylene, cycloalkylene, heteroarylene, and heterocyclylene.

In certain embodiments, $A^2$ is

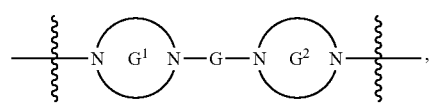

wherein each G is independently absent or a ring selected from arylene, cycloalkylene, heteroarylene, and heterocyclylene; and each $G^1$ and $G^2$ are independently heteroarylene or heterocyclylene ring.

In certain embodiments, $A^2$ is

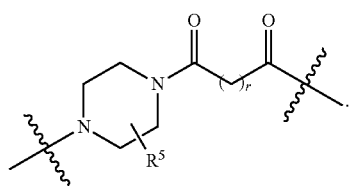

In certain embodiments, $A^2$ is
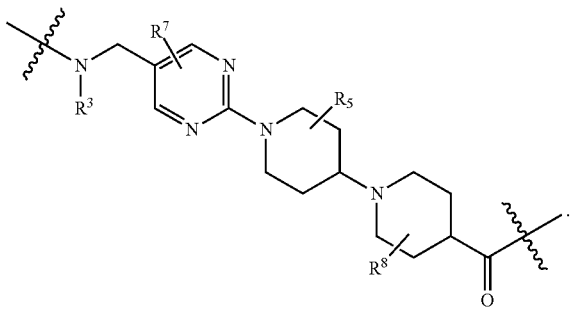
In certain embodiments, $A^2$ is
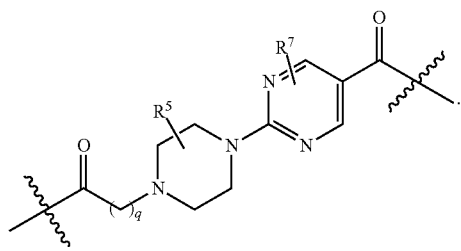
As described above, each B is independently selected from
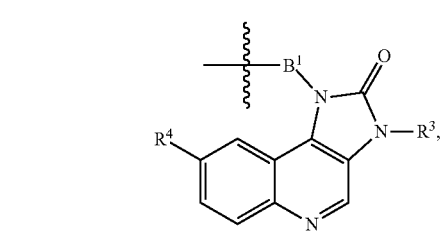
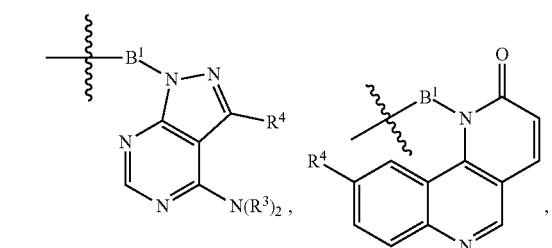
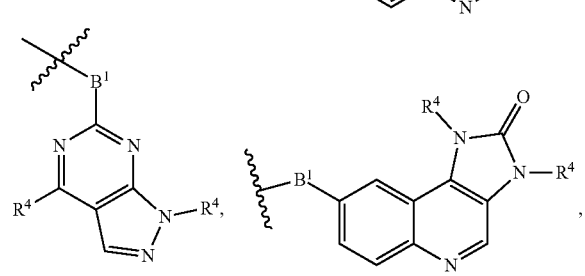
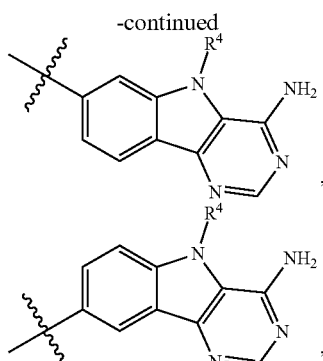
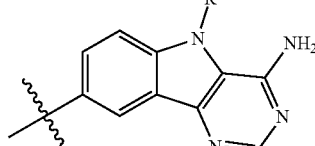
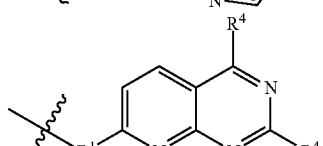
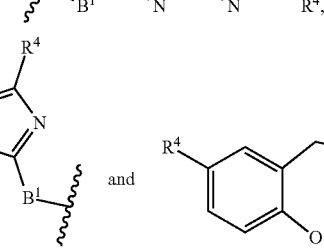
In certain embodiments, B is
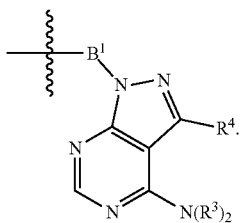
In certain embodiments, B is
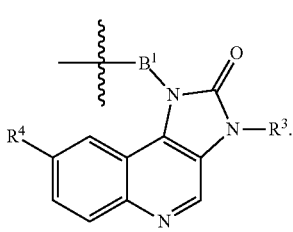
In certain embodiments, B is
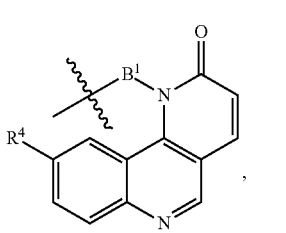, 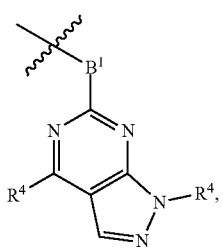

-continued
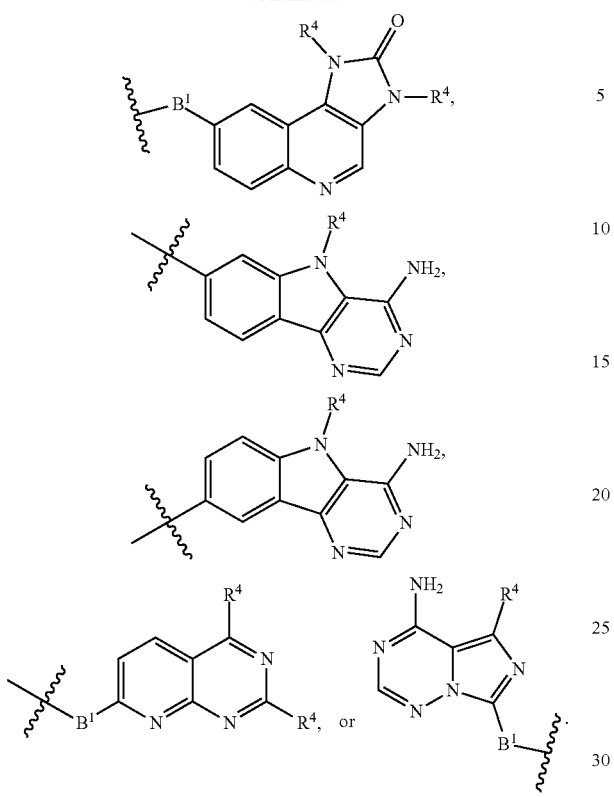
In certain embodiments, B is
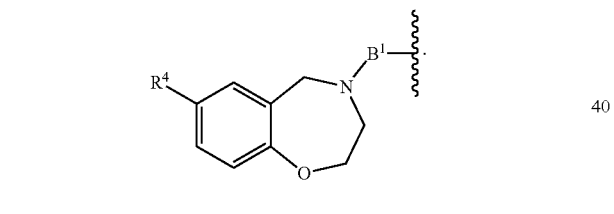
As described above, each $B^1$ is independently selected from
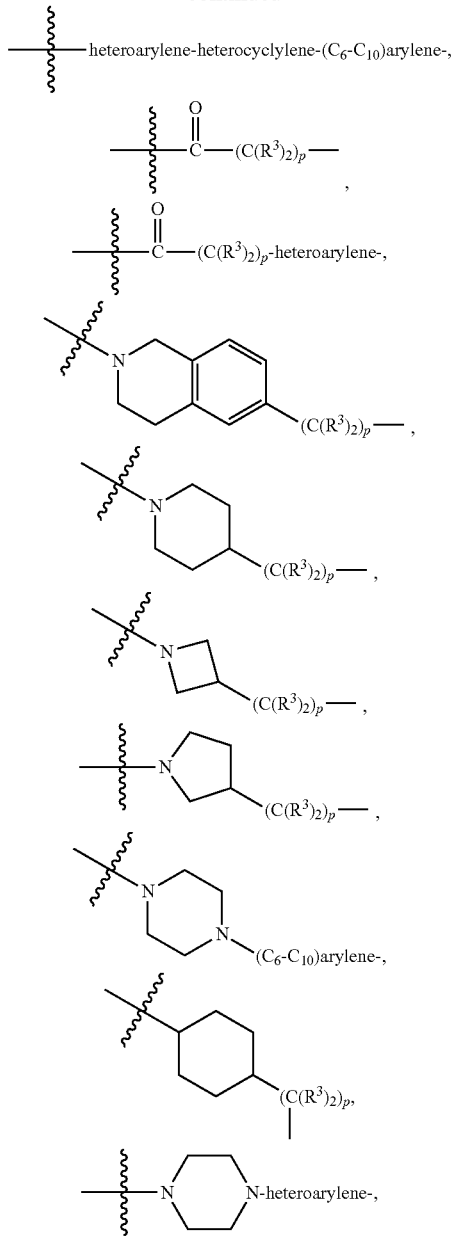
-continued
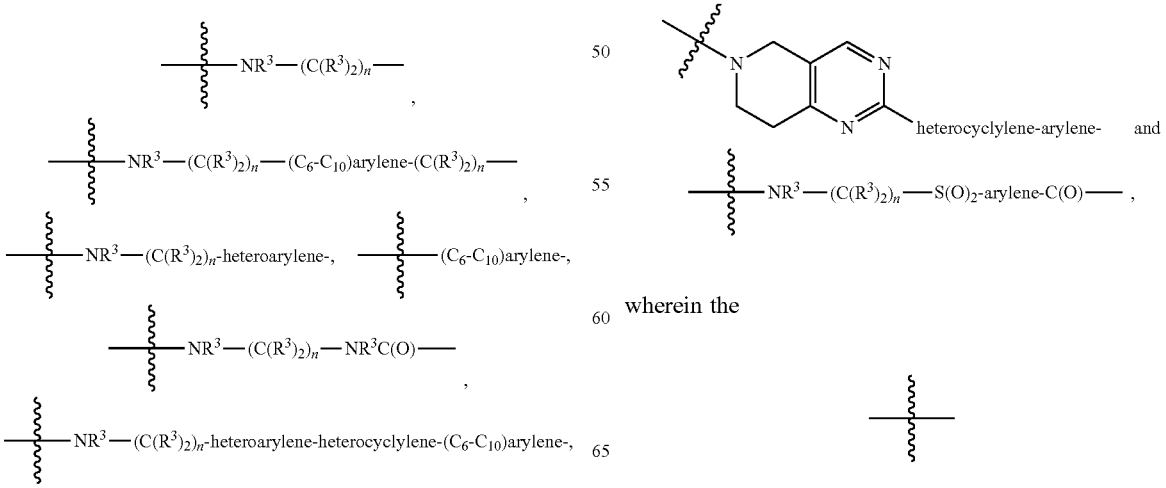
wherein the bond on the left side of $B^1$, as drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl.

In certain embodiments, $B^1$ is

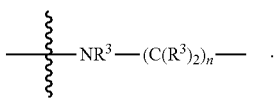

In certain embodiments, $B^1$ is

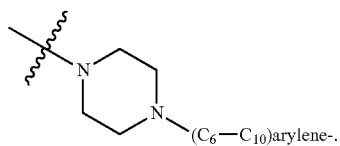

In certain embodiments, $B^1$ is

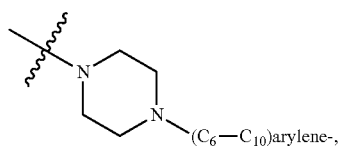

wherein arylene are optionally substituted with haloalkyl.

In certain embodiments, $B^1$ is

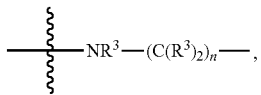

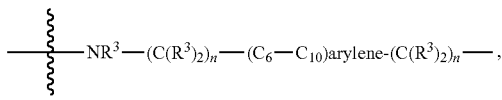

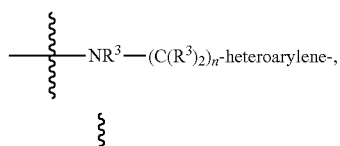

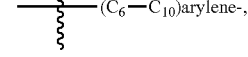

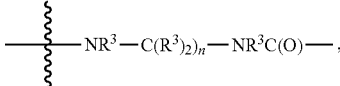

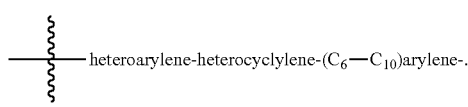

In certain embodiments, $B^1$ is

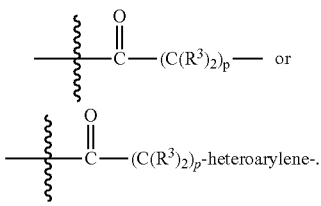

In certain embodiments, $B^1$ is

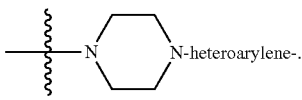

In certain embodiments, $B^1$ is

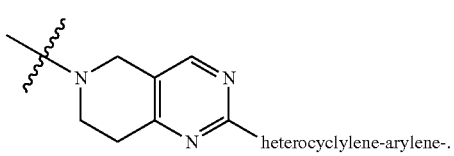

In certain embodiments, $B^1$ is

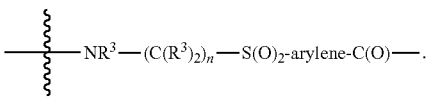

In certain embodiments, in $B^1$, the heteroaryl, heterocyclyl, and arylene are optionally substituted with alkyl, hydroxyalkyl, haloalkyl, alkoxy, halogen, or hydroxyl.

In certain embodiments, $R^3$ is H. In certain embodiments, $R^3$ is $(C_1-C_6)$alkyl.

In certain embodiments, $R^4$ is H. In certain embodiments, $R^4$ is $(C_1-C_6)$alkyl. In certain embodiments, $R^4$ is halogen. In certain embodiments, $R^4$ is 5-12 membered heteroaryl, 5-12 membered heterocyclyl, or $(C_6-C_{10})$aryl, wherein the heteroaryl, heterocyclyl, and aryl are optionally substituted with —$N(R^3)_2$, —$OR^3$, halogen, $(C_1-C_6)$alkyl, —$(C_1-C_6)$alkylene-heteroaryl, —$(C_1-C_6)$alkylene-CN, or —$C(O)$NR$^3$-heteroaryl. In certain embodiments, $R^4$ is —$C(O)NR^3$-heterocyclyl. In certain embodiments, $R^4$ is 5-12 membered heteroaryl, optionally substituted with —$N(R^3)_2$ or —$OR^3$.

As described above, each $R^5$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$. In certain embodiments, $R^5$ is H. In certain embodiments, $R^5$ is $(C_1-C_6)$alkyl, wherein the alkyl is optionally substituted with —$N(R^3)_2$ or —$OR^3$. In certain embodiments, $R^5$ is —$C(O)OR^3$. In certain embodiments, $R^5$ is —$N(R^3)_2$.

As described above, each $R^6$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$. In certain embodiments, $R^6$ is H. In certain embodiments, $R^6$ is $(C_1-C_6)$alkyl, wherein the alkyl is optionally substituted with —$N(R^3)_2$ or —$OR^3$. In certain embodiments, $R^6$ is —$C(O)OR^3$. In certain embodiments, $R^6$ is —$N(R^3)_2$.

As described above, each $R^7$ is independently H, $(C_1-C_6)$alkyl, —$C(O)OR^3$, or —$N(R^3)_2$, wherein the alkyl of $(C_1$-

$C_6$)alkyl is optionally substituted with —N(R$^3$)$_2$ or —OR$^3$. In certain embodiments, R$^7$ is H. In certain embodiments, R$^7$ is ($C_1$-$C_6$)alkyl, wherein the alkyl is optionally substituted with —N(R$^3$)$_2$ or —OR$^3$. In certain embodiments, R$^7$ is —C(O)OR$^3$. In certain embodiments, R$^7$ is —N(R$^3$)$_2$.

As described above, each R$^8$ is independently H, ($C_1$-$C_6$) alkyl, —C(O)OR$^3$, or —N(R$^3$)$_2$, wherein the alkyl of ($C_1$-$C_6$)alkyl is optionally substituted with —N(R$^3$)$_2$ or —OR$^3$. In certain embodiments, R$^8$ is H. In certain embodiments, R$^8$ is ($C_1$-$C_6$)alkyl, wherein the alkyl is optionally substituted with —N(R$^3$)$_2$ or —OR$^3$. In certain embodiments, R$^8$ is —C(O)OR$^3$. In certain embodiments, R$^8$ is —N(R$^3$)$_2$.

As described above, each Y is independently C(R$^3$)$_2$ or a bond. In certain embodiments, Y is C(R$^3$)$_2$. In certain embodiments, Y is CH$_2$. In certain embodiments, Y is a bond.

In certain embodiments, n is 1, 2, 3, 4, 5, 6, 7, or 8, or any range derivable therein. In certain embodiments, n is 1, 2, 3, or 4. In certain embodiments, n is 5, 6, 7, or 8. In certain embodiments, n is 9, 10, 11, or 12.

In certain embodiments, o is an integer from zero to 10, or any range derivable therein. In certain embodiments, o is 0, 1, 2, 3, 4, or 5. In certain embodiments, o is 6, 7, 8, 9, or 10. In certain embodiments, o is one to 7. In certain embodiments, o is one to 8. In certain embodiments, o is one to 9. In certain embodiments, o is 3 to 8.

In certain embodiments, o is an integer from zero to 30, or any range derivable therein. In certain embodiments, o is an integer from zero to 30, 29, 28, 27, or 26. In certain embodiments, o is an integer from zero to 25, 24, 23, 22, or 21. In certain embodiments, o is an integer from zero to 20, 19, 18, 17, or 16. In certain embodiments, o is an integer from zero to 15, 14, 13, 12, or 11.

In certain embodiments, p is 0, 1, 2, 3, 4, 5, or 6, or any range derivable therein. In certain embodiments, p is 7, 8, 9, 10, 11, or 12. In certain embodiments, p is 0, 1, 2, or 3. In certain embodiments, p is 4, 5, or 6.

In certain embodiments, q is an integer from zero to 10, or any range derivable therein. In certain embodiments, q is 0, 1, 2, 3, 4, or 5. In certain embodiments, q is 6, 7, 8, 9, or 10. In certain embodiments, q is one to 7. In certain embodiments, q is one to 8. In certain embodiments, q is one to 9. In certain embodiments, q is 3 to 8.

In certain embodiments, q is an integer from zero to 30, or any range derivable therein. In certain embodiments, q is an integer from zero to 30, 29, 28, 27, or 26. In certain embodiments, q is an integer from zero to 25, 24, 23, 22, or 21. In certain embodiments, q is an integer from zero to 20, 19, 18, 17, or 16. In certain embodiments, q is an integer from zero to 15, 14, 13, 12, or 11.

As described above, r is an integer from one to 6, or any range derivable therein. In certain embodiments, r is one. In certain embodiments, r is 2. In certain embodiments, r is 3. In certain embodiments, r is 4. In certain embodiments, r is 5. In certain embodiments, r is 6.

The present disclosure provides a compound of formula (I) or (Ia),

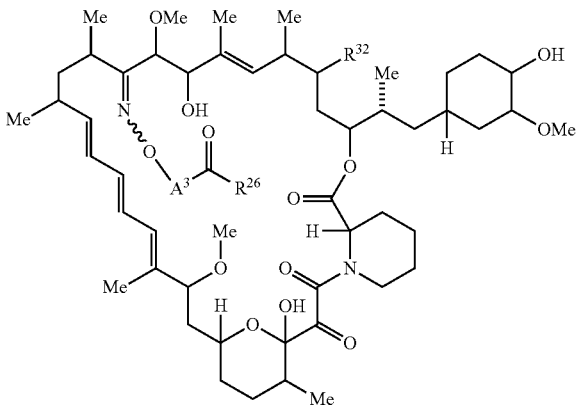

(I)

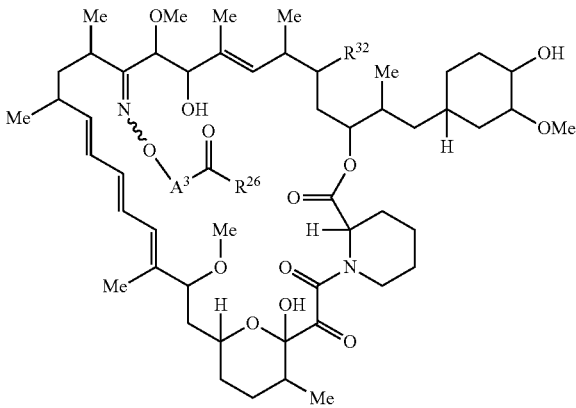

(Ia)

or a pharmaceutically acceptable salt or tautomer thereof, having one, two, three, or four of the following features:

a) A$^3$ is —[C(R$^3$)$_2$]$_n$—, such as CH$_2$;
b) R$^{26}$ is -A$^1$-L$^1$-A$^2$-B;
c) L$^1$ is

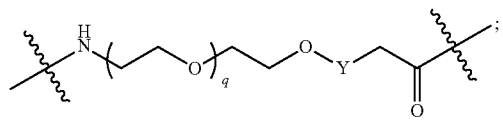

d) A$^2$ is

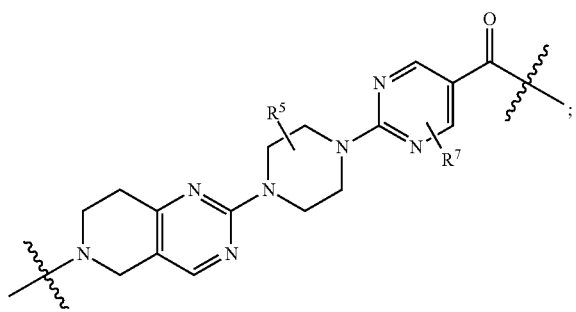

e) B is

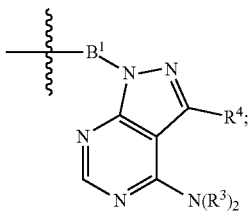

f) B¹ is

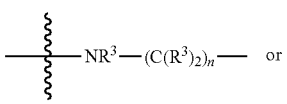

or

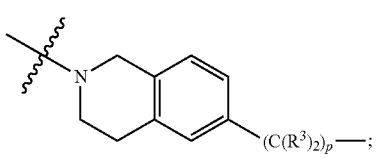

g) R⁴ is 5-12 membered heteroaryl, optionally substituted with —N(R³)₂ or —OR³; and h) R³² is —OH.

The present disclosure provides a compound of formula (I) or (Ia),

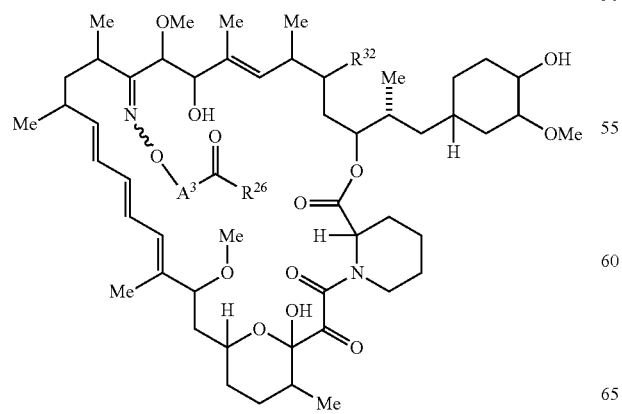

(I)

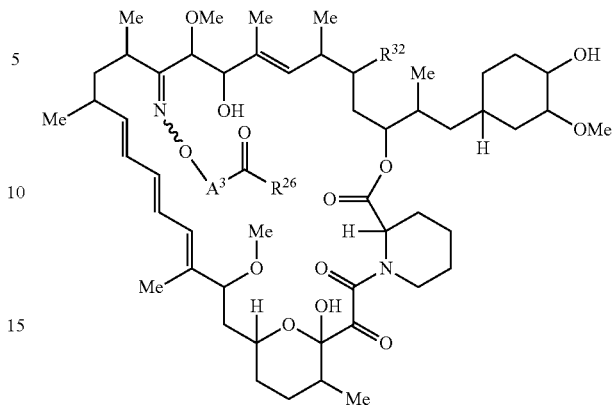

(Ia)

or a pharmaceutically acceptable salt or tautomer thereof, having one, two, three, or four of the following features:

a) A³ is —[C(R³)₂]ₙ—, such as CH₂;
b) R²⁶ is -A¹-L¹-A²-B;
c) A¹ is absent;
d) A² is absent;
e) L¹ is

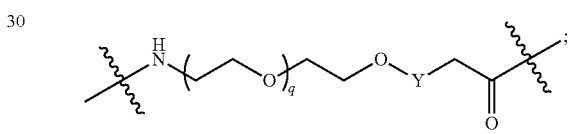

f) B is

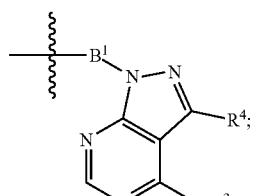

g) B¹ is

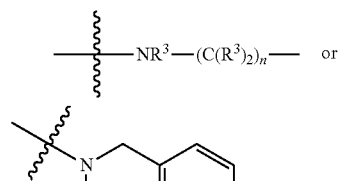

h) R⁴ is 5-12 membered heteroaryl, optionally substituted with —N(R³)₂ or —OR³; and i) R³² is —OH.

The present disclosure provides a compound of formula (Ia),

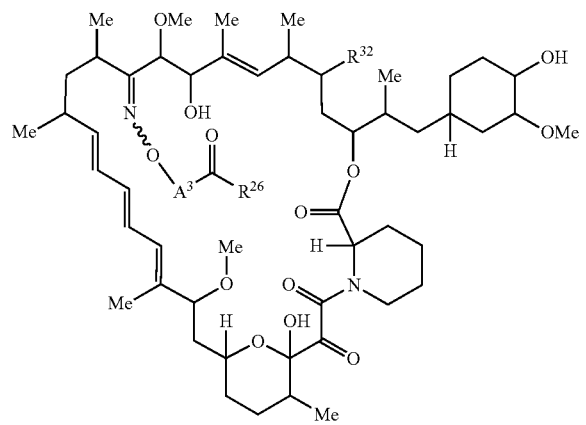

(Ia)

or a pharmaceutically acceptable salt or tautomer thereof, having one, two, three, or four of the following features:

a) $A^3$ is —[C(R$^3$)$_2$]$_n$—, such as CH$_2$;
b) $R^{26}$ is -A$^1$-L$^1$-A$^2$-B;
C) $A^1$ is

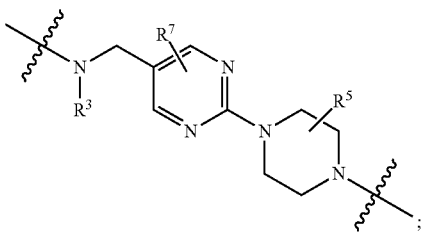

d) $A^2$ is

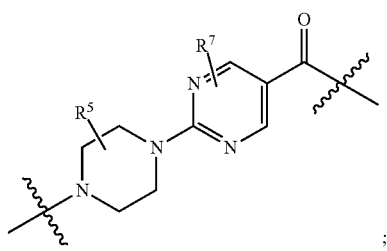

e) $L^1$ is

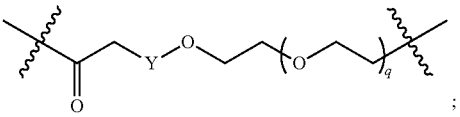

f) B is

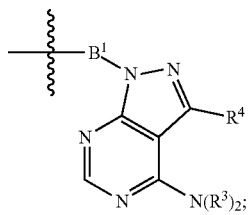

g) $B^1$ is

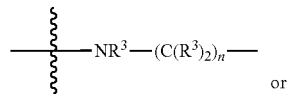

or

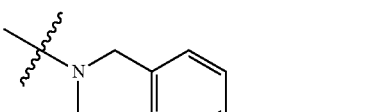

h) $R^4$ is 5-12 membered heteroaryl, optionally substituted with —N(R$^3$)$_2$ or —OR$^3$; and
i) $R^{32}$ is —OH.

In certain embodiments, the present disclosure provides for a compound selected from below, or a pharmaceutically acceptable salt or tautomer thereof, Example 1
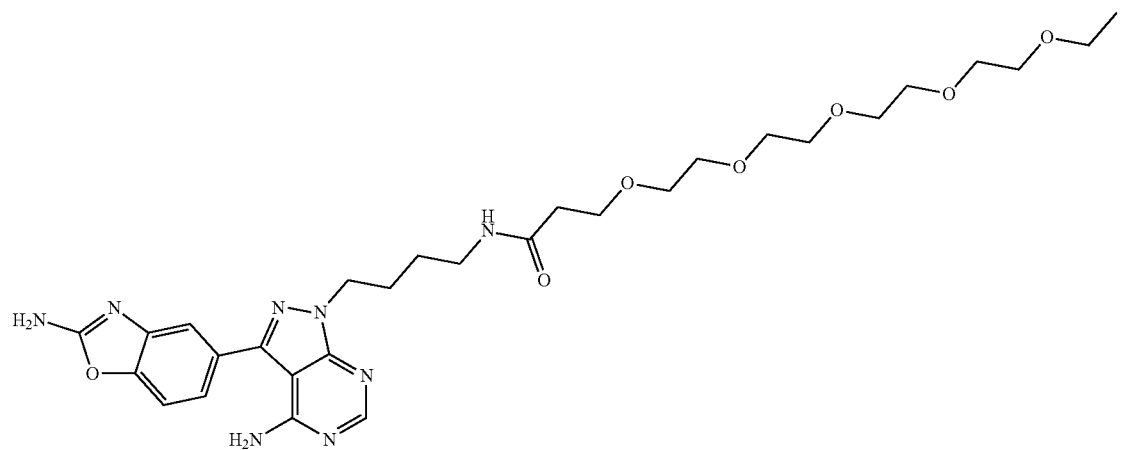
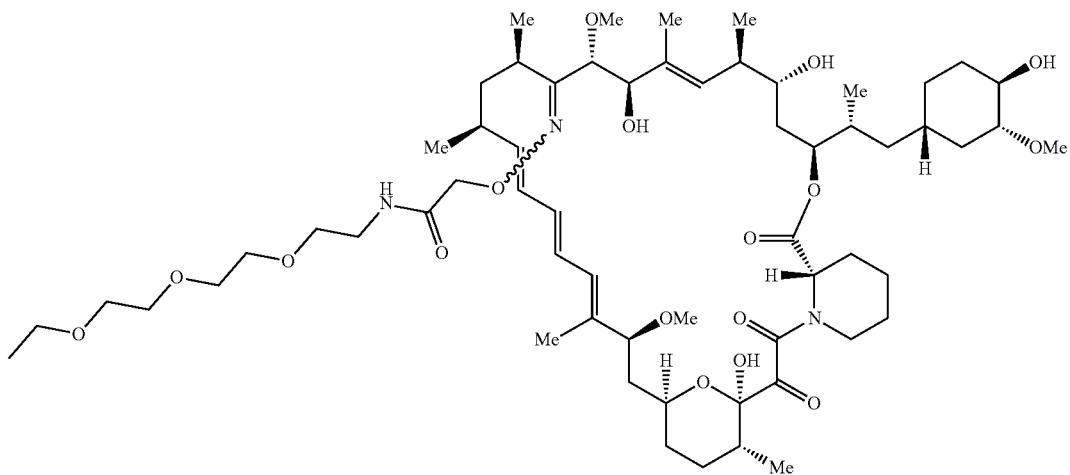
Example 2
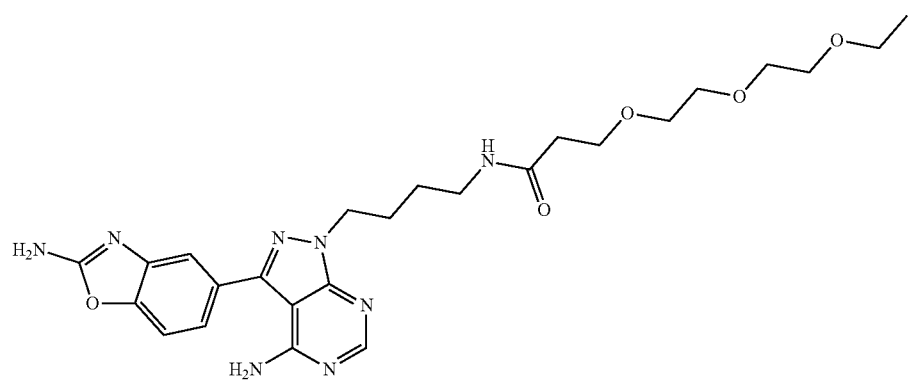

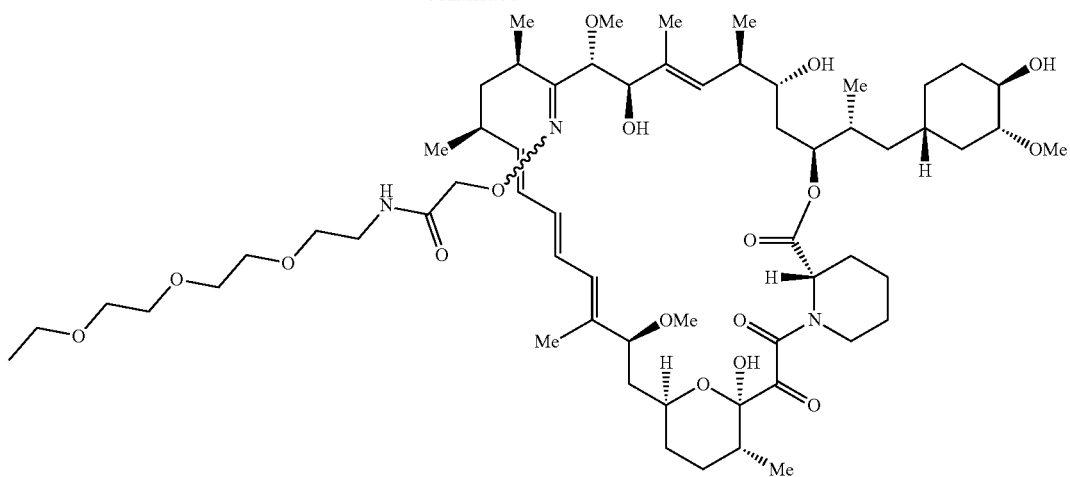
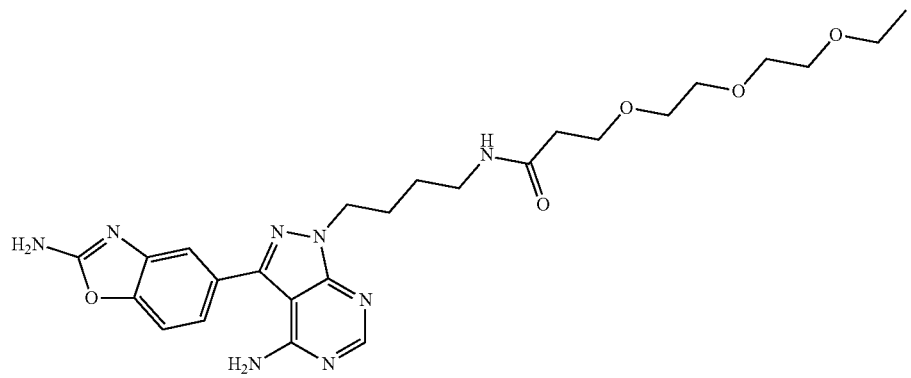
Example 3
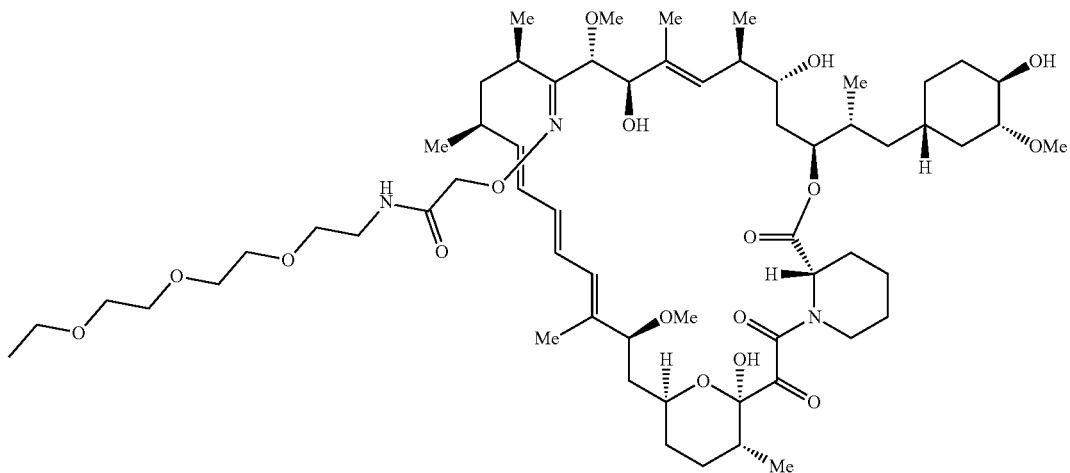

Example 4
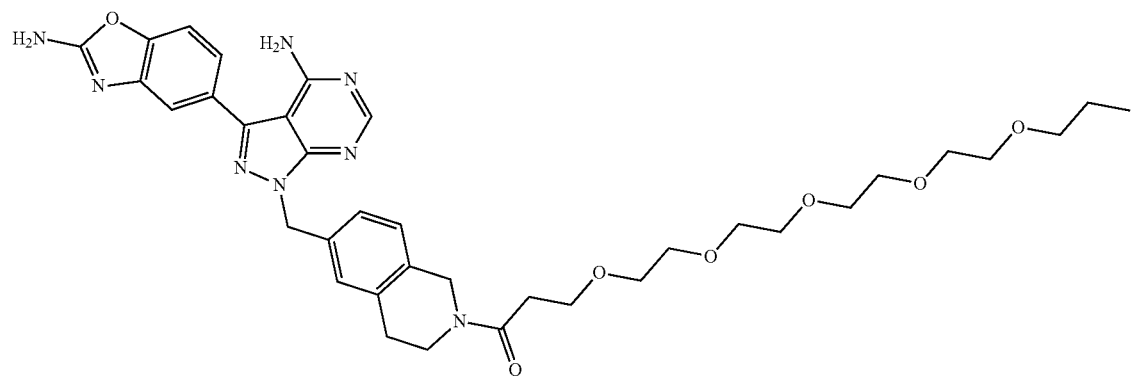
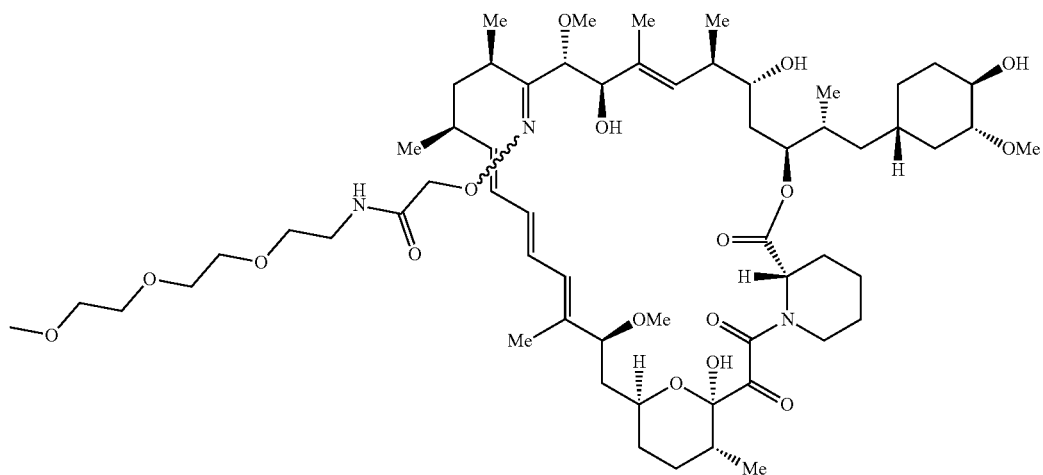
Example 5
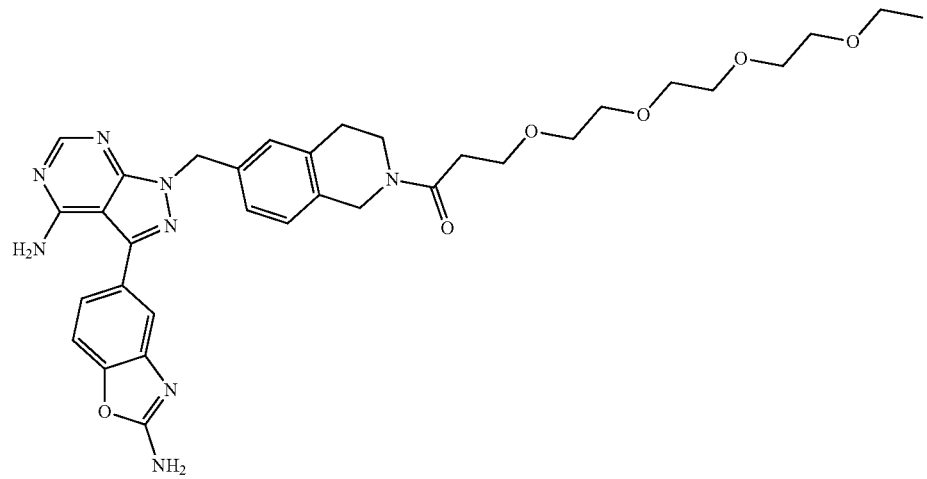

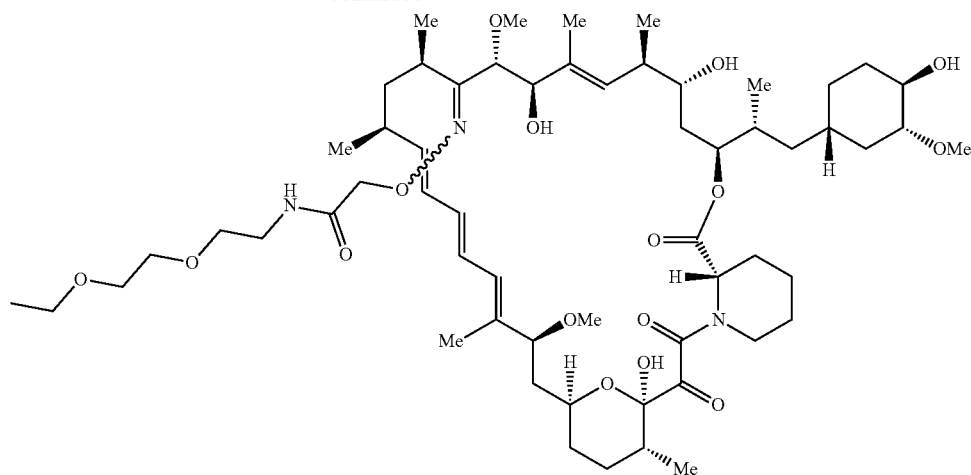
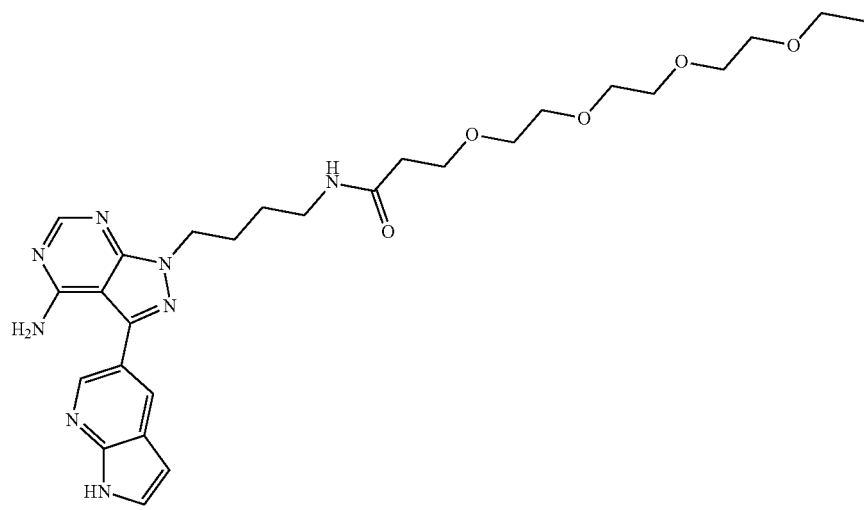
Example 6
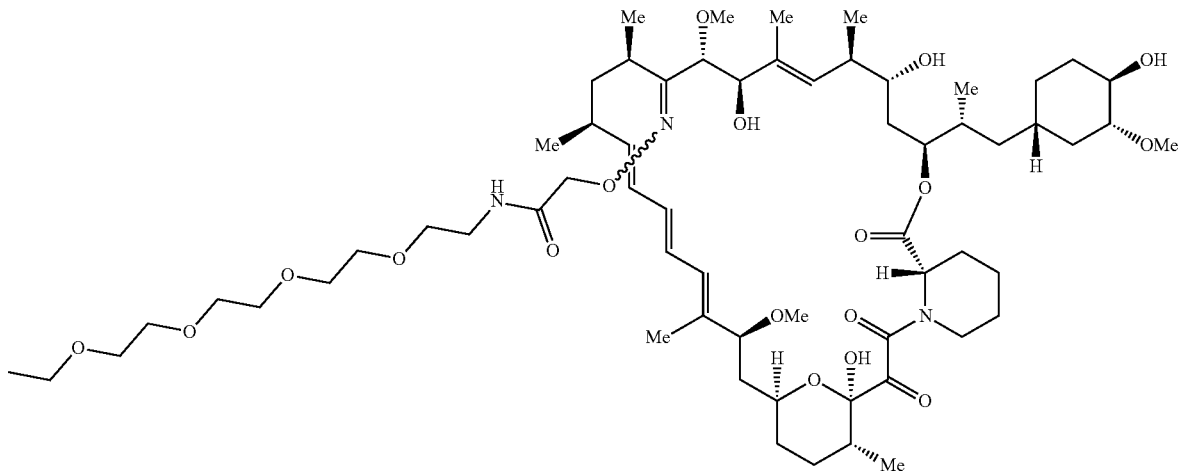

Example 7
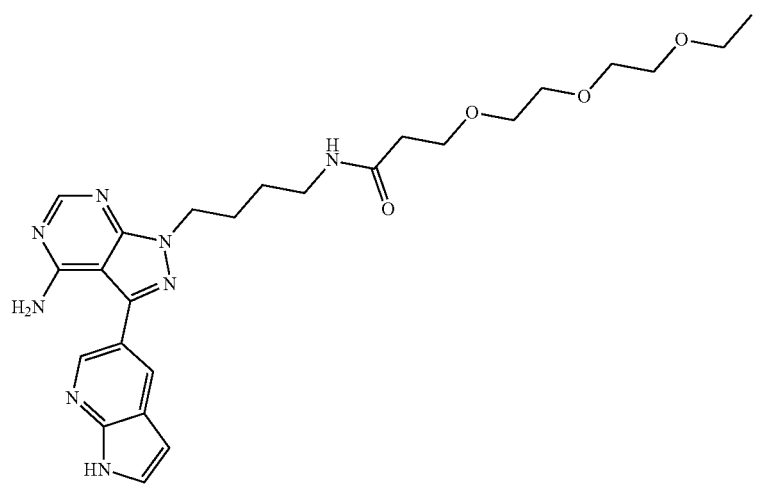
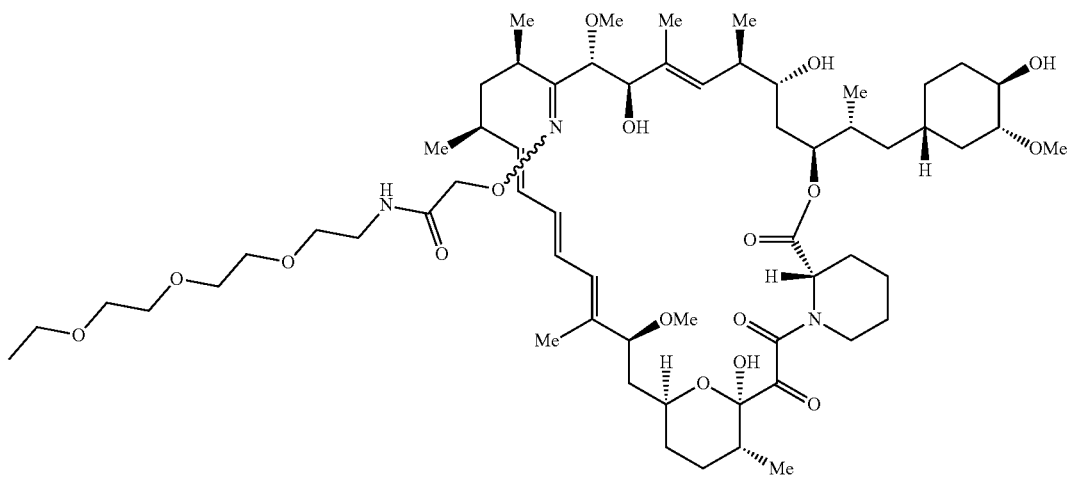
Example 8
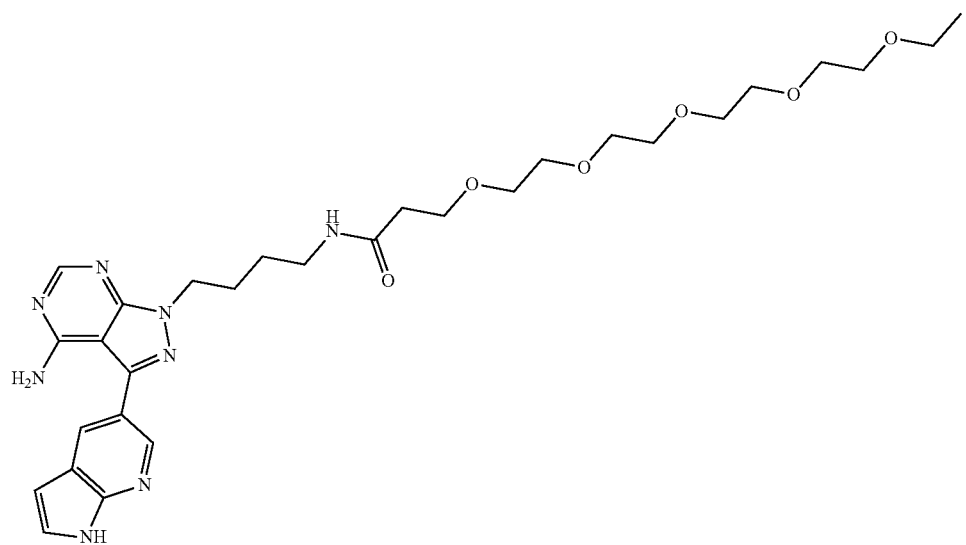

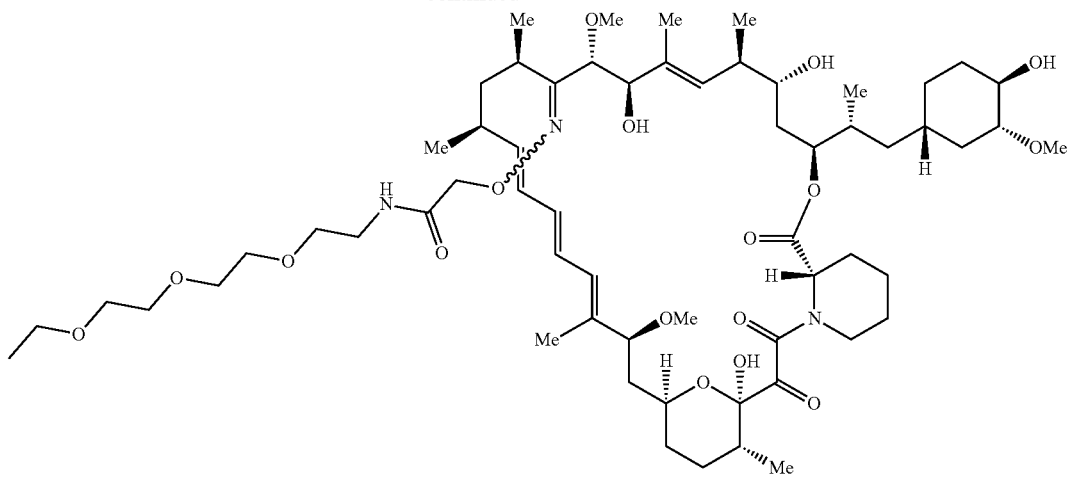
Example 9
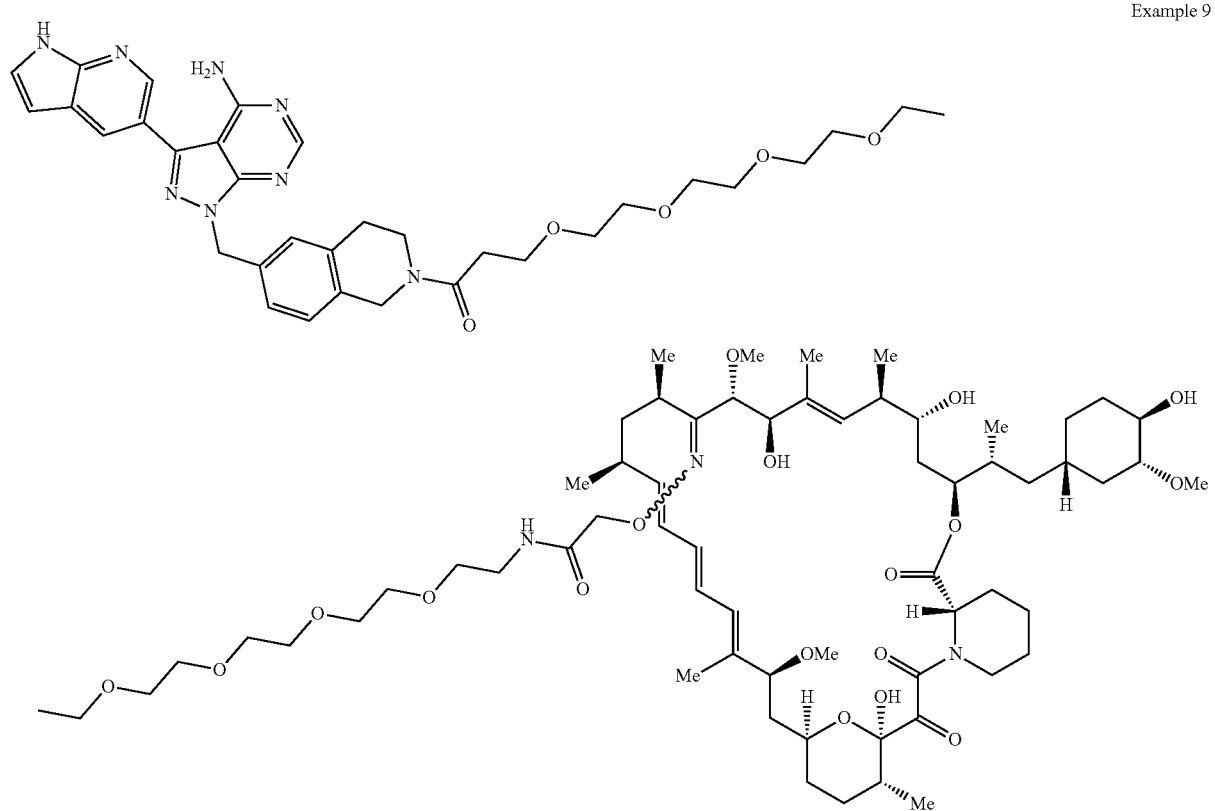
Example 10
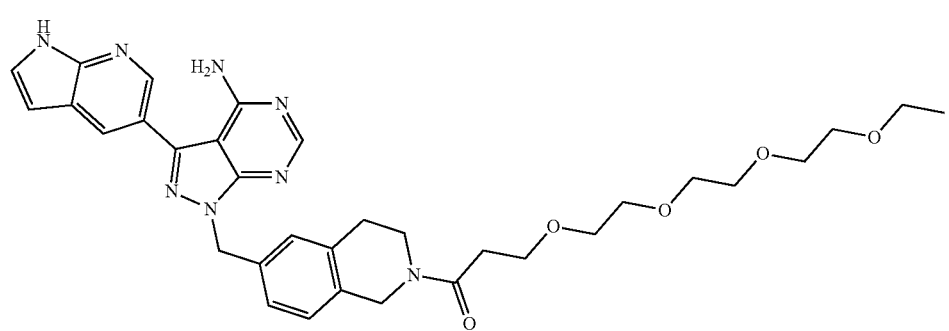

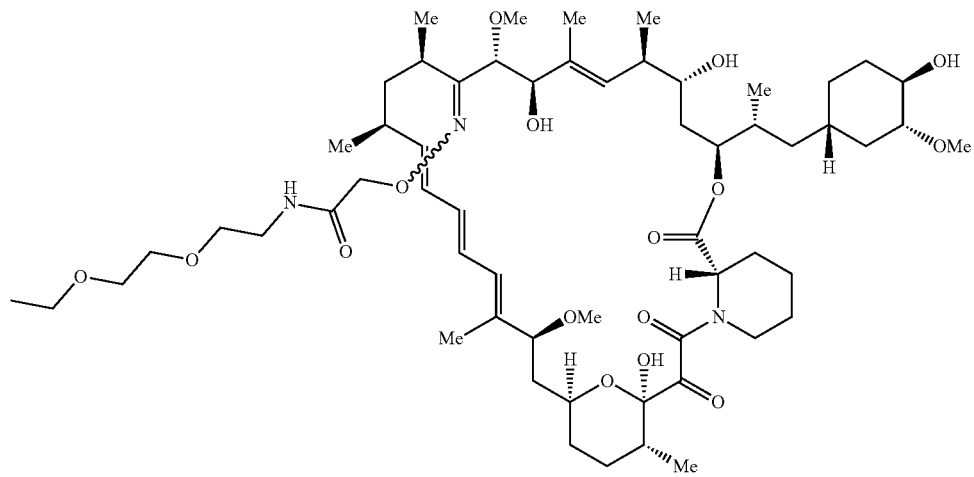
Example 11
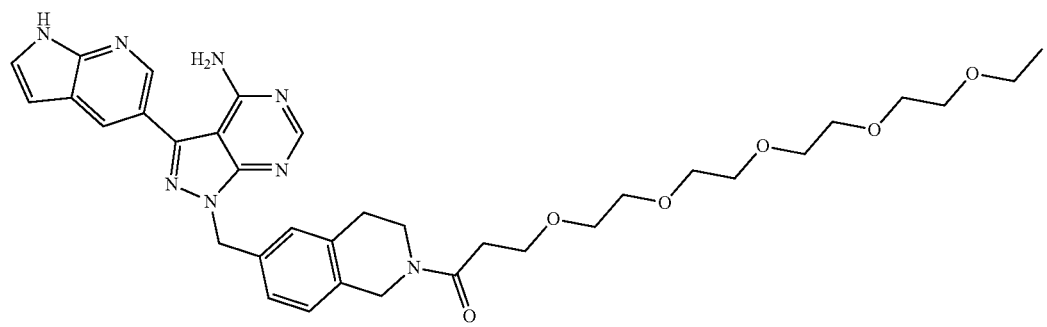
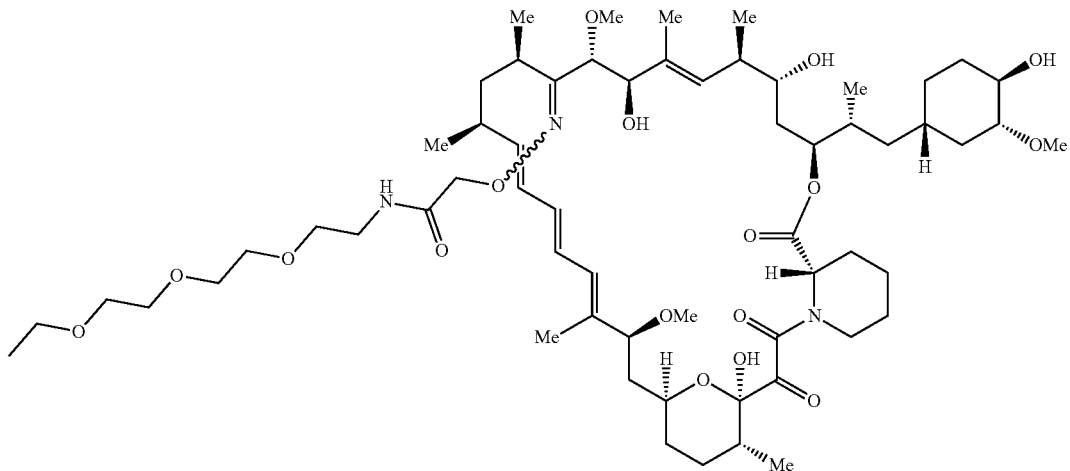
Example 12
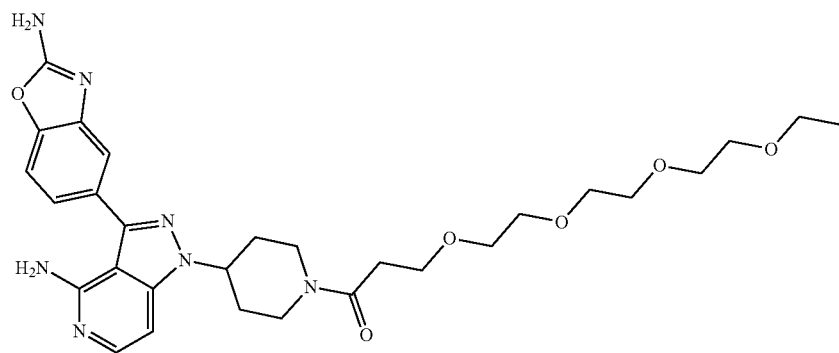

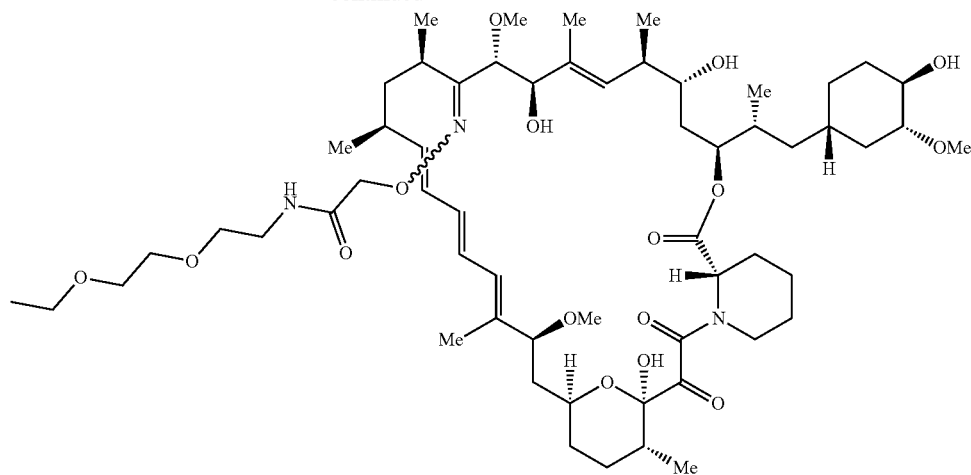
Example 13
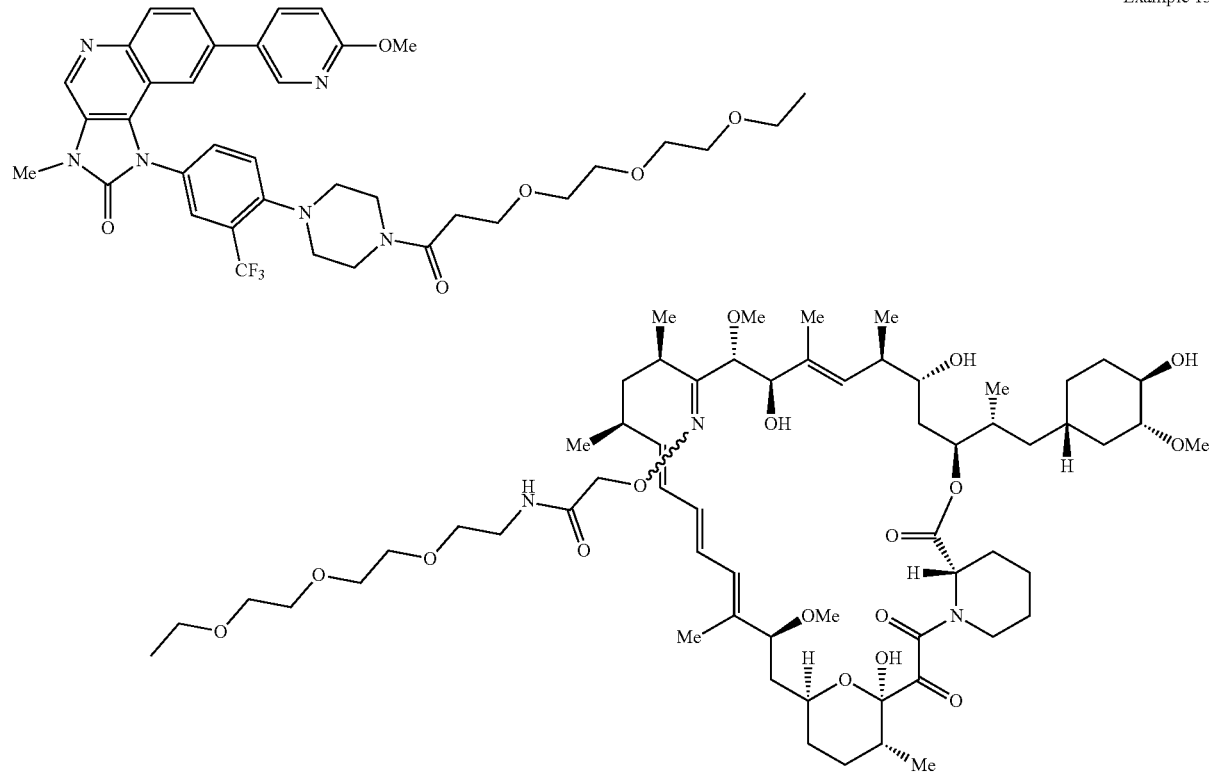
Example 14
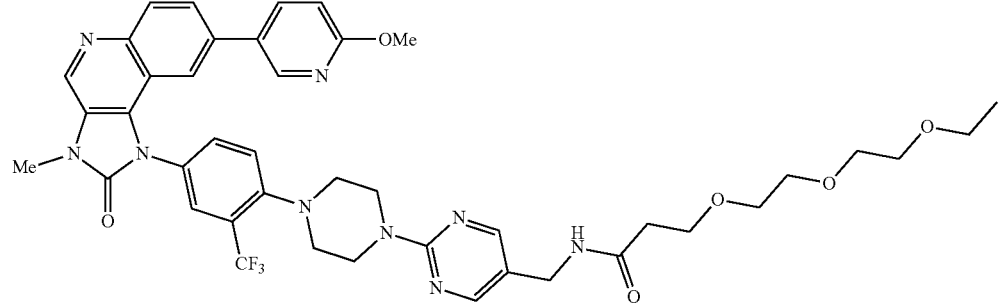

-continued
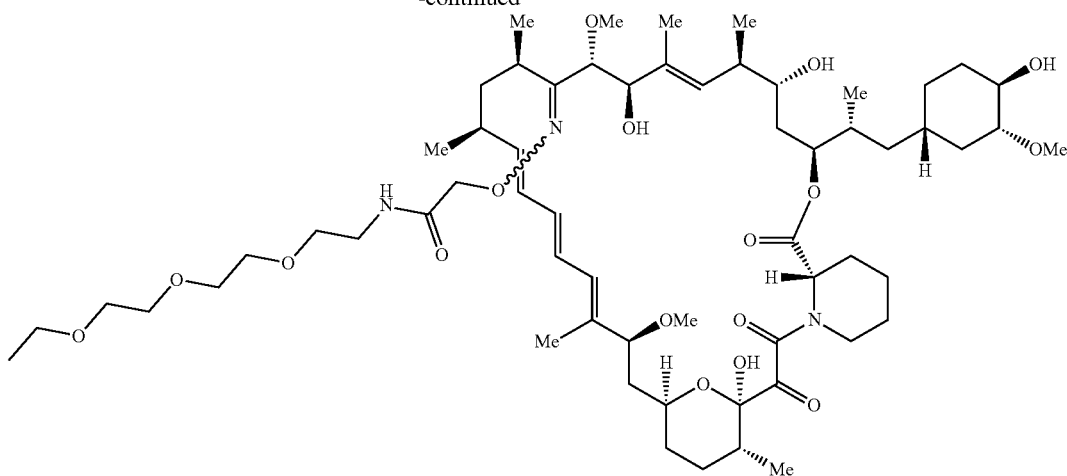
Example 15
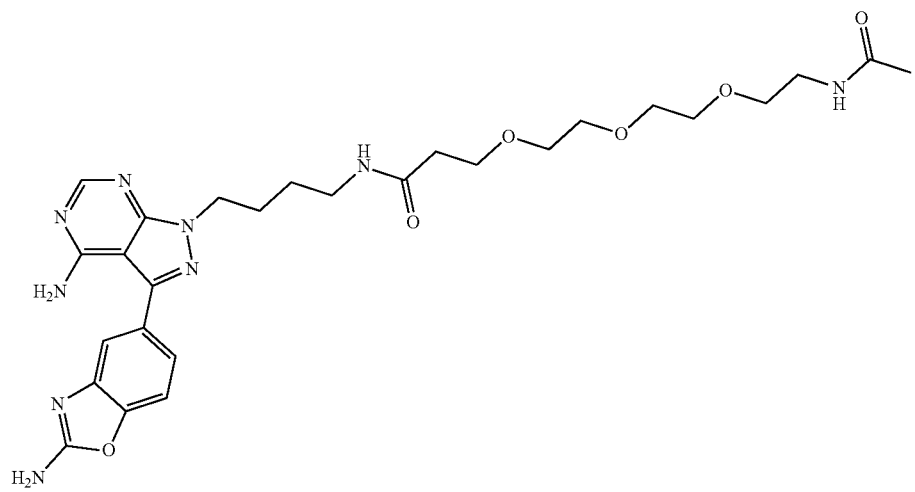
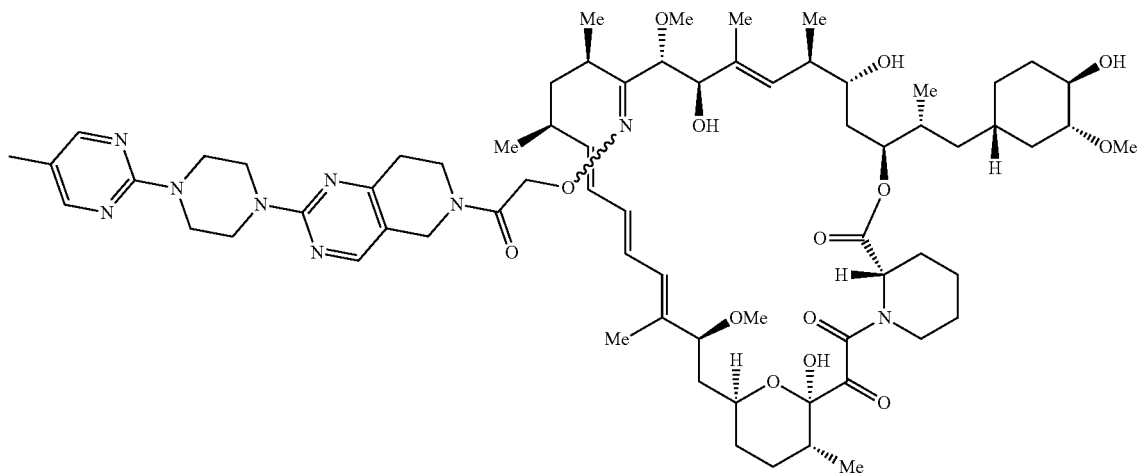

Example 16
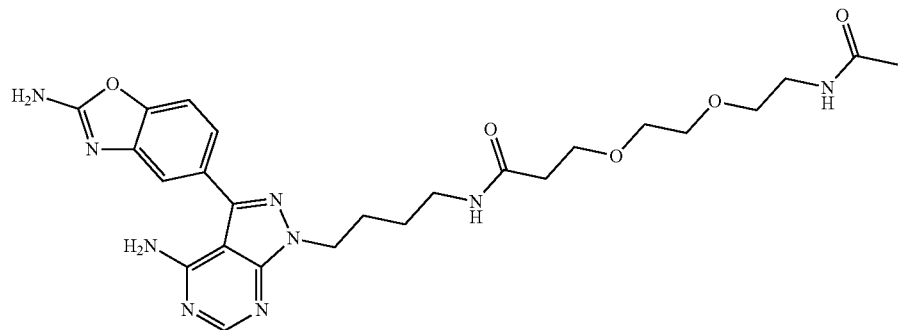
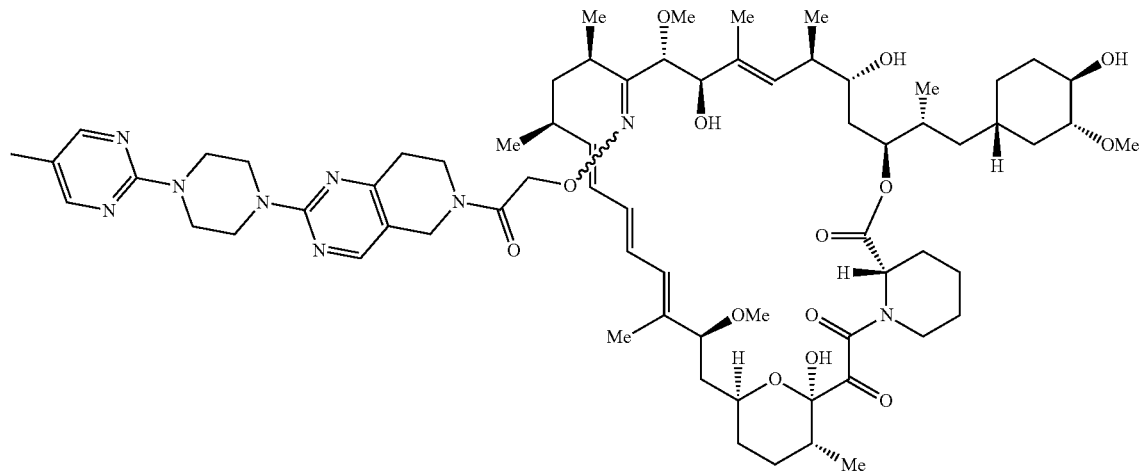
Example 17
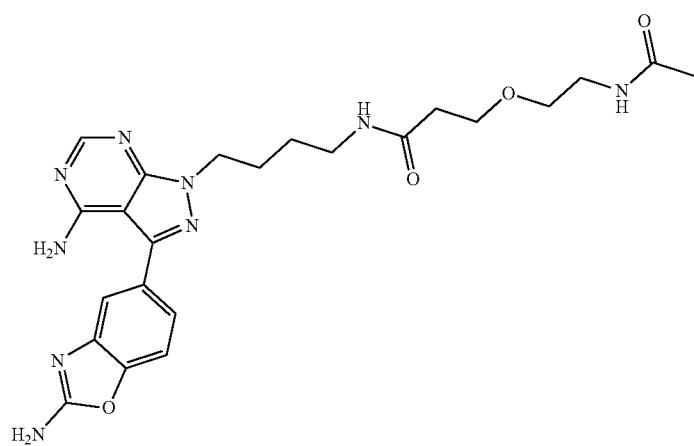

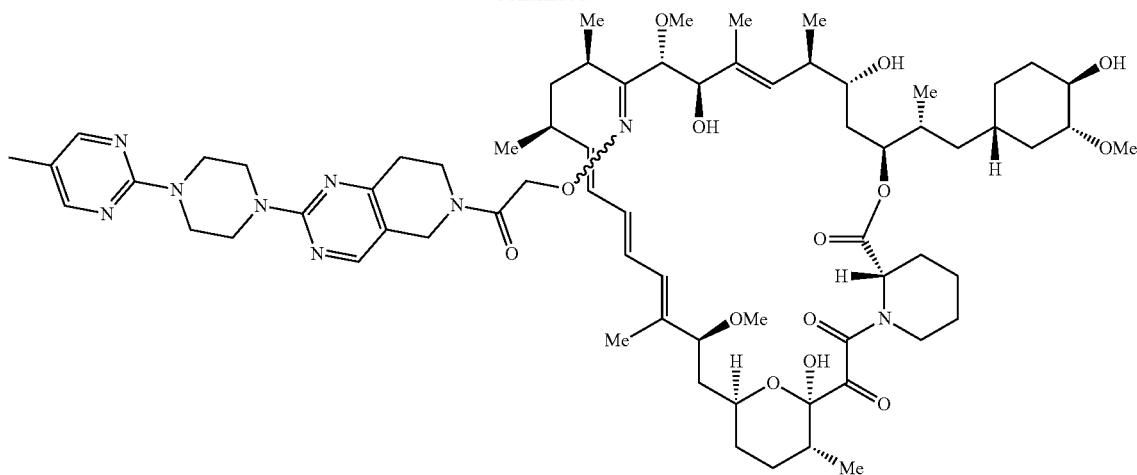
Example 18
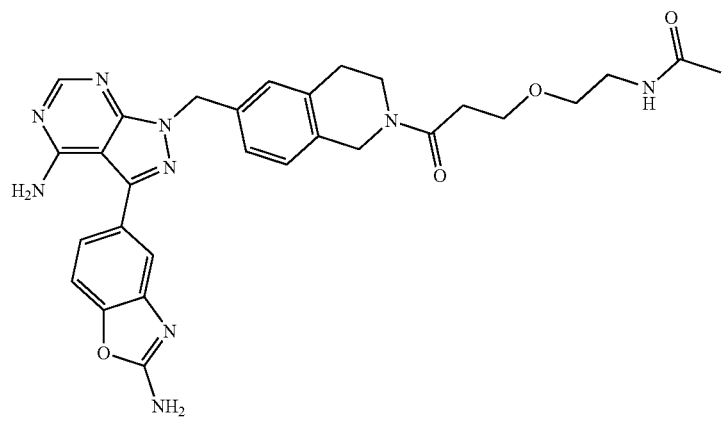
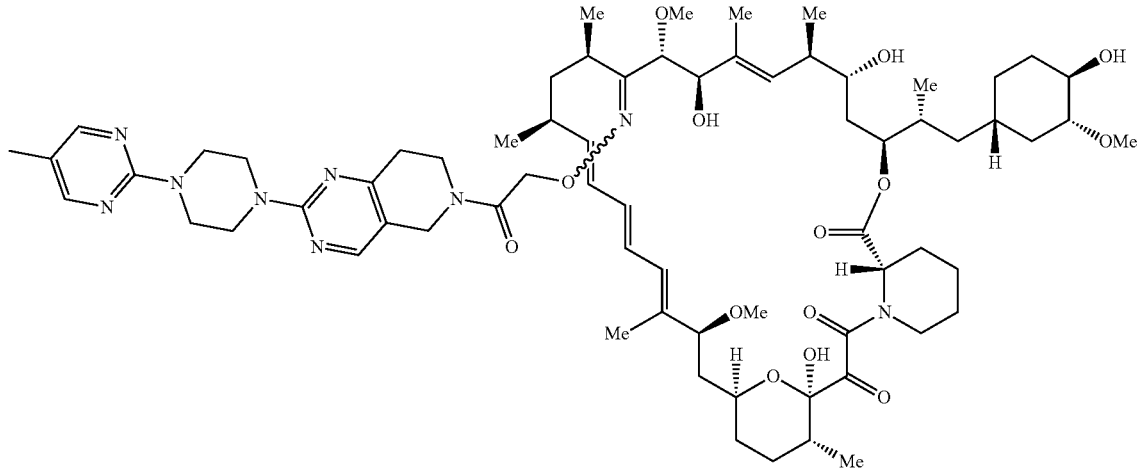
Example 19
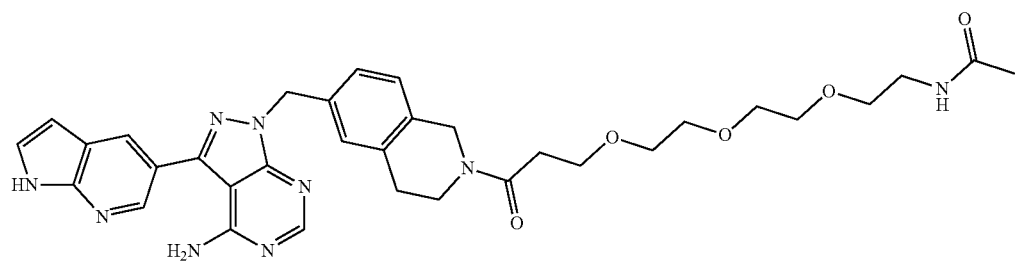

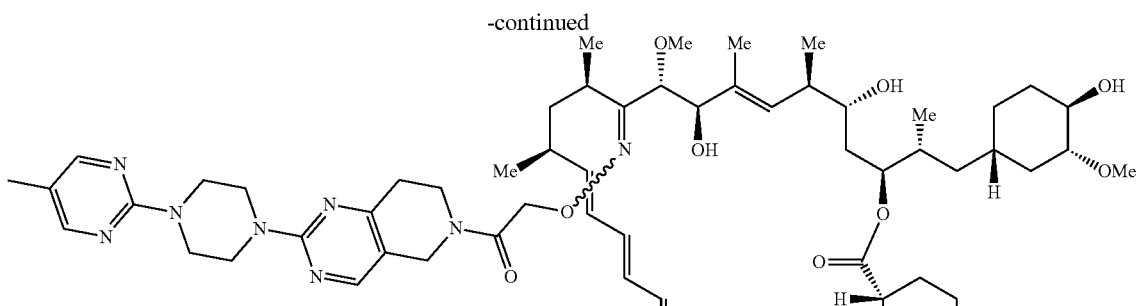
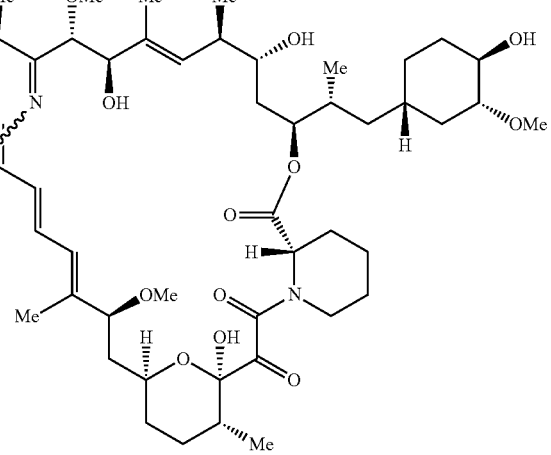
Example 20
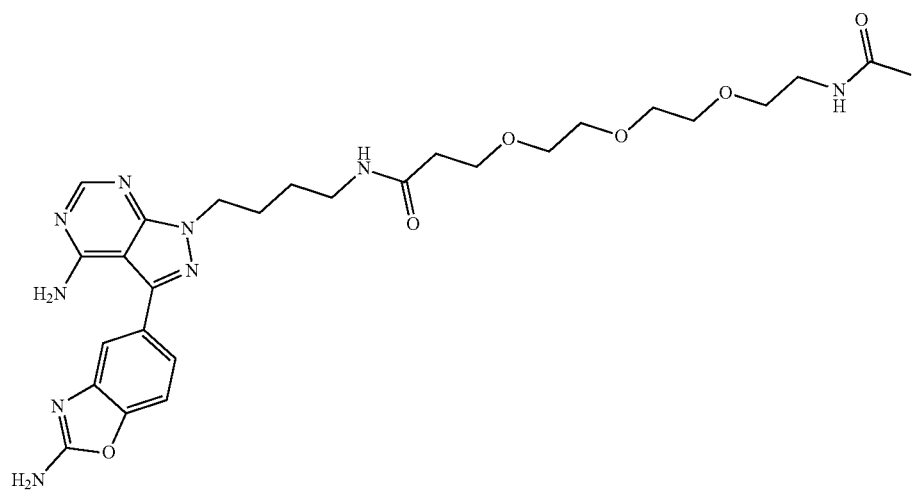
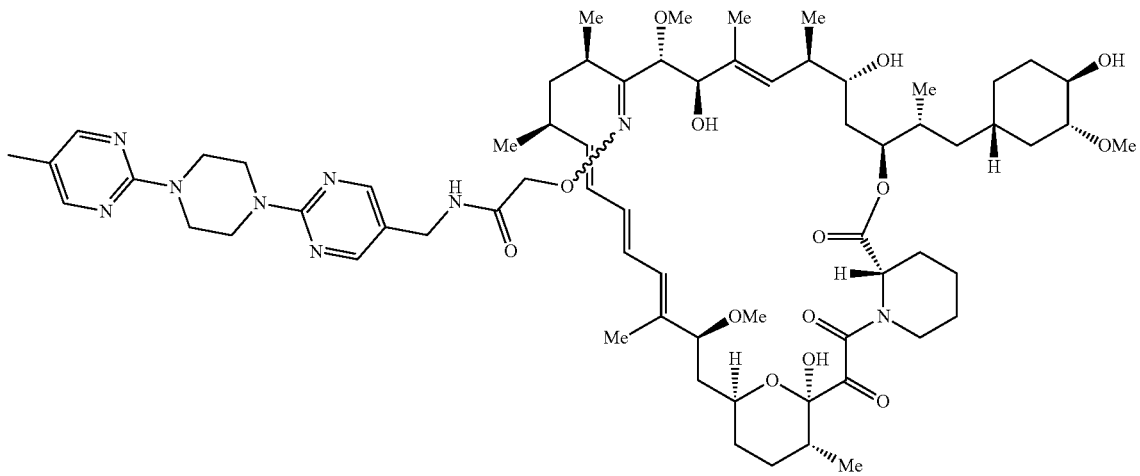
Example 21
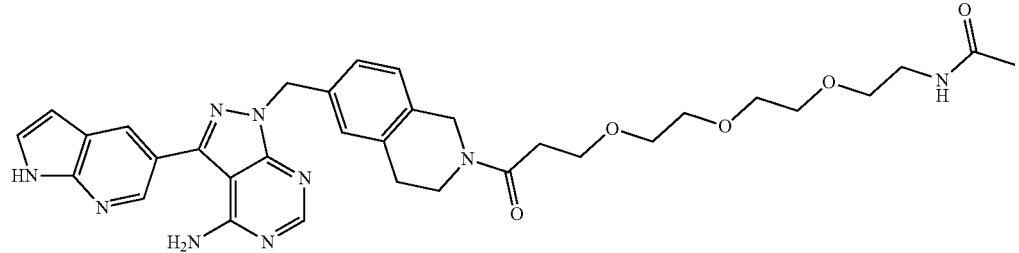

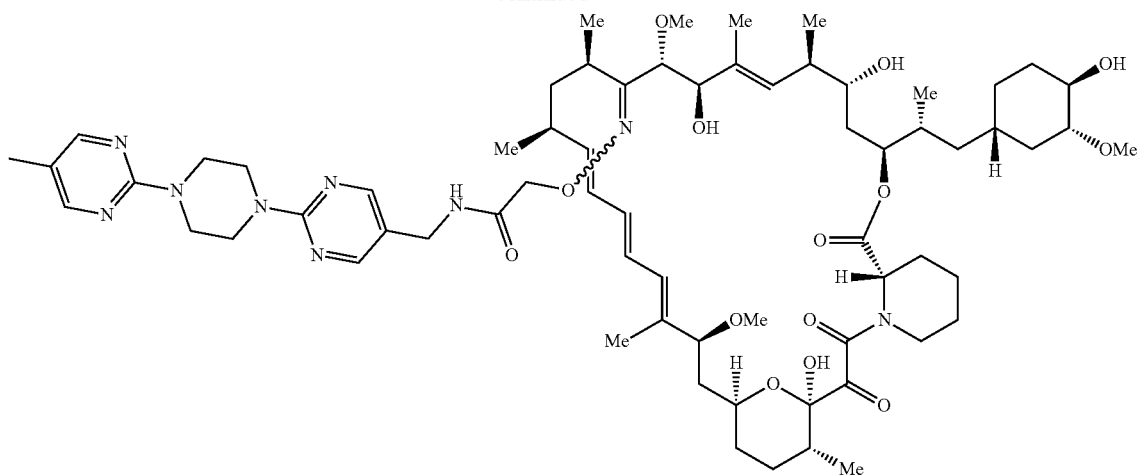
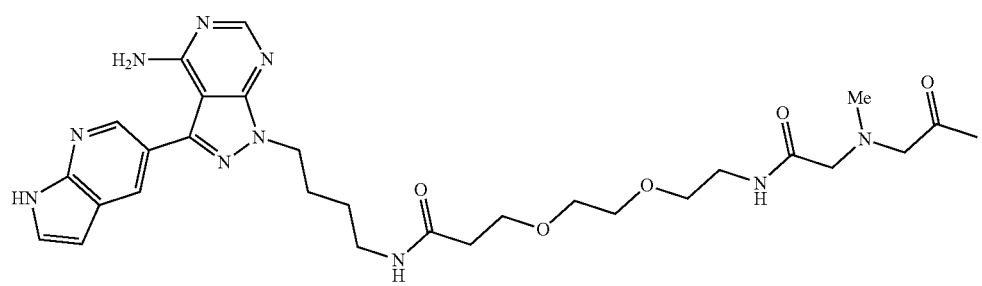
Example 22
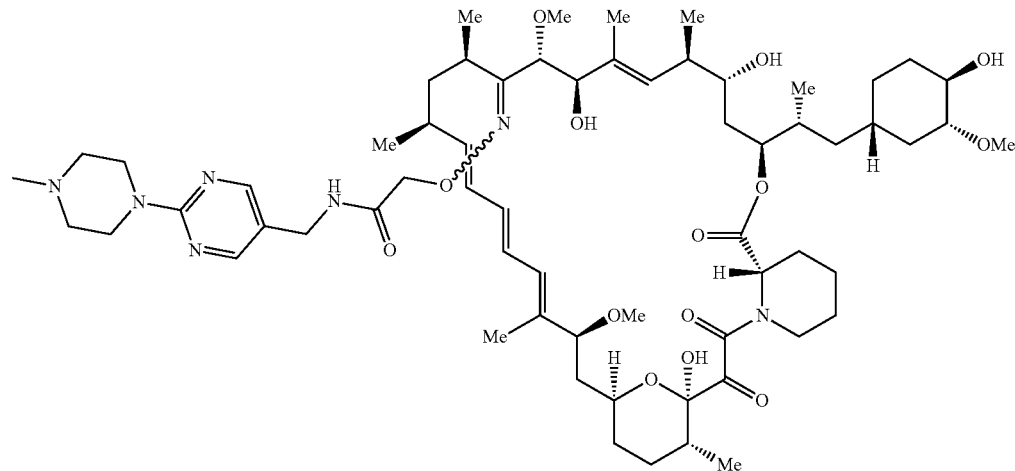

Example 23
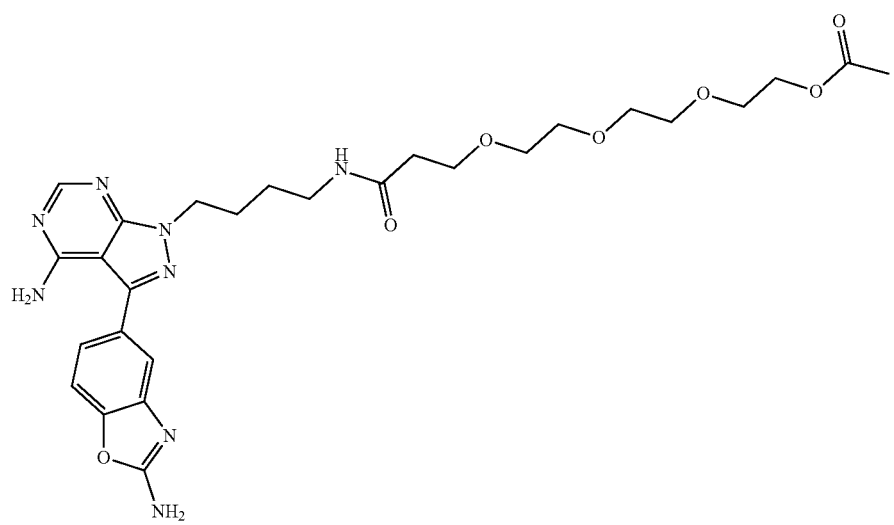
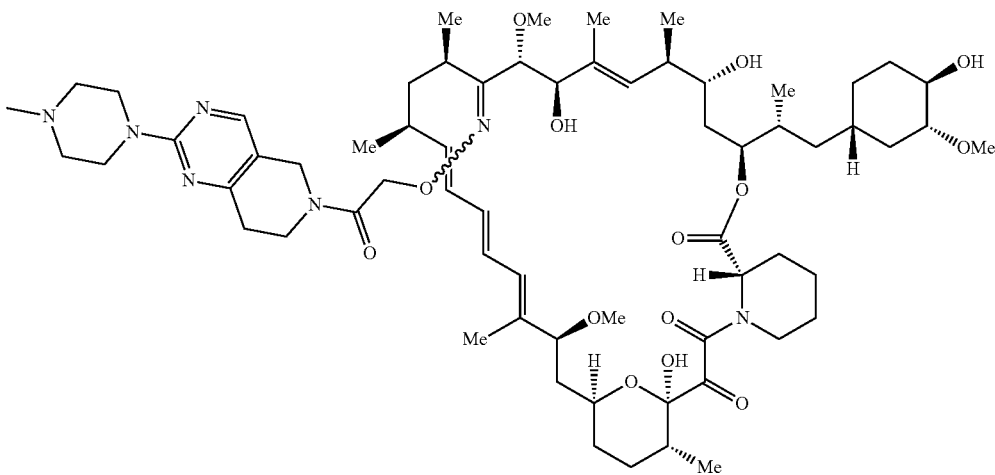
Example 24
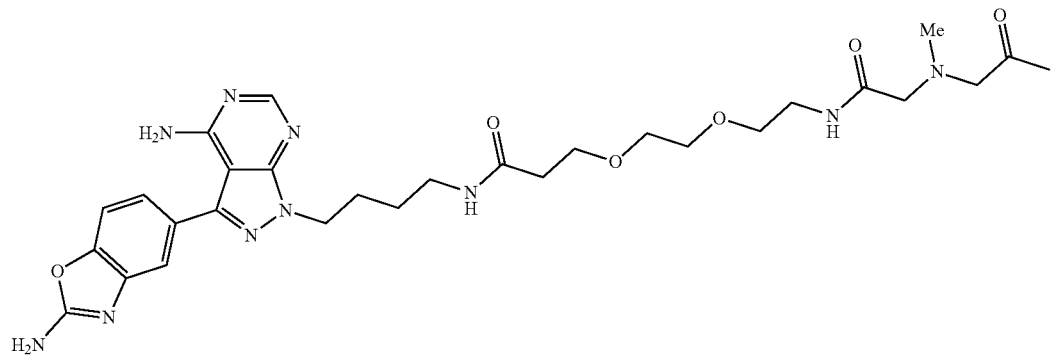

-continued
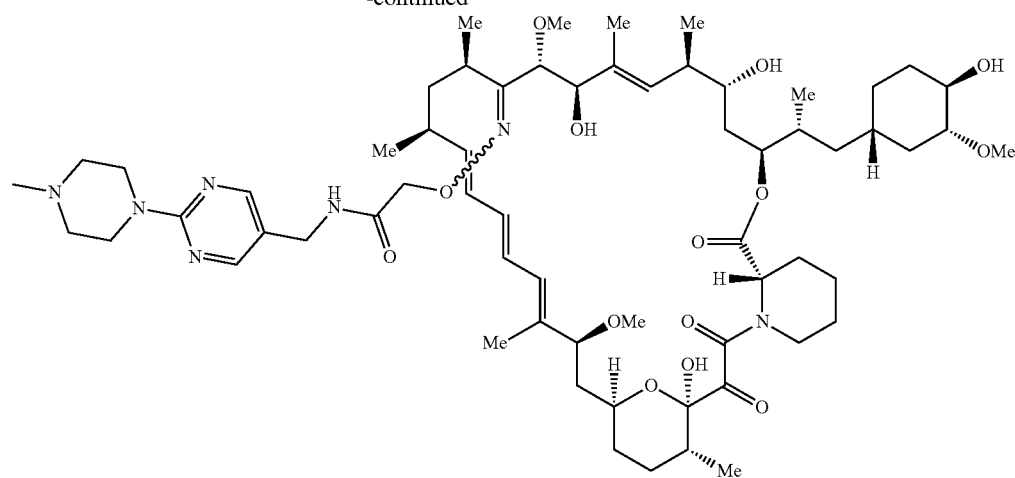
Example 25
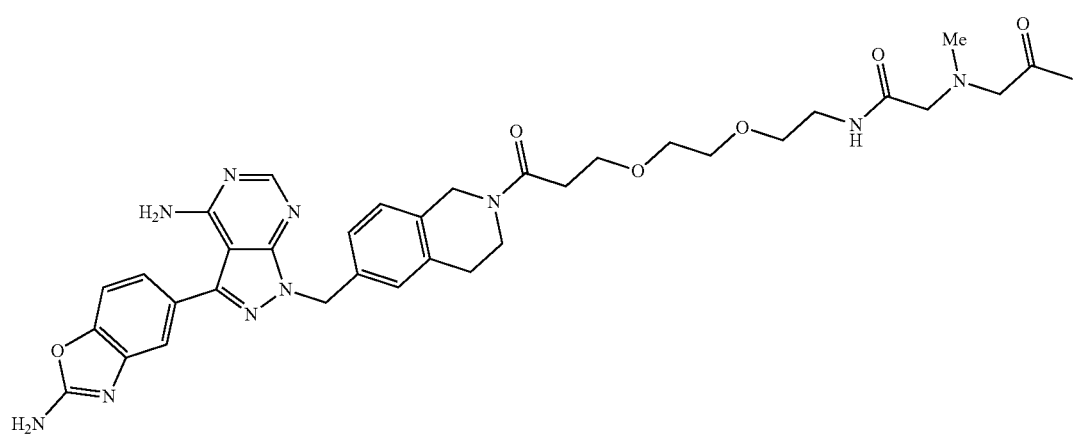
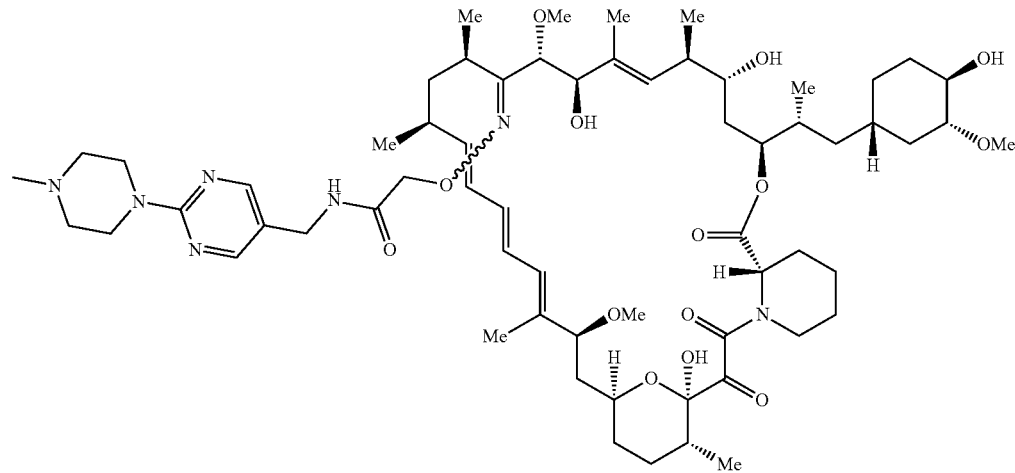

Example 26
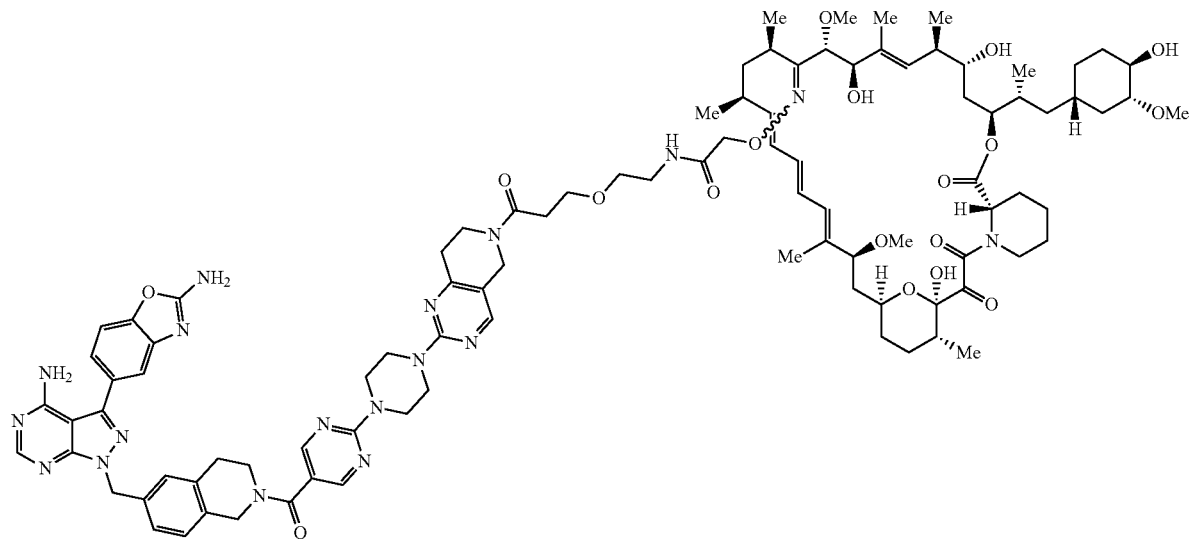
Example 27
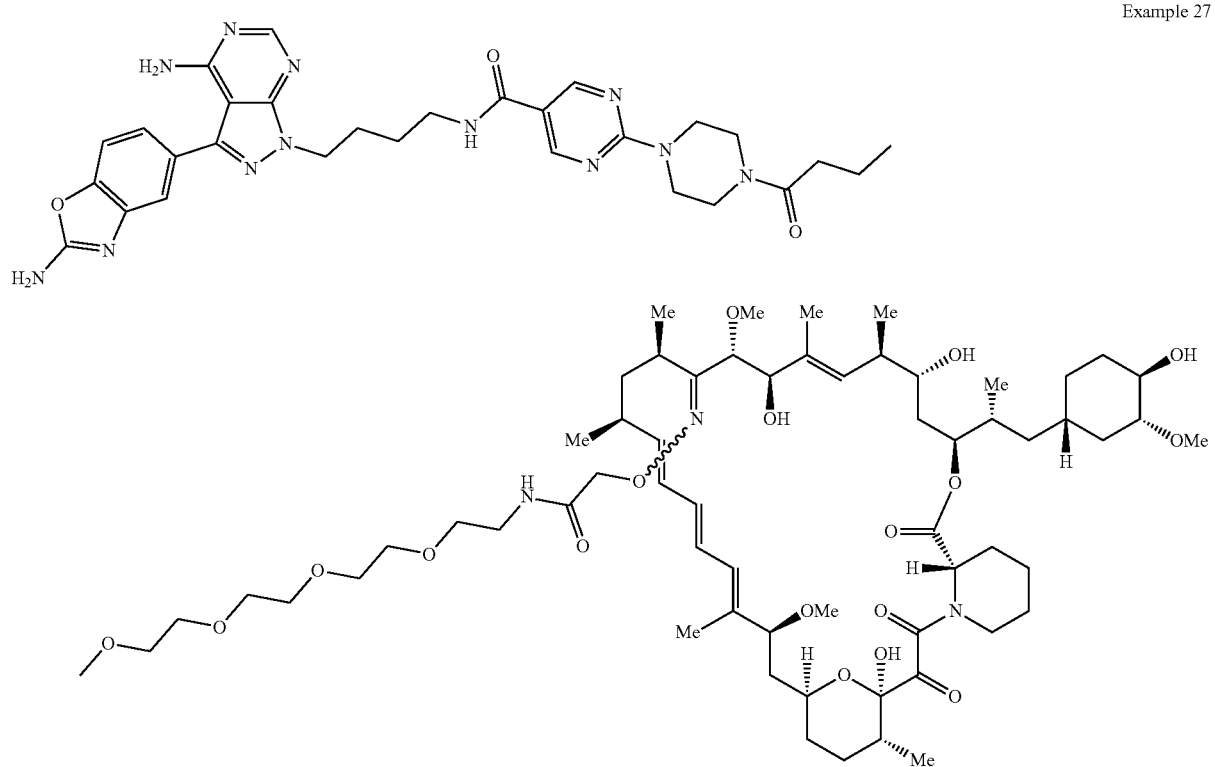
Example 28
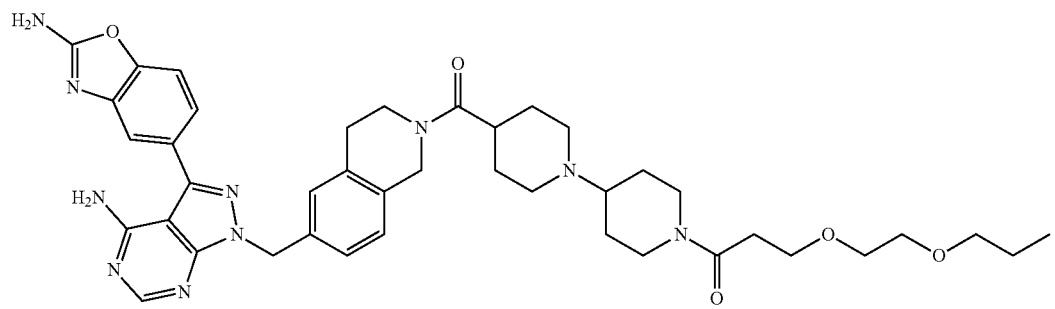

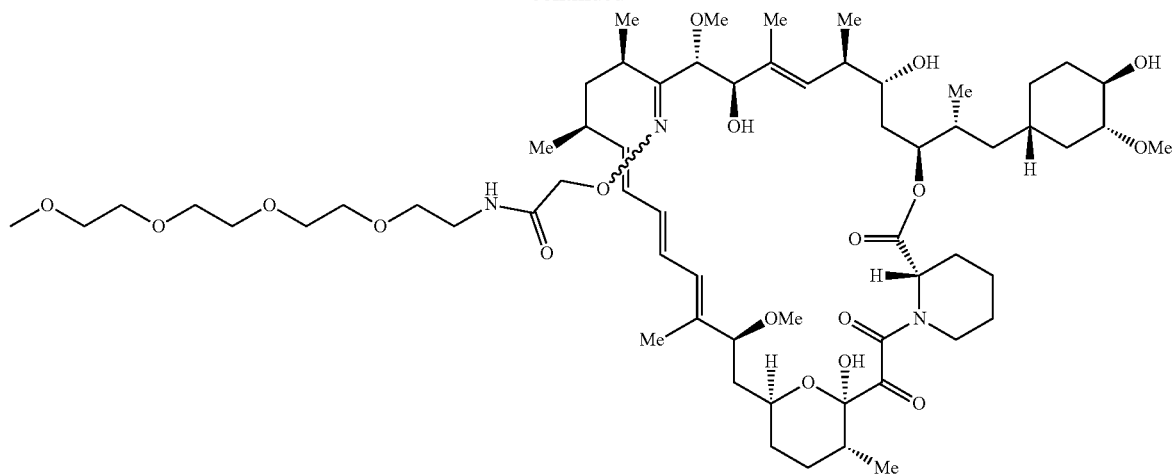
Example 29
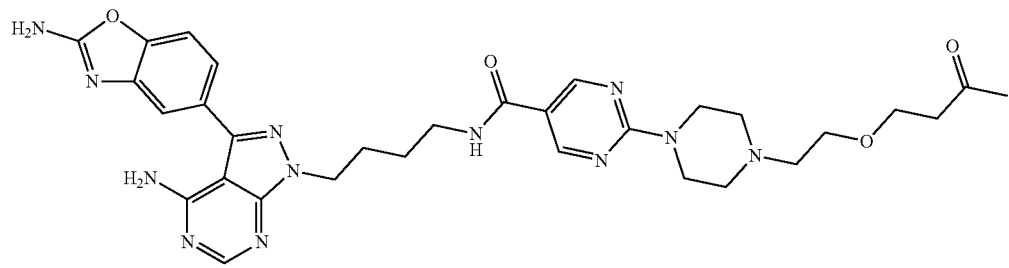
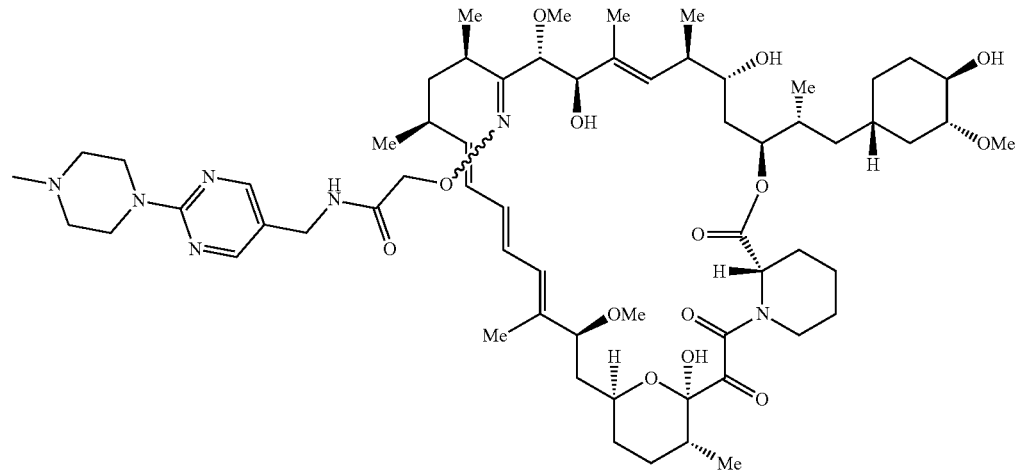
Example 30
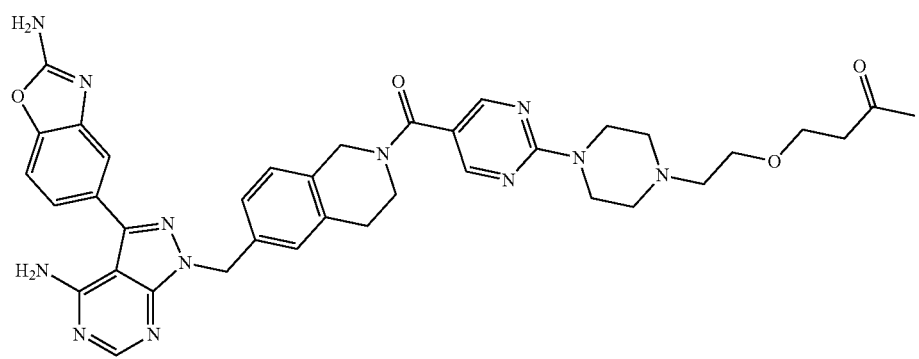

-continued
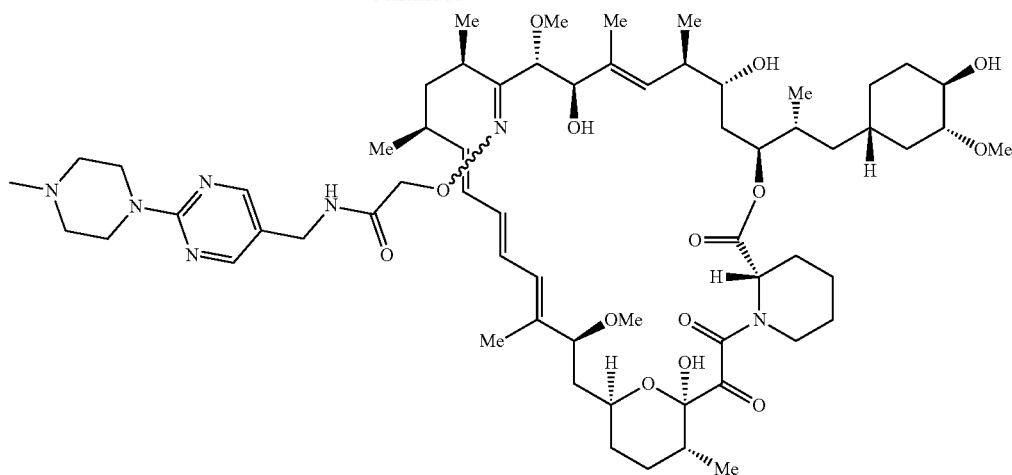
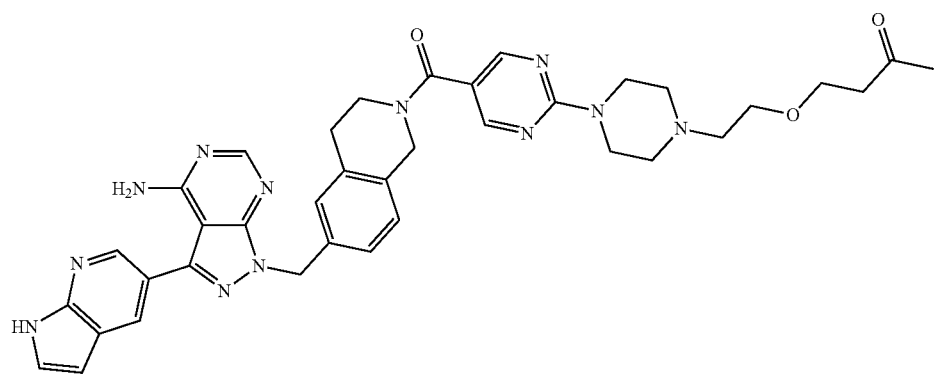
Example 31
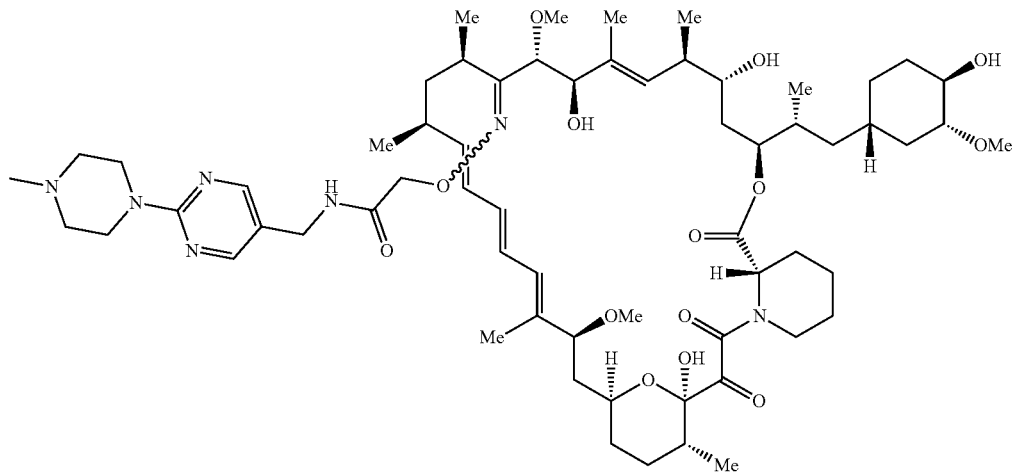

Example 32
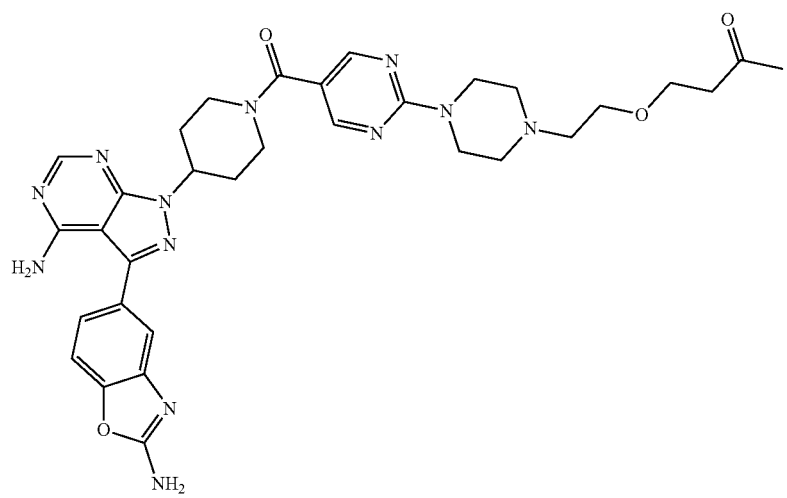
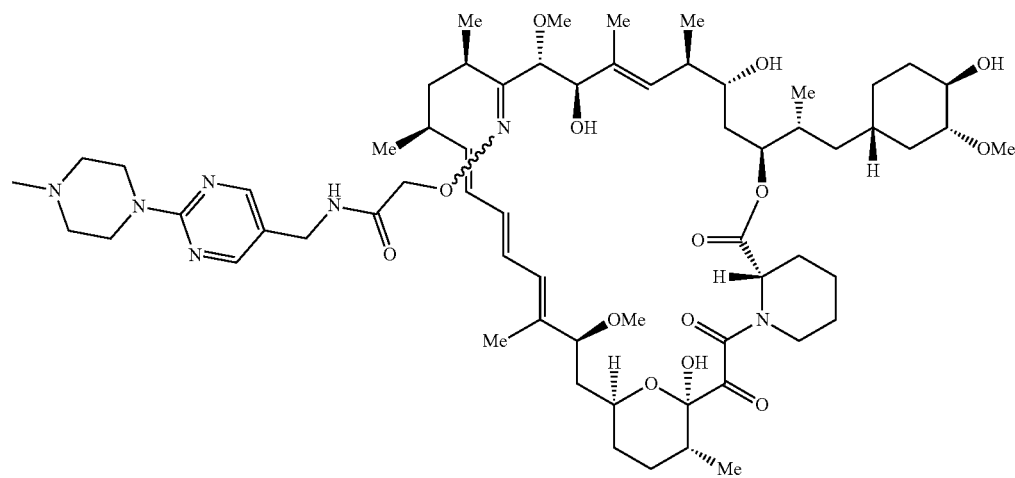
Example 33
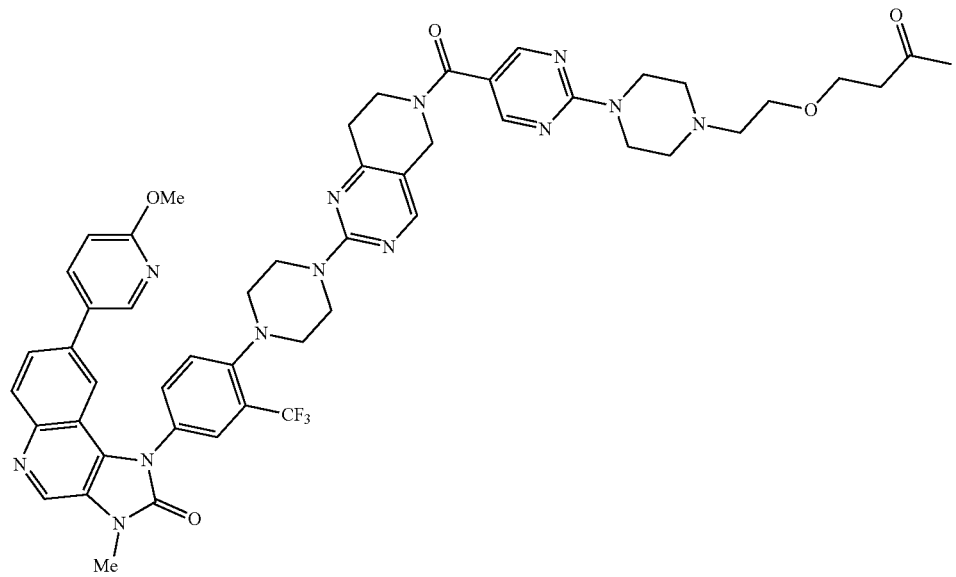

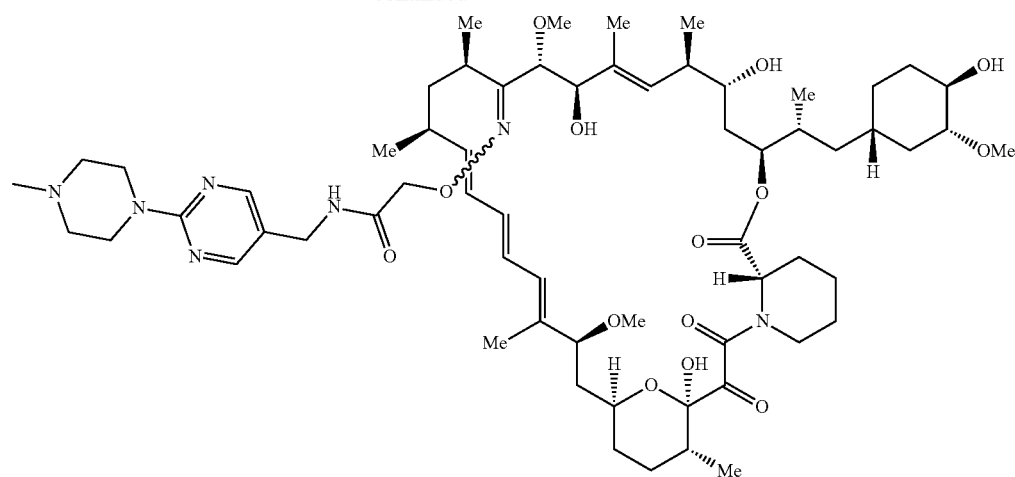
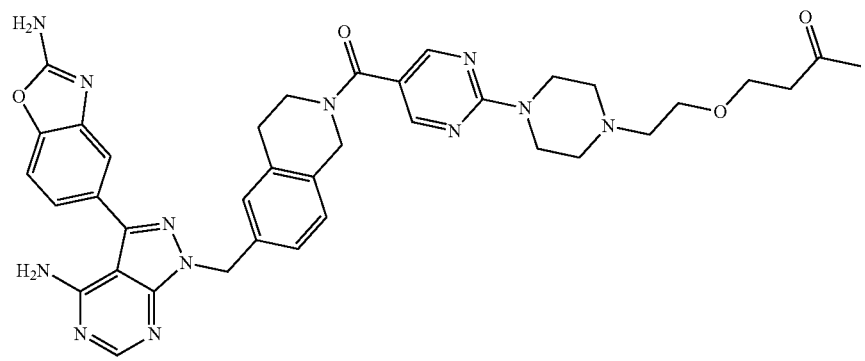
Example 34
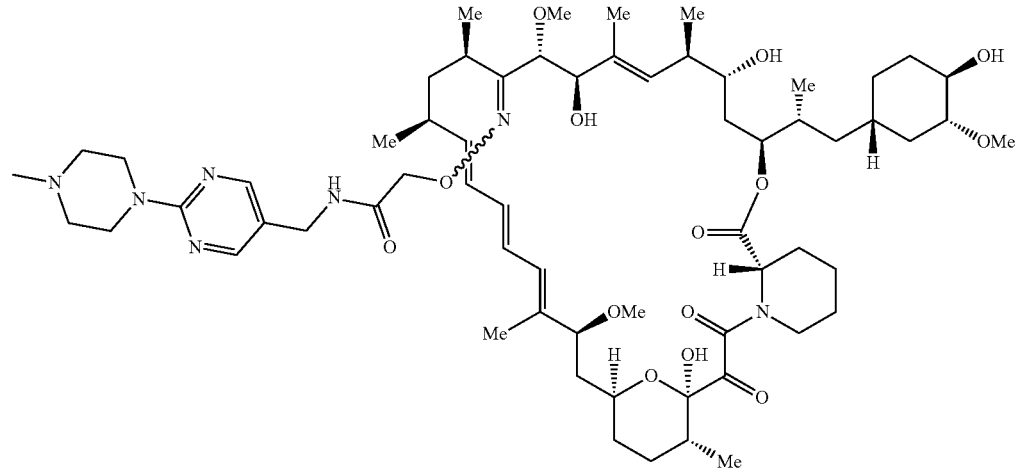
Example 35
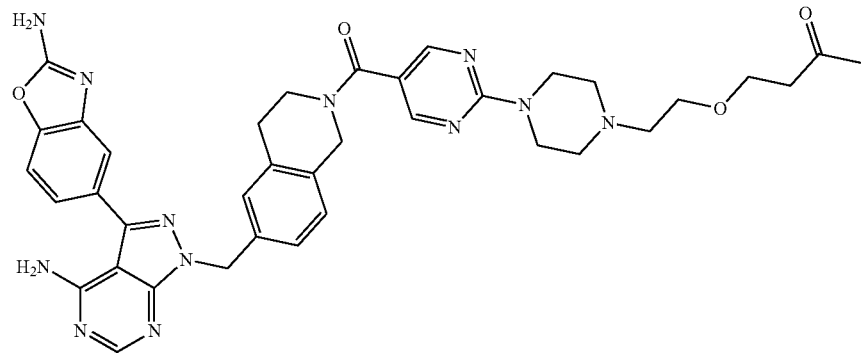

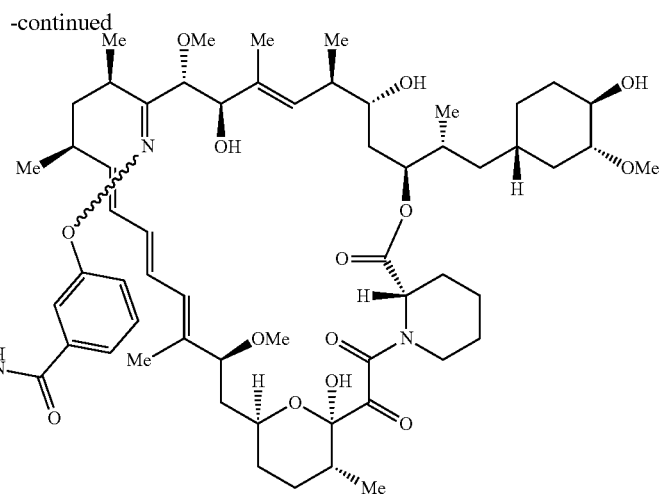
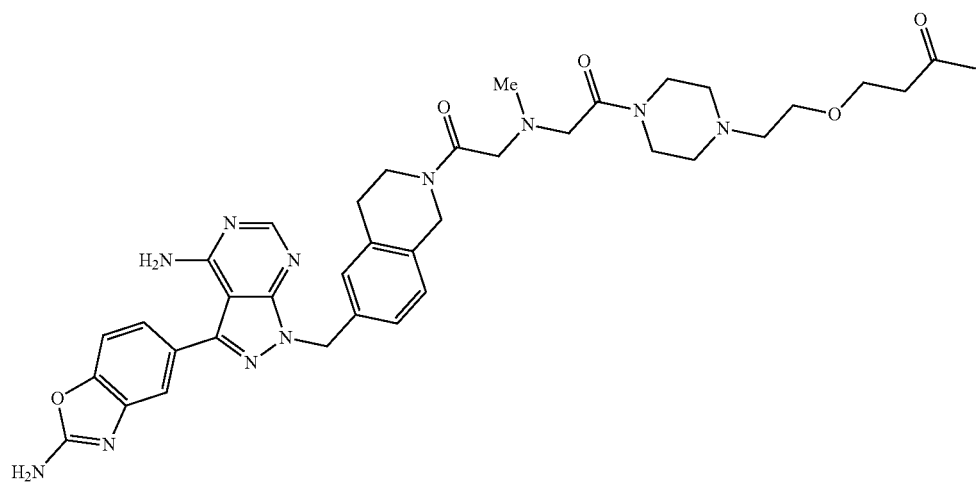
Example 36
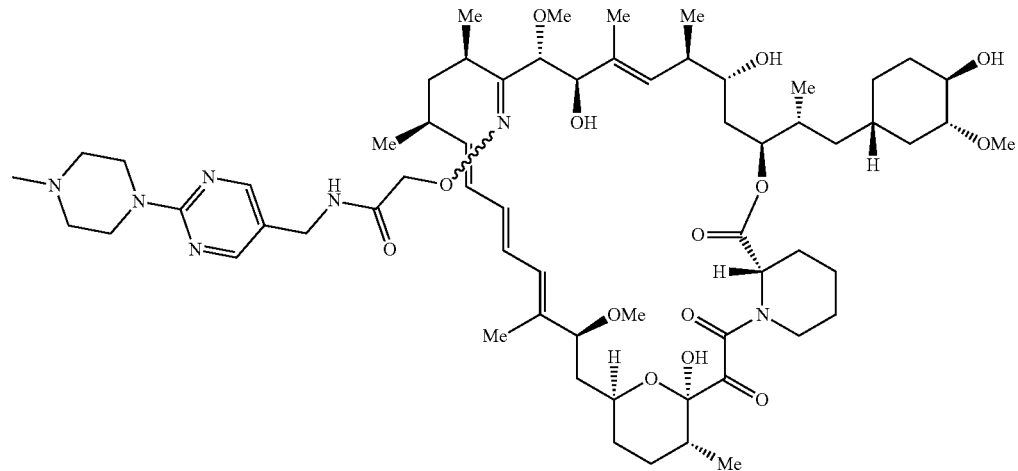

Example 37
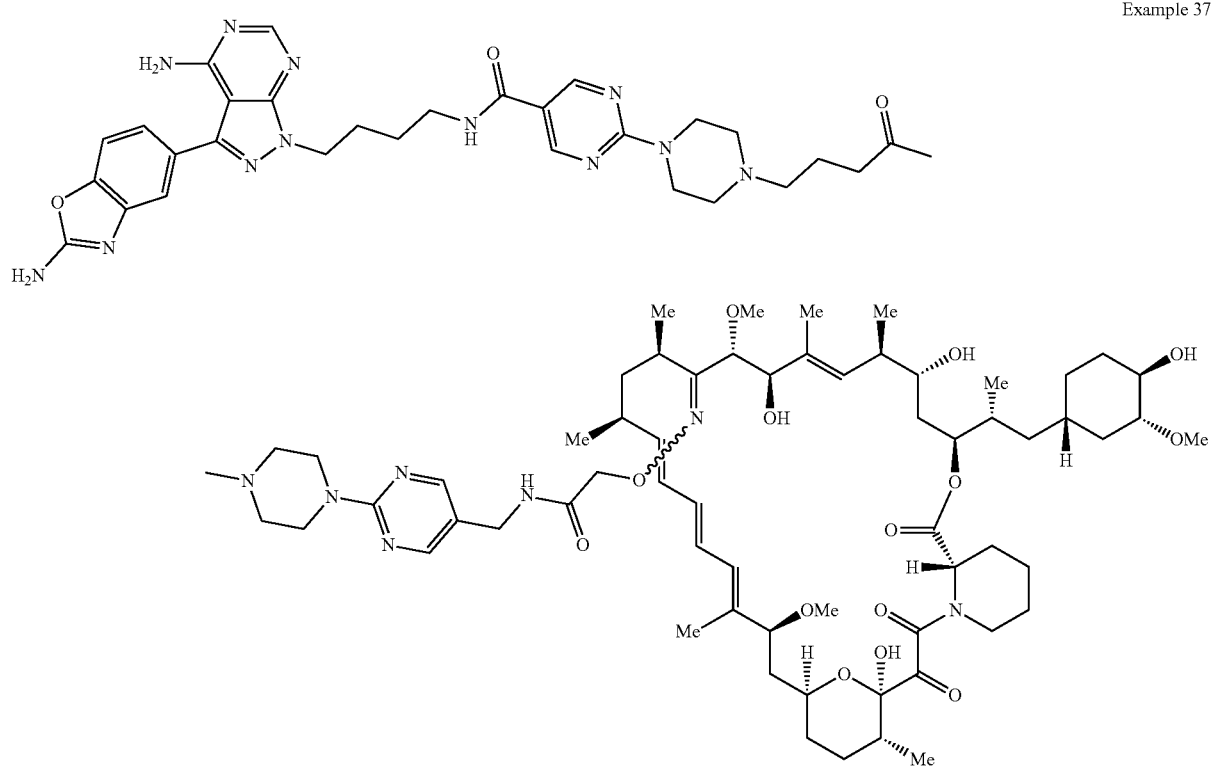
Example 38
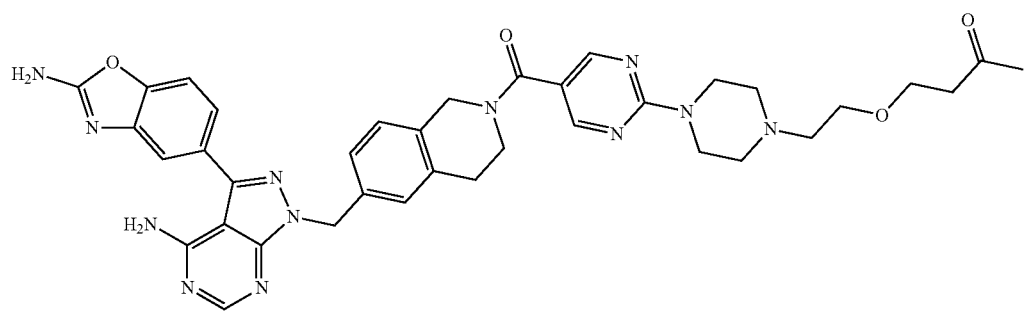
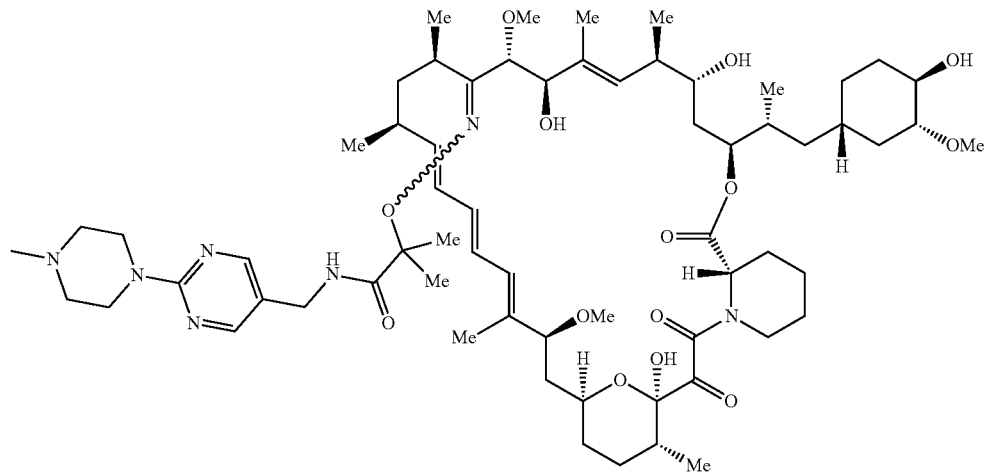

-continued
Example 39
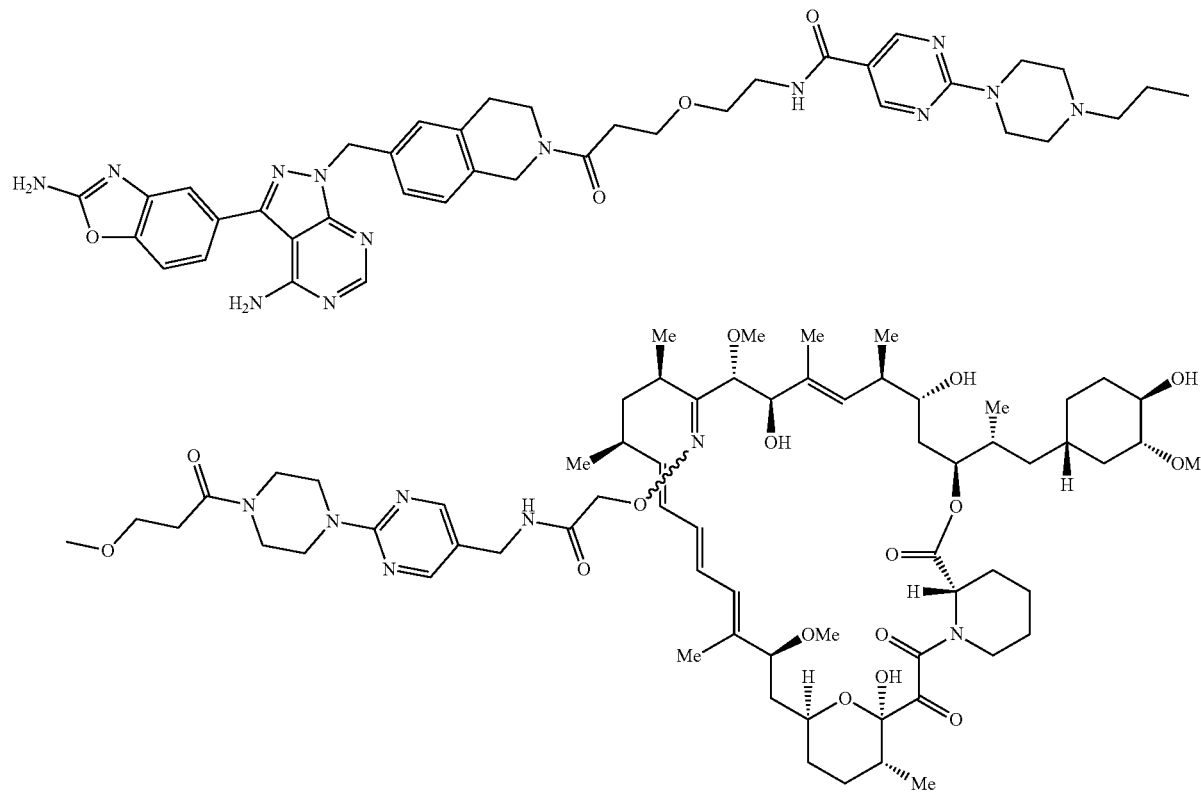
Example 40
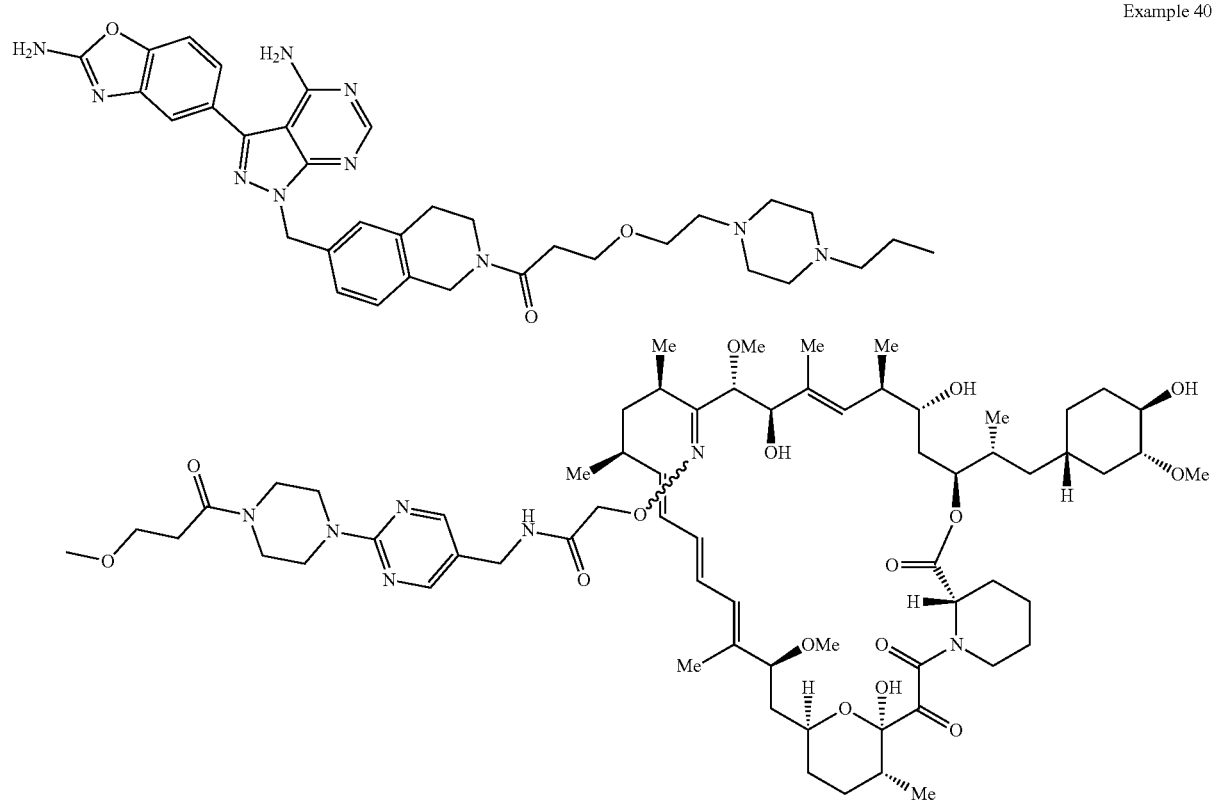

-continued
Example 41
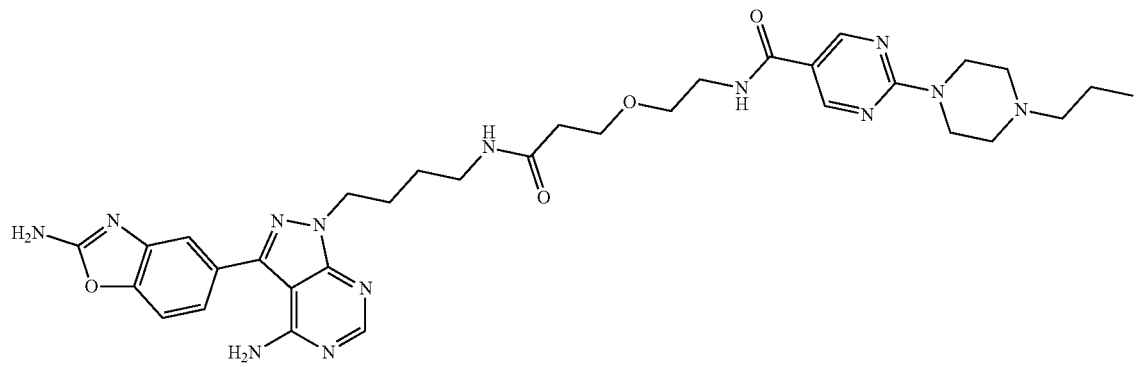
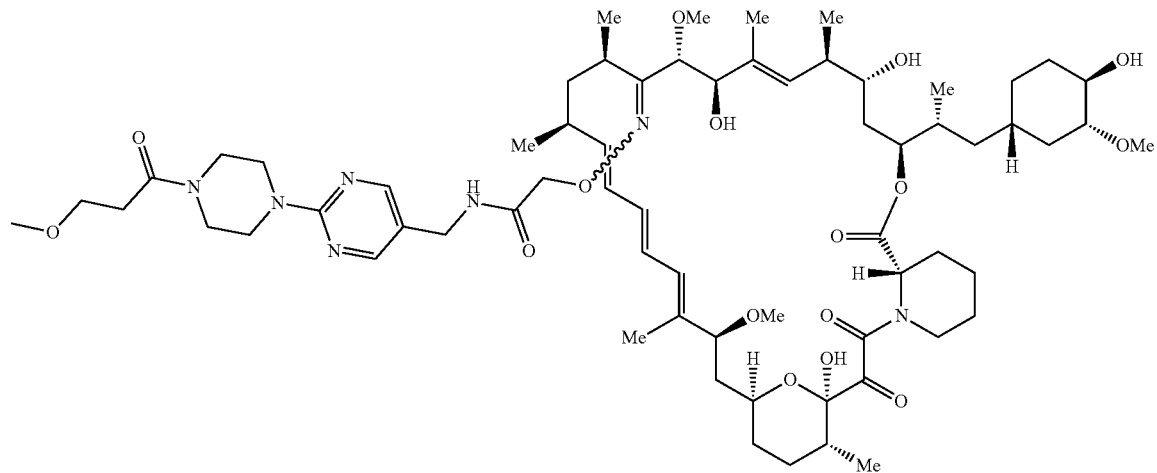
Example 42
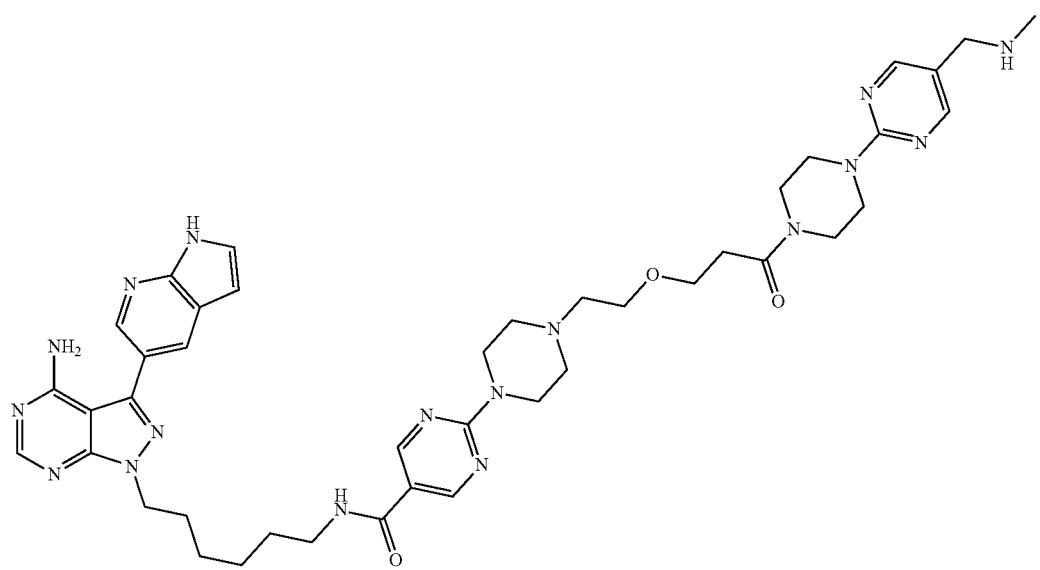

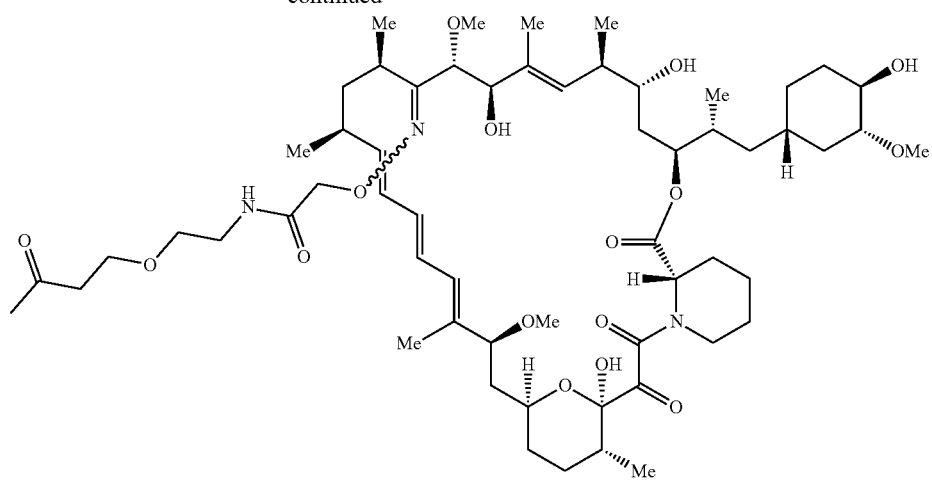
Example 43
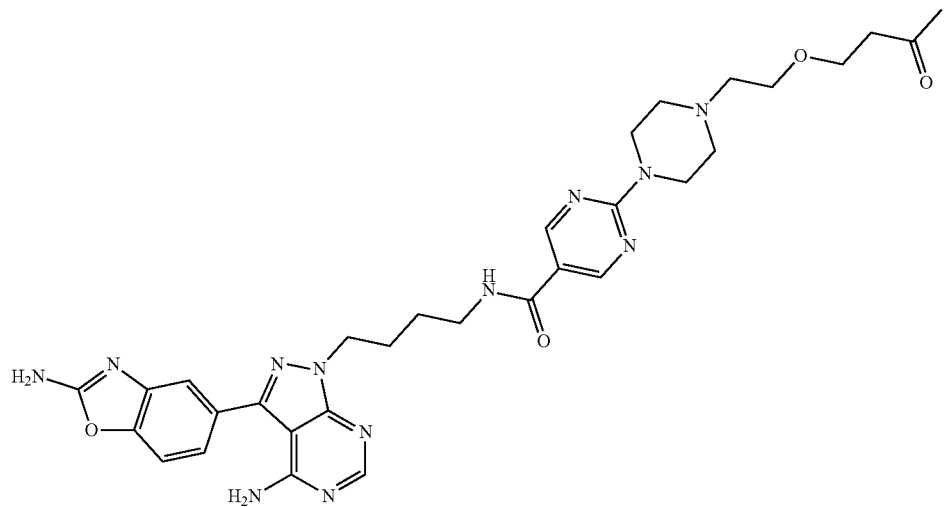
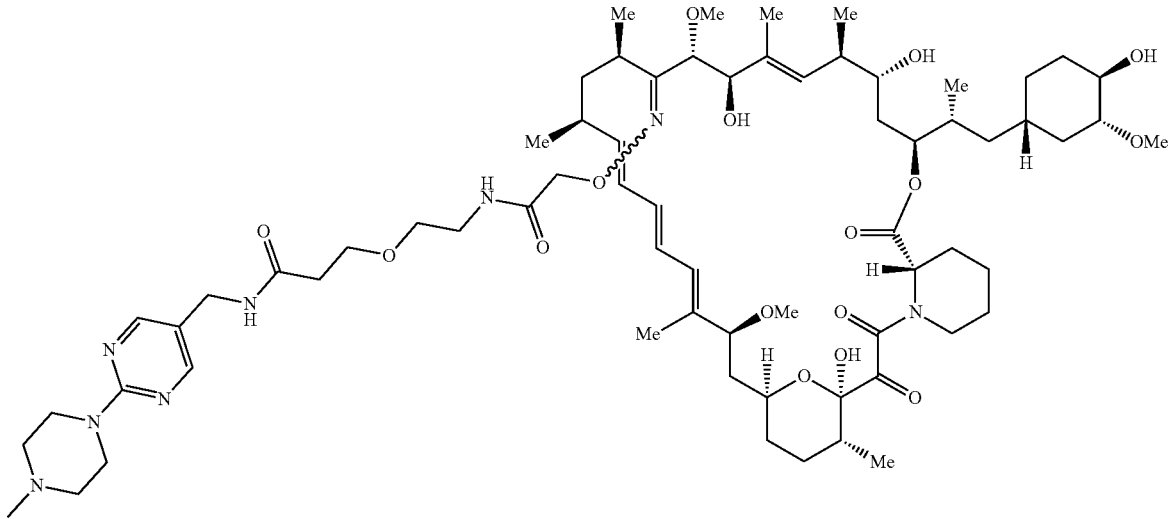

Example 44
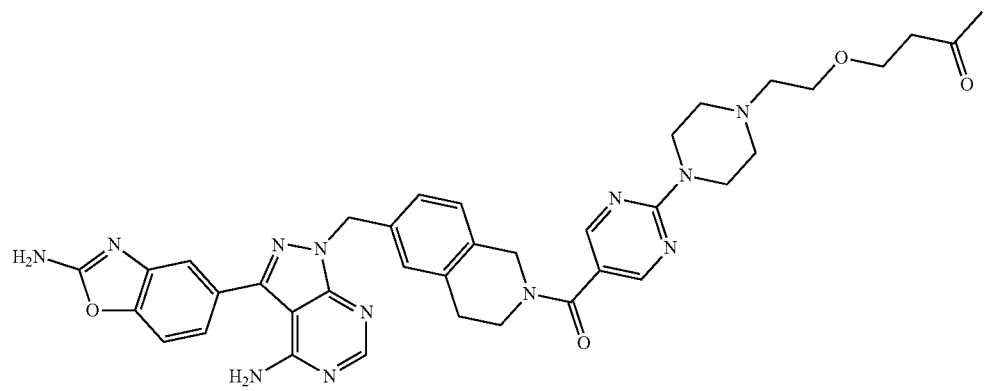
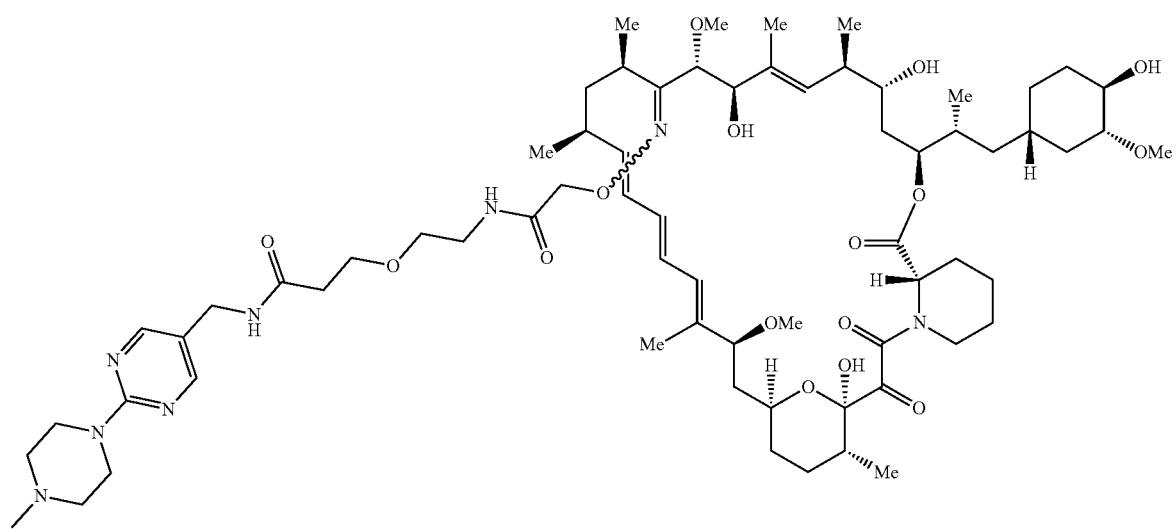
In certain embodiments, the present disclosure provides for a compound selected from below or a pharmaceutically acceptable salt or tautomer thereof,
Example 45
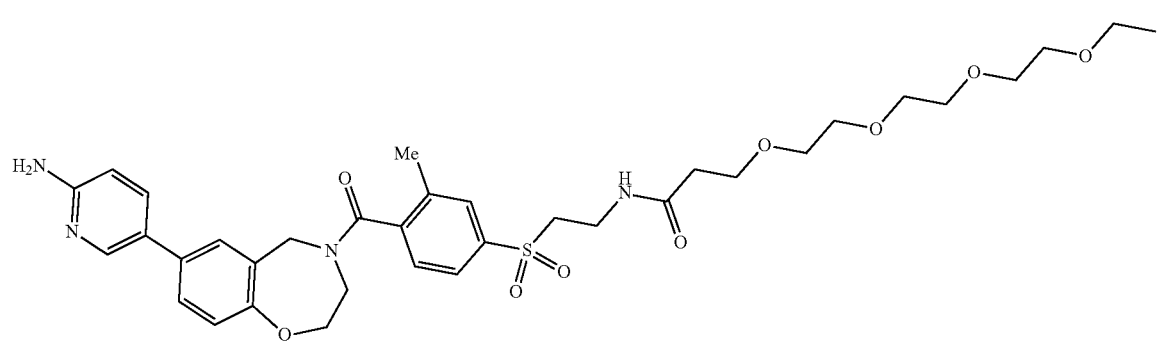

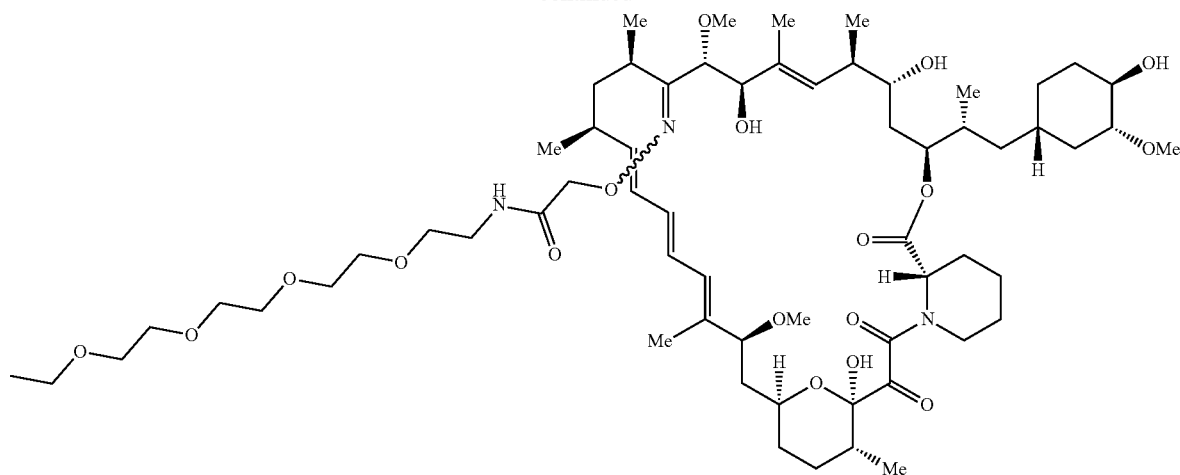
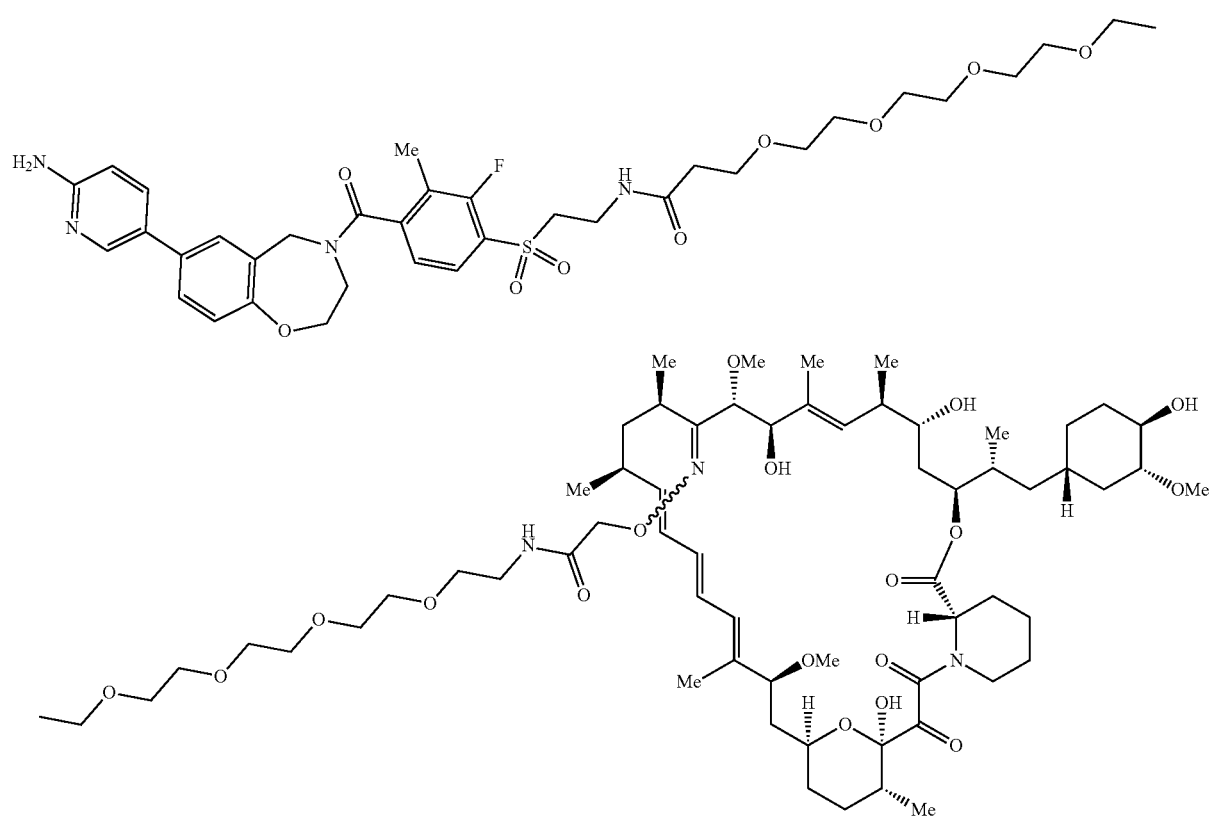
Example 46
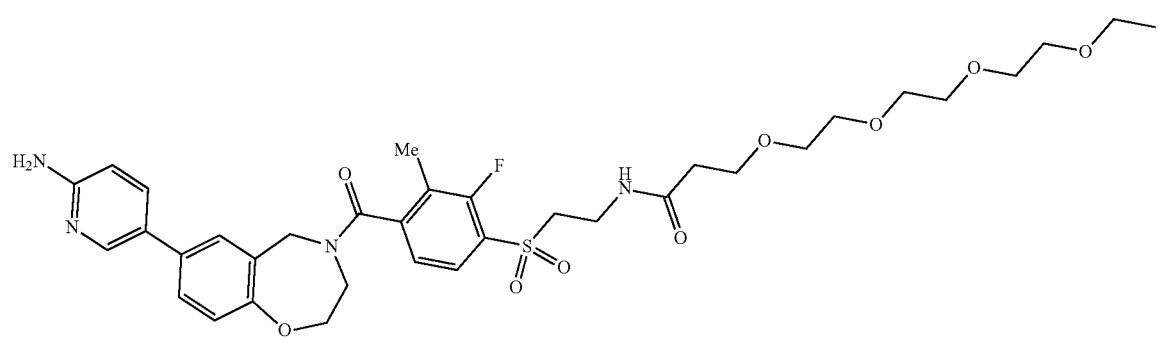
Example 47

-continued
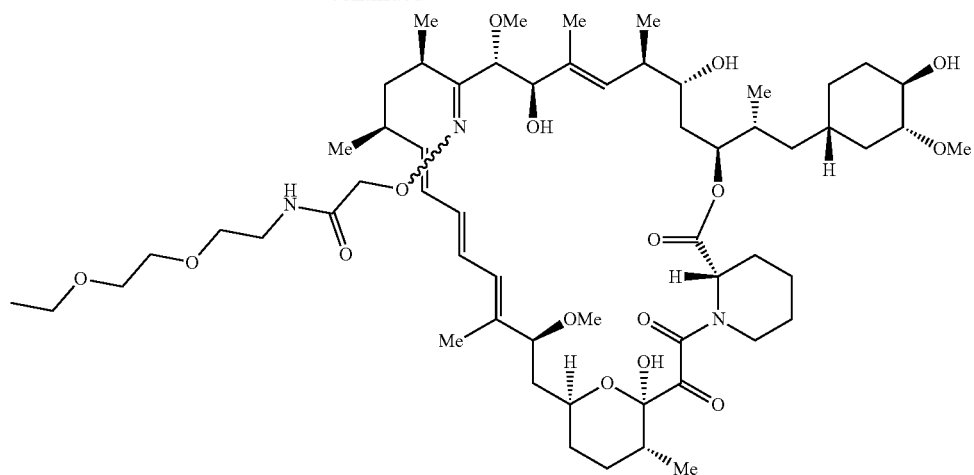
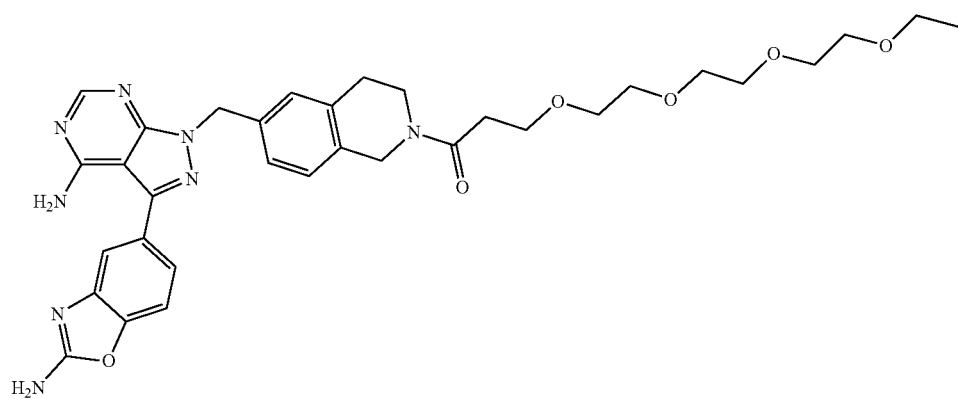
Example 48
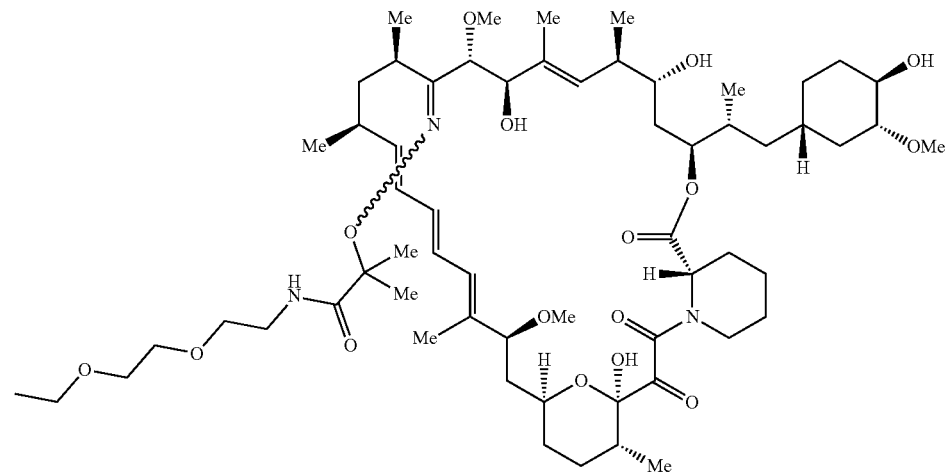

Example 49
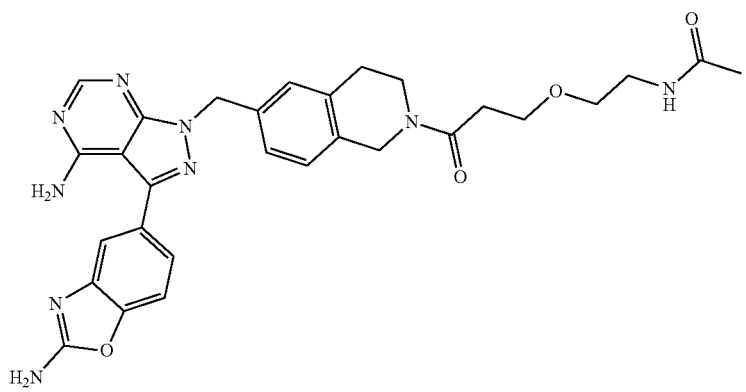
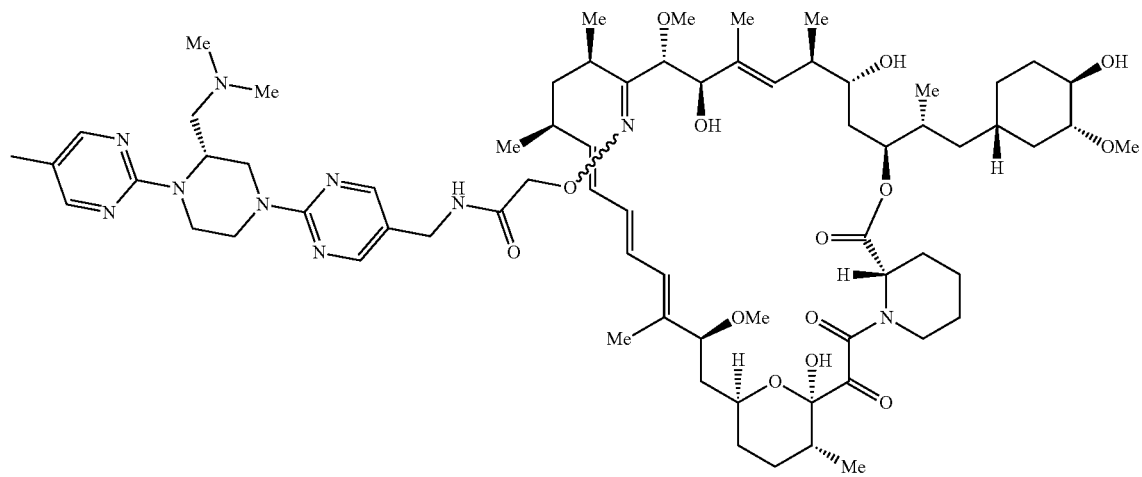
Example 50
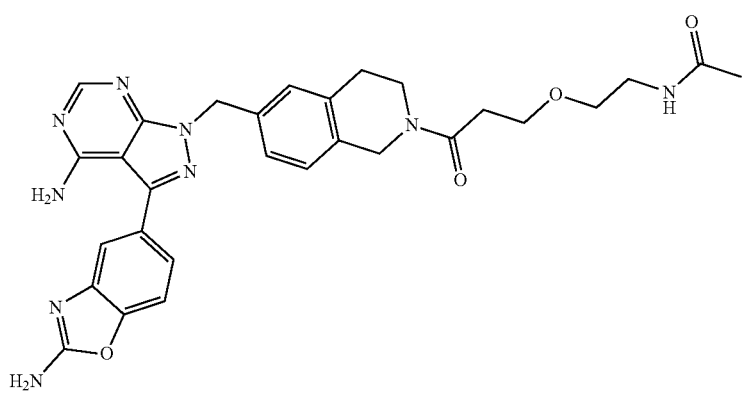

-continued
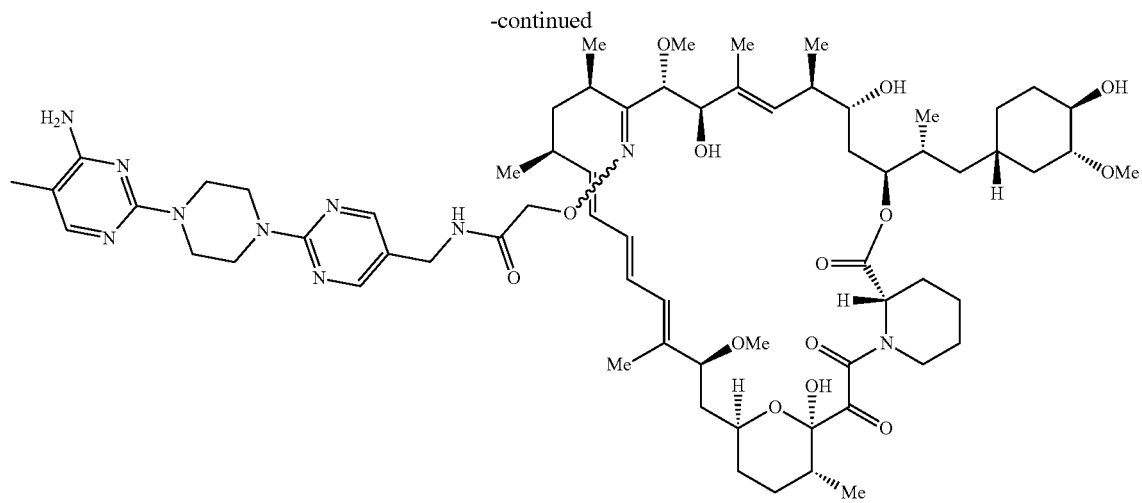
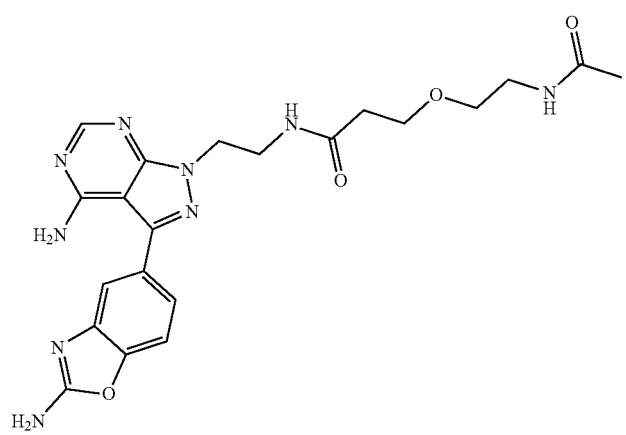
Example 51
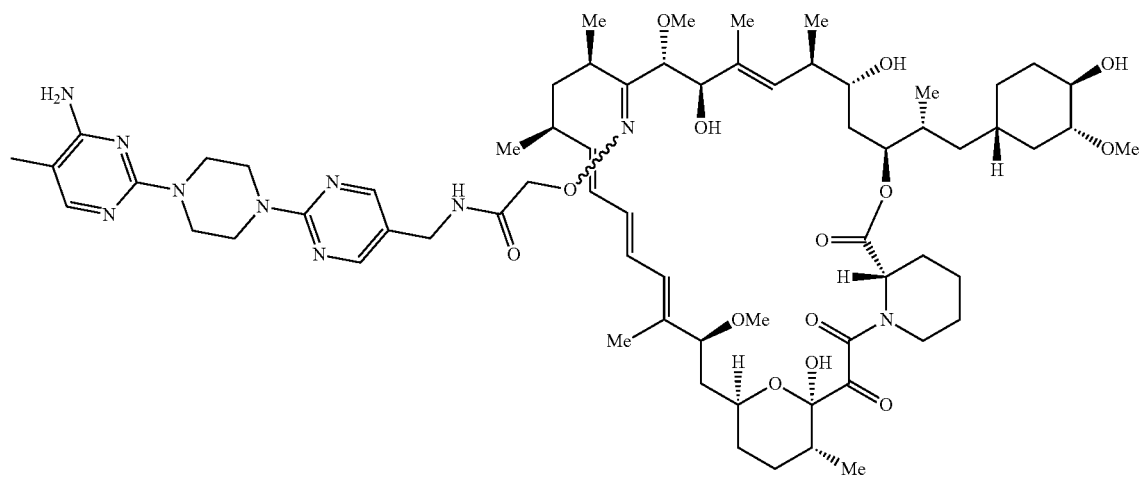

Example 52
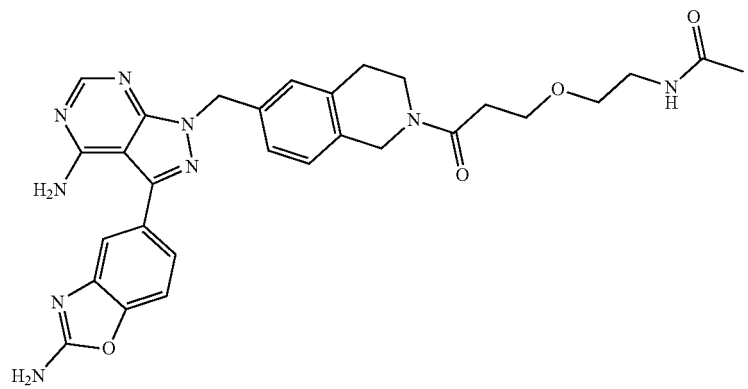
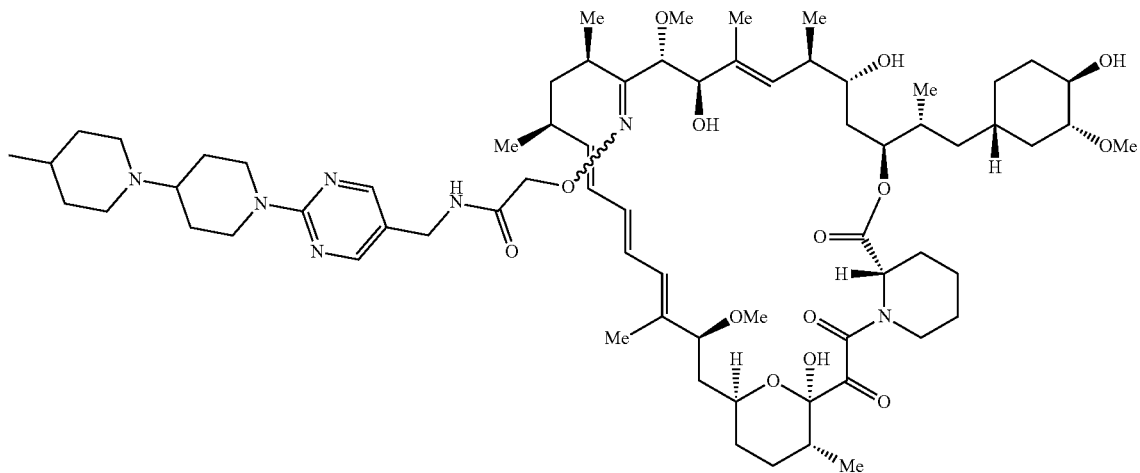
Example 53
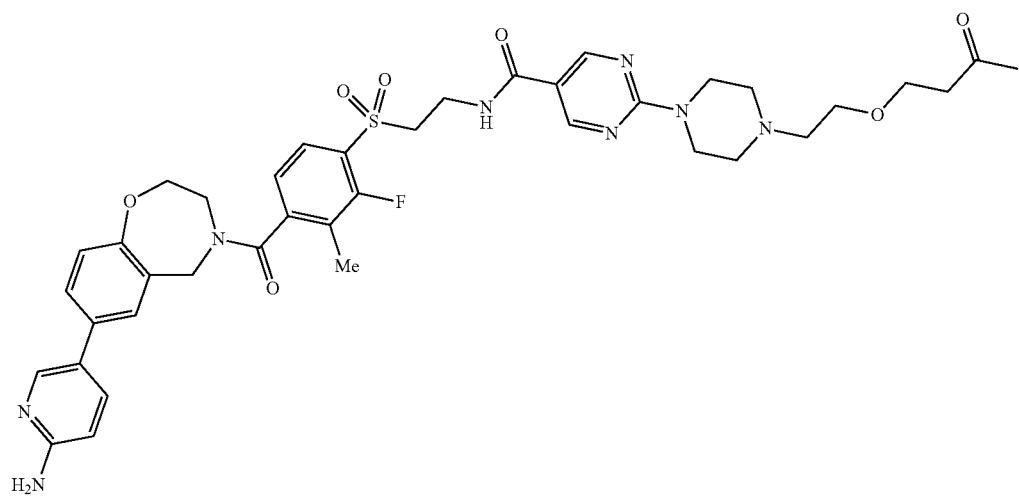

-continued
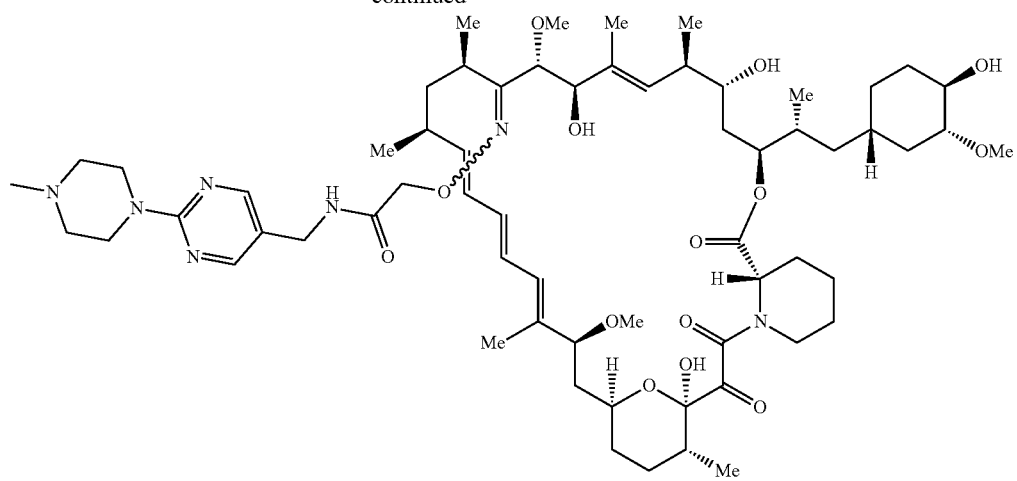
Example 54
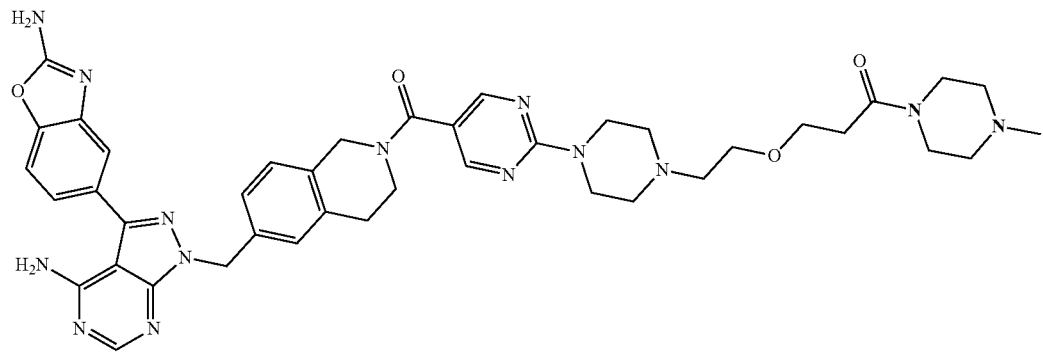
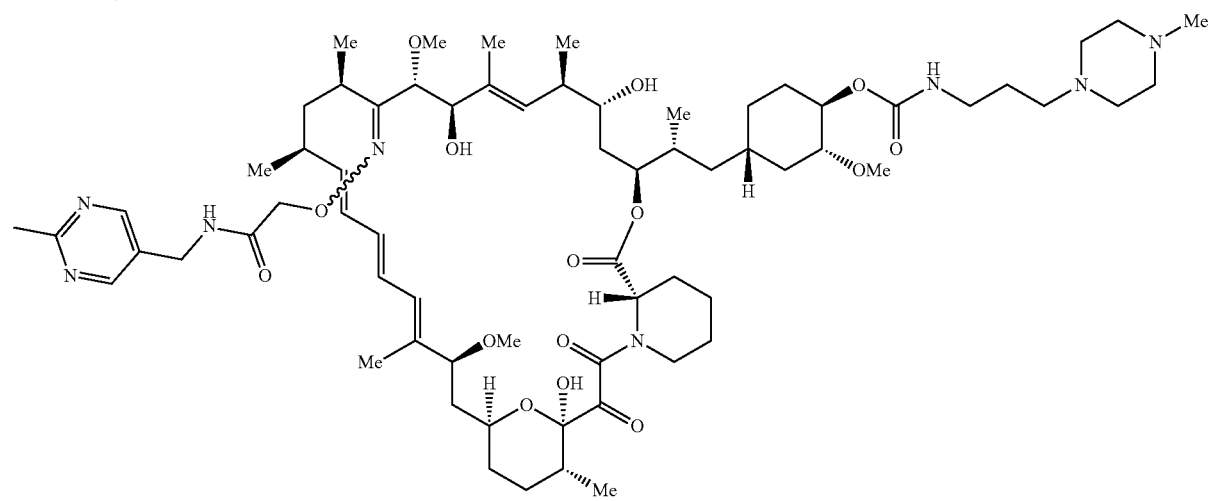
Example 55
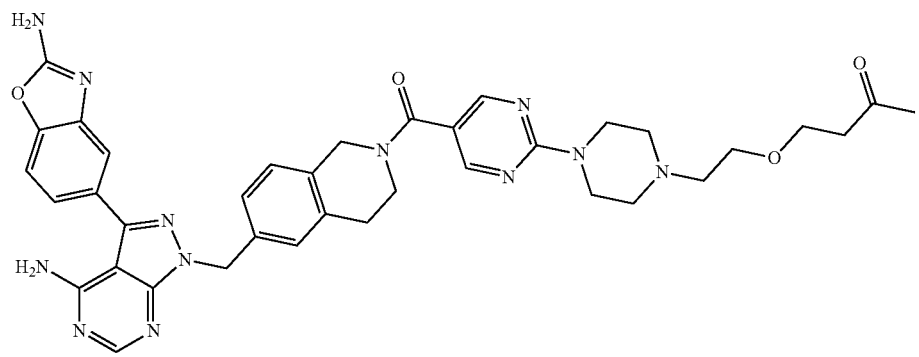

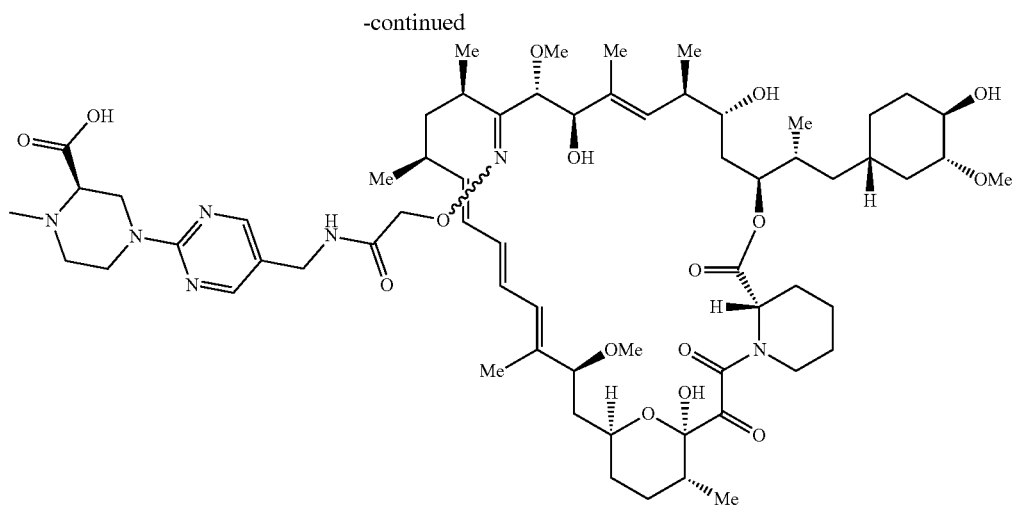
Example 56
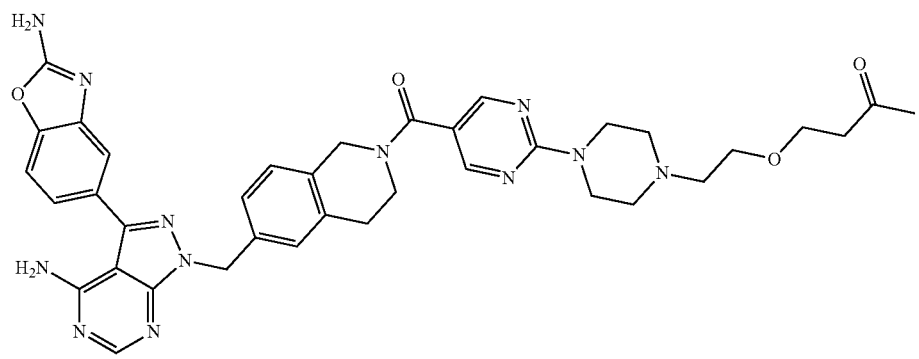
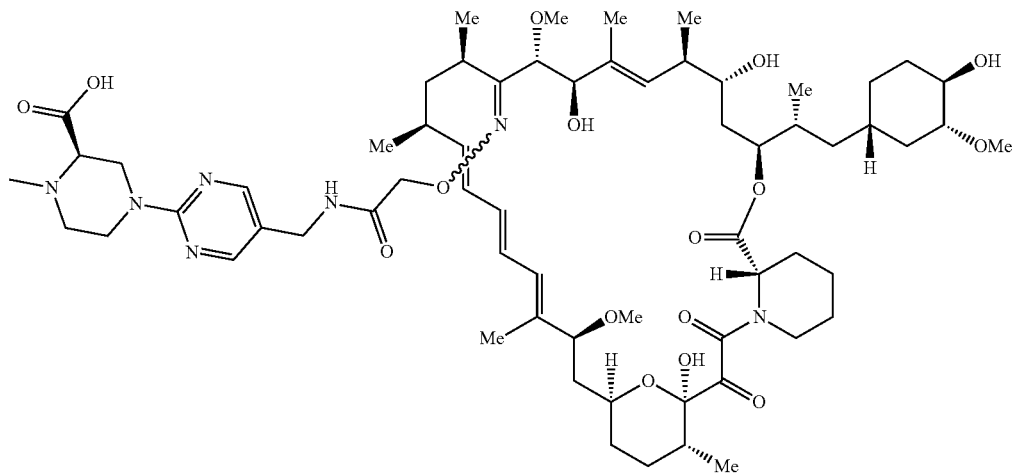
Example 57
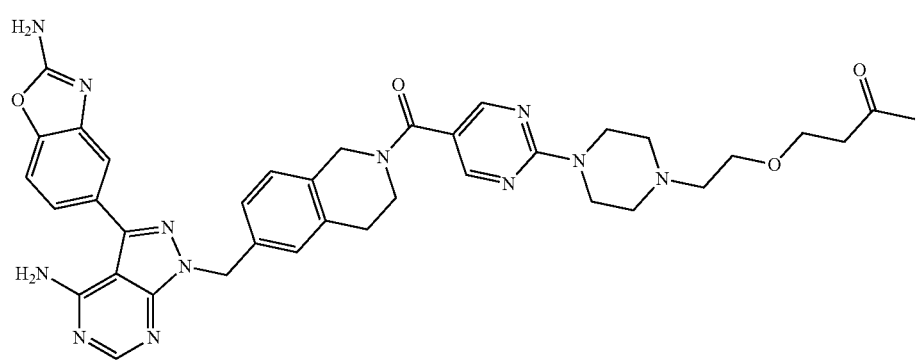

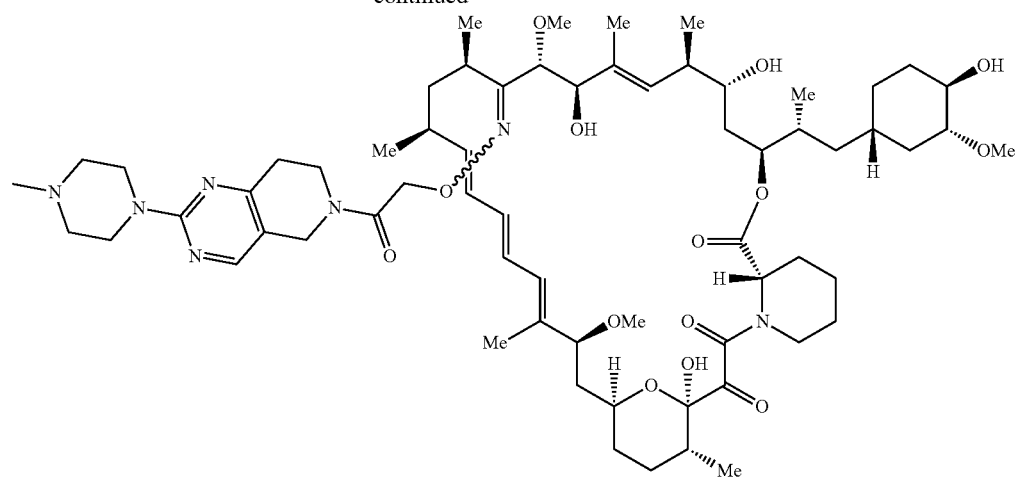
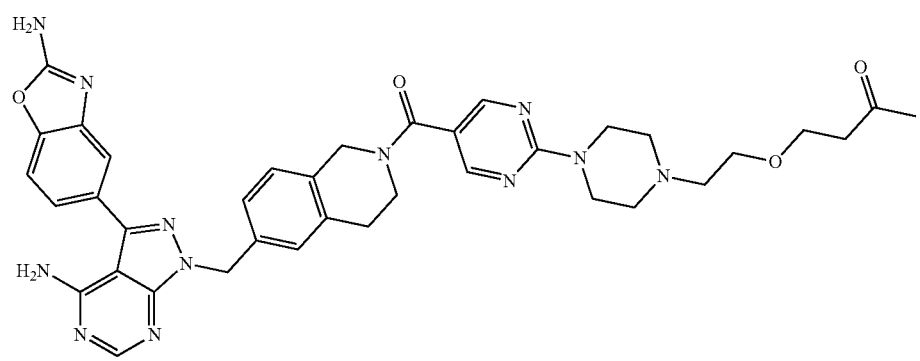
Example 58
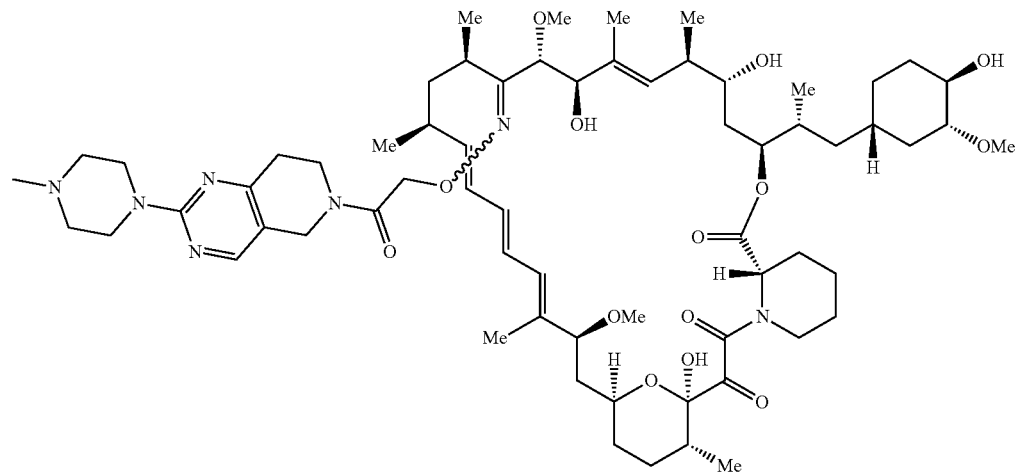

Example 59
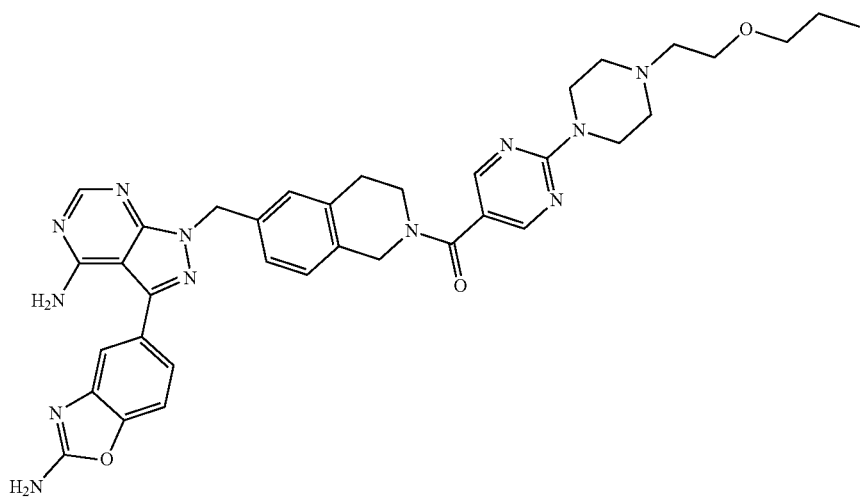
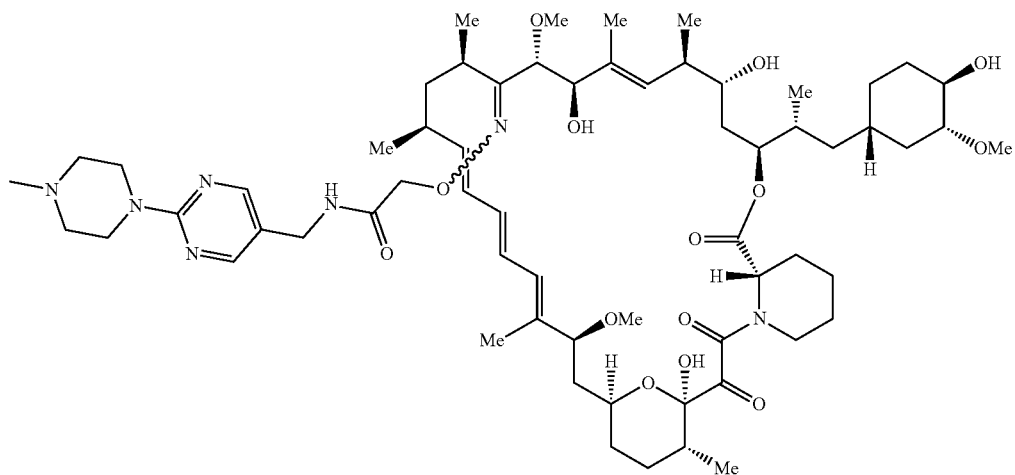
Example 60
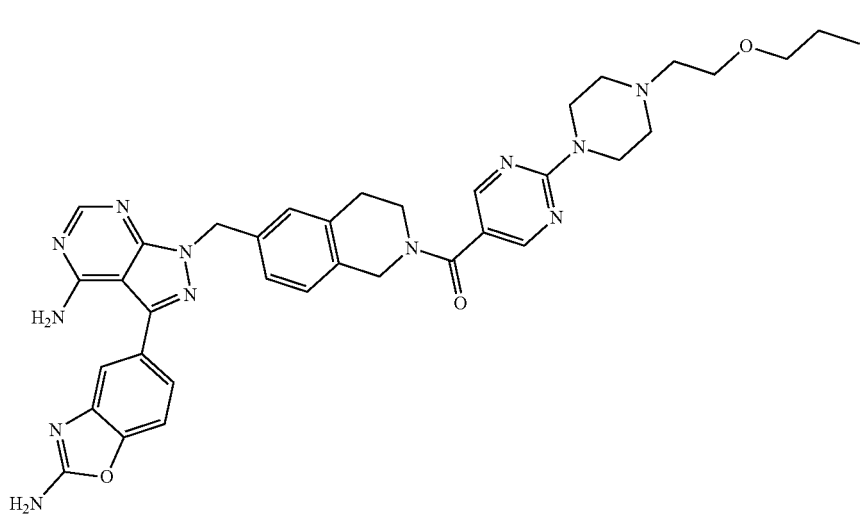

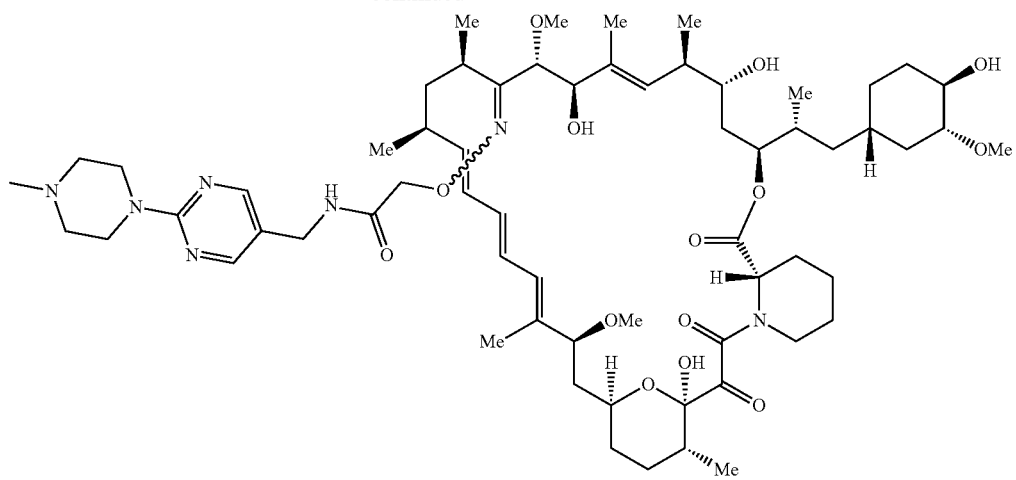
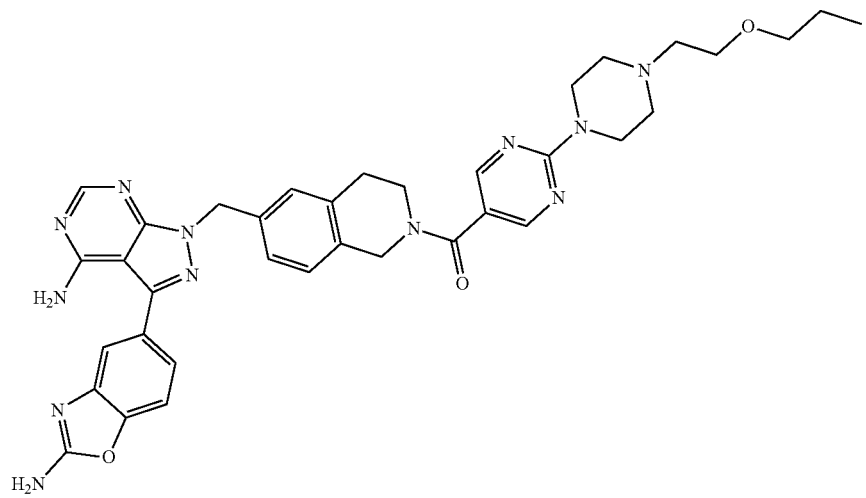
Example 61
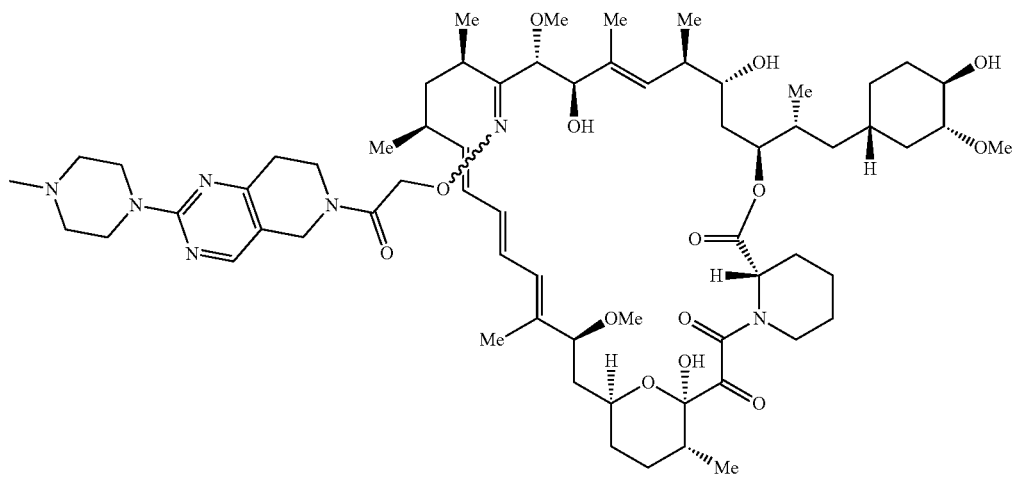

Example 62
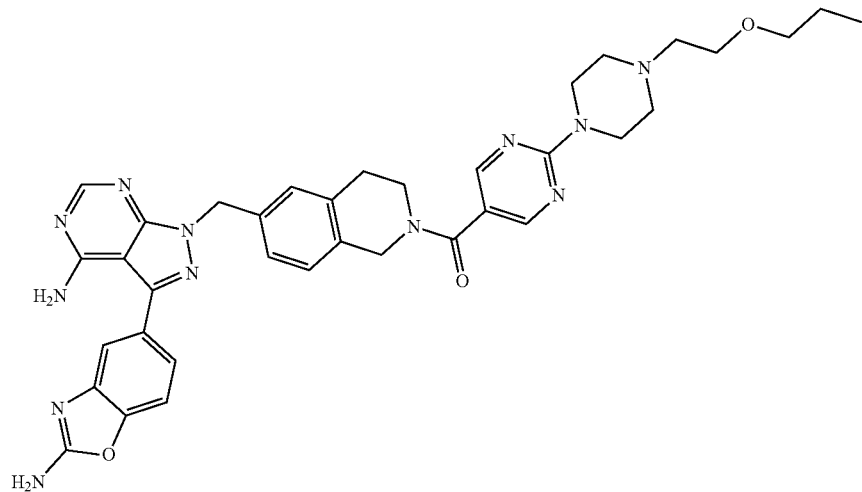
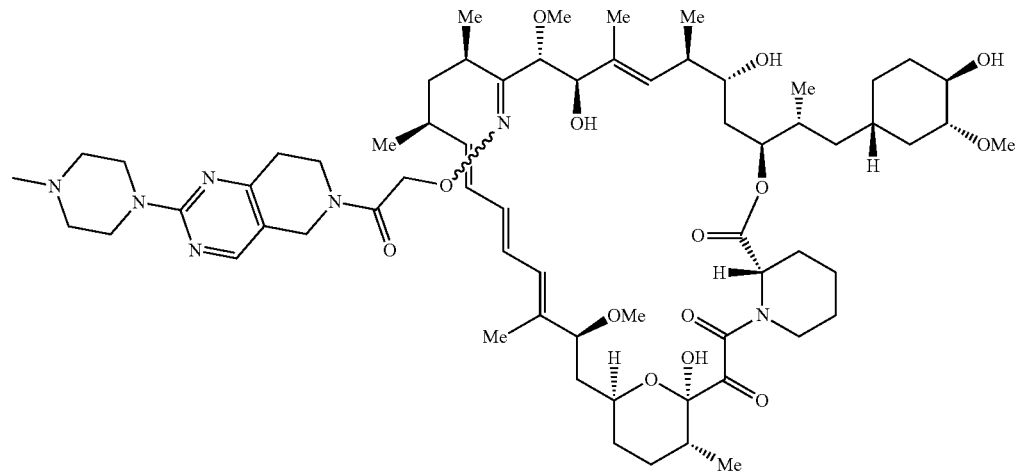
Example 63
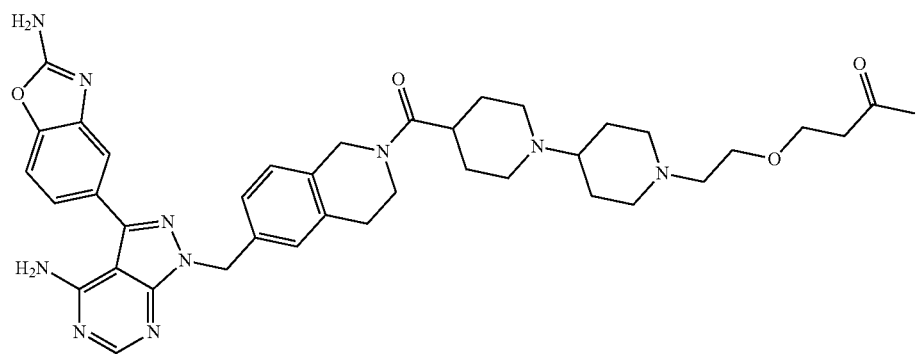

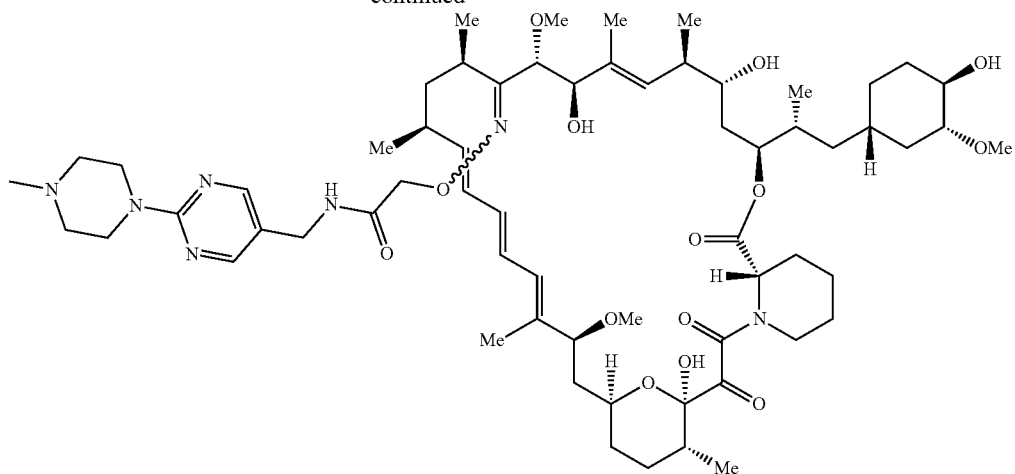
Example 64
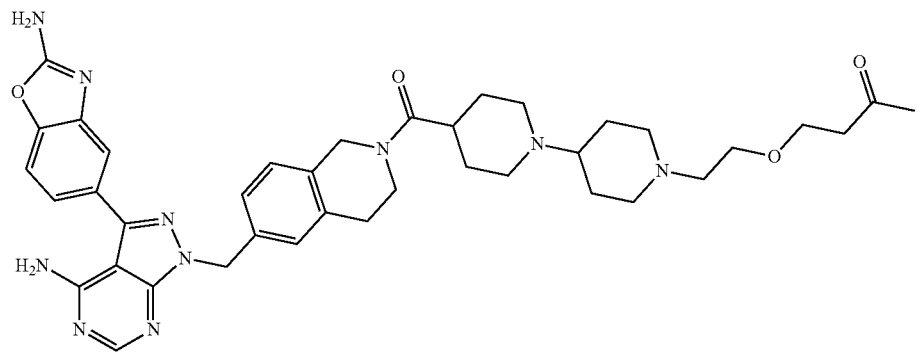
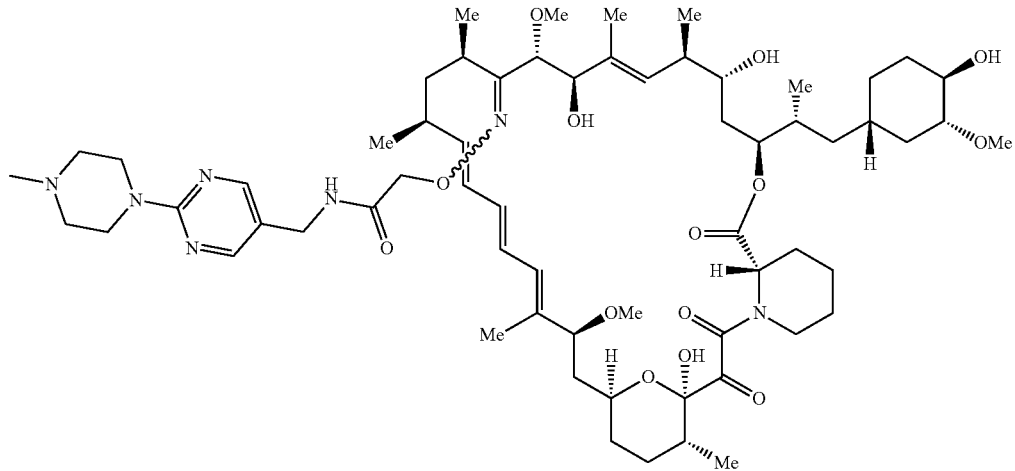
Example 65
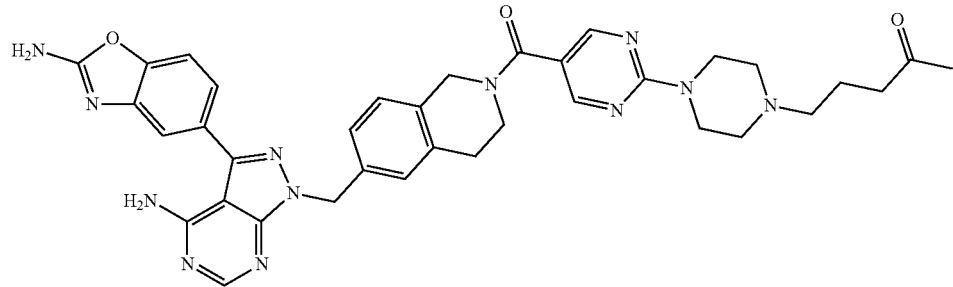

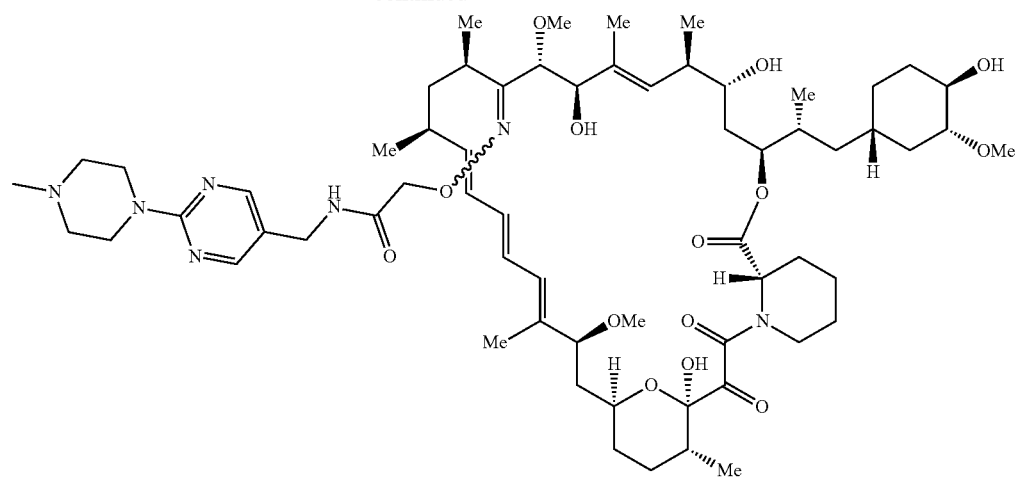
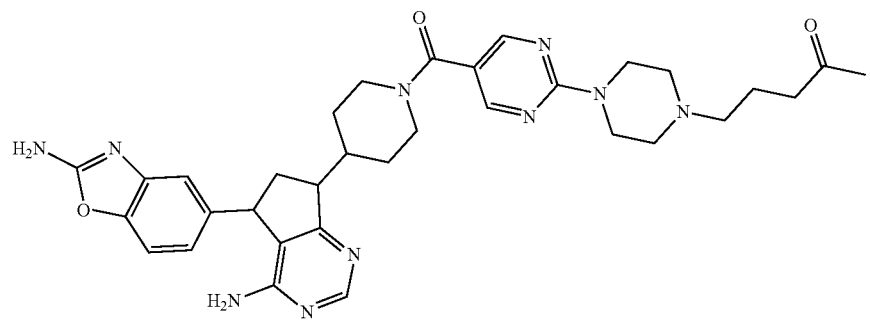
Example 66
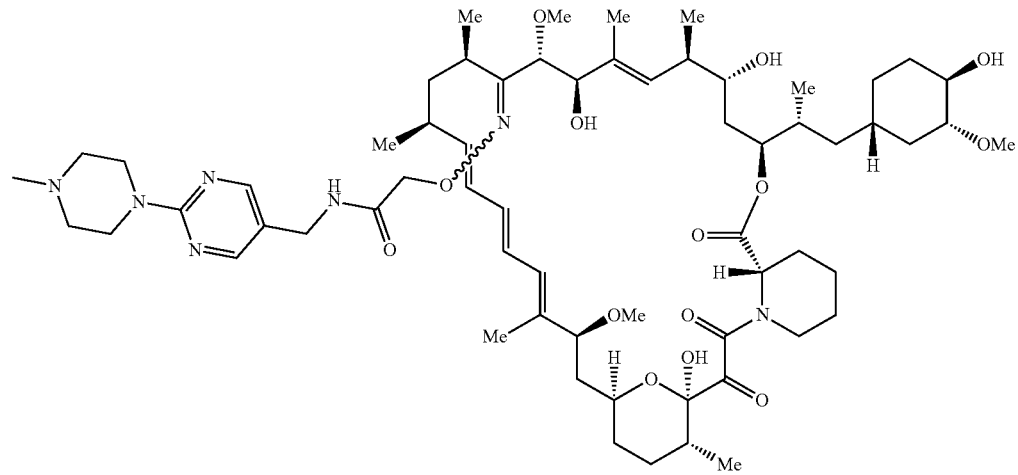

In certain embodiments, the present disclosure provides for a compound selected from below or a pharmaceutically acceptable salt or tautomer thereof,
Example 67
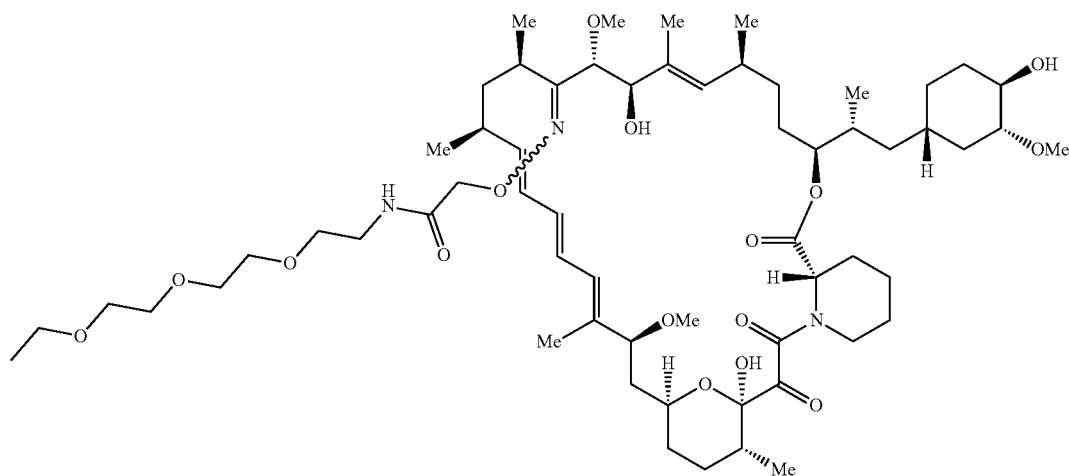
Example 68
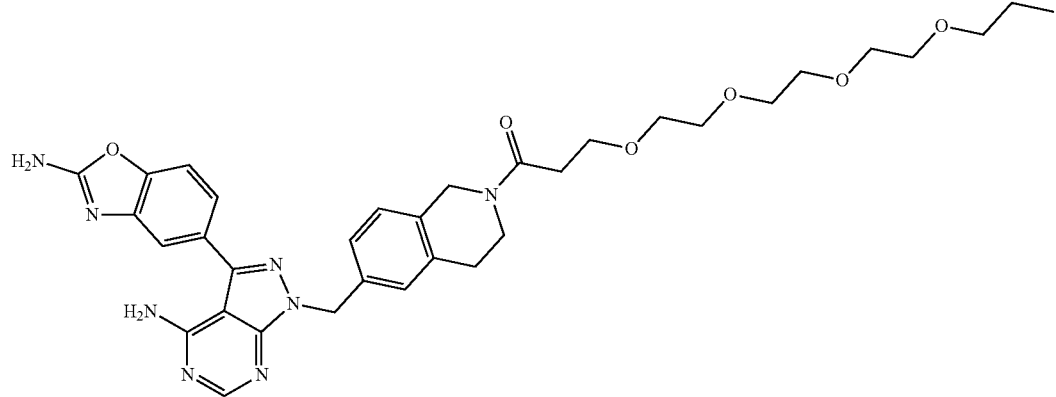

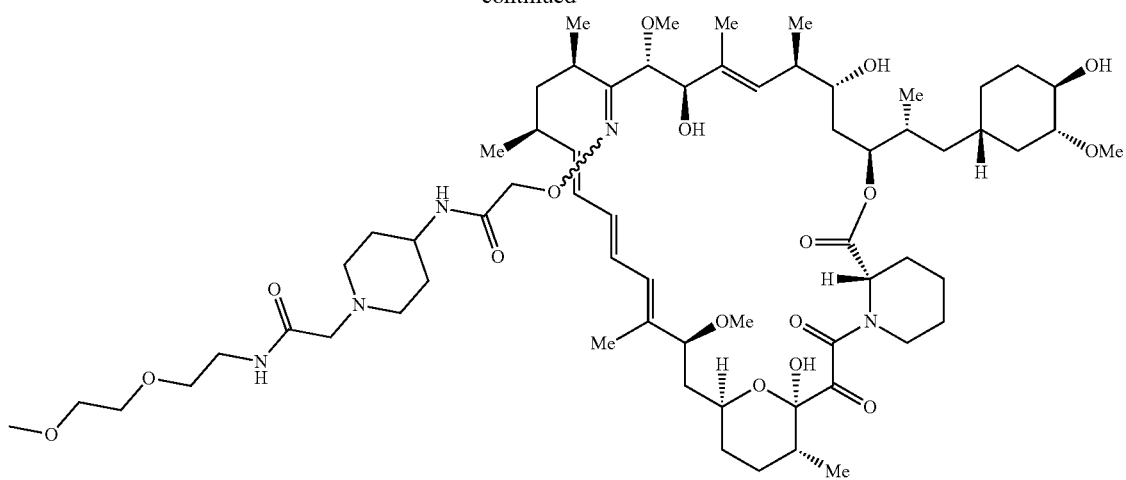
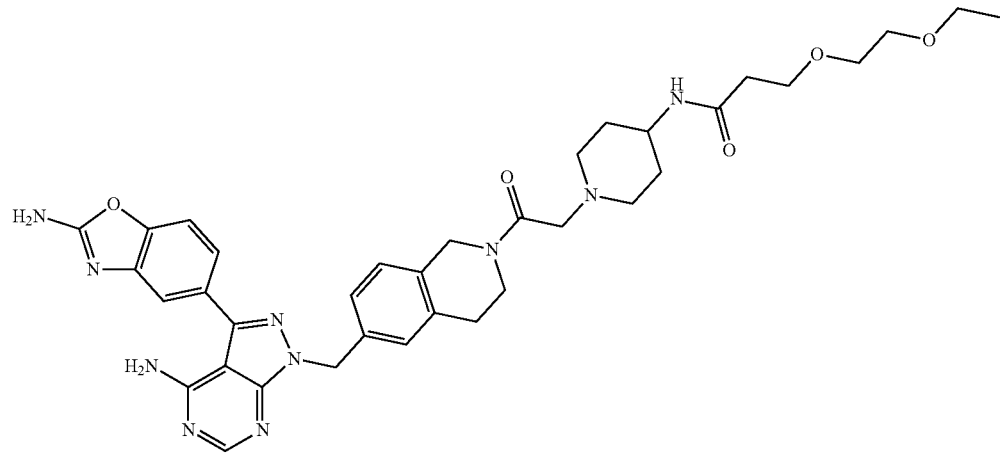
Example 69
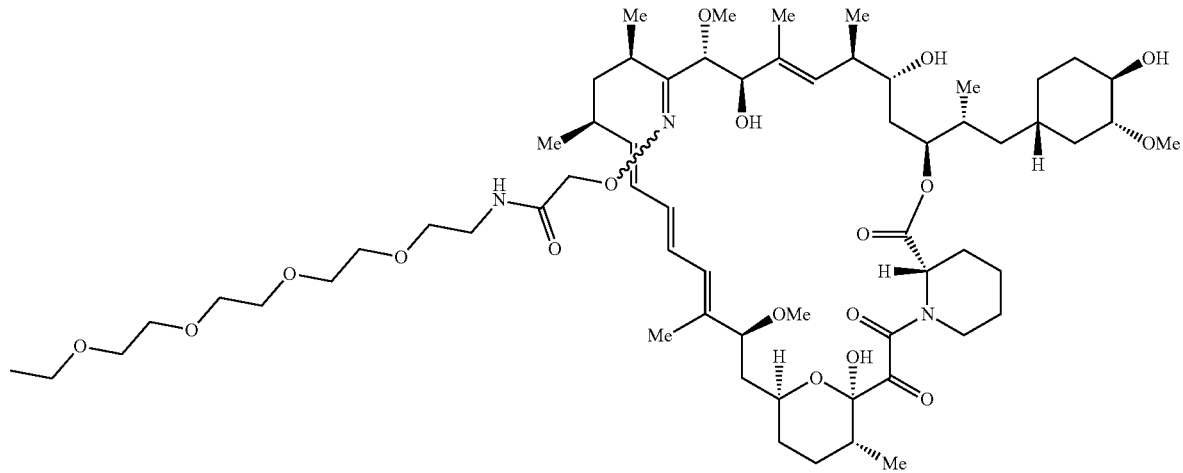

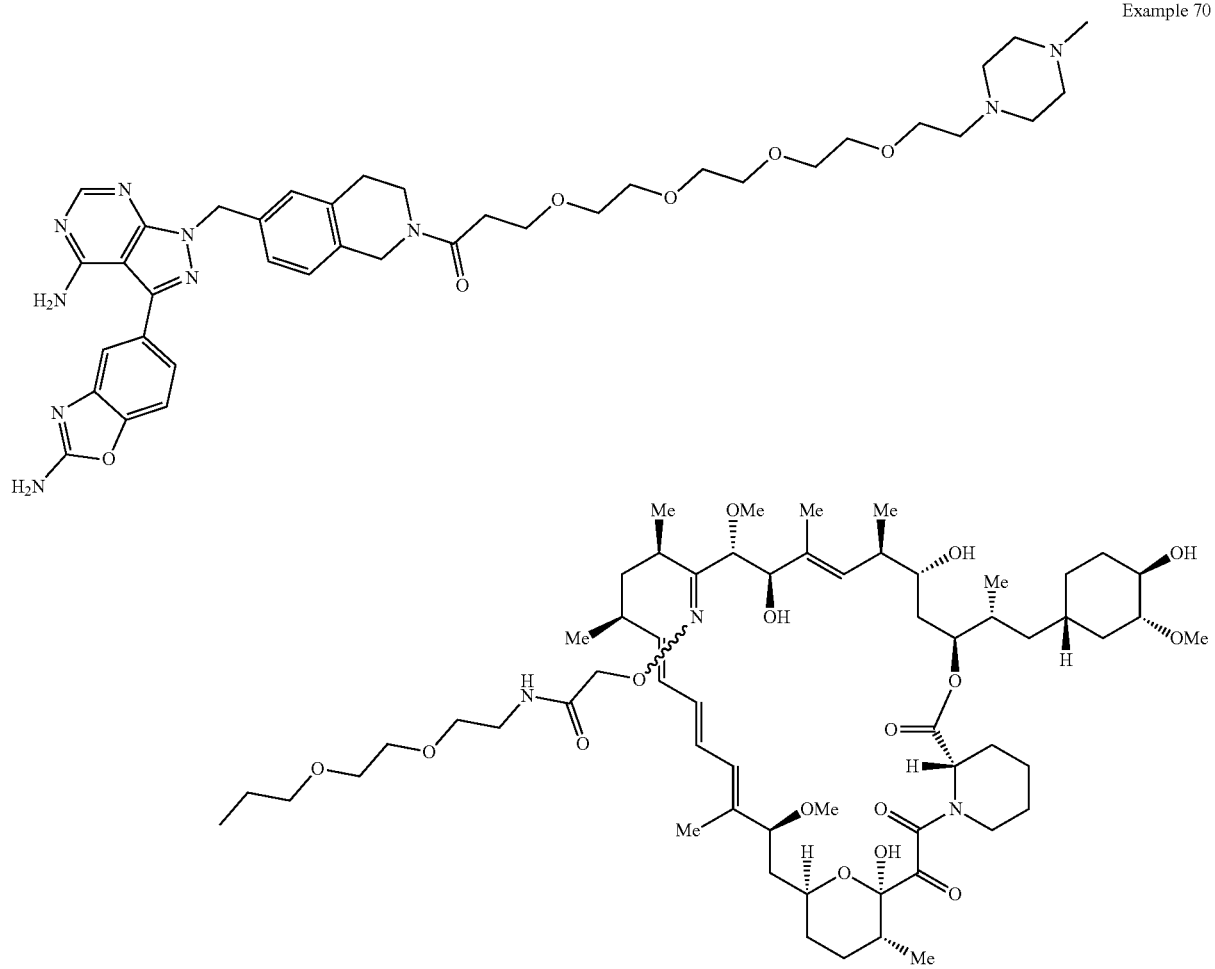

Example 70

The compounds of the disclosure may include pharmaceutically acceptable salts of the compounds disclosed herein. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Unless otherwise stated, structures depicted herein may also include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the disclosure. Such isotopically labeled compounds are useful as research or diagnostic tools.

In some embodiments, one or more deuterium atoms may be introduced into the PEG moiety of any compound of the present invention. Mechanisms for such modifications are known in the art starting from commercially available starting materials, such as isotopically enriched hydroxylamine building blocks. In some embodiments, a tritium or a deuterium may be introduced at the C32 position of compounds of the present invention using, for example, a commercially available isotopically pure reducing agent and methods known to those in the art. In some embodiments, an isotope such as deuterium or tritium may be introduced into the $R^{26}$ substituent of a compound of Formula I, Ia, or Ib using commercially available starting materials and methods known to those of skill in the art.

Methods of Synthesizing Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I, or a pharmaceutically acceptable salt or tautomer of any of the foregoing.

The compounds of any of the formulae described herein may be prepared by methods which avoid the use of metal-mediated cycloaddition reactions which require the use of azide-containing compounds. Azide containing compounds present potential safety hazards associated with their preparation and storage (e.g., explosion due to high energy decomposition). Also, the reaction schemes herein can avoid the use of copper or ruthenium metals in the penultimate or ultimate synthetic steps, which can be advantageous. Avoiding the use of copper or ruthenium metals in the penultimate or ultimate synthetic steps reduces the potential for contamination of the final compounds with undesirable metal impurities.

Those skilled in the art will recognize if a stereocenter exists in any of the compounds of the present disclosure. Accordingly, the present disclosure may include both possible stereoisomers (unless specified in the synthesis) and may include not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the disclosure can be synthesized using the methods described below, together with synthetic methods known in the art of synthetic organic chemistry, or variations thereon as appreciated by those skilled in the art. These methods may include but are not limited to those methods described below.

The term "tautomers" may refer to a set of compounds that have the same number and type of atoms, but differ in bond connectivity and are in equilibrium with one another. A "tautomer" is a single member of this set of compounds. Typically a single tautomer is drawn but it may be understood that this single structure may represent all possible tautomers that might exist. Examples may include enol-ketone tautomerism. When a ketone is drawn it may be understood that both the enol and ketone forms are part of the disclosure.

In addition to tautomers that may exist at all amide, carbonyl, and oxime groups within compounds of Formula I, Ia, or Ib, compounds in this family readily interconvert via a ring-opened species between two major isomeric forms, known as the pyran and oxepane isomers (shown below). This interconversion can be promoted by magnesium ions, mildly acidic conditions, or alkylamine salts, as described in the following references: i) Hughes, P. F.; Musser, J.; Conklin, M.; Russo, R. 1992. Tetrahedron Lett. 33(33): 4739-32. ii) Zhu, T. 2007. U.S. Pat. No. 7,241,771; Wyeth. iii) Hughes, P. F. 1994. U.S. Pat. No. 5,344,833; American Home Products Corp. The scheme below shows an interconversion between the pyran and oxepane isomers in compounds of Formula I, Ia, or Ib.

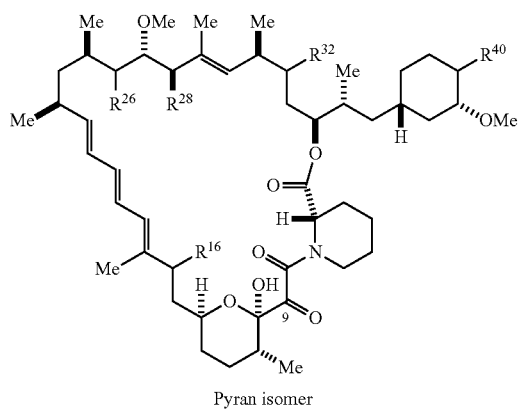

Pyran isomer

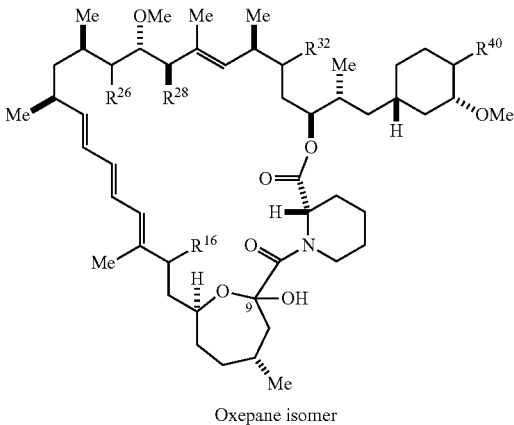

Oxepane isomer

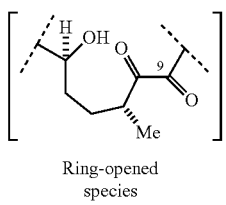

Ring-opened species

As this interconversion occurs under mild condition, and the thermodynamic equilibrium position may vary between different members of compounds of Formula I, Ia, or Ib, both isomers are contemplated for the compounds of Formula I, Ia, or Ib. For the sake of brevity, the pyran isomer form of all intermediates and compounds of Formula I is shown.

General Assembly Approaches For Bifunctional Rapalogs

With reference to the schemes below, rapamycin is Formula RAP, (RAP)

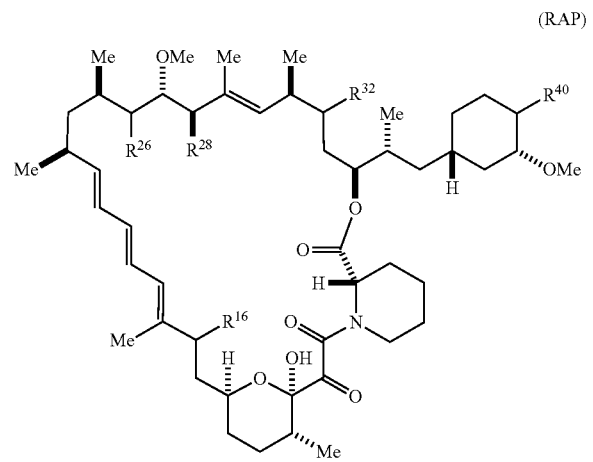

where $R^{16}$ is —$OCH_3$; $R^{26}$ is =O; $R^{28}$ is —OH; $R^{32}$ is =O; and $R^{40}$ is —OH. A "rapalog" refers to an analog or derivative of rapamycin. For example, with reference to the schemes below, a rapalog can be rapamycin that is substituted at any position, such as $R^{16}$, $R^{26}$, $R^{28}$, $R^{32}$, or $R^{40}$. An active site inhibitor (AS inhibitor) is an active site mTOR inhibitor. In certain embodiments, AS inhibitor is depicted by B, in Formula I, Ia, or Ib.

Series 1 bifunctional Rapalogs

A general structure of Series 1 bifunctional rapalogs is shown in Scheme 1 below. Scheme 1. For these types of bifunctional rapalogs, the linker may include variations where q=0 to 30, such as q=1 to 7, and r=1 to 6. The linker amine can include substitutions, such as R═H and C1-C6 alkyl groups. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Series 1 bifunctional rapalogs.

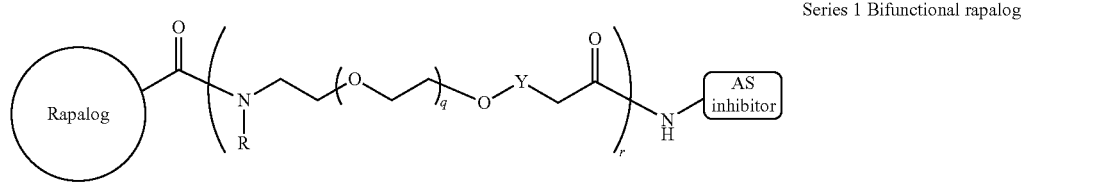

Series 1 Bifunctional rapalog

Series 2 bifunctional rapalogs

A general structure of Series 2 bifunctional rapalogs is shown in Scheme 2 below. For these types of bifunctional rapalogs, the linker may include variations where q=0 to 30, such as q=1 to 7. The linker amine can include substitutions, such as R=H and C1-C6 alkyl groups. The pre-linker amine can include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 2. Series 2 bifunctional rapalogs.

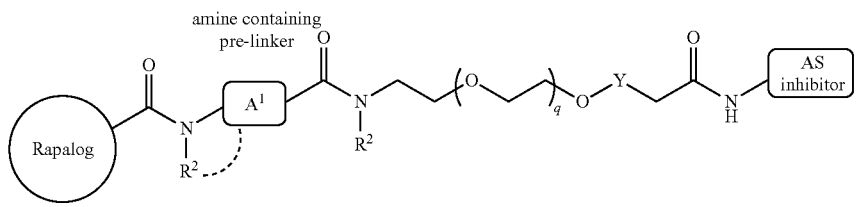

Series 2 Bifunctional rapalog

Series 3 bifunctional rapalogs

A general structure of Series 3 bifunctional rapalogs is shown in Scheme 3 below. For these types of bifunctional rapalogs, the linker may include variations where q=0 to 30, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 3. Series 3 bifunctional rapalogs

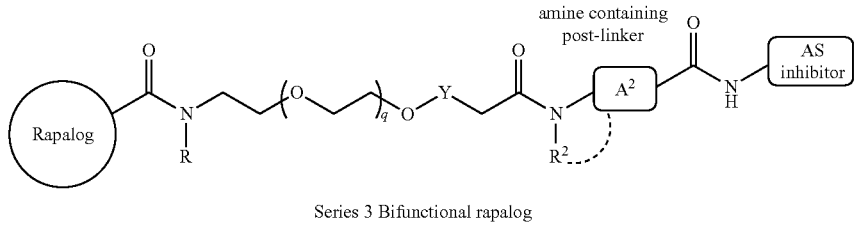

Series 3 Bifunctional rapalog

Series 4 Bifunctional Rapalogs

A general structure of Series 4 bifunctional rapalogs is shown in Scheme 4 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 4. Series 4 bifunctional rapalogs

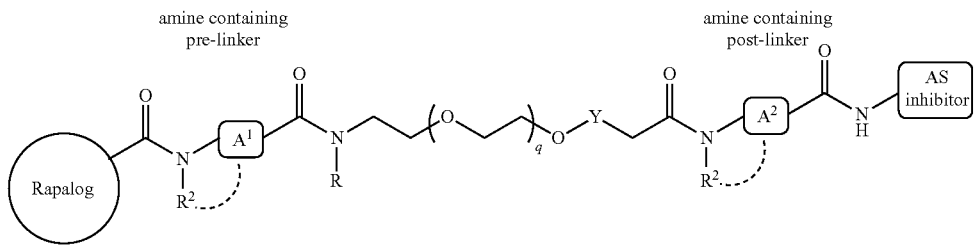

Series 4 Bifunctional rapalog

Series 5 Bifunctional Rapalogs

A general structure of Series 5 bifunctional rapalogs is shown in Scheme 5 below. For these types of bifunctional rapalogs, the pre-linker amine can include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 5. Series 5 bifunctional rapalogs

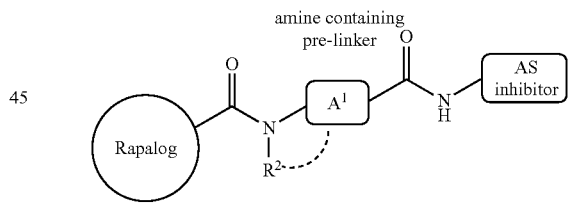

Series 5 Bifunction rapalog

Series 6 Bifunctional Rapalogs

A general structure of Series 6 bifunctional rapalogs is shown in Scheme 6 below. For these types of bifunctional rapalogs, the linker may include variations where q=0 to 30, such as q=1 to 7. The linker amines can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 6. Series 6 bifunctional rapalogs.

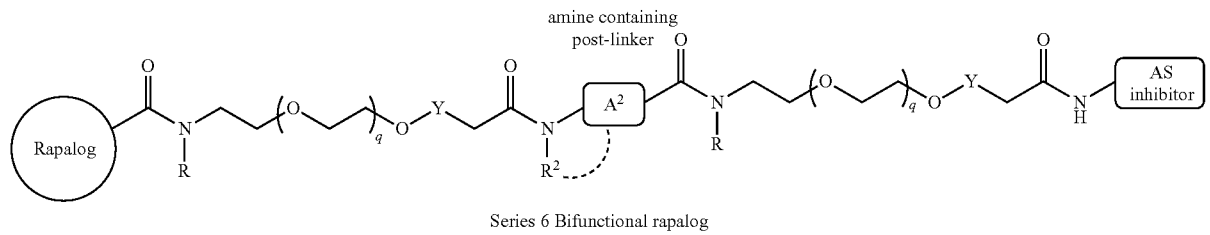

Series 6 Bifunctional rapalog

Series 7 bifunctional rapalogs

A general structure of Series 7 bifunctional rapalogs is shown in Scheme 7 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 7. Series 7 bifunctional rapalog

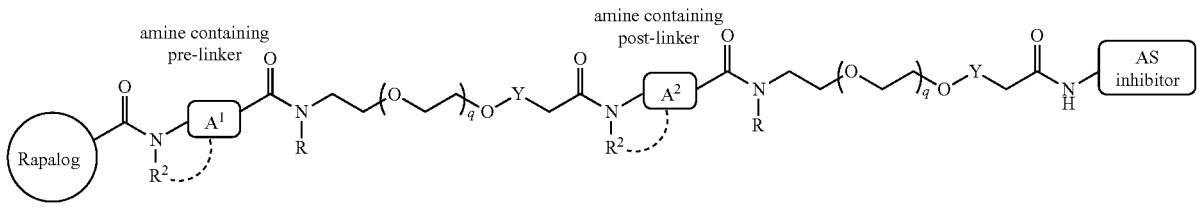

Series 7 Bifunctional rapalog

Series 8 bifunctional rapalogs

A general structure of Series 8 bifunctional rapalogs is shown in Scheme 8 below. For these types of bifunctional rapalogs, the linker may include variations where q=0 to 10, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I, Ia, or Ib), via an oxime linkage fragment including variations found in Table 1 in the Examples Section. An mTOR active site inhibitor can attach to the linker via a primary or secondary amine, and may include variations found in Table 2 in the Examples Section.

Scheme 8. Series 8 bifunctional rapalog

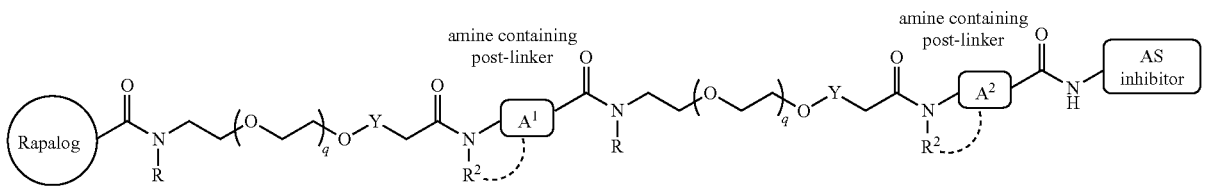

Series 8 Bifunctional rapalog

Pharmaceutical Compositions

Another aspect provides a pharmaceutical composition including a pharmaceutically acceptable excipient and a compound, or pharmaceutically acceptable salt or tautomer thereof.

In embodiments of the pharmaceutical compositions, a compound of the present invention, or a pharmaceutically acceptable salt or tautomer thereof, may be included in a therapeutically effective amount.

Administration of the disclosed compounds or compositions can be accomplished via any mode of administration for therapeutic agents. These modes may include systemic or local administration such as oral, nasal, parenteral, transdermal, subcutaneous, vaginal, buccal, rectal, topical, intrathecal, or intracranial administration modes.

In certain embodiments, administering can include oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration can be by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, J. Biomater Set Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46: 1576-1587, 1989). The compositions of the present disclosure can also be delivered as nanoparticles.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure relates to a pharmaceutical composition comprising a compound, or a pharmaceutically acceptable salt or tautomer thereof, of the present disclosure and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The compounds described herein can be used in combination with one another, with other active agents known to be useful in treating cancer, autoimmune disease, inflammatory disease, metabolic disease, neurodegenerative disease, fungal infection, or transplant rejection, or with adjunctive agents that may not be effective alone, but may contribute to the efficacy of the active agent. The compounds described herein can be used in combination with other active agents known to be longevity agents or anti-aging agents.

In embodiments of the pharmaceutical compositions, the pharmaceutical composition may include a second agent (e.g., therapeutic agent). In embodiments of the pharmaceutical compositions, the pharmaceutical composition may include a second agent (e.g., therapeutic agent) in a therapeutically effective amount. In embodiments, the second agent is an anti-cancer agent. In embodiments, the second agent is an immunotherapeutic agent. In embodiments, the second agent is an immune-oncological agent. In embodiments, the second agent is an anti-autoimmune disease agent. In embodiments, the second agent is an anti-inflammatory disease agent. In embodiments, the second agent is an anti-neurodegenerative disease agent. In embodiments, the second agent is an anti-metabolic disease agent. In embodiments, the second agent is an anti-cardiovascular disease agent. In embodiments, the second agent is an anti-aging agent. In embodiments, the second agent is a longevity agent. In embodiments, the second agent is an agent for treating or preventing transplant rejection. In embodiments, the second agent is an agent for treating or preventing fungal infection. In embodiments, the second agent is immune system repressor. In embodiments, the second agent is an mTOR modulator. In embodiments, the second agent is an mTOR inhibitor. In embodiments, the second agent is an active site mTOR inhibitor. In embodiments, the second agent is a rapamycin. In embodiments, the second agent is a rapamycin analog. In embodiments, the second agent is an mTOR pathway inhibitor. In certain embodiments, the second agent is CDK4/6 inhibitor; anti-PD1/PD-L1, PI3K inhibitor; or Ras inhibitor.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anticancer agent is an agent approved by the FDA or similar regulatory agency of a country other than the USA, for treating cancer. Examples of anti-cancer agents include, but are not limited to, rapamycin, rapamycin analog, bevacizumab, PP242, FN 128, MLN0128, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1 120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/ PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, FNK128, PP242, PP121, MLN0128, AZD8055, AZD2014, VP-BEZ235, BGT226, SF1 126, Torin 1, Torin 2, WYE 687, WYE 687 salt (e.g., hydrochloride), PF04691502, PI-103, CC-223, OSI-027, XL388, KU-0063794, GDC-0349, PKI-587, rapamycin, deforolimus (AP23573, MK-8669, ridaforolimus), temsirolimus (CCI-779), ABT478, everolimus (RAD001) or the like.

mTOR and Methods of Treatment

The term "mTOR" refers to the protein "mechanistic target of rapamycin (serine/threonine kinase)" or "mammalian target of rapamycin." The term "mTOR" may refer to the nucleotide sequence or protein sequence of human mTOR (e.g., Entrez 2475, Uniprot P42345, RefSeq NM 004958, or RefSeq NP 004949) (SEQ ID NO: 1). The term "mTOR" may include both the wild-type form of the nucleotide sequences or proteins as well as any mutants thereof. In some embodiments, "mTOR" is wild-type mTOR. In some embodiments, "mTOR" is one or more mutant forms. The term "mTOR" XYZ may refer to a nucleotide sequence or protein of a mutant mTOR wherein the Y numbered amino acid of mTOR that normally has an X amino acid in the wildtype, instead has a Z amino acid in the mutant. In embodiments, an mTOR is the human mTOR. In embodiments, the mTOR has the nucleotide sequence corresponding to reference number GL206725550 (SEQ ID NO:2). In embodiments, the mTOR has the nucleotide sequence corresponding to RefSeq NM 004958.3 (SEQ ID NO:2). In embodiments, the mTOR has the protein sequence corresponding to reference number GL4826730 (SEQ ID NO: 1). In embodiments, the mTOR has the protein sequence corresponding to RefSeq NP 004949.1 (SEQ ID NO: 1). In embodiments, the mTOR has the following amino acid sequence:

```
                                         (SEQ ID NO: 1)
MLGTGPAAATTAATTSSNVSVLQQFASGLKSRNEETRAKAAKELQHYVTM

ELREMSQEESTRFYDQLNHHIFELVSSSDANERKGGILAIASLIGVEGGN

ATRIGRFANYLRNLLPSNDPWMEMASKAIGRLAMAGDTFTAEYVEFEVKR

ALEWLGADRNEGRRHAAVLVLRELAISVPTFFFQQVQPFFDNIFVAVWDP

KQAIREGAVAALRACLILTTQREPKEMQKPQWYRHTFEEAEKGFDETLAK

EKGMNRDDRIHGALLILNELVRISSMEGERLREEMEEITQQQLVHDKYCK

DLMGFGTKPRHITPFTSFQAVQPQQSNALVGLLGYSSHQGLMGFGTSPSP

AKSTLVESRCCRDLMEEKFDQVCQWVLKCRNSKNSLIQMTILNLLPRLAA

FRPSAFTDTQYLQDTMNHVLSCVKKEKERTAAFQALGLLSVAVRSEFKVY

LPRVLDIIRAALPPKDFAHKRQKAMQVDATVFTCISMLARAMGPGIQQDI

KELLEPMLAVGLSPALTAVLYDLSRQIPQLKKDIQDGLLKMLSLVLMHKP

LRHPGMPKGLAHQLASPGLTTLPEASDVGSITLALRTLGSFEFEGHSLTQ

FVRHCADHFLNSEHKEIRMEAARTCSRLLTPSIHLISGHAHVVSQTAVQV

VADVLSKLLWGITDPDPDIRYCVLASLDERFDAHLAQAENLQALFVALND

QVFEIRELAICTVGRLSSMNPAFVMPFLRKMLIQILTELEHSGIGRIKEQ

SARMLGHLVSNAPRLIRPYMEPILKALILKLKDPDPDPNPGVINNVLATI

GELAQVSGLEMRKWVDELFIIIMDMLQDSSLLAKRQVALWTLGQLVASTG

YVVEPYRKYPTLLEVLLNFLKTEQNQGTRREAIRVLGLLGALDPYKHKVN
```

-continued

IGMIDQSRDASAVSLSESKSSQDSSDYSTSEMLVNMGNLPLDEFYPAVSM

VALMRIFRDQSLSHHHTMVVQAITFIFKSLGLKCVQFLPQVMPTFLNVIR

VCDGAIREFLFQQLGMLVSFVKSHIRPYMDEIVTLMREFWVMNTSIQSTI

ILLIEQIVVALGGEFKLYLPQLIPHMLRVFMHDNSPGRIVSIKLLAAIQL

FGANLDDYLHLLLPPIVKLFDAPEAPLPSRKAALETVDRLTESLDFTDYA

SRIIHPIVRTLDQSPELRSTAMDTLSSLVFQLGKKYQIFIPMVNKVLVRH

RINHQRYDVLICRIVKGYTLADEEEDPLIYQHRMLRSGQGDALASGPVET

GPMKKLHVSTINLQKAWGAARRVSKDDWLEWLRRLSLELLKDSSSPSLRS

CWALAQAYNPMARDLFNAAFVSCWSELNEDQQDELIRSIELALTSQDIAE

VTQTLLNLAEFMEHSDKGPLPLRDDNGIVLLGERAAKCRAYAKALHYKEL

EFQKGPTPAILESLISINNKLQQPEAAAGVLEYAMKHFGELEIQATWYEK

LHEWEDALVAYDKKMDTNKDDPELMLGRMRCLEALGEWGQLHQQCCEKWT

LVNDETQAKMARMAAAAAWGLGQWDSMEEYTCMIPRDTHDGAFYRAVLAL

HQDLFSLAQQCIDKARDLLDAELTAMAGESYSRAYGAMVSCHMLSELEEV

IQYKLVPERREIIRQIWWERLQGCQRIVEDWQKILMVRSLVVSPHEDMRT

WLKYASLCGKSGRLALAHKTLVLLLGVDPSRQLDHPLPTVHPQVTYAYMK

NMWKSARKIDAFQHMQHFVQTMQQQAQHAIATEDQQHKQELHKLMARCFL

KLGEWQLNLQGINESTIPKVLQYYSAATEHDRSWYKAWHAWAVMNFEAVL

HYKHQNQARDEKKKLRHASGANITNATTAATTAATATTTASTEGSNSESE

AESTENSPTPSPLQKKVTEDLSKTLLMYTVPAVQGFFRSISLSRGNNLQD

TLRVLTLWFDYGHWPDVNEALVEGVKAIQIDTWLQVIPQLIARIDTPRPL

VGRLIHQLLTDIGRYHPQALIYPLTVASKSTTTARHNAANKILKNMCEHS

NTLVQQAMMVSEELIRVAILWHEMWHEGLEEASRLYFGERNVKGMFEVLE

PLHAMMERGPQTLKETSFNQAYGRDLMEAQEWCRKYMKSGNVKDLTQAWD

LYYHVFRRISKQLPQLTSLELQYVSPKLLMCRDLELAVPGTYDPNQPIIR

IQSIAPSLQVITSKQRPRKLTLMGSNGHEFVFLLKGHEDLRQDERVMQLF

GLVNTLLANDPTSLRKNLSIQRYAVIPLSTNSGLIGWVPHCDTLHALIRD

YREKKKILLNIEHRIMLRMAPDYDHLTLMQKVEVFEHAVNNTAGDDLAKL

LWLKSPSSEVWFDRRTNYTRSLAVMSMVGYILGLGDRHPSNLMLDRLSGK

ILHIDFGDCFEVAMTREKFPEKIPFRLTRMLTNAMEVTGLDGNYRITCHT

VMEVLREHKDSVMAVLEAFVYDPLLNWRLMDTNTKGNKRSRTRTDSYSAG

QSVEILDGVELGEPAHKKTGTTVPESIHSFIGDGLVKPEALNKKAIQIIN

RVRDKLTGRDFSHDDTLDVPTQVELLIKQATSHENLCQCYIGWCPFW

In embodiments, the mTOR is a mutant mTOR. In embodiments, the mutant mTOR is associated with a disease that is not associated with wildtype mTOR. In embodiments, the mTOR may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to the sequence above.

The term "mTORC1" refers to the protein complex including mTOR and Raptor (regulatory-associated protein of mTOR). mTORC1 may also include MLST8 (mammalian lethal with SEC 13 protein 8), PRAS40, and/or DEPTOR. mTORC1 may function as a nutrient/energy/redox sensor and regulator of protein synthesis. The term "mTORC1 pathway" or "mTORC1 signal transduction pathway" may refer to a cellular pathway including mTORC1. An mTORC1 pathway includes the pathway components upstream and downstream from mTORC1. An mTORC1 pathway is a signaling pathway that is modulated by modulation of mTORC1 activity. In embodiments, an mTORC1 pathway is a signaling pathway that is modulated by modulation of mTORC1 activity but not by modulation of mTORC2 activity. In embodiments, an mTORC1 pathway is a signaling pathway that is modulated to a greater extent by modulation of mTORC1 activity than by modulation of mTORC2 activity.

The term "mTORC2" refers to the protein complex including mTOR and RICTOR (rapamycin-insensitive companion of mTOR). mTORC2 may also include GβL, mSIN1 (mammalian stress-activated protein kinase interacting protein 1), Protor 1/2, DEPTOR, TTI1, and/or TEL2. mTORC2 may regulate cellular metabolism and the cytoskeleton. The term "mTORC2 pathway" or "mTORC2 signal transduction pathway" may refer to a cellular pathway including mTORC2. An mTORC2 pathway includes the pathway components upstream and downstream from mTORC2. An mTORC2 pathway is a signaling pathway that is modulated by modulation of mTORC2 activity. In embodiments, an mTORC2 pathway is a signaling pathway that is modulated by modulation of mTORC2 activity but not by modulation of mTORC1 activity. In embodiments, an mTORC2 pathway is a signaling pathway that is modulated to a greater extent by modulation of mTORC2 activity than by modulation of mTORC1 activity.

The term "rapamycin" or "sirolimus" refers to a macrolide produced by the bacteria *Streptomyces hygroscopicus*. Rapamycin may prevent the activation of T cells and B cells. Rapamycin has the IUPAC name (3S,6R,7E,9R, 10R, 12R, 14S, 15E, 17E, 19E,21S,23S,26R,27R,34aS)-9, 10, 12, 13, 14,21,22,23,24,25,26,27,32,33,34,34a-hexadecahydro-9,27-dihydroxy-3-[(1R)-2-[(1 S,3R,4R)-4-hydroxy-3-methoxycyclohexyl]-1-methylethyl]-10,21-dimethoxy-6,8, 12, 14,20,26-hexamethyl-23,27-epoxy-3H-pyrido[2, 1-c][1,4]-oxaazacyclohentriacontine-1,5,11,28,29(4H,6H,31H)-pentone. Rapamycin has the CAS number 53123-88-9. Rapamycin may be produced synthetically (e.g., by chemical synthesis) or through use of a production method that does not include use of *Streptomyces hygroscopicus*.

"Analog" is used in accordance with its plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof.

The term "rapamycin analog" or "rapalog" refers to an analog or derivative (e.g., a prodrug) of rapamycin.

The terms "active site mTOR inhibitor" and "ATP mimetic" refers to a compound that inhibits the activity of mTOR (e.g., kinase activity) and binds to the active site of mTOR (e.g., the ATP binding site, overlapping with the ATP binding site, blocking access by ATP to the ATP binding site of mTOR). Examples of active site mTOR inhibitors include, but are not limited to, FNK128, PP242, PP121, MLN0128, AZD8055, AZD2014, NVP-BEZ235, BGT226, SF1126, Torin 1, Torin 2, WYE 687, WYE 687 salt (e.g., hydrochloride), PF04691502, PI-103, CC-223, OSI-027, XL388, KU-0063794, GDC-0349, and PKI-587. In embodiments, an active site mTOR inhibitor is an asTORi. In some embodiments, "active site inhibitor" may refer to "active site mTOR inhibitor."

The term "FKBP" refers to the protein Peptidyl-prolyl cis-trans isomerase. For non-limiting examples of FKBP, see Cell Mol Life Sci. 2013 September; 70(18):3243-75. In embodiments, "FKBP" may refer to "FKBP-12" or "FKBP 12" or "FKBP 1 A." In embodiments, "FKBP" may refer to the human protein. Included in the term "FKBP" is the wildtype and mutant forms of the protein. In embodiments, "FKBP" may refer to the wildtype human protein. In embodiments, "FKBP" may refer to the wildtype human nucleic acid. In embodiments, the FKBP is a mutant FKBP. In embodiments, the mutant FKBP is associated with a disease that is not associated with wildtype FKBP. In embodiments, the FKBP includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP.

The term "FKBP-12" or "FKBP 12" or "FKBP1A" may refer to the protein "Peptidyl-prolyl cis-trans isomerase FKBP 1 A." In embodiments, "FKBP-12" or "FKBP 12" or "FKBP 1 A" may refer to the human protein. Included in the term "FKBP-12" or "FKBP 12" or "FKBP 1 A" are the wildtype and mutant forms of the protein. In embodiments, "FKBP-12" or "FKBP 12" or "FKBP 1 A" may refer to the protein associated with Entrez Gene 2280, OMIM 186945, UniProt P62942, and/or RefSeq (protein) NP 000792 (SEQ ID NO:3). In embodiments, the reference numbers immediately above may refer to the protein, and associated nucleic acids, known as of the date of filing of this application. In embodiments, "FKBP-12" or "FKBP 12" or "FKBP 1 A" may refer to the wildtype human protein. In embodiments, "FKBP-12" or "FKBP 12" or "FKBP1A" may refer to the wildtype human nucleic acid. In embodiments, the FKBP-12 is a mutant FKBP-12. In embodiments, the mutant FKBP-12 is associated with a disease that is not associated with wildtype FKBP-12. In embodiments, the FKBP-12 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype FKBP-12. In embodiments, the FKBP-12 has the protein sequence corresponding to reference number GI:206725550. In embodiments, the FKBP-12 has the protein sequence corresponding to RefSeq NP 000792.1 (SEQ ID NO:3).

The term "4E-BP1" or "4EBP1" or "EIF4EBP1" refers to the protein "Eukaryotic translation initiation factor 4E-binding protein 1." In embodiments, "4E-BP1" or "4EBP1" or "EIF4EBP 1" may refer to the human protein. Included in the term "4E-BP 1" or "4EBP 1" or "EIF4EBP1" are the wildtype and mutant forms of the protein. In embodiments, "4E-BP1" or "4EBP1" or "EIF4EBP1" may refer to the protein associated with Entrez Gene 1978, OMIM 602223, UniProt Q13541, and/or RefSeq (protein) NP 004086 (SEQ ID NO:4). In embodiments, the reference numbers immediately above may refer to the protein, and associated nucleic acids, known as of the date of filing of this application. In embodiments, "4E-BP 1" or "4EBP1" or "EIF4EBP1" may refer to the wildtype human protein. In embodiments, "4E-BP1" or "4EBP1" or "EIF4EBP1" may refer to the wildtype human nucleic acid. In embodiments, the 4EBP1 is a mutant 4EBP1. In embodiments, the mutant 4EBP1 is associated with a disease that is not associated with wildtype 4EBP1. In embodiments, the 4EBP1 may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype 4EBP1. In embodiments, the 4EBP1 has the protein sequence corresponding to reference number GL4758258. In embodiments, the 4EBP1 has the protein sequence corresponding to RefSeq NP 004086.1 (SEQ ID NO:4).

The term "Akt" refers to the serine/threonine specific protein kinase involved in cellular processes such as glucose metabolism, apoptosis, proliferation, and other functions, also known as "protein kinase B" (PKB) or "Akt1." In embodiments, "Akt" or "AM" or "PKB" may refer to the human protein. Included in the term "Akt" or "Akt1" or "PKB" are the wildtype and mutant forms of the protein. In embodiments, "Akt" or "Akt1" or "PKB" may refer to the protein associated with Entrez Gene 207, OMIM 164730, UniProt P31749, and/or RefSeq (protein) NP 005154 (SEQ ID NO:5). In embodiments, the reference numbers immediately above may refer to the protein, and associated nucleic acids, known as of the date of filing of this application. In embodiments, "Akt" or "Akt1" or "PKB" may refer to the wildtype human protein. In embodiments, "Akt" or "Akt1" or "PKB" may refer to the wildtype human nucleic acid. In embodiments, the Akt is a mutant Akt. In embodiments, the mutant Akt is associated with a disease that is not associated with wildtype Akt. In embodiments, the Akt may include at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, or any range derivable therein) compared to wildtype Akt. In embodiments, the Akt has the protein sequence corresponding to reference number GI: 62241011. In embodiments, the Akt has the protein sequence corresponding to RefSeq NP 005154.2 (SEQ ID NO:5).

The present disclosure provides a method of treating a disease or disorder mediated by mTOR comprising administering to the subject suffering from or susceptible to developing a disease or disorder mediated by mTOR a therapeutically effective amount of one or more disclosed compositions or compounds. The present disclosure provides a method of preventing a disease or disorder mediated by mTOR comprising administering to the subject suffering from or susceptible to developing a disease or disorder mediated by mTOR a therapeutically effective amount of one or more disclosed compositions or compounds. The present disclosure provides a method of reducing the risk of a disease or disorder mediated by mTOR comprising administering to the subject suffering from or susceptible to developing a disease or disorder mediated by mTOR a therapeutically effective amount of one or more disclosed compositions or compounds.

In some embodiments, the disease is cancer or an immune-mediated disease. In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

The present disclosure provides a method of treating cancer comprising administering to the subject a therapeutically effective amount of one or more disclosed compositions or compounds. In some embodiments, the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors. In some embodiments, the disorder is liver cirrhosis. In certain embodiments, the disease is tuberous sclerosis complex (TSC). In certain embodiments, the disease is pancreatic neuroendocrine tumor (PNET), mantle cell lymphoma (MCL), colorectal cancer or bowel cancer (CRC), uterine cancer, ovarian cancer, bladder cancer, genitourinary tract cancer, or renal cell carcinoma (RCC).

In certain embodiments, cancer includes human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In certain embodiments, the disease is multiple myeloma. In certain embodiments, the disease is breast cancer. In certain embodiments, the disease is triple negative breast cancer.

In certain embodiments, cancer includes cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head and neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In certain embodiments, the disease is leukemia. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of aberrant cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

In certain embodiments, the disease is sarcoma. The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

In certain embodiments, the disease is melanoma. The term "melanoma" is taken to mean a tumor arising from the melanocyte system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

In certain embodiments, the disease is carcinoma. The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The present disclosure provides a method of treating an immune-mediated disease comprising administering to the subject a therapeutically effective amount of one or more disclosed compositions or compounds. In some embodiments, the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

In certain embodiments, the disease is autoimmune disease. As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The present disclosure provide a method of treating an age related condition comprising administering to the subject a therapeutically effective amount of one or more disclosed compositions or compounds. In certain embodiments, the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

In certain embodiments, the disclosed compositions or compounds can be used with regard to immunosenescence. Immunosenescence may refer to a decrease in immune function resulting in impaired immune response, e.g., to cancer, vaccination, infectious pathogens, among others. It involves both the host's capacity to respond to infections and the development of long-term immune memory, especially by vaccination. This immune deficiency is ubiquitous and found in both long- and short-lived species as a function of their age relative to life expectancy rather than chronological time. It is considered a major contributory factor to the increased frequency of morbidity and mortality among the elderly. Immunosenescence is not a random deteriorative phenomenon, rather it appears to inversely repeat an evolutionary pattern and most of the parameters affected by immunosenescence appear to be under genetic control. Immunosenescence can also be sometimes envisaged as the result of the continuous challenge of the unavoidable exposure to a variety of antigens such as viruses and bacteria. Immunosenescence is a multifactorial condition leading to many pathologically significant health problems, e.g., in the aged population. Age-dependent biological changes such as depletion of hematopoietic stem cells, an increase in PD1+ lymphocytes, a decline in the total number of phagocytes and NK cells and a decline in humoral immunity contribute to the onset of immunosenescence. In one aspect, immunosenescence can be measured in an individual by measuring telomere length in immune cells (See, e.g., U.S. Pat. No. 5,741,677). Immunosenescence can also be determined by documenting in an individual a lower than normal number of naive CD4 and/or CD8 T cells, T cell repertoire, the number of PD1-expressing T cells, e.g., a lower than normal number of PD-1 negative T cells, or response to vaccination in a subject greater than or equal to 65 years of age. In certain embodiments, mTOR selective modulation of certain T-cell populations may improve vaccine efficacy in the aging population and enhance effectiveness of cancer immunotherapy. The present disclosure provides a method of treating immunosenescence comprising administering to the subject a therapeutically effective amount of one or more disclosed compositions or compounds.

In certain embodiments, a disease that may be treated with a compound, pharmaceutical composition, or method described herein is organ or tissue transplant rejection (e.g. heart, lung, combined heart-lung, liver, kidney, pancreatic, skin or corneal transplants; graft-versus-host disease), restenosis, Hamartoma syndromes (e.g., tuberous sclerosis or Cowden Disease), Lymphangioleiomyomatosis, Retinitis pigmentosis, encephalomyelitis, insulin-dependent diabetes mellitus, lupus, dermatomyositis, arthritis, rheumatic diseases, Steroid-resistant acute Lymphoblastic Leukemia, fibrosis, scleroderma, pulmonary fibrosis, renal fibrosis, cystic fibrosis, Pulmonary hypertension, Multiple sclerosis, VHL syndrome, Carney complex, Familial adenonamtous polyposis, Juvenile polyposis syndrome, Birt-Hogg-Duke syndrome, Familial hypertrophic cardiomyopathy, Wolf-Parkinson-White syndrome, Parkinson's disease, Huntingtin's disease, Alzheimer's disease, dementias caused by tau mutations, spinocerebellar ataxia type 3, motor neuron disease caused by SOD1 mutations, neuronal ceroid lipofucinoses/Batten disease (pediatric neurodegeneration), wet macular degeneration, dry macular degeneration, muscle wasting (atrophy, cachexia), myopathies (e.g., Danon's disease), bacterial infection, viral infection, *M. tuberculosis*, group A *streptococcus*, HSV type I, HIV infection, Neurofibromatosis (e.g., Neurofibromatosis type 1), or Peutz-Jeghers syndrome.

In certain embodiments, the disease is neurodegenerative disease. As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In certain embodiments, the disease is metabolic disease. As used herein, the term "metabolic disease" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

In certain embodiments, the disease is fungal disease. As used herein, the term "fungal disease" refers to a disease or condition associated with a fungus infection of the subject. Examples of fungal diseases that may be treated with a compound, pharmaceutical composition, or method described herein include infection with *Mucor circinelloides*, zygomycetes, *Cryptococcus neoformans*, *Candida albicans*, yeast, and *Saccharomyces cerevisiae* among others.

In certain embodiments, the disease is inflammatory disease. As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In certain embodiments, the disease is cardiovascular disease. As used herein, the term "cardiovascular disease" refers to a disease or condition in which the function of a subject's cardiovascular system becomes impaired. Examples of cardiovascular diseases that may be treated with a compound, pharmaceutical composition, or method described herein include congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

In an aspect is provided a method of treating a disease associated with an aberrant level of mTOR activity in a subject in need of such treatment. The disease may be caused by an upregulation of mTOR. The method may include administering to the subject one or more compositions or compounds described herein. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating a disease caused by an upregulation of mTOR. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of a disease caused by aberrant levels of mTORC1 activity in a subject in need of such treatment. The disease may be caused by an upregulation of mTORC1. The use may include administering to the subject one or more compositions or compounds described herein. The use may include administering to the subject a therapeutically effective amount of one or more compositions or compounds described herein (e.g., an mTORC1 modulator (e.g., inhibitor) as described above).

Upregulation of mTOR can result in an increased amount of mTOR activity compared to normal levels of mTOR activity in a particular subject or a population of healthy subjects. The increased amount of mTOR activity may result in, for example, excessive amounts of cell proliferation thereby causing the disease state.

The subject of treatment for the disease is typically a mammal. The mammal treated with the compound (e.g., compound described herein, mTOR modulator (e.g., inhibitor)) may be a human, nonhuman primate, and/or nonhuman mammal (e.g., rodent, canine).

In another aspect is provided a method of treating an mTOR activity-associated disease in a subject in need of such treatment, the method including administering one or more compositions or compounds as described herein, including embodiments (e.g., a claim, embodiment, example, table, figure, or claim) to the subject.

In another aspect is provided one or more compositions or compounds as described herein for use as a medicament. In embodiments, the medicament may be useful for treating an mTORC1 activity-associated disease in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds for use in the treatment of an mTOR activity-associated disease in a subject in need of such treatment. In embodiments, the use may include administering one or more compositions or compounds as described herein, including embodiments (e.g., an aspect, embodiment, example, table, figure, or claim) to the subject.

In embodiments, the mTOR activity-associated disease or disease associated with aberrant levels of mTOR activity is cancer. In embodiments, the mTOR activity-associated disease or disease associated with aberrant levels of mTOR activity is an autoimmune disease. In embodiments, the mTOR activity-associated disease or disease associated with aberrant levels of mTOR activity is an inflammatory disease. In embodiments, the mTOR activity-associated disease or disease associated with aberrant levels of mTOR activity is a neurodegenerative disease. In embodiments, the mTOR activity-associated disease or disease associated with aberrant levels of mTOR activity is a metabolic disease. In embodiments, the mTOR activity-associated disease or disease associated with aberrant levels of mTOR activity is transplant rejection. In embodiments, the mTOR activity-associated disease or disease associated with aberrant levels of mTOR activity is fungal infection. In embodiments, the mTOR activity-associated disease or disease associated with aberrant levels of mTOR activity is a cardiovascular disease.

In embodiments, the mTOR activity-associated disease or disease associated with aberrant levels of mTOR activity is aging. In embodiments, the mTOR activity-associated disease or disease associated with aberrant levels of mTOR activity is dying of an age-related disease. In embodiments, the mTOR activity-associated disease or disease associated with aberrant levels of mTOR activity is an age-related condition. In certain embodiments, the age related condition is selected from the group consisting of sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes. In certain embodiments, mTOR selective modulation of certain T-cell populations may improve vaccine efficacy in the aging population and enhance effectiveness of cancer immunotherapy. The present disclosure provides a method of treating immunosenescence comprising administering to the subject a therapeutically effective amount of one or more disclosed compounds.

In embodiments, the mTOR activity-associated disease or disease associated with aberrant levels of mTOR activity is cancer (e.g., carcinomas, sarcomas, adenocarcinomas, lymphomas, leukemias, solid cancers, lymphoid cancers; cancer of the kidney, breast, lung, bladder, colon, gastrointestinal, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), multiple myeloma, and breast cancer (e.g., triple negative breast cancer)).

In embodiments, the mTOR activity-associated disease or disease associated with aberrant levels of mTOR activity is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressier's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatry Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HTV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation).

In an aspect is provided a method of treating a disease including administering an effective amount of one or more compositions or compounds as described herein. In an aspect is provided one or more compositions or compounds as described herein for use as a medicament (e.g., for treatment of a disease). In an aspect is provided one or more compositions or compounds as described herein for use in the treatment of a disease (e.g., including administering an effective amount of one or more compositions or compounds as described herein). In embodiments, the disease is cancer. In embodiments, the disease is an autoimmune disease. In embodiments, the disease is an inflammatory disease. In embodiments, the disease is a neurodegenerative disease. In embodiments, the disease is a metabolic disease. In embodiments, the disease is fungal infection. In embodiments, the disease is transplant rejection. In embodiments, the disease is a cardiovascular disease.

In embodiments, the disease is cancer (e.g., carcinomas, sarcomas, adenocarcinomas, lymphomas, leukemias, solid cancers, lymphoid cancers; cancer of the kidney, breast, lung, bladder, colon, ovarian, prostate, pancreas, stomach, brain, head and neck, skin, uterine, esophagus, liver; testicular cancer, glioma, hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CIVIL), multiple myeloma, and breast cancer (e.g., triple negative breast cancer)).

In embodiments, the disease is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (i.e., Granulomatosis with Polyangiitis (GPA), traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, atopic dermatitis, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HTV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, diabetes (e.g., type I or type II), obesity, metabolic syndrome, a mitochondrial disease (e.g., dysfunction of mitochondria or aberrant mitochondrial function), fungal infection, transplant rejection, or a cardiovascular disease (e.g., congestive heart failure; arrhythmogenic syndromes (e.g., paroxysomal tachycardia, delayed after depolarizations, ventricular tachycardia, sudden tachycardia, exercise-induced arrhythmias, long QT syndromes, or bidirectional tachycardia); thromboembolic disorders (e.g., arterial cardiovascular thromboembolic disorders, venous cardiovascular thromboembolic disorders, or thromboembolic disorders in the chambers of the heart); atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); myocardial infarction (first or recurrent); acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis, cerebral embolism; kidney embolism; pulmonary embolism; thrombosis (e.g., associated with prosthetic valves or other implants, indwelling catheters, stents, cardiopulmonary bypass, hemodialysis); thrombosis (e.g., associated with atherosclerosis, surgery, prolonged immobilization, arterial fibrillation, congenital thrombophilia, cancer, diabetes, hormones, or pregnancy); or cardiac arrhythmias (e.g., supraventricular arrhythmias, atrial arrhythmias, atrial flutter, or atrial fibrillation). In embodiments, the disease is a polycystic disease. In embodiments, the disease is polycystic kidney disease. In embodiments, the disease is stenosis. In embodiments, the disease is restenosis. In embodiments, the disease is neointimal proliferation. In embodiments, the disease is neointimal hyperplasia.

In another aspect is provided a method of treating aging in a subject in need of such treatment, the method including administering one or more compositions or compounds as described herein, including embodiments (e.g., a claim, embodiment, example, table, figure, or claim) to the subject. The present disclosure provides a method of treating immunosenescence comprising administering to the subject a therapeutically effective amount of one or more disclosed compounds or compositions.

In another aspect is provided one or more compositions or compounds as described herein for use as a medicament. In embodiments, the medicament may be useful for treating aging in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds disclosed herein for use in the treatment of aging in a subject in need of such treatment. In embodiments, the use may include administering one or more compositions or compounds as described herein, including embodiments (e.g., an aspect, embodiment, example, table, figure, or claim) to the subject.

In another aspect is provided a method of extending life span or inducing longevity in a subject in need of such treatment, the method including administering one or more compositions or compounds as described herein, including embodiments (e.g., a claim, embodiment, example, table, figure, or claim) to the subject.

In another aspect is provided one or more compositions or compounds as described herein for use as a medicament. In embodiments, the medicament may be useful for extending life span or inducing longevity in a subject in need of such treatment. In embodiments, the use may include administering one or more compositions or compounds as described herein, including embodiments (e.g., an aspect, embodiment, example, table, figure, or claim) to the subject.

In another aspect is provided one or more compositions or compounds for use in extending life span or inducing longevity in a subject in need of such treatment. In embodiments, the use may include administering one or more compositions or compounds as described herein, including embodiments (e.g., an aspect, embodiment, example, table, figure, or claim) to the subject.

In an aspect is provided a method of treating a polycystic disease in a subject in need of such treatment. The polycystic disease may be polycystic kidney disease. The method may include administering to the subject one or more compositions or compounds described herein. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating a polycystic disease. The polycystic disease may be polycystic kidney disease. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of a polycystic disease in a subject in need of such treatment. The polycystic disease may be polycystic kidney disease. The use may include administering to the subject one or more compositions or compounds described herein. The use may include administering to the subject a therapeutically effective amount of one or more compositions or compounds described herein (e.g., an mTOR modulator (e.g., inhibitor) as described above).

In an aspect is provided a method of treating stenosis in a subject in need of such treatment. The stenosis may be restenosis. The method may include administering to the subject one or more compositions or compounds described herein. In embodiments the one or more compositions or compounds are administered in a drug eluting stent. The method may include administering to the subject a therapeutically effective amount of one or more compositions or compounds described herein (e.g., an mTOR modulator (e.g., inhibitor) as described above).

In an aspect is provided one or more compositions or compounds as described herein for use as a medicament. In embodiments, the medicament is useful for treating stenosis. The stenosis may be restenosis. The use may include administering to the subject one or more compositions or compounds described herein. In embodiments the compound is administered in a drug eluting stent. The use may include administering to the subject a therapeutically effective amount of one or more compositions or compounds described herein (e.g., an mTOR modulator (e.g., inhibitor) as described above).

In an aspect is provided one or more compositions or compounds as described herein for use in the treatment of stenosis in a subject in need of such treatment. The stenosis may be restenosis. The use may include administering to the subject one or more compositions or compounds described herein. In embodiments the one or more compositions or compounds are administered in a drug eluting stent. The use may include administering to the subject a therapeutically effective amount of one or more compositions or compounds described herein (e.g., an mTOR modulator (e.g., inhibitor) as described above).

In embodiments, the disease is a disease described herein and the compound is a compound described herein and the composition is a composition described herein.

Methods of Modulating mTOR

In some embodiments, compounds disclosed herein are more selective inhibitors of mTORC1 versus mTORC2. In some embodiments, compounds disclosed herein are more selective inhibitors of mTORC2 versus mTORC1. In some embodiments, compounds disclosed herein exhibit no selectivity difference between mTORC1 and mTORC2.

In another aspect is provided a method of modulating mTORC1 activity in a subject in need thereof, including administering to the subject an effective amount of a compound as described herein, or a pharmaceutically acceptable salt thereof. In embodiments, the method includes inhibiting mTORC1 activity. In embodiments, the method includes inhibiting mTORC1 activity and not inhibiting mTORC2 activity.

In embodiments, the method includes inhibiting mTORC1 activity more than inhibiting mTORC2 activity. In embodiments, the method includes inhibiting mTORC1 activity at least 1.1 fold as much as inhibiting mTORC2 activity (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In another aspect is provided a method of modulating mTORC2 activity in a subject in need thereof, including administering to the subject an effective amount of a compound as described herein, or a pharmaceutically acceptable salt thereof. In embodiments, the method includes inhibiting mTORC2 activity. In embodiments, the method includes inhibiting mTORC2 activity and not inhibiting mTORC1 activity.

In embodiments, the method includes inhibiting mTORC2 activity more than inhibiting mTORC1 activity. In embodiments, the method includes inhibiting mTORC2 activity at least 1.1 fold as much as inhibiting mTORC1 activity (e.g., at least 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 10000, 20000, 30000, 40000, 50000, 60000, 70000, 80000, 90000, 100000, 100000, 200000, 300000, 400000, 500000, 600000, 700000, 800000, 900000, or 1000000 fold).

In some embodiments, the mTOR is in a cell. In some embodiments, the cell is a mammalian cell, such as a human cell. The cell may be isolated in vitro, form part of a tissue in vitro, or may form part of an organism.

EXEMPLARY EMBODIMENTS

Some embodiments of this disclosure are Embodiment I, as follows:

Embodiment I-1. A compound of Formula I:

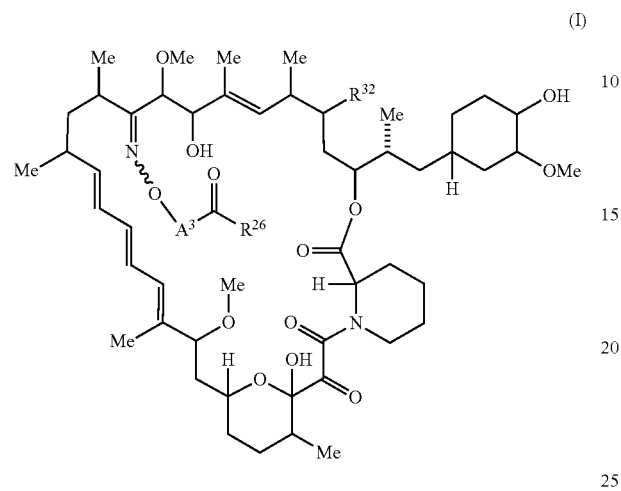

(I)

or a pharmaceutically acceptable salt or tautomer thereof, wherein:

$R^{32}$ is H, =O, or —$OR^3$;

$A^3$ is —$[C(R^3)_2]_n$—, ($C_6$-$C_{10}$)arylene, cycloalkylene, heteroarylene, or heterocyclylene;

$R^{26}$ is -$A^1$-$L^1$-$A^2$-B; -$A^1$-$A^2$-B; -$L^2$-$A^1$-$L^1$-$A^2$-$L^3$-B; or —OH;

$A^1$ and $A^2$ are independently absent or are independently selected from

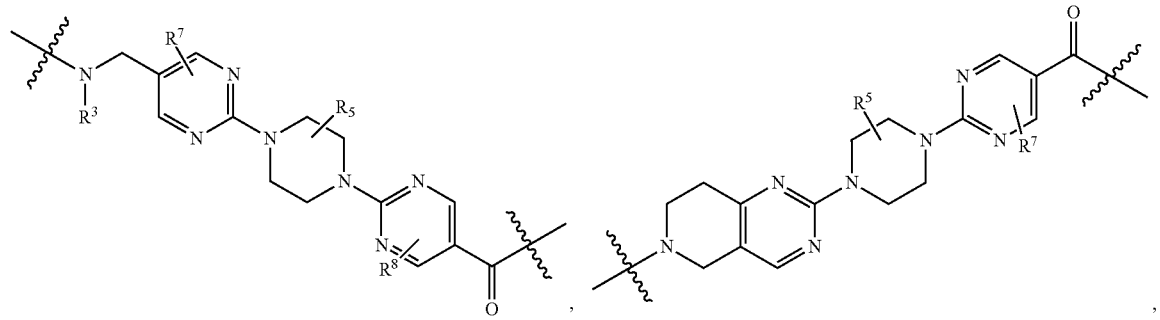

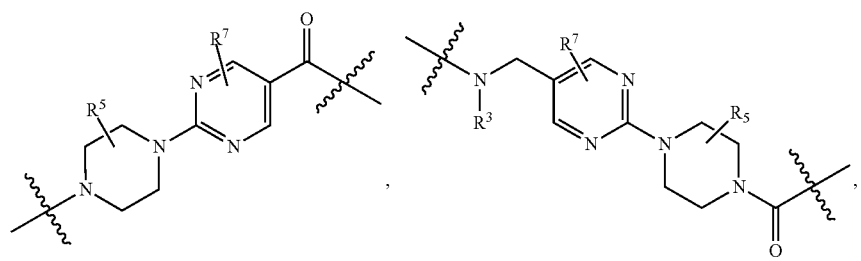

-continued
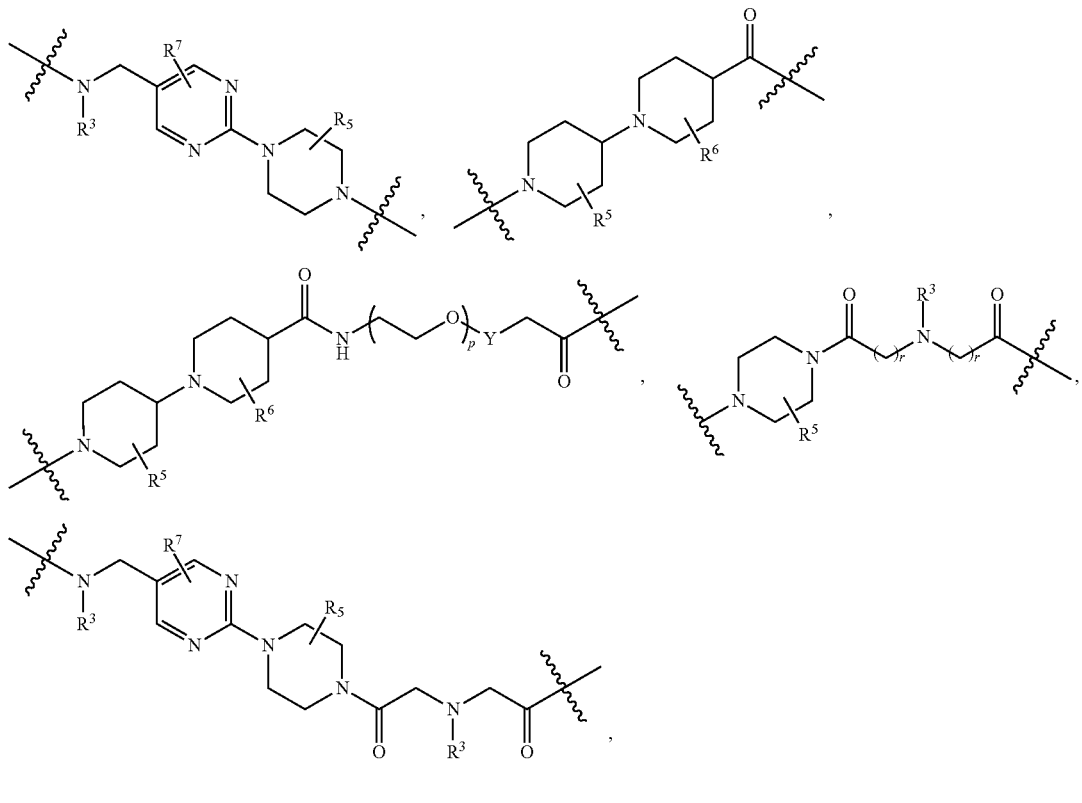
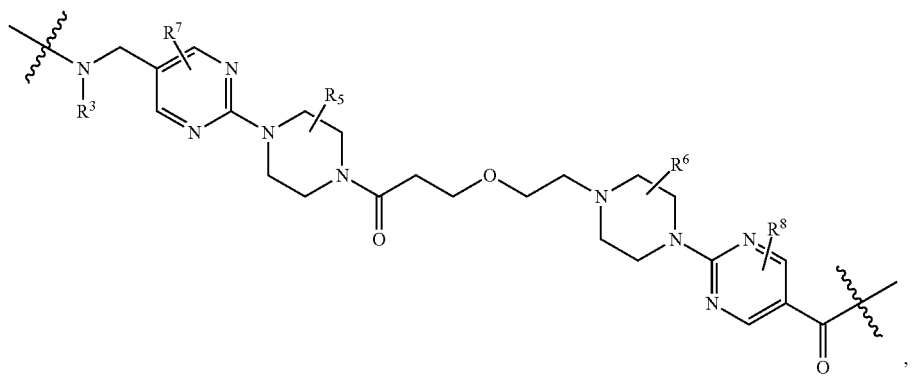
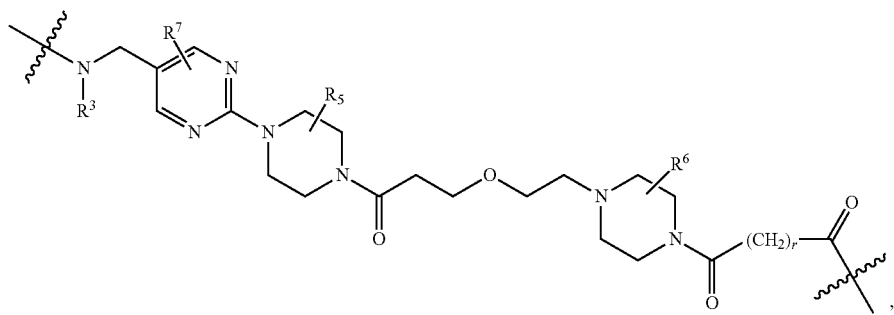

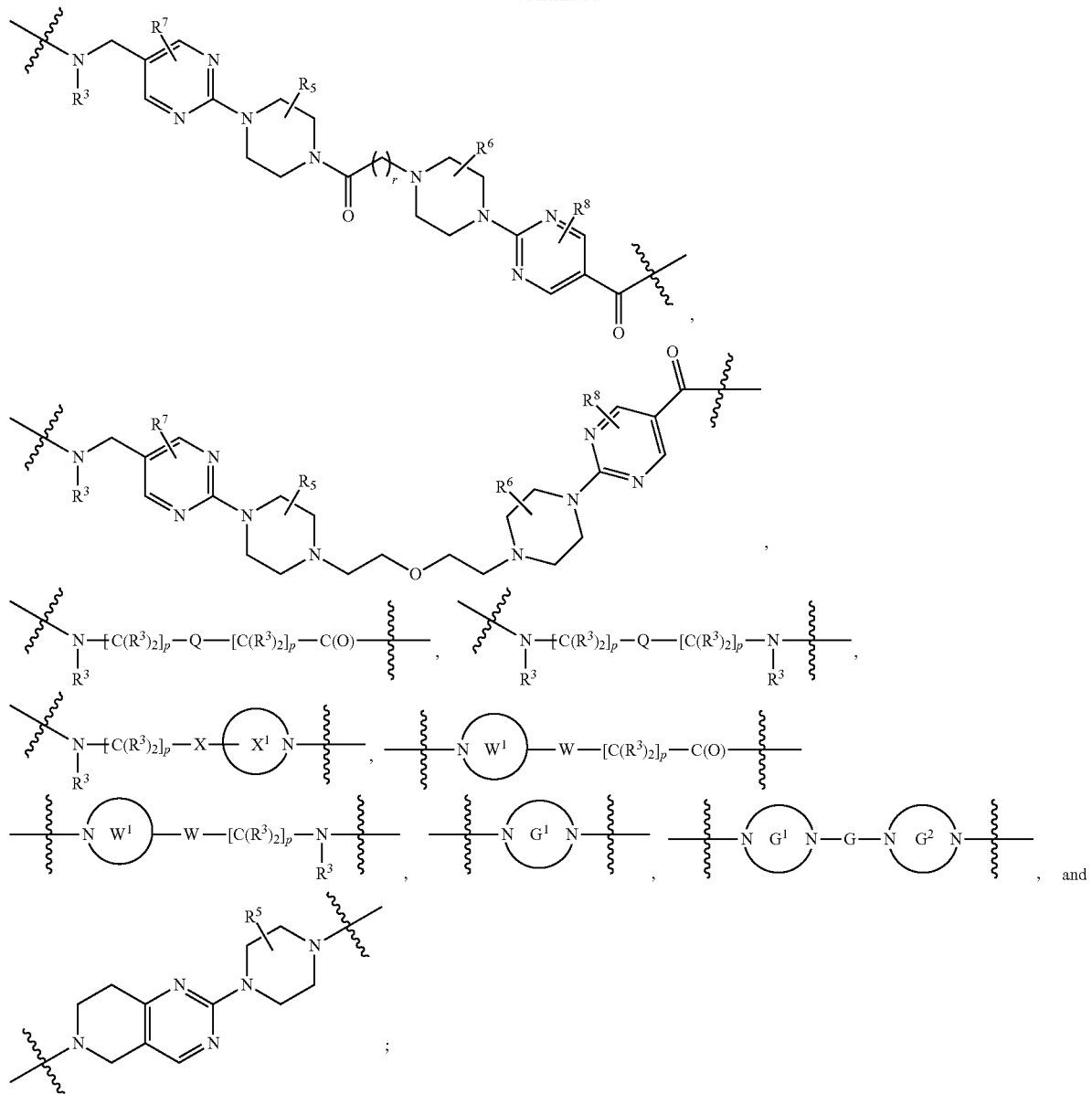

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is a heteroarylene or heterocyclylene ring;

each W is independently absent or 1 to 2 rings selected from arylene, cycloalkylene, heteroarylene, and heterocyclylene;

each $W^1$ is a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

$L^1$ is selected from

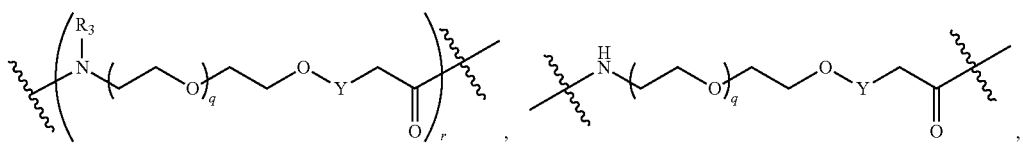

-continued
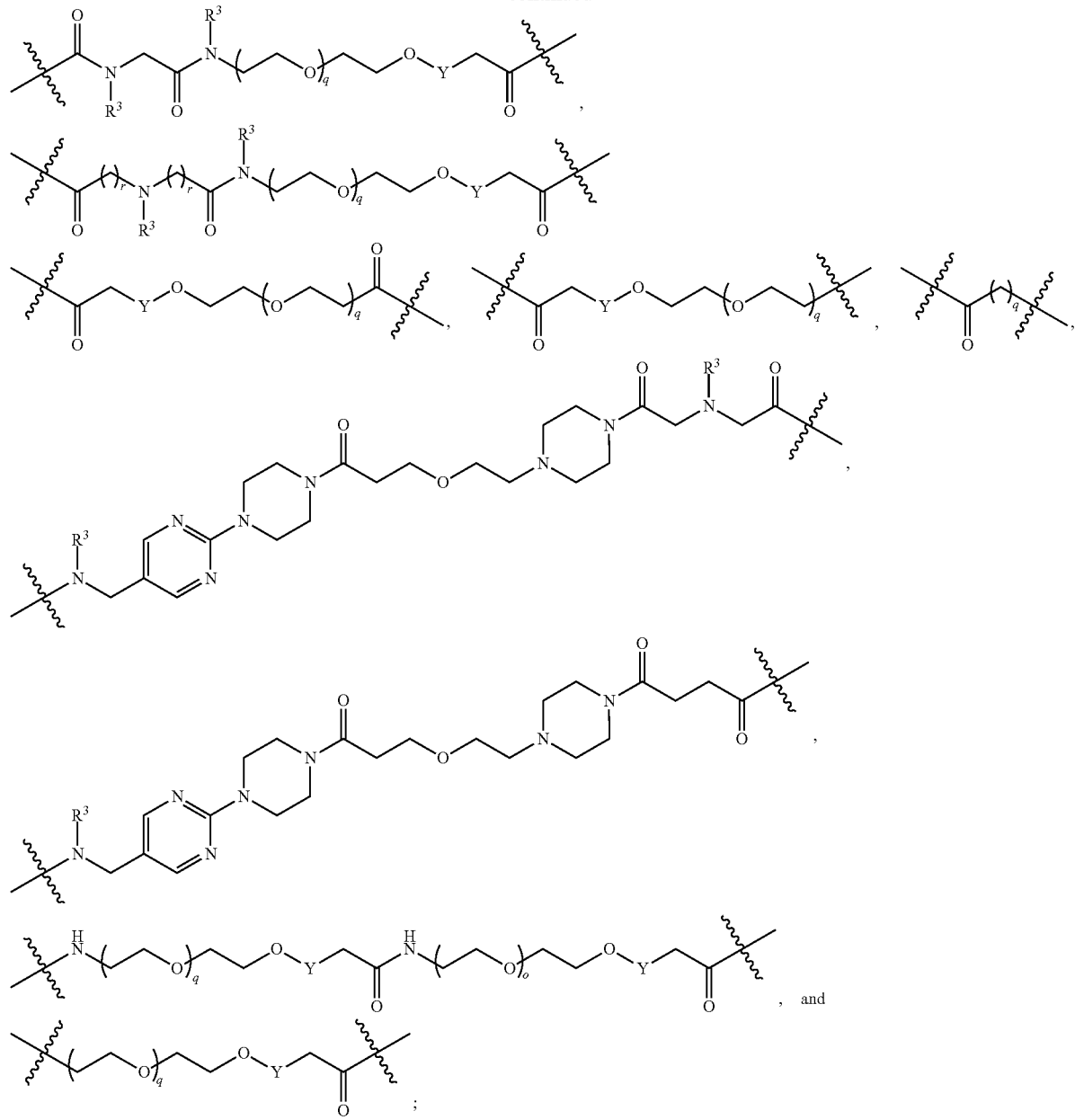
$L^2$ and $L^3$ are independently absent or are independently selected from
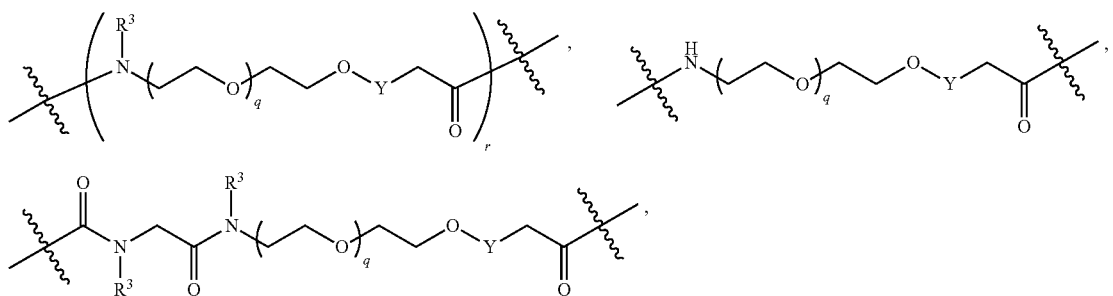

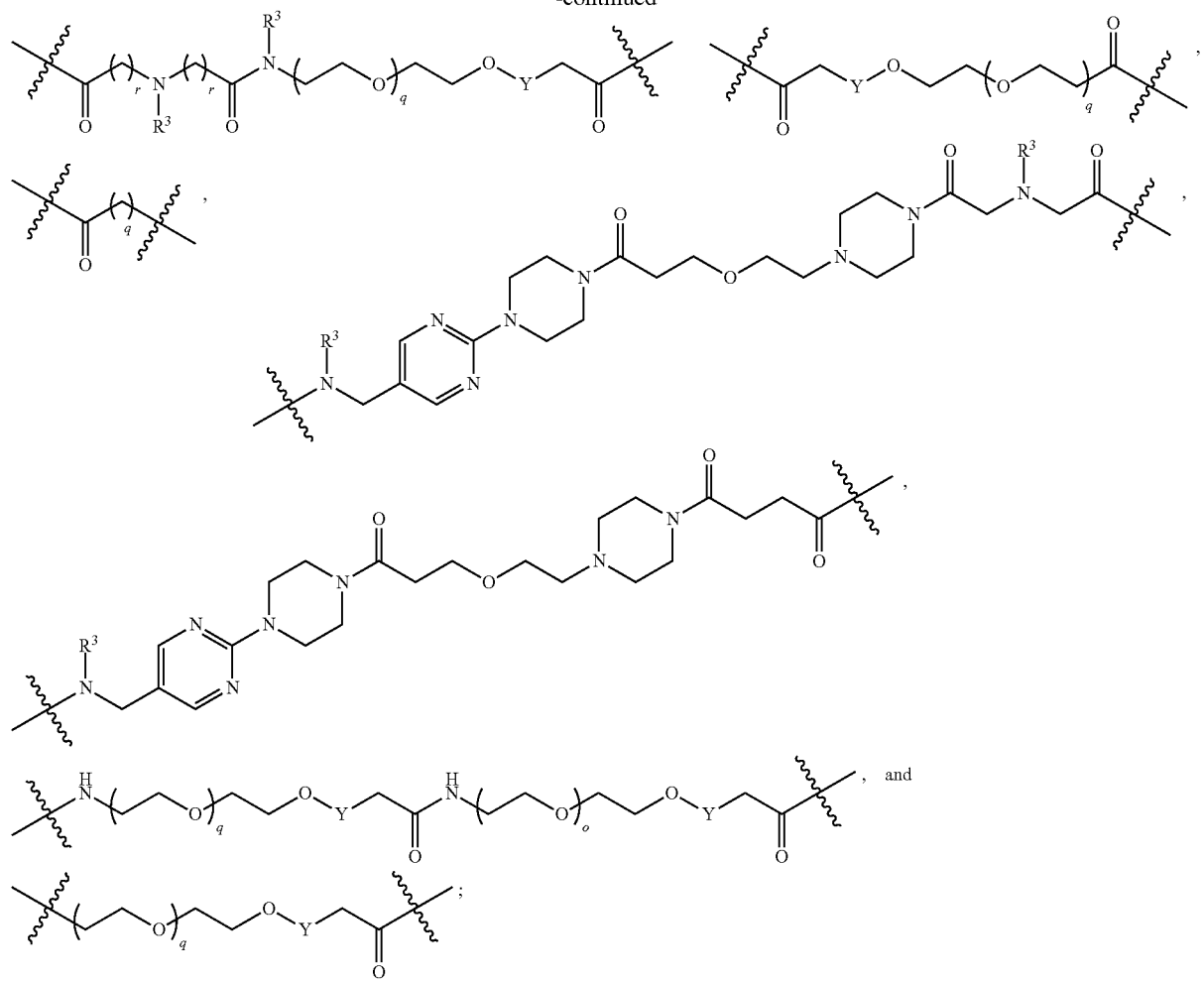
B is selected from
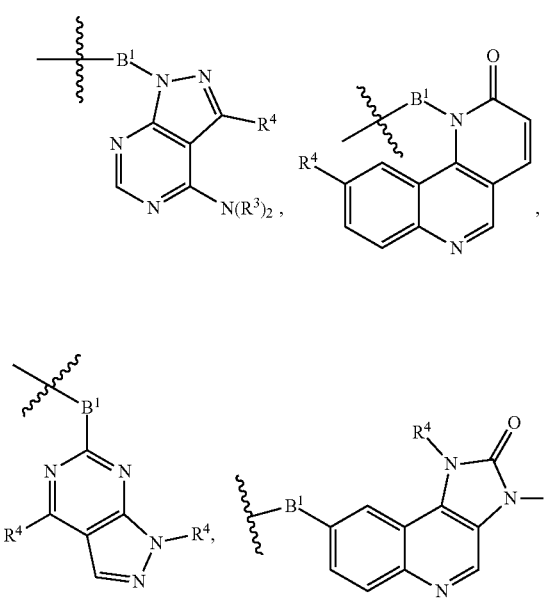
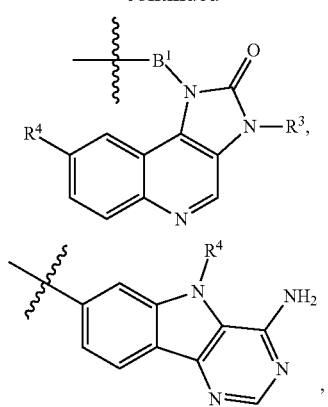
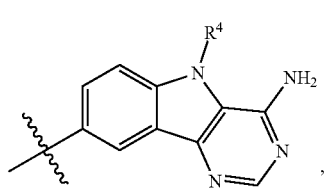

-continued

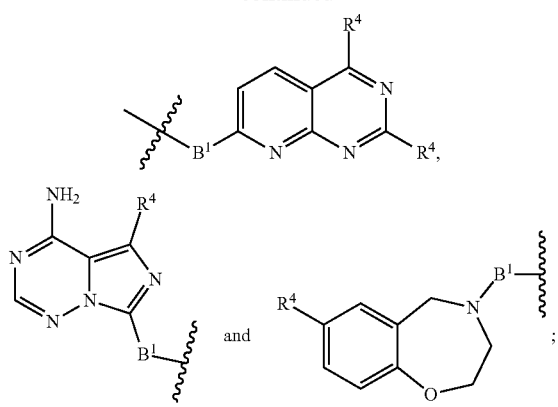

$B^1$ is selected from

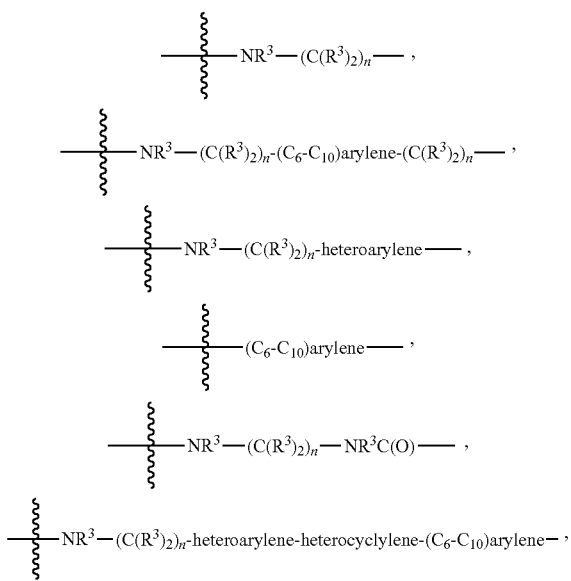

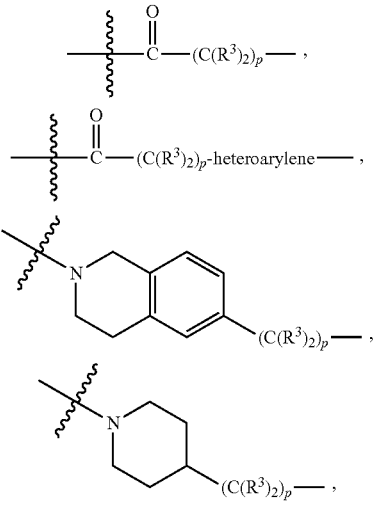

-continued

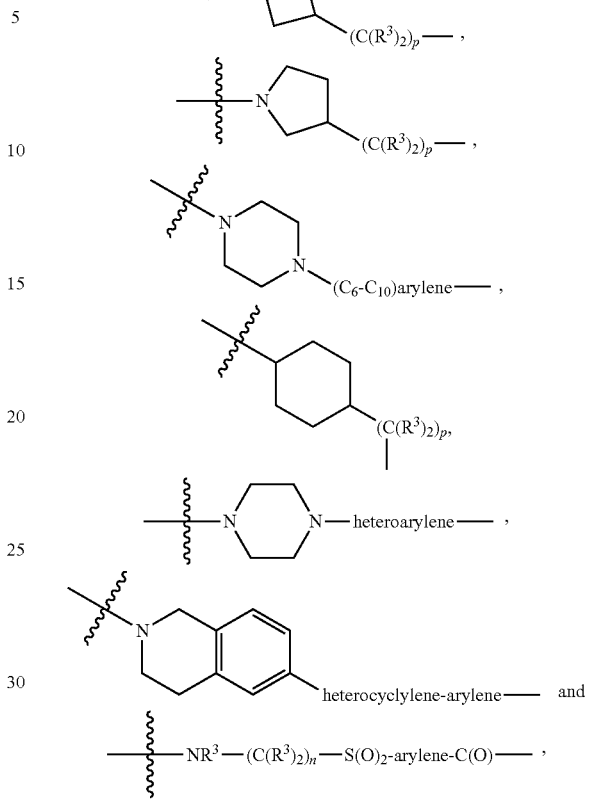

wherein the

bond on the left side of $B^1$, as drawn, is bound to $A^2$ or $L^1$; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with —$N(R^3)_2$, —$OR^3$, halogen, $(C_1\text{-}C_6)$alkyl, —$(C_1\text{-}C_6)$alkylene-heteroaryl, —$(C_1\text{-}C_6)$alkylene-CN, —$C(O)NR^3$-heteroaryl, or —$C(O)NR^3$-heterocyclyl;

each $R^5$ is independently H, $(C_1\text{-}C_6)$alkyl, —$C(O)OR^3$, or —$N(R^3)_2$, wherein the alkyl is optionally substituted with —$N(R^3)_2$ or —$OR^3$;

each $R^6$ is independently H, $(C_1\text{-}C_6)$alkyl, —$C(O)OR^3$, or —$N(R^3)_2$, wherein the alkyl is optionally substituted with —$N(R^3)_2$ or —$OR^3$;

each $R^7$ is independently H, $(C_1\text{-}C_6)$alkyl, —$C(O)OR^3$, or —$N(R^3)_2$, wherein the alkyl is optionally substituted with —$N(R^3)_2$ or —$OR^3$;

each $R^8$ is independently H, $(C_1\text{-}C_6)$alkyl, —$C(O)OR^3$, or —$N(R^3)_2$, wherein the alkyl is optionally substituted with —$N(R^3)_2$ or —$OR^3$;

each Y is independently $C(R^3)_2$ or a bond;
each n is independently an integer from one to 12;
each o is independently an integer from zero to 30;
each p is independently an integer from zero to 12;
each q is independently an integer from zero to 30; and
each r is independently an integer from one to 6.

Embodiment I-2. The compound of Embodiment I-1, wherein $R^{32}$ is =O.

Embodiment I-3. The compound of Embodiment I-1, wherein $R^{32}$ is —$OR^3$.

Embodiment I-4. The compound of any one of Embodiments I-1 to I-3, wherein $A^3$ is —$[C(R^3)_2]_n$—.

Embodiment I-5. The compound of any one of Embodiments I-1 to I-3, wherein $A^3$ is —$(C_6$-$C_{10})$arylene-.

Embodiment I-6. The compound of any one of Embodiments I-1 to I-5, wherein $R^{26}$ is -$A^1$-$L^1$-$A^2$-B, wherein $A^1$ and $A^2$ are absent.

Embodiment I-7. The compound of any one of Embodiments I-1 to I-5, wherein $R^{26}$ is -$A^1$-$L^1$-$A^2$-B, wherein $A^2$ is absent.

Embodiment I-8. The compound of any one of Embodiments I-1 to I-5, wherein $R^{26}$ is $A^1$-$L^1$-$A^2$-B, wherein $A^1$ is absent.

Embodiment I-9. The compound of any one of Embodiments I-1 to I-5, wherein $R^{26}$ is -$A^1$-$L^1$-$A^2$-B.

Embodiment I-10. The compound of any one of Embodiments I-1 to I-5, wherein $R^{26}$ is -$A^1$-$A^2$-B.

Embodiment I-11. The compound of any one of Embodiments I-1 to I-5, wherein $R^{26}$ is -$L^2$-$A^1$-$L^1$-$A^2$-$L^3$-B.

Embodiment I-12. The compound of any one of Embodiments I-1 to I-5, wherein $R^{26}$ is —OH.

Embodiment I-13. The compound of any one of Embodiments I-1 to I-11, wherein $L^1$ is

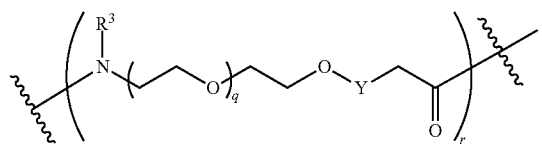

Embodiment I-14. The compound of any one of Embodiments I-1 to I-11, wherein $L^1$ is

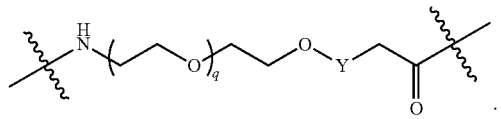

Embodiment I-15. The compound of any one of Embodiments I-1 to I-11, wherein $L^1$ is

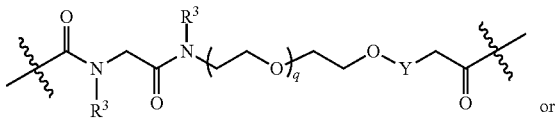

or

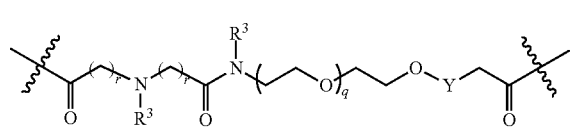

Embodiment I-16. The compound of any one of Embodiments I-1 to I-11, wherein $L^1$ is

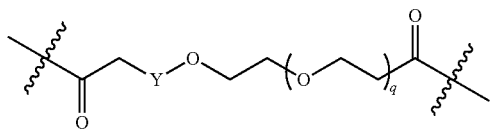

Embodiment I-17. The compound of any one of Embodiments I-1 to I-11, wherein $L^1$ is

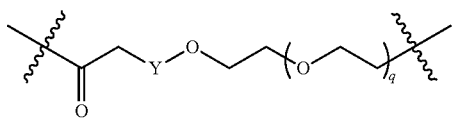

Embodiment I-18. The compound of any one of Embodiments I-1 to I-11, wherein $L^1$ is

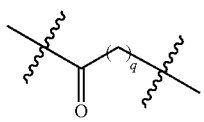

Embodiment I-19. The compound of any one of Embodiments I-1 to I-11, wherein $L^1$ is

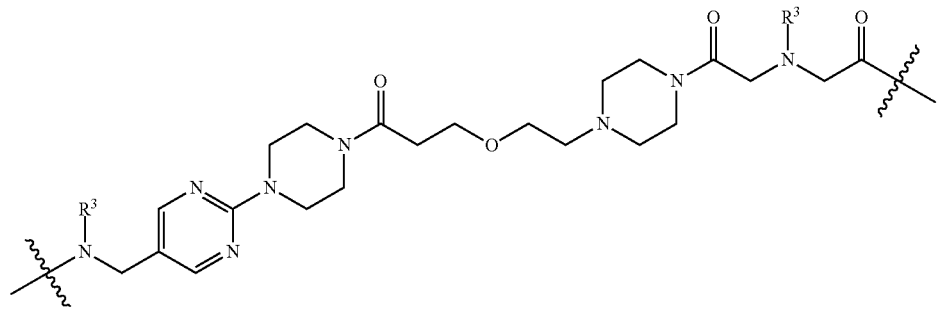

Embodiment I-20. The compound of any one of Embodiments I-1 to I-11, wherein L¹ is

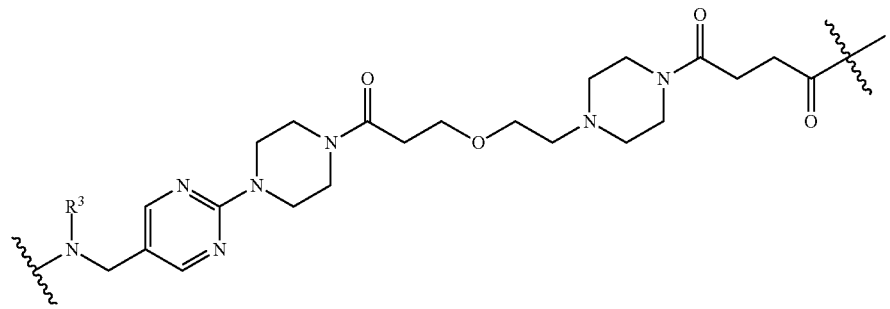

Embodiment I-21. The compound of any one of Embodiments I-1 to I-11 and I-13 to I-20, wherein A¹ is absent.

Embodiment I-22. The compound of any one of Embodiments I-1 to I-5, I-7, I-9 to I-11 and I-13 to I-20, wherein A¹ is

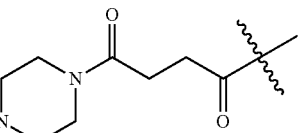

Embodiment I-23. The compound of any one of Embodiments I-1 to I-5, I-7, I-9 to I-11 and I-13 to I-20, wherein A¹ is

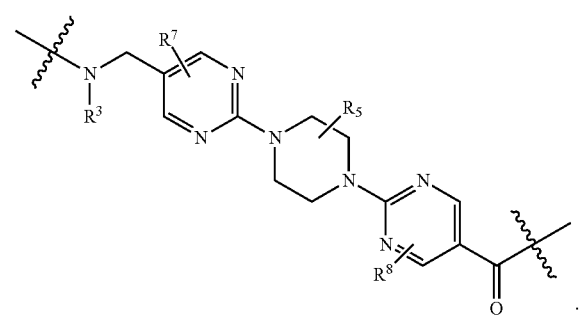

Embodiment I-24. The compound of any one of Embodiments I-1 to I-5, I-7, I-9 to I-11 and I-13 to I-20, wherein A¹ is

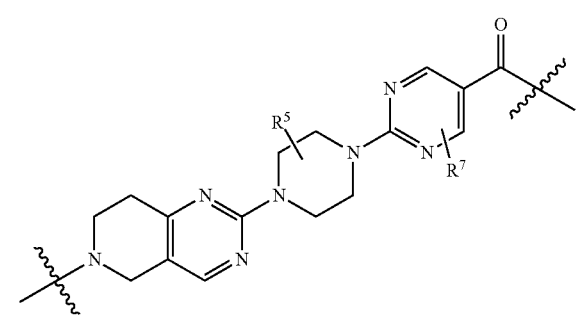

Embodiment I-25. The compound of any one of Embodiments I-1 to I-5, I-7, I-9 to I-11 and I-13 to I-20, wherein A¹ is

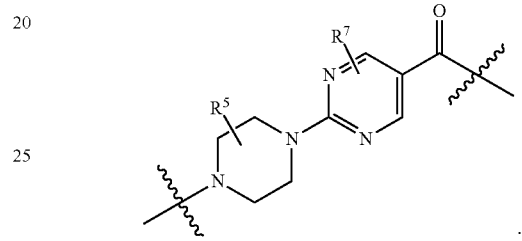

Embodiment I-26. The compound of any one of Embodiments I-1 to I-5, I-7, I-9 to I-11 and I-13 to I-20, wherein A¹ is

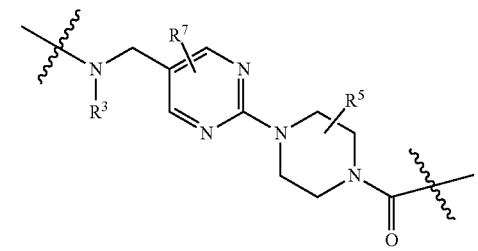

Embodiment I-27. The compound of any one of Embodiments I-1 to I-11 and I-13 to I-24, wherein A² is absent.

Embodiment I-28. The compound of any one of Embodiments I-1 to I-5, I-8 to I-11 and I-13 to I-24, wherein A² is

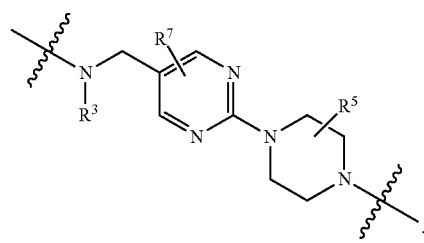

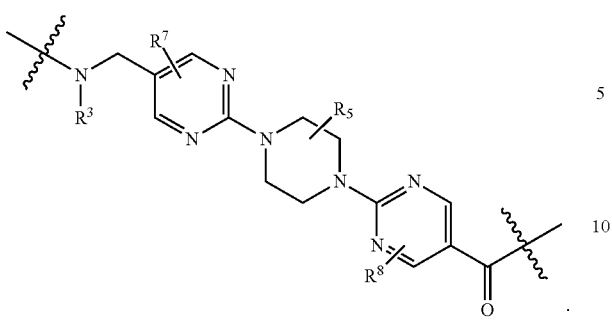

Embodiment I-29. The compound of any one of Embodiments I-1 to I-5, I-8 to I-11 and I-13 to I-24, wherein $A^2$ is

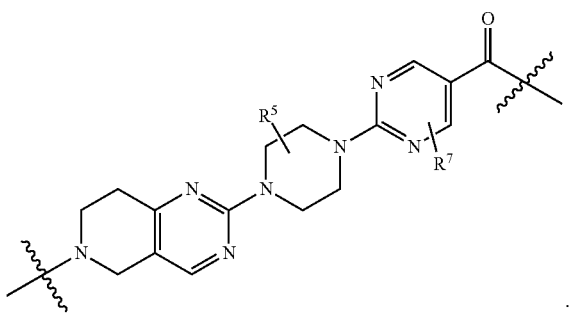

Embodiment I-30. The compound of any one of Embodiments I-1 to I-5, I-8 to I-11 and I-13 to I-24, wherein $A^2$ is

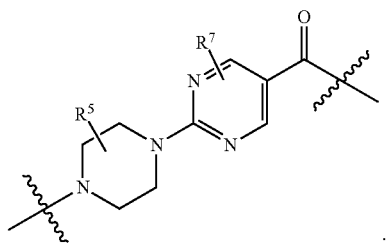

Embodiment I-31. The compound of any one of Embodiments I-1 to I-5, I-8 to I-11 and I-13 to I-24, wherein $A^2$ is

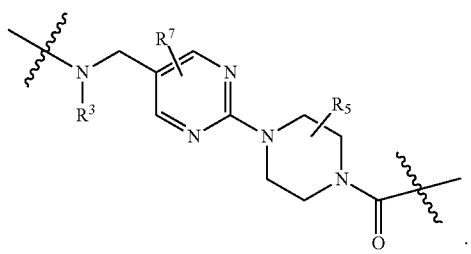

Embodiment I-32. The compound of any one of Embodiments I-1 to I-5, I-8 to I-11 and I-13 to I-24, wherein $A^2$ is

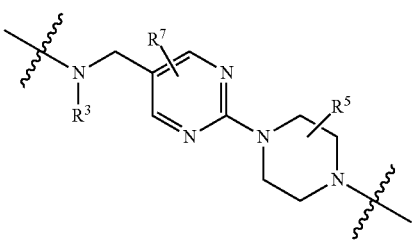

Embodiment I-33. The compound of any one of Embodiments I-1 to I-11 and I-13 to I-30, wherein B is

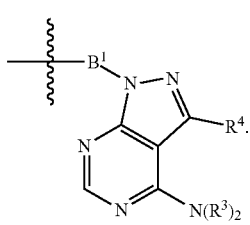

Embodiment I-34. The compound of any one of Embodiments I-1 to I-11 and I-13 to I-30, wherein B is

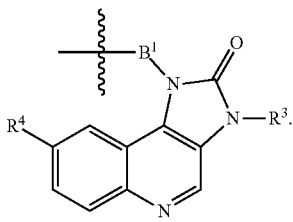

Embodiment I-35. The compound of any one of Embodiments I-1 to I-11 and I-13 to I-34, wherein $B^1$ is

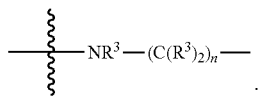

Embodiment I-36. The compound of any one of Embodiments I-1 to I-11 and I-13 to I-34, wherein $B^1$ is

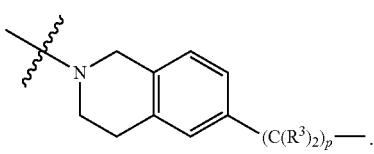

Embodiment I-37. The compound of any one of Embodiments I-1 to I-11 and I-13 to I-36, wherein $R^4$ is 5-12 membered heteroaryl, optionally substituted with —N($R^3$)$_2$, —O$R^3$, halogen, ($C_1$-$C_6$)alkyl, —($C_1$-$C_6$)alkylene-heteroaryl, —($C_1$-$C_6$)alkylene-CN, or —C(O)N$R^3$-heteroaryl.

Embodiment I-38. The compound of any one of Embodiments I-1 to I-37, or a pharmaceutically acceptable salt or tautomer thereof, wherein compound has the following formula:

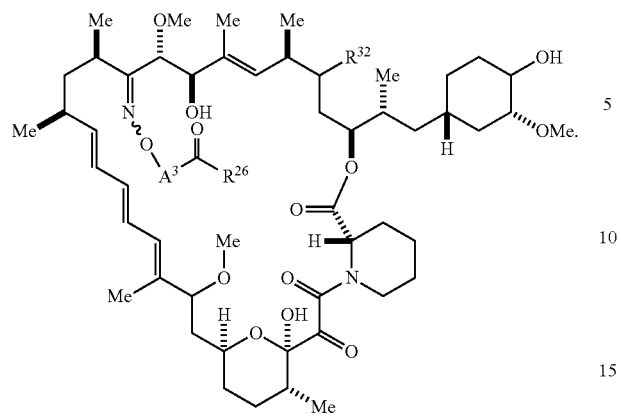
Embodiment I-39. A compound selected from the group consisting of:
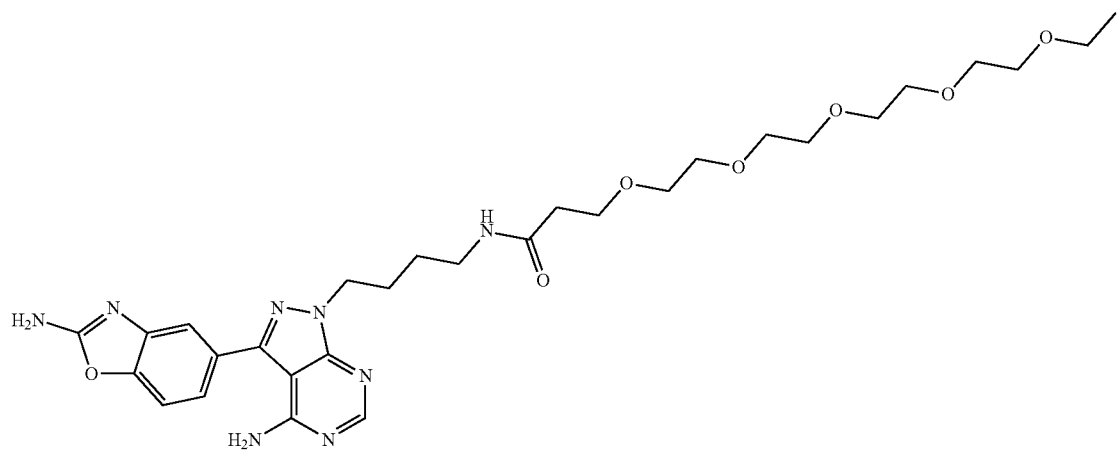
Example 1
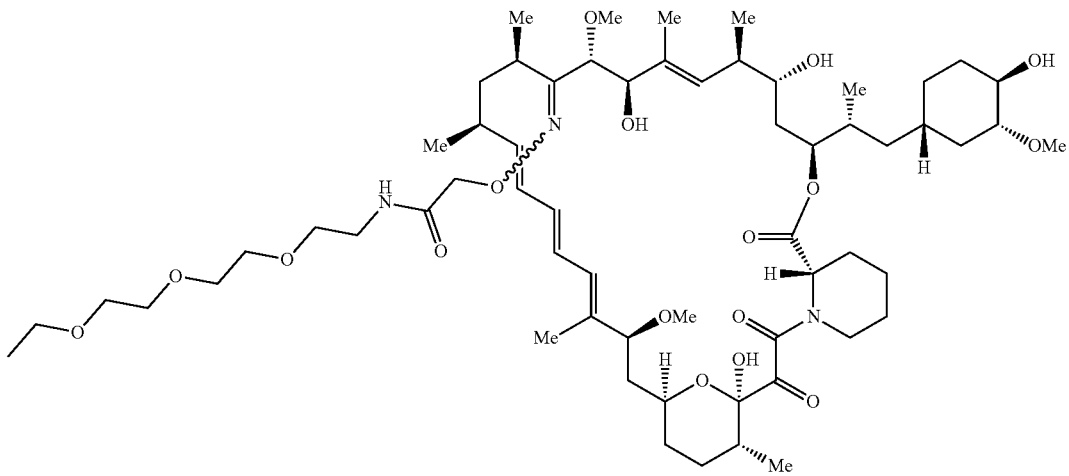

Example 2
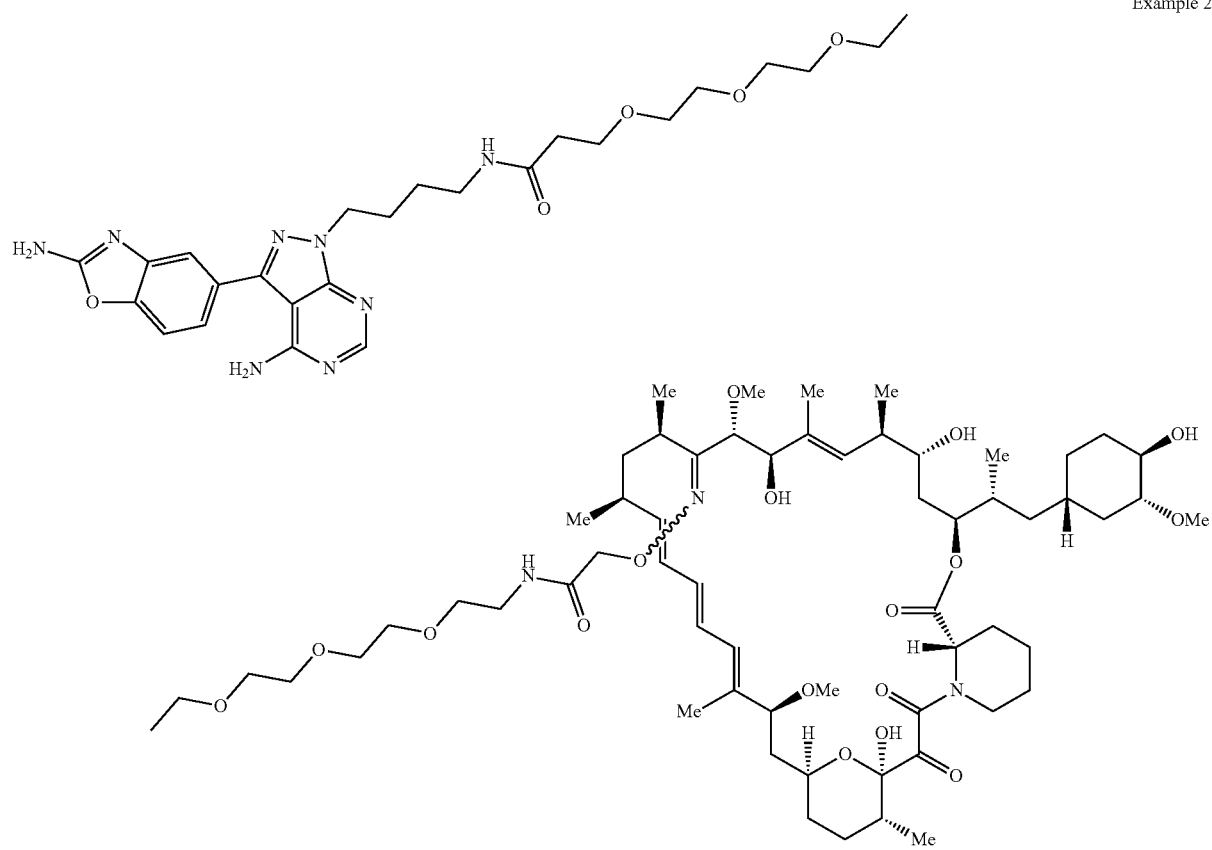
Example 3
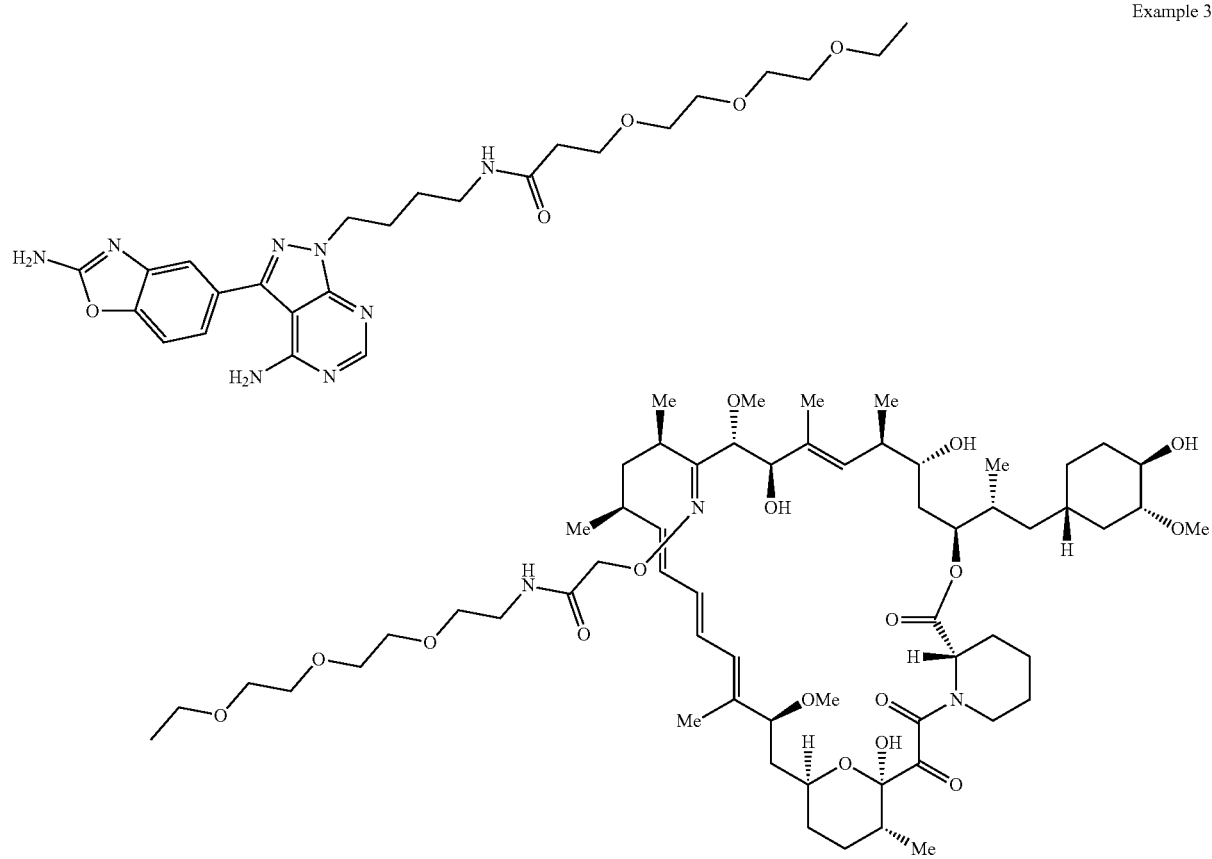

Example 4
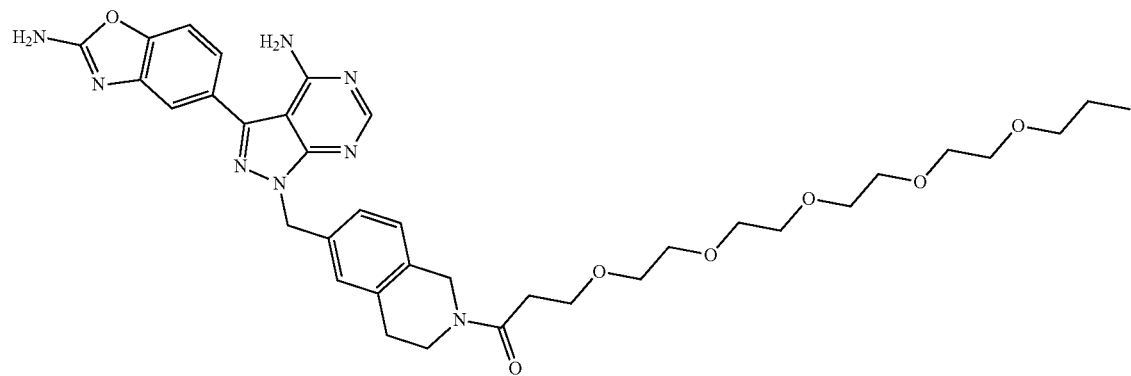
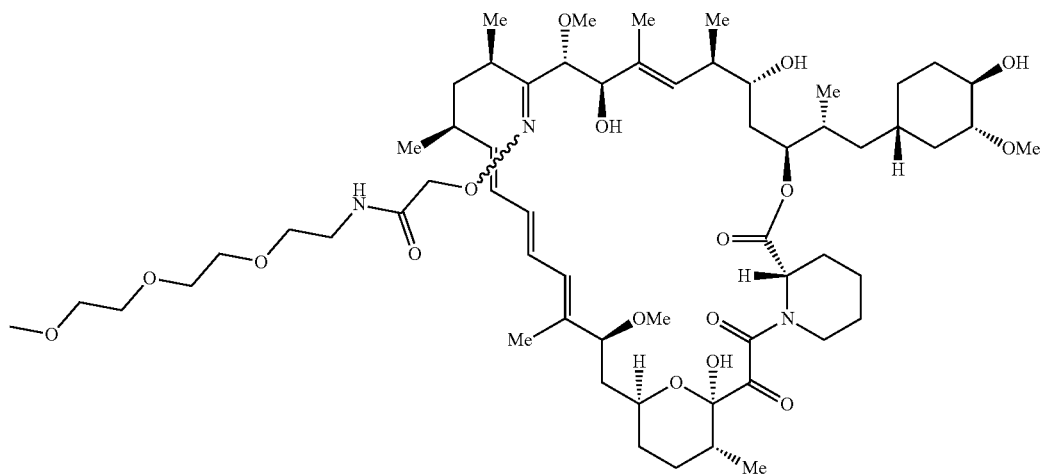
Example 5
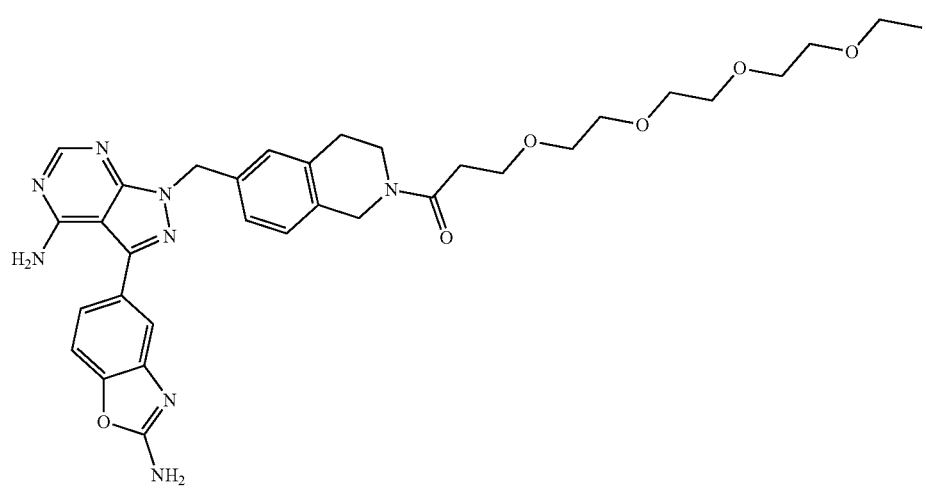

223 224
-continued
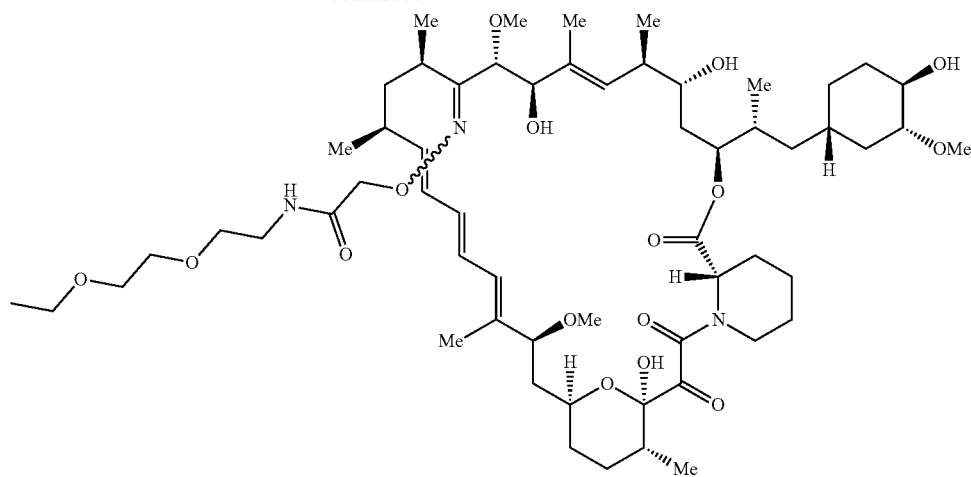
Example 6
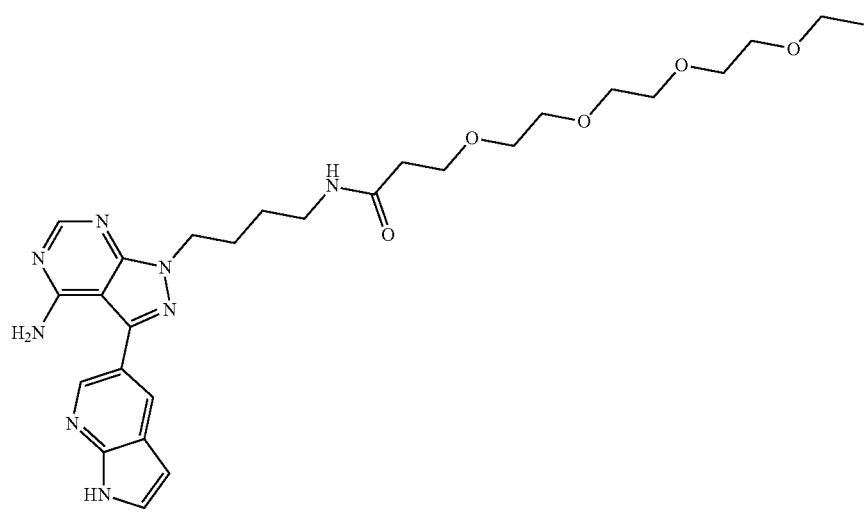
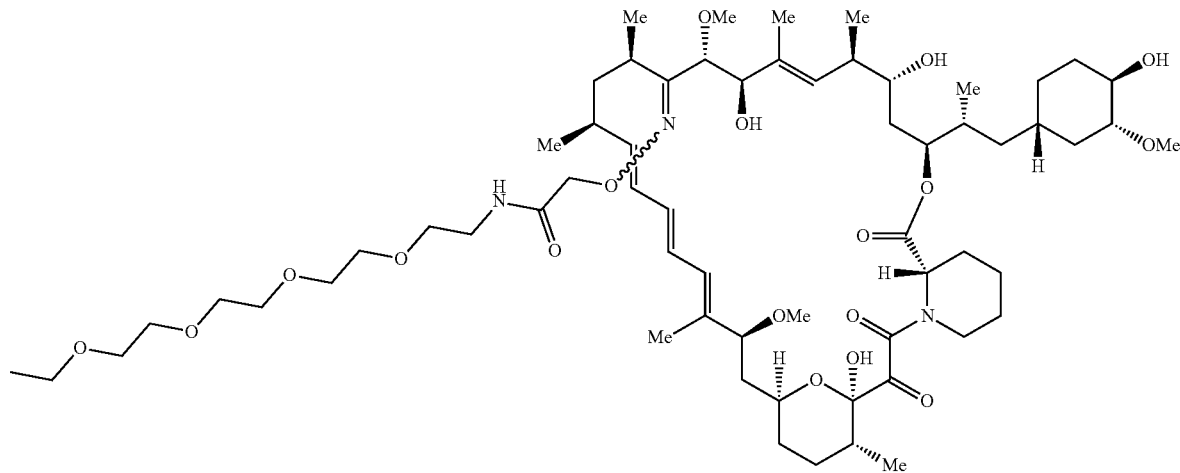

Example 7
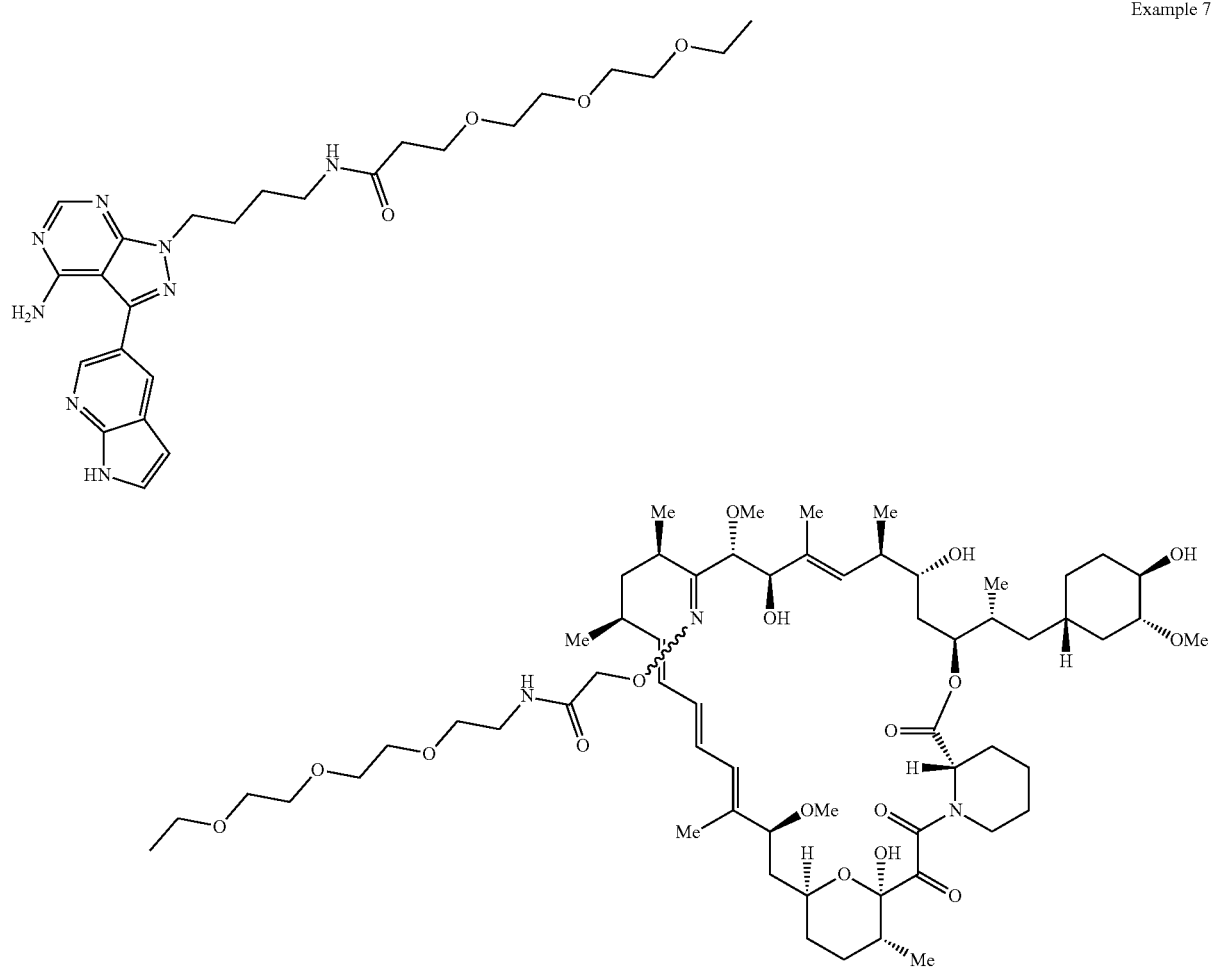
Example 8
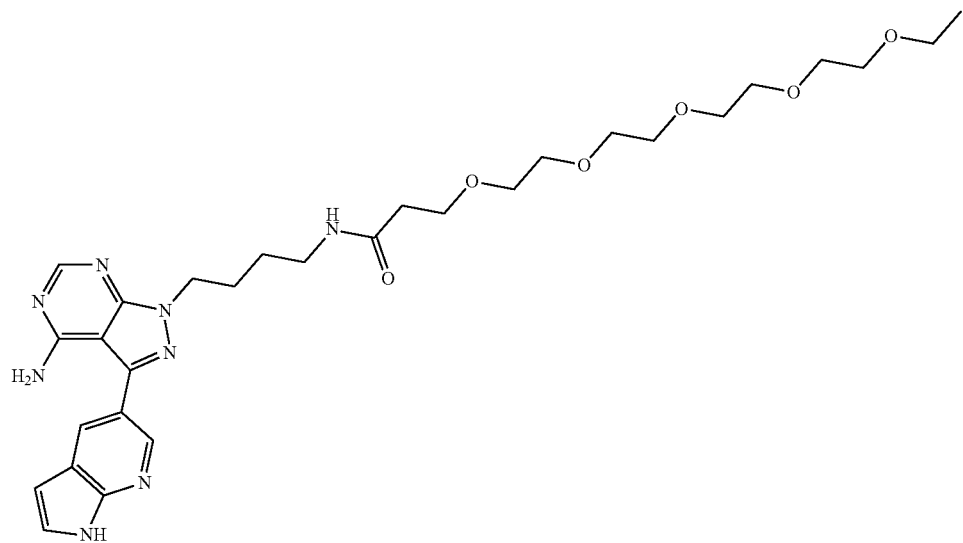

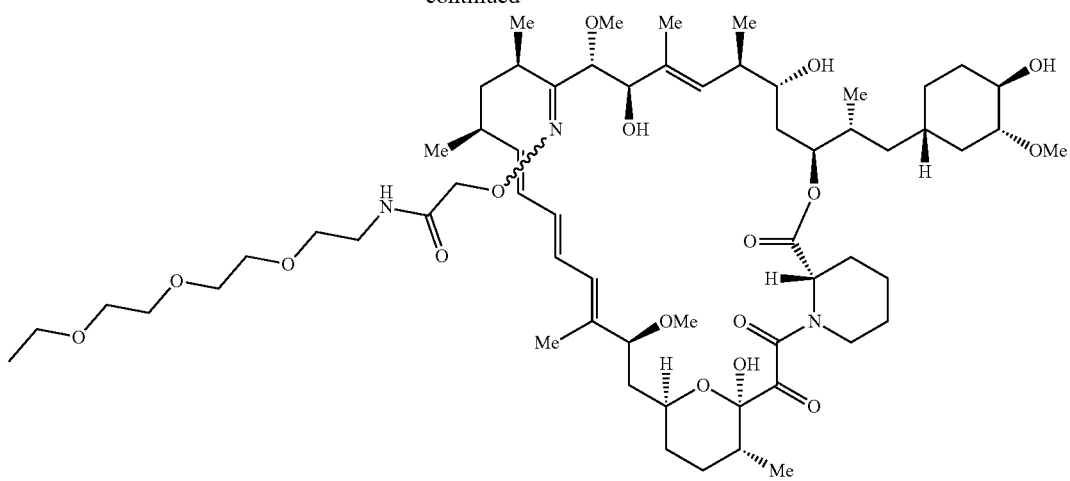
Example 9
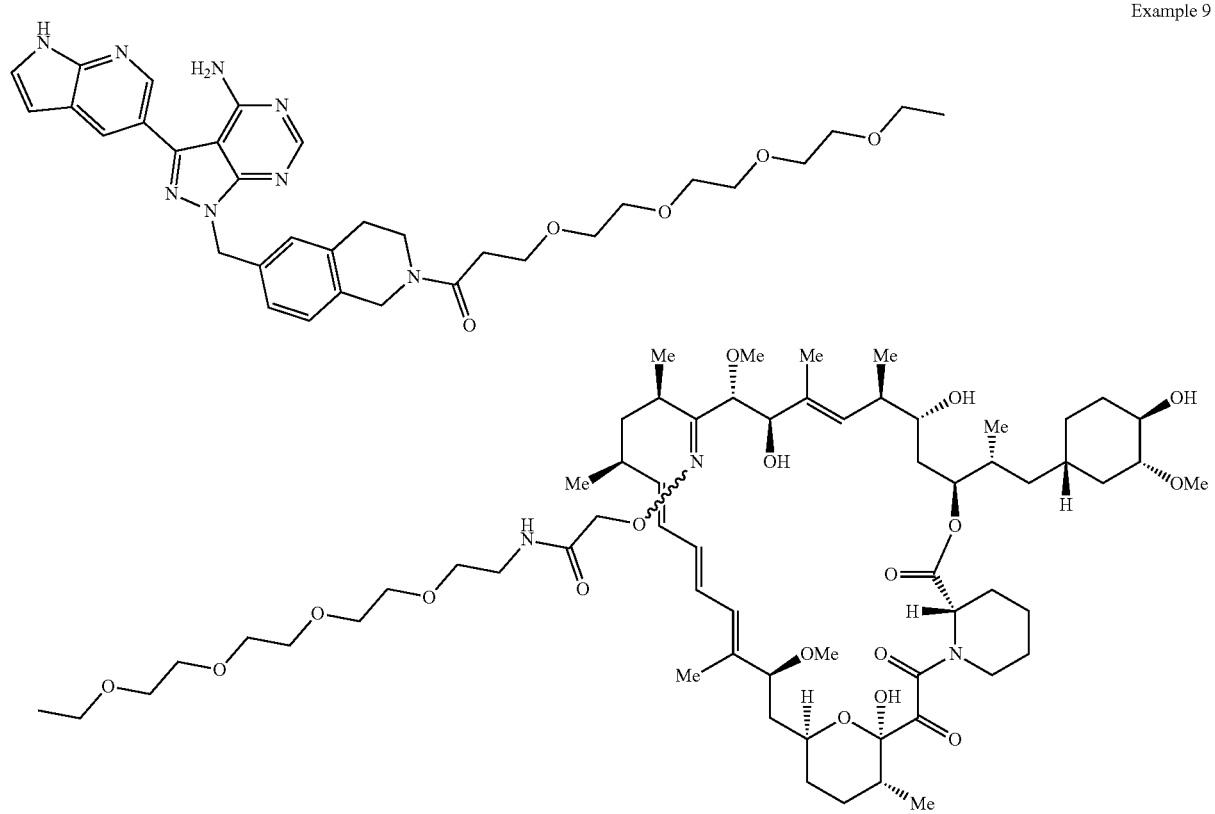
Example 10
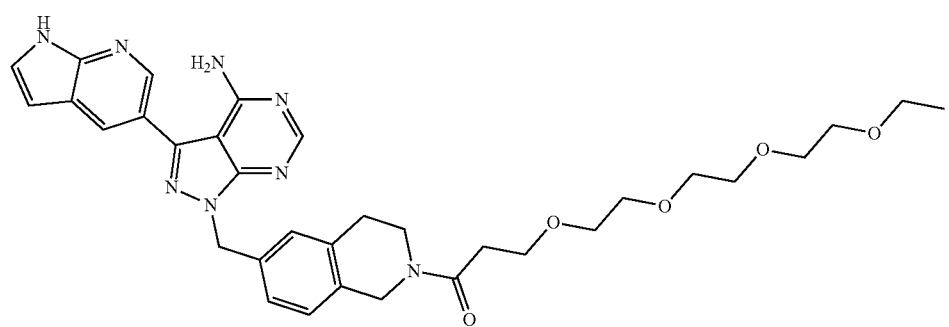

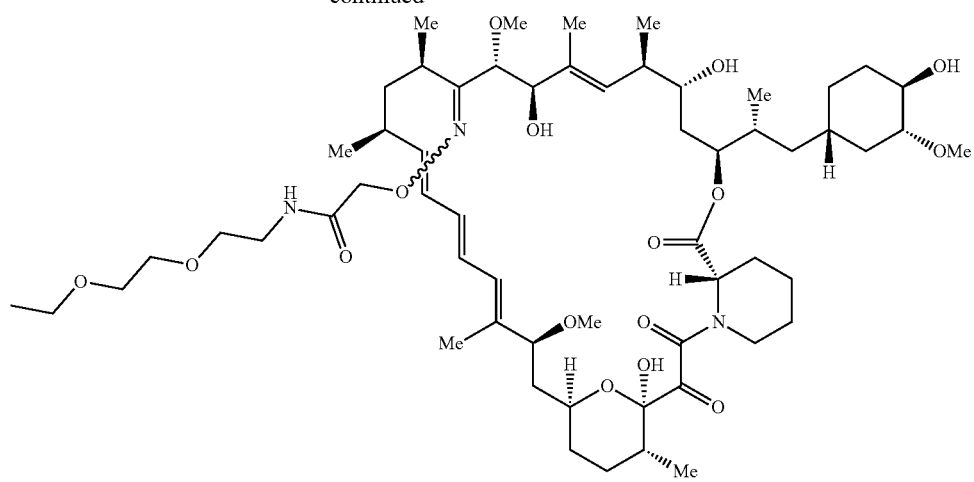
Example 11
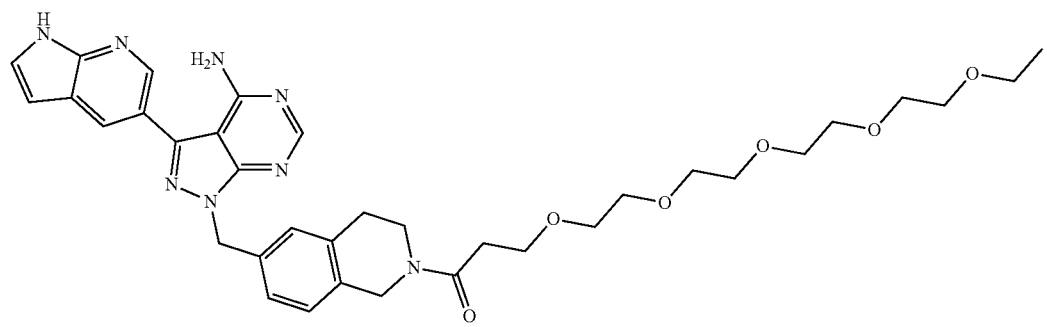
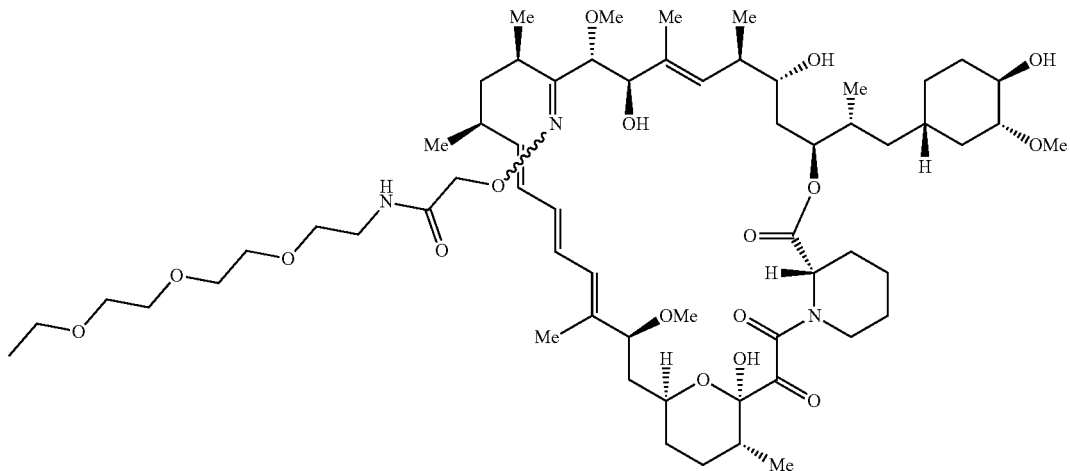
Example 12
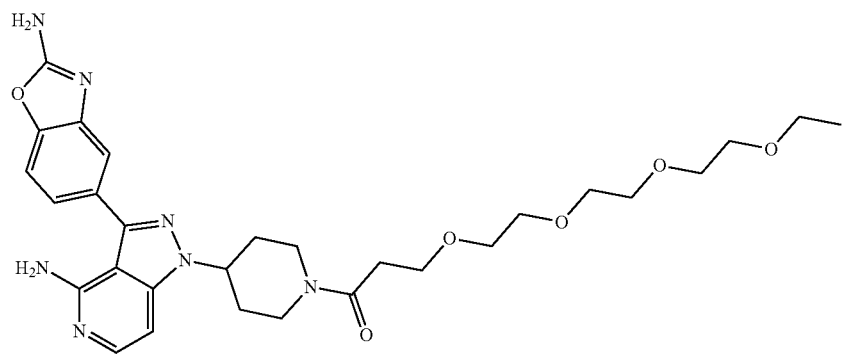

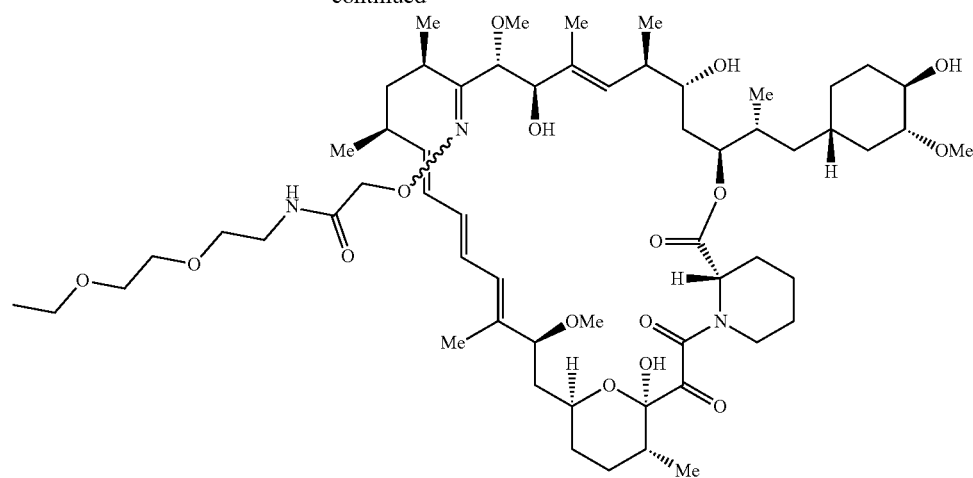
Example 13
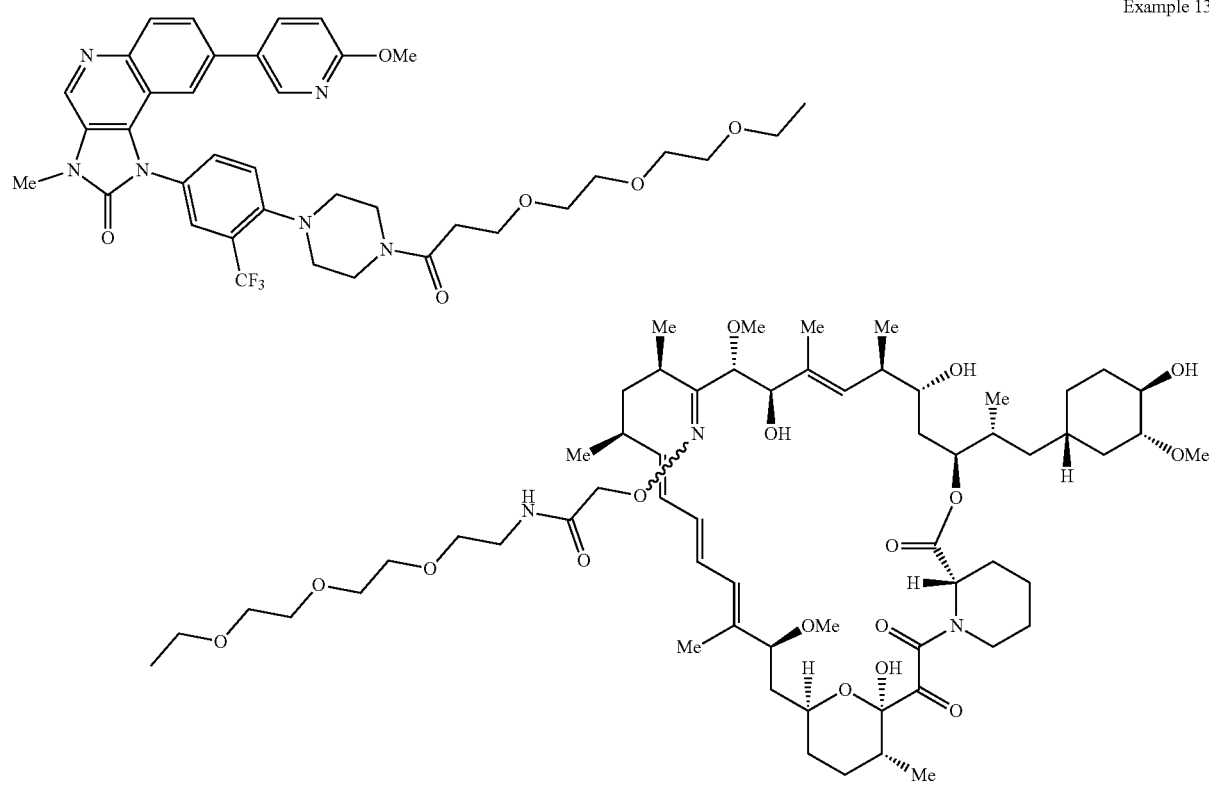
Example 14
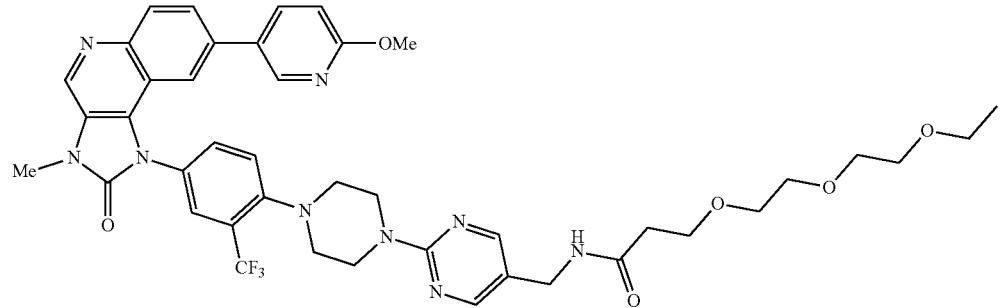

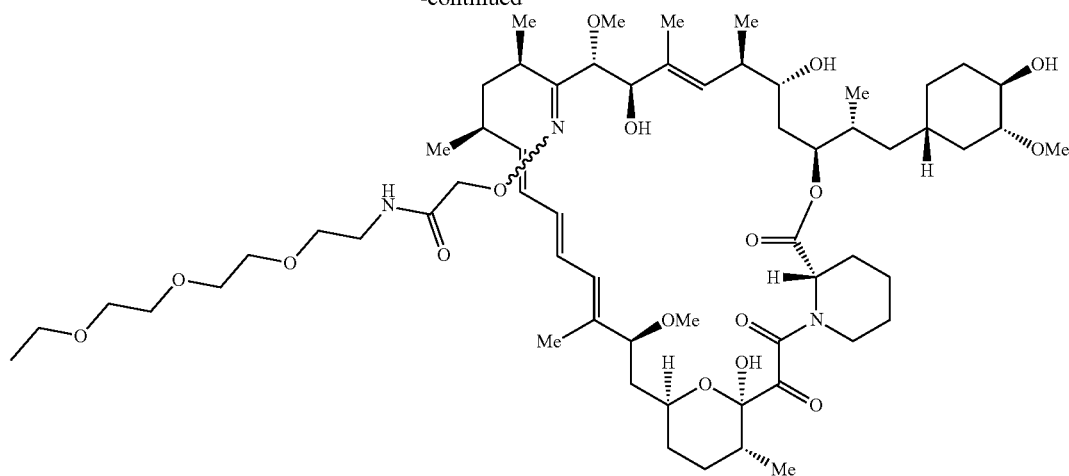
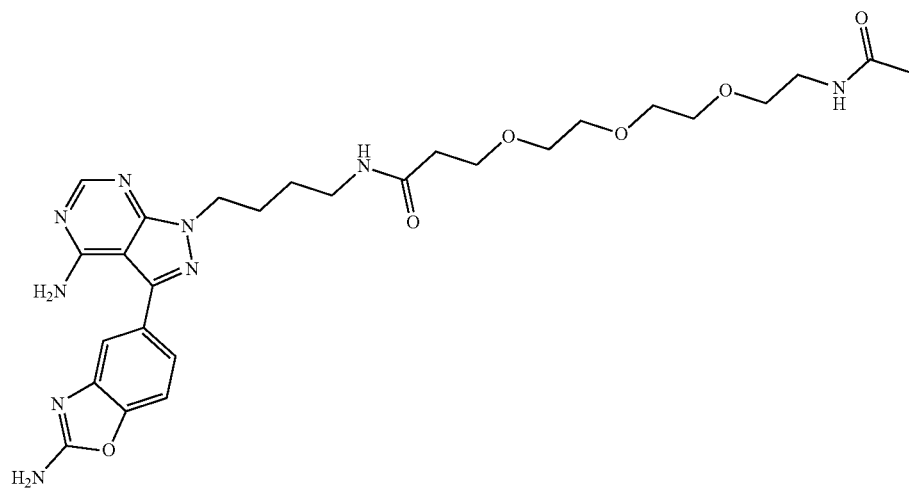
Example 15
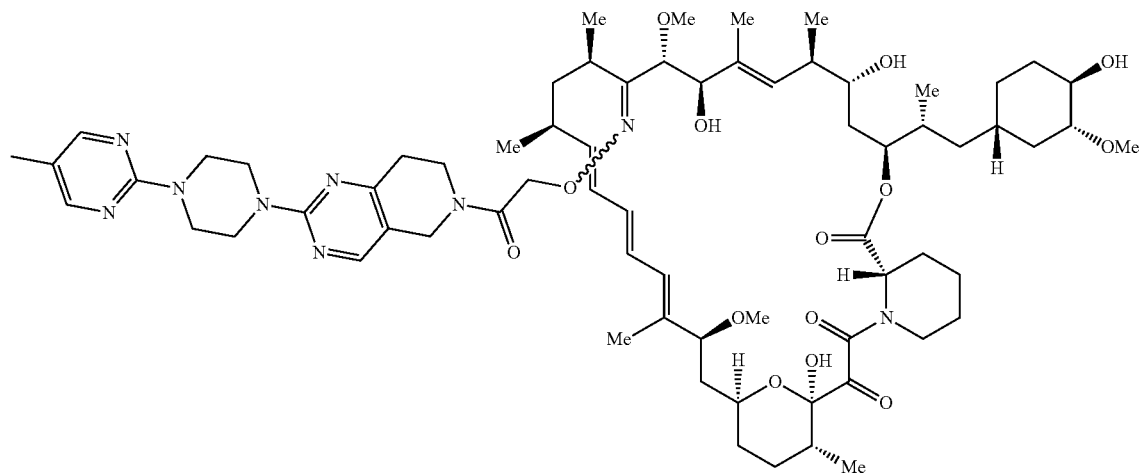

Example 16
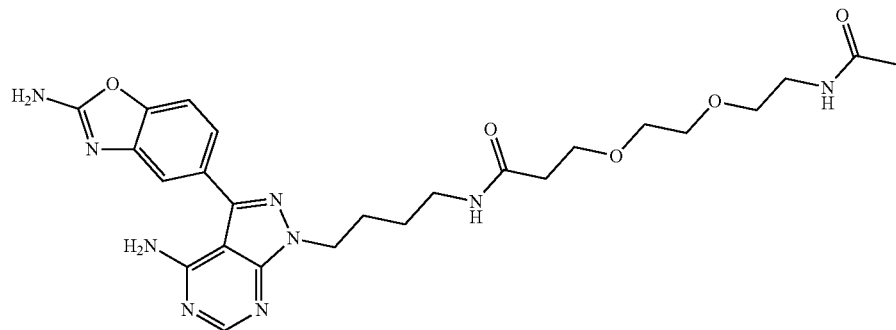
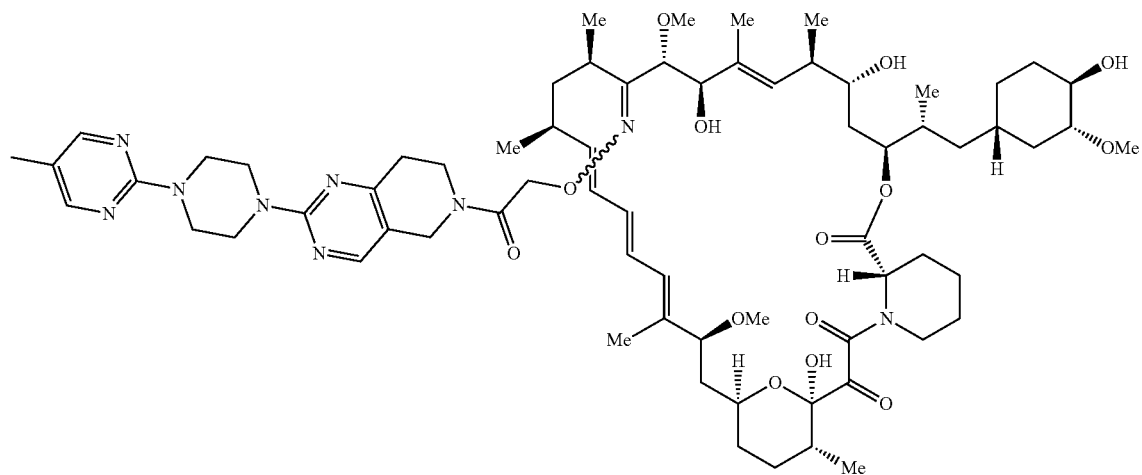
Example 17
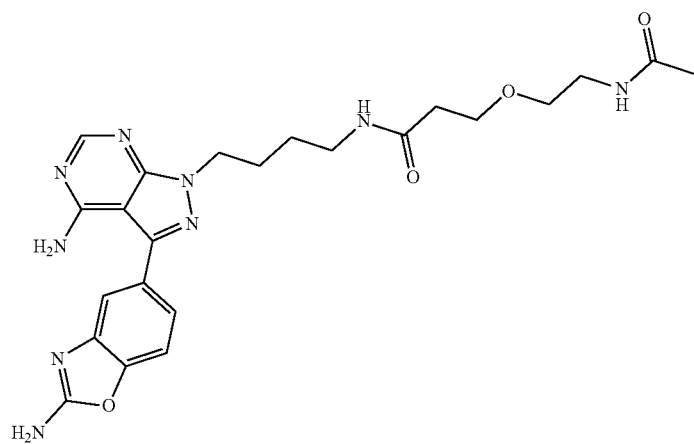

-continued
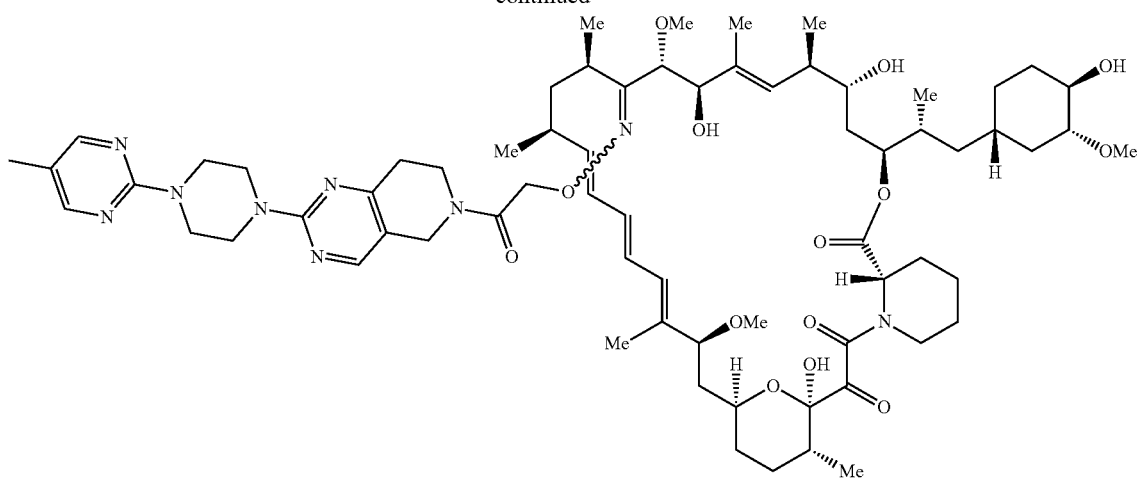
Example 18
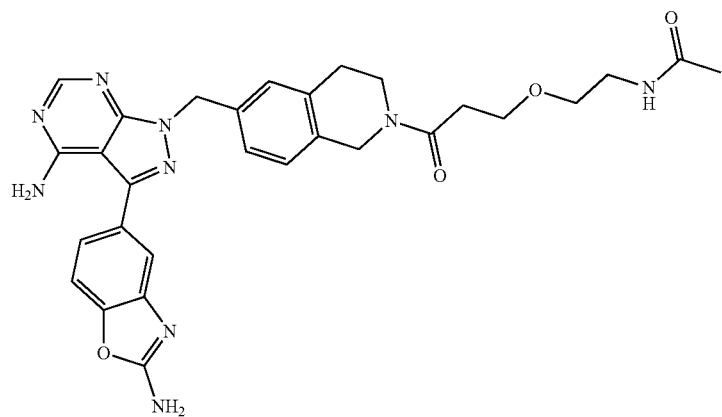
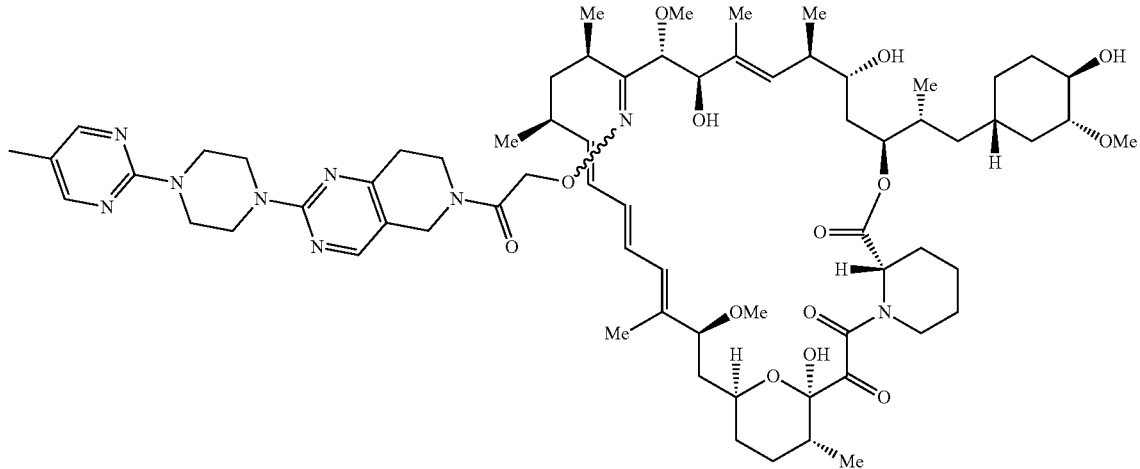
Example 19
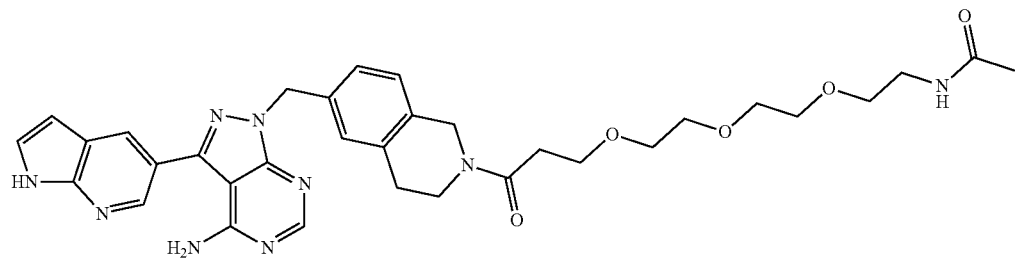

-continued
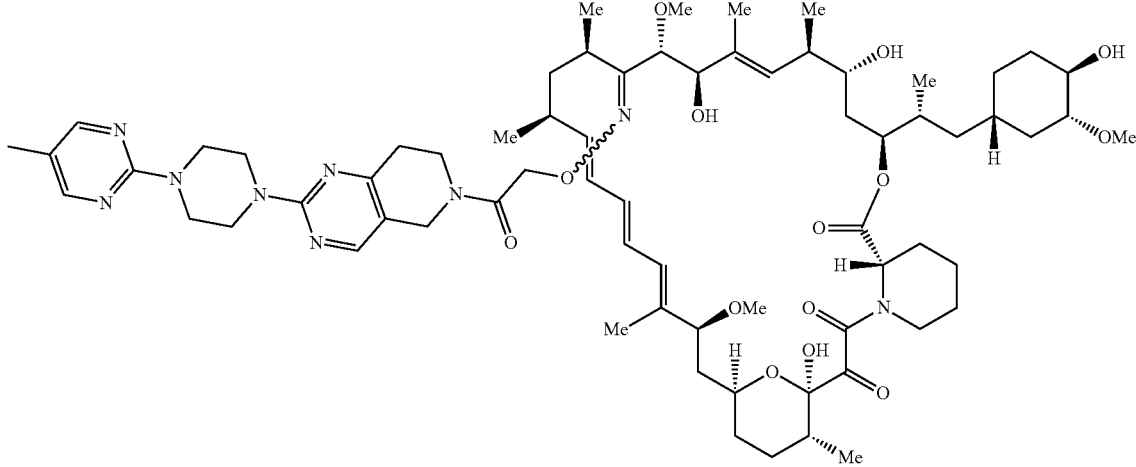
Example 20
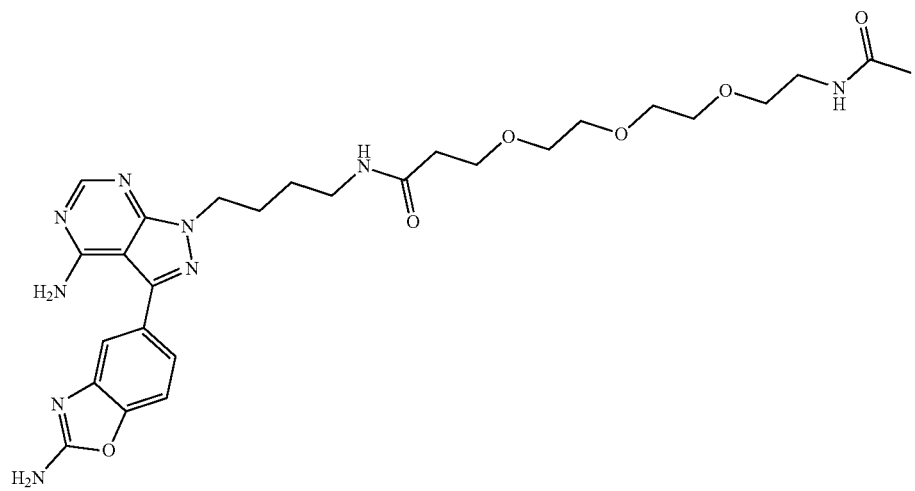
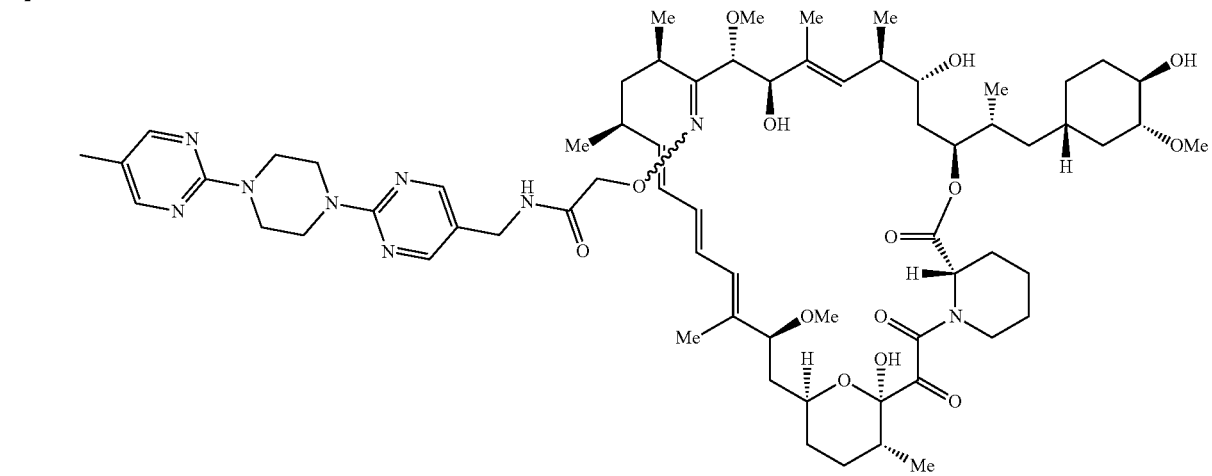
Example 21
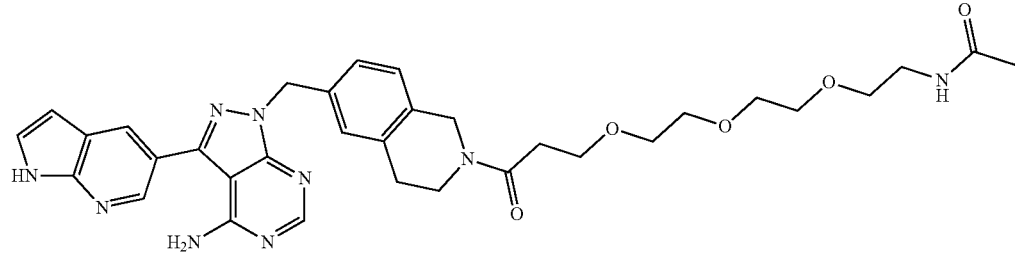

-continued
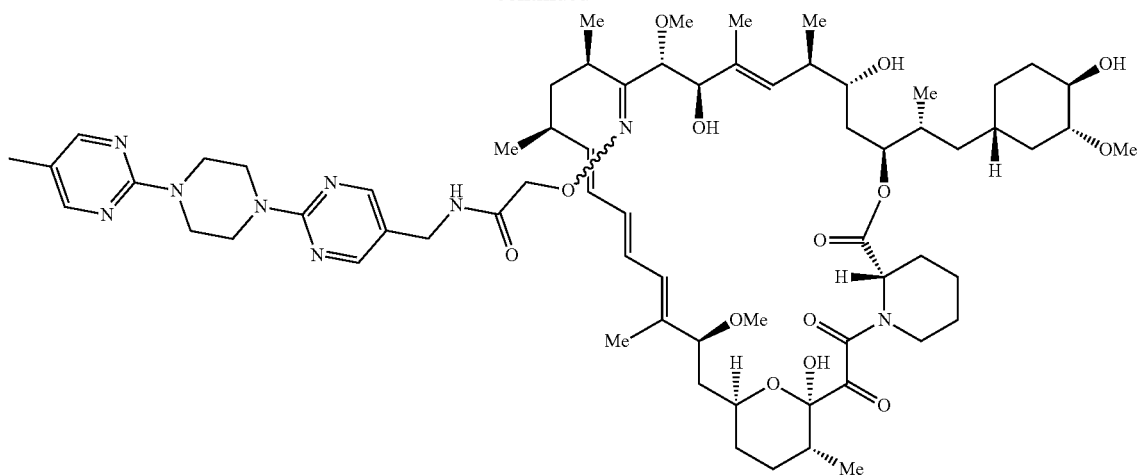
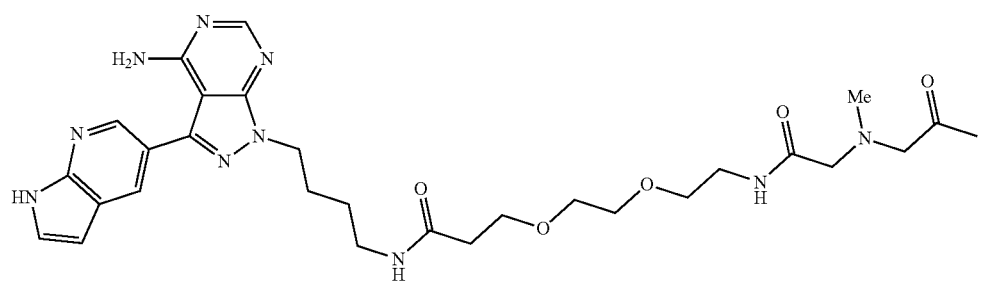
Example 22
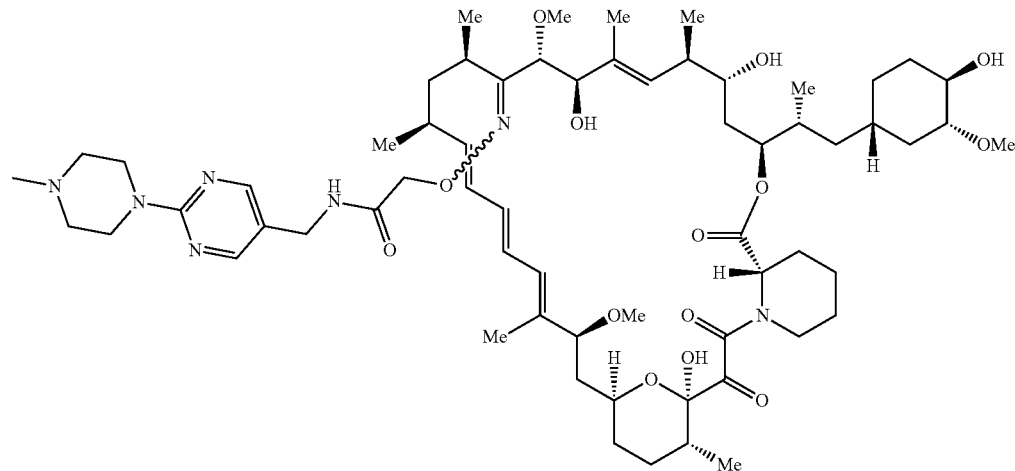

Example 23
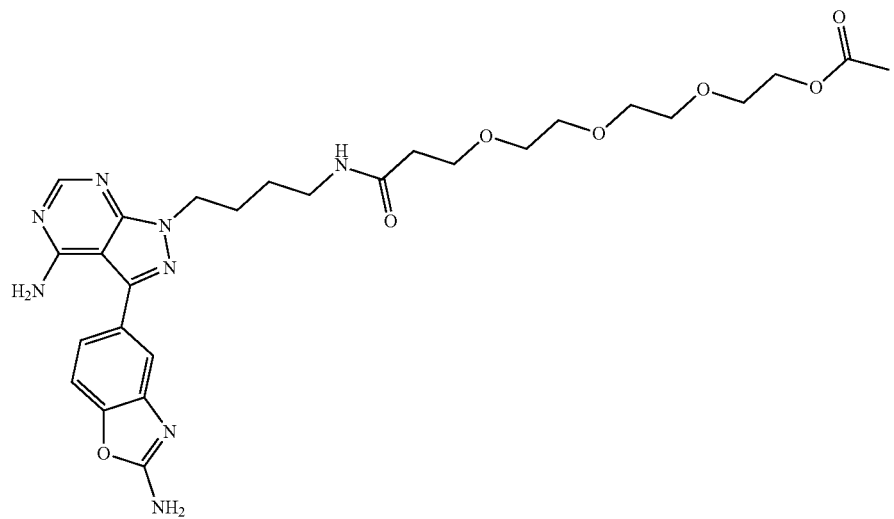
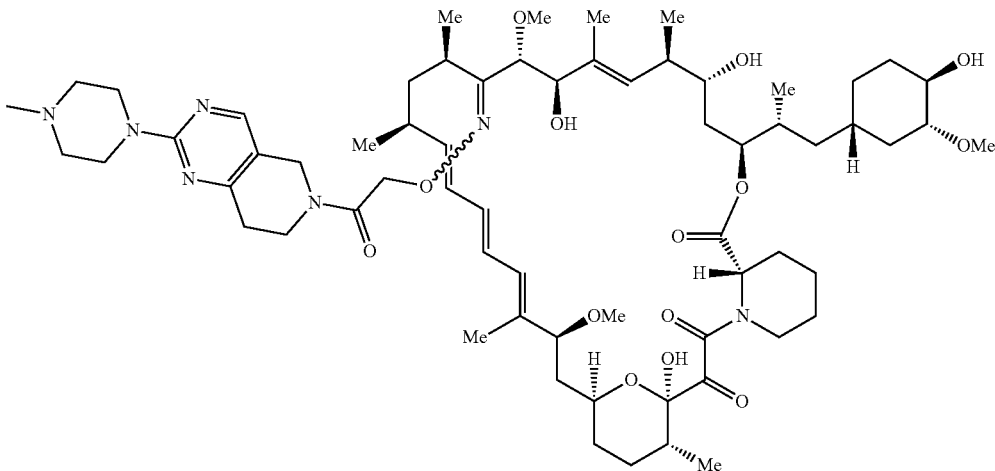
Example 24
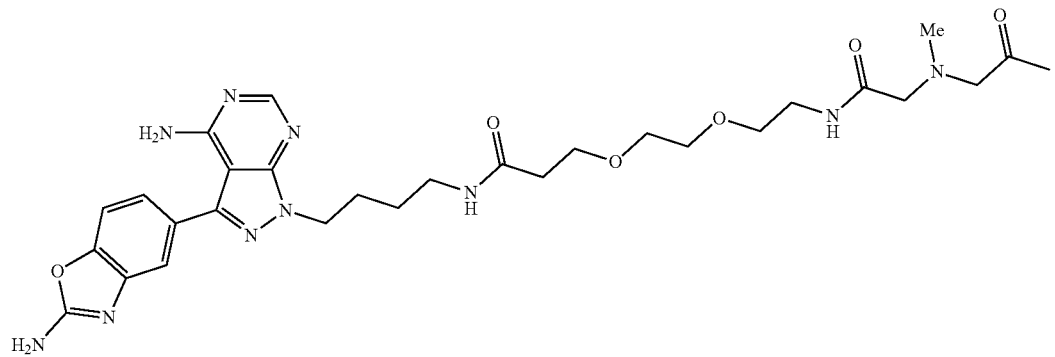

-continued
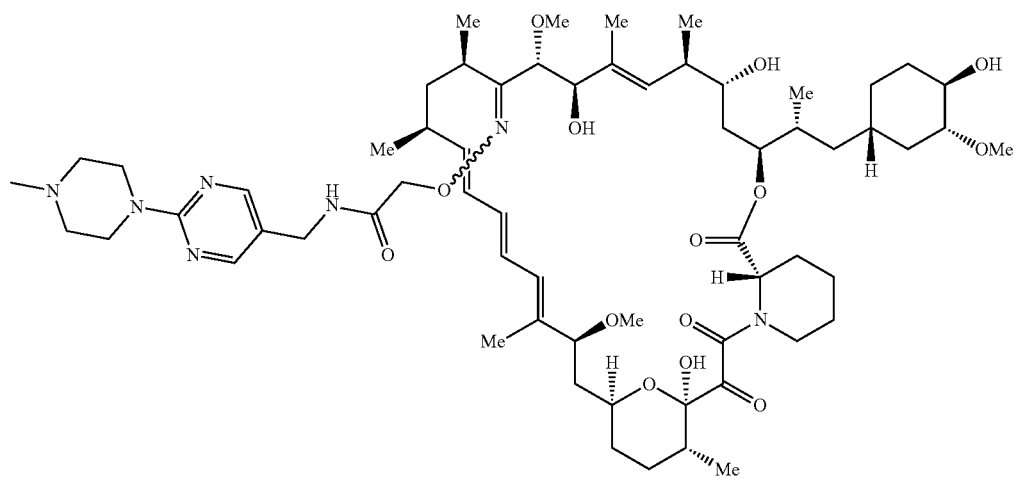
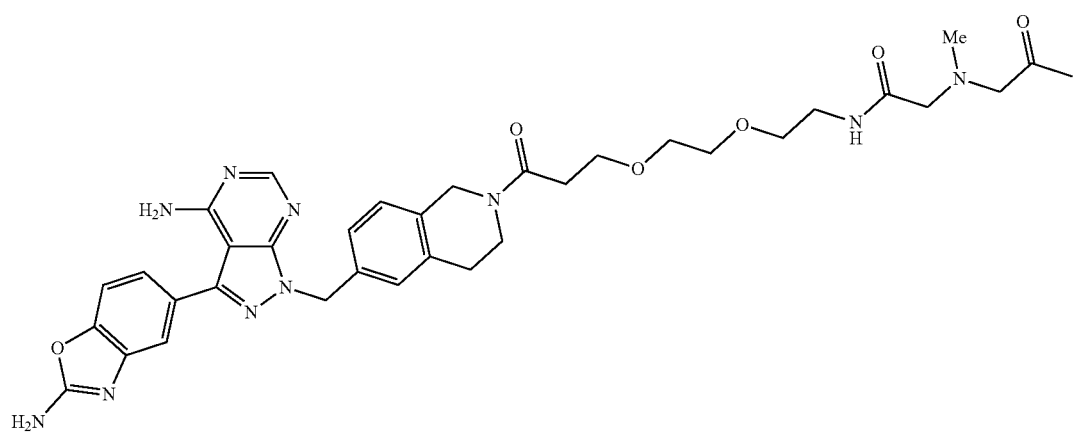
Example 25
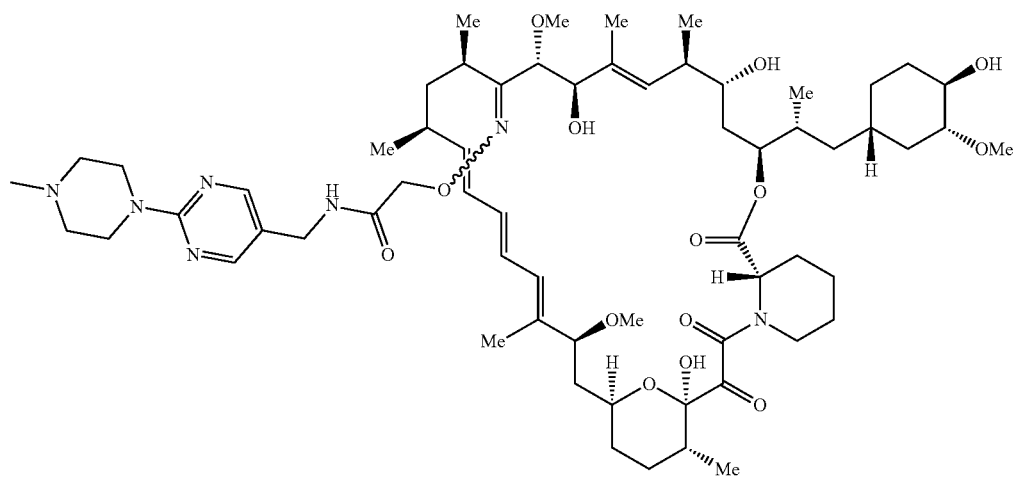

Example 26
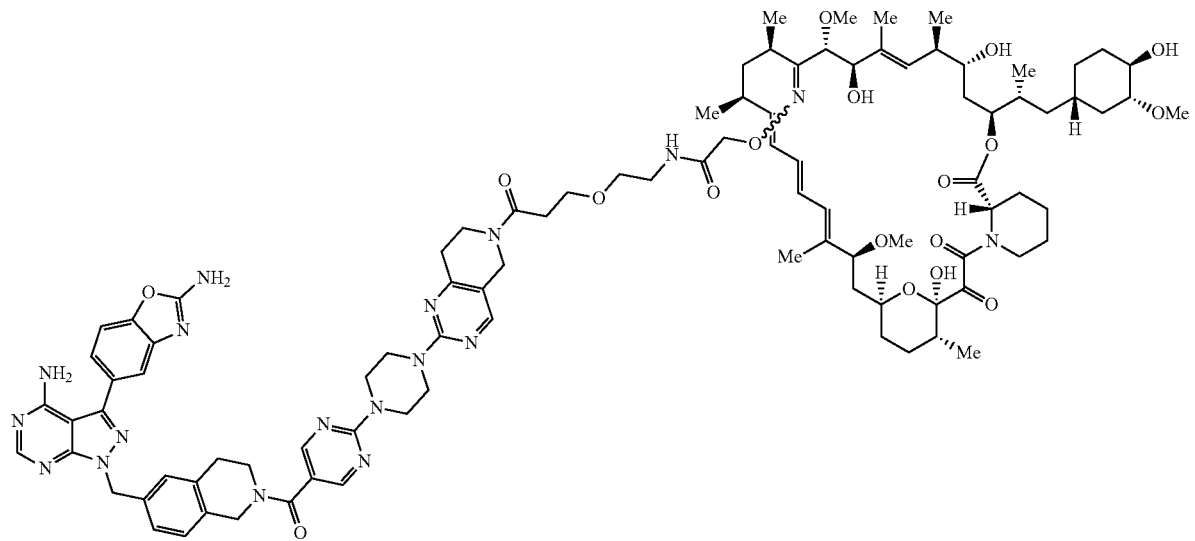
Example 27
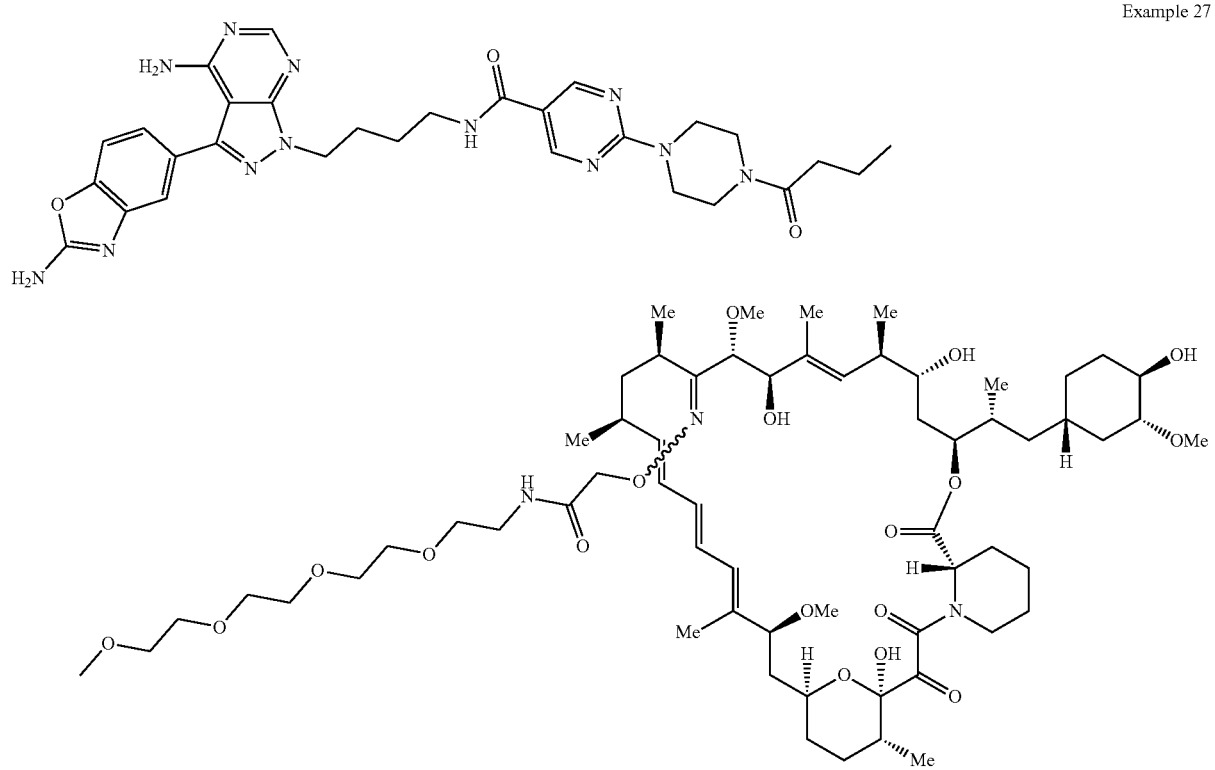
Example 28
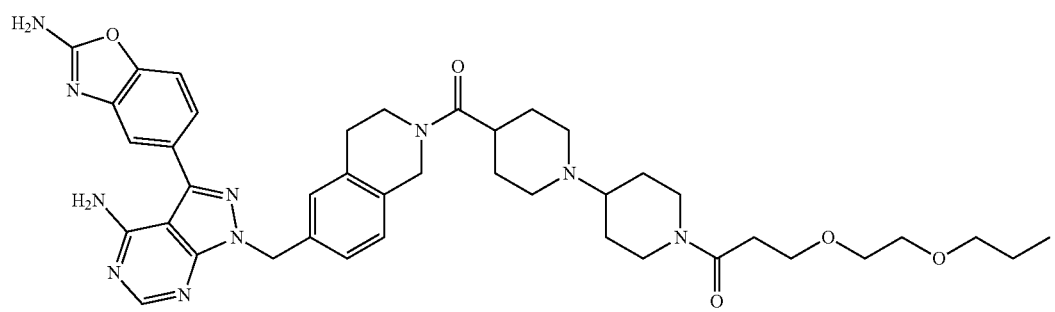

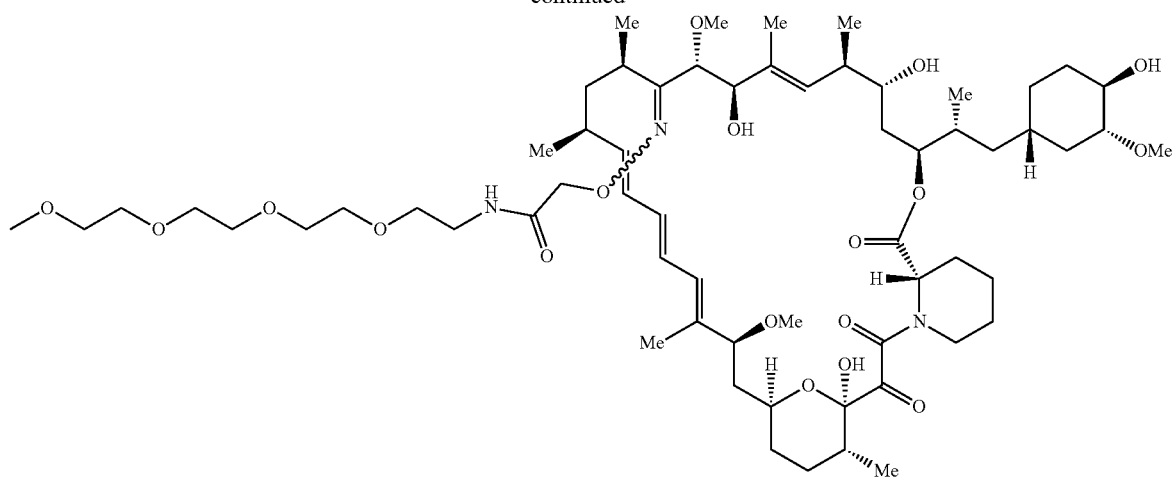
-continued
Example 29
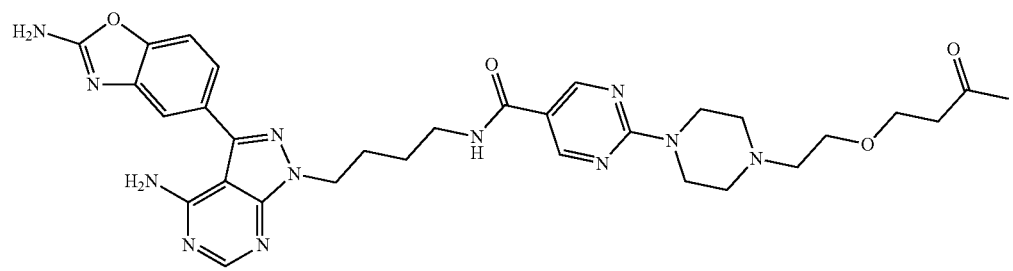
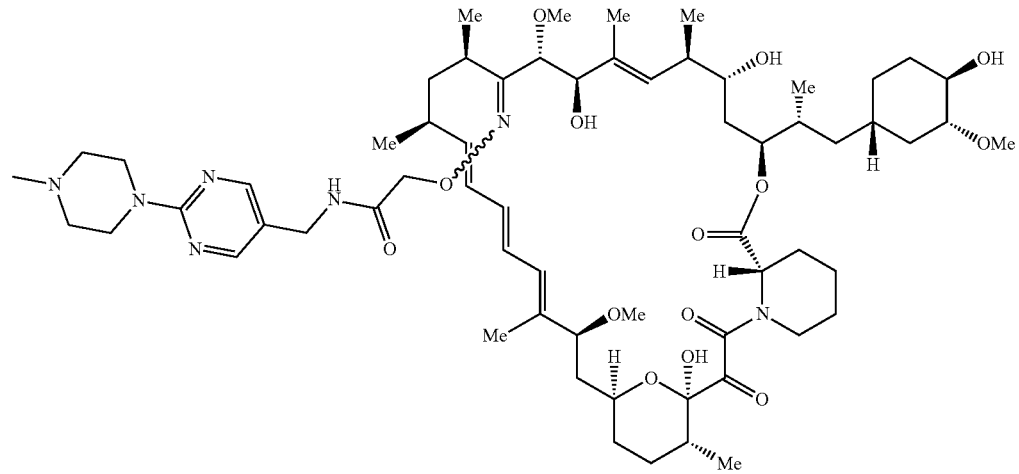
Example 30
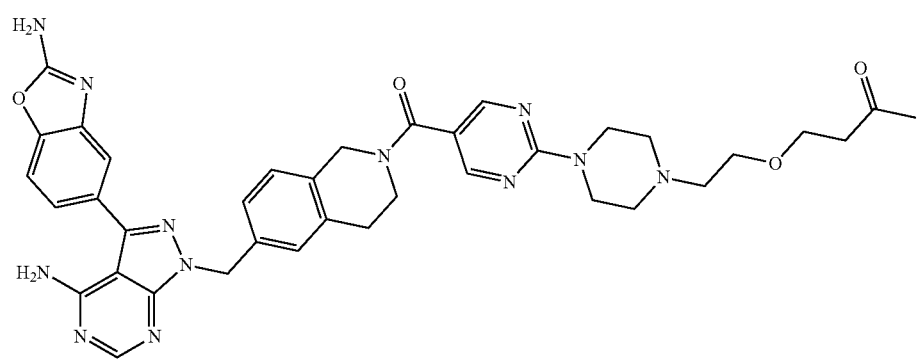

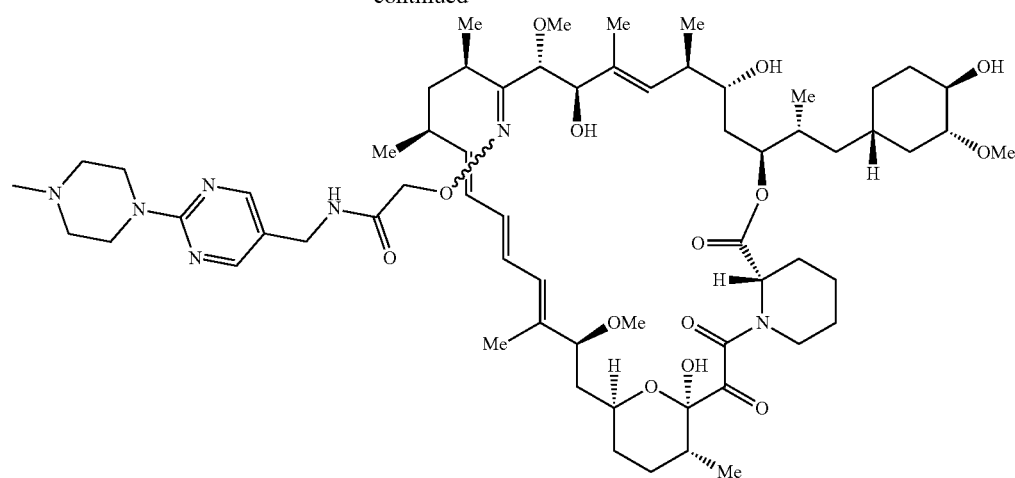
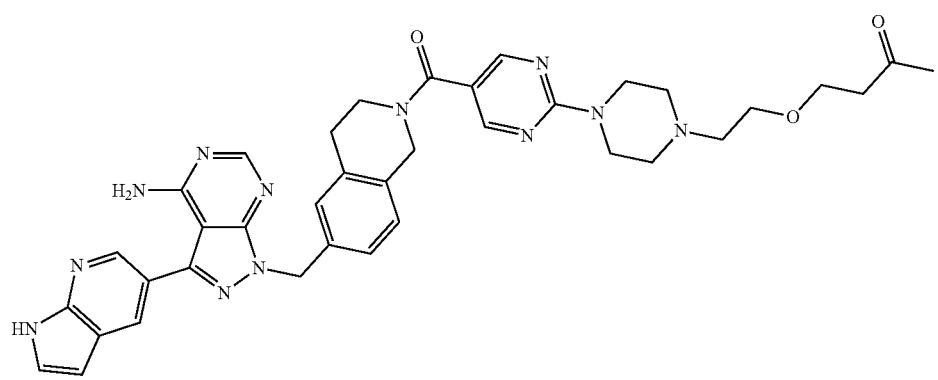
Example 31
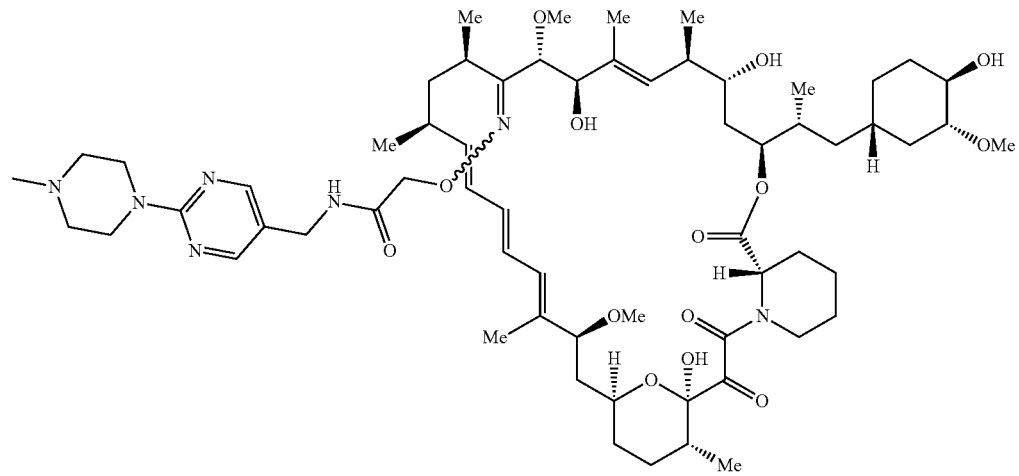

Example 32
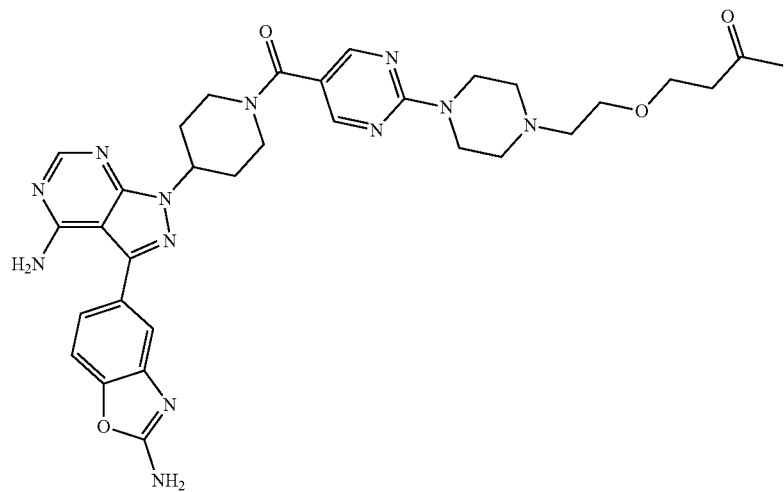
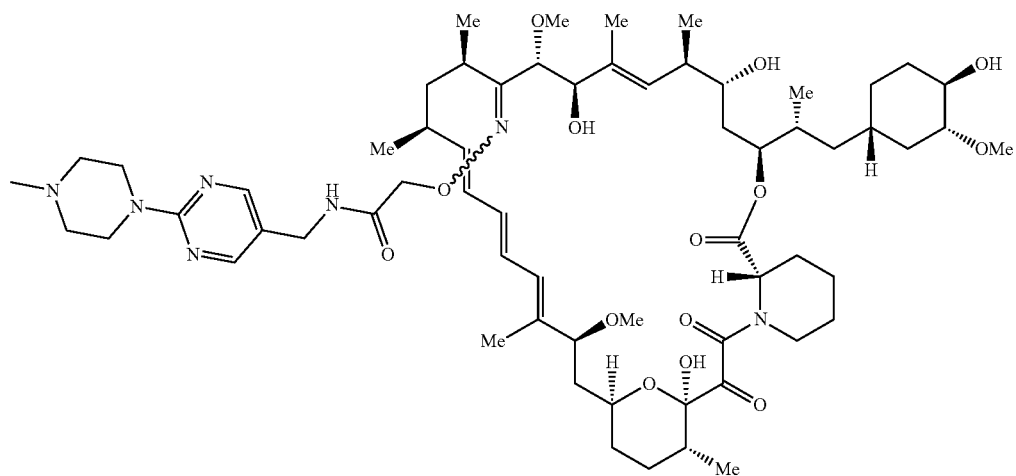
Example 33
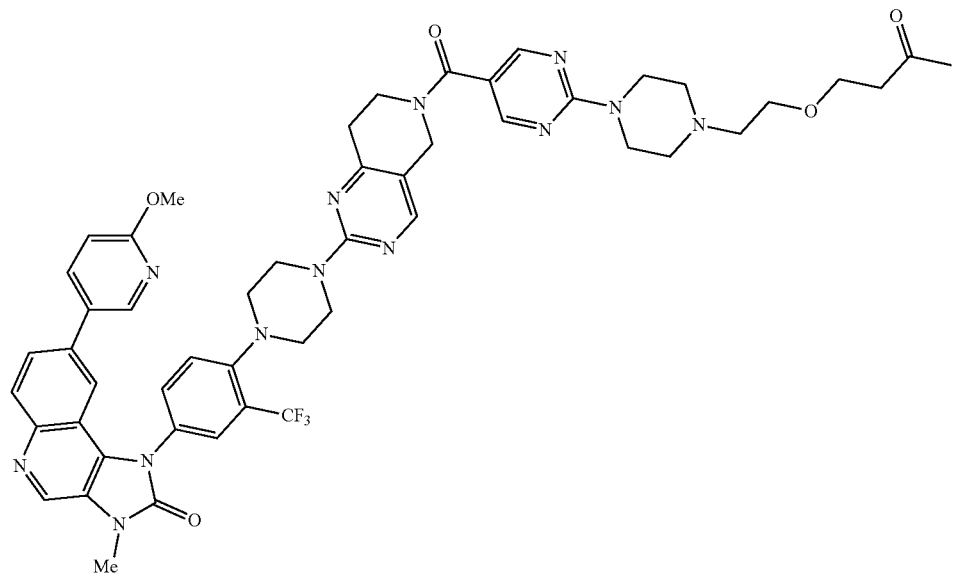

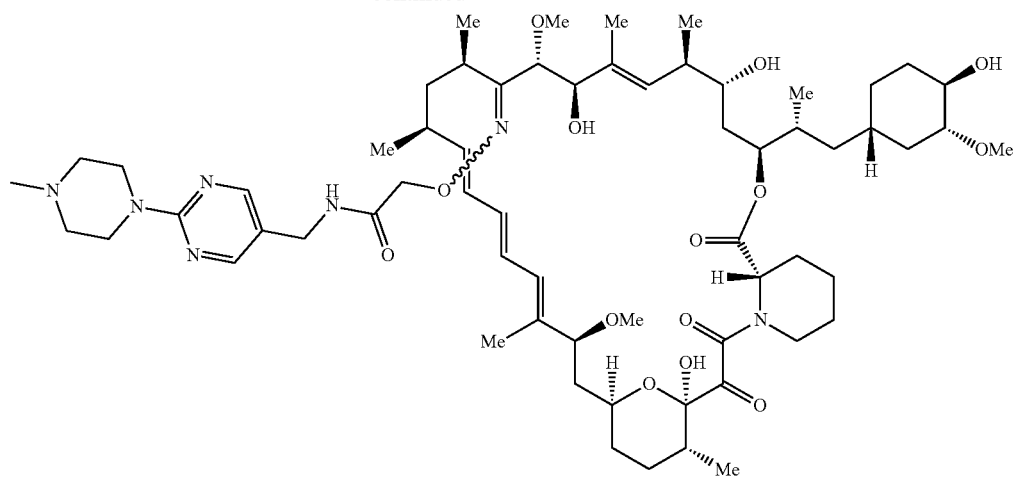
Example 34
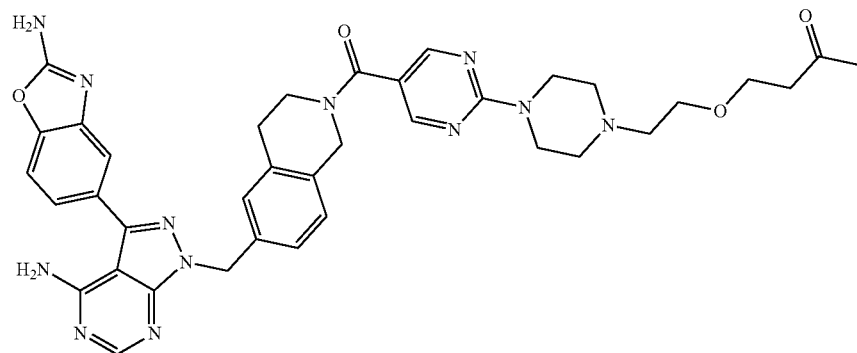
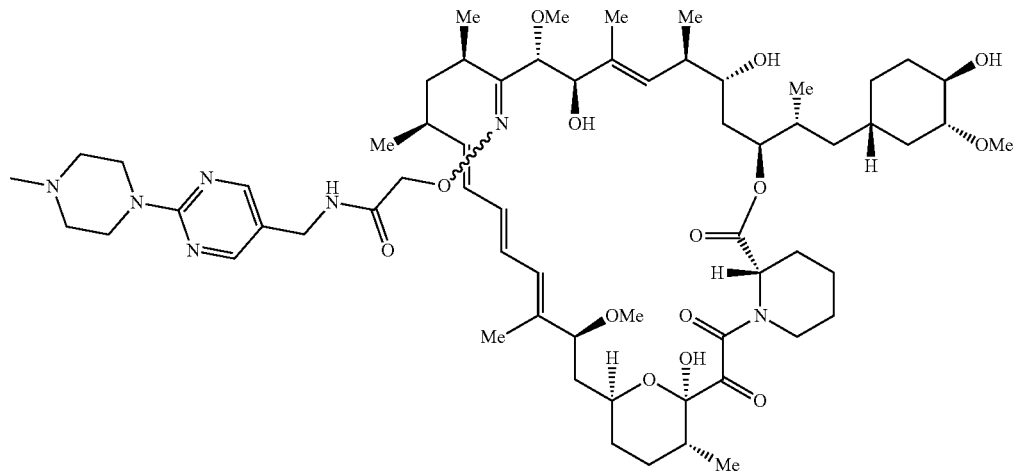
Example 35
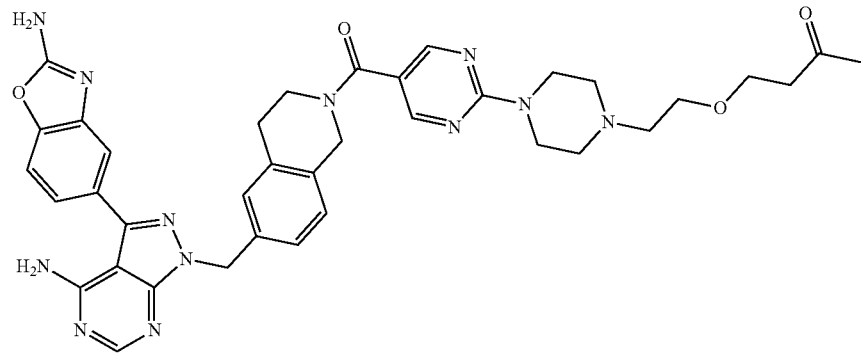

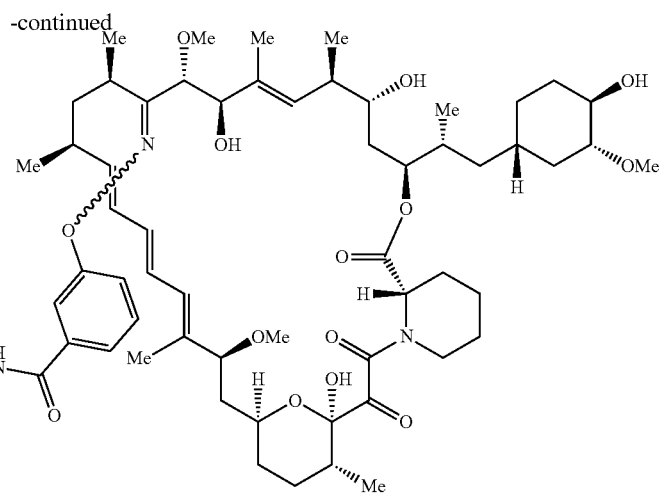
Example 36
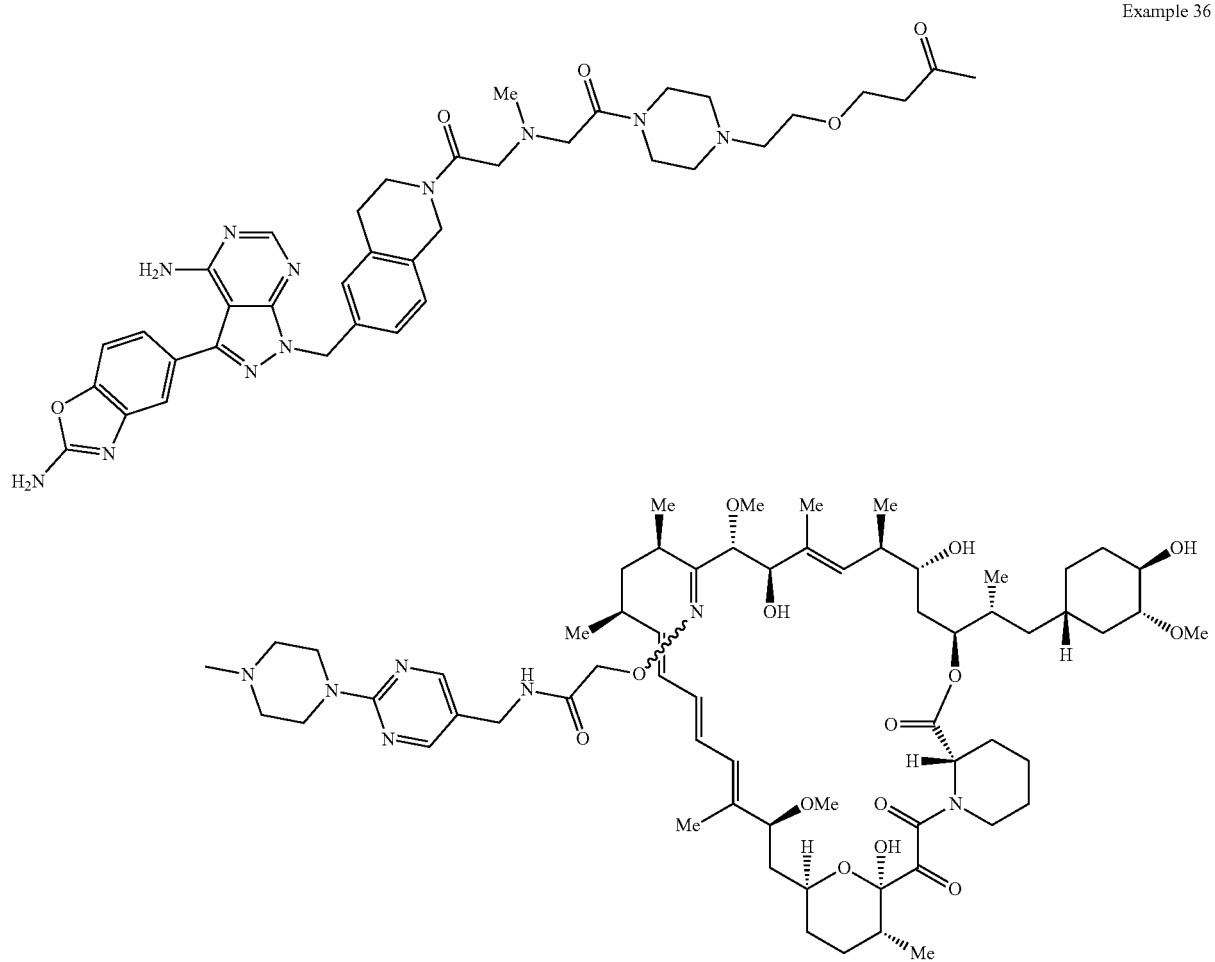
Example 37
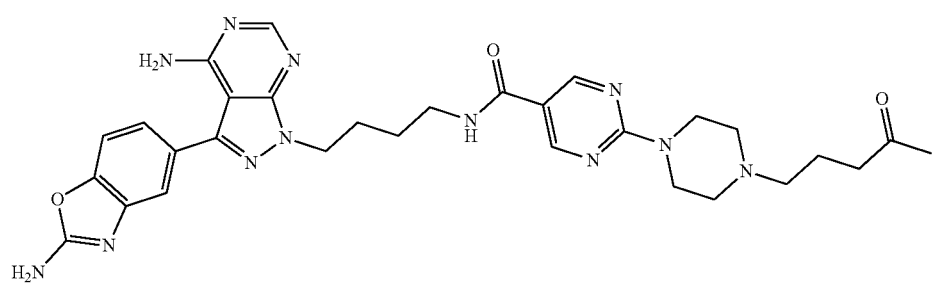

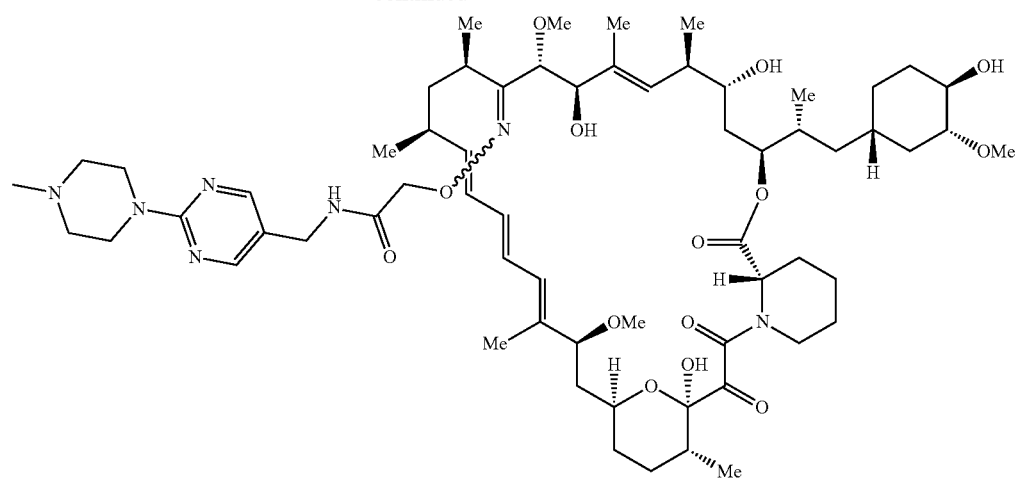
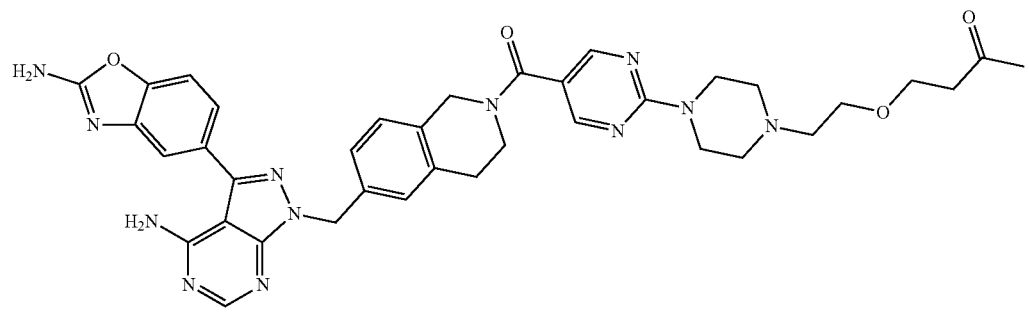
Example 38
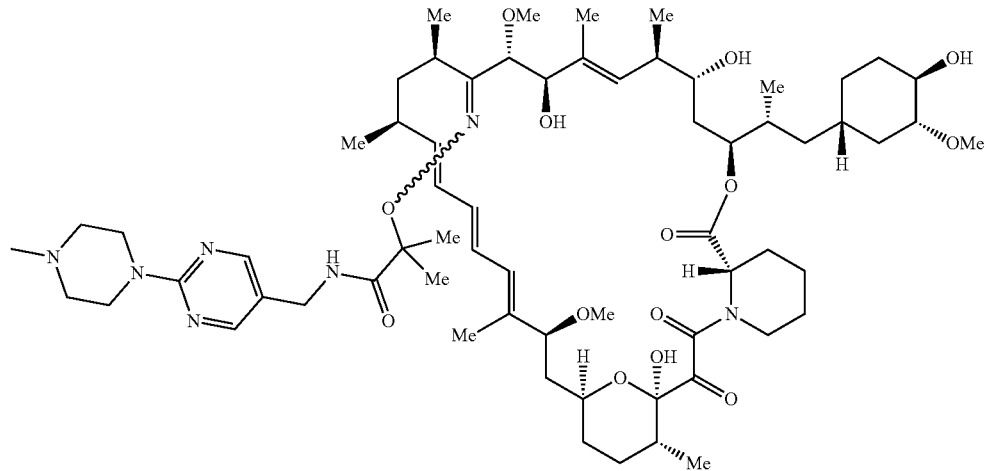
Example 39
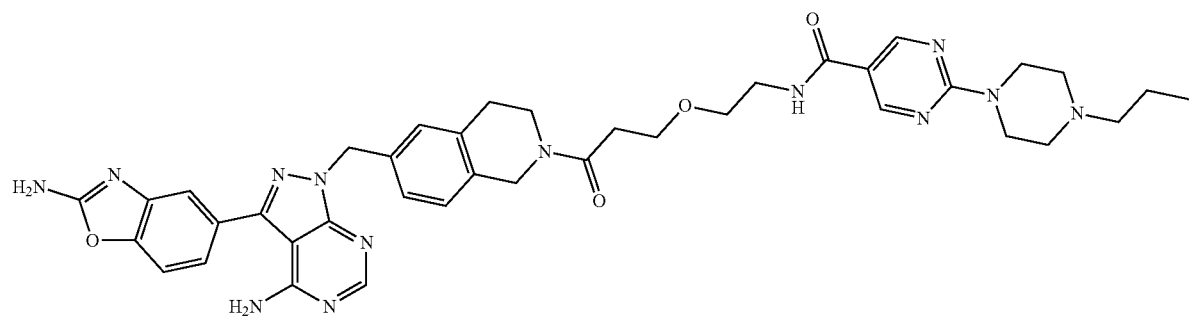

261 262
-continued
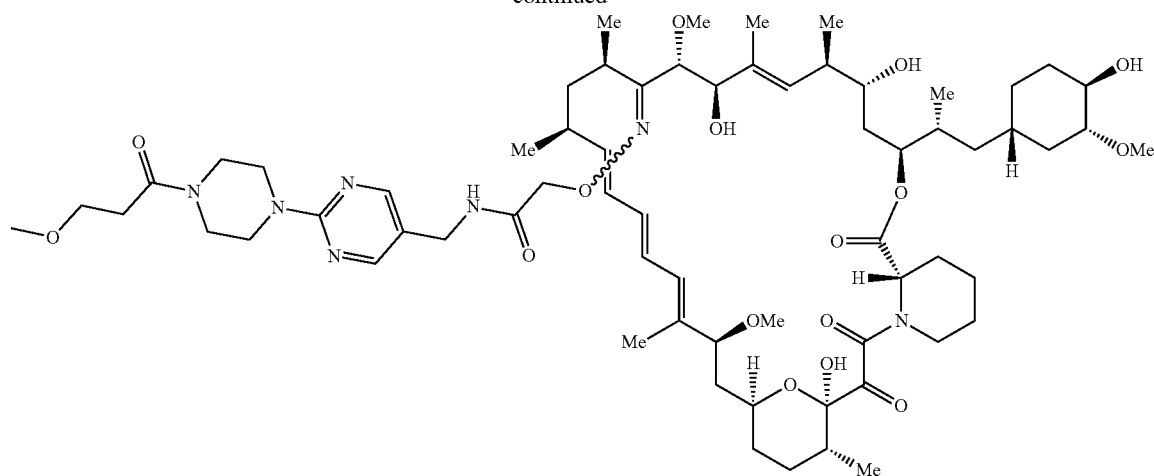
Example 40
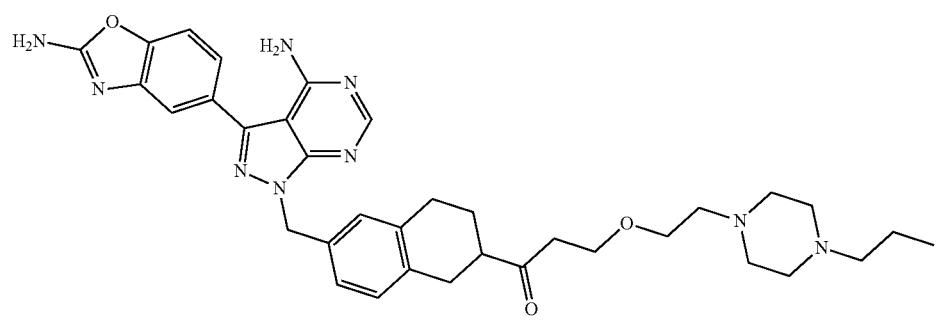
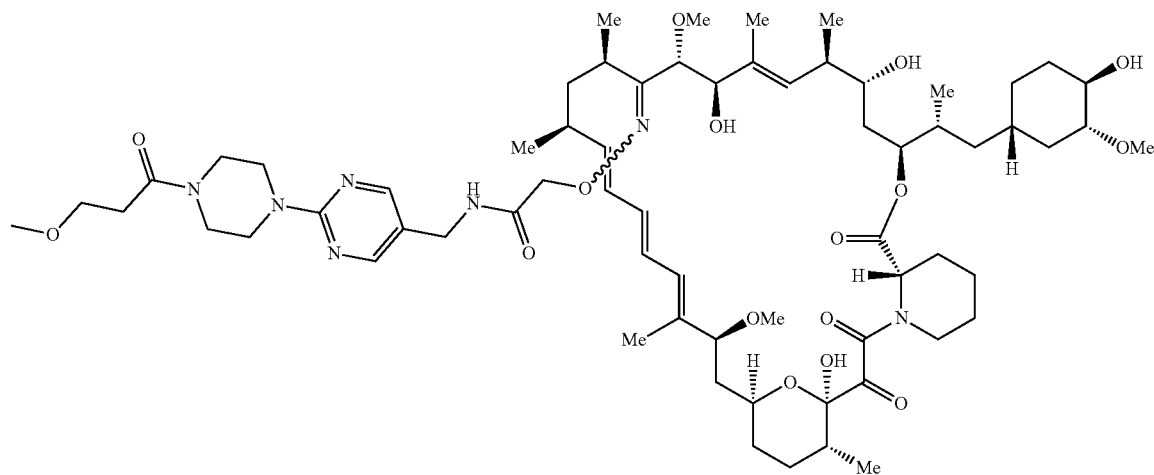
Example 41
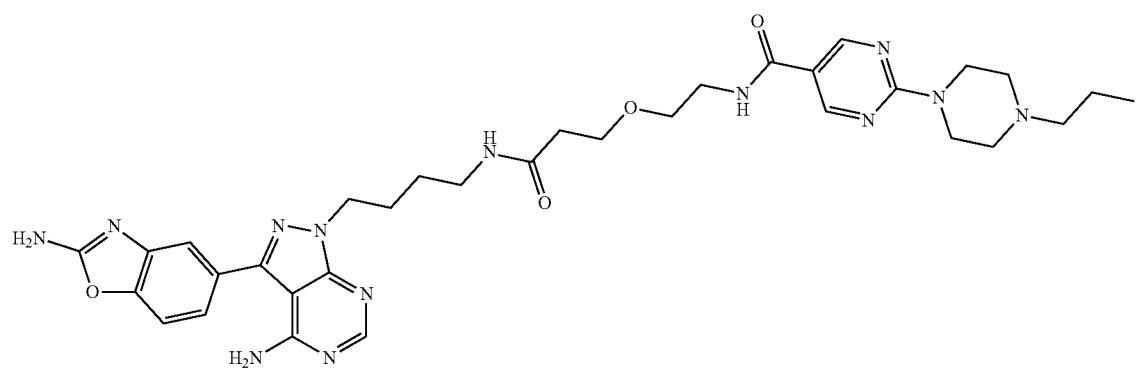

-continued

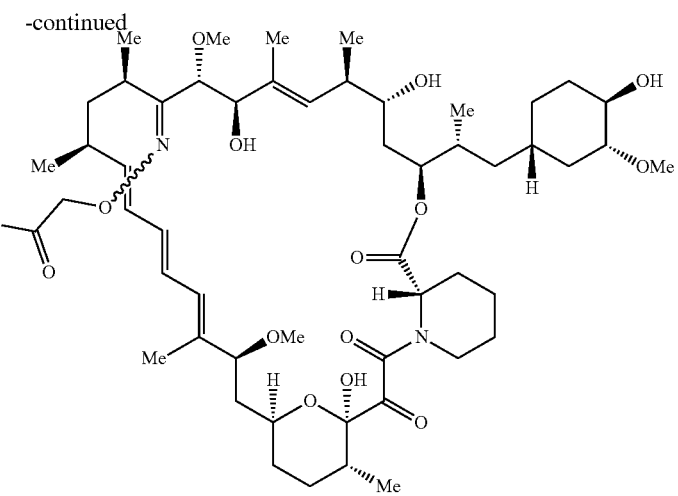

Example 42

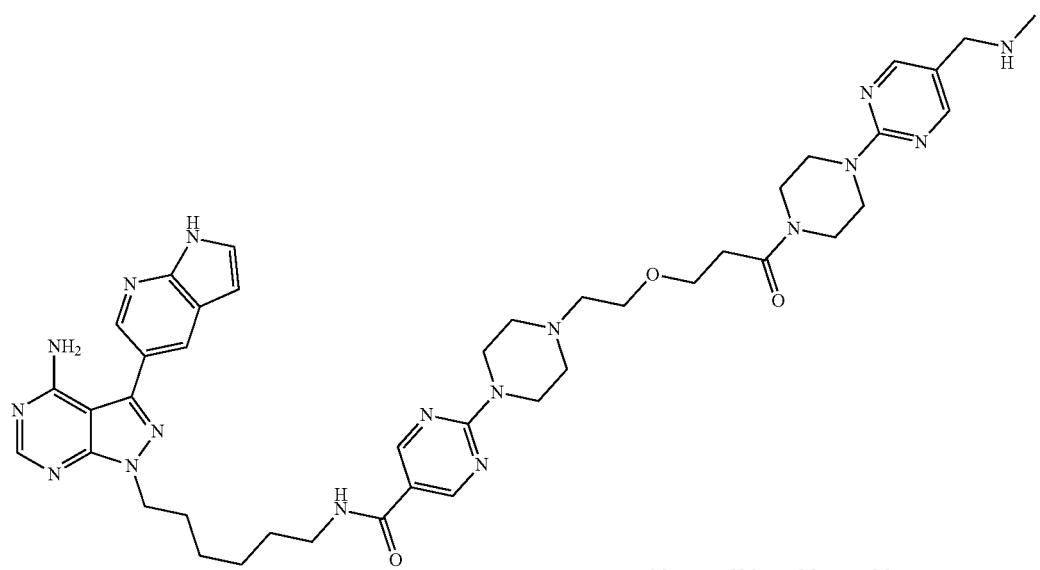

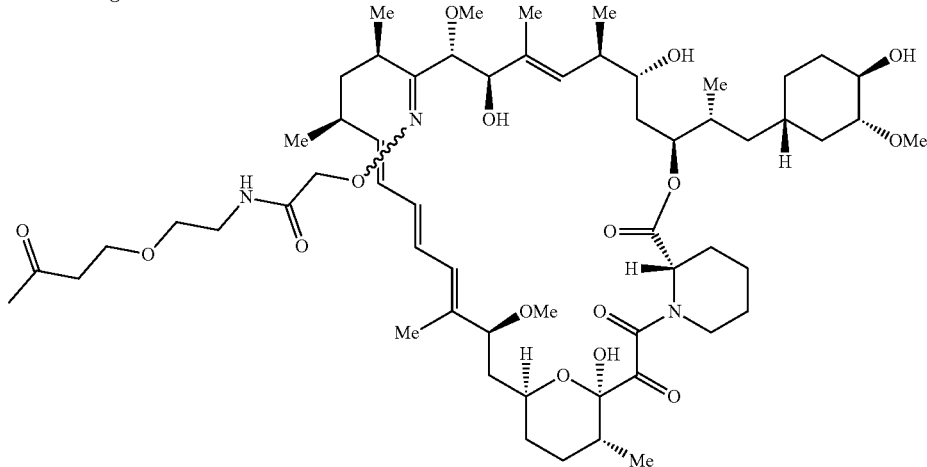

or a pharmaceutically acceptable salt or isomer thereof

Embodiment I-40. A pharmaceutical composition comprising a compound of any one of Embodiments I-1 to I-39, or a pharmaceutically acceptable salt thereof, and at least one of a pharmaceutically acceptable carrier, diluent, or excipient.

Embodiment I-41. A method of treating a disease or disorder mediated by mTOR comprising administering to the subject suffering from or susceptible to developing a disease or disorder mediated by mTOR a therapeutically effective amount of one or more compounds of any one of Embodiments I-1 to I-39, or a pharmaceutically acceptable salt thereof.

Embodiment I-42. A method of preventing a disease or disorder mediated by mTOR comprising administering to the subject suffering from or susceptible to developing a disease or disorder mediated by mTOR a therapeutically effective amount of one or more compounds of any one of Embodiments I-1 to I-39, or a pharmaceutically acceptable salt thereof.

Embodiment I-43. A method of reducing the risk of a disease or disorder mediated by mTOR comprising administering to the subject suffering from or susceptible to developing a disease or disorder mediated by mTOR a therapeutically effective amount of one or more compounds of any one of Embodiments I-1 to I-39, or a pharmaceutically acceptable salt thereof.

Embodiment I-44. The method of any one of Embodiments I-41 to I-43, wherein the disease is cancer or an immune-mediated disease.

Embodiment I-45. The method of Embodiment I-44, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment I-46. The method of Embodiment I-44, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment I-47. A method of treating cancer comprising administering to the subject a therapeutically effective amount of one or more compounds of any one of Embodiments I-1 to I-39, or a pharmaceutically acceptable salt thereof.

Embodiment I-48. The method of Embodiment I-47, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment I-49. A method of treating an immune-mediated disease comprising administering to the subject a therapeutically effective amount of one or more compounds of any one of Embodiments I-1 to I-39, or a pharmaceutically acceptable salt thereof.

Embodiment I-50. The method of Embodiment I-49, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment I-51. A method of treating an age related condition comprising administering to the subject a therapeutically effective amount of one or more compounds of any one of Embodiments I-1 to I-39, or a pharmaceutically acceptable salt thereof.

Embodiment I-52. The method of Embodiment I-51, wherein the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

Embodiment I-53. A compound of any one of Embodiments I-1 to I-39, or a pharmaceutically acceptable salt thereof, for use in treating, preventing, or reducing the risk of a disease or condition mediated by mTOR.

Embodiment I-54. Use of a compound of any of Embodiments I-1 to I-39, or a pharmaceutically acceptable salt thereof, in the manufacture of a medicament for treating, preventing, or reducing the risk of a disease or disorder mediated by mTOR.

Embodiment I-55. A compound of any one of Embodiments I-1 to I-39, or a pharmaceutically acceptable salt thereof, for use in treating cancer.

Embodiment I-Embodiment I-56. Use of a compound of any one of Embodiments I-1 to I-39, or a pharmaceutically acceptable salt thereof, in the manufacture of a medicament for treating cancer.

Embodiment I-57. A compound of any one of Embodiments I-1 to I-39, or a pharmaceutically acceptable salt thereof, for use in treating an immune-mediated disease.

Embodiment I-58. Use of a compound of any one of Embodiments I-1 to I-39, or a pharmaceutically acceptable salt thereof, in the manufacture of a medicament for treating an immune-mediated disease.

Embodiment I-59. A compound of any one of Embodiments I-1 to I-39, or a pharmaceutically acceptable salt thereof, for use in treating an age related condition.

Embodiment I-60. Use of a compound of any one of Embodiments I-1 to I-39, or a pharmaceutically acceptable salt thereof, in the manufacture of a medicament for treating an age related condition.

Some embodiments of this disclosure are Embodiment II, as follows:

Embodiment II-1. A compound of Formula Ia:
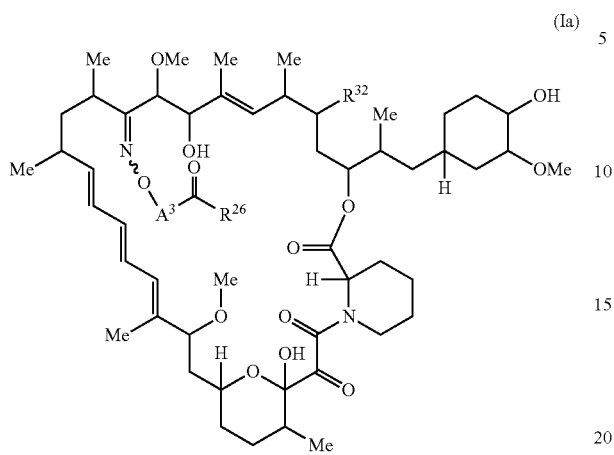
or a pharmaceutically acceptable salt or tautomer thereof, wherein:
$R^{32}$ is H, =O, —$OR^3$, or —$N_3$;
$A^3$ is —$[C(R^3)_2]_n$—, ($C_6$-$C_{10}$)arylene, cycloalkylene, heteroarylene, or heterocyclylene;
$R^{26}$ is $A^1$-$L^1$-$A^2$-B; -$A^1$-$A^2$-B; -$L^2$-$A^1$-$L^1$-$A^2$-$L^3$-B; or —OH;
$A^1$ and $A^2$ are independently absent or are independently selected from
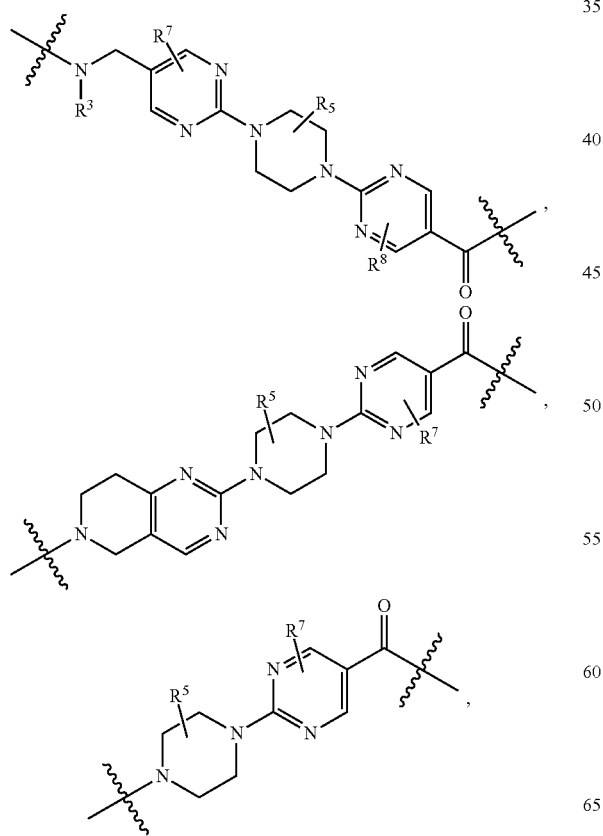
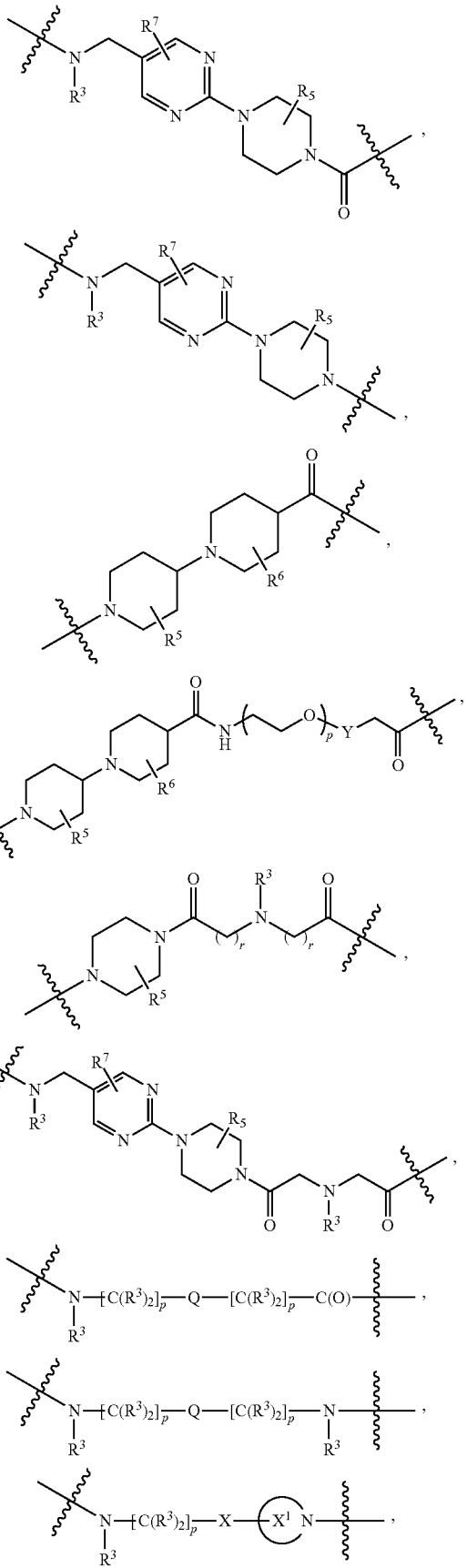

269
-continued

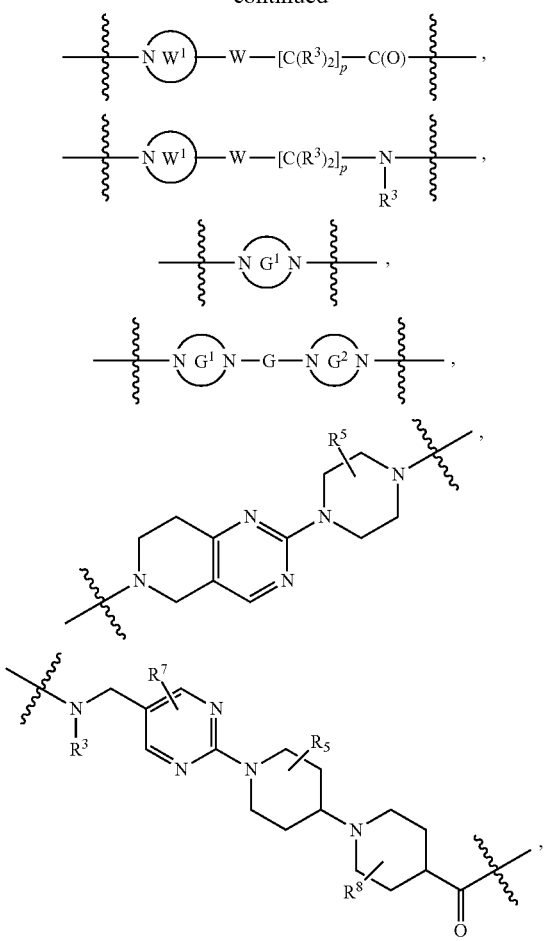

270
-continued

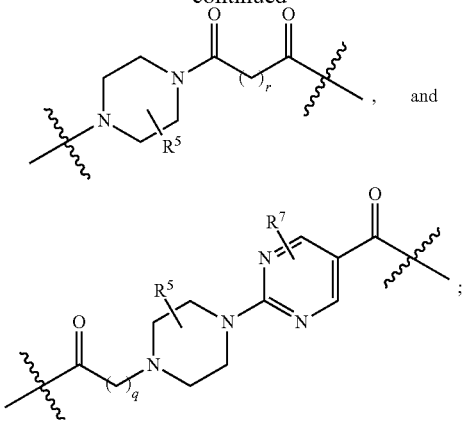

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

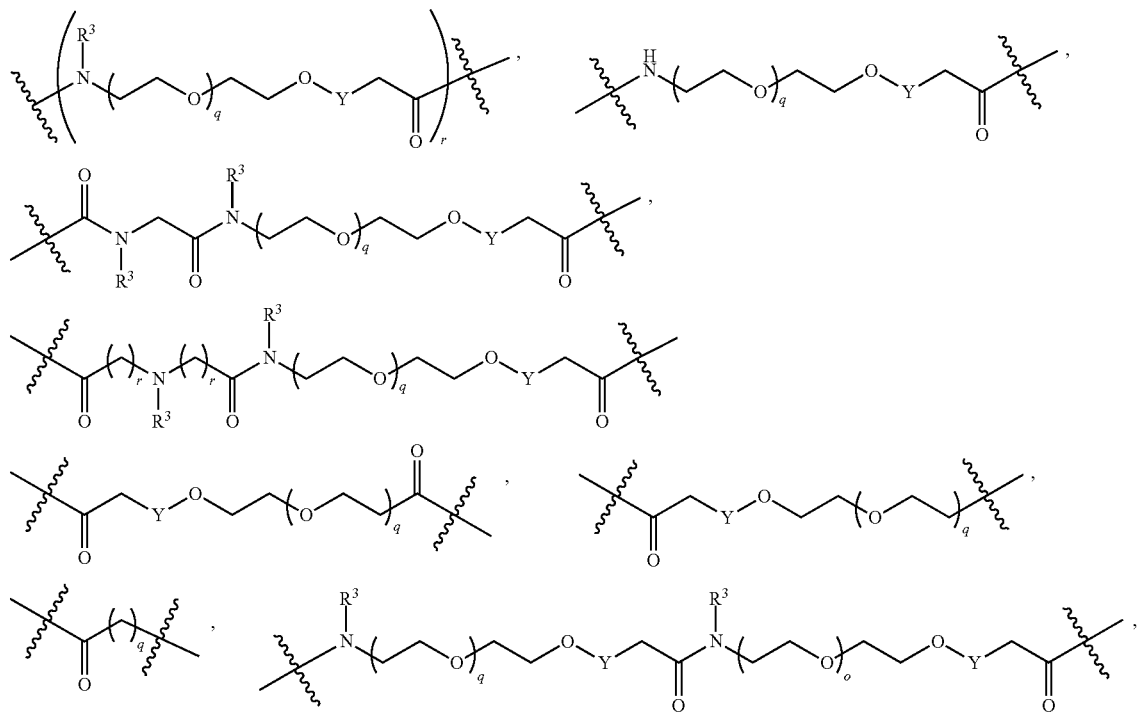

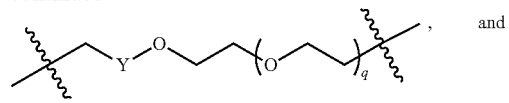
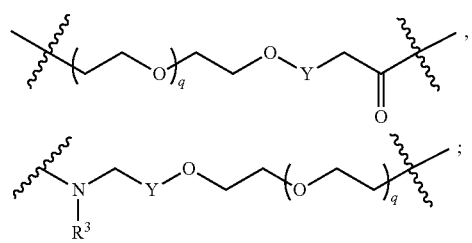
$L^2$ and $L^3$ are independently absent or are independently selected from
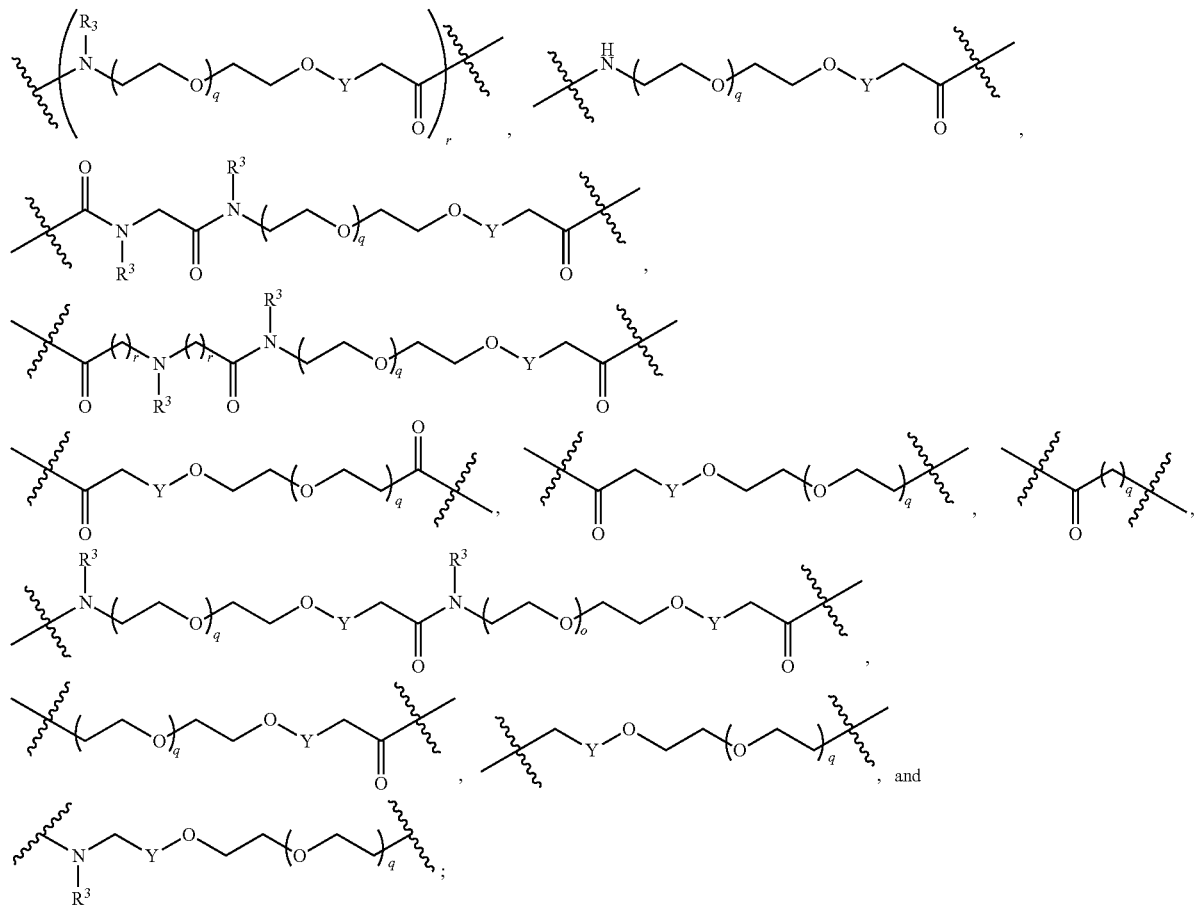
each B is independently selected from
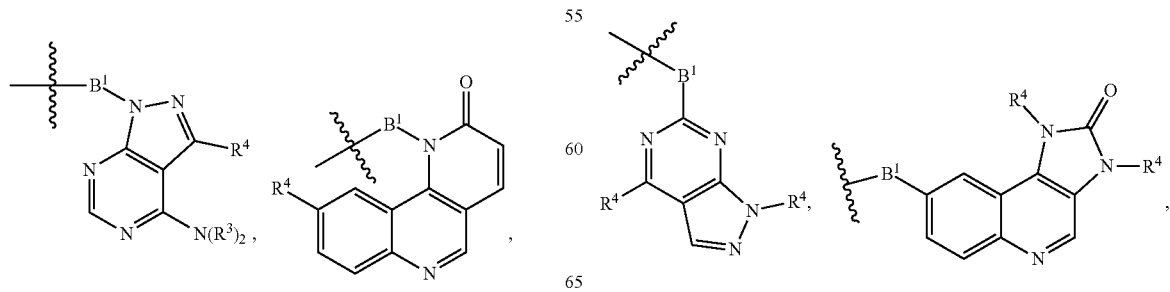

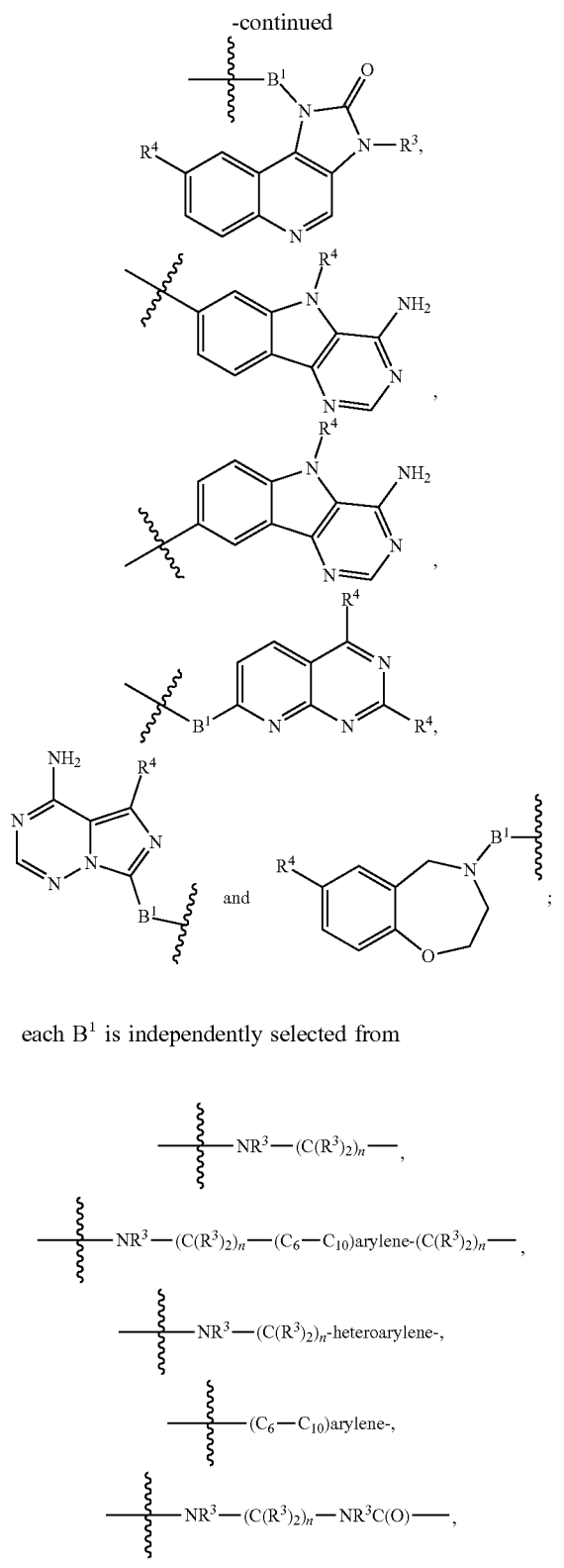
each B¹ is independently selected from
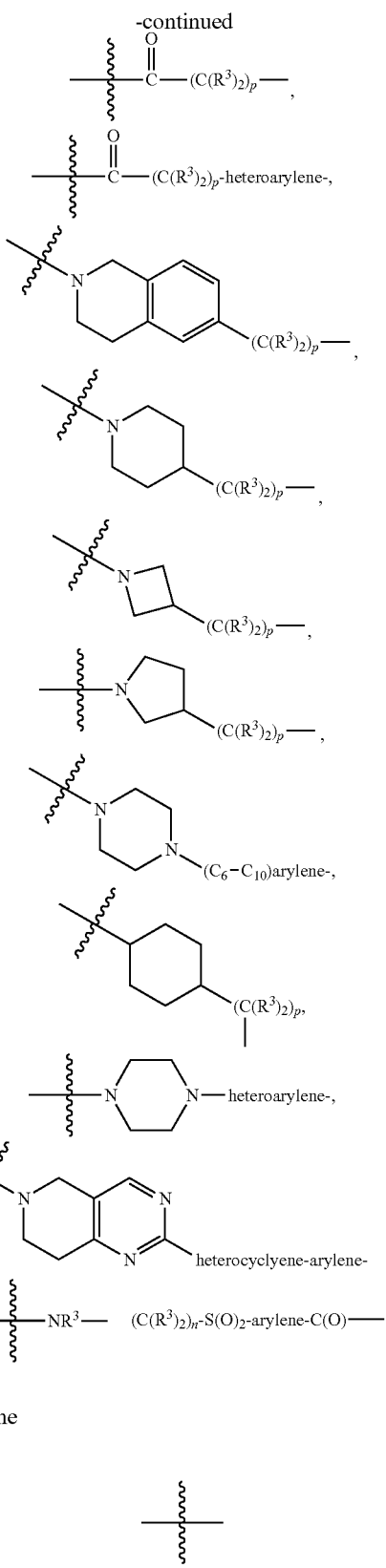
wherein the
bond on the left side of B¹, as drawn is bound to A² or L¹; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1-C_6)$alkyl;

each $R^4$ is independently H, $(C_1-C_6)$alkyl, halogen, 5-12 membered heteroaryl, 5-12 membered heterocyclyl, $(C_6-C_{10})$aryl, wherein the heteroaryl, heterocyclyl, and aryl are each independently optionally substituted with —$N(R^3)_2$, —$OR^3$, halogen, $(C_1-C_6)$alkyl, —$(C_1-C_6)$alkylene-heteroaryl, —$(C_1-C_6)$alkylene-CN, —$C(O)NR^3$-heteroaryl, or —$C(O)NR^3$-heterocyclyl;

each $R^5$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^6$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^7$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each $R^8$ is independently H, $(C_1-C_6)$alkyl, —$C(O)OR^3$, or —$N(R^3)_2$, wherein the alkyl of $(C_1-C_6)$alkyl is optionally substituted with —$N(R^3)_2$ or —$OR^3$;

each Y is independently $C(R^3)_2$ or a bond;
each n is independently an integer from one to 12;
each o is independently an integer from zero to 30;
each p is independently an integer from zero to 12;
each q is independently an integer from zero to 30; and
each r is independently an integer from one to 6.

Embodiment II-2. The compound of Embodiment II-1, wherein $R^{32}$ is =O.

Embodiment II-3. The compound of Embodiment II-1, wherein $R^{32}$ is —$OR^3$.

Embodiment II-4. The compound of any one of Embodiments II-1 to II-3, wherein $A^3$ is —$[C(R^3)_2]_n$—.

Embodiment II-5. The compound of any one of Embodiments II-1 to II-3, wherein $A^3$ is —$(C_6-C_{10})$arylene-.

Embodiment II-6. The compound of any one of Embodiments II-1 to II-5, wherein $R^{26}$ is $-A^1-L^2-A^2-B$, wherein $A^1$ and $A^2$ are absent.

Embodiment II-7. The compound of any one of Embodiments II-1 to II-5, wherein $R^{26}$ is $-A^1-L^1-A^2-B$, wherein $A^2$ is absent.

Embodiment II-8. The compound of any one of Embodiments II-1 to II-5, wherein $R^{26}$ is $-A^1-L^2-A^2-B$, wherein $A^1$ is absent.

Embodiment II-9. The compound of any one of Embodiments II-1 to II-5, wherein $R^{26}$ is $-A^1-L^1-A^2-B$.

Embodiment II-10. The compound of any one of Embodiments II-1 to II-5, wherein $R^{26}$ is $-A^1-L^1-A^2-B$.

Embodiment II-11. The compound of any one of Embodiments II-1 to II-5, wherein $R^{26}$ is $-L^2-A^1-L^1-A^2-L^3-B$.

Embodiment II-12. The compound of any one of Embodiments II-1 to II-5, wherein $R^{26}$ is —OH.

Embodiment II-13. The compound of any one of Embodiments II-1 to II-11, wherein $L^1$ is

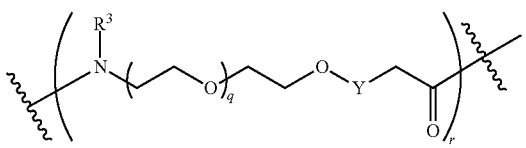

Embodiment II-14. The compound of any one of Embodiments II-1 to II-11, wherein $L^1$ is

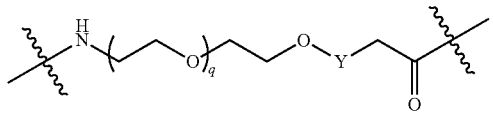

Embodiment II-15. The compound of any one of Embodiments II-1 to II-11, wherein $L^1$ is

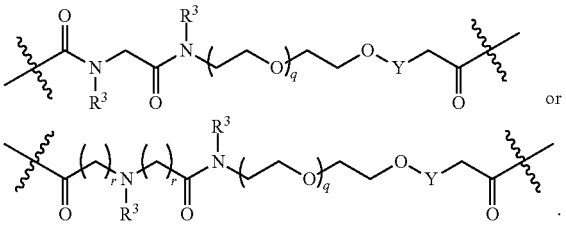

or

Embodiment II-16. The compound of any one of Embodiments II-1 to II-11, wherein $L^1$ is

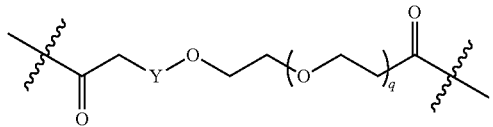

Embodiment II-17. The compound of any one of Embodiments II-1 to II-11, wherein $L^1$ is

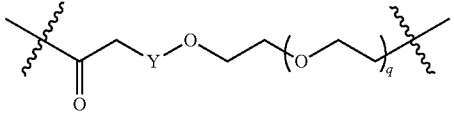

Embodiment II-18. The compound of any one of Embodiments II-1 to II-11, wherein $L^1$ is

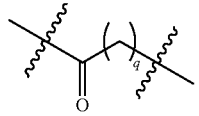

Embodiment II-19. The compound of any one of Embodiments II-1 to II-11, wherein $L^1$ is

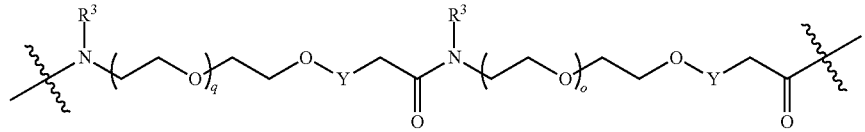

Embodiment II-20. The compound of any one of Embodiments II-1 to II-11, wherein L¹ is

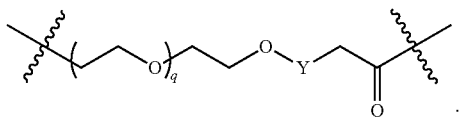

Embodiment II-21. The compound of any one of Embodiments II-1 to II-11, wherein L¹ is

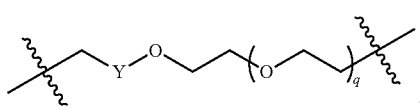

Embodiment II-22. The compound of any one of Embodiments II-1 to II-11 and II-13 to II-21, wherein A¹ is absent.

Embodiment II-23. The compound of any one of Embodiments II-1 to II-5, II-7, II-9 to II-11 and II-13 to II-21, wherein A¹ is

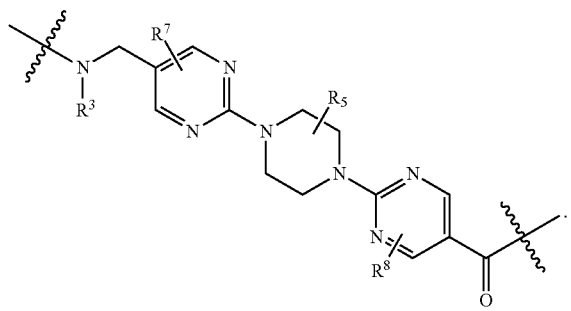

Embodiment II-24. The compound of any one of Embodiments II-1 to II-5, II-7, II-9 to II-11 and II-13 to II-21, wherein A¹ is

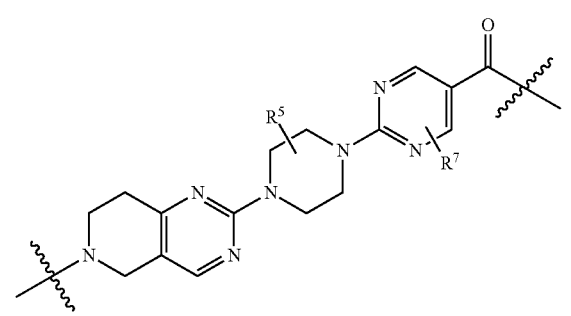

Embodiment II-25. The compound of any one of Embodiments II-1 to II-5, II-7, II-9 to II-11 and II-13 to II-21, wherein A¹ is

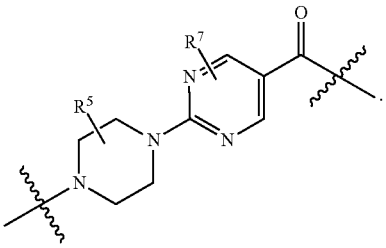

Embodiment II-26. The compound of any one of Embodiments II-1 to II-5, II-7, II-9 to II-11 and II-13 to II-21, wherein A¹ is

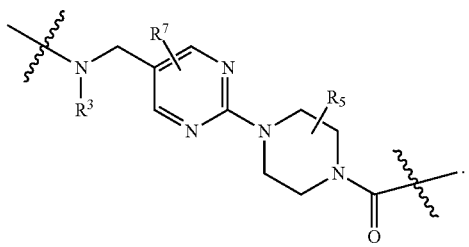

Embodiment II-27. The compound of any one of Embodiments II-1 to II-5, II-7, II-9 to II-11 and II-13 to II-21, wherein A¹ is

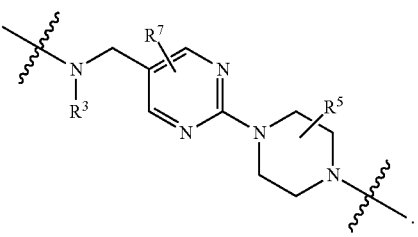

Embodiment II-28. The compound of any one of Embodiments II-1 to II-5, II-7, II-9 to II-11 and II-13 to II-21, wherein A¹ is

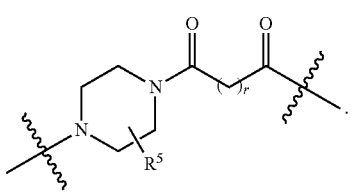

Embodiment II-29. The compound of any one of Embodiments II-1 to II-5, II-7, II-9 to II-11 and II-13 to II-21, wherein A¹ is

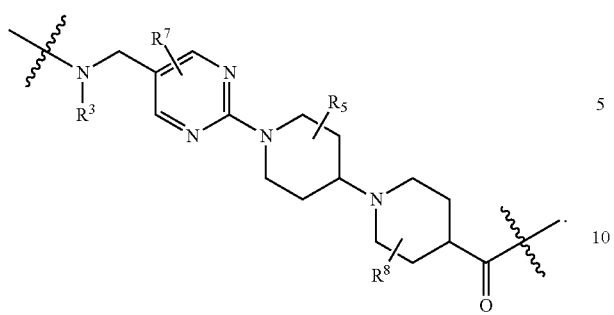

Embodiment II-30. The compound of any one of Embodiments II-1 to II-11 and II-13 to II-29, wherein A² is absent.

Embodiment II-31. The compound of any one of Embodiments II-1 to II-5, II-8 to II-11 and II-13 to II-29, wherein A² is

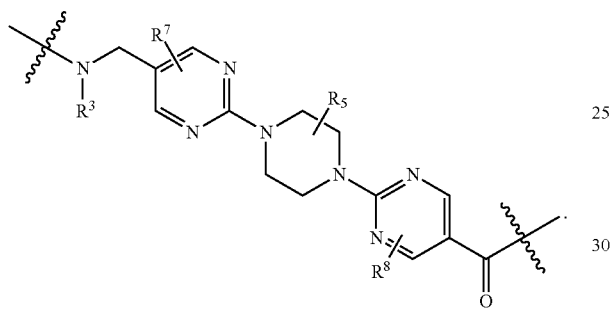

Embodiment II-32. The compound of any one of Embodiments II-1 to II-5, II-8 to II-11 and II-13 to II-29, wherein A² is

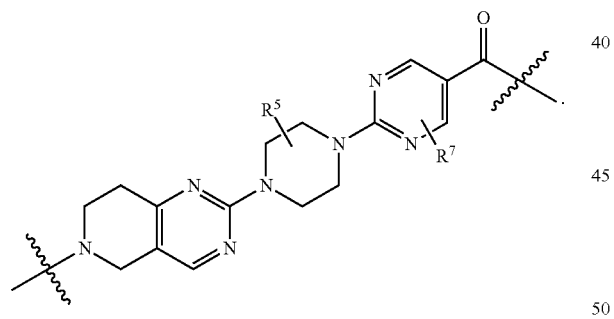

Embodiment II-33. The compound of any one of Embodiments II-1 to II-5, II-8 to II-11 and II-13 to II-29, wherein A² is

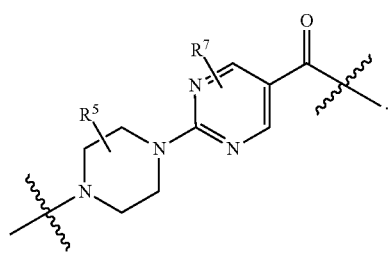

Embodiment II-34. The compound of any one of Embodiments II-1 to II-5, II-8 to II-11 and II-13 to II-29, wherein A² is

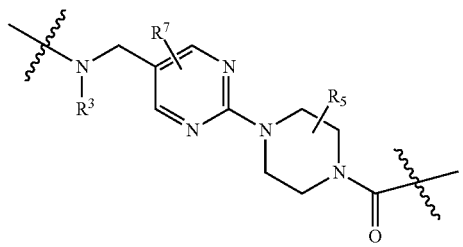

Embodiment II-35. The compound of any one of Embodiments II-1 to II-5, II-8 to II-11 and II-13 to II-29, wherein A² is

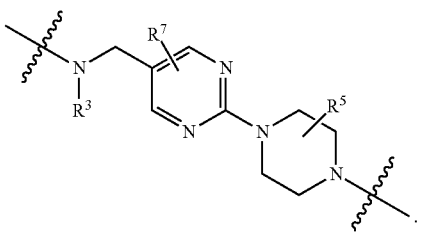

Embodiment II-36. The compound of any one of Embodiments II-1 to II-5, II-8 to II-11 and II-13 to II-29, wherein A² is

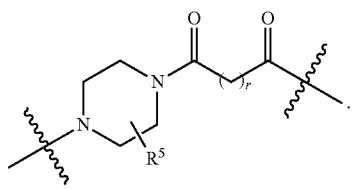

Embodiment II-37. The compound of any one of Embodiments II-1 to II-5, II-8 to II-11 and II-13 to II-29, wherein A² is

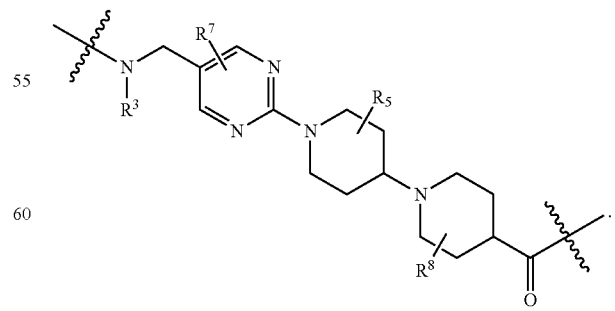

Embodiment II-38. The compound of any one of Embodiments II-1 to II-11 and II-13 to II-37, wherein B is

281

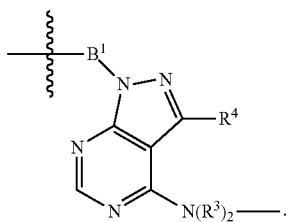

Embodiment II-39. The compound of any one of Embodiments II-1 to II-11 and II-13 to II-37, wherein B is

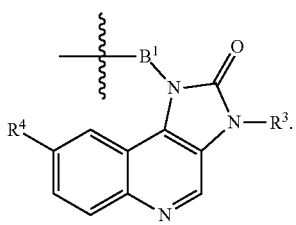

Embodiment II-40. The compound of any one of Embodiments II-1 to II-11 and II-13 to II-39, wherein $B^1$ is

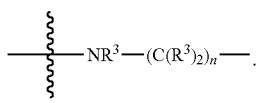

Embodiment II-41. The compound of any one of Embodiments II-1 to II-11 and II-13 to II-39, wherein $B^1$ is

282

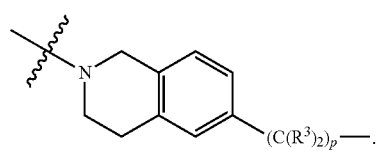

Embodiment II-42. The compound of any one of Embodiments II-1 to II-11 and II-13 to II-41, wherein $R^4$ is 5-12 membered heteroaryl, optionally substituted with —$N(R^3)_2$, —$OR^3$, halogen, ($C_1$-$C_6$)alkyl, —($C_1$-$C_6$)alkylene-heteroaryl, —($C_1$-$C_6$)alkylene-CN, or —C(O)$NR^3$-heteroaryl.

Embodiment II-43. The compound of any one of Embodiments II-1 to II-42, or a pharmaceutically acceptable salt or tautomer thereof, wherein compound has the following formula:

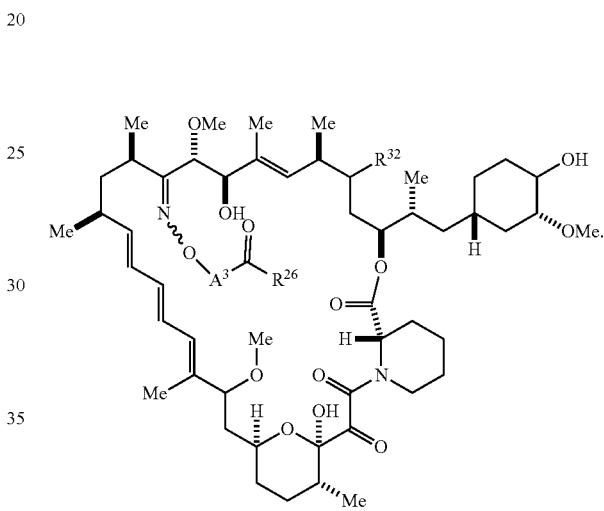

Embodiment II-44. A compound selected from the group consisting of:

Example 1

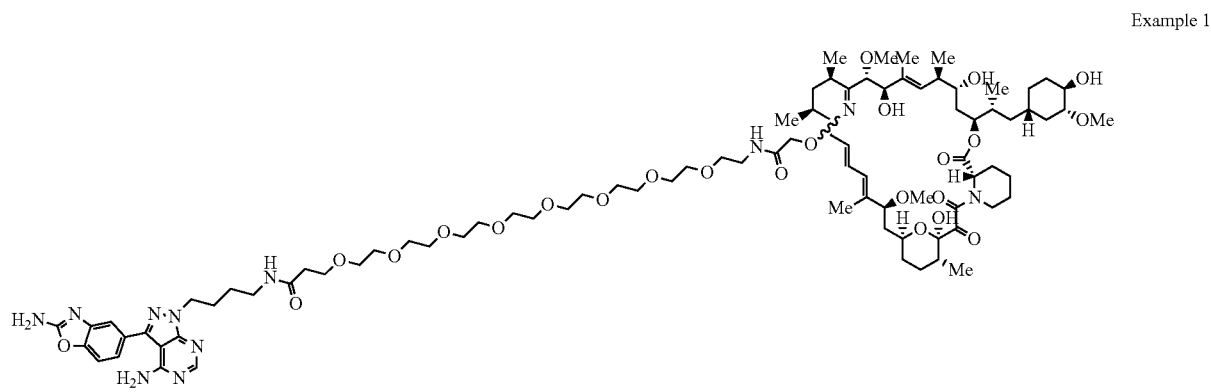

-continued
Example 2
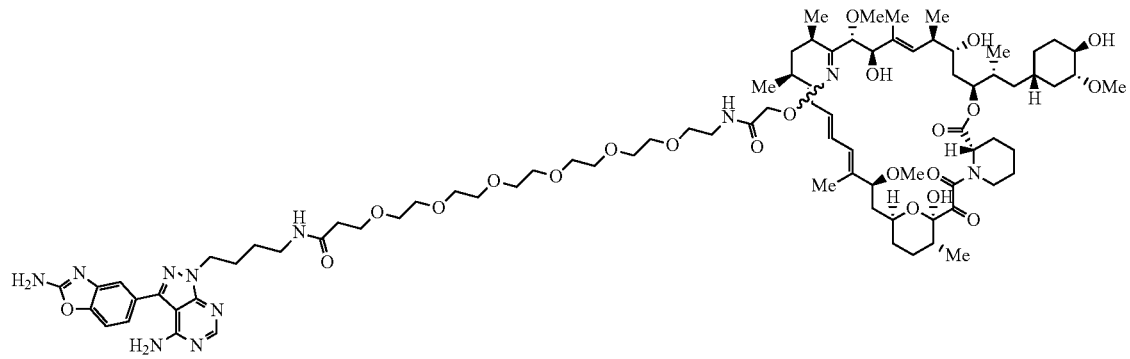
Example 3
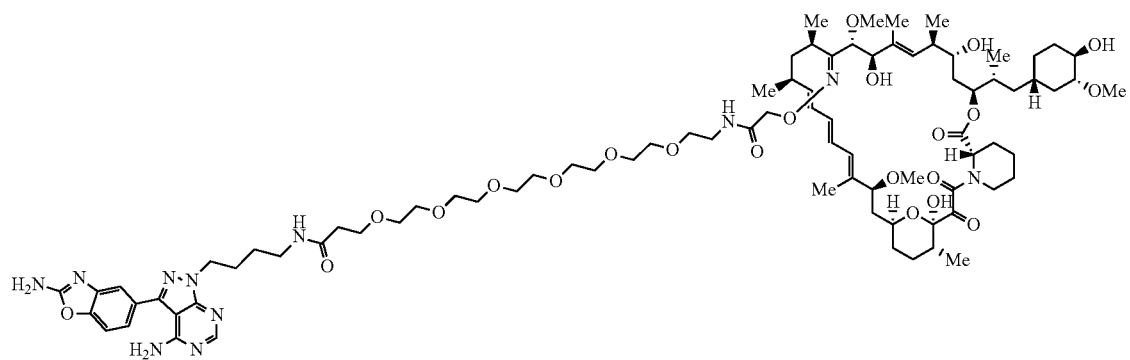
Example 4
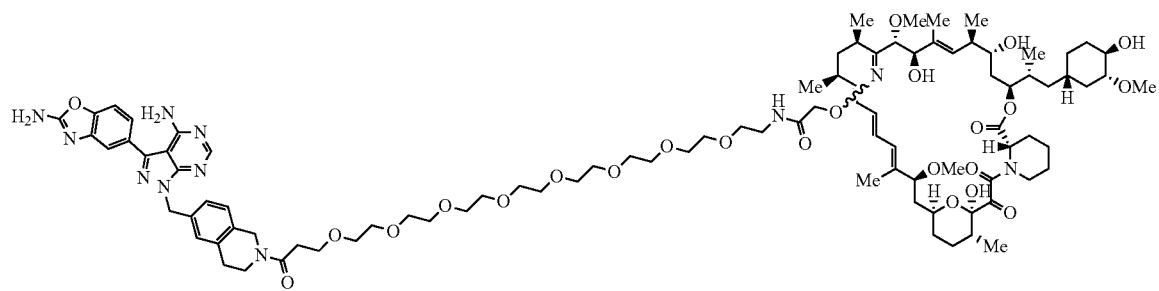
Example 5
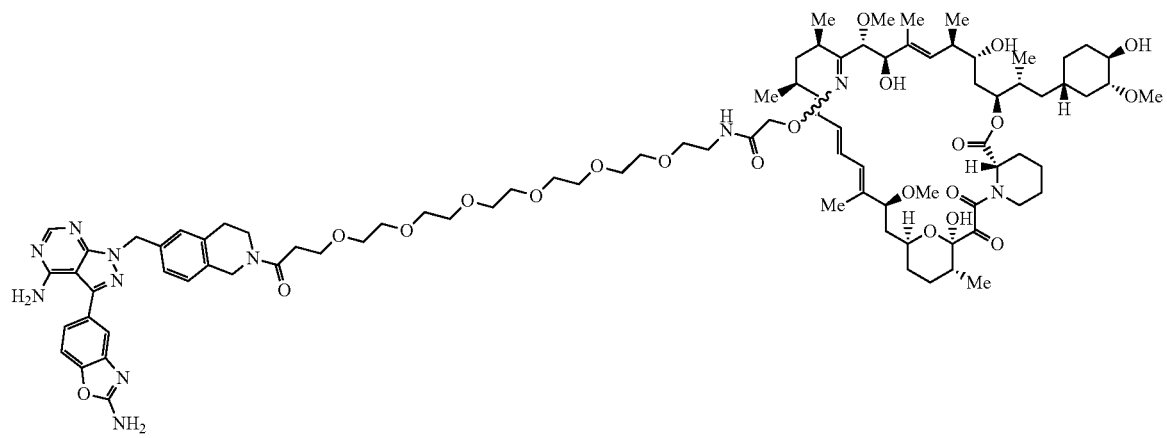

-continued
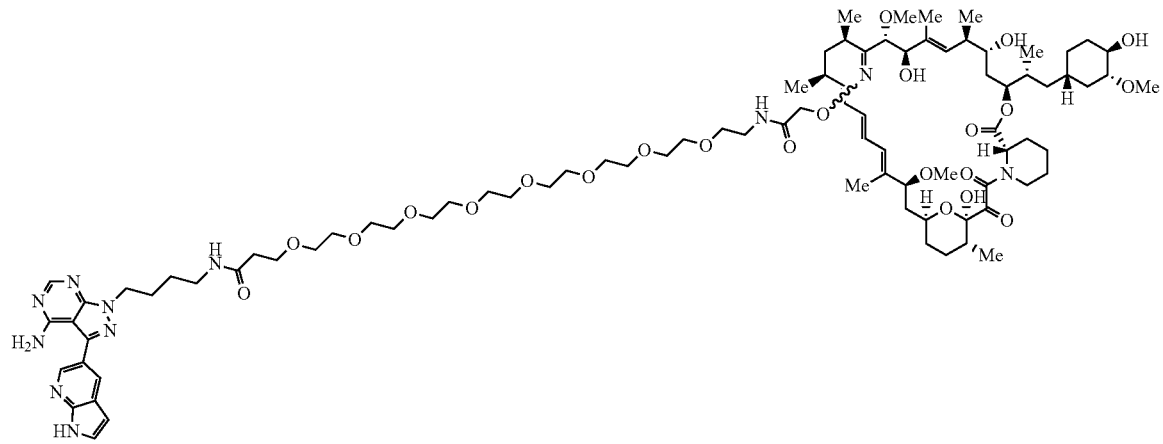
Example 6
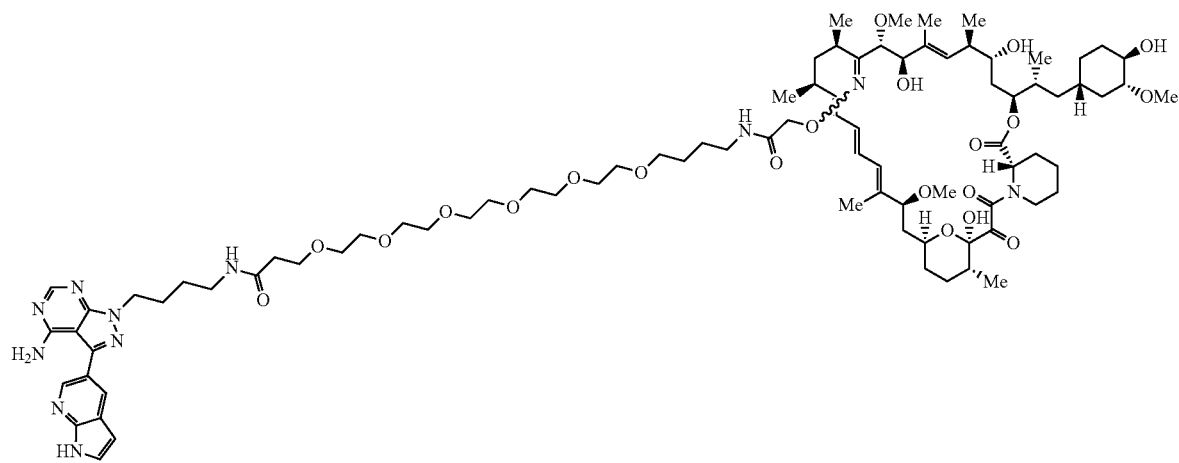
Example 7
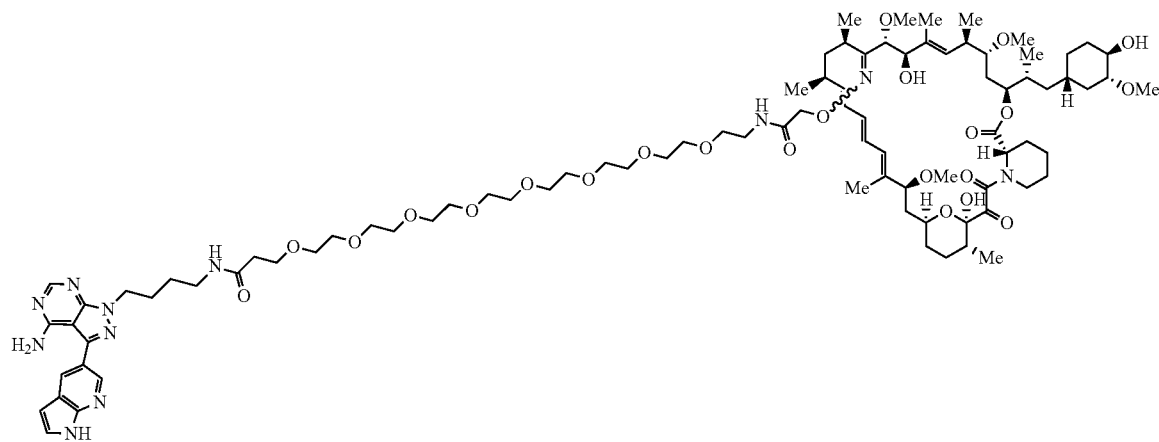
Example 8

-continued
Example 9
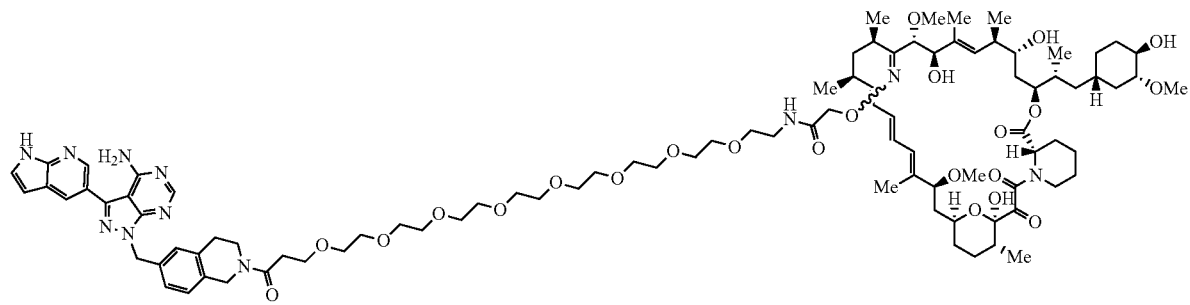
Example 10
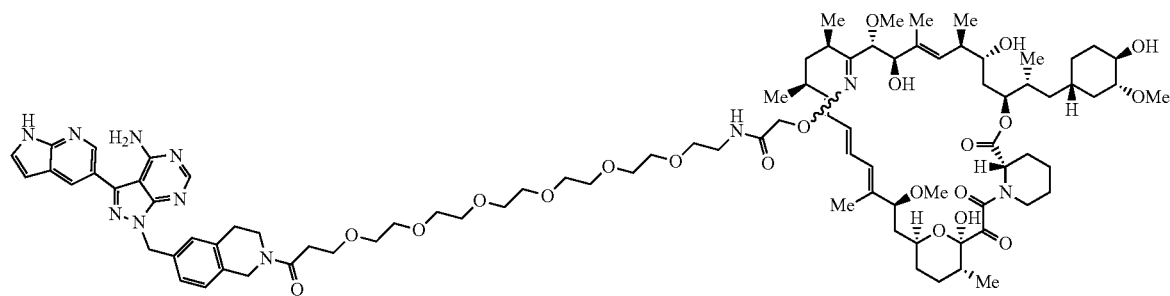
Example 11
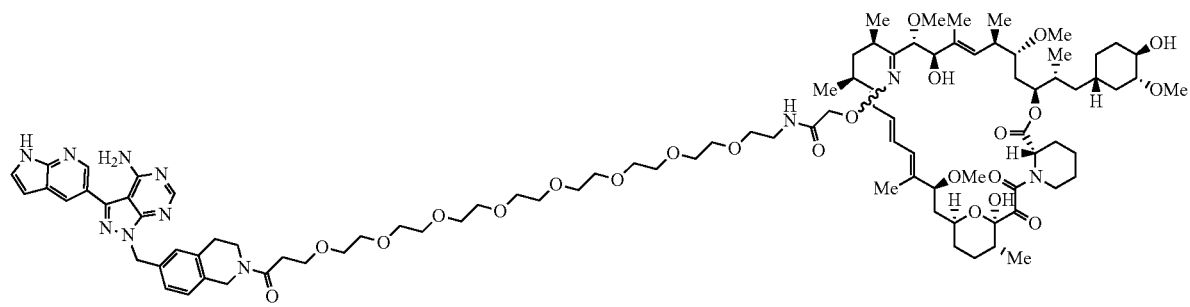
Example 12
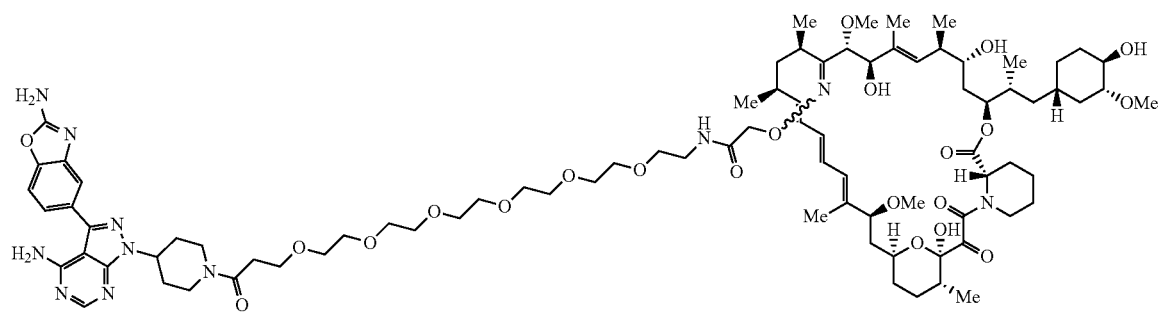
Example 13
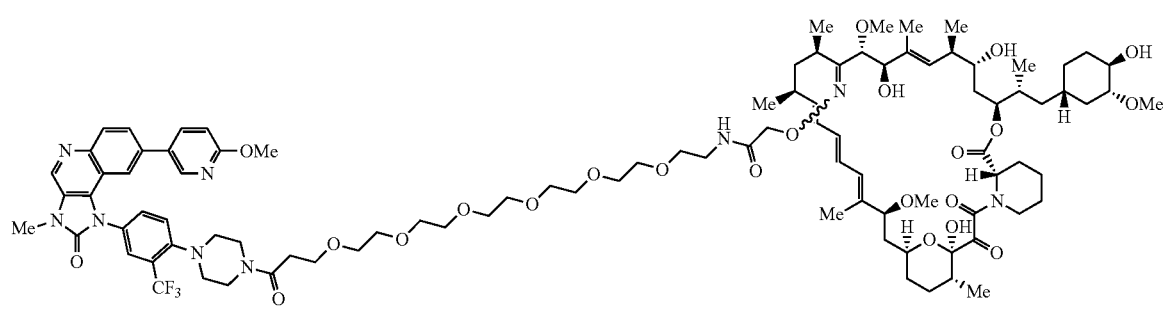

-continued
Example 14
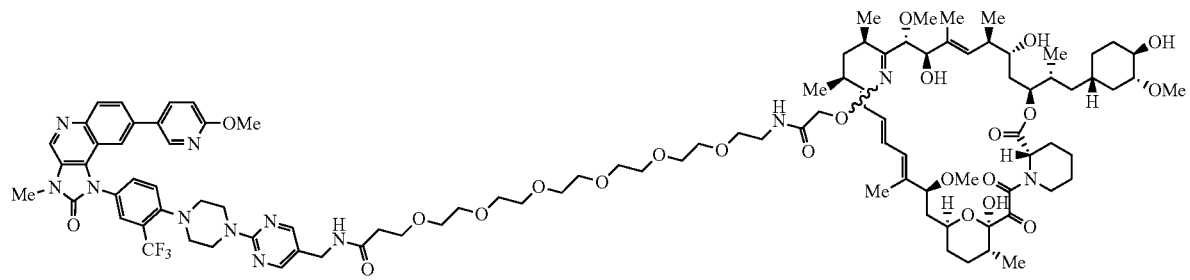
Example 15
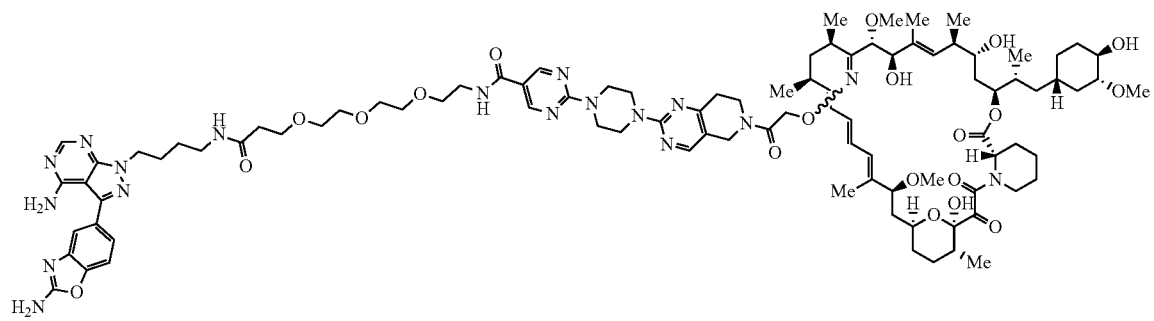
Example 16
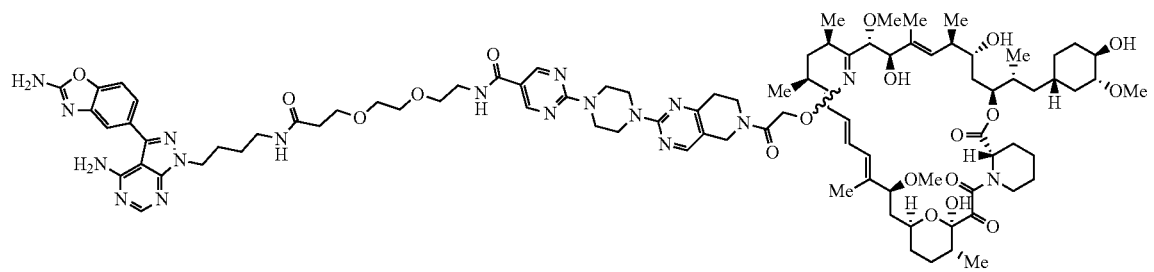
Example 17
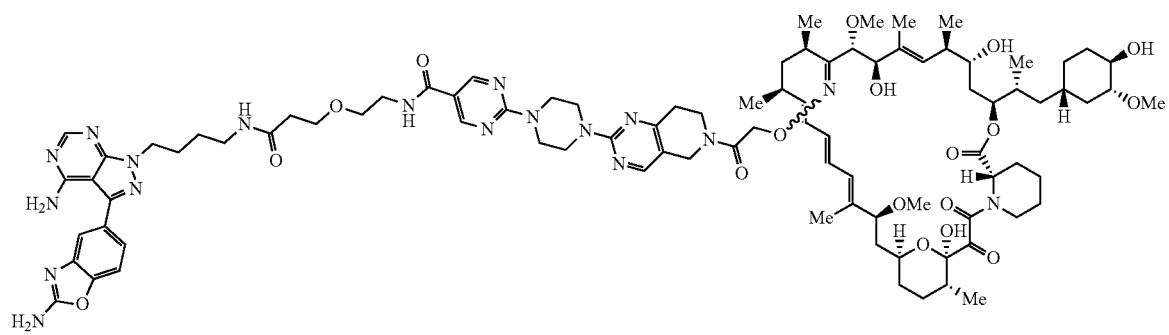
Example 18
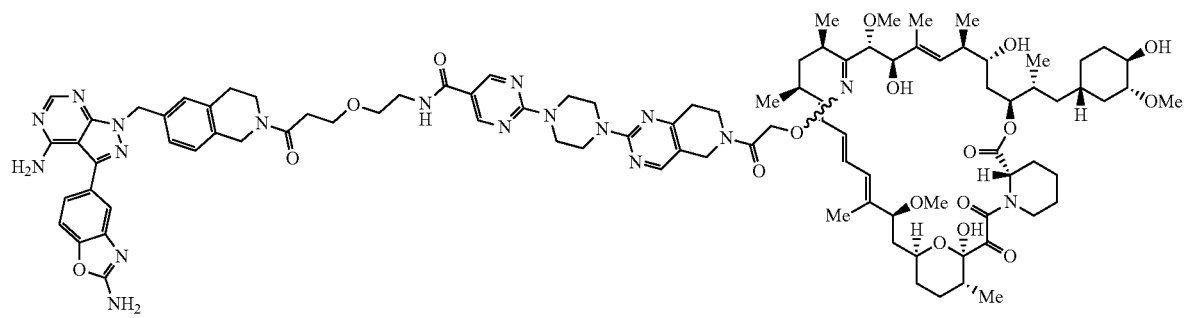

Example 19
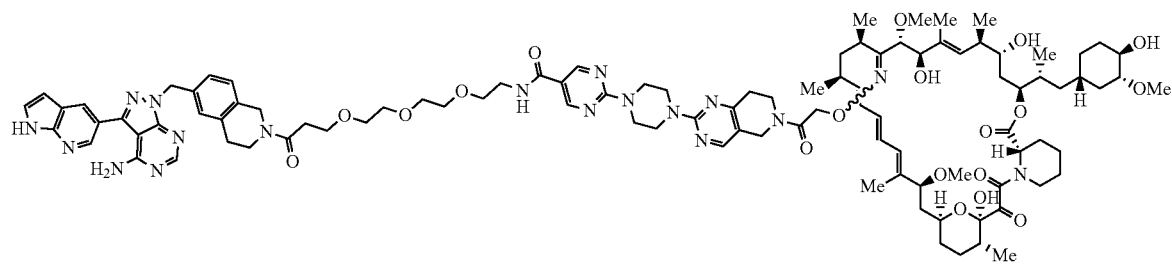
Example 20
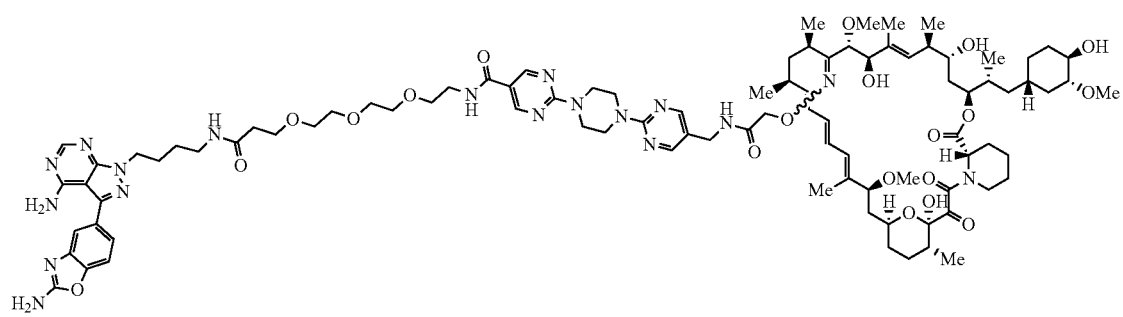
Example 21
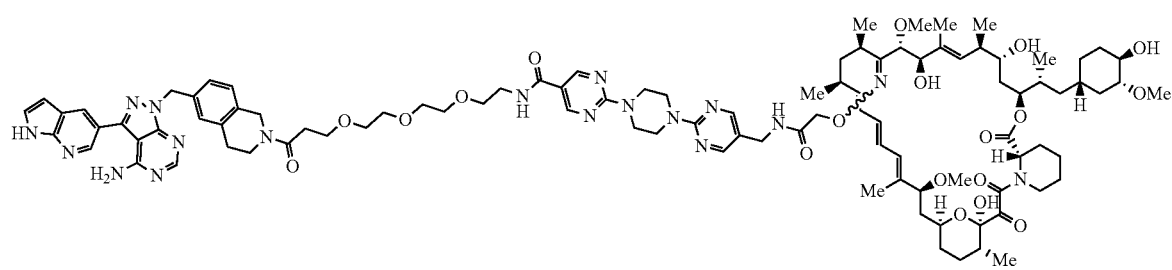
Example 22
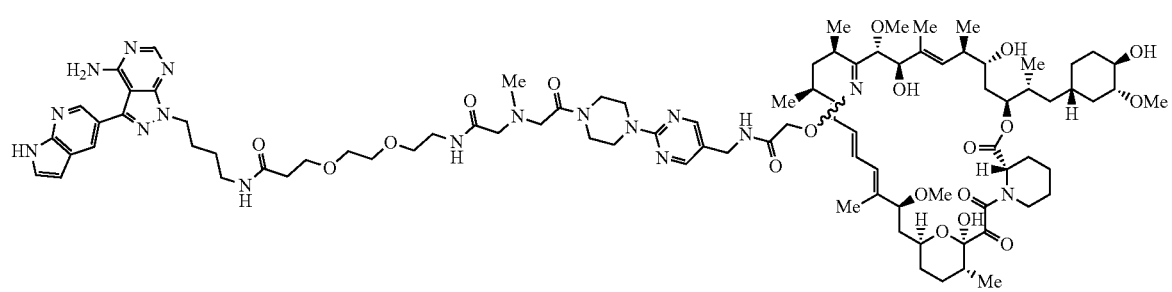
Example 23
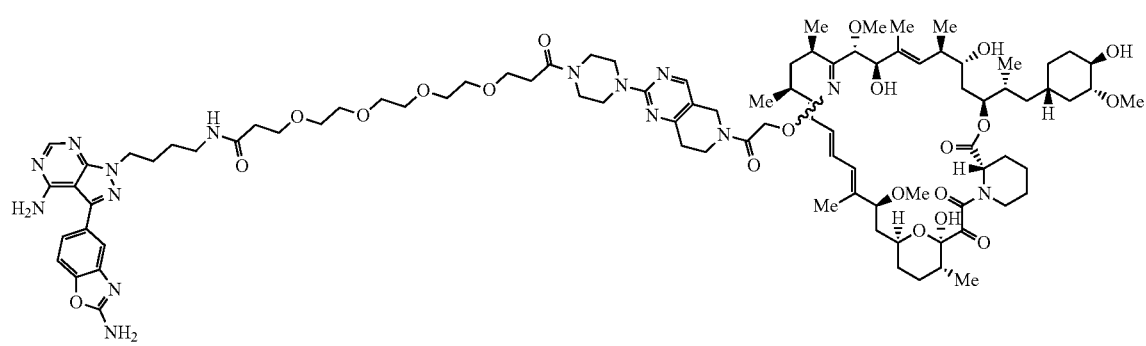

-continued
Example 24
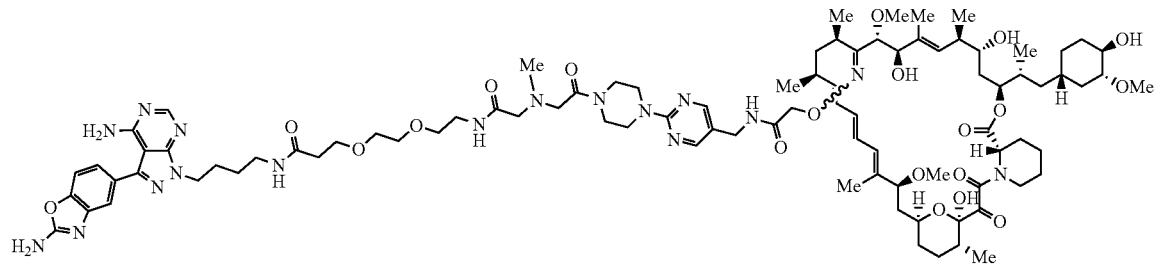
Example 25
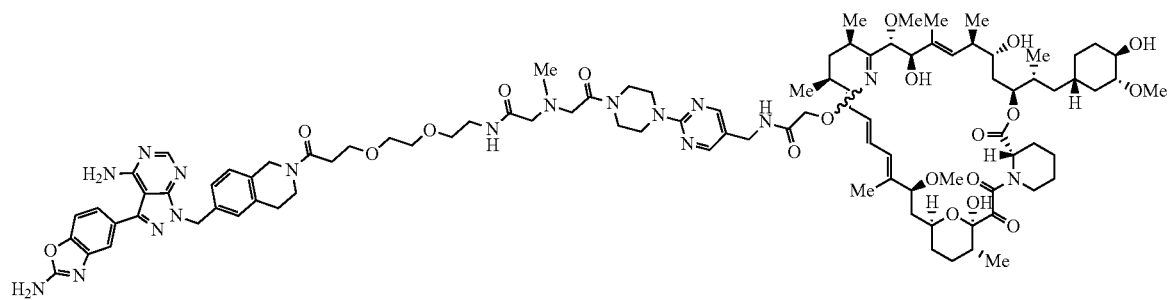
Example 26
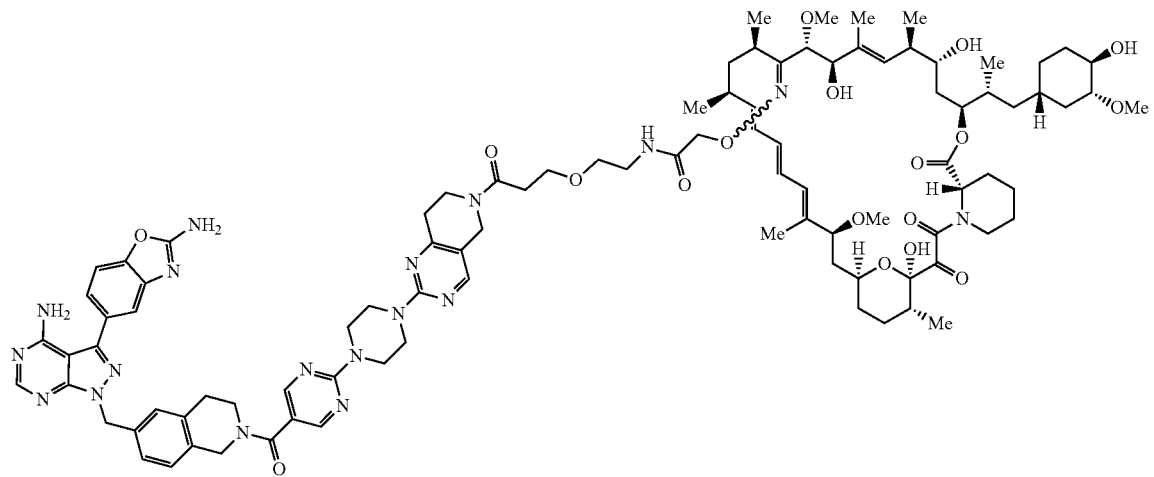
Example 27
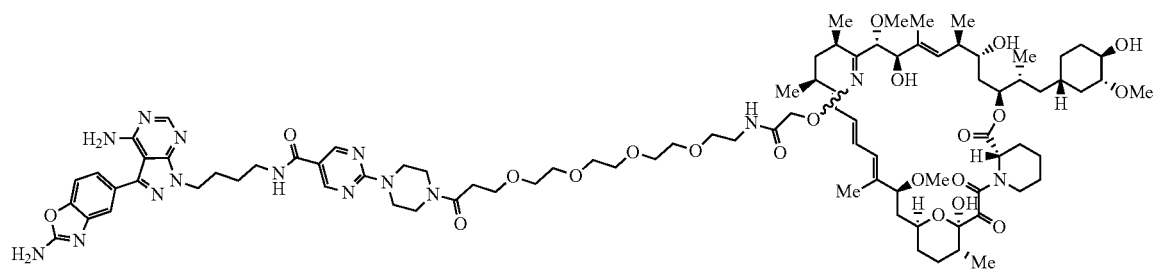

Example 28
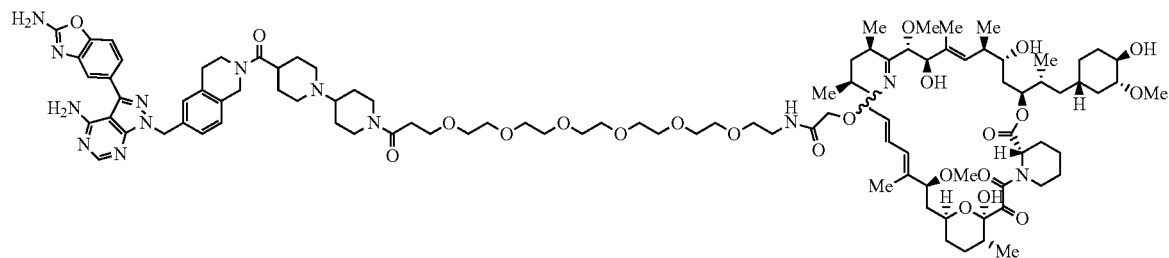
Example 29
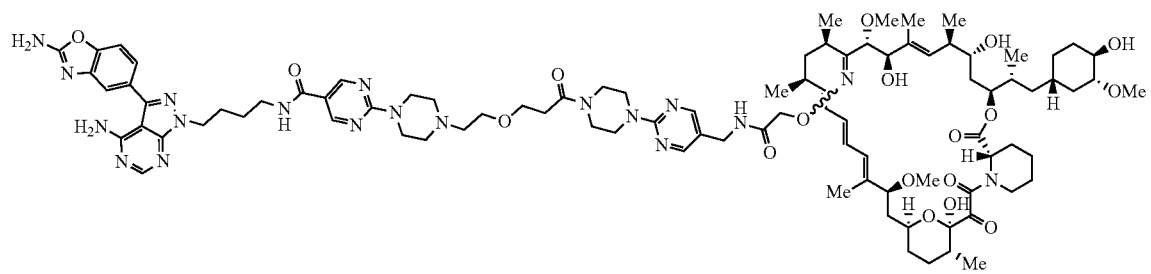
Example 30
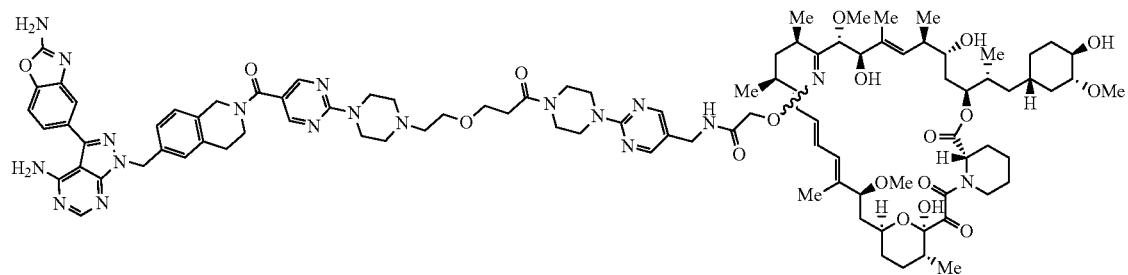
Example 31
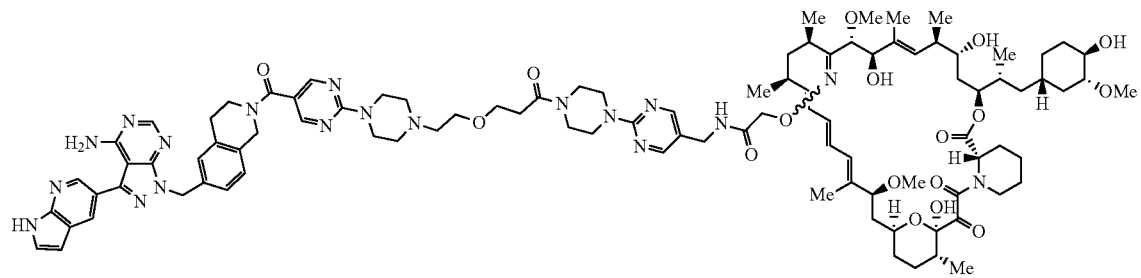
Example 32
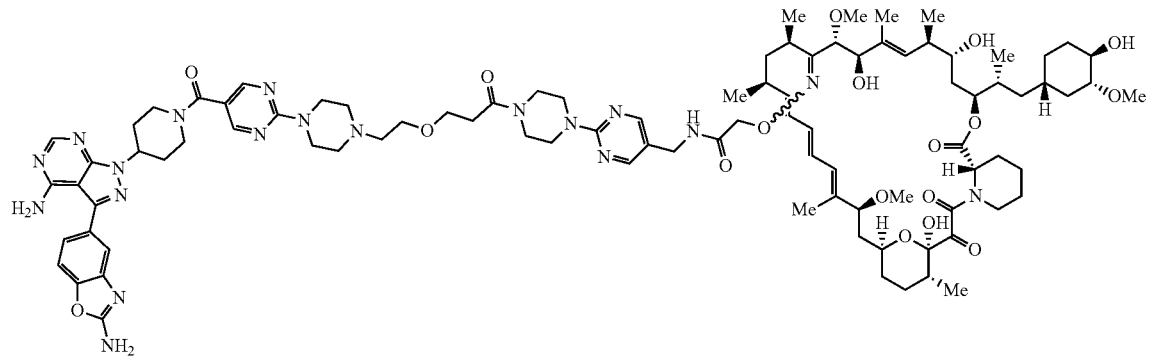

Example 33
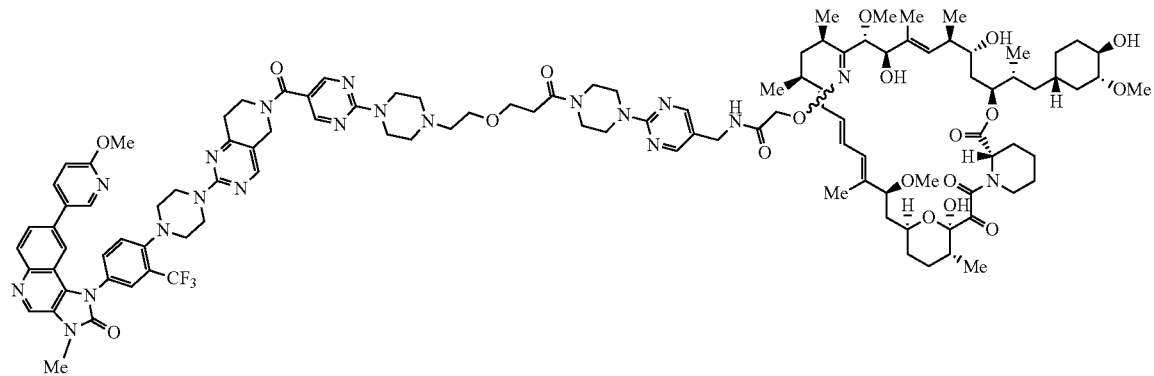
Example 34
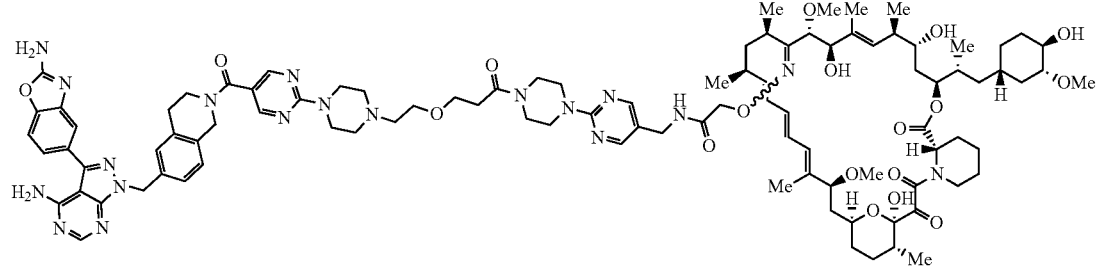
Example 35
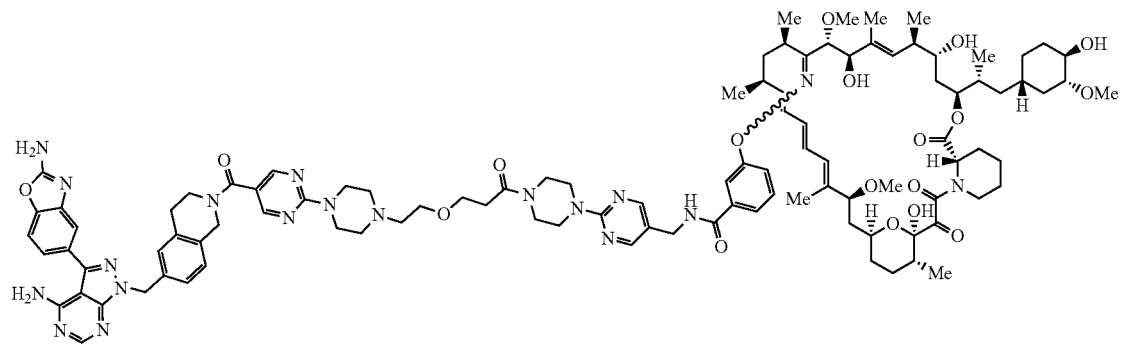
Example 36
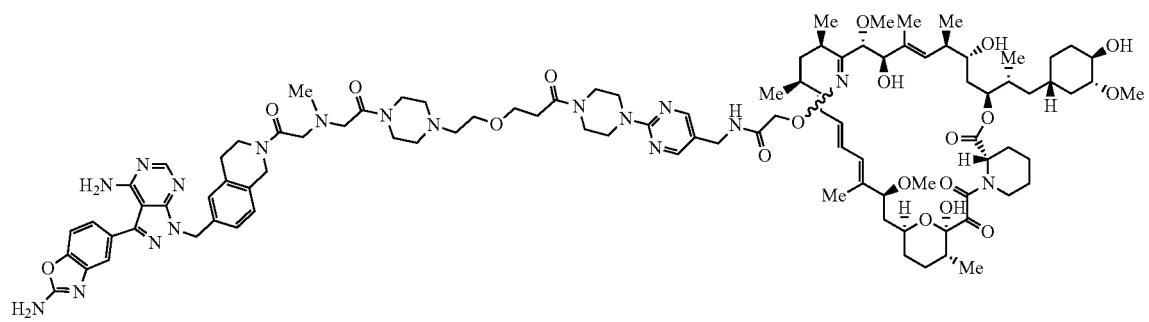

-continued
Example 37
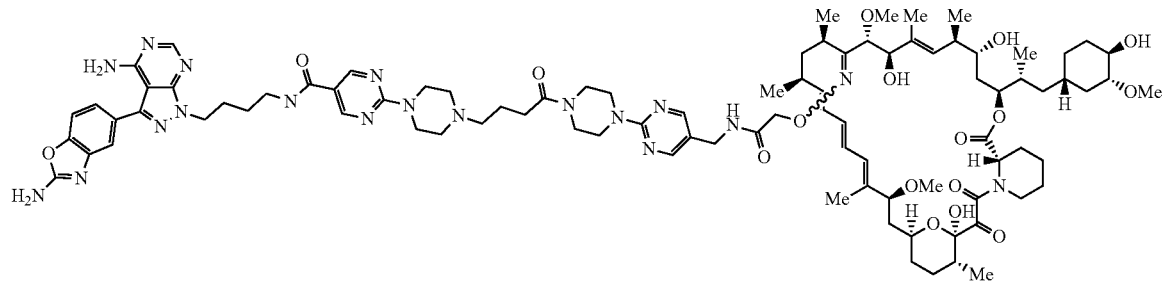
Example 38
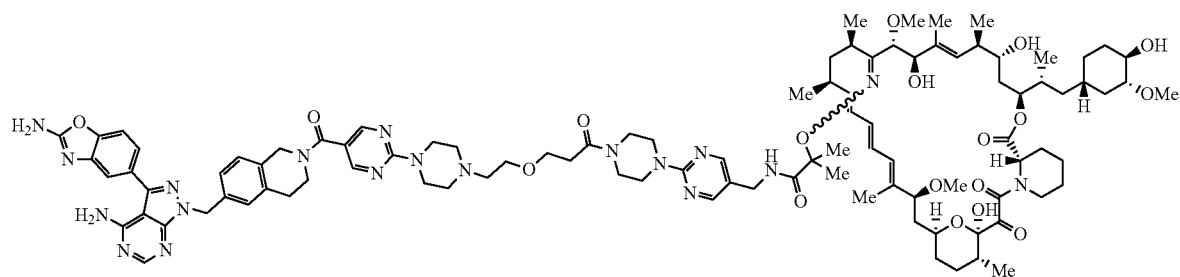
Example 39
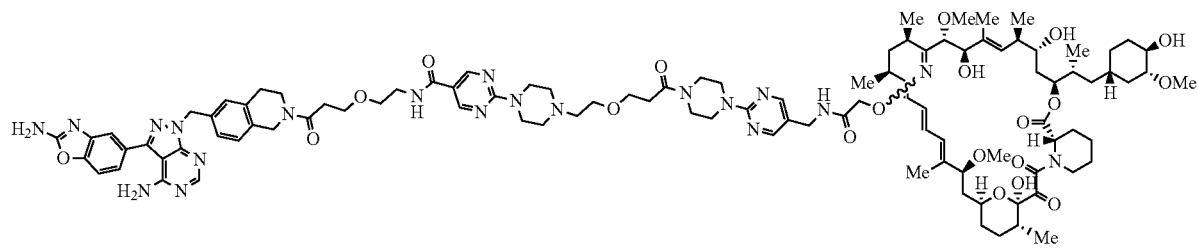
Example 40
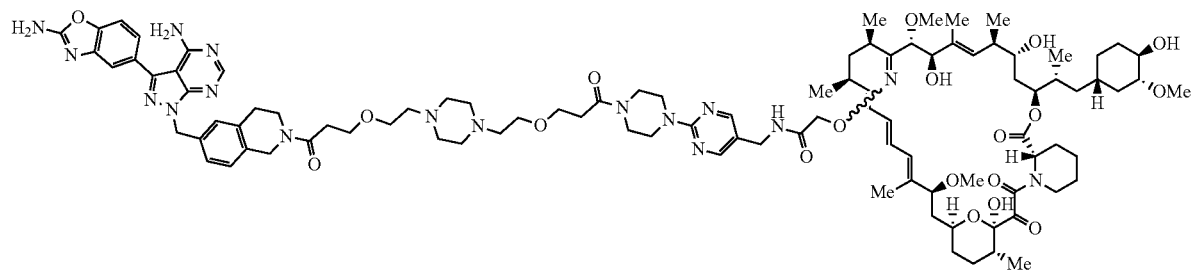
Example 41
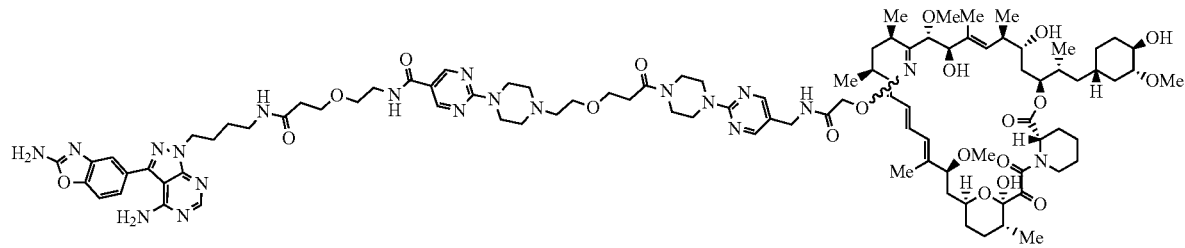

Example 42
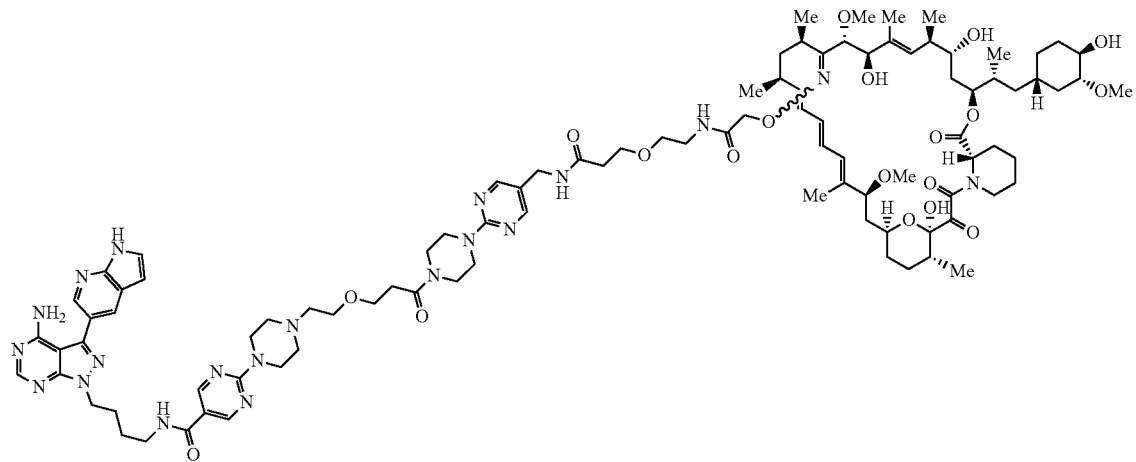
Example 43
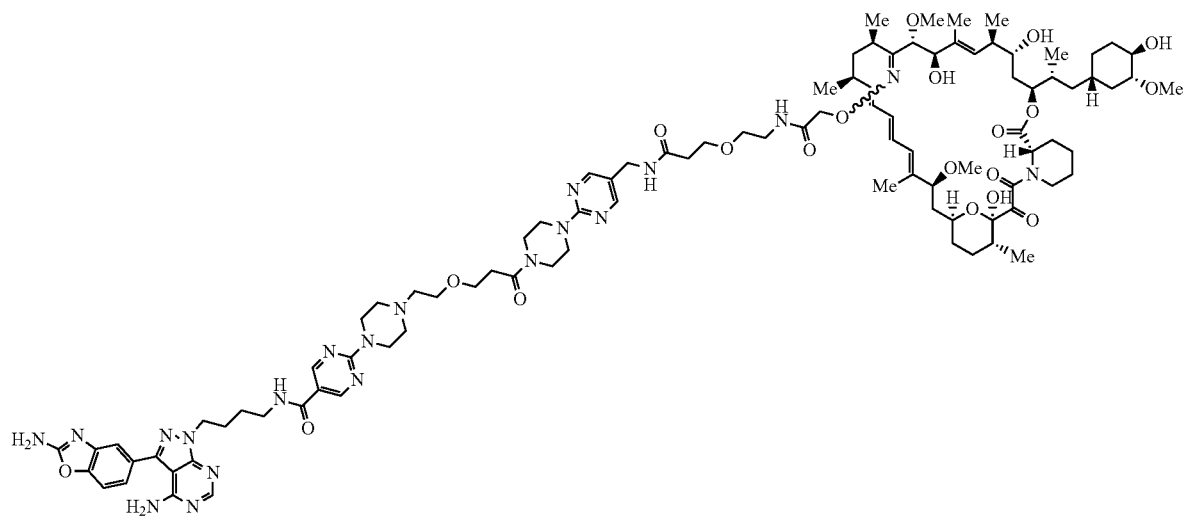
Example 44
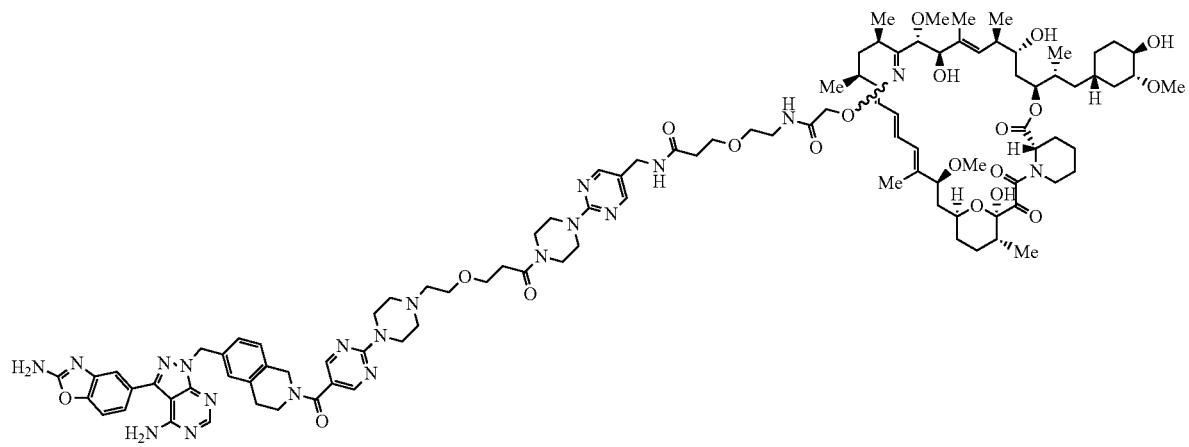
or a pharmaceutically acceptable salt or tautomer thereof.

Embodiment II-45. A compound selected from the group consisting of:
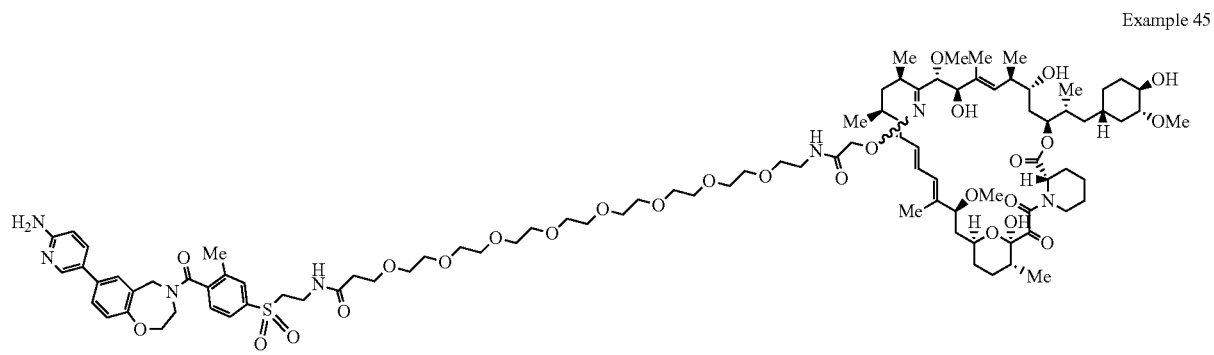
Example 45
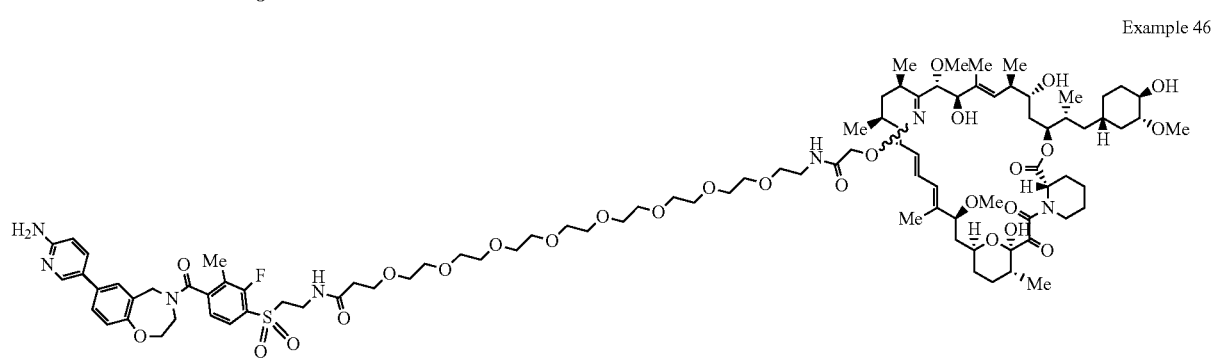
Example 46
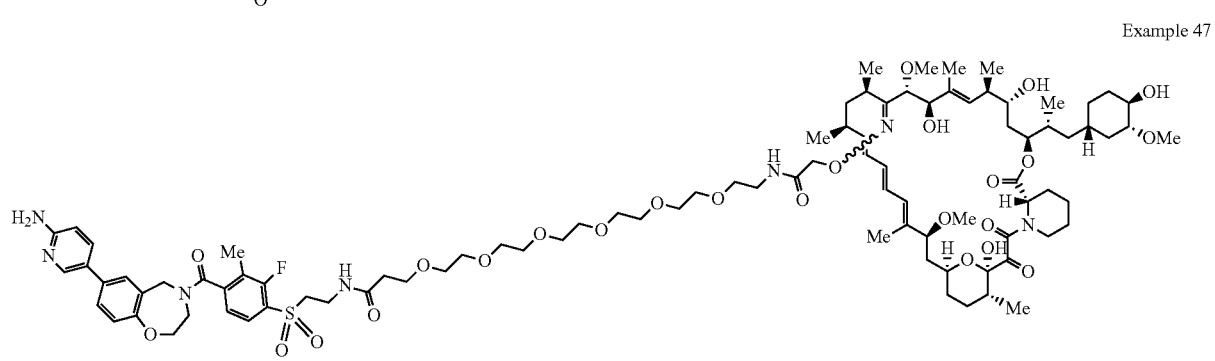
Example 47
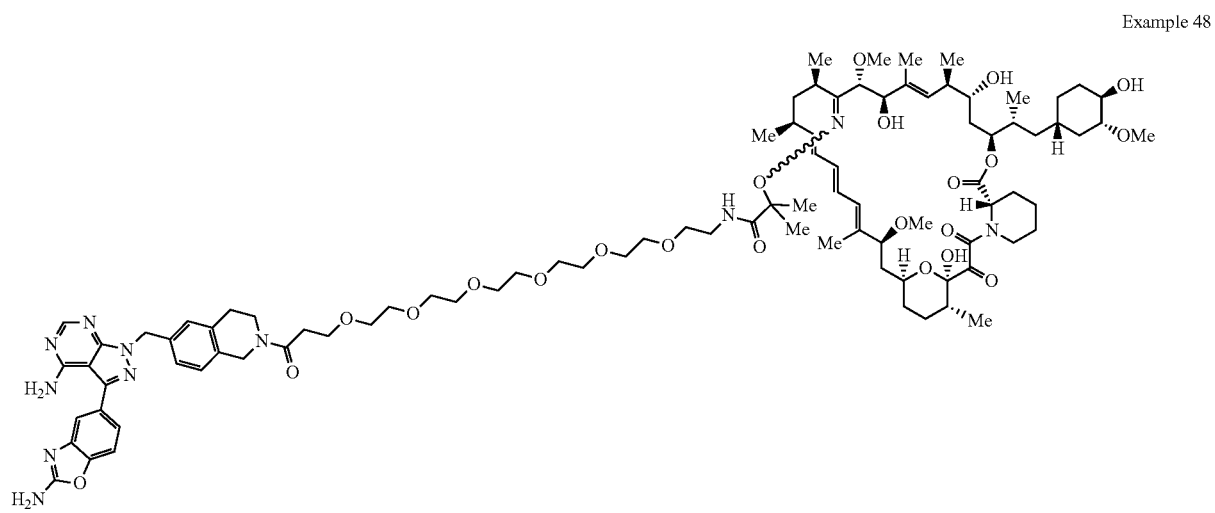
Example 48

-continued
Example 49
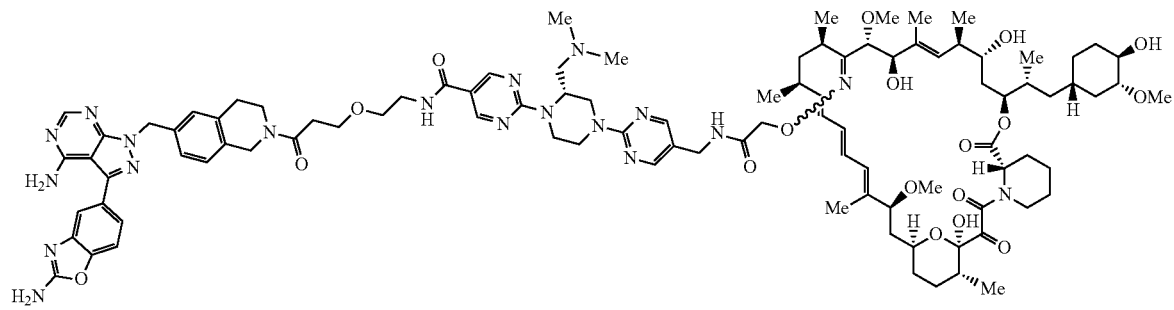
Example 50
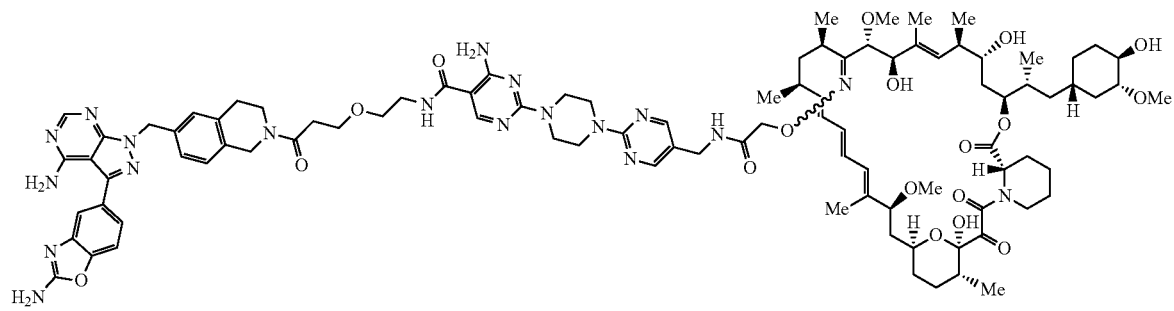
Example 51
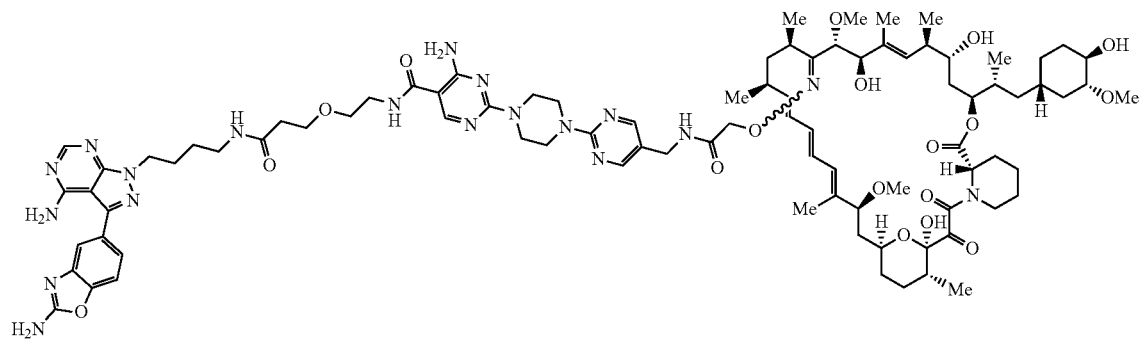
Example 52
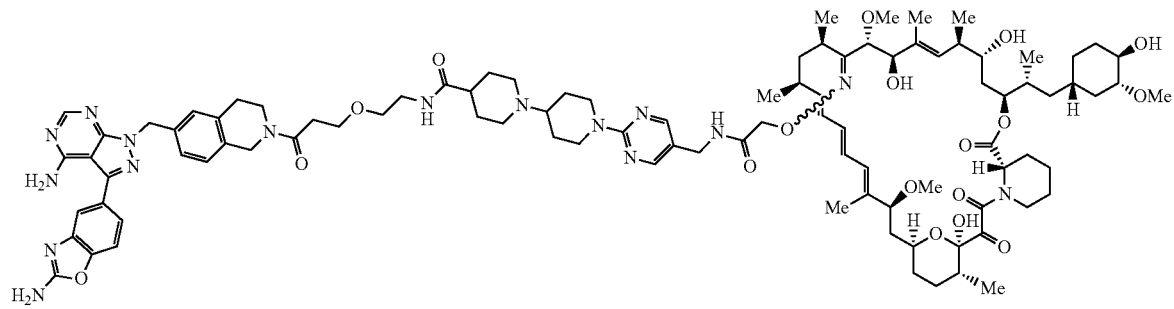

Example 53
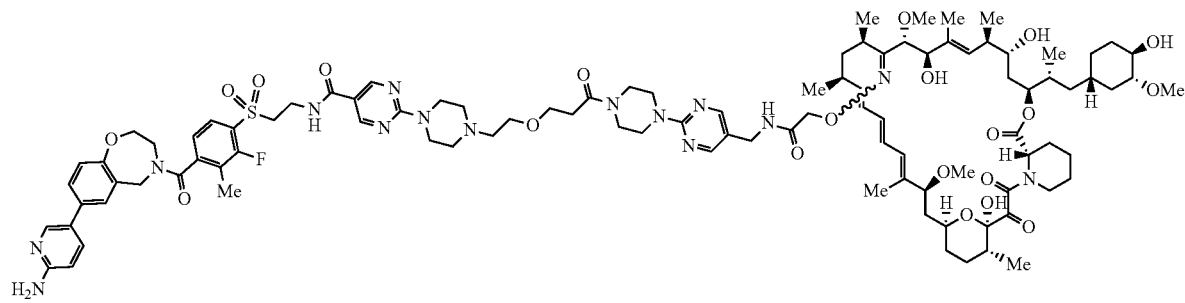
Example 54
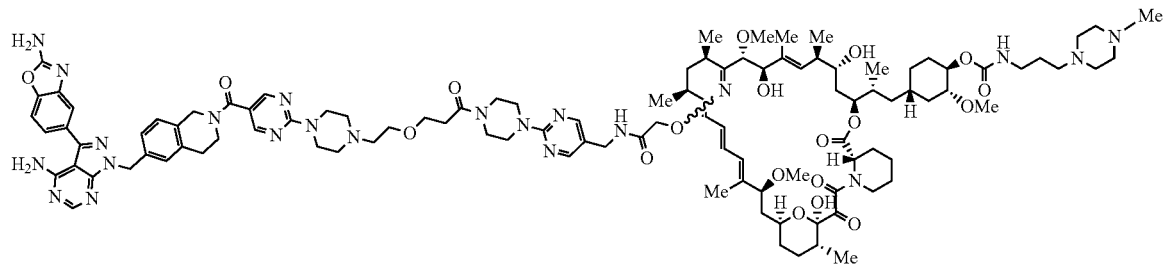
Example 55
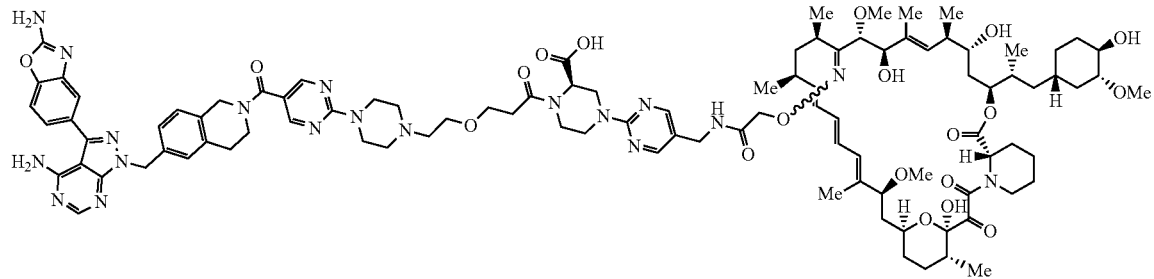
Example 56
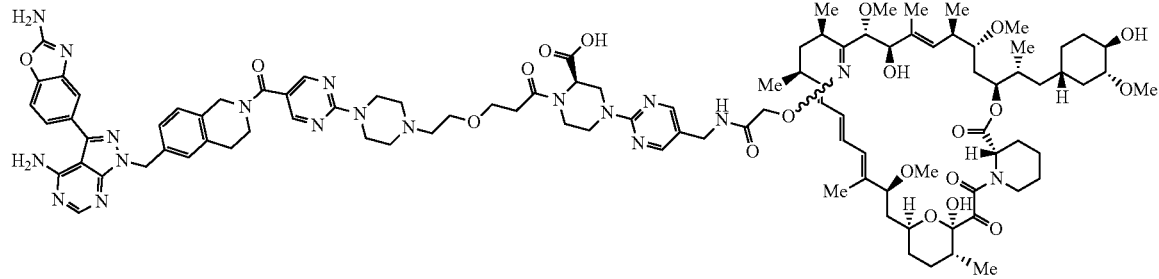
Example 57
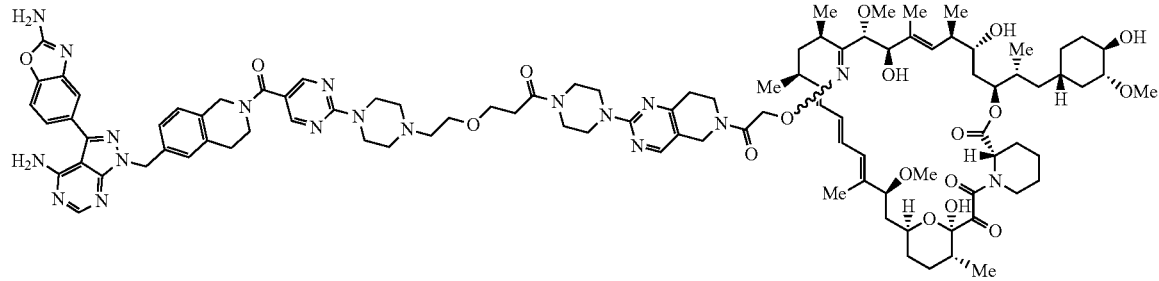

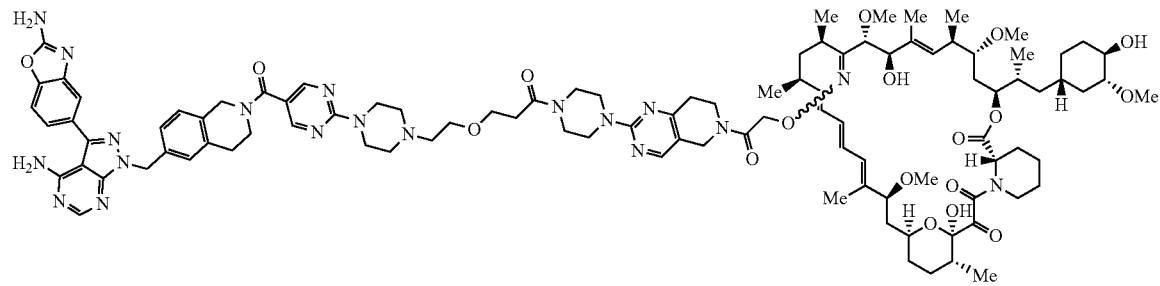
Example 58
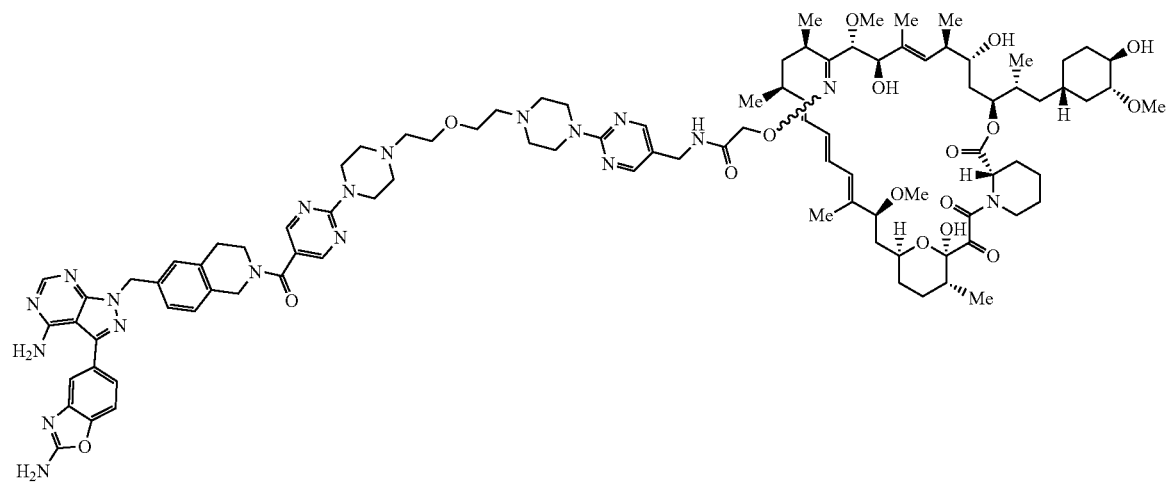
Example 59
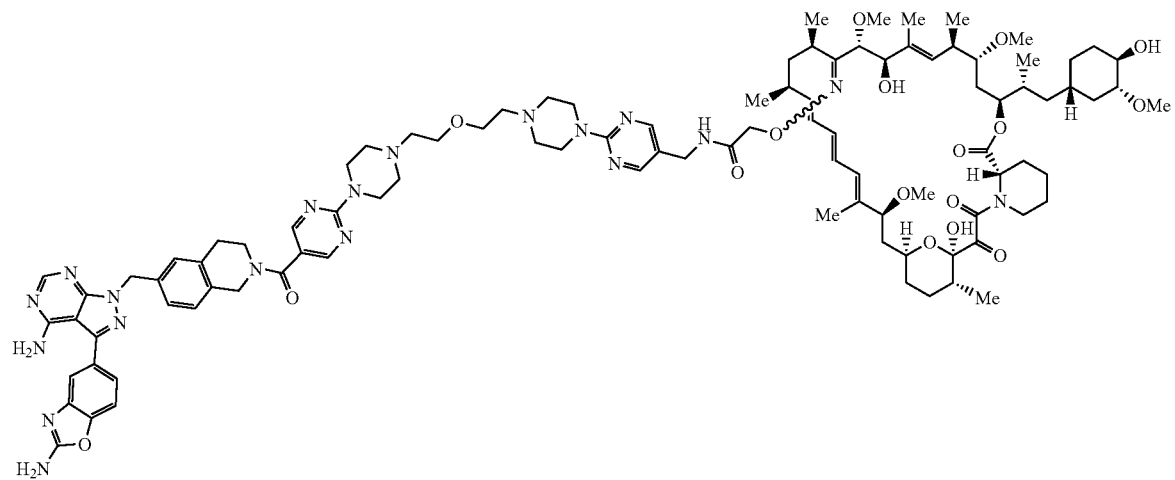
Example 60

-continued
Example 61
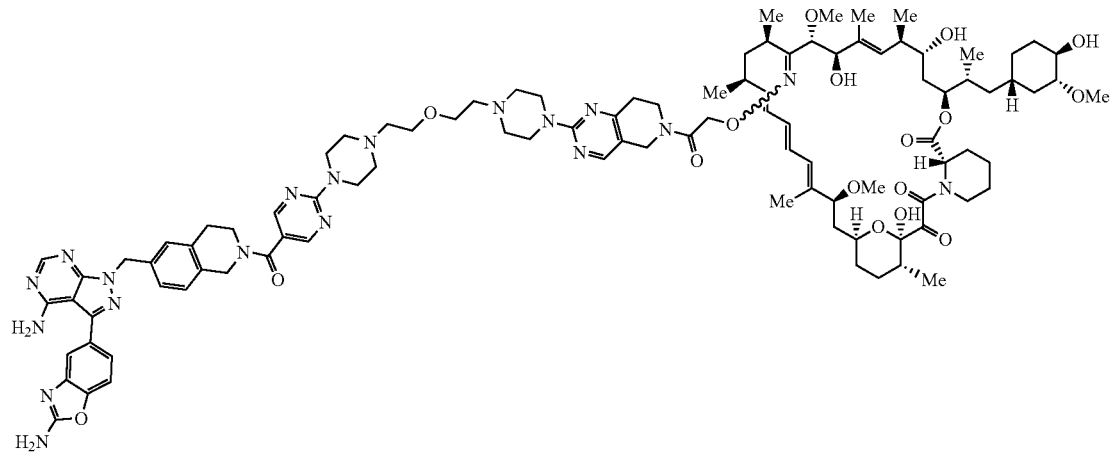
Example 62
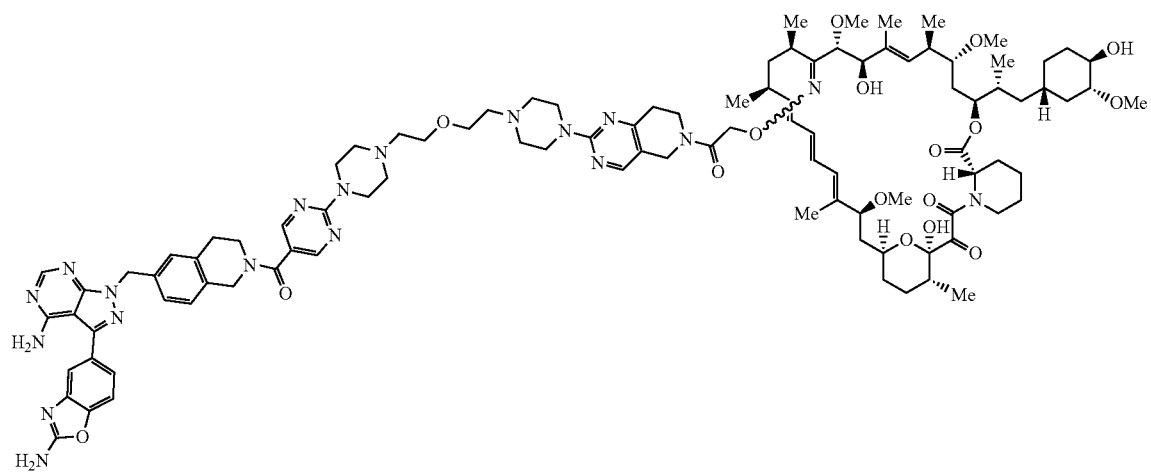
Example 63
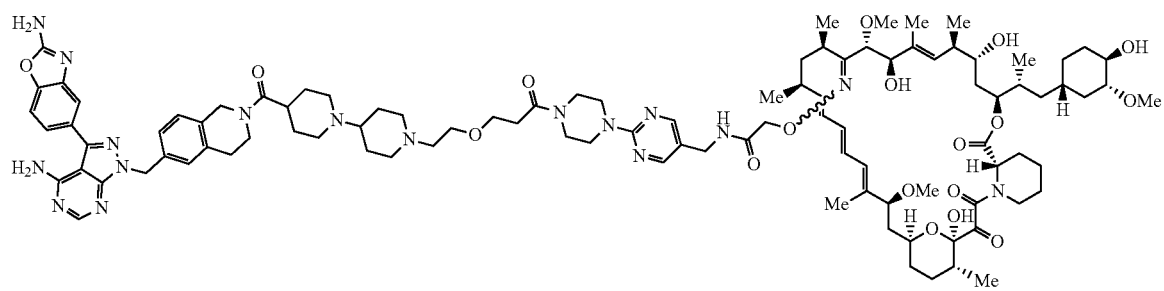
Example 64
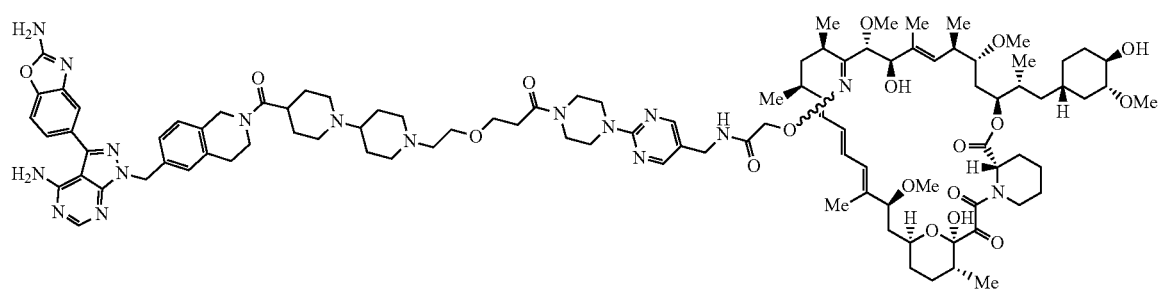

-continued
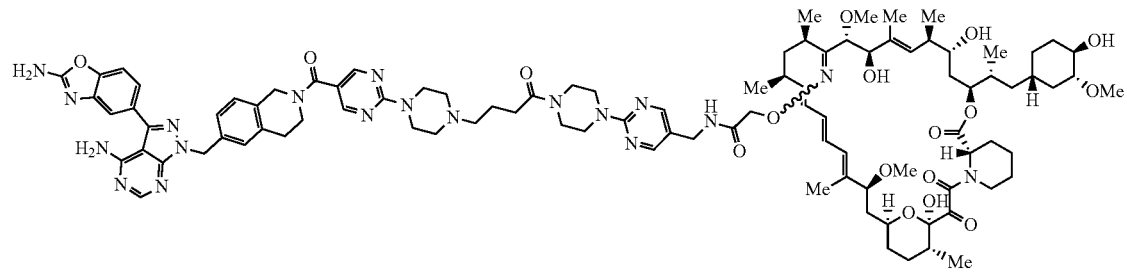
Example 65
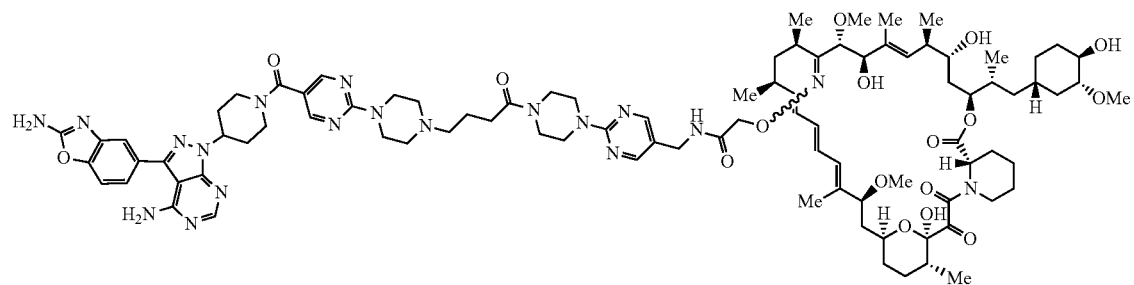
Example 66
or a pharmaceutically acceptable salt or tautomer thereof.
Embodiment II-46. A compound selected from the group consisting of:
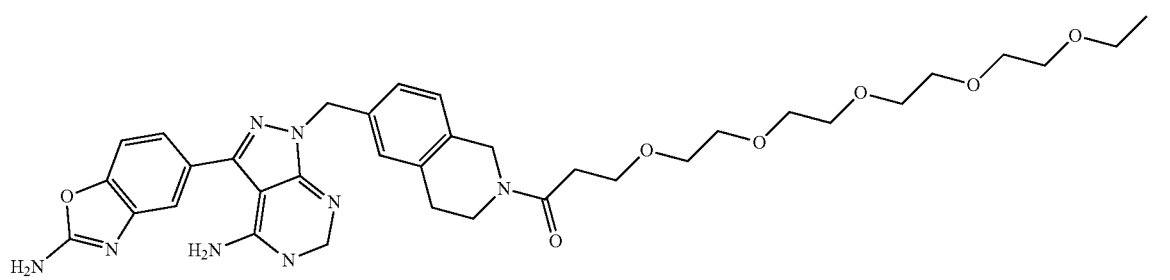
Example 67
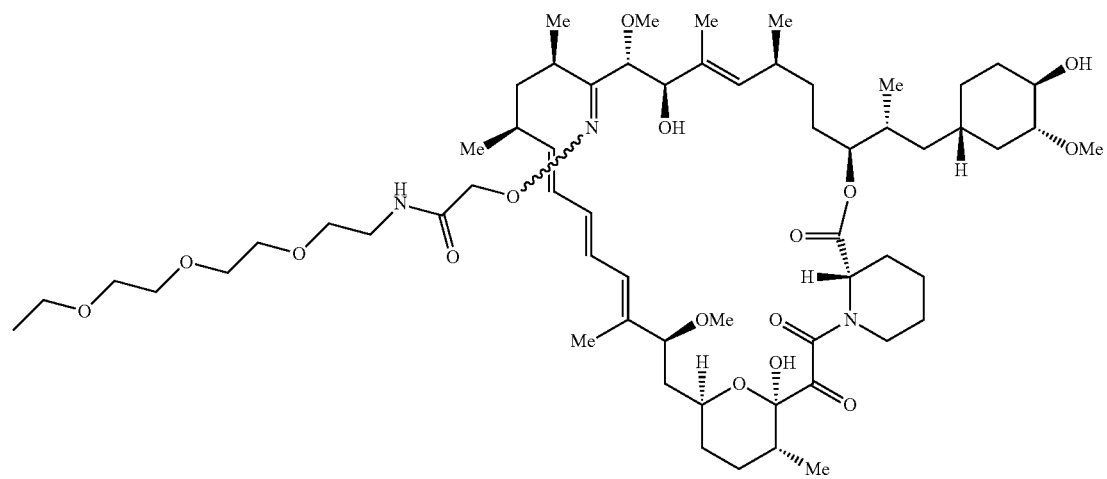

Example 68
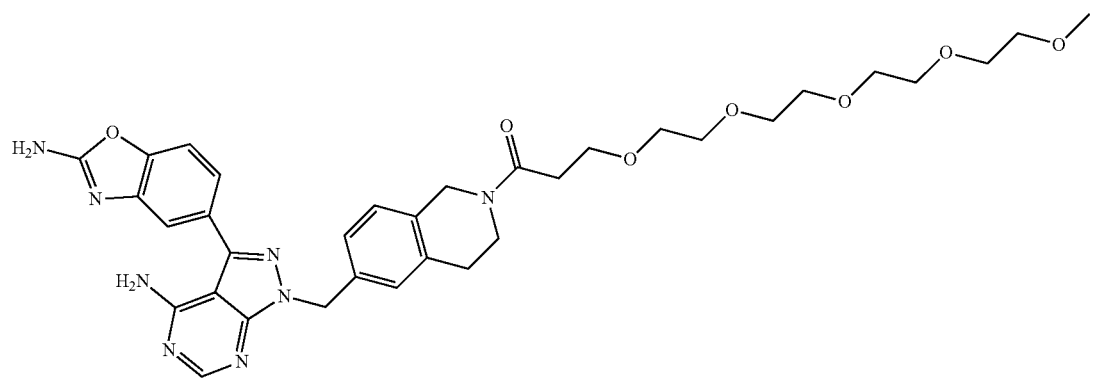
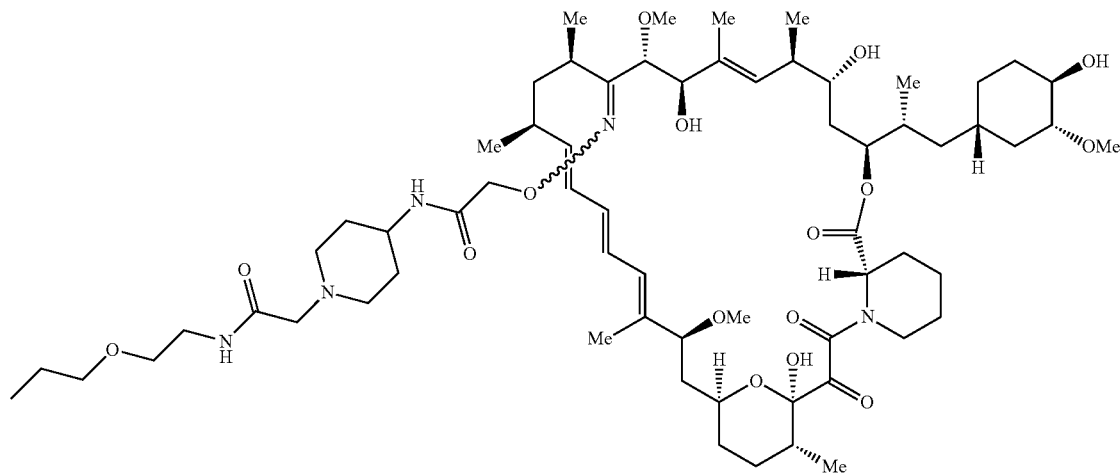
Example 69
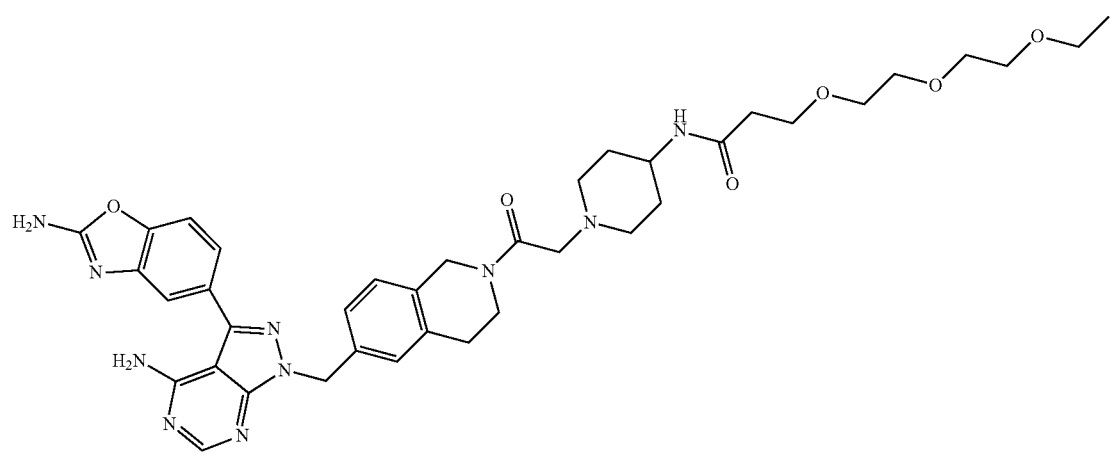

-continued

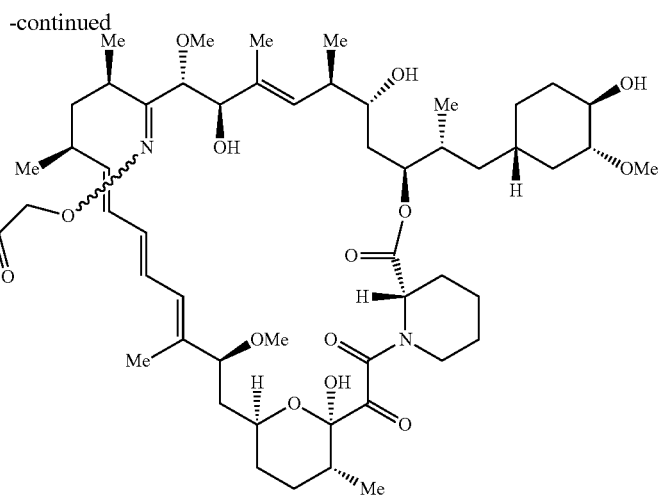

Example 70

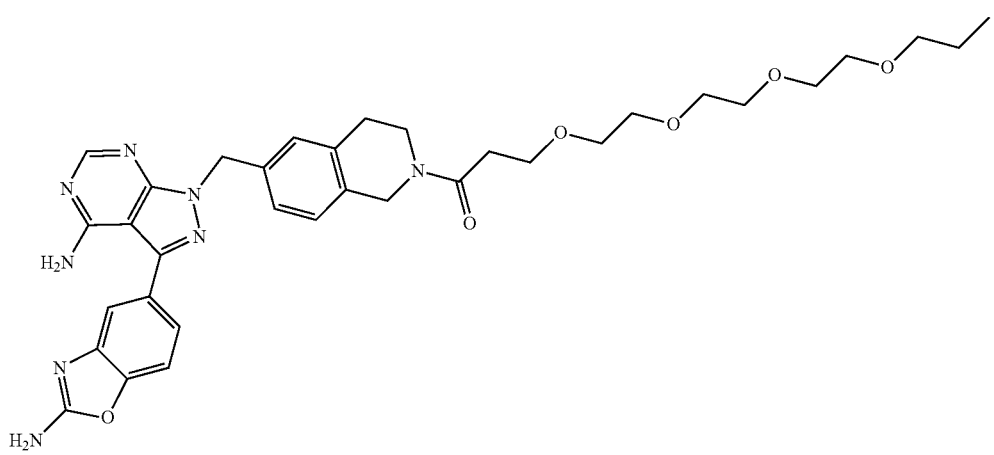

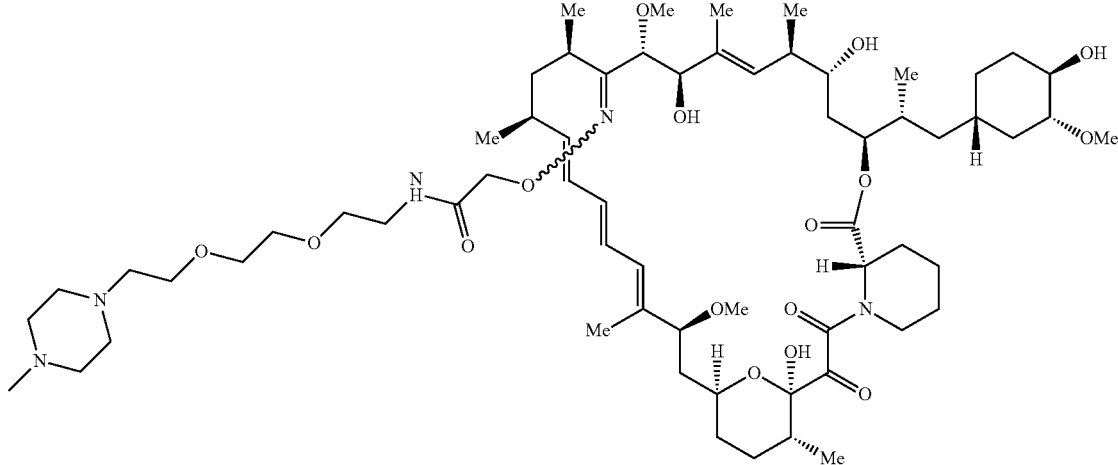

or a pharmaceutically acceptable salt or tautomer thereof.

Embodiment II-47. A pharmaceutical composition comprising a compound of any one of Embodiments II-1 to II-46, or a pharmaceutically acceptable salt thereof, and at least one of a pharmaceutically acceptable carrier, diluent, or excipient.

Embodiment II-48. A method of treating a disease or disorder mediated by mTOR comprising administering to the subject suffering from or susceptible to developing a disease or disorder mediated by mTOR a therapeutically effective amount of one or more compounds of any one of Embodiments II-1 to II-46, or a pharmaceutically acceptable salt thereof.

Embodiment II-49. A method of preventing a disease or disorder mediated by mTOR comprising administering to the subject suffering from or susceptible to developing a disease or disorder mediated by mTOR a therapeutically effective amount of one or more compounds of any one of Embodiments II-1 to II-46, or a pharmaceutically acceptable salt thereof.

Embodiment II-50. A method of reducing the risk of a disease or disorder mediated by mTOR comprising administering to the subject suffering from or susceptible to developing a disease or disorder mediated by mTOR a therapeutically effective amount of one or more compounds of any one of Embodiments II-1 to II-46, or a pharmaceutically acceptable salt thereof.

Embodiment II-51. The method of any one of Embodiments II-47 to II-49, wherein the disease is cancer or an immune-mediated disease.

Embodiment II-52. The method of Embodiment II-51, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment II-53. The method of Embodiment II-51, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment II-54. A method of treating cancer comprising administering to the subject a therapeutically effective amount of one or more compounds of any one of Embodiments II-1 to II-46, or a pharmaceutically acceptable salt thereof.

Embodiment II-55. The method of Embodiment II-54, wherein the cancer is selected from brain and neurovascular tumors, head and neck cancers, breast cancer, lung cancer, mesothelioma, lymphoid cancer, stomach cancer, kidney cancer, renal carcinoma, liver cancer, ovarian cancer, ovary endometriosis, testicular cancer, gastrointestinal cancer, prostate cancer, glioblastoma, skin cancer, melanoma, neuro cancers, spleen cancers, pancreatic cancers, blood proliferative disorders, lymphoma, leukemia, endometrial cancer, cervical cancer, vulva cancer, prostate cancer, penile cancer, bone cancers, muscle cancers, soft tissue cancers, intestinal or rectal cancer, anal cancer, bladder cancer, bile duct cancer, ocular cancer, gastrointestinal stromal tumors, and neuro-endocrine tumors.

Embodiment II-56. A method of treating an immune-mediated disease comprising administering to the subject a therapeutically effective amount of one or more compounds of any one of Embodiments II-1 to II-46, or a pharmaceutically acceptable salt thereof.

Embodiment II-57. The method of Embodiment II-56, wherein the immune-mediated disease is selected from resistance by transplantation of heart, kidney, liver, medulla ossium, skin, cornea, lung, pancreas, intestinum tenue, limb, muscle, nerves, duodenum, small-bowel, or pancreatic-islet-cell; graft-versus-host diseases brought about by medulla ossium transplantation; rheumatoid arthritis, systemic lupus erythematosus, Hashimoto's thyroiditis, multiple sclerosis, myasthenia gravis, type I diabetes, uveitis, allergic encephalomyelitis, and glomerulonephritis.

Embodiment II-58. A method of treating an age related condition comprising administering to the subject a therapeutically effective amount of one or more compounds of any one of Embodiments II-1 to II-46, or a pharmaceutically acceptable salt thereof.

Embodiment II-59. The method of Embodiment II-58, wherein the age related condition is selected from sarcopenia, skin atrophy, muscle wasting, brain atrophy, atherosclerosis, arteriosclerosis, pulmonary emphysema, osteoporosis, osteoarthritis, high blood pressure, erectile dysfunction, dementia, Huntington's disease, Alzheimer's disease, cataracts, age-related macular degeneration, prostate cancer, stroke, diminished life expectancy, impaired kidney function, and age-related hearing loss, aging-related mobility disability (e.g., frailty), cognitive decline, age-related dementia, memory impairment, tendon stiffness, heart dysfunction such as cardiac hypertrophy and systolic and diastolic dysfunction, immunosenescence, cancer, obesity, and diabetes.

Embodiment II-60. A compound of any one of Embodiments II-1 to II-46, or a pharmaceutically acceptable salt thereof, for use in treating, preventing, or reducing the risk of a disease or condition mediated by mTOR.

Embodiment II-61. Use of a compound of any of Embodiments II-1 to II-46, or a pharmaceutically acceptable salt thereof, in the manufacture of a medicament for treating, preventing, or reducing the risk of a disease or disorder mediated by mTOR.

Embodiment II-62. A compound of any one of Embodiments II-1 to II-46, or a pharmaceutically acceptable salt thereof, for use in treating cancer.

Embodiment II-63. Use of a compound of any one of Embodiments II-1 to II-46, or a pharmaceutically acceptable salt thereof, in the manufacture of a medicament for treating cancer.

Embodiment II-64. A compound of any one of Embodiments II-1 to II-46, or a pharmaceutically acceptable salt thereof, for use in treating an immune-mediated disease.

Embodiment II-65. Use of a compound of any one of Embodiments II-1 to II-46, or a pharmaceutically acceptable salt thereof, in the manufacture of a medicament for treating an immune-mediated disease.

Embodiment II-66. A compound of any one of Embodiments II-1 to II-46, or a pharmaceutically acceptable salt thereof, for use in treating an age related condition.

Embodiment II-67. Use of a compound of any one of Embodiments II-1 to II-46, or a pharmaceutically acceptable salt thereof, in the manufacture of a medicament for treating an age related condition.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

| | |
|---|---|
| $CH_2Cl_2$, DCM | Methylene chloride, Dichloromethane |
| $CH_3CN$, MeCN | Acetonitrile |
| DIPEA | Diisopropylethyl amine |
| DMA | Dimethylacetamide |
| DME | Dimethoxyethane |
| DMF | N,N-Dimethylformamide |
| EDCI | 1-Ethyl-3-(3-dimethylaminopropyl)carbodiimide |
| EtOAc | Ethyl acetate |
| h | hour |
| $H_2O$ | Water |
| HCl | Hydrochloric acid |
| HOBt | Hydroxybenzotriazole |
| HPLC | High-performance liquid chromatography |
| LCMS | Liquid chromatography-mass spectrometry |
| MeOH | Methanol |
| MTBE | Methyl tert-butyl ether |
| $Na_2SO_4$ | Sodium sulfate |
| PEG | Polyethylene glycol |
| TBDMS | tert-butyldimethylsilyl |
| TFA | Trifluoroacetic acid |
| THF | Tetrahydrofuran |
| TMS | Tetramethylsilane |

Series 1 bifunctional rapalogs

A general structure of Series 1 bifunctional rapalogs is shown in Scheme 1 below. Scheme 1. For these types of bifunctional rapalogs, the linker may include variations where q=0 to 30, such as q=1 to 7, and r=1 to 6. The linker amine can include substitutions, such as R=H and C1-C6 alkyl groups. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section. Series 1 bifunctional rapalogs.

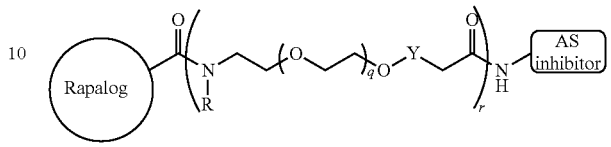

Series 1 Bifunctional rapalog

Series 2 Bifunctional Rapalogs

A general structure of to Series 2 bifunctional rapalogs is shown in Scheme 2 below. For these types of bifunctional rapalogs, the linker may include variations where q=0 to 30, such as q=1 to 7. The linker amine can include substitutions, such as R=H and C1-C6 alkyl groups. The pre-linker amine can include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 2. Series 2 bifunctional rapalogs.

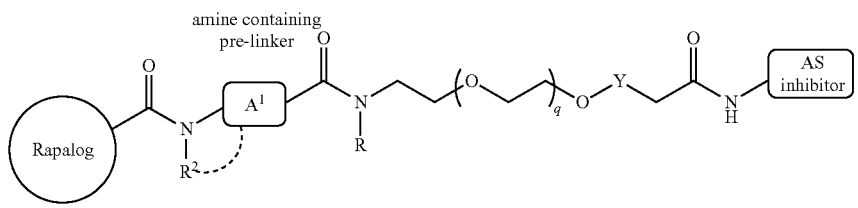

Series 2 Bifunctional rapalog

Series 3 Bifunctional Rapalogs

A general structure of Series 3 bifunctional rapalogs is shown in Scheme 3 below. For these types of bifunctional rapalogs, the linker may include variations where q=0 to 30, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 3. Series 3 bifunctional rapalogs

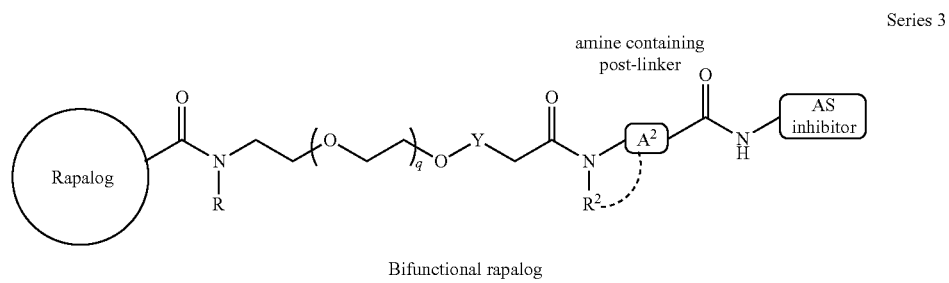

Series 3

Bifunctional rapalog

Series 4 Bifunctional Rapalogs

A general structure of Series 4 bifunctional rapalogs is shown in Scheme 4 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 4. Series 4 bifunctional rapalogs

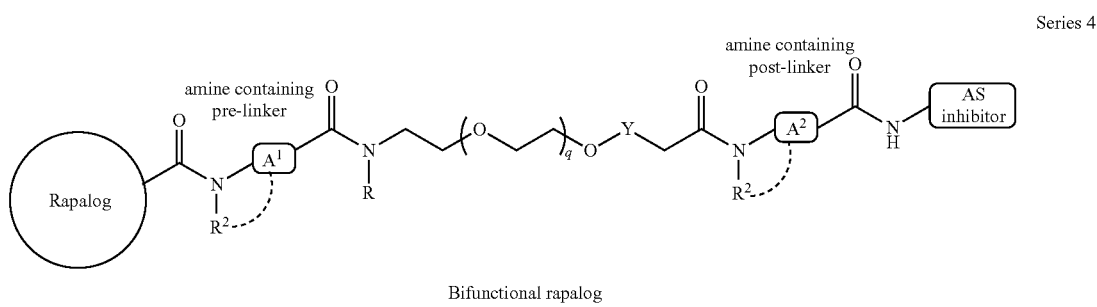

Series 4

Bifunctional rapalog

Series 5 Bifunctional Rapalogs

A general structure of Series 5 bifunctional rapalogs is shown in Scheme 5 below. For these types of bifunctional rapalogs, the pre-linker amine can include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 5. Series 5 bifunctional rapalogs

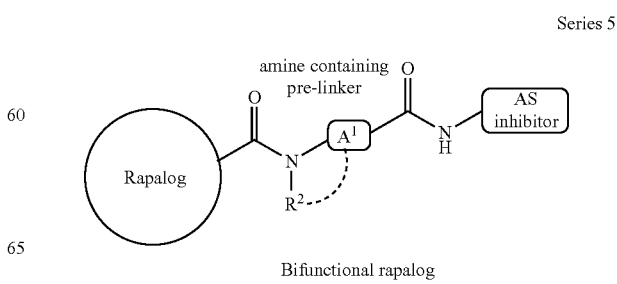

Series 5

Bifunctional rapalog

Series 6 Bifunctional Rapalogs

A general structure of Series 6 bifunctional rapalogs is shown in Scheme 6 below. For these types of bifunctional rapalogs, the linker may include variations where q=0 to 30, such as q=1 to 7. The linker amines can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 6. Series 6 bifunctional rapalogs.

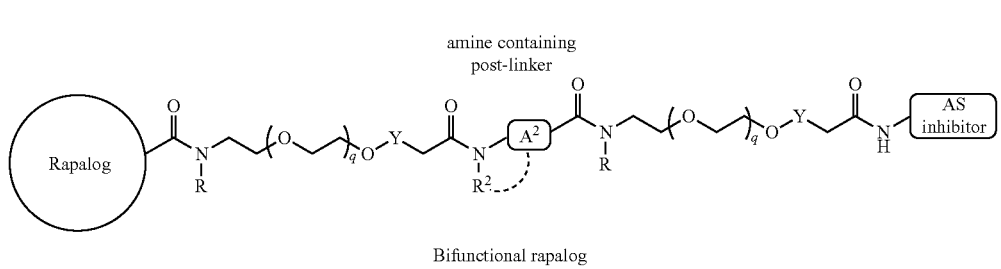

Bifunctional rapalog

Series 7 Bifunctional Rapalogs

A general structure of Series 7 bifunctional rapalogs is shown in Scheme 7 below. For these types of bifunctional rapalogs, the linker may include variations where q=0 to 30, such as q=1 to 7. The linker amine can include substitutions, such as R=H and C1-C6 alkyl groups. The pre- and post-linker amines can each include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 7. Series 7 bifunctional rapalogs

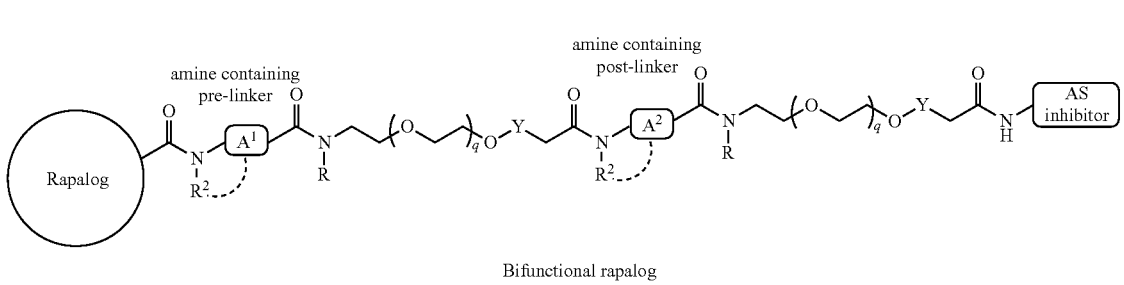

Bifunctional rapalog

Series 8 Bifunctional Rapalogs

A general structure of Series 8 bifunctional rapalogs is shown in Scheme 8 below. For these types of bifunctional rapalogs, the linker may include variations where q=0 to 30, such as q=1 to 7. The linker amine can include substitutions, such as R=H and C1-C6 alkyl groups. The post-linker amine can include substitutions, such as $R^2$=H, C1-C6 alkyl groups, and cycloalkyl including 4 to 8-membered rings. The amide moiety can be attached to the rapalog at $R^{26}$ (Formula I), via an oxime linkage fragment including variations found in Table 1 in the Examples Section. An mTOR active site inhibitor can attach to the linker via a primary or secondary amine, and may include variations found in Table 2 in the Examples Section.

Scheme 8. Series 8 bifunctional rapalogs
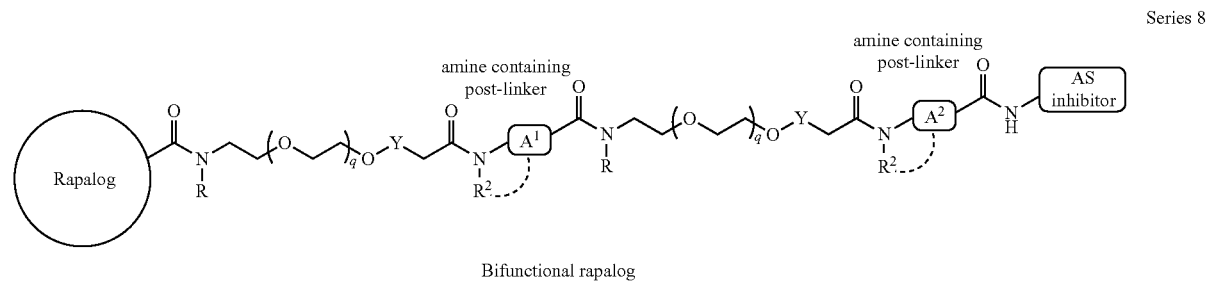
Bifunctional rapalog
TABLE 1
Carboxylic acid containing rapalog monomers.
Carboxylic acid containing rapalog
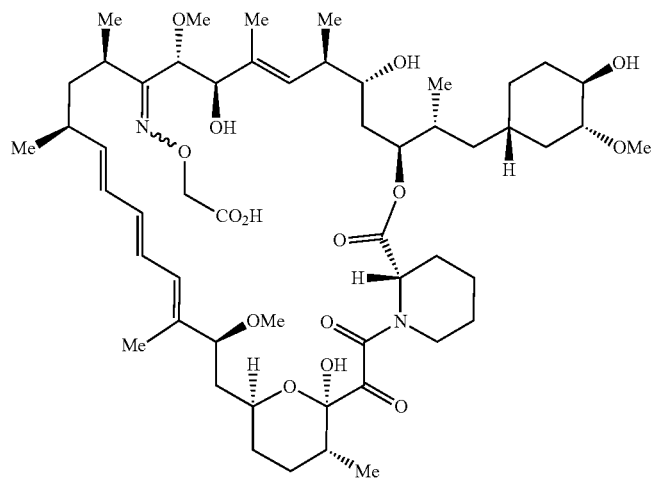
Monomer 1
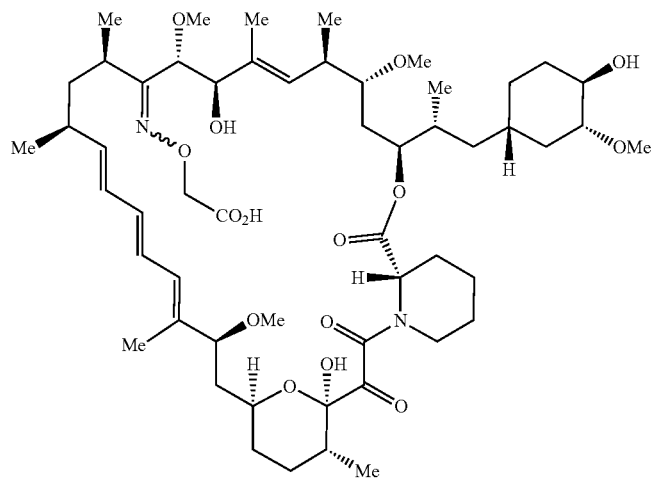
Monomer 2

TABLE 1-continued
Carboxylic acid containing rapalog monomers.
Carboxylic acid containing rapalog
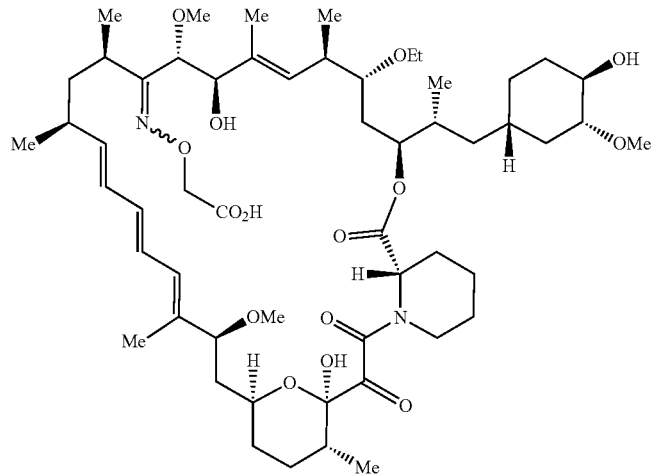
Monomer 3
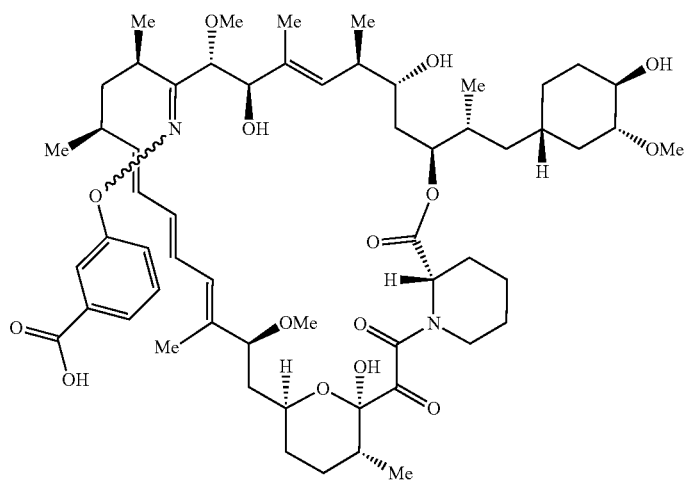 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)C[C@@H](O)[C@H](C)/C=C(\C)[C@@H](O)[C@@H](OC)C(=NOc2cccc(C(=O)O)c2)[C@H](C)C[C@H](C)/C=C/C=C/C=C/1C]
Monomer 4
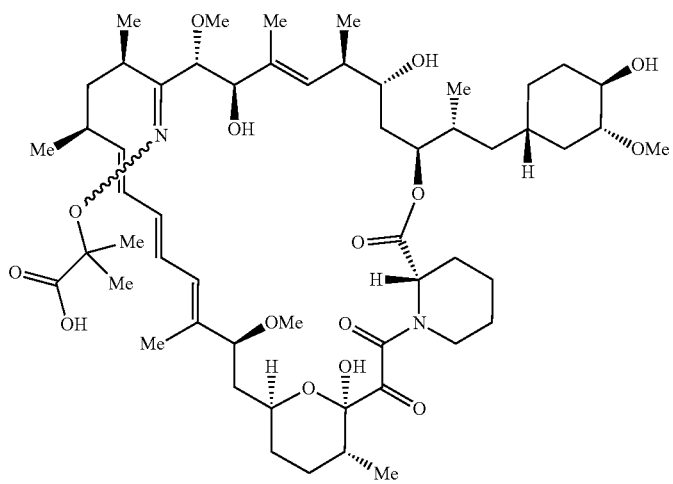 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)C[C@@H](O)[C@H](C)/C=C(\C)[C@@H](O)[C@@H](OC)C(=NOC(C)(C)C(=O)O)[C@H](C)C[C@H](C)/C=C/C=C/C=C/1C]
Monomer 5

TABLE 1-continued
Carboxylic acid containing rapalog monomers.
Carboxylic acid containing rapalog
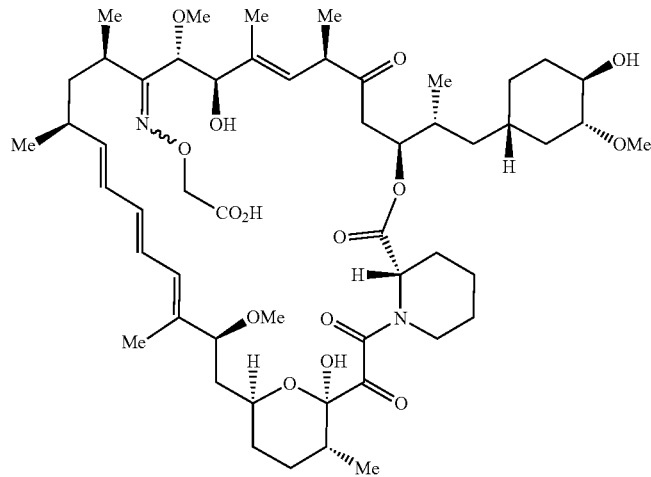
Monomer 6
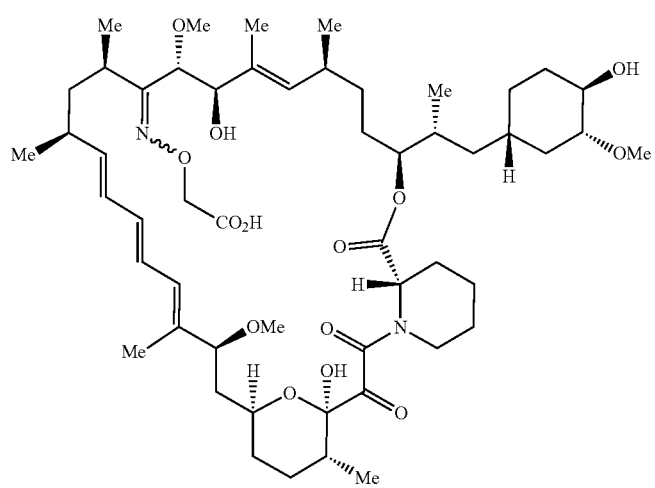
Monomer 7
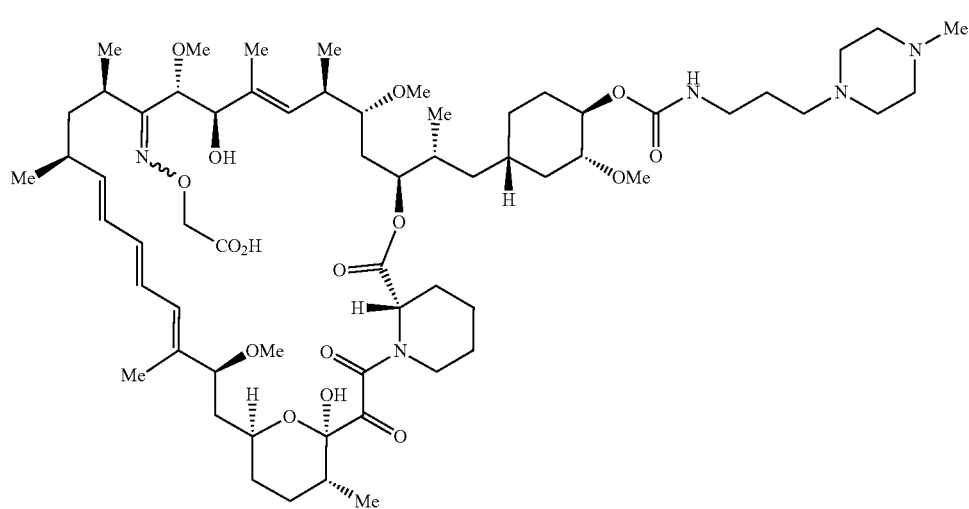
Monomer 8

TABLE 2
Active Site inhibitor monomers.
Active Site inhibitor monomers
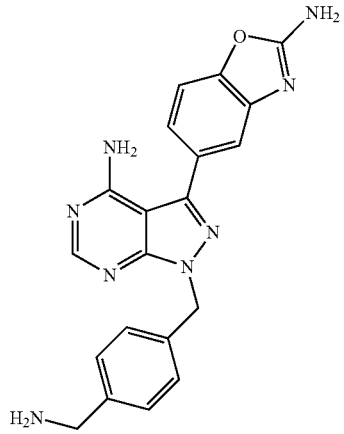 [SMILES: NCc1ccc(Cn2nc(-c3ccc4oc(N)nc4c3)c3c(N)ncnc32)cc1]
Monomer A
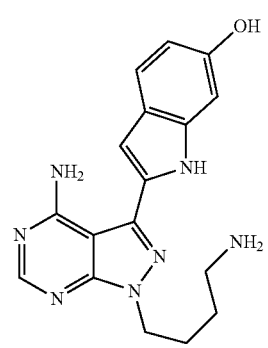 [SMILES: NCCCCn1nc(-c2cc3ccc(O)cc3[nH]2)c2c(N)ncnc21]
Monomer B
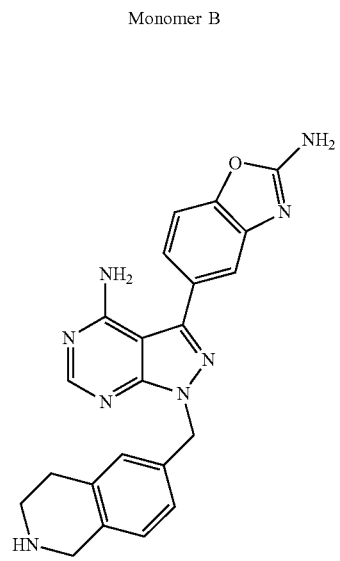
Monomer C
TABLE 2-continued
Active Site inhibitor monomers.
Active Site inhibitor monomers
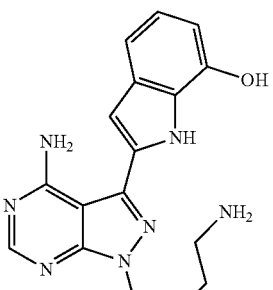
Monomer D
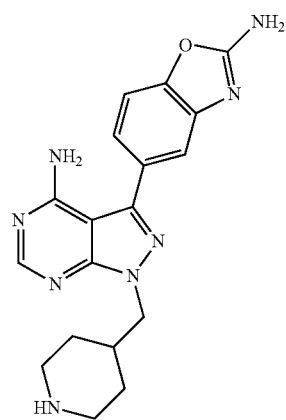 [SMILES: Nc1nc2cc(-c3nn(CC4CCNCC4)c4ncnc(N)c34)ccc2o1]
Monomer E
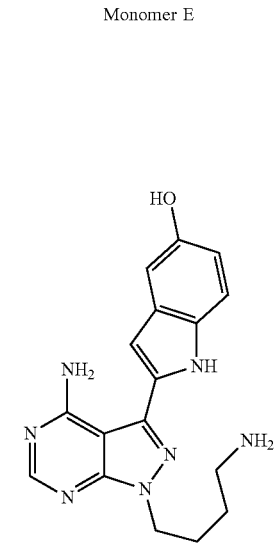
Monomer F TABLE 2-continued
Active Site inhibitor monomers.
Active Site inhibitor monomers
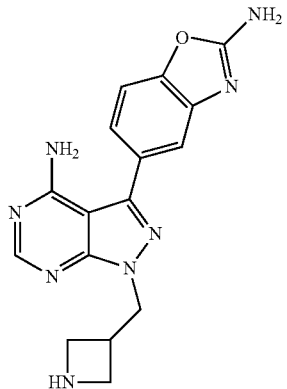 [SMILES: Nc1nc2cc(-c3nn(CC4CNC4)c4ncnc(N)c34)ccc2o1]
Monomer G
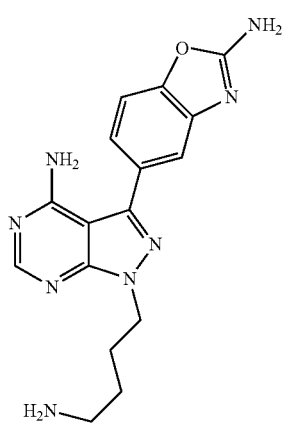 [SMILES: NCCCCn1nc(-c2ccc3oc(N)nc3c2)c2c(N)ncnc21]
Monomer H
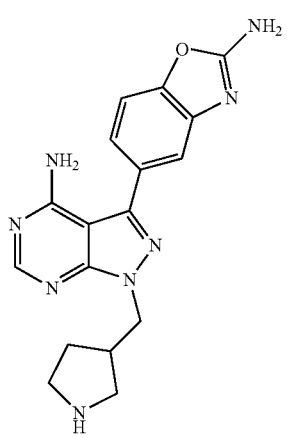 [SMILES: Nc1nc2cc(-c3nn(CC4CCNC4)c4ncnc(N)c34)ccc2o1]
Monomer I
TABLE 2-continued
Active Site inhibitor monomers.
Active Site inhibitor monomers
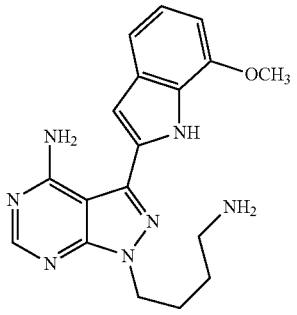 [SMILES: COc1cccc2cc(-c3nn(CCCCN)c4ncnc(N)c34)[nH]c12]
Monomer J
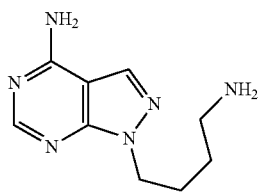 [SMILES: NCCCCn1ncc2c(N)ncnc21]
Monomer K
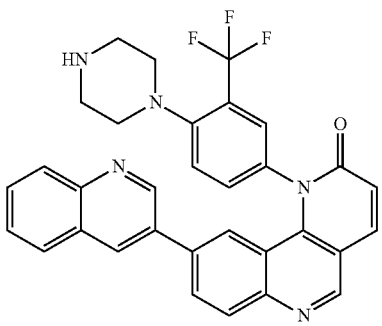 [SMILES: O=c1ccc2cnc3ccc(-c4cnc5ccccc5c4)cc3c2n1-c1ccc(N2CCNCC2)c(C(F)(F)F)c1]
Monomer L
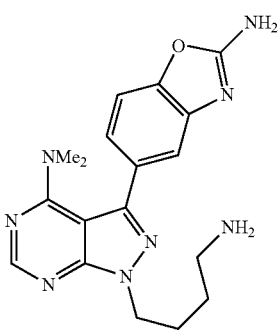 [SMILES: CN(C)c1ncnc2c1c(-c1ccc3oc(N)nc3c1)nn2CCCCN]
Monomer M TABLE 2-continued
Active Site inhibitor monomers.
Active Site inhibitor monomers
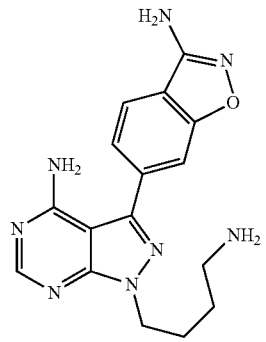 [SMILES: NCCCCn1nc(-c2ccc3c(N)noc3c2)c2c(N)ncnc21]
Monomer N
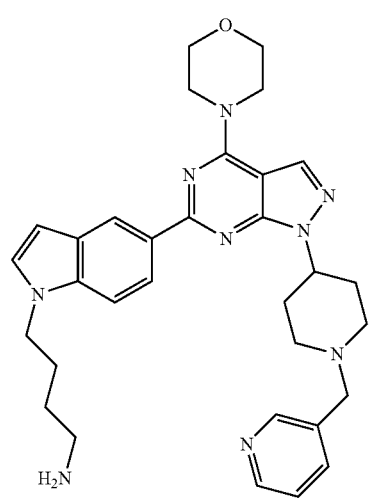 [SMILES: NCCCCn1ccc2cc(-c3nc(N4CCOCC4)c4cnn(C5CCN(Cc6cccnc6)CC5)c4n3)ccc21]
Monomer O
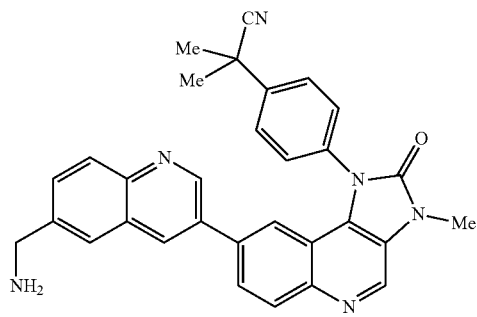 [SMILES: Cn1c(=O)n(-c2ccc(C(C)(C)C#N)cc2)c2c3cc(-c4cnc5ccc(CN)cc5c4)ccc3ncc21]
Monomer P
TABLE 2-continued
Active Site inhibitor monomers.
Active Site inhibitor monomers
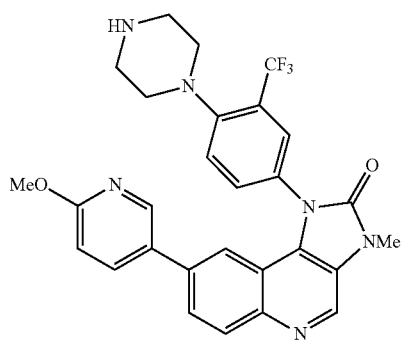 [SMILES: COc1ccc(-c2ccc3ncc4c(c3c2)n(-c2ccc(N3CCNCC3)c(C(F)(F)F)c2)c(=O)n4C)cn1]
Monomer Q
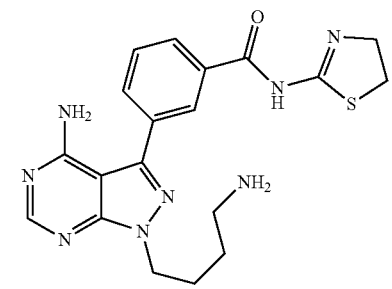 [SMILES: NCCCCn1nc(-c2cccc(C(=O)NC3=NCCS3)c2)c2c(N)ncnc21]
Monomer R
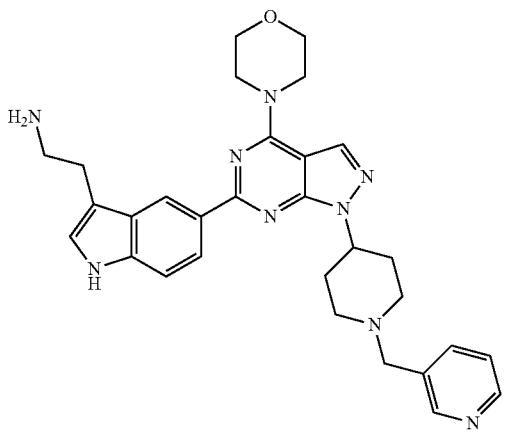 [SMILES: NCCc1c[nH]c2ccc(-c3nc(N4CCOCC4)c4cnn(C5CCN(Cc6cccnc6)CC5)c4n3)cc12]
Monomer S
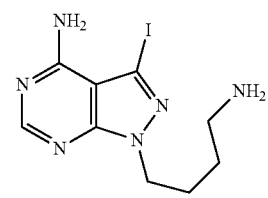 [SMILES: NCCCCn1nc(I)c2c(N)ncnc21]
Monomer T TABLE 2-continued
Active Site inhibitor monomers.
Active Site inhibitor monomers
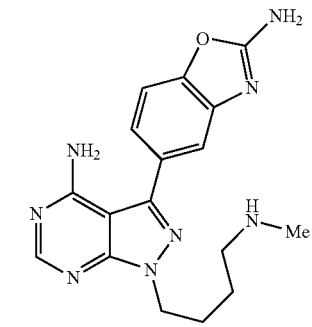 [SMILES: CNCCCCn1nc(-c2ccc3oc(N)nc3c2)c2c(N)ncnc21]
Monomer U
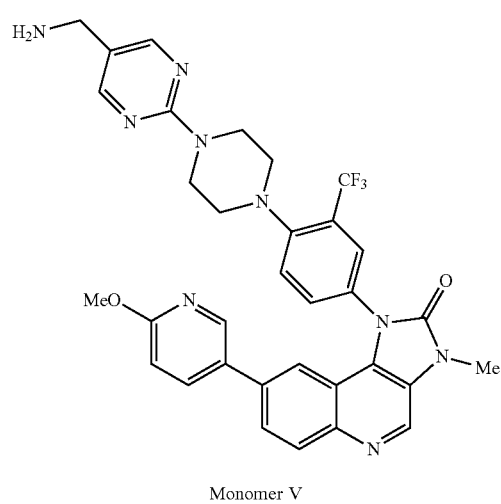
Monomer V
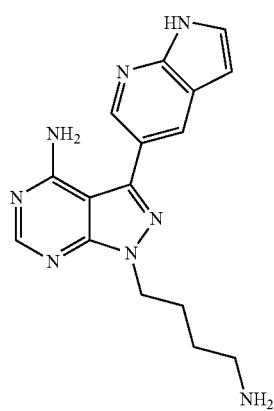 [SMILES: NCCCCn1nc(-c2cnc3[nH]ccc3c2)c2c(N)ncnc21]
Monomer W
TABLE 2-continued
Active Site inhibitor monomers.
Active Site inhibitor monomers
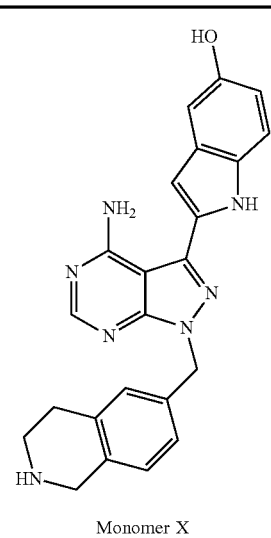
Monomer X
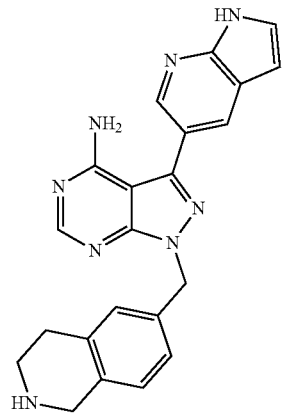 [SMILES: Nc1ncnc2c1c(-c1cnc3[nH]ccc3c1)nn2Cc1ccc2c(c1)CCNC2]
Monomer Y
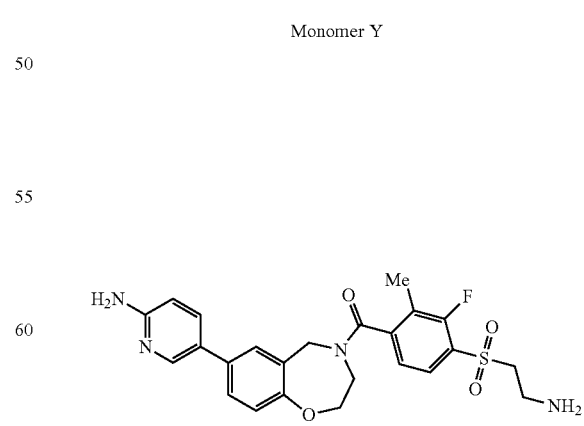
Monomer Z TABLE 2-continued
Active Site inhibitor monomers.
Active Site inhibitor monomers
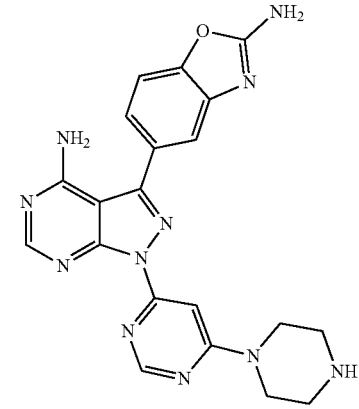 [SMILES: Nc1nc2cc(-c3nn(-c4cc(N5CCNCC5)ncn4)c4ncnc(N)c34)ccc2o1]
Monomer AA
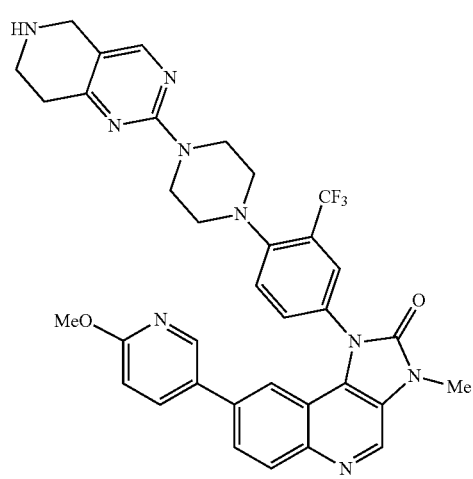 [SMILES: COc1ccc(-c2ccc3ncc4c(c3c2)n(-c2ccc(N3CCN(c5ncc6c(n5)CCNC6)CC3)c(C(F)(F)F)c2)c(=O)n4C)cn1]
Monomer AB
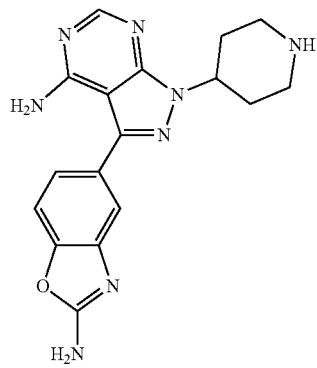 [SMILES: Nc1nc2cc(-c3nn(C4CCNCC4)c4ncnc(N)c34)ccc2o1]
Monomer AC
TABLE 2-continued
Active Site inhibitor monomers.
Active Site inhibitor monomers
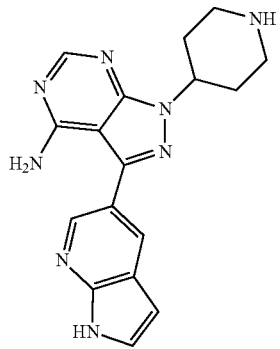 [SMILES: Nc1ncnc2c1c(-c1cnc3[nH]ccc3c1)nn2C1CCNCC1]
Monomer AD
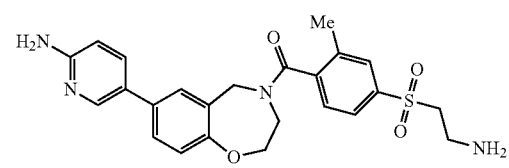 [SMILES: Cc1cc(S(=O)(=O)CCN)ccc1C(=O)N1CCOc2ccc(-c3ccc(N)nc3)cc2C1]
Monomer AE
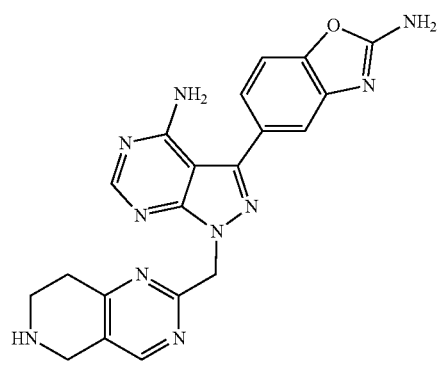 [SMILES: Nc1nc2cc(-c3nn(Cc4ncc5c(n4)CCNC5)c4ncnc(N)c34)ccc2o1]
Monomer AF
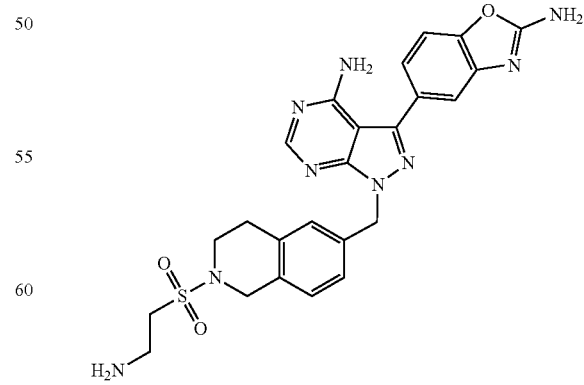
Monomer AG

TABLE 2-continued
Active Site inhibitor monomers.
Active Site inhibitor monomers
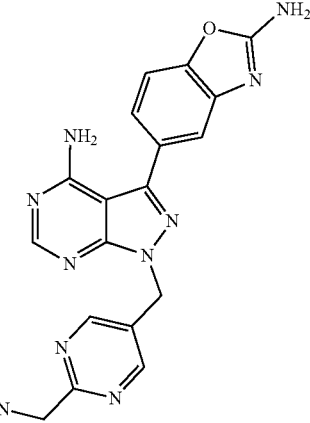
Monomer AH
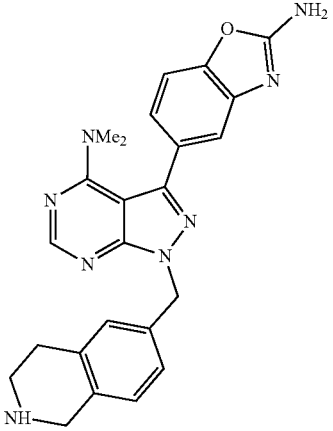 [SMILES: CN(C)c1ncnc2c1c(-c1ccc3oc(N)nc3c1)nn2Cc1ccc2c(c1)CCNC2]
Monomer AI
TABLE 3
Active Site inhibitor monomers
Active Site Inhibitor
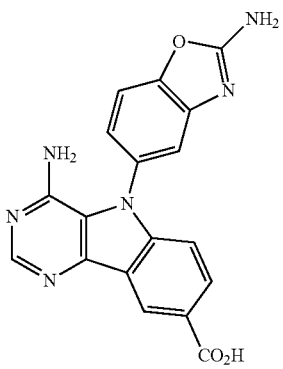 [SMILES: Nc1nc2cc(-n3c4ccc(C(=O)O)cc4c4ncnc(N)c43)ccc2o1]
Monomer AJ
TABLE 3-continued
Active Site inhibitor monomers
Active Site Inhibitor
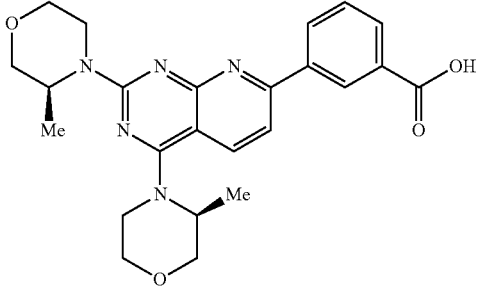 [SMILES: C[C@H]1COCCN1c1nc(N2CCOC[C@@H]2C)c2ccc(-c3cccc(C(=O)O)c3)nc2n1]
Monomer AK
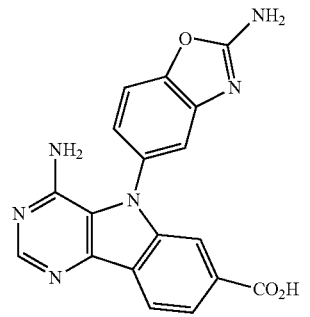
Monomer AL
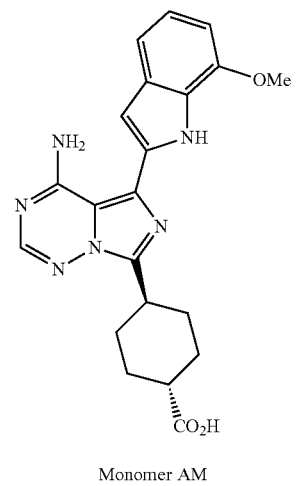
Monomer AM TABLE 3-continued
Active Site inhibitor monomers
Active Site Inhibitor
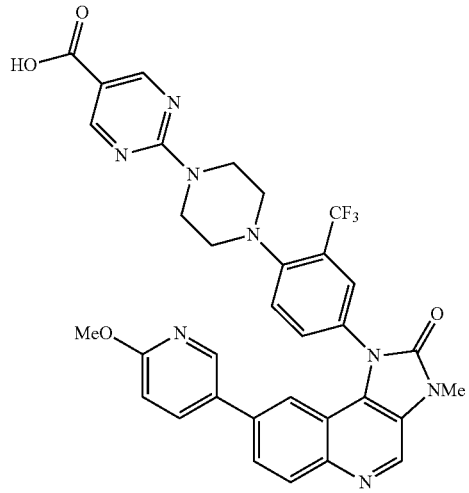 [SMILES: COc1ccc(-c2ccc3ncc4c(c3c2)n(-c2ccc(N3CCN(c5ncc(C(=O)O)cn5)CC3)c(C(F)(F)F)c2)c(=O)n4C)cn1]
Monomer AN
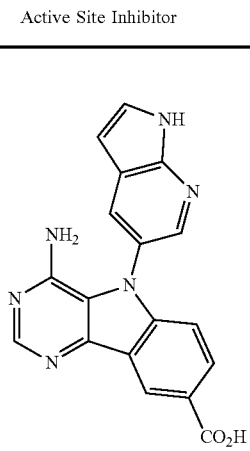
Monomer AO
TABLE 4
Amine containing pre- and post-linkers.
Amide containing block
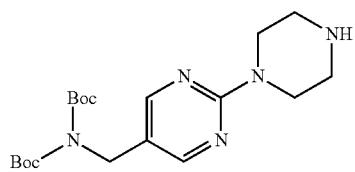 [SMILES: CC(C)(C)OC(=O)N(Cc1cnc(N2CCNCC2)nc1)C(=O)OC(C)(C)C]
Building block A
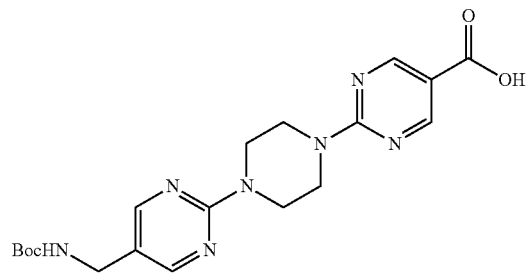 [SMILES: CC(C)(C)OC(=O)NCc1cnc(N2CCN(c3ncc(C(=O)O)cn3)CC2)nc1]
Building block B
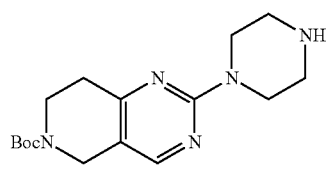 [SMILES: CC(C)(C)OC(=O)N1CCc2nc(N3CCNCC3)ncc2C1]
Building block C TABLE 4-continued
Amine containing pre- and post-linkers.
Amide containing block
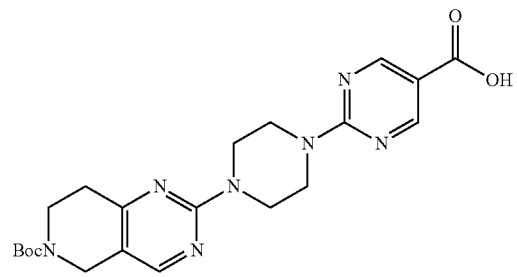 [SMILES: CC(C)(C)OC(=O)N1CCc2nc(N3CCN(c4ncc(C(=O)O)cn4)CC3)ncc2C1]
Building block D
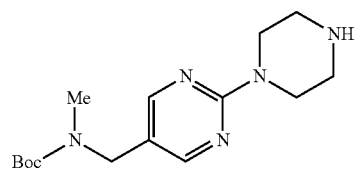 [SMILES: CN(Cc1cnc(N2CCNCC2)nc1)C(=O)OC(C)(C)C]
Building block E
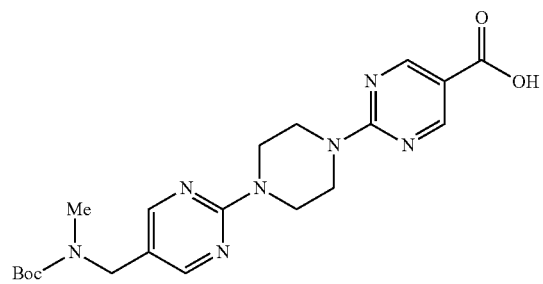 [SMILES: CN(Cc1cnc(N2CCN(c3ncc(C(=O)O)cn3)CC2)nc1)C(=O)OC(C)(C)C]
Building block F
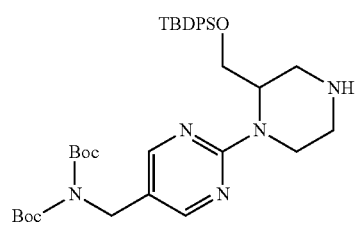
Building block G
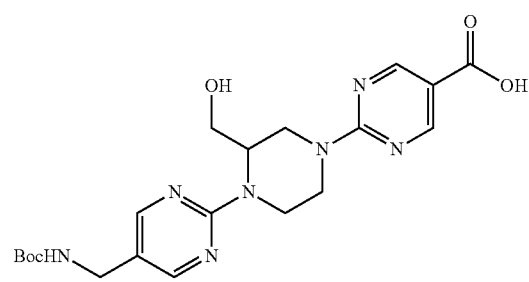 [SMILES: CC(C)(C)OC(=O)NCc1cnc(N2CCN(c3ncc(C(=O)O)cn3)CC2CO)nc1]
Building block H TABLE 4-continued
Amine containing pre- and post-linkers.
Amide containing block
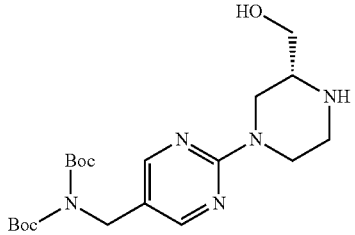 [SMILES: CC(C)(C)OC(=O)N(Cc1cnc(N2CCN[C@@H](CO)C2)nc1)C(=O)OC(C)(C)C]
Building block I
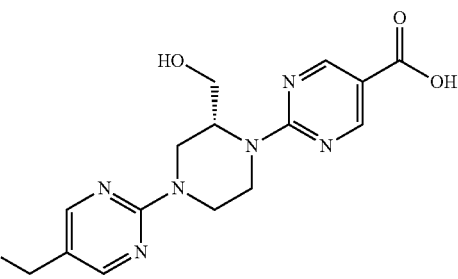
Building block J
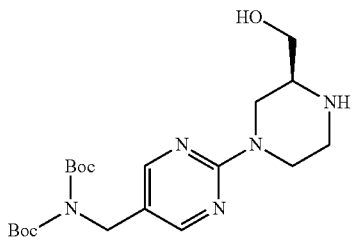 [SMILES: CC(C)(C)OC(=O)N(Cc1cnc(N2CCN[C@H](CO)C2)nc1)C(=O)OC(C)(C)C]
Building block K
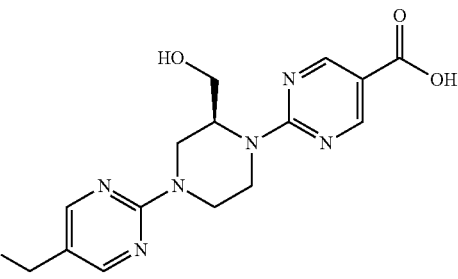
Building block L
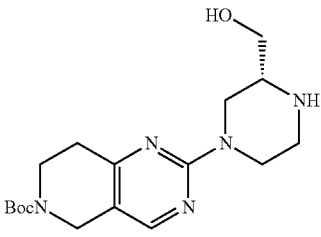 [SMILES: CC(C)(C)OC(=O)N1CCc2nc(N3CCN[C@@H](CO)C3)ncc2C1]
Building block M TABLE 4-continued Amine containing pre- and post-linkers.

Amide containing block

Building block N

Building block O

Building block P

Building block Q

Building block R

TABLE 4-continued
Amine containing pre- and post-linkers.
Amide containing block
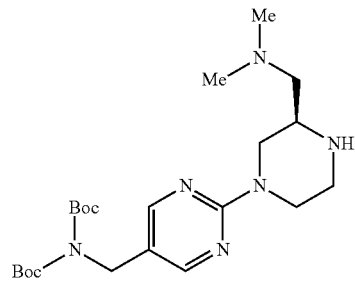 [SMILES: CN(C)C[C@@H]1CN(c2ncc(CN(C(=O)OC(C)(C)C)C(=O)OC(C)(C)C)cn2)CCN1]
Building block S
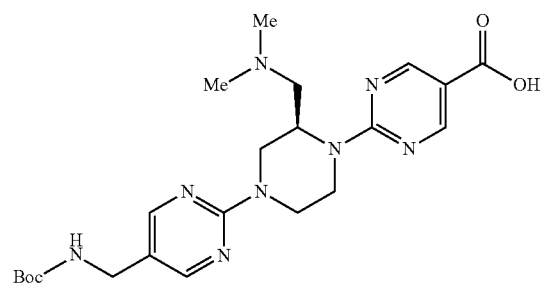 [SMILES: CN(C)C[C@@H]1CN(c2ncc(CNC(=O)OC(C)(C)C)cn2)CCN1c1ncc(C(=O)O)cn1]
Building block T
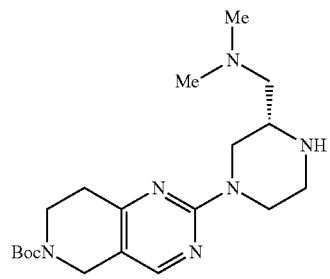 [SMILES: CN(C)C[C@H]1CN(c2ncc3c(n2)CCN(C(=O)OC(C)(C)C)C3)CCN1]
Building block U
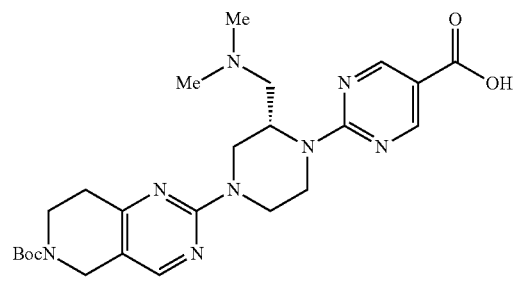 [SMILES: CN(C)C[C@H]1CN(c2ncc3c(n2)CCN(C(=O)OC(C)(C)C)C3)CCN1c1ncc(C(=O)O)cn1]
Building block V TABLE 4-continued Amine containing pre- and post-linkers.

Amide containing block

Building block W

Building block X

Building block Y

Building block Z

Building block AA

TABLE 4-continued
Amine containing pre- and post-linkers.
Amide containing block
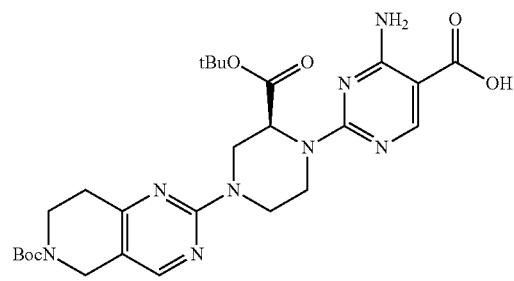 [SMILES: CC(C)(C)OC(=O)[C@@H]1CN(c2ncc3c(n2)CCN(C(=O)OC(C)(C)C)C3)CCN1c1ncc(C(=O)O)c(N)n1]
Building block AB
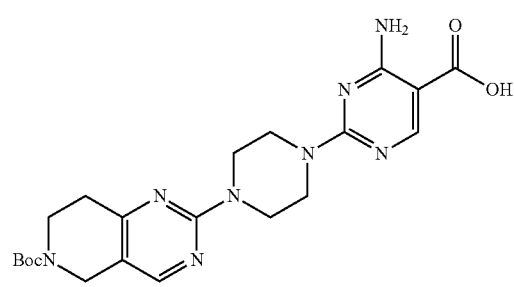 [SMILES: CC(C)(C)OC(=O)N1CCc2nc(N3CCN(c4ncc(C(=O)O)c(N)n4)CC3)ncc2C1]
Building block AC
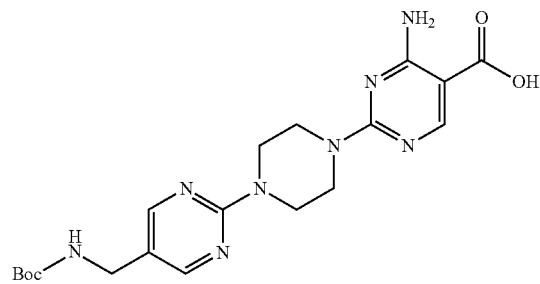 [SMILES: CC(C)(C)OC(=O)NCc1cnc(N2CCN(c3ncc(C(=O)O)c(N)n3)CC2)nc1]
Building block AD
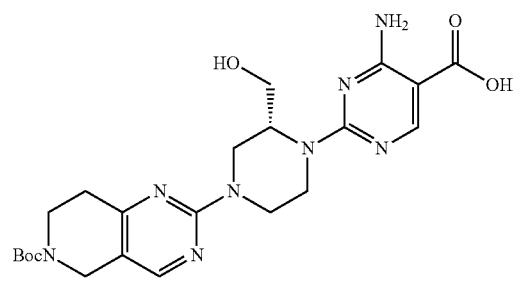 [SMILES: CC(C)(C)OC(=O)N1CCc2nc(N3CCN(c4ncc(C(=O)O)c(N)n4)[C@@H](CO)C3)ncc2C1]
Building block AE TABLE 4-continued
Amine containing pre- and post-linkers.
Amide containing block
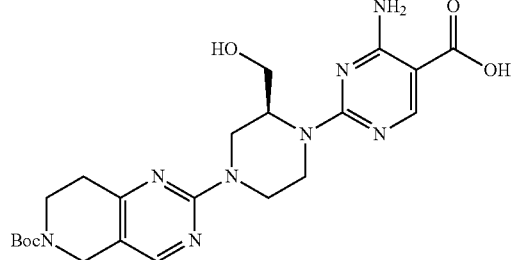 [SMILES: CC(C)(C)OC(=O)N1CCc2nc(N3CCN(c4ncc(C(=O)O)c(N)n4)[C@H](CO)C3)ncc2C1]
Building block AF
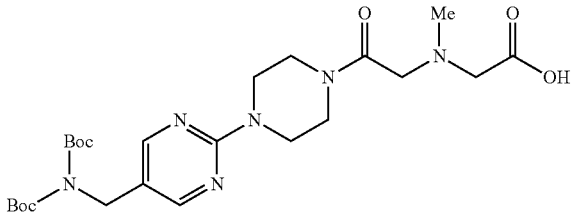 [SMILES: CN(CC(=O)O)CC(=O)N1CCN(c2ncc(CN(C(=O)OC(C)(C)C)C(=O)OC(C)(C)C)cn2)CC1]
Building block AG
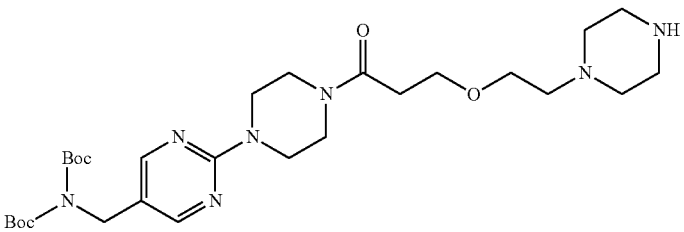 [SMILES: CC(C)(C)OC(=O)N(Cc1cnc(N2CCN(C(=O)CCOCCN3CCNCC3)CC2)nc1)C(=O)OC(C)(C)C]
Building block AH
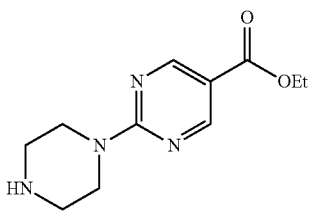
Building block AI
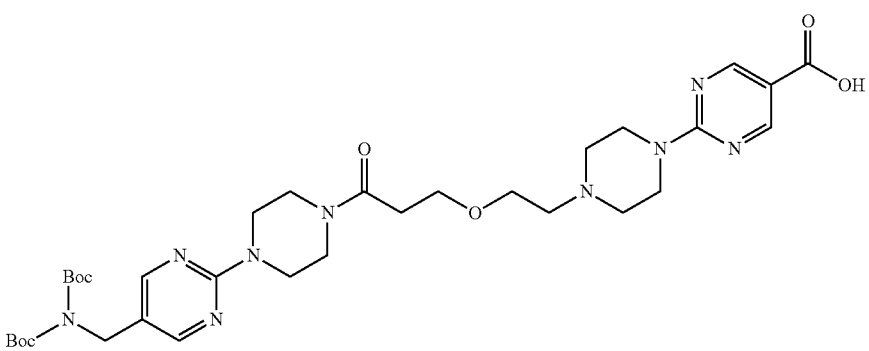 [SMILES: CC(C)(C)OC(=O)N(Cc1cnc(N2CCN(C(=O)CCOCCN3CCN(c4ncc(C(=O)O)cn4)CC3)CC2)nc1)C(=O)OC(C)(C)C]
Building block AJ TABLE 4-continued
Amine containing pre- and post-linkers.
Amide containing block
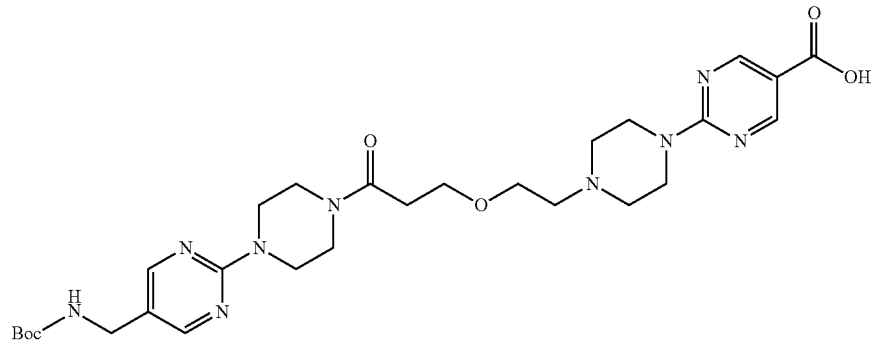 [SMILES: CC(C)(C)OC(=O)NCc1cnc(N2CCN(C(=O)CCOCCN3CCN(c4ncc(C(=O)O)cn4)CC3)CC2)nc1]
Building block AK
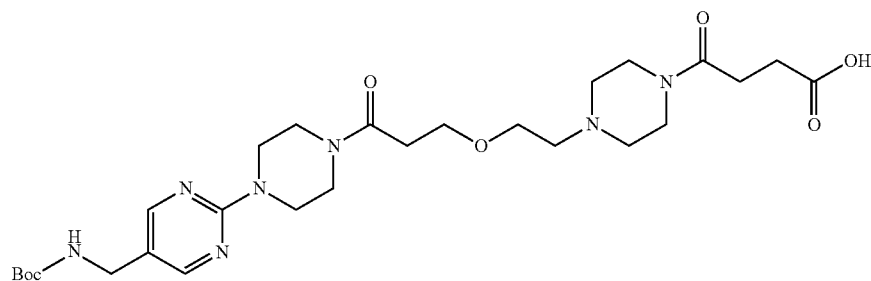 [SMILES: CC(C)(C)OC(=O)NCc1cnc(N2CCN(C(=O)CCOCCN3CCN(C(=O)CCC(=O)O)CC3)CC2)nc1]
Building block AL
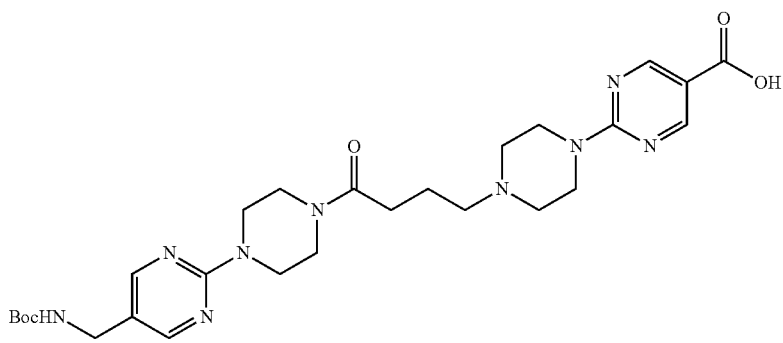 [SMILES: CC(C)(C)OC(=O)NCc1cnc(N2CCN(C(=O)CCCN3CCN(c4ncc(C(=O)O)cn4)CC3)CC2)nc1]
Building block AM
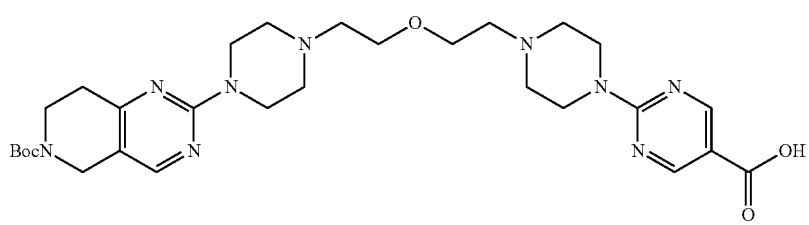 [SMILES: CC(C)(C)OC(=O)N1CCc2nc(N3CCN(CCOCCN4CCN(c5ncc(C(=O)O)cn5)CC4)CC3)ncc2C1]
Building block AN TABLE 4-continued
Amine containing pre- and post-linkers.
Amide containing block
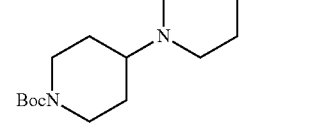
Building block AO
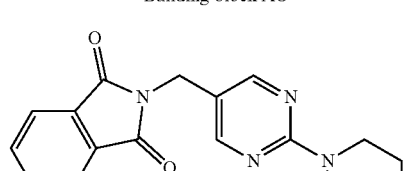
Building block AP
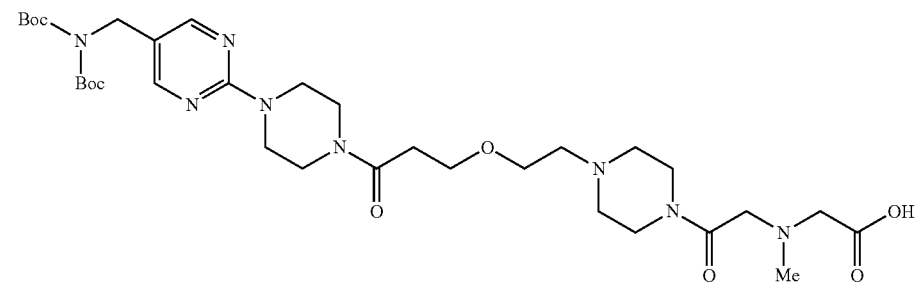 [SMILES: CN(CC(=O)O)CC(=O)N1CCN(CCOCCC(=O)N2CCN(c3ncc(CN(C(=O)OC(C)(C)C)C(=O)OC(C)(C)C)cn3)CC2)CC1]
Building block AQ
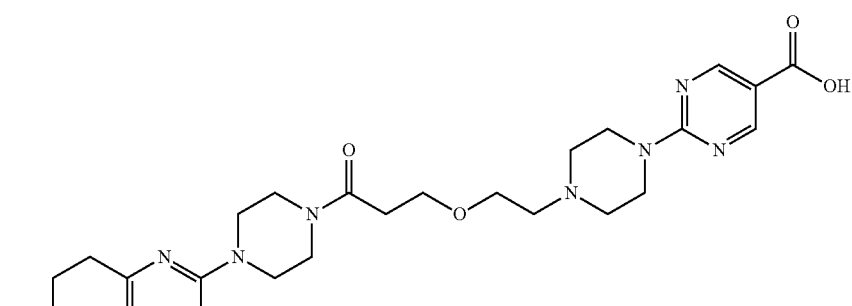
Building block AR
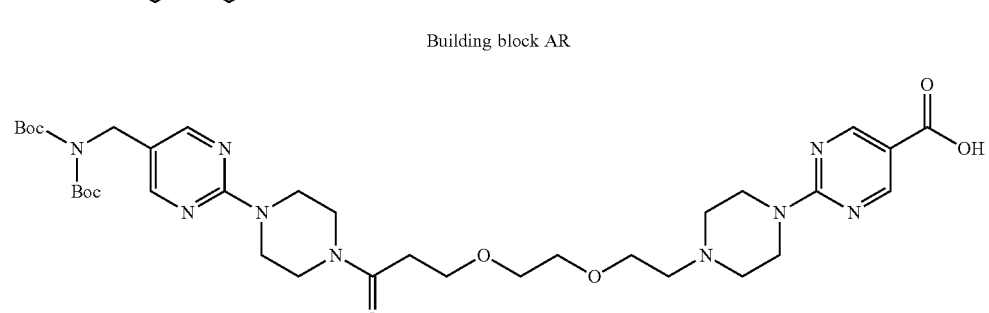
Building block AS TABLE 4-continued
Amine containing pre- and post-linkers.
Amide containing block
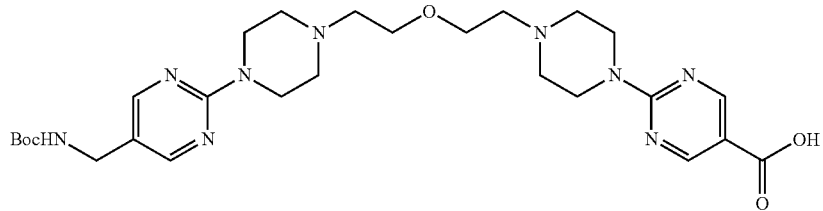 [SMILES: CC(C)(C)OC(=O)NCc1cnc(N2CCN(CCOCCN3CCN(c4ncc(C(=O)O)cn4)CC3)CC2)nc1]
Building block AT
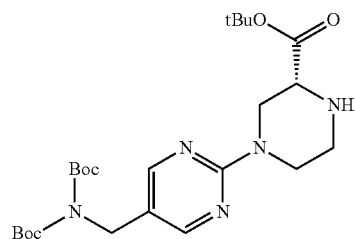 [SMILES: CC(C)(C)OC(=O)[C@H]1CN(c2ncc(CN(C(=O)OC(C)(C)C)C(=O)OC(C)(C)C)cn2)CCN1]
Building block AU
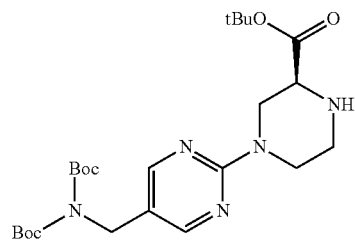 [SMILES: CC(C)(C)OC(=O)[C@@H]1CN(c2ncc(CN(C(=O)OC(C)(C)C)C(=O)OC(C)(C)C)cn2)CCN1]
Building block AV
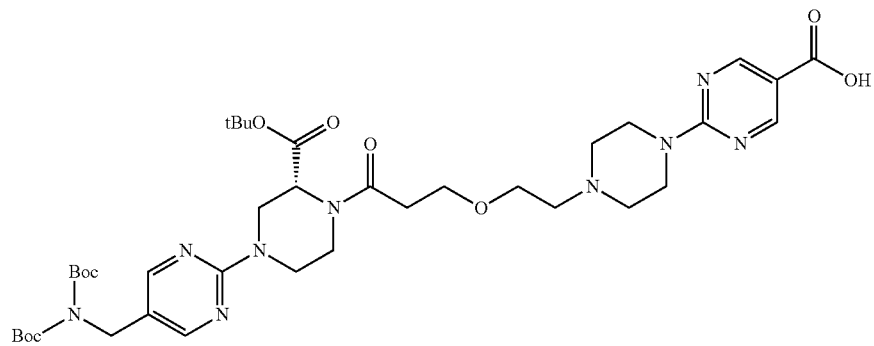 [SMILES: CC(C)(C)OC(=O)[C@H]1CN(c2ncc(CN(C(=O)OC(C)(C)C)C(=O)OC(C)(C)C)cn2)CCN1C(=O)CCOCCN1CCN(c2ncc(C(=O)O)cn2)CC1]
Building block AW TABLE 4-continued
Amine containing pre- and post-linkers.
Amide containing block
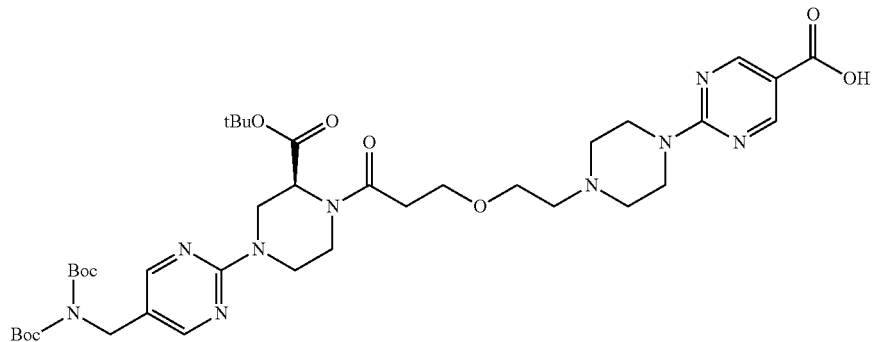 [SMILES: CC(C)(C)OC(=O)[C@@H]1CN(c2ncc(CN(C(=O)OC(C)(C)C)C(=O)OC(C)(C)C)cn2)CCN1C(=O)CCOCCN1CCN(c2ncc(C(=O)O)cn2)CC1]
Building block AX
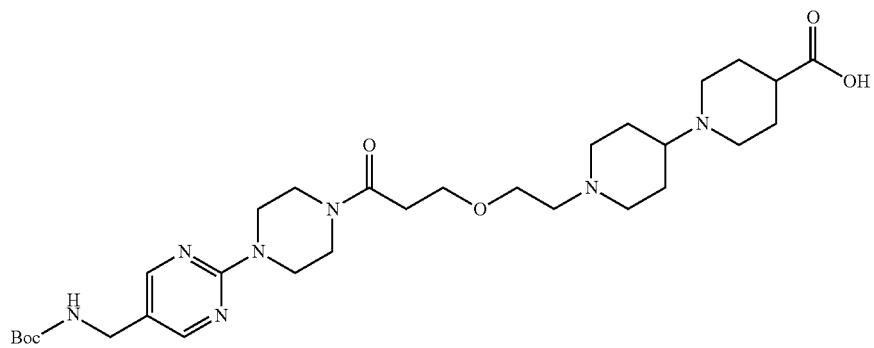 [SMILES: CC(C)(C)OC(=O)NCc1cnc(N2CCN(C(=O)CCOCCN3CCC(N4CCC(C(=O)O)CC4)CC3)CC2)nc1]
Building block AY
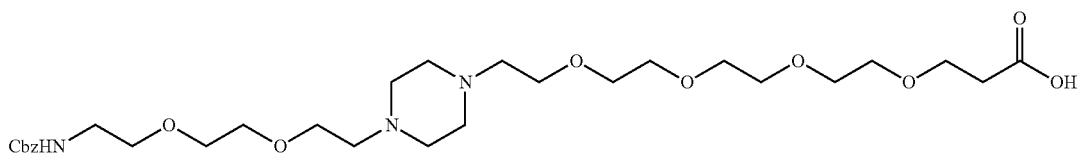 [SMILES: O=C(O)CCOCCOCCOCCOCCN1CCN(CCOCCOCCNC(=O)OCc2ccccc2)CC1]
Building block AZ
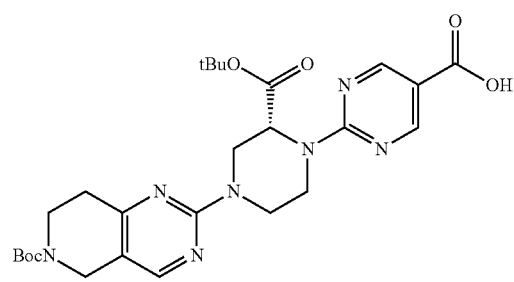 [SMILES: CC(C)(C)OC(=O)[C@H]1CN(c2ncc3c(n2)CCN(C(=O)OC(C)(C)C)C3)CCN1c1ncc(C(=O)O)cn1]
Building block BA TABLE 4-continued
Amine containing pre- and post-linkers.
Amide containing block
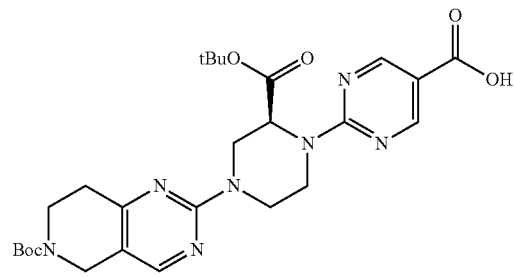 [SMILES: CC(C)(C)OC(=O)[C@@H]1CN(c2ncc3c(n2)CCN(C(=O)OC(C)(C)C)C3)CCN1c1ncc(C(=O)O)cn1]
Building block BB
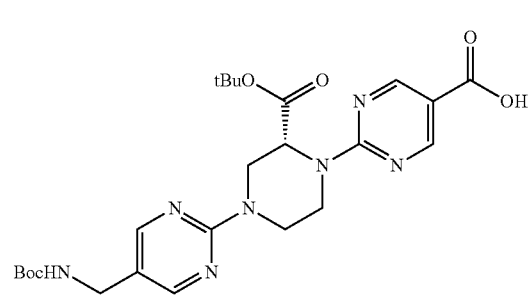 [SMILES: CC(C)(C)OC(=O)NCc1cnc(N2CCN(c3ncc(C(=O)O)cn3)[C@@H](C(=O)OC(C)(C)C)C2)nc1]
Building block BC
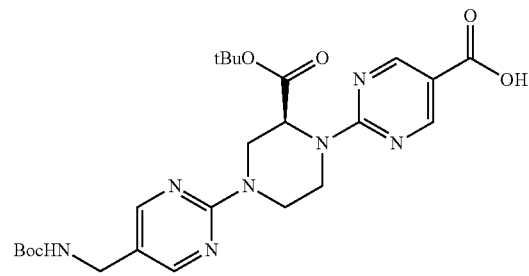 [SMILES: CC(C)(C)OC(=O)NCc1cnc(N2CCN(c3ncc(C(=O)O)cn3)[C@H](C(=O)OC(C)(C)C)C2)nc1]
Building block BD
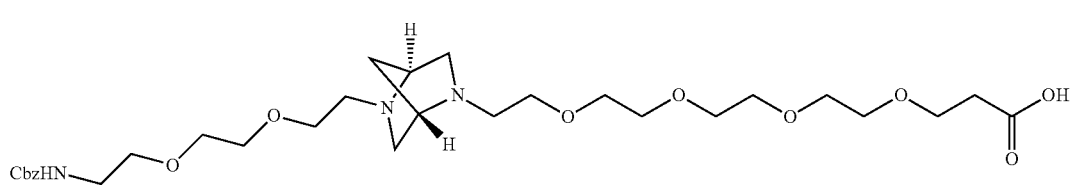 [SMILES: O=C(O)CCOCCOCCOCCOCCN1C[C@@H]2C[C@H]1CN2CCOCCOCCNC(=O)OCc1ccccc1]
Building block BE
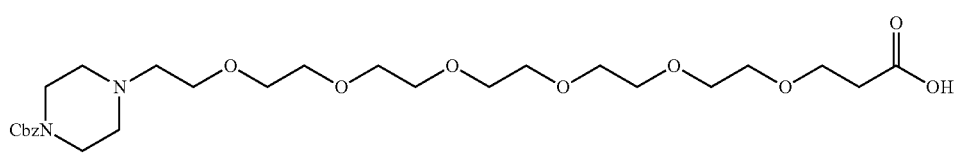 [SMILES: O=C(O)CCOCCOCCOCCOCCOCCOCCN1CCN(C(=O)OCc2ccccc2)CC1]
Building block BF

Preparation of Active Site Inhibitor Monomers

Monomer A. 5-(4-amino-1-(4-(aminomethyl)benzyl)-1H-pyrazolo[3,4-d]pyrimidin-3-yl)benzo[d]oxazol-2-amine trifluoroacetic acid salt

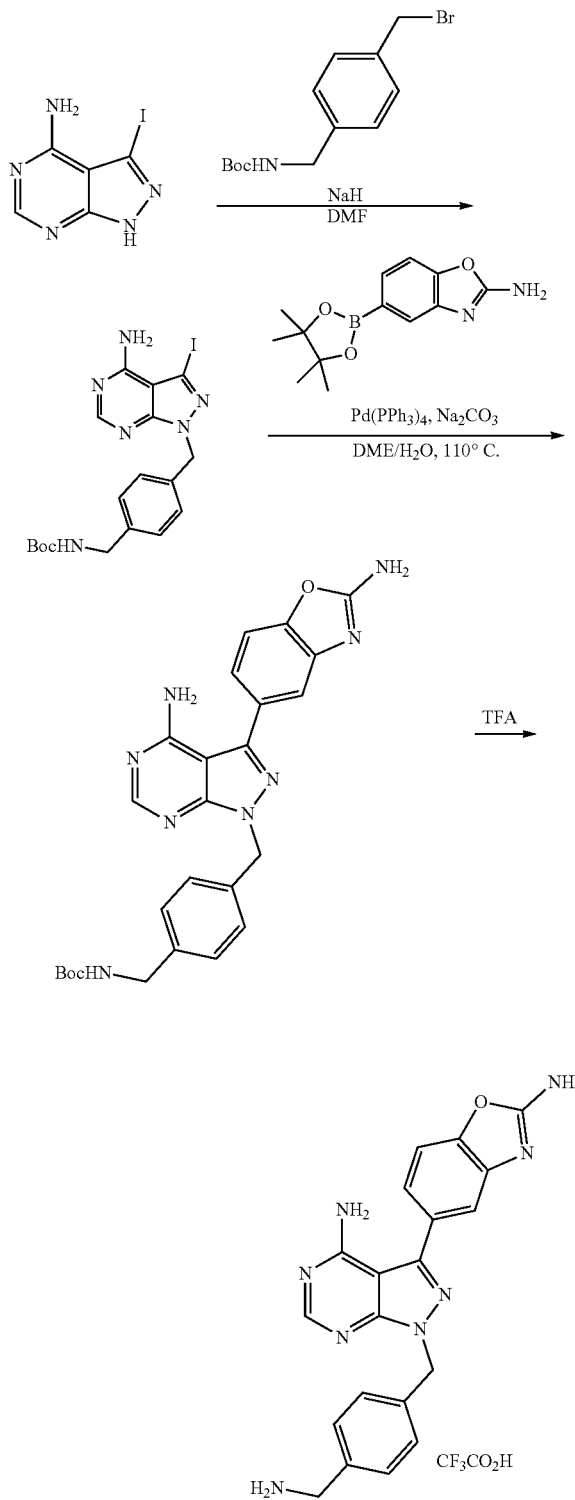

Step 1: Synthesis of tert-butyl 4-((4-amino-3-iodo-1H-pyrazolo[3,4-d]pyrimidin-1-yl)methyl)benzylcarbamate To a solution of 3-iodo-1H-pyrazolo[3,4-d]pyrimidin-4-amine (3.8 g, 14.56 mmol, 1.0 equiv) in DMF (20 mL) was added NaH (582.27 mg, 14.56 mmol, 60 wt. %, 1.0 equiv) at 0° C. and the reaction solution was stirred at this temperature for 30 min, then tert-butyl 4-(bromomethyl)benzylcarbamate (4.59 g, 15.29 mmol, 1.05 equiv) was added to the reaction at 0° C. and the reaction solution was stirred at room temperature for 2 h. The solution was poured into $H_2O$ (80 mL) and the solid that precipitated out was filtered. The solid cake was washed with $H_2O$ (2×10 mL) and then dried under reduced pressure to give tert-butyl 4-((4-amino-3-iodo-1H-pyrazolo[3,4-d]pyrimidin-1-yl)methyl)benzylcarbamate (5 g, 53% yield) as a yellow solid. LCMS (ESI) m/z: [M+Na] calcd for $C_{18}H_{21}IN_6O_2$: 503.07; found 503.2.

Step 2: Synthesis of tert-butyl 4-((4-amino-3-(2-aminobenzo[d]oxazol-5-yl)-1H-pyrazolo[3,4-d]pyrimidin-1-yl)methyl)benzylcarbamate To a bi-phasic suspension of tert-butyl 4-((4-amino-3-iodo-1H-pyrazolo[3,4-d]pyrimidin-1-yl)methyl)benzylcarbamate (5 g, 7.68 mmol, 1.0 equiv), 5-(4,4,5,5-tetramethyl-1,3,2-dioxaborolan-2-yl)benzo[d]oxazol-2-amine (2.40 g, 9.22 mmol, 1.2 equiv) and $Pd(PPh_3)_4$ (887.66 mg, 768.16 μmol, 0.1 equiv) in DME (100 mL) and $H_2O$ (50 mL) was added $Na_2CO_3$ (1.91 g, 23.04 mmol, 3.0 equiv) at room temperature under $N_2$. The mixture was stirred at 110° C. for 3 h. The reaction mixture was cooled to room temperature and filtered, the filtrate was extracted by EtOAc (3×50 mL). The organic phases were combined and washed with brine (10 mL), dried over $Na_2SO_4$, filtered, and the filtrate was concentrated under reduced pressure to give a residue. The residue was purified by silica gel chromatography (0→20% MeOH/EtOAc) to give tert-butyl 4-((4-amino-3-(2-aminobenzo[d]oxazol-5-yl)-1H-pyrazolo[3,4-d]pyrimidin-1-yl)methyl)benzylcarbamate (4.5 g, 82% yield) as a yellow solid. LCMS (ESI) m/z: [M+H] calcd for $C_{25}H_{26}N_8O_3$: 487.22; found 487.2.

Step 3: Synthesis of 5-(4-amino-1-(4-(aminomethyl)benzyl)-1H-pyrazolo[3,4-d] pyrimidin-3-yl)benzo[d]oxazol-2-amine To a solution of tert-butyl 4-((4-amino-3-(2-aminobenzo[d]oxazol-5-yl)-1H-pyrazolo[3,4-d]pyrimidin-1-yl)methyl)benzylcarbamate (4.5 g, 6.29 mmol, 1.0 equiv) in DCM (50 mL) was added TFA (30.80 g, 270.12 mmol, 20 mL, 42.95 equiv) at 0° C. The reaction solution was stirred at room temperature for 2 h. The reaction solution was concentrated under reduced pressure to give a residue, which was dissolved in 10 mL of MeCN, then poured into MTBE (100 mL). The solid that precipitated was then filtered and the solid cake was dried under reduced pressure to give 5-[4-amino-1-[[4-(aminomethyl)phenyl]methyl]pyrazolo[3,4-d]pyrimidin-3-yl]-1,3-benzoxazol-2-amine (2.22 g, 71% yield) as a yellow solid. LCMS (ESI) m/z: [M+H] calcd for $C_{20}H_{18}N_8O$: 387.16; found 387.1.

Monomer B. 2-(4-amino-1-(4-aminobutyl)-1H-pyrazolo[3,4-d]pyrimidin-3-yl)-1H-indol-6-ol trifluoroacetic acid salt

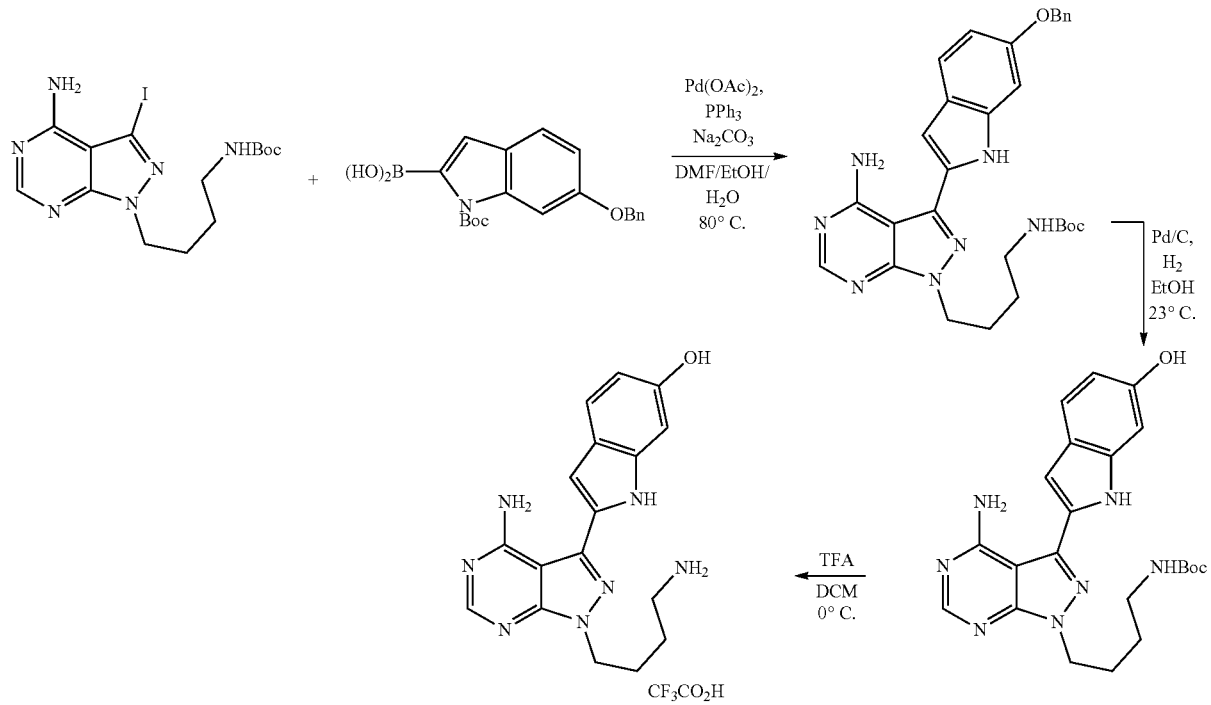

Step 1: Synthesis of tert-butyl N-(4-{4-amino-3-[6-(benzyloxy)-1H-indol-2-yl]-1H-pyrazolo[3,4-d]pyrimidin-1-yl}butyl)carbamate To a mixture of tert-butyl (4-(4-amino-3-iodo-1H-pyrazolo[3,4-d]pyrimidin-1-yl)butyl)carbamate (300 mg, 694 μmol, 1.0 equiv) and (6-(benzyloxy)-1-(tert-butoxycarbonyl)-1H-indol-2-yl)boronic acid (763 mg, 2.08 mmol, 3.0 equiv) in DMF (2.6 mL), EtOH (525 μL), and H$_2$O (350 μL) were added Pd(OAc)$_2$ (15.5 mg, 69 μmol, 0.1 equiv), triphenylphosphine (36.1 mg, 138 μmol, 0.2 equiv), and sodium carbonate (440 mg, 4.16 mmol, 6.0 equiv). The reaction was heated at 80° C. for 20 h, cooled to room temperature, and quenched with H$_2$O (10 mL) and EtOAc (10 mL). The mixture was transferred to a separatory funnel and the aqueous phase was extracted with EtOAc (3×20 mL). The combined organic phase was washed with sat. aq. NaCl (1×20 mL), dried over Na$_2$SO$_4$, filtered, and concentrated under reduced pressure. The crude material was purified by silica gel chromatography (20→85% EtOAc/heptane) to provide the product (201 mg, 46% yield) as an orange solid. LCMS (ESI) m/z: [M+H] calcd for C$_{29}$H$_{33}$N$_7$O$_3$: 528.27; found 528.2.

Step 2: Synthesis of tert-butyl (4-(4-amino-3-(6-hydroxy-1H-indol-2-yl)-1H-pyrazolo[3,4-d]pyrimidin-1-yl)butyl)carbamate To a solution of tert-butyl N-(4-{4-amino-3-[6-(benzyloxy)-1H-indol-2-yl]-1H-pyrazolo[3,4-d]pyrimidin-1-yl}butyl)carbamate (1.0 equiv) in EtOH is added Pd/C (10 mol %). The reaction is purged with H$_2$ and the reaction is stirred under an atmosphere of H$_2$ until consumption of starting material, as determined by LCMS. The reaction is then diluted with EtOAc, filtered over Celite, and concentrated under reduced pressure. The resulting residue is purified by silica gel chromatography to afford the desired product.

Step 3: Synthesis of 2-(4-amino-1-(4-aminobutyl)-1H-pyrazolo[3,4-d]pyrimidin-3-yl)-1H-indol-6-ol To a solution of tert-butyl (4-(4-amino-3-(6-hydroxy-1H-indol-2-yl)-1H-pyrazolo[3,4-d]pyrimidin-1-yl)butyl)carbamate (1.0 equiv) in anhydrous DCM is added TFA (50 equiv.) dropwise at 0° C. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under N$_2$ to give 2-(4-amino-1-(4-aminobutyl)-1H-pyrazolo[3,4-d]pyrimidin-3-yl)-1H-indol-6-ol.

Monomer C. 5-(4-amino-1-((1,2,3,4-tetrahydroisoquinolin-6-yl)methyl)-1H-pyrazolo[3,4-d]pyrimidin-3-yl)benzo[d]oxazol-2-amine trifluoroacetic acid salt

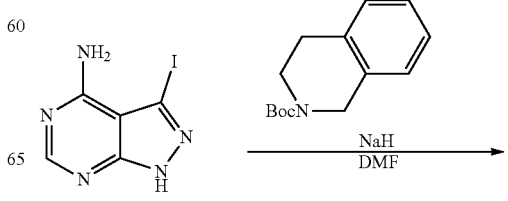

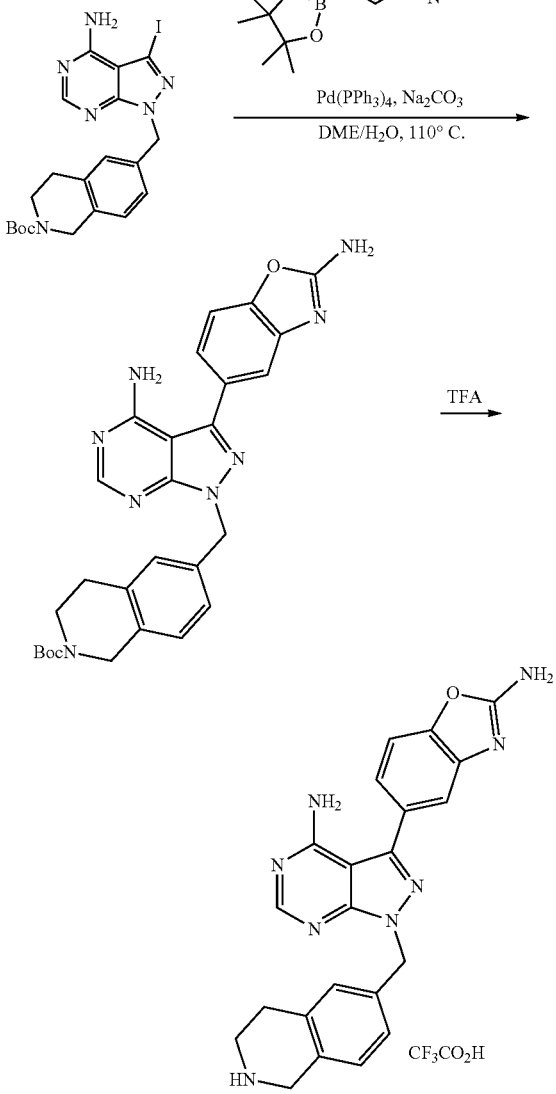

Step 1: Synthesis of tert-butyl 6-((4-amino-3-iodo-1H-pyrazolo[3,4-d]pyrimidin-1-yl)methyl)-3,4-dihydroisoquinoline-2(1H)-carboxylate To a suspension of 3-iodo-1H-pyrazolo[3,4-d]pyrimidin-4-amine (5 g, 19.16 mmol, 1.0 equiv) in DMF (50.0 mL) was added NaH (766.22 mg, 19.16 mmol, 60 wt. %, 1.0 equiv) at 4° C. The mixture was stirred at 4° C. for 30 min. To the reaction mixture was added tert-butyl 6-(bromomethyl)-3,4-dihydroisoquinoline-2(1H)-carboxylate (6.87 g, 21.07 mmol, 1.1 equiv) in DMF (30 mL) at 4° C. The mixture was stirred at room temperature for 2 h. The mixture was then cooled to 4° C. and H₂O (400 mL) was added and the mixture was stirred for 30 min. The resulting precipitate was collected by filtration to give crude tert-butyl 6-((4-amino-3-iodo-1H-pyrazolo[3,4-d]pyrimidin-1-yl)methyl)-3,4-dihydroisoquinoline-2(1H)-carboxylate (9.7 g, 76% yield) as a light yellow solid. The crude product was used for the next step directly.

Step 2: Synthesis of tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate To a bi-phasic suspension of tert-butyl 6-((4-amino-3-iodo-1H-pyrazolo[3,4-d]pyrimidin-1-yl)methyl)-3,4-dihydroisoquinoline-2(1H)-carboxylate (9.7 g, 14.63 mmol, 1.0 equiv), 5-(4,4,5,5-tetramethyl-1,3,2-dioxaborolan-2-yl)benzo[d]oxazol-2-amine (4.57 g, 17.55 mmol, 1.2 equiv), and Na₂CO₃ (7.75 g, 73.14 mmol, 5.0 equiv) in DME (120.0 mL) and H₂O (60 mL) was added Pd(PPh₃)₄ (1.69 g, 1.46 mmol, 0.1 equiv) at room temperature under N₂. The mixture was stirred at 110° C. for 3 h. The reaction mixture was then cooled to room temperature and partitioned between EtOAc (100 mL) and H₂O (100 mL). The aqueous layer was separated and extracted with EtOAc (2×60 mL). The organic layers were combined, washed with brine (80 mL) and dried over anhydrous Na₂SO₄, filtered and the filtrate was concentrated under reduced pressure. The residue was purified by silica gel chromatography (1→100% EtOAc/petroleum ether, then 20→50% MeOH/EtOAc) to afford tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate (4.5 g, 58% yield,) as a light yellow solid.

Step 3: Synthesis of 5-(4-amino-1-((1,2,3,4-tetrahydroisoquinolin-6-yl)methyl)-1H-pyrazolo[3,4-d]pyramidin-3-yl)benzo[d]oxazol-2-amine To neat TFA (32.5 mL, 438.97 mmol, 50.0 equiv) was added tert-butyl 6-((4-amino-3-(2-aminobenzo[d]oxazol-5-yl)-1H-pyrazolo[3,4-d]pyrimidin-1-yl)methyl)-3,4-dihydroisoquinoline-2(1H)-carboxylate (4.5 g, 8.78 mmol, 1.0 equiv) at room temperature. The mixture was stirred for 30 min and then concentrated under reduced pressure. The oily residue was triturated with MeCN (8 mL), then dripped into MTBE (350 mL) over 10 min. The supernatant was removed and then the precipitate was collected by filtration under N₂ to give 5-(4-amino-1-((1,2,3,4-tetrahydroisoquinolin-6-yl)methyl)-1H-pyrazolo[3,4-d]pyrimidin-3-yl)benzo[d]oxazol-2-amine (5.72 g, over 100% yield) as a light pink solid. LCMS (ESI) m/z: [M+H] calcd for $C_{22}H_{20}N_8O$: 413.18; found 413.2.

Monomer D. 2-(4-amino-1-(4-aminobutyl)-1H-pyrazolo[3,4-d]pyrimidin-3-yl)-1H-indol-7-ol trifluoroacetic acid salt

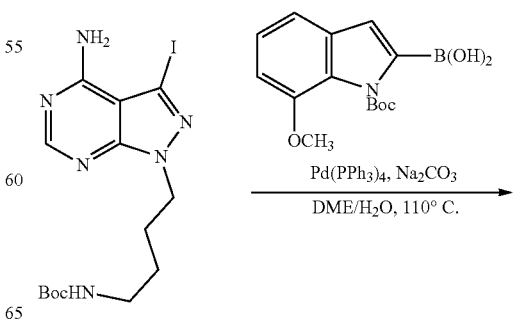

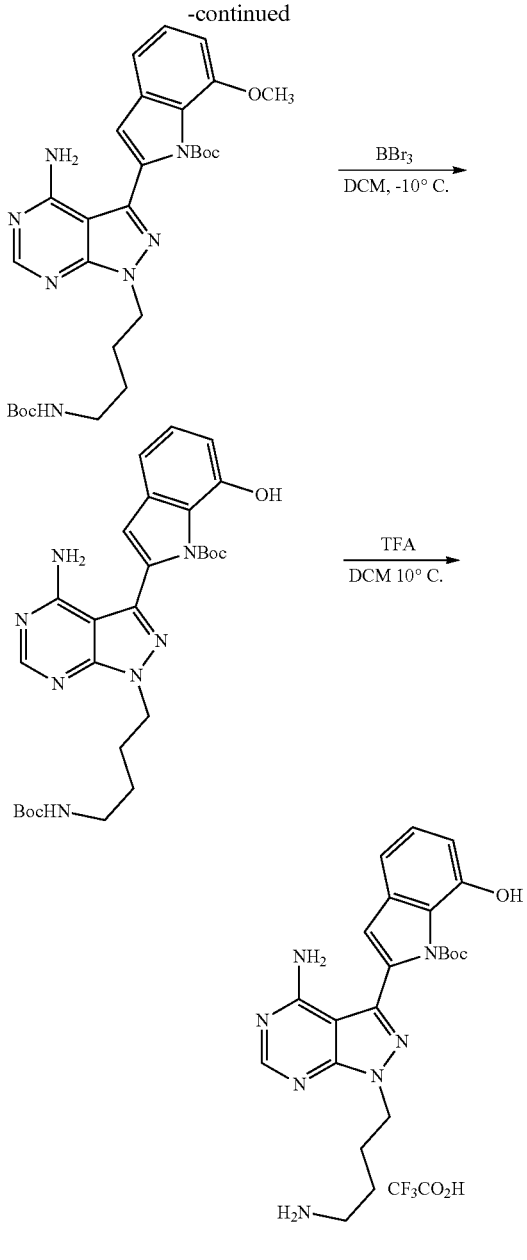

Step 1: Synthesis of tert-butyl 2-(4-amino-1-(4-((tert-butoxycarbonyl)amino)butyl)-1H-pyrazolo[3,4-d]pyrimidin-3-yl)-7-methoxy-1H-indole-1-carboxylate To a mixture of tert-butyl (4-(4-amino-3-iodo-1H-pyrazolo[3,4-d]pyrimidin-1-yl)butyl)carbamate (1.0 equiv) and (1-(tert-butoxycarbonyl)-7-methoxy-1H-indol-2-yl)boronic acid (3.0 equiv) in DME and $H_2O$ is added $Pd(PPh_3)_4$ (0.1 equiv) and sodium carbonate (6.0 equiv). The reaction is heated at 80° C. until completion, as determined by LCMS and TLC analysis. The reaction is then quenched with $H_2O$ and EtOAc. The mixture is transferred to a separatory funnel and the aqueous phase is extracted with EtOAc. The organic phase is washed with sat. aq. NaCl, dried over $Na_2SO_4$, filtered, and concentrated under reduced pressure. The desired product is isolated after chromatography on silica gel.

Step 2: Synthesis of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate To a solution of tert-butyl 2-(4-amino-1-(4-((tert-butoxycarbonyl)amino)butyl)-1H-pyrazolo[3,4-d]pyrimidin-3-yl)-7-methoxy-1H-indole-1-carboxylate (1.0 equiv) in DCM at −10° C. is added $BBr_3$ (2.0 equiv). The reaction is allowed to stir until consumption of starting material, as determined by LCMS. The reaction is quenched by slow addition of sat. aq. $NaHCO_3$, transferred to a separatory funnel and the mixture is extracted with DCM. The organic phase is washed with sat. aq. NaCl, dried over $Na_2SO_4$, filtered, and concentrated under reduced pressure. The desired product is isolated after chromatography on silica gel.

Step 3: Synthesis of 2-(4-amino-1-(4-aminobutyl)-1H-pyrazolo[3,4-d]pyrimidin-3-yl)-1H-indol-7-ol To a solution of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate (1.0 equiv) in DCM at 0° C. is added TFA dropwise. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under $N_2$ to give 2-(4-amino-1-(4-aminobutyl)-1H-pyrazolo[3,4-d]pyrimidin-3-yl)-1H-indol-7-ol.

Monomer E. 5-(4-amino-1-(piperidin-4-ylmethyl)-1H-pyrazolo[3,4-d]pyrimidin-3-yl)benzo[d]oxazol-2-amine trifluoroacetic acid salt

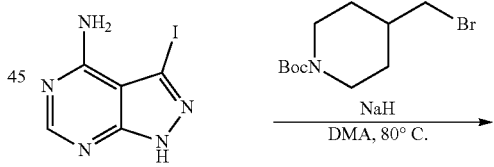

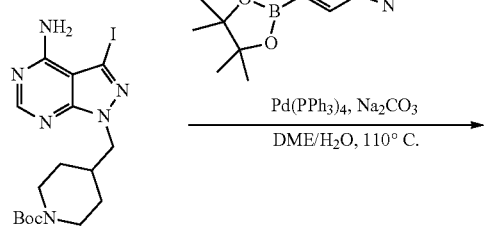

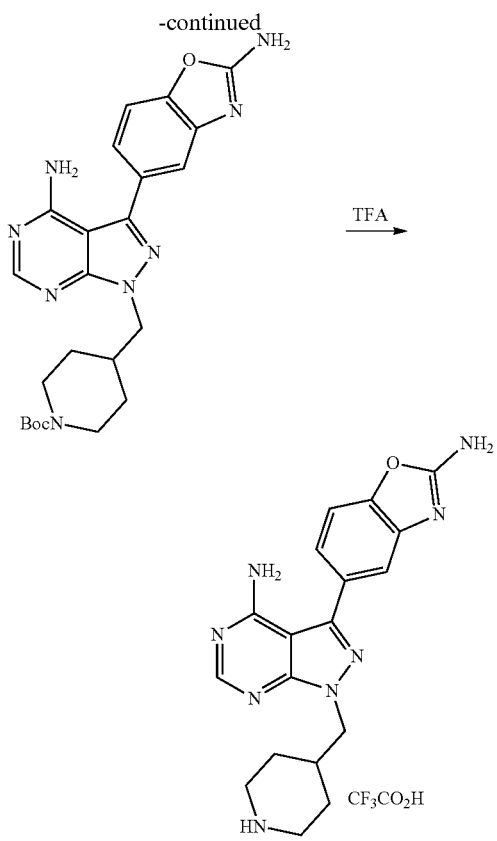

Step 1: Synthesis of tert-butyl 4-((4-amino-3-iodo-1H-pyrazolo[3,4-d]pyrimidin-1-yl)methyl)piperidine-1-carboxylate To a solution of 3-iodo-1H-pyrazolo[3,4-d]pyrimidin-4-amine (3 g, 11.49 mmol, 1.0 equiv) in DMA (30 mL) was added tert-butyl 4-(bromomethyl)piperidine-1-carboxylate (3.36 g, 12.07 mmol, 1.05 equiv) and $K_2CO_3$ (4.77 g, 34.48 mmol, 3.0 equiv), then the reaction was stirred at 80° C. for 3 h. The reaction mixture was filtered to remove $K_2CO_3$ and the filtrate was poured into $H_2O$ (200 mL). A solid precipitated was then filtered to give tert-butyl 4-((4-amino-3-iodo-1H-pyrazolo[3,4-d]pyrimidin-1-yl)methyl)piperidine-1-carboxylate (3 g, 57% yield) as light yellow solid. LCMS (ESI) m/z: [M+H] calcd for $C_{16}H_{23}IN_6O_2$: 459.10; found 459.1.

Step 2: Synthesis of tert-butyl 4-((4-amino-3-(2-aminobenzo[d]oxazol-5-yl)-1H-pyrazolo[3,4-d]pyrimidin-1-yl)methyl)piperidine-1-carboxylate To a bi-phasic suspension of tert-butyl 4-((4-amino-3-iodo-1H-pyrazolo[3,4-d]pyrimidin-1-yl)methyl)piperidine-1-carboxylate (3 g, 6.55 mmol, 1.0 equiv) and 5-(4,4,5,5-tetramethyl-1,3,2-dioxaborolan-2-yl)benzo[d]oxazol-2-amine (2.04 g, 7.86 mmol, 1.2 equiv) and $Na_2CO_3$ (3.47 g, 32.73 mmol, 5.0 equiv) in DME (60 mL) and $H_2O$ (30 mL) was added $Pd(PPh_3)_4$ (756.43 mg, 654.60 µmol, 0.1 equiv) at room temperature under $N_2$. The mixture was stirred at 110° C. for 3 h. Two batches were combined together. The reaction mixture was cooled and partitioned between EtOAc (500 mL) and $H_2O$ (500 mL). The aqueous layer was separated and extracted with EtOAc (3×300 mL). All the organic layers were combined, washed with brine (20 mL), dried over anhydrous $Na_2SO_4$, filtered, and the filtrate was concentrated under reduced pressure to give tert-butyl 4-((4-amino-3-(2-aminobenzo[d]oxazol-5-yl)-1H-pyrazolo[3,4-d]pyrimidin-1-yl)methyl)piperidine-1-carboxylate (4.5 g, 74% yield) as a yellow solid. LCMS (ESI) m/z: [M+H] calcd for $C_{23}H_{28}N_8O_3$: 465.24; found 465.2.

Step 3: Synthesis of 5-(4-amino-1-(piperidin-4-ylmethyl)-1H-pyrazolo[3,4-d]pyrimidin-3-yl)benzo[d]oxazol-2-amine A solution of tert-butyl 4-((4-amino-3-(2-aminobenzo[d]oxazol-5-yl)-1H-pyrazolo[3,4-d]pyrimidin-1-yl)methyl)piperidine-1-carboxylate (2.5 g, 5.38 mmol, 1.0 equiv) in TFA (25 mL) was stirred at room temperature for 30 min. The reaction solution was concentrated under reduced pressure to remove TFA. The residue was added to MTBE (400 mL) and a solid precipitated, which was then filtered to give 5-(4-amino-1-(piperidin-4-ylmethyl)-1H-pyrazolo[3,4-d]pyrimidin-3-yl)benzo[d]oxazol-2-amine (2.7 g, over 100% yield) as a yellow solid. LCMS (ESI) m/z: [M+H] calcd for $C_{18}H_{20}N_8O$: 365.18; found 365.1.

Monomer F. 2-(4-amino-1-(4-aminobutyl)-1H-pyrazolo[3,4-d]pyrimidin-3-yl)-1H-indol-5-ol trifluoroacetic acid salt

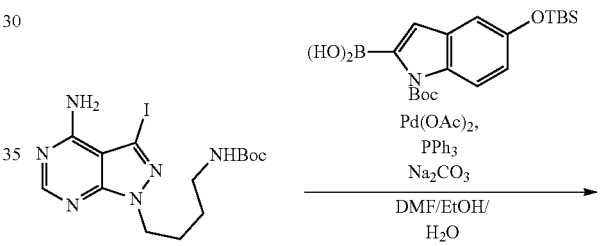

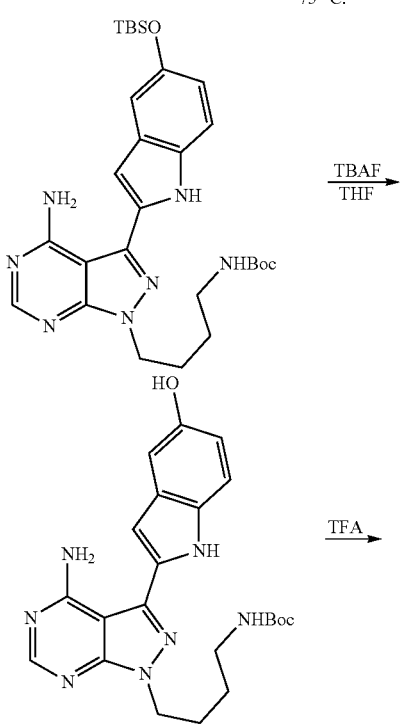

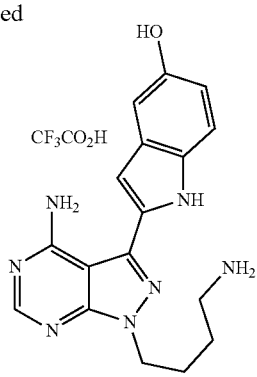

Step 1: Synthesis of tert-butyl (4-(4-amino-3-(5-((tert-butyldimethylsilyl)oxy)-1H-indol-2-yl)-1H-pyrazolo[3,4-d]pyrimidin-1-yl)butyl)carbamate To a solution of tert-butyl (4-(4-amino-3-iodo-1H-pyrazolo[3,4-d]pyrimidin-1-yl)butyl)carbamate (1.0 g, 2.31 mmol, 1.0 equiv) in dioxane (10.5 mL) and H$_2$O (3.5 mL) was added (1-(tert-butoxycarbonyl)-5-((tert-butyldimethylsilyl)oxy)-1H-indol-2-yl)boronic acid (1.54 g, 2.78 mmol, 1.2 equiv), K$_3$PO$_4$ (1.47 g, 6.94 mmol, 3.0 equiv), Pd$_2$(dba)$_3$ (211.84 mg, 231.34 µmol, 0.1 equiv), and SPhos (189.95 mg, 462.69 µmol, 0.2 equiv) at room temperature under N$_2$. The sealed tube was heated at 150° C. for 20 min in a microwave. This was repeated for 9 additional batches. The 10 batches were combined and the reaction mixture was cooled and partitioned between EtOAc (60 mL) and H$_2$O (80 mL). The aqueous layer was separated and extracted with EtOAc (2×50 mL). The organic layers were combined, washed with brine (60 mL) and dried over anhydrous Na$_2$SO$_4$. The suspension was filtered and the filtrate was concentrated under reduced pressure. The crude material was purified by silica gel chromatography (1→75% EtOAc/petroleum ether). The desired fractions were combined and evaporated under reduced pressure to give tert-butyl (4-(4-amino-3-(5-((tert-butyldimethylsilyl)oxy)-1H-indol-2-yl)-1H-pyrazolo[3,4-d]pyrimidin-1-yl)butyl)carbamate (10 g, 60% yield) as a light yellow solid.

Step 2: Synthesis of tert-butyl (4-(4-amino-3-(5-hydroxy-1H-indol-2-yl)-1H-pyrazolo[3,4-d] pyrimidin-1-yl)butyl)carbamate To a mixture of tert-butyl (4-(4-amino-3-(5-((tert-butyldimethylsilyl)oxy)-1H-indol-2-yl)-1H-pyrazolo[3,4-d]pyrimidin-1-yl)butyl)carbamate (10 g, 18.12 mmol, 1.0 equiv) in THF (100 mL) was added TBAF·3H$_2$O (1 M, 54.37 mL, 3.0 equiv) in one portion at room temperature under N$_2$. The mixture was stirred for 1 h and then H$_2$O (100 mL) was added to the reaction mixture. The layers were separated and the aqueous phase was extracted with EtOAc (2×80 mL). The combined organic phase was washed with brine (100 mL), dried with anhydrous Na$_2$SO$_4$, filtered and concentrated under reduced pressure. The residue was purified by silica gel chromatography (1→67% EtOAc/petroleum ether) to afford tert-butyl (4-(4-amino-3-(5-hydroxy-1H-indol-2-yl)-1H-pyrazolo[3,4-d]pyrimidin-1-yl)butyl)carbamate (7 g, 87% yield) as a light pink solid.

Step 3: Synthesis of 2-[4-amino-1-(4-aminobutyl)pyrazolo[3,4-d]pyrimidin-3-yl]-1H-indol-5-ol To TFA (50.0 mL, 675.26 mmol, 38.9 equiv) was added tert-butyl (4-(4-amino-3-(5-hydroxy-1H-indol-2-yl)-1H-pyrazolo[3,4-d]pyrimidin-1-yl)butyl)carbamate (7.6 g, 17.37 mmol, 1.0 equiv) at room temperature. The mixture was stirred for 40 min and was then concentrated under reduced pressure. The oily residue was triturated with MeCN (20 mL), then added dropwise into MTBE (300 mL) for 10 min. The supernatant was removed and then the precipitate was collected by filtration under N$_2$ to give 2-[4-amino-1-(4-aminobutyl)pyrazolo[3,4-d]pyrimidin-3-yl]-1H-indol-5-ol (7.79 g, 91% yield) as light yellow solid. LCMS (ESI) m/z: [M+H] calcd for C$_{17}$H$_{19}$N$_7$O: 338.17; found 338.2.

Monomer G. 5-(4-amino-1-(azetidin-3-ylmethyl)-1H-pyrazolo[3,4-d]pyrimidin-3-yl)benzo[d]oxazol-2-amine trifluoroacetic acid salt

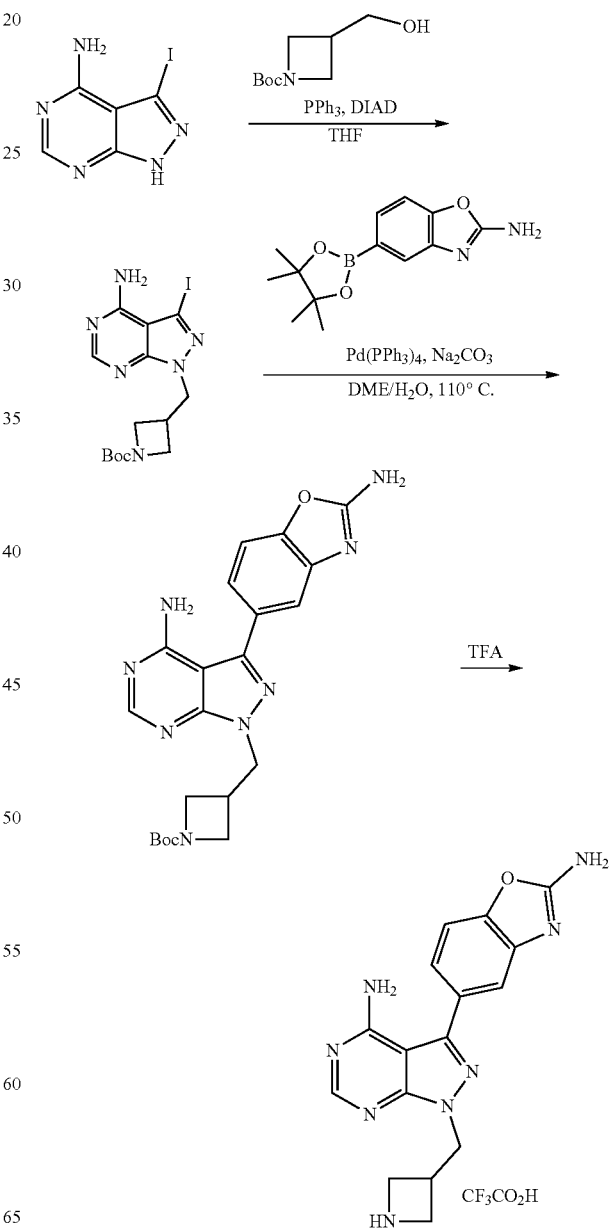

Step 1: Synthesis of tert-butyl 3-((4-amino-3-iodo-1H-pyrazolo[3,4-d]pyrimidin-1-yl) methyl)azetidine-1-carboxylate To a solution of 3-iodo-1H-pyrazolo[3,4-d]pyrimidin-4-amine (4 g, 15.32 mmol, 1.0 equiv), tert-butyl 3-(hydroxymethyl)azetidine-1-carboxylate (3.01 g, 16.09 mmol, 1.05 equiv) and PPh$_3$ (6.03 g, 22.99 mmol, 1.5 equiv) in THF (80 mL) cooled to 0° C. was added DIAD (4.47 mL, 22.99 mmol, 1.5 equiv), dropwise. After the addition was complete, the reaction was stirred at room temperature for 14 h. The reaction was poured into H$_2$O (200 mL) and then extracted with EtOAc (3×50 mL). The organic layers were combined and washed with brine (2×50 mL). The organic phase was dried over Na$_2$SO$_4$, filtered, the filtrate was concentrated under reduced pressure to give a residue. The residue was purified by silica gel chromatography (0→100% EtOAc/petroleum ether) to give tert-butyl 3-((4-amino-3-iodo-1H-pyrazolo[3,4-d]pyrimidin-1-yl)methyl) azetidine-1-carboxylate (4.2 g, 64% yield) as a white solid. LCMS (ESI) m/z: [M+H] calcd for C$_{14}$H$_{19}$IN$_6$O$_2$: 431.07; found 431.0.

Step 2: Synthesis of tert-butyl 3-((4-amino-3-(2-aminobenzo[d]oxazol-5-yl)-1H-pyrazolo [3,4-d]pyrimidin-1-yl)methyl)azetidine-1-carboxylate To a bi-phasic suspension of tert-butyl 3-((4-amino-3-iodo-1H-pyrazolo[3,4-d]pyrimidin-1-yl) methyl)azetidine-1-carboxylate (4 g, 9.30 mmol, 1.0 equiv), 5-(4,4,5,5-tetramethyl-1,3,2-dioxaborolan-2-yl)benzo[d]oxazol-2-amine (2.90 g, 11.16 mmol, 1.2 equiv) and Na$_2$CO$_3$ (4.93 g, 46.49 mmol, 5.0 equiv) in DME (100 mL) and H$_2$O (50 mL) was added Pd(PPh$_3$)$_4$ (1.07 g, 929.71 µmol, 0.1 equiv) at room temperature under N$_2$. The mixture was stirred at 110° C. for 3 h. The reaction mixture was then cooled to room temperature and filtered, and the filtrate was extracted by EtOAc (3×50 mL). The organic layers were combined and washed with brine (10 mL), dried over Na$_2$SO$_4$, filtered and the filtrate was concentrated under reduced pressure to give a residue. The residue was purified by silica gel chromatography (0→20% MeOH/EtOAc) to give tert-butyl 3-((4-amino-3-(2-aminobenzo[d]oxazol-5-yl)-1H-pyrazolo[3,4-d]pyrimidin-1-yl)methyl)azetidine-1-carboxylate (3.5 g, 80% yield) as a yellow solid. LCMS (ESI) m/z: [M+H] calcd for C$_{21}$H$_{24}$N$_8$O$_3$: 437.20; found 437.2.

Step 3: Synthesis of 5-(4-amino-1-(azetidin-3-ylmethyl)-1H-pyrazolo[3,4-d]pyrimidin-3-yl)benzo[d]oxazol-2-amine To a solution of tert-butyl 3-((4-amino-3-(2-aminobenzo[d]oxazol-5-yl)-1H-pyrazolo[3,4-d] pyrimidin-1-yl)methyl) azetidine-1-carboxylate (3.29 g, 6.87 mmol, 1.0 equiv) in DCM (20 mL) was added TFA (7.50 mL, 101.30 mmol, 14.7 equiv) at 0° C. The reaction was warmed to room temperature and stirred for 2 h. The reaction solution was concentrated under reduced pressure to give a residue. The residue was dissolved in MeCN (6 mL) and then poured into MTBE (80 mL). A solid precipitated, which was filtered and the solid cake was dried under reduced pressure to give 5-[4-amino-1-(azetidin-3-ylmethyl)pyrazolo[3,4-d]pyrimidin-3-yl]-1,3-benzoxazol-2-amine (4.34 g, over 100% yield, TFA) as a yellow solid. LCMS (ESI) m/z: [M+H] calcd for C$_{16}$H$_{16}$N$_8$O: 337.15; found 337.1.

Monomer H. 5-(4-amino-1-(4-aminobutyl)-1H-pyrazolo[3,4-d]pyrimidin-3-yl)benzo[d]-oxazol-2-amine trifluoroacetic acid salt

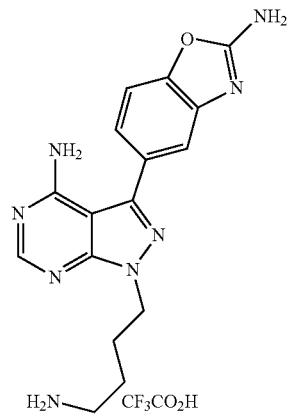 [SMILES: NCCCCn1nc(-c2ccc3oc(N)nc3c2)c2c(N)ncnc21 ; "CF3CO2H"]

This monomer was synthesized following the procedures outlined in Nature 2015, 534, 272-276, which is incorporated by reference in its entirety.

Monomer I. 5-(4-amino-1-(pyrrolidin-3-ylmethyl)-1H-pyrazolo[3,4-d]pyrimidin-3-yl)benzo[d]oxazol-2-amine trifluoroacetic acid salt

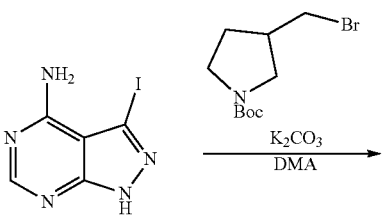

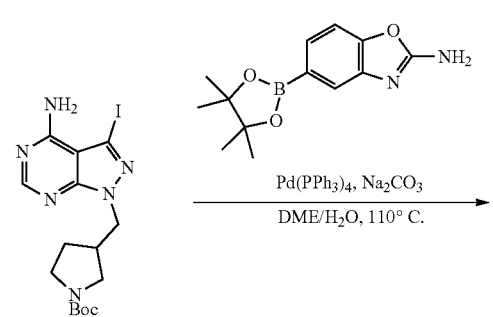

-continued

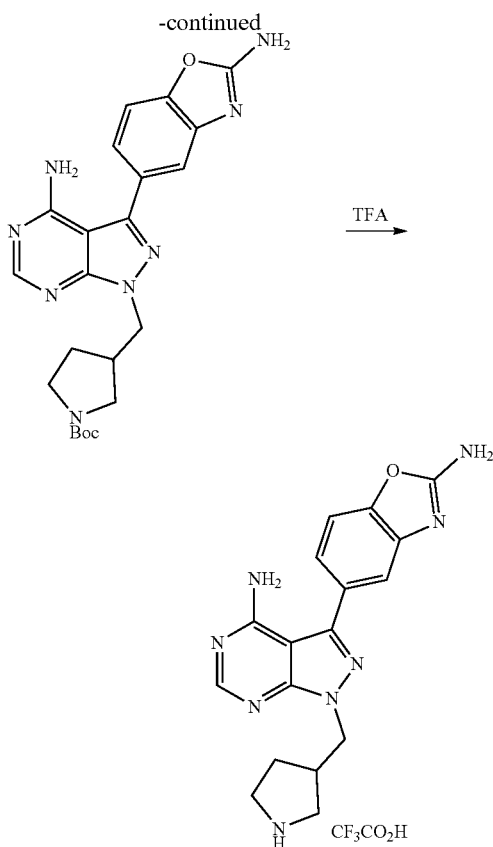

Step 1: Synthesis of tert-butyl 3-((4-amino-3-iodo-1H-pyrazolo[3,4-d]pyrimidin-1-yl) methyl)pyrrolidine-1-carboxylate A suspension of 3-iodo-1H-pyrazolo[3,4-d]pyrimidin-4-amine (4.5 g, 17.24 mmol, 1.0 equiv), tert-butyl 3-(bromomethyl)pyrrolidine-1-carboxylate (4.78 g, 18.10 mmol, 1.05 equiv) and $K_2CO_3$ (7.15 g, 51.72 mmol, 3.0 equiv) in DMA (40 mL) was heated to 85° C. The reaction was stirred at 85° C. for 3 h, at which point the solution was cooled to room temperature. Then, $H_2O$ (80 mL) was added to the reaction, and a solid precipitated out. The mixture was filtered, and the solid cake was washed with $H_2O$ (2×40 mL), and then dried under reduced pressure to give tert-butyl 3-((4-amino-3-iodo-1H-pyrazolo[3,4-d]pyrimidin-1-yl) methyl)pyrrolidine-1-carboxylate (6 g, 78% yield) as a yellow solid. LCMS (ESI) m/z: [M+H] calcd for $C_{15}H_{21}IN_6O_2$: 445.08; found 445.1.

Step 2: Synthesis of tert-butyl 3-[[4-amino-3-(2-amino-1,3-benzoxazol-5-yl)pyrazolo[3,4-d] pyrimidin-1-yl]methyl]pyrrolidine-1-carboxylate To a bi-phasic suspension of tert-butyl 3-((4-amino-3-iodo-1H-pyrazolo[3,4-d]pyrimidin-1-yl) methyl)pyrrolidine-1-carboxylate (4 g, 9.00 mmol, 1.0 equiv), 5-(4,4,5,5-tetramethyl-1,3,2-dioxaborolan-2-yl)benzo[d]oxazol-2-amine (2.81 g, 10.80 mmol, 1.2 equiv) and $Na_2CO_3$ (4.77 g, 45.02 mmol, 5.0 equiv) in DME (120 mL) and $H_2O$ (60 mL) was added $Pd(PPh_3)_4$ (1.04 g, 900.35 µmol, 0.1 equiv) at room temperature under $N_2$. The mixture was stirred at 110° C. for 3 h. The reaction mixture was cooled to room temperature and filtered and the filtrate was extracted with EtOAc (3×50 mL). The organic phases were combined and washed with brine (50 mL), dried over $Na_2SO_4$, filtered and concentrated under reduced pressure to give a residue. The residue was purified by silica gel chromatography (0→20% MeOH/EtOAc) to give tert-butyl 3-((4-amino-3-(2-aminobenzo[d]oxazol-5-yl)-1H-pyrazolo[3,4-d]pyrimidin-1-yl) methyl)pyrrolidine-1-carboxylate (3 g, 64% yield) as a yellow solid. LCMS (ESI) m/z: [M+H] calcd for $C_{22}H_{26}N_8O_3$: 451.21, found 451.2.

Step 3: Synthesis of 5-(4-amino-1-(pyrrolidin-3-ylmethyl)-1H-pyrazolo[3,4-d]pyrimidin-3-yl)benzo [d]oxazol-2-amine To a solution of tert-butyl 3-((4-amino-3-(2-aminobenzo [d]oxazol-5-yl)-1H-pyrazolo[3,4-d]pyrimidin-1-yl)methyl) pyrrolidine-1-carboxylate (3 g, 6.66 mmol, 1.0 equiv) in DCM (40 mL) was added TFA (20 mL) at 0° C., dropwise. The reaction mixture was warmed to room temperature and stirred for 2 h. The reaction solution was then concentrated under reduced pressure to give a residue. The residue was dissolved in MeCN (4 mL), then poured into MTBE (100 mL), and a solid precipitated out. The solid was filtered and the cake was dried under reduced pressure to give 5-(4-amino-1-(pyrrolidin-3-ylmethyl)-1H-pyrazolo[3,4-d]pyrimidin-3-yl)benzo[d]oxazol-2-amine (4.00 g, over 100% yield, TFA) as a yellow solid. LCMS (ESI) m/z: [M+H] calcd for $C_{17}H_{18}N_8O$: 351.17; found 351.2.

Monomer J. 1-(4-aminobutyl)-3-(7-methoxy-1H-indol-2-yl)-1H-pyrazolo[3,4-d]pyrimidin-4-aminetrifluoroacetic acid salt

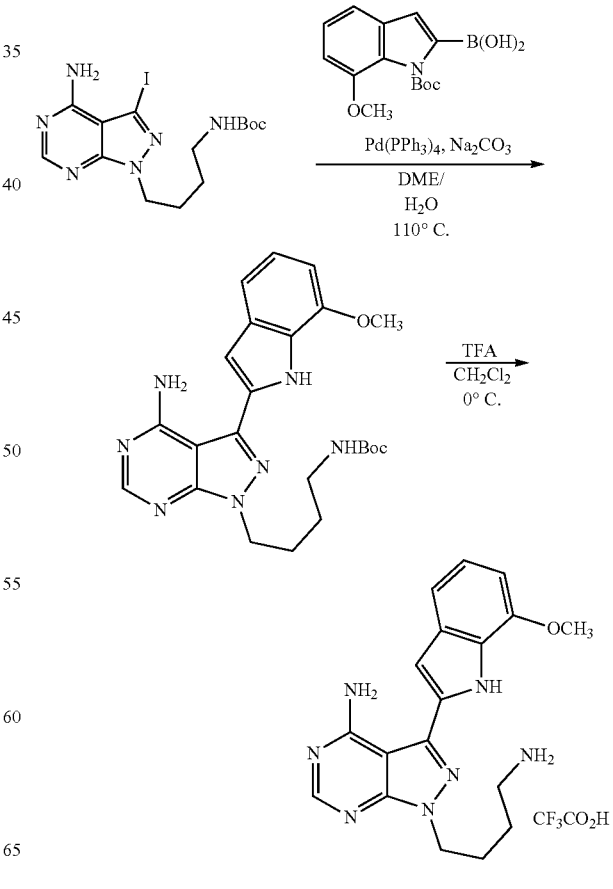

Step 1: Synthesis of tert-butyl 2-(4-amino-1-(4-((tert-butoxycarbonyl)amino)butyl)-1H-pyrazolo[3,4-d]pyrimidin-3-yl)-7-methoxy-1H-indole-1-carboxylate To a mixture of tert-butyl (4-(4-amino-3-iodo-1H-pyrazolo[3,4-d]pyrimidin-1-yl)butyl)carbamate (1.0 equiv) and (1-(tert-butoxycarbonyl)-7-methoxy-1H-indol-2-yl)boronic acid (3.0 equiv) in DME and H₂O is added Pd(PPh₃)₄ (0.1 equiv) and sodium carbonate (6.0 equiv). The reaction is heated at 80° C. until completion, as determined by LCMS and TLC analysis. The reaction is then quenched with H₂O and EtOAc. The mixture is transferred to a separatory funnel and the aqueous phase is extracted with EtOAc. The organic phase is washed with sat. aq. NaCl, dried over Na₂SO₄, filtered, and concentrated under reduced pressure. The desired product is isolated after chromatography on silica gel.

Step 2: Synthesis of 1-(4-aminobutyl)-3-(7-methoxy-1H-indol-2-yl)-1H-pyrazolo[3,4-d]pyrimidin-4-amine To a solution of tert-butyl 2-(4-amino-1-(4-((tert-butoxycarbonyl)amino)butyl)-1H-pyrazolo[3,4-d]pyrimidin-3-yl)-7-hydroxy-1H-indole-1-carboxylate (1.0 equiv) in DCM at 0° C. is added TFA dropwise. The reaction is stirred at 0° C. and warmed to room temperature. Once the reaction is complete, as determined by LCMS, the reaction is concentrated under reduced pressure. The residue is triturated with MeCN, then dripped into MTBE over 10 min. The supernatant is removed and the precipitate is collected by filtration under N₂ to give 1-(4-aminobutyl)-3-(7-methoxy-1H-indol-2-yl)-1H-pyrazolo[3,4-d]pyrimidin-4-amine.

Monomer K. Synthesis of 1-(4-aminobutyl)-1H-pyrazolo[3,4-d]pyrimidin-4-amine trifluoroacetic acid salt

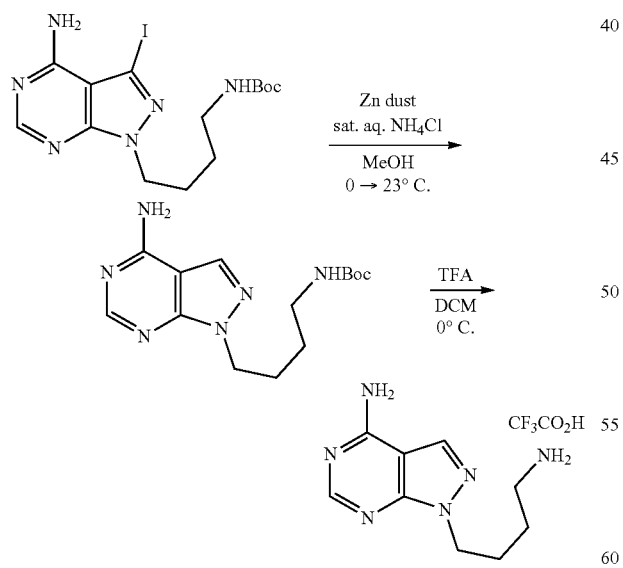

Step 1: Synthesis of tert-butyl (4-(4-amino-1H-pyrazolo[3,4-d]pyrimidin-1-yl)butyl)carbamate To a mixture of tert-butyl (4-(4-amino-3-iodo-1H-pyrazolo[3,4-d]pyrimidin-1-yl)butyl)carbamate (300 mg, 694 µmol, 1.0 equiv) in MeOH (14 mL) at 0° C. was added zinc dust (226 mg, 3.46 mmol, 5.0 equiv). Sat. aq. NH₄Cl (14 mL) was added to the reaction mixture and the reaction was warmed to room temperature and stirred for 18 h. The reaction was quenched by EtOAc (40 mL) and H₂O (10 mL) and the mixture was transferred to a separatory funnel. The aqueous phase was extracted with EtOAc (3×20 mL) and the combined organic phases were washed with sat. aq. NaHCO₃ (15 mL), dried over Na₂SO₄, filtered, and concentrated under reduced pressure to provide the product (210 mg, 99% yield) as a light yellow solid that was used without further purification. LCMS (ESI) m/z: [M+H] calcd for C₁₄H₂₂N₆O₂: 307.19; found 307.1.

Step 2: Synthesis of 1-(4-aminobutyl)-1H-pyrazolo[3,4-d]pyrimidin-4-amine

To a solution of tert-butyl (4-(4-amino-1H-pyrazolo[3,4-d]pyrimidin-1-yl)butyl)carbamate (210 mg, 691 µmol) in DCM (3.5 mL) at 0° C. was added TFA (3.5 mL), dropwise. After 3 h, the reaction was warmed to room temperature and concentrated under reduced pressure to provide the trifluoroacetate salt of the product (220 mg, 99% yield) as a brown oil, which was used without further purification. LCMS (ESI) m/z: [M+H] calcd for C₉H₁₄N₆: 207.13; found 207.1.

Monomer L. 1-[4-(piperazin-1-yl)-3-(trifluoromethyl)phenyl]-9-(quinolin-3-yl)-1H,2H-benzo[h][1,6-naphthyridin-2-one

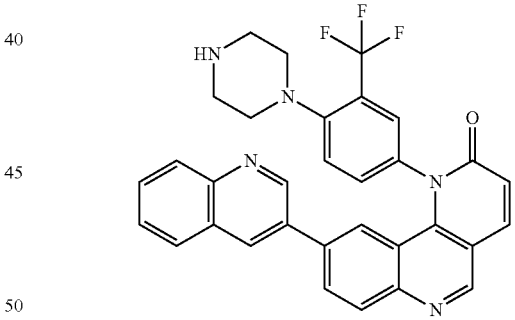

The preparation of this monomer has been previously reported in the literature. See the following references: i) Liu, Qingsong; Chang, Jae Won; Wang, Jinhua; Kang, Seong A.; Thoreen, Carson C.; Markhard, Andrew; Hur, Wooyoung; Zhang, Jianming; Sim, Taebo; Sabatini, David M.; et al From Journal of Medicinal Chemistry (2010), 53(19), 7146-7155. ii) Gray, Nathanael; Chang, Jae Won; Zhang, Jianming; Thoreen, Carson C.; Kang, Seong Woo Anthony; Sabatini, David M.; Liu, Qingsong From PCT Int. Appl. (2010), WO 2010044885A2, which are incorporated by reference in their entirety.

Monomer M. 5-(1-(4-aminobutyl)-4-(dimethyl-amino)-1H-pyrazolo[3,4-d]pyrimidin-3-yl)benzo[d]oxazol-2-amine trifluoroacetic acid salt

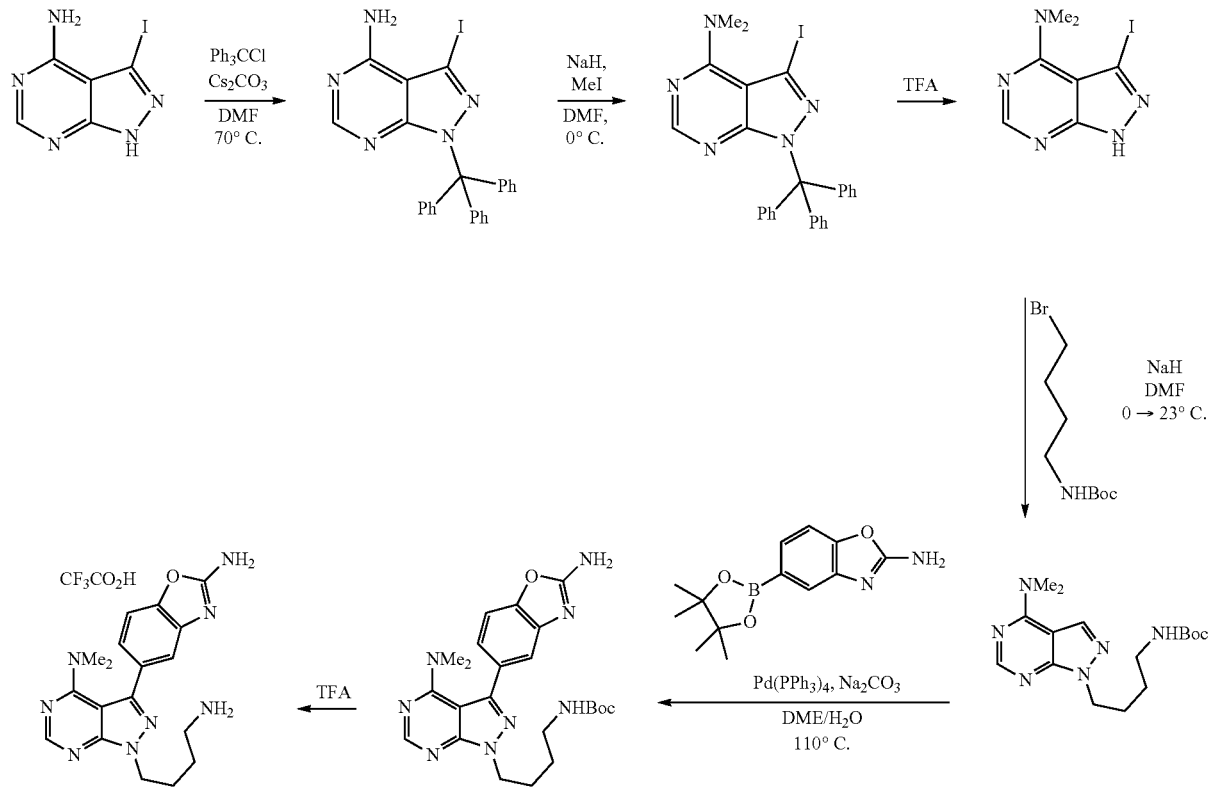

Step 1: Synthesis of 3-iodo-1-trityl-1H-pyrazolo[3,4-d]pyrimidin-4-amine

A suspension of 3-iodo-1H-pyrazolo[3,4-d]pyrimidin-4-amine (10.5 g, 40.23 mmol, 1.0 equiv) in DMF (170.0 mL) was treated with $Cs_2CO_3$ (19.7 g, 60.34 mmol, 1.5 equiv) and [chloro(diphenyl)methyl]benzene (13.5 g, 48.27 mmol, 1.2 equiv) at room temperature. The reaction mixture was stirred at 70° C. for 4 h under a nitrogen atmosphere. The reaction mixture was added to $H_2O$ (1200 mL). The precipitate was filtered and washed with $H_2O$. The residue was purified by silica gel chromatography (0→60% EtOAc/petroleum ether) to afford 3-iodo-1-trityl-1H-pyrazolo[3,4-d]pyrimidin-4-amine (15.40 g, 73.5% yield) as a white solid.

Step 2: Synthesis of 3-iodo-N,N-dimethyl-1-trityl-1H-pyrazolo[3,4-d]pyrimidin-4-amine To a suspension of NaH (2.98 g, 74.50 mmol, 60 wt. %, 2.5 equiv) in DMF (150 mL) was added the solution of 3-iodo-1-trityl-1H-pyrazolo[3,4-d]pyrimidin-4-amine (15.0 g, 29.80 mmol, 1.0 equiv) in DMF (50 mL) at 0° C. The mixture was stirred at 0° C. for 10 min. To the reaction mixture was then added iodomethane (16.92 g, 119.20 mmol, 7.42 mL, 4.0 equiv) at 0° C. The mixture was stirred at room temperature for 2 h, at which point $H_2O$ (1400 mL) was added at 0° C. The mixture was stirred for an additional 10 min at 0 C. The resulting precipitate was collected by filtration to give curde product, which was purified by silica gel chromatography (1% 25% EtOAc/petroleum ether) twice to afford 3-iodo-N,N-dimethyl-1-trityl-1H-pyrazolo[3,4-d]pyrimidin-4-amine (9.0 g, 89% yield) as a white solid.

Step 3: Synthesis of 3-iodo-N,N-dimethyl-1H-pyrazolo[3,4-d]pyrimidin-4-amine To a cooled solution of TFA (19.1 mL, 258.1 mmol, 15.0 equiv) in DCM (100.0 mL) was added 3-iodo-N,N-dimethyl-1-trityl-1H-pyrazolo[3,4-d]pyrimidin-4-amine (9.10 g, 17.12 mmol, 1.0 equiv) at 4° C. The mixture was stirred at room temperature for 1 h. The residue was poured into $H_2O$ (100 mL) and the aqueous phase was extracted with DCM (2×50 mL). To the aqueous phase was then added a saturated aqueous solution of $NaHCO_3$ until the solution was pH 8. The resulting precipitate was collected by filtration to give 3-iodo-N,N-dimethyl-1H-pyrazolo[3,4-d]pyrimidin-4-amine (3.40 g, 68.7% yield) as a white solid.

Step 4: Synthesis of tert-butyl (4-(4-(dimethyl-amino)-3-iodo-1H-pyrazolo[3,4-d]pyrimidin-1-yl)butyl)carbamate To a suspension of 3-iodo-N,N-dimethyl-1H-pyrazolo[3,4-d]pyrimidin-4-amine (1.7 g, 5.88 mmol, 1.0 equiv) in DMF (20 mL) was added NaH (247 mg, 6.17 mmol, 60 wt. %, 1.05 equiv) at 4° C. The mixture was stirred at 4° C. for 30 min. To the reaction mixture was then added tert-butyl N-(4-bromobutyl)carbamate (2.22 g, 8.82 mmol, 1.81 mL, 1.5 equiv) in DMF (10 mL) at 4° C. The mixture was stirred at room temperature for 2 h. To the mixture was then added $H_2O$ (100 mL) at 4° C. The mixture was stirred for an additional 30 min at 4° C. and the resulting precipitate was collected by filtration to give crude product. The residue was purified by silica gel chromatography (0→75% EtOAc/petroleum ether) to afford tert-butyl(4-(4-(dimethylamino)-3-iodo-1H-pyrazolo[3,4-d]pyrimidin-1-yl)butyl)carbamate (2.0 g, 56% yield) as a white solid.

Step 5: Synthesis of tert-butyl (4-(3-(2-aminobenzo[d]oxazol-5-yl)-4-(dimethylamino)-1H-pyrazolo[3,4-d]pyrimidin-1-yl)butyl)carbamate To a bi-phasic suspension of tert-butyl (4-(4-(dimethylamino)-3-iodo-1H-pyrazolo[3,4-d]pyrimidin-1-yl)butyl)carbamate (4.0 g, 8.69 mmol, 1.0 equiv), 5-(4,4,5,5-tetramethyl-1,3,2-dioxaborolan-2-yl)benzo[d]oxazol-2-amine (3.4 g, 13.03 mmol, 1.5 equiv), and Na$_2$CO$_3$ (4.6 g, 43.45 mmol, 5.0 equiv) in DME (80.0 mL) and H$_2$O (40.0 mL) was added Pd(PPh$_3$)$_4$ (1.0 g, 868.98 µmol, 0.1 equiv) at room temperature under N$_2$. The mixture was stirred at 110° C. for 3 h. The reaction mixture was then cooled and partitioned between EtOAc (300 mL) and H$_2$O (600 mL). The aqueous layer was separated and extracted with EtOAc (2×100 mL). The organic layers were combined, washed with brine (2×60 mL) and dried over anhydrous Na$_2$SO$_4$, filtered, and concentrated under reduced pressure. The crude material was purified by silica gel column chromatography (50% EtOAc/hexanes followed by 20% MeOH/EtOAc). The desired fractions were combined and concentrated under reduced pressure to give tert-butyl (4-(3-(2-aminobenzo[d]oxazol-5-yl)-4-(dimethylamino)-1H-pyrazolo[3,4-d]pyramidin-1-yl)butyl)carbamate (3.2 g, 78.9% yield) as a light brown solid.

Step 6: Synthesis of 5-(1-(4-aminobutyl)-4-(dimethylamino)-1H-pyrazolo[3,4-d]pyrimidin-3-yl)benzo[d]oxazol-2-amine To TFA (20.82 mL, 281.27 mmol, 36.5 equiv) was added tert-butyl (4-(3-(2-aminobenzo[d]oxazol-5-yl)-4-(dimethylamino)-1H-pyrazolo[3,4-d]pyrimidin-1-yl)butyl)carbamate (3.6 g, 7.72 mmol, 1.0 equiv) at room temperature. The mixture was stirred for 30 min, at which point the mixture was concentrated under reduced pressure. The oily residue was triturated with MeCN (8 mL) and MTBE (60 mL) for 10 min. The supernatant was removed and then the precipitate was collected by filtration under N$_2$ to give 5-(1-(4-aminobutyl)-4-(dimethylamino)-1H-pyrazolo[3,4-d]pyrimidin-3-yl)benzo[d]oxazol-2-amine (4.0 g, crude, TFA) as a light brown solid.

To 1M NaOH (107.2 mL, 14.7 equiv) was added 5-(1-(4-aminobutyl)-4-(dimethylamino)-1H-pyrazolo[3,4-d]pyrimidin-3-yl)benzo[d]oxazol-2-amine (3.5 g, crude, TFA) at room temperature. The mixture was stirred for 10 min and then the aqueous phase was extracted with DCM (3×50 mL). The combined organic phase was washed with brine (50 mL), dried with anhydrous Na$_2$SO$_4$, filtered and concentrated under reduced pressure. TFA (539.37 µL, 7.28 mmol, 1.0 equiv) was added and concentrated under reduced pressure. MeCN (10 mL) was then added, followed by MTBE (150 mL). The resulting precipitate was collected by filtration to give 5-(1-(4-aminobutyl)-4-(dimethylamino)-1H-pyrazolo[3,4-d]pyrimidin-3-yl)benzo[d]oxazol-2-amine (1.3 g, 36.6% yield, TFA) as a light brown product. LCMS (ESI) m/z: [M+H] calcd for C$_{18}$H$_{22}$N$_8$O: 367.19; found 367.1.

Monomer N. 6-(4-amino-1-(4-aminobutyl)-1H-pyrazolo[3,4-d]pyrimidin-3-yl)benzo-[d]isoxazol-3-amine trifluoroacetic acid salt

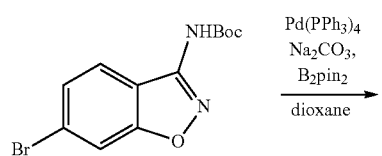

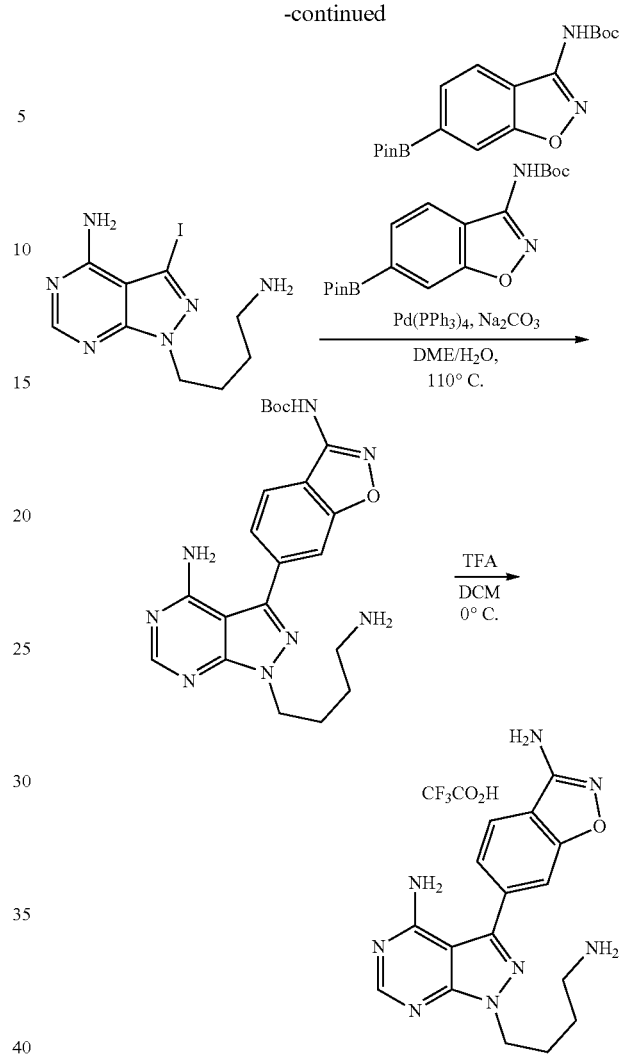

Step 1: Synthesis of tert-butyl (6-(4,4,5,5-tetramethyl-1,3,2-dioxaborolan-2-yl)benzo[d]isoxazol-3-yl)carbamate To a solution of tert-butyl (6-bromobenzo[d]isoxazol-3-yl)carbamate (1.0 equiv) in dioxane is added Pd(PPh$_3$)$_4$ (0.1 equiv), sodium carbonate (6.0 equiv), and bis(pinacolato)diboron (3.0 equiv). The reaction mixture is stirred and heated until completion, as determined by LCMS and TLC analysis. The reaction is cooled to room temperature, quenched with sat. aq. NaHCO$_3$, and the mixture transferred to a separatory funnel. The aqueous phase is extracted with EtOAc and the organic phase is washed with sat. aq. NaCl, dried over Na$_2$SO$_4$, filtered, and concentrated under reduced pressure. The desired product is isolated after purification by silica gel chromatography.

Step 2: Synthesis of tert-butyl (4-(4-amino-3-(3-((tert-butoxycarbonyl)amino)benzo[d]isoxazol-6-yl)-1H-pyrazolo[3,4-d]pyrimidin-1-yl)butyl)carbamate To a mixture of tert-butyl (4-(4-amino-3-iodo-1H-pyrazolo[3,4-d]pyrimidin-1-yl)butyl)carbamate (1.0 equiv) and tert-butyl (6-(4,4,5,5-tetramethyl-1,3,2-dioxaborolan-2-yl)

benzo[d]isoxazol-3-yl)carbamate (3.0 equiv) in DME and H₂O is added Pd(PPh₃)₄ (0.1 equiv) and sodium carbonate (6.0 equiv). The reaction is heated at 80° C. until completion, as determined by LCMS and TLC analysis. The reaction is then quenched with H₂O and EtOAc. The mixture is transferred to a separatory funnel and the aqueous phase is extracted with EtOAc. The organic phase is washed with sat. aq. NaCl, dried over Na₂SO₄, filtered, and concentrated under reduced pressure. The desired product is isolated after chromatography on silica gel.

Step 3: Synthesis of 6-(4-amino-1-(4-aminobutyl)-1H-pyrazolo[3,4-d]pyrimidin-3-yl)benzo-[d]isoxazol-3-amine To a solution of tert-butyl (4-(4-amino-3-(3-((tert-butoxycarbonyl)amino)benzo[d]isoxazol-6-yl)-1H-pyrazolo[3,4-d]pyrimidin-1-yl)butyl)carbamate (1.0 equiv) in DCM at 0° C. is added TFA, dropwise. The reaction is stirred at 0° C. and warmed to room temperature. Once the reaction is complete, as determined by LCMS, the reaction is concentrated under reduced pressure. The residue is triturated with MeCN, then added dropwise into MTBE over 10 min. The supernatant is removed and the precipitate is collected by filtration under N₂ to give 6-(4-amino-1-(4-aminobutyl)-1H-pyrazolo[3,4-d]pyrimidin-3-yl)benzo-[d]isoxazol-3-amine.

Monomer O. 4-(5-(4-morpholino-1-(1-(pyridin-3-ylmethyl)piperidin-4-yl)-1H-pyrazolo[3,4-d]pyrimidin-6-yl)-1H-indol-1-yl)butan-1-amine trifluoroacetic acid salt

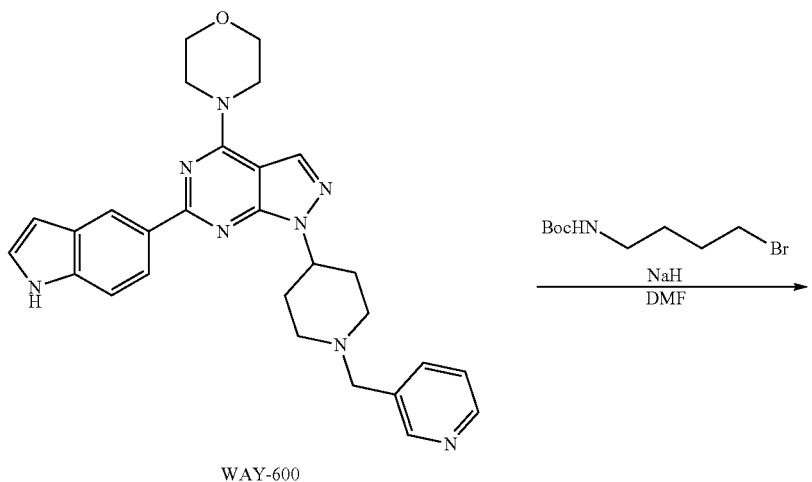

WAY-600

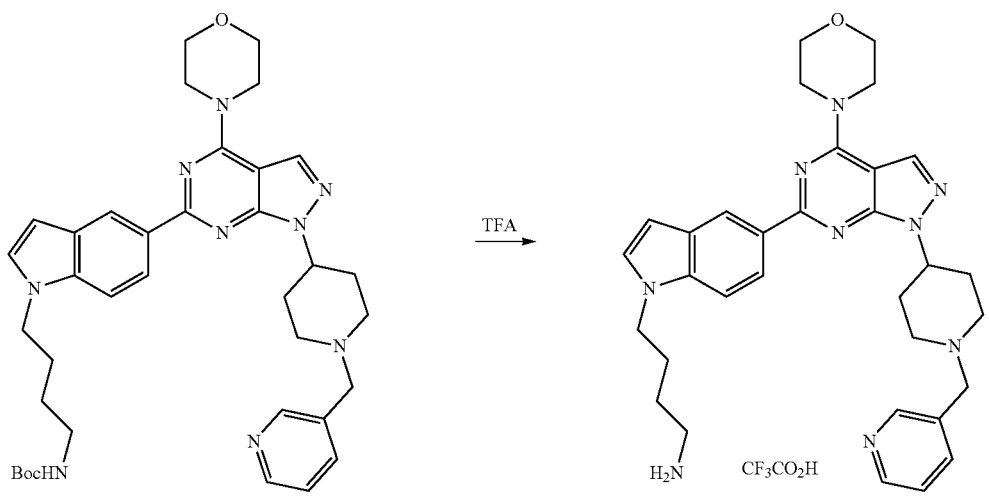

The synthesis of this monomer proceeds by alkylation of WAY-600 (CAS #1062159-35-6) with tert-butyl (4-bromobutyl)carbamate under basic conditions, followed by Boc-deprotection using TFA to produce the TFA salt.

Reference for preparation of WAY-600: Discovery of Potent and Selective Inhibitors of the Mammalian Target of Rapamycin (mTOR) Kinase: Nowak, P.; Cole, D. C.; Brooijmans, N.; Bursavich, M. G.; Curran, K. J.; Ellingboe, J. W.; Gibbons, J. J.; Hollander, I.; Hu, Y.; Kaplan, J.; Malwitz, D. J.; Toral-Barza, L.; Verheijen, J. C.; Zask, A.; Zhang, W.-G.; Yu, K. 2009; Journal of Medicinal Chemistry Volume 52, Issue 22, 7081-89, which is incorporated by reference in its entirety.

Monomer P. 2-(4-(8-(6-(aminomethyl)quinolin-3-yl)-3-methyl-2-oxo-2,3-dihydro-1H-imidazo[4,5-c]quinolin-1-yl)phenyl)-2-methylpropanenitrile trifluoroacetic acid salt

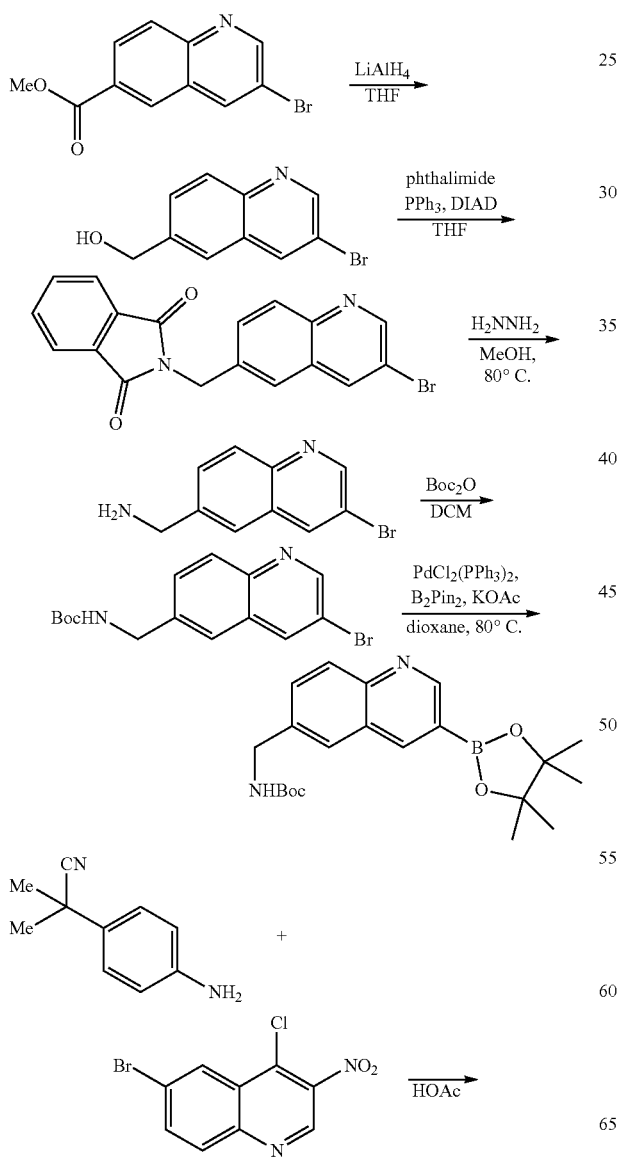

-continued

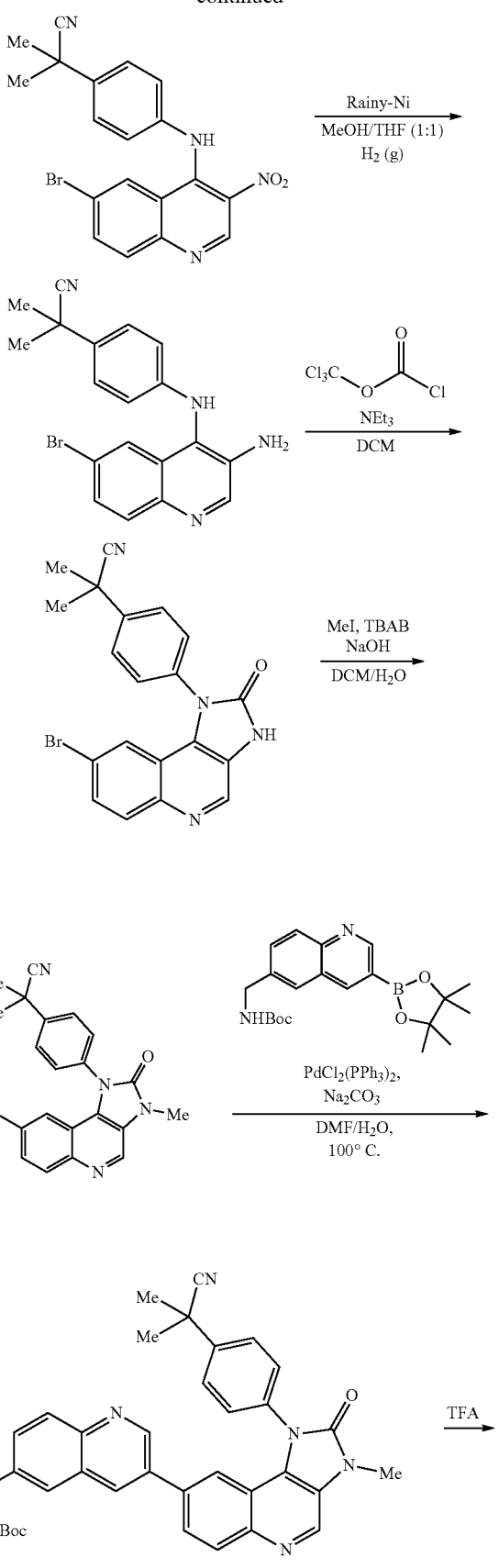

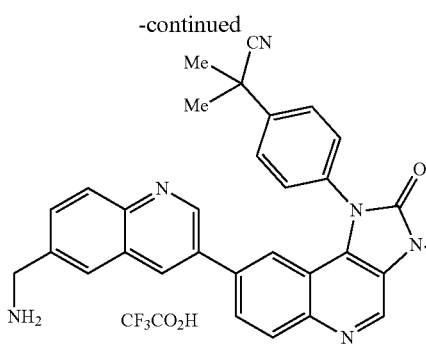

The synthesis of this monomer proceeds first by synthesis of the Suzuki reaction coupling partner (3-(4,4,5,5-tetramethyl-1,3,2-dioxaborolane)quinolin-6-yl)-N-boc-methanamine starting from methyl 3-bromoquinoline-6-carboxylate. Reduction of the methyl ester with lithium aluminum hydride followed by Mitsunobu reaction with phthalimide and hydrazine cleavage provides the benzylic amine. Protection of the benzylic amine with di-tert-butyl dicarbonate followed by a Miyaura borylation reaction provides (3-(4,4,5,5-tetramethyl-1,3,2-dioxaborolane)quinolin-6-yl)-N-boc-methanamine.

An $S_NAr$ reaction of 2-(4-aminophenyl)-2-methylpropanenitrile with 6-bromo-4-chloro-3-nitroquinoline provides the substituted amino-nitro-pyridine. Reduction of the nitro group with Raney-Ni under a hydrogen atmosphere followed by cyclization with trichloromethyl chloroformate provides the aryl-substituted urea. Substitution of the free N—H of the urea with methyl iodide mediated by tetrabutylammonium bromide and sodium hydroxide followed by Suzuki coupling of (3-(4,4,5,5-tetramethyl-1,3,2-dioxaborolane)quinolin-6-yl)-N-boc-methanamine and then Boc-deprotection using TFA produces the TFA salt.

Reference for preparation of 2-[4-(8-bromo-3-methyl-2-oxo-2,3-dihydro-imidazo [4,5-c]quinolin-1-yl)-phenyl]-2-methyl-propionitrile: Vannucchi, A. M.; Bogani, C.; Bartalucci, N. 2016. JAK PI3K/mTOR combination therapy. U.S. Pat. No. 9,358,229. Novartis Pharma AG, Incyte Corporation, which is incorporated by reference in its entirety.

Monomer Q. 8-(6-methoxypyridin-3-yl)-3-methyl-1-[4-(piperazin-1-yl)-3-(trifluoromethyl)phenyl]-1H,2H,3H-imidazo[4,5-c]quinolin-2-one

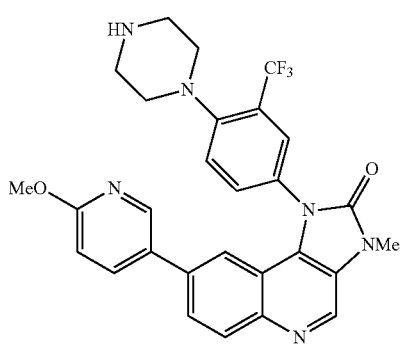 [SMILES: COc1ccc(-c2ccc3ncc4c(c3c2)n(-c2ccc(N3CCNCC3)c(C(F)(F)F)c2)c(=O)n4C)cn1]

This monomer is a commercially available chemical known as BGT226(CAS #1245537-68-1). At the time this application was prepared, it was available for purchase from several vendors as the free amine.

Monomer R. 3-(4-amino-1-(4-aminobutyl)-1H-pyrazolo[3,4-d]pyrimidin-3-yl)-N-(4,5-dihydrothiazol-2-yl)benzamide trifluoroacetic acid salt

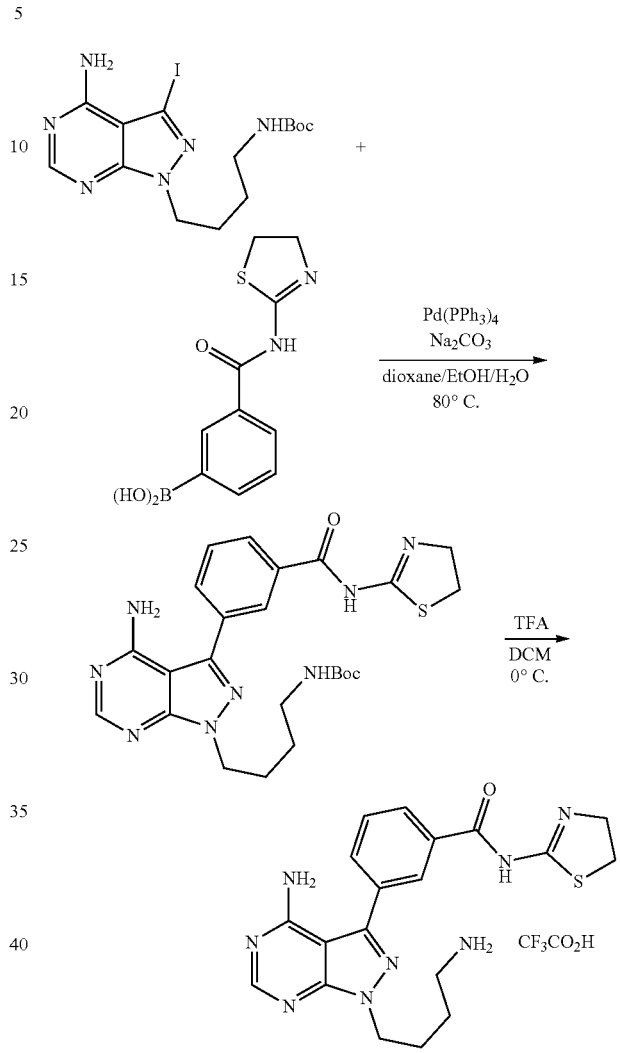

Step 1: Synthesis of tert-butyl (4-(4-amino-3-(3-((4,5-dihydrothiazol-2-yl)carbamoyl)phenyl)-1H-pyrazolo[3,4-d]pyrimidin-1-yl)butyl)carbamate To a solution of (3-((4,5-dihydrothiazol-2-yl)carbamoyl)phenyl)boronic acid (500 mg, 1.15 mmol, 1.0 equiv) and tert-butyl (4-(4-amino-3-iodo-1H-pyrazolo[3,4-d]pyrimidin-1-yl)butyl)carbamate (575 mg, 2.30 mmol, 2.0 equiv) in dioxane (19.1 mL), EtOH (3.8 mL), and H$_2$O (2.3 mL) was added Pd(PPh$_3$)$_4$ (265 mg, 230 µmol, 0.2 equiv) and sodium carbonate (730 mg, 6.89 mmol, 6.0 equiv). The reaction mixture was sonicated until formation of a clear, yellow solution, which was subsequently heated at 80° C. for 14 h. The reaction was then diluted with sat. aq. NaCl (30 mL) and the mixture transferred to a separatory funnel. The aqueous phase was extracted with DCM (3×25 mL). The combined organic phases were dried over Na$_2$SO$_4$, filtered, and concentrated under reduced pressure. The desired product was isolated as a yellow solid (324 mg, 53% yield) after silica gel chromatography (0→15% MeOH/DCM). LCMS (ESI) m/z: [M+H] calcd for C$_{24}$H$_{30}$N$_8$O$_3$S: 511.22; found 511.2.

Step 2: Synthesis of 3-(4-amino-1-(4-aminobutyl)-1H-pyrazolo[3,4-d]pyrimidin-3-yl)-N-(4,5-dihydrothiazol-2-yl)benzamide To a solution of tert-butyl (4-(4-amino-3-(3-((4,5-dihydrothiazol-2-yl)carbamoyl)phenyl)-1H-pyrazolo[3,4-d]pyrimidin-1-yl)butyl)carbamate (324 mg, 614 µmol) in DCM (4.1 mL) at 0° C. was added TFA (1.5 mL), dropwise. After 1 h, the reaction was warmed to room temperature and concentrated under reduced pressure to provide the trifluoroacetate salt of the product as a yellow solid (320 mg, 99%). Used without further purification. LCMS (ESI) m/z: [M+H] calcd for $C_{19}H_{22}N_8OS$: 411.16; found 411.1.

Monomer S. 2-(5-(4-morpholino-1-(1-(pyridin-3-ylmethyl)piperidin-4-yl)-1H-pyrazolo[3,4-d]pyrimidin-6-yl)-1H-indol-3-yl)ethan-1-amine

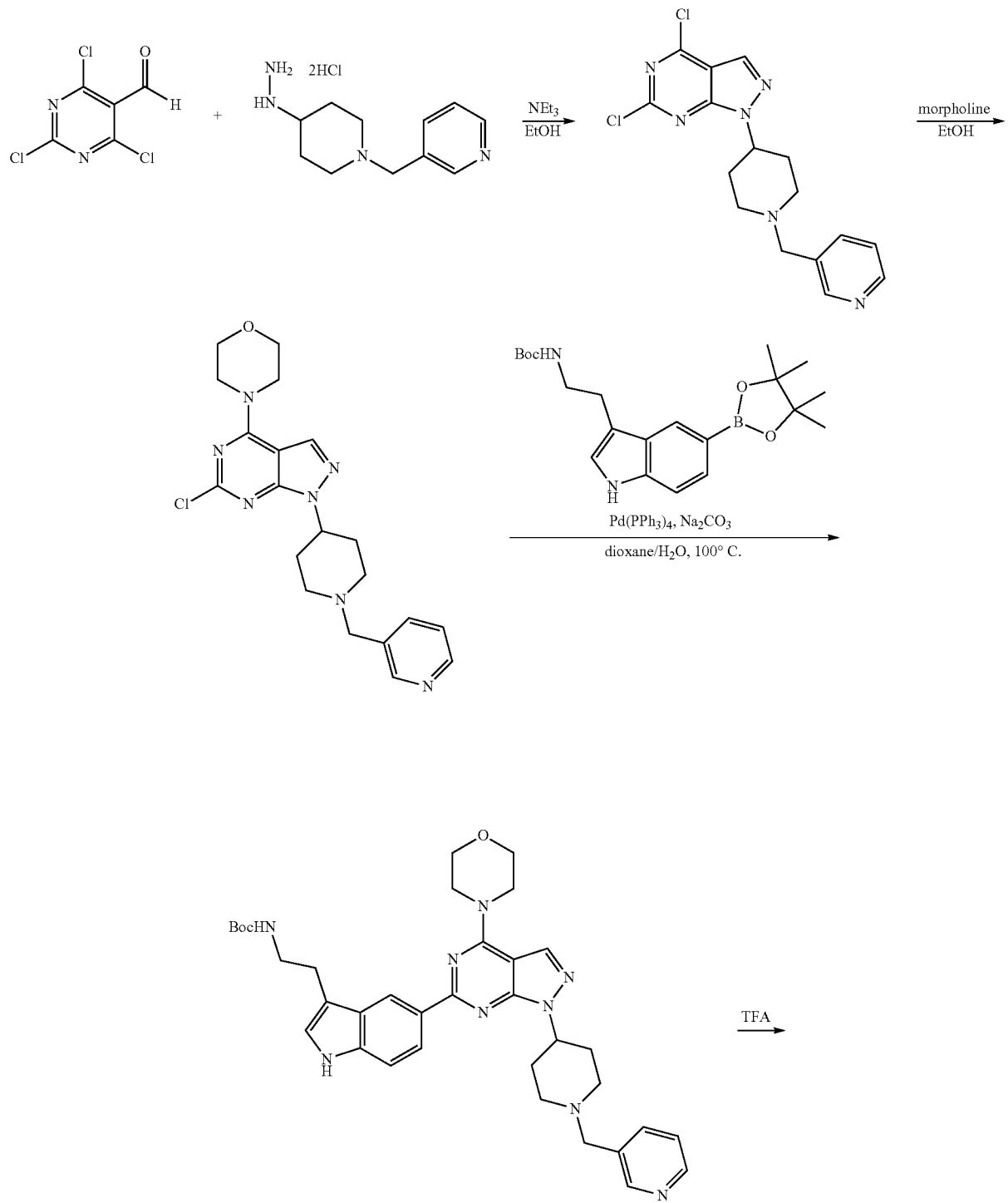

-continued

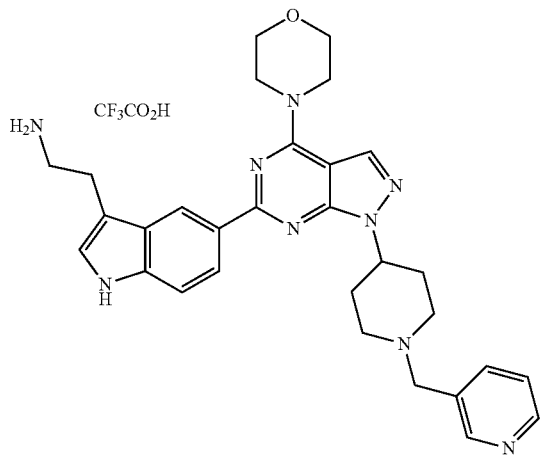

The synthesis of this monomer proceeds by condensation of 2,4,6-trichloropyrimidine-5-carbaldehyde with 3-((4-hydrazineylpiperidin-1-yl)methyl)pyridine hydrochloride. Reaction of the product with morpholine followed by a Suzuki reaction with boronic ester gives the Boc-protected amine. Final deprotection with TFA gives the monomer. This synthesis route follows closely to the reported preparation of highly related structures in the following references: i) Nowak, Pawel; Cole, Derek C.; Brooijmans, Natasj a; Curran, Kevin J.; Ellingboe, John W.; Gibbons, James J.; Hollander, Irwin; Hu, Yong Bo; Kaplan, Joshua; Malwitz, David J.; et al From Journal of Medicinal Chemistry (2009), 52(22), 7081-7089. ii) Zask, Arie; Nowak, Pawel Wojciech; Verheij en, Jeroen; Curran, Kevin J.; Kaplan, Joshua; Malwitz, David; Bursavich, Matthew Gregory; Cole, Derek Cecil; Ayral-Kaloustian, Semiramis; Yu, Ker; et al From PCT Int. Appl. (2008), WO 2008115974 A2 20080925, which are incorporated by reference in their entirety.

Monomer T. 1-(4-aminobutyl)-3-iodo-1H-pyrazolo[3,4-d]pyrimidin-4-amine trifluoroacetic acid salt

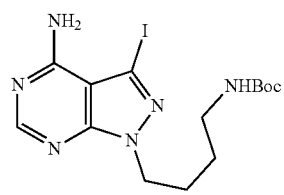

To a mixture of tert-butyl (4-(4-amino-3-iodo-1H-pyrazolo[3,4-d]pyrimidin-1-yl)butyl)carbamate (496 mg, 1.14 mmol, 1.0 equiv) in DCM (5.7 mL) at 0° C. was added TFA (1.5 mL) dropwise. The reaction was allowed to stir at 0° C. for 1 h, at which time the reaction was concentrated under reduced pressure to provide a yellow solid (505 mg, 99% yield) which was taken on without further purification. LCMS (ESI) m/z: [M+H] calcd for $C_9H_{13}IN_6$: 333.02; found 332.9.

Monomer U. 5-(4-amino-1-(4-(methylamino)butyl)-1H-pyrazolo[3,4-d]pyrimidin-3-yl)benzo[d]oxazol-2-amine trifluoroacetic acid salt

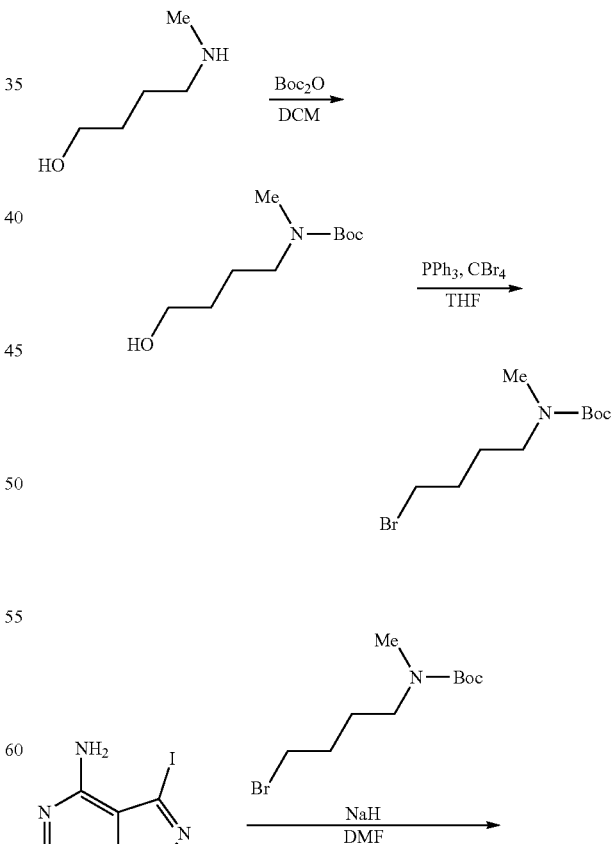

403

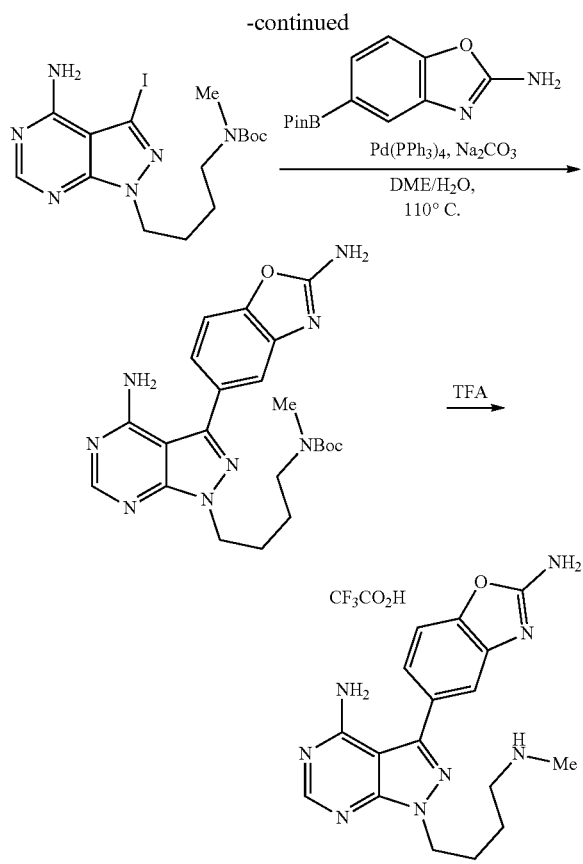

Step 1: Synthesis of tert-butyl (4-hydroxybutyl)(methyl)carbamate

To a solution of 4-(methylamino)butan-1-ol (0.5 g, 4.85 mmol, 104.2 mL, 1.0 equiv) in DCM (10 mL) at room temperature was added Boc$_2$O (1.06 g, 4.85 mmol, 1.11 mL, 1.0 equiv). The mixture was stirred for 3 h at room temperature and then the mixture was concentrated under reduced pressure at 30° C. The residue was purified by silica gel chromatography (100/1 to 3/1 petroleum ether/EtOAc) to afford tert-butyl (4-hydroxybutyl)(methyl)carbamate (0.9 g, 91.4% yield) as a colorless oil.

Step 2: Synthesis of tert-butyl (4-bromobutyl)(methyl)carbamate

To a solution of tert-butyl (4-hydroxybutyl)(methyl)carbamate (0.9 g, 4.43 mmol, 1.0 equiv) in THF (20 mL) at room temperature was added PPh$_3$ (2.21 g, 8.41 mmol, 1.9 equiv) and CBr$_4$ (2.79 g, 8.41 mmol, 1.9 equiv). The mixture was stirred for 1 h and then the reaction mixture was filtered and concentrated. The residue was purified by silica gel chromatography (I/O to 4/1 petroleum ether/EtOAc) to afford tert-butyl (4-bromobutyl)(methyl) carbamate (1.1 g, 93.3% yield) as a colorless oil.

Step 3: Synthesis of tert-butyl (4-(4-amino-3-iodo-1H-pyrazolo[3,4-d]pyrimidin-1-yl) butyl) (methyl) carbamate To a suspension of 3-iodo-1H-pyrazolo[3,4-d]pyrimidin-4-amine (0.9 g, 3.45 mmol, 1.0 equiv) in DMF (10 mL) at

404

4° C. was added NaH (137.92 mg, 3.45 mmol, 60 wt. %, 1.0 equiv). The mixture was stirred at 4° C. for 30 min and then a solution of tert-butyl (4-bromobutyl)(methyl)carbamate (1.01 g, 3.79 mmol, 25.92 mL, 1.1 equiv) in DMF (3 mL) was added. The mixture was stirred at room temperature for 3 h, at which point H$_2$O (100 mL) was added. The aqueous phase was extracted with EtOAc (3×30 mL) and the combined organic phases were washed with brine (20 mL), dried with anhydrous Na$_2$SO$_4$, filtered and concentrated under reduced pressure. The residue was purified by silica gel chromatography (1/0 to 0/1 petroleum ether/EtOAc) to afford tert-butyl (4-(4-amino-3-iodo-1H-pyrazolo[3,4-d]pyrimidin-1-yl)butyl) (methyl) carbamate (1.2 g, 78% yield) as a white solid. LCMS (ESI) m/z: [M+H] calcd for C$_{15}$H$_{23}$IN$_6$O$_2$: 447.10; found 447.1.

Step 4: Synthesis of tert-butyl (4-(4-amino-3-(2-aminobenzo[d]oxazol-5-yl)-1H-pyrazolo[3,4-d]pyrimidin-1-yl)butyl)(methyl)carbamate To a bi-phasic suspension of tert-butyl (4-(4-amino-3-iodo-1H-pyrazolo[3,4-d] pyrimidin-1-yl)butyl)(methyl)carbamate (1.2 g, 2.69 mmol, 1.0 equiv), 5-(4,4,5,5-tetramethyl-1,3,2-dioxaborolan-2-yl)benzo[d]oxazol-2-amine (1.19 g, 3.23 mmol, 1.2 equiv), and Na$_2$CO$_3$ (1.42 g, 13.44 mmol, 5.0 equiv) in DME (20 mL) and H$_2$O (10 mL) at room temperature was added Pd(PPh$_3$)$_4$ (310.71 mg, 268.89 μmol, 0.1 equiv) under N$_2$. The mixture was stirred at 110° C. for 3 h and then the reaction mixture was cooled and partitioned between EtOAc (20 mL) and H$_2$O (15 mL). The aqueous layer was separated and extracted with EtOAc (3×20 mL). The combined organic layers were washed with brine (2×20 mL), dried over anhydrous Na$_2$SO$_4$, filtered and concentrated under reduced pressure. The crude product was purified by silica gel chromatography (1/0 to 4/1 EtOAc/MeOH) to give tert-butyl (4-(4-amino-3-(2-aminobenzo[d]oxazol-5-yl)-1H-pyrazolo [3,4-d]pyrimidin-1-yl)butyl)(methyl) carbamate (0.78 g, 62.5% yield) as an orange solid.

Step 5: Synthesis of 5-(4-amino-1-(4-(methylamino) butyl)-1H-pyrazolo[3,4-d] pyrimidin-3-yl) benzo[d] oxazol-2-amine A solution of tert-butyl(4-(4-amino-3-(2-aminobenzo[d]oxazol-5-yl)-1H-pyrazolo[3,4-d]pyrimidin-1-yl)butyl) (methyl)carbamate (0.78 g, 1.72 mmol, 1.0 equiv) in TFA (5 mL) at room temperature was stirred for 30 min. The solution was concentrated under reduced pressure and the oily residue was triturated with MeCN (1 mL) and then added to MTBE (100 mL). The supernatant was removed and then the precipitate was collected by filtration under N$_2$ to give 5-(4-amino-1-(4-(methylamino) butyl)-1H-pyrazolo [3,4-d]pyrimidin-3-yl)benzo[d]oxazol-2-amine bis-trifluorosulfonate (0.959 g, 93% yield) as an orange solid. LCMS (ESI) m/z: [M+H] calcd for C$_{17}$H$_{20}$N$_8$O: 353.18; found 353.1.

Monomer V. 1-(4-(4-(5-(aminomethyl)pyrimidin-2-yDpiperazin-1-yl)-3-(trifluoromethyDphenyD-8-(6-methoxypyridin-3-yl)-3-methyl-1,3-dihydro-211-imidazo[4,5-c]quinolin-2-one

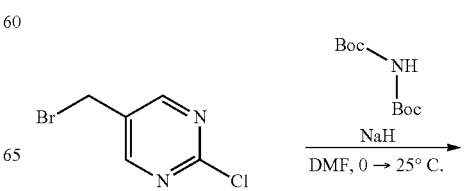

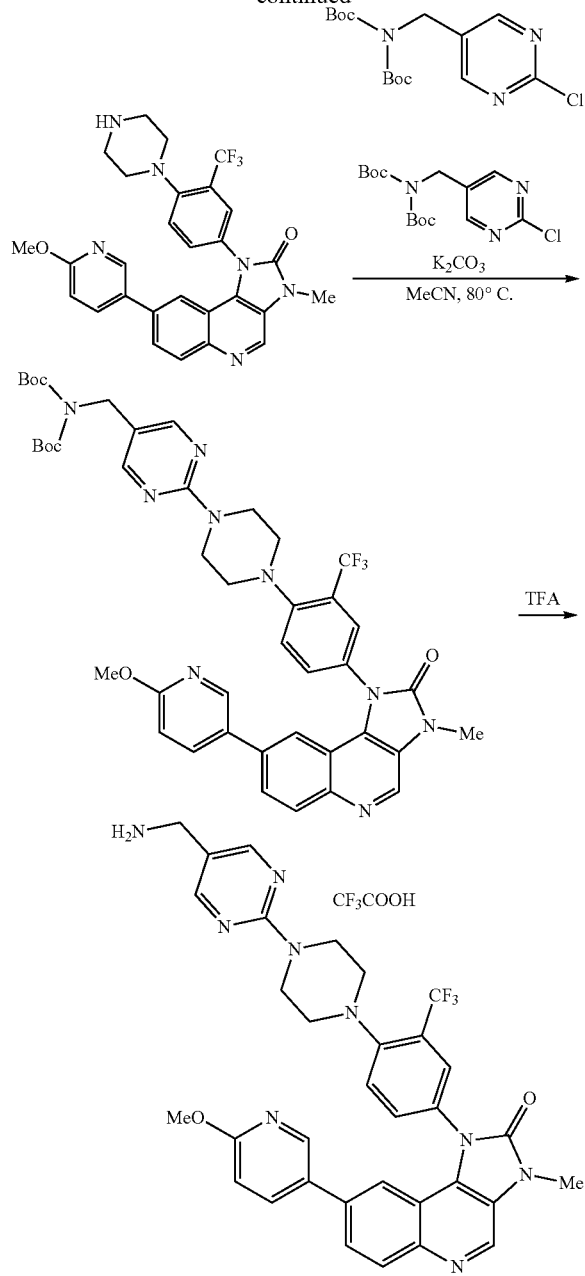

chromatography (20:1 to 1:1 petroleum ether/EtOAc) to afford tert-butyl N-tert-butoxycarbonyl-N-[(2-chloro pyrimidin-5-yl)methyl]carbamate (7.0 g, 60.3% yield) as a white solid. LCMS (ESI) m/z: [M+H] calcd for $C_{15}H_{22}ClN_3O_4$: 344.14; found 344.2.

Step 2: Synthesis of tert-butyl N-tert-butoxycarbonyl-N-[[2-[4-[4-[8-(6-methoxy-3-pyridyl)-3-methyl-2-oxo-imidazo[4,5-c]quinolin-1-yl]-2-(trifluoromethyl)phenyl]piperazin-1-yl]pyrimidin-5-yl]methyl] carbamate To a solution of 8-(6-methoxy-3-pyridyl)-3-methyl-1-[4-piperazin-1-yl-3-(trifluoromethyl)phenyl]imidazo[4,5-c]quinolin-2-one (0.4 g, 748.32 µmol, 1.0 equiv) in MeCN (7 mL) was added tert-butyl N-tert-butoxycarbonyl-N-[(2-chloropyrimidin-5-yl)methyl]carbamate (514.55 mg, 1.50 mmol, 2.0 equiv) and $K_2CO_3$ (413.69 mg, 2.99 mmol, 4 equiv) at room temperature. The reaction mixture was stirred at 80° C. for 14 h and then the mixture was cooled to room temperature, filtered and concentrated under reduced pressure. The residue was purified by washing with MTBE (5 mL) to give tert-butyl N-tert-butoxycarbonyl-N-[[2-[4-[4-[8-(6-methoxy-3-pyridyl)-3-methyl-2-oxo-imidazo[4,5-c]quinolin-1-yl]-2-(trifluoromethyl)phenyl]piperazin-1-yl]pyrimidin-5-yl]methyl]carbamate (0.57 g, 90.5% yield) as a light yellow solid. LCMS (ESI) m/z: [M+H] calcd for $C_{43}H_{46}F_3N_9O_6$: 842.36; found 842.7.

Step 3: Synthesis of 1-[4-[4-[5-(aminomethyl)pyrimidin-2-yl]piperazin-1-yl]-3-(trifluoromethyl) phenyl]-8-(6-methoxy-3-pyridyl)-3-methyl-imidazo[4,5-c]quinolin-2-one A solution of tert-butyl N-tert-butoxycarbonyl-N-[[2-[4-[4-[8-(6-methoxy-3-pyridyl)-3-methyl-2-oxo-imidazo[4,5-c]quinolin-1-yl]-2-(trifluoromethyl)phenyl]piperazin-1-yl]pyrimidin-5-yl]methyl]carbamate (0.95 g, 1.13 mmol, 1 equiv) in TFA (10 mL) was stirred at room temperature for 1 h, at which point the solvent was concentrated under reduced pressure. The residue was dissolved in MeCN (10 mL) and then the solution was added to MTBE (150 mL), dropwise. The precipitate was collected to give 1-[4-[4-[5-(aminomethyl)pyrimidin-2-yl]piperazin-1-yl]-3-(trifluoromethyl)phenyl]-8-(6-methoxy-3-pyridyl)-3-methyl-imidazo[4,5-c]quinolin-2-one trifluoromethanesulfonate (0.778 g, 84.8% yield) as a yellow solid. LCMS (ESI) m/z: [M+H] calcd for C33H30F3N9O2: 642.26; found 642.4.

Monomer W. 1-(4-aminobutyl)-3-(1H-pyrrolo[2,3-b]pyridin-5-yl)pyrazolo[3,4-d]pyrimidin-4-amine Step 1: Synthesis of tert-butyl N-tert-butoxycarbonyl-N-[(2-chloropyrimidin-5-yl)methyl] carbamate To a solution of tert-butyl N-tert-butoxycarbonylcarbamate (7.33 g, 33.74 mmol, 1.0 equiv) in DMF (80 mL) was added NaH (1.62 g, 40.49 mmol, 60 wt. %, 1.2 equiv) at 0° C. The mixture was stirred at 0° C. for 30 min and then 5-(bromomethyl)-2-chloropyrimidine (7 g, 33.74 mmol, 1 equiv) was added. The reaction mixture was stirred at room temperature for 1.5 h and then the mixture was poured into sat. $NH_4Cl$ (300 mL) and stirred for 5 min. The aqueous phase was extracted with EtOAc (3×80 mL) and the combined organic phases were washed with brine (50 mL), dried over anhydrous $Na_2SO_4$, filtered and concentrated under reduced pressure. The residue was purified by silica gel

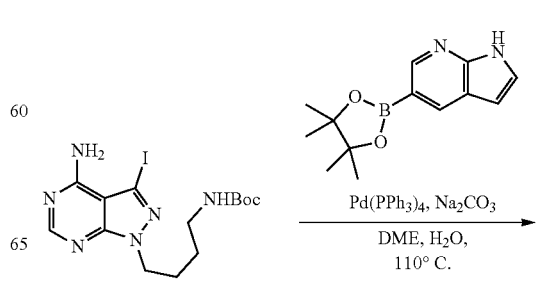

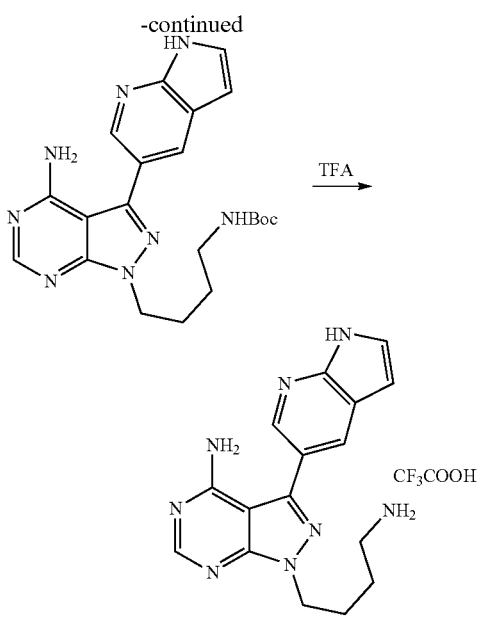

Step 1: Synthesis of tert-butyl N-[4-[4-amino-3-(1H-indol-5-yl)pyrazolo[3,4-d]pyrimidin-1-yl]butyl] carbamate To a bi-phasic suspension of tert-butyl N-[4-(4-amino-3-iodo-pyrazolo[3,4-d]pyrimidin-1-yl)butyl]carbamate (8 g, 18.51 mmol, 1 equiv), 5-(4,4,5,5-tetramethyl-1,3,2-dioxaborolan-2-yl)-1H-pyrrolo[2,3-b]pyridine (5.42 g, 22.21 mmol, 1.2 equiv) and $Na_2CO_3$ (9.81 g, 92.54 mmol, 5 equiv) in diglyme (160 mL) and $H_2O$ (80 mL) was added $Pd(PPh_3)_4$ (2.14 g, 1.85 mmol, 0.1 equiv) at room temperature under $N_2$. The mixture was stirred at 110° C. for 3 h. The reaction mixture was cooled to room temperature, filtered and the filtrate was partitioned between EtOAc (500 mL) and $H_2O$ (500 mL). The aqueous layer was separated and extracted with EtOAc (3×300 mL). The organic layers were combined, washed with brine (20 mL) and dried over anhydrous $Na_2SO_4$, then filtered and the filtrate was concentrated under reduced pressure. The residue was purified by silica gel chromatography (1/0 to 0/1 petroleum ether/EtOAc then 4/1 EtOAc/MeOH) to give tert-butyl N-[4-[4-amino-3-(1H-indol-5-yl)pyrazolo[3,4-d]pyrimidin-1-yl]butyl]carbamate (6.6 g, 84.6% yield) as a yellow solid. LCMS (ESI) m/z: [M+H] calcd for $C_{22}H_{27}N_7O_2$: 422.22; found 423.3.

Step 2: Synthesis of 1-(4-aminobutyl)-3-(1H-pyrrolo[2,3-b]pyridin-5-yl)pyrazolo[3,4-d]pyrimidin-4-amine To tert-butyl N-[4-[4-amino-3-(1H-indol-5-yl)pyrazolo[3,4-d]pyrimidin-1-yl]butyl]carbamate (6.6 g, 15.66 mmol, 1 equiv) was added TFA (66 mL), which was then stirred at room temperature for 30 min. The reaction solution was concentrated under reduced pressure to remove TFA and then MTBE (400 mL) was added to the residue. The suspension was stirred for 15 min, at which point the yellow solid was filtered, and the solid cake dried under reduced pressure to give 1-(4-aminobutyl)-3-(1H-pyrrolo[2,3-b]pyridin-5-yl)pyrazolo[3,4-d]pyrimidin-4-amine (10.2 g, 97.1% yield) as a yellow solid. LCMS (ESI) m/z: [M+H] calcd for $C_{16}H_{18}N_8$: 323.17; found 323.1.

Monomer X. 2-(4-amino-1((1,2,3,4-tetrahydroisoquinolin-6-yl)methyl)-1H-pyrazolo[3,4-d]pyrimidin-3-yl)-1H-indol-5-ol 2,2,2-trifluoroacetate

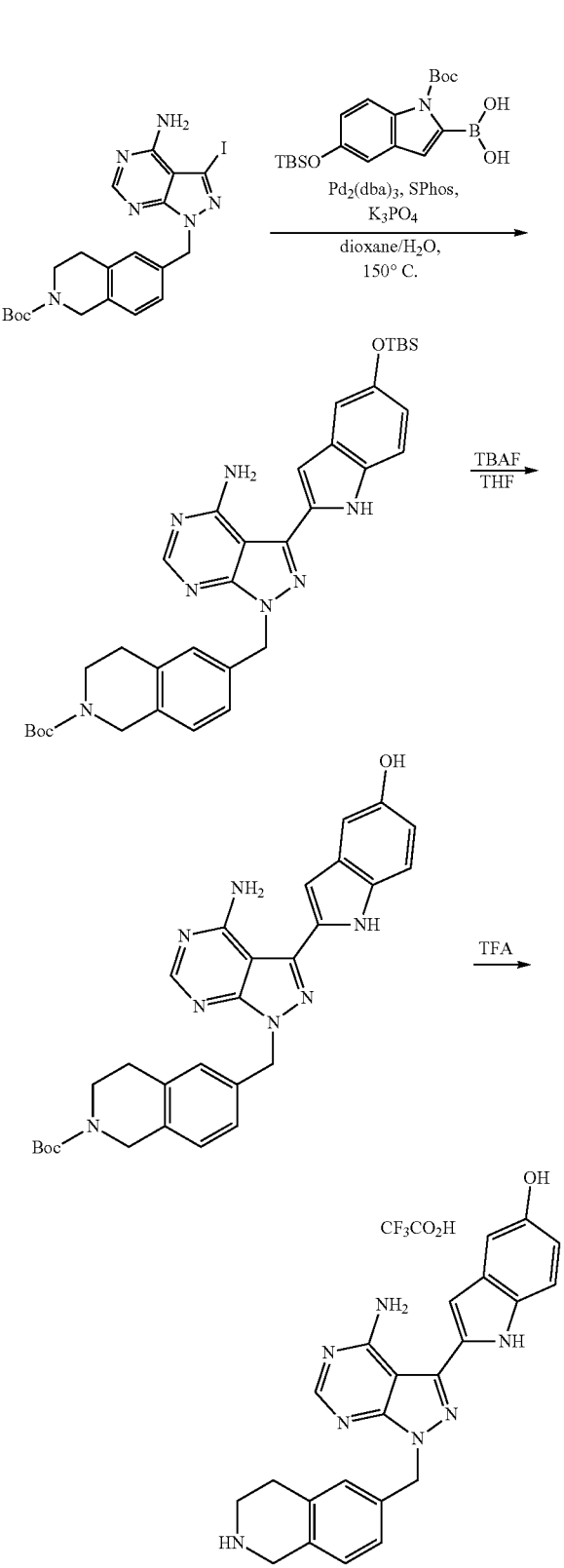

Step 1: Synthesis of tert-butyl 6-((4-amino-3-(5-((tert-butyldimethylsilyl)oxy)-1H-indol-2-yl)-1H-pyrazolo[3,4-d]pyrimidin-1-yl)methyl)-3,4-dihydroisoquinoline-2(1H)-carboxylate To a solution of tert-butyl 6-((4-amino-3-iodo-1H-pyrazolo[3,4-d]pyrimidin-1-yl)methyl)-3,4-dihydroisoquinoline-2(1H)-carboxylate (1 g, 1.97 mmol, 1.0 equiv) in dioxane (10.5 mL) and H$_2$O (3.5 mL) was added (1-(tert-butoxycarbonyl)-5-((tert-butyldimethylsilyl)oxy)-1H-indol-2-yl)boronic acid (1.16 g, 2.96 mmol, 1.5 equiv), K$_3$PO$_4$ (1.26 g, 5.92 mmol, 3.0 equiv), Pd$_2$(dba)$_3$ (180.85 mg, 197.50 µmol, 0.1 equiv), and SPhos (162.16 mg, 394.99 µmol, 0.2 equiv) at room temperature under N$_2$. The sealed tube was heated at 150° C. for 20 min under microwave. The reaction mixture was then cooled and 6 separate batches were combined together. The reaction mixture was partitioned between EtOAc (100 mL) and H$_2$O (100 mL). The aqueous layer was separated and extracted with EtOAc (3×80 mL). The organic layers were combined, washed with brine (100 mL) and dried over anhydrous Na$_2$SO$_4$. The solution was filtered and the filtrate was concentrated under reduced pressure. The crude material was purified by silica gel column chromatography (100/1 to 1/4 petroleum ether/EtOAc) to give tert-butyl 6-((4-amino-3-(5-((tert-butyldimethylsilyl)oxy)-1H-indol-2-yl)-1H-pyrazolo [3,4-d]pyrimidin-1-yl)methyl)-3,4-dihydroisoquinoline-2(1H)-carboxylate (6.17 g, 82.9% yield) as a light yellow solid.

Step 2: Synthesis of tert-butyl 6-((4-amino-3-(5-hydroxy-1H-indol-2-yl)-1H-pyrazolo[3,4-d]pyrimidin-1-yl)methyl)-3,4-dihydroisoquinoline-2(1H)-carboxylate To a mixture of tert-butyl 6-((4-amino-3-(5-((tert-butyldimethylsilyl)oxy)-1H-indol-2-yl)-1H-pyrazolo[3,4-d]pyrimidin-1-yl)methyl)-3,4-dihydroisoquinoline-2(1H)-carboxylate (6.17 g, 9.86 mmol, 1.0 equiv) in THF (100 mL) was added tetrabutylammonium fluoride trihydrate (1 M, 10.84 mL, 1.1 equiv) in one portion at 0° C. under N$_2$. The mixture was stirred at 0° C. for 1 h and was then added to H$_2$O (100 mL). The aqueous phase was extracted with EtOAc (3×80 mL) and the combined organic phase was washed with brine (2×80 mL), dried with anhydrous Na$_2$SO$_4$, filtered and concentrated under reduced pressure. The residue was purified by silica gel chromatography (1/1 to 0/1 petroleum ether/EtOAc) to afford tert-butyl 6-((4-amino-3-(5-hydroxy-1H-indol-2-yl)-1H-pyrazolo[3,4-d]pyrimidin-1-yl)methyl)-3,4-dihydroisoquinoline-2(1H)-carboxylate (4 g, 79.3% yield) as a light pink solid. LCMS (ESI) m/z: [M+H] calcd for C$_{28}$H$_{29}$N$_7$O$_3$: 512.24; found 512.3.

Step 3: Synthesis of 2-(4-amino-1-((1,2,3,4-tetrahydroisoquinolin-6-yl)methyl)-1H-pyrazolo[3,4-d]pyrimidin-3-yl)-1H-indol-5-ol 2,2,2-trifluoroacetate To a solution of tert-butyl 6-((4-amino-3-(5-hydroxy-1H-indol-2-yl)-1H-pyrazolo [3,4-d]pyrimidin-1-yl)methyl)-3,4-dihydroisoquinoline-2(1H)-carboxylate (4.5 g, 8.80 mmol, 1.0 equiv) in MeOH (50 mL) was added HCl in MeOH (4 M, 50 mL, 22.7 equiv) at room temperature. The mixture was stirred at room temperature overnight and was then concentrated under reduced pressure. To the crude product was added EtOAc (100 mL) and the resulting precipitate was collected by filtration under N$_2$ to give 2-(4-amino-1-((1,2,3,4-tetrahydroisoquinolin-6-yl)methyl)-1H-pyrazolo [3,4-d]pyrimidin-3-yl)-1H-indol-5-ol 2,2,2-trifluoroacetate (4.1 g, 85.0% yield, 3HCl) as a light yellow solid. LCMS (ESI) m/z: [M+H] calcd for C$_{23}$H$_{21}$N$_7$O: 412.19; found 412.1.

Monomer Y. 3-(1H-pyrrolo[2,3-b]pyridin-5-yl)-1((1,2,3,4-tetrahydroisoquinolin-6-yl)methyl)-1H-pyrazolo[3,4-d]pyrimidin-4-amine 2,2,2-trifluoroacetate

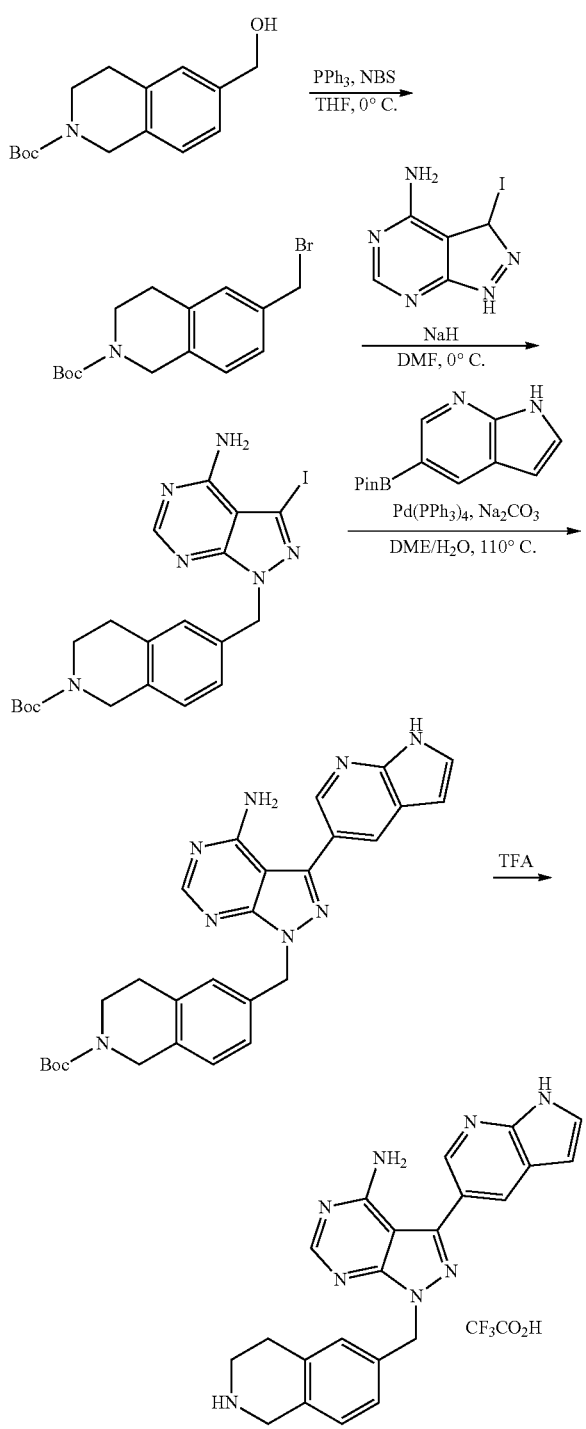

Step 1: Synthesis of tert-butyl 6-(bromomethyl)-3,4-dihydroisoquinoline-2(1H)-carboxylate A solution of NBS (34.07 g, 191.39 mmol, 4 equiv) in THF (200 mL) was added in portions to a solution of tert-butyl 6-(hydroxymethyl)-3,4-dihydroisoquinoline-2(1H)-carboxylate (12.6 g, 47.85 mmol, 1.0 equiv) and triphenylphosphine (37.65 g, 143.55 mmol, 3.0 equiv) in THF (200 mL) at 0° C. After the addition was complete, the mixture was stirred for 1 h at room temperature. EtOAc (150 mL) was added and the mixture was washed with $H_2O$ (200 mL) and brine (150 mL), dried over anhydrous $Na_2SO_4$ and concentrated under reduced pressure. The residue was purified by silica gel chromatography (100/1 to 10/1 petroleum ether/EtOAc) to afford tert-butyl 6-(bromomethyl)-3,4-dihydroisoquinoline-2(1H)-carboxylate (8.56 g, 54.8% yield) as a light yellow solid.

Step 2: Synthesis of tert-butyl 6-((4-amino-3-iodo-1H-pyrazolo[3,4-d]pyrimidin-1-yl) methyl)-3,4-dihydroisoquinoline-2(1H)-carboxylate To a suspension of 3-iodo-1H-pyrazolo[3,4-d]pyrimidin-4-amine (9.5 g, 36.40 mmol, 1.0 equiv) in DMF (110 mL) was added NaH (1.46 g, 36.40 mmol, 60 wt. %, 1.0 equiv) at 0° C. The mixture was stirred at 0° C. for 30 min at which point a solution of tert-butyl 6-(bromomethyl)-3,4-dihydroisoquinoline-2(1H)-carboxylate (12.47 g, 38.22 mmol, 1.05 equiv) in DMF (40 mL) was added at 0° C. The mixture was stirred at room temperature for 1 h and then $H_2O$ (1000 mL) was added at 0° C. The mixture stirred at 0° C. for 30 min and then the resulting precipitate was collected by filtration to give tert-butyl 6-((4-amino-3-iodo-1H-pyrazolo[3,4-d] pyrimidin-1-yl)methyl)-3,4-dihydroisoquinoline-2(1H)-carboxylate (17.8 g, 76.3% yield) as a light yellow solid, which was used the next step directly. LCMS (ESI) m/z: [M+H] calcd for $C_{20}H_{23}IN_6O_2$: 507.10; found 507.1.

Step 3: Synthesis of tert-butyl 6-((4-amino-3-(1H-pyrrolo[2,3-b]pyridin-5-yl)-1H-pyrazolo[3,4-d]pyrimidin-1-yl)methyl)-3,4-dihydroisoquinoline-2(1H)-carboxylate To a bi-phasic suspension of tert-butyl 6-((4-amino-3-iodo-1H-pyrazolo [3,4-d] pyrimidin-1-yl)methyl)-3,4-dihydroisoquinoline-2(1H)-carboxylate (6.5 g, 10.14 mmol, 1.0 equiv), 5-(4,4,5,5-tetramethyl-1,3,2-dioxaborolan-2-yl)-1H-pyrrolo[2,3-b] pyridine (2.97 g, 12.16 mmol, 1.2 equiv), and $Na_2CO_3$ (5.37 g, 50.68 mmol, 5.0 equiv) in diglyme (100 mL) and $H_2O$ (50 mL) was added $Pd(PPh_3)_4$ (1.17 g, 1.01 mmol, 0.1 equiv) at room temperature under $N_2$. The mixture was stirred at 110° C. for 3 h. The reaction mixture was then cooled and partitioned between EtOAc (100 mL) and $H_2O$ (100 mL). The aqueous layer was separated and extracted with EtOAc (2×100 mL). The combined organic phase was washed with brine (100 mL), dried with anhydrous $Na_2SO_4$, filtered and concentrated under reduced pressure. The residue was purified by silica gel chromatography (0/1 to 1/4 MeOH/EtOAc) to afford tert-butyl 6-((4-amino-3-(1H-pyrrolo[2,3-b]pyridin-5-yl)-1H-pyrazolo[3,4-d]pyrimid in-1-yl) methyl)-3,4-dihydroisoquinoline-2(1H)-carboxylate (3.77 g, 72.1% yield) as a light yellow solid. LCMS (ESI) m/z: [M+H] calcd for $C_{27}H_{28}N_8O_2$: 497.24; found 497.3.

Step 4: Synthesis of 3-(1H-pyrrolo[2,3-b]pyridin-5-yl)-1-((1,2,3,4-tetrahydroiso quinolin-6-yl)methyl)-1H-pyrazolo[3,4-d]pyrimidin-4-amine 2,2,2-trifluoroacetate tert-Butyl 6-((4-amino-3-(1H-pyrrolo[2,3-b]pyridin-5-yl)-1H-pyrazolo[3,4-d] pyrimidin-1-yl)methyl)-3,4-dihydroisoquinoline-2(1H)-carboxylate (3.77 g, 7.59 mmol, 1.0 equiv) was added to TFA (85.36 mL, 1.15 mol, 151.8 equiv) at room temperature. The reaction mixture was stirred for 1 h. It was then concentrated under reduced pressure and the oily residue was triturated with MeCN (3 mL), then dripped into MTBE (200 mL) for 5 min. The supernatant was removed and then the precipitate was collected by filtration under $N_2$ to give the product, which was dissolved in MeCN (20 mL), and finally concentrated under reduced pressure to give 3-(1H-pyrrolo[2,3-b]pyridin-5-yl)-1-((1,2,3,4-tetrahydroisoquinolin-6-yl)methyl)-1H-pyrazolo[3,4-d]pyrimidin-4-amine 2,2,2-trifluoroacetate (4.84 g, 85.0% yield, 3TFA) as a light yellow solid. LCMS (ESI) m/z: [M+H] calcd for $C_{22}H_{20}N_8$: 397.19; found 397.2.

Monomer Z. (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate

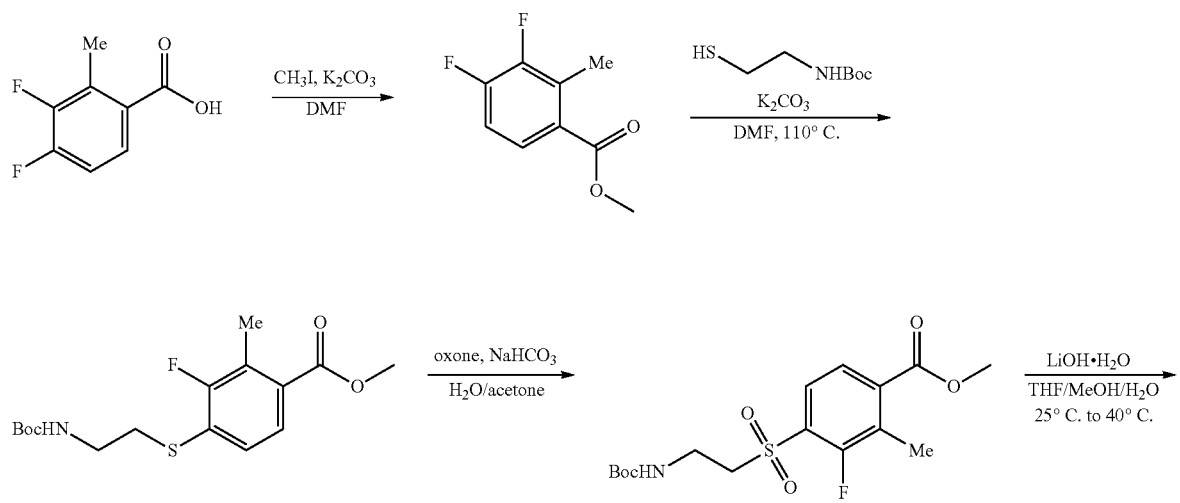

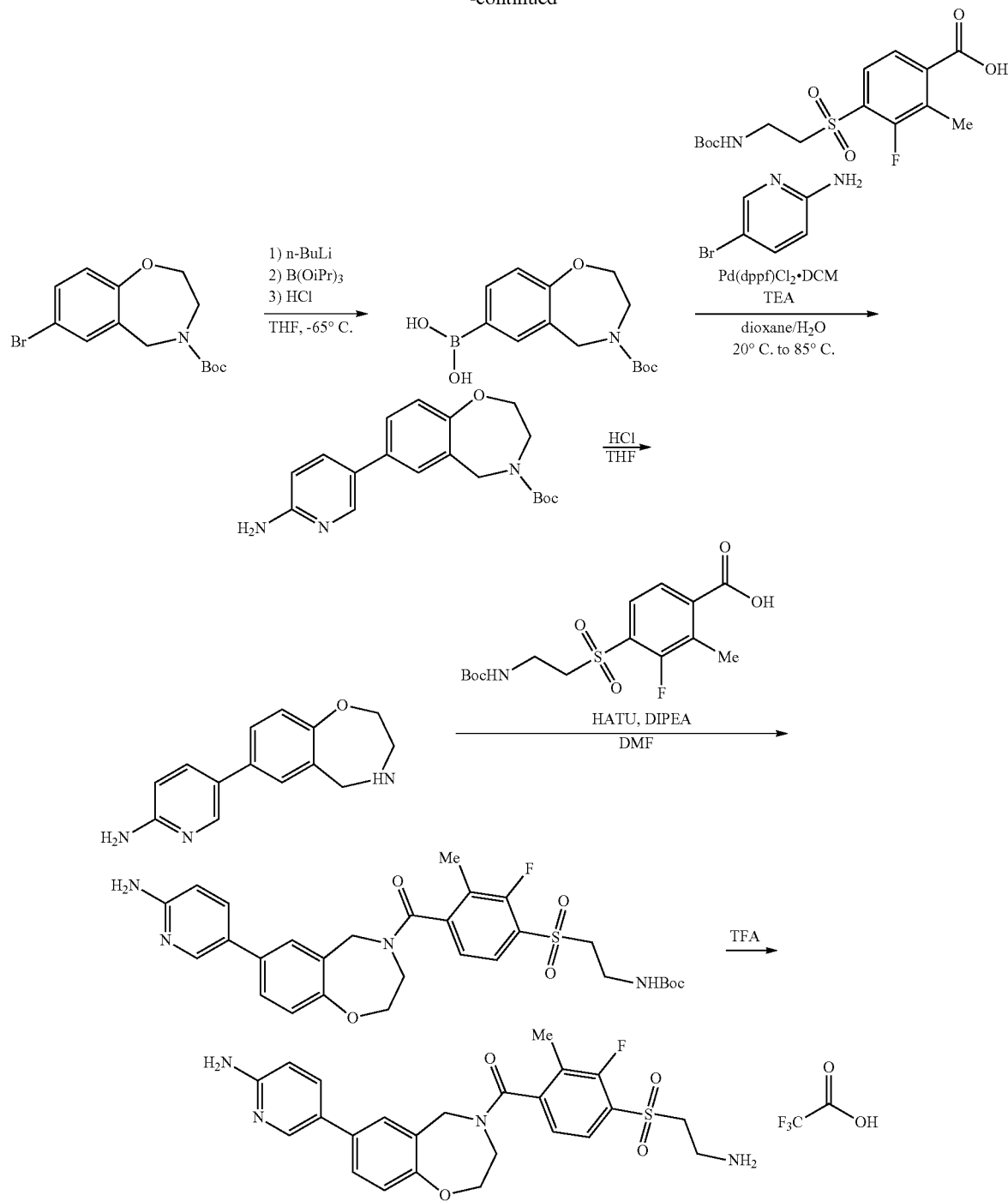

Step 1: Synthesis of methyl 3,4-difluoro-2-methylbenzoate

To a solution of 3,4-difluoro-2-methylbenzoic acid (2 g, 11.62 mmol, 1.0 equiv) in DMF (20 mL) was added K₂CO₃ (4.82 g, 34.86 mmol, 3.0 equiv) and iodomethane (3.26 mL, 52.29 mmol, 4.5 equiv) at room temperature. The mixture was stirred at room temperature for 3 h. The solution of methyl 3,4-difluoro-2-methylbenzoate in DMF (20 mL) was used directly in the next step.

Step 2: Synthesis of methyl 4-((2-((tert-butoxycarbonyl)amino)ethyl)thio)-3-fluoro-2-methylbenzoate To a solution of methyl 3,4-difluoro-2-methylbenzoate (2.16 g, 11.28 mmol, 1.0 equiv) in DMF (20 mL) was added tert-butyl (2-mercaptoethyl)carbamate (2.0 g, 11.28 mmol, 1 equiv) and K₂CO₃ (3.12 g, 22.56 mmol, 2.0 equiv) at room temperature. The reaction was stirred at 110° C. for 12 h, at which point the mixture was added to H₂O (50 mL). The aqueous solution was then extracted with EtOAc (3×30 mL) and the organic phase was combined and concentrated under reduced pressure. The residue was purified by silica gel chromatography (1/0 to 3/1 petroleum ether/EtOAc) to afford methyl 4-((2-((tert-butoxycarbonyl)amino)ethyl)thio)-3-fluoro-2-methylbenzoate (3 g, 76.0% yield) as light yellow solid.

Step 3: Synthesis of methyl 4-((2-((tert-butoxycarbonyl)amino)ethyl)sulfonyl)-3-fluoro-2-methylbenzoate To a solution of methyl 4-((2-((tert-butoxycarbonyl)amino)ethyl)thio)-3-fluoro-2-methylbenzoate (3.3 g, 9.61 mmol, 1.0 equiv), NaOH (2 M, 4.80 mL, 1.0 equiv), and NaHCO$_3$ (2.42 g, 28.83 mmol, 3.0 equiv) in acetone (30 mL) was added potassium peroxymonosulfate (12.35 g, 20.08 mmol, 2.1 equiv). The mixture was stirred for 12 that room temperature and then the mixture was acidified to pH 5 by addition of 1N HCl. The aqueous layer was extracted with EtOAc (3×30 mL) and the combined organic phase was washed with brine (20 mL), dried with anhydrous Na$_2$SO$_4$, filtered and concentrated under reduced pressure. The residue was purified by silica gel chromatography (1/0 to 3/1 petroleum ether/EtOAc) to afford methyl 4-((2-((tert-butoxycarbonyl)amino)ethyl)sulfonyl)-3-fluoro-2-methylbenzoate (2.1 g, 58.2% yield) as a yellow solid. LCMS (ESI) m/z: [M-56+H] calcd for C$_{16}$H$_{22}$FNO$_6$S: 320.12; found 320.1.

Step 4: Synthesis of 4-((2-((tert-butoxycarbonyl)amino)ethyl)sulfonyl)-3-fluoro-2-methylbenzoic acid To a solution of methyl 4-((2-((tert-butoxycarbonyl)amino)ethyl)sulfonyl)-3-fluoro-2-methylbenzoate (2.1 g, 5.59 mmol, 1.0 equiv) in THF (20 mL), MeOH (10 mL) and H$_2$O (10 mL) was added LiOH.H$_2$O (704.16 mg, 16.78 mmol, 3.0 equiv) at room temperature. The reaction mixture was stirred at 40° C. for 4 h. The mixture was then concentrated under reduced pressure to remove THF and MeOH. The aqueous phase was neutralized with 0.5N HCl and was then extracted with EtOAc (5×20 mL). The combined organic phase was washed with brine (2×20 mL), dried with anhydrous Na$_2$SO$_4$, filtered and concentrated under reduced pressure to give 4-((2-((tert-butoxycarbonyl)amino)ethyl)sulfonyl)-3-fluoro-2-methylbenzoic acid (2.01 g, 97.1% yield) as a white solid. LCMS (ESI) m/z: [M-100+H] calcd for C$_{15}$H$_{20}$FNO$_6$S: 262.11; found 262.1.

Step 5: Synthesis of (4-(tert-butoxycarbonyl)-2,3,4,5-tetrahydrobenzo[f][1,4] oxazepin-7-yl)boronic acid To a solution of tert-butyl 7-bromo-2,3-dihydrobenzo[f][1,4]oxazepine-4(5H)-carboxylate (4 g, 12.19 mmol, 1.0 equiv) in THF (80 mL) at −60° C. was added B(OiPr)$_3$ (4.58 g, 24.38 mmol, 5.60 mL, 2.0 equiv) followed by dropwise addition of n-BuLi (2.5 M, 12.19 mL, 2.5 equiv) in n-hexane. The reaction was stirred at −65° C. for 1 h. The reaction mixture was quenched with 1N HCl (12.25 mL) and allowed to warm to room temperature. The reaction mixture was extracted with EtOAc (3×30 mL), dried over anhydrous Na$_2$SO$_4$, filtered and concentrated under reduced pressure to give (4-(tert-butoxycarbonyl)-2,3,4,5-tetrahydrobenzo[f][1,4]oxazepin-7-yl)boronic acid (3.5 g, crude) as light yellow oil, which was used to the next step directly. LCMS (ESI) m/z: [M-100+H] calcd for C$_{14}$H$_{20}$BNO$_5$: 194.15; found 194.2.

Step 6: Synthesis of tert-butyl 7-(6-aminopyridin-3-yl)-2,3-dihydrobenzo[f][1,4] oxazepine-4(5H)-carboxylate To a solution of (4-(tert-butoxycarbonyl)-2,3,4,5-tetrahydrobenzo[f][1,4]oxazepin-7-yl)boronic acid (4.2 g, 14.33 mmol, 1.0 equiv) in H$_2$O (20 mL) and dioxane (60 mL) was added 5-bromopyridin-2-amine (2.48 g, 14.33 mmol, 1.0 equiv), Pd(dppf)Cl$_2$.DCM (1.17 g, 1.43 mmol, 0.1 equiv) and Et$_3$N (4.35 g, 42.99 mmol, 5.98 mL, 3.0 equiv) at room temperature. The mixture was stirred at 85° C. for 12 h. The mixture was then cooled to room temperature and the residue was poured into H$_2$O (15 mL). The aqueous phase was extracted with EtOAc (3×40 mL) and the combined organic phase was washed with brine (2×40 mL), dried with anhydrous Na$_2$SO$_4$, filtered and concentrated under reduced pressure. The residue was purified by silica gel chromatography (1/0 to 1/8 petroleum ether/EtOAc) to afford tert-butyl 7-(6-aminopyridin-3-yl)-2,3-dihydrobenzo[f][1,4] oxazepine-4(5H)-carboxylate (3.3 g, 65.0% yield) as light yellow solid. LCMS (ESI) m/z: [M+H] calcd for C$_{19}$H$_{23}$N$_3$O$_3$: 342.18; found 342.2.

Step 7: Synthesis of 5-(2,3,4,5-tetrahydrobenzo[f][1,4]oxazepin-7-yl)pyridin-2-amine To a solution of tert-butyl 7-(6-aminopyridin-3-yl)-2,3-dihydrobenzo[f][1,4] oxazepine-4(5H)-carboxylate (3.3 g, 9.67 mmol, 1.0 equiv) in THF (40 mL) was added HCl in EtOAc (4 M, 100 mL, 41.38 equiv) at room temperature. The mixture was stirred for 3 h. The reaction mixture was filtered and the filter cake was washed with EtOAc (3×15 mL) and then dried under reduced pressure to give 5-(2,3,4,5-tetrahydrobenzo [f][1,4]oxazepin-7-yl)pyridin-2-amine (3 g, 95.1% yield, 2HCl) as a light yellow solid.

Step 8: Synthesis of tert-butyl (2-((4-(7-(6-aminopyridin-3-yl)-2,3,4,5-tetrahydrobenzo[f][1,4] oxazepine-4-carbonyl)-2-fluoro-3-methylphenyl)sulfonyl)ethyl)carbamate To a solution of 4-((2-((tert-butoxycarbonyl)amino)ethyl)sulfonyl)-3-fluoro-2-methylbenzoic acid (690.08 mg, 1.91 mmol, 1.0 equiv) in DMF (10 mL) was added HATU (1.09 g, 2.86 mmol, 1.5 equiv) and DIPEA (1.66 mL, 9.55 mmol, 5 equiv). The reaction was stirred at room temperature for 30 min and then 5-(2,3,4,5-tetrahydrobenzo[f][1,4]oxazepin-7-yl)pyridin-2-amine (0.6 g, 1.91 mmol, 1.0 equiv, 2HCl) was added. The mixture was stirred for 2 h, at which point H$_2$O (40 mL) was added. The mixture was stirred for 5 min and the resulting precipitate was collected by filtration to give the crude product. The residue was purified by silica gel chromatography (1/0 to 10/1 EtOAc/MeOH) to afford tert-butyl (2-((4-(7-(6-aminopyridin-3-yl)-2,3,4,5-tetrahydrobenzo[f][1,4] oxazepine-4-carbonyl)-2-fluoro-3-methylphenyl)sulfonyl)ethyl)carbamate (0.538 g, 47.4% yield) as a light yellow solid. LCMS (ESI) m/z: [M+H] calcd for C$_{29}$H$_{33}$FN$_4$O$_6$S: 585.22; found 585.3.

Step 9: Synthesis of (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate A solution tert-butyl (2-((4-(7-(6-aminopyridin-3-yl)-2,3,4,5-tetrahydrobenzo[f][1,4] oxazepine-4-carbonyl)-2-fluoro-3-methylphenyl)sulfonyl)ethyl)carbamate (0.538 g, 920.20 1.0 equiv) in TFA (10.35 mL, 139.74 mmol, 151.85 equiv) was stirred at room temperature for 2 h. The solution was then concentrated under reduced pressure. The oily residue was triturated with MeCN (1 mL) and then dripped into MTBE (30 mL) for 10 min. The supernatant was removed and then the precipitate was collected by filtration under $N_2$ to give (4-((2-aminoethyl)sulfonyl)-3-fluoro-2-methylphenyl)(7-(6-aminopyridin-3-yl)-2,3-dihydrobenzo[f][1,4]oxazepin-4(5H)-yl)methanone 2,2,2-trifluoroacetate (0.50 g, 87.4% yield) as a light brown solid. LCMS (ESI) m/z: [M+H] calcd for $C_{24}H_{25}FN_4O_4S$: 485.17; found 485.1.

Monomer AA. 5-(4-amino-1-(6-(piperazin-1-yl)pyrimidin-4-yl)-1H-pyrazolo[3,4-d]pyrimidin-3-yl)benzo[d]oxazol-2-amine trifluoroacetic acid salt

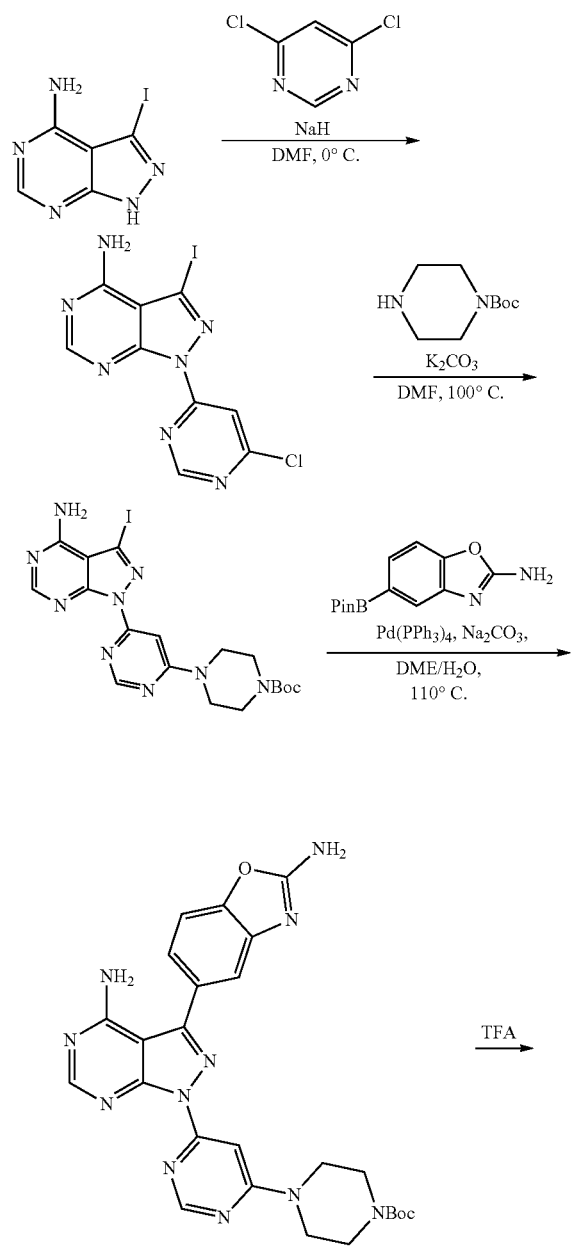

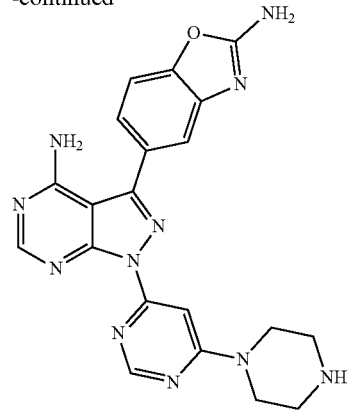

Step 1: Synthesis of 1-(6-chloropyrimidin-4-yl)-3-iodo-1H-pyrazolo[3,4-d]pyrimidin-4-amine To a suspension of 3-iodo-1H-pyrazolo[3,4-d]pyrimidin-4-amine (5 g, 19.16 mmol, 1.0 equiv) in DMF (60 mL) was added NaH (804.53 mg, 20.11 mmol, 60 wt. %, 1.05 equiv) at 0° C. The mixture was stirred at 0° C. for 30 min. To the reaction mixture was then added 4,6-dichloropyrimidine (3.42 g, 22.99 mmol, 1.2 equiv) at 0° C. The mixture was stirred at room temperature for 2.5 h, at which point the reaction mixture was added to $H_2O$ (600 mL). The suspension was then filtered to give the product (7.1 g, 99.2% yield) as a yellow solid. LCMS (ESI) m/z: [M+H] calcd for $C_9H_5C_{11}N_7$: 373.94; found 373.9.

Step 2: Synthesis of tert-butyl 4-(6-(4-amino-3-iodo-1H-pyrazolo[3,4-d]pyrimidin-1-yl)pyrimidin-4-yl)piperazine-1-carboxylate To a solution of 1-(6-chloropyrimidin-4-yl)-3-iodo-1H-pyrazolo[3,4-d]pyrimidin-4-amine (5 g, 13.39 mmol, 1.0 equiv) and tert-butyl piperazine-1-carboxylate (2.99 g, 16.06 mmol, 1.2 equiv) in DMF (50 mL) was added $K_2CO_3$ (3.70 g, 26.77 mmol, 2.0 equiv). The reaction mixture was stirred at 100° C. for 4 h, at which point it was added to $H_2O$ (500 mL). The suspension was then filtered to give the product (6.2 g, 88.5% yield) as a yellow solid. LCMS (ESI) m/z: [M+H] calcd for $C_{18}H_{22}IN_9O_2$: 524.09; found 524.2.

Step 3: Synthesis of tert-butyl 4-(6-(4-amino-3-(2-aminobenzo[d]oxazol-5-yl)-1H-pyrazolo[3,4-d]pyrimidin-1-yl)pyrimidin-4-yl)piperazine-1-carboxylate To a bi-phasic suspension of 5-(4,4,5,5-tetramethyl-1,3,2-dioxaborolan-2-yl)benzo[d]oxazol-2-amine (3.08 g, 11.85 mmol, 1.0 equiv), tert-butyl 4-(6-(4-amino-3-iodo-1H-pyrazolo[3,4-d]pyrimidin-1-yl)pyrimidin-4-yl)piperazine-1-carboxylate (6.2 g, 11.85 mmol, 1.0 equiv) and $Na_2CO_3$ (6.28 g, 59.24 mmol, 5.0 equiv) in $H_2O$ (100 mL) and DME (200 mL) was added $Pd(PPh_3)_4$ (1.37 g, 1.18 mmol, 0.1 equiv) at room temperature under $N_2$. The mixture was stirred at 110° C. for 24 h and then the mixture was filtered to give a solid cake. The solid was added to dioxane (20 mL) and stirred at 110° C. for 60 min, then filtered to give the product (3.5 g, 55.8% yield) as a brown solid. LCMS (ESI) m/z: [M+H] calcd for $C_{25}H_{27}N_{11}O_3$: 530.24; found 530.3.

Step 4: Synthesis of 5-(4-amino-1-(6-(piperazin-1-yl)pyrimidin-4-yl)-1H-pyrazolo[3,4-d]pyrimidin-3-yl)benzo[d]oxazol-2-amine trifluoroacetic acid salt A solution of tert-butyl 4-(6-(4-amino-3-(2-aminobenzo[d]oxazol-5-yl)-1H-pyrazolo[3,4-d]pyrimidin-1-yl)pyrimidin-4-yl)piperazine-1-carboxylate (3.5 g, 6.61 mmol, 1.0 equiv) in TFA (35 mL) was stirred at room temperature for 1 h. The reaction solution was concentrated under reduced pressure and the resulting crude material was dissolved in MeCN (20 mL) and added dropwise to MTBE (500 mL). The resulting solid was then filtered to give the product (5.5 g, 91.9% yield) as a brown solid. LCMS (ESI) m/z: [M+H] calcd for $C_{20}H_{19}N_{11}O$: 430.19; found 430.1.

Monomer AB. 8-(6-methoxypyridin-3-yl)-3-methyl-1-(4-(4-(5,6,7,8-tetrahydropyrido[4,3-d]pyrimidin-2-yl)piperazin-1-yl)-3-(trifluoromethyl)phenyl)-1H-imidazo[4,5-c]quinolin-2(3H)-one trifluoroacetic acid salt

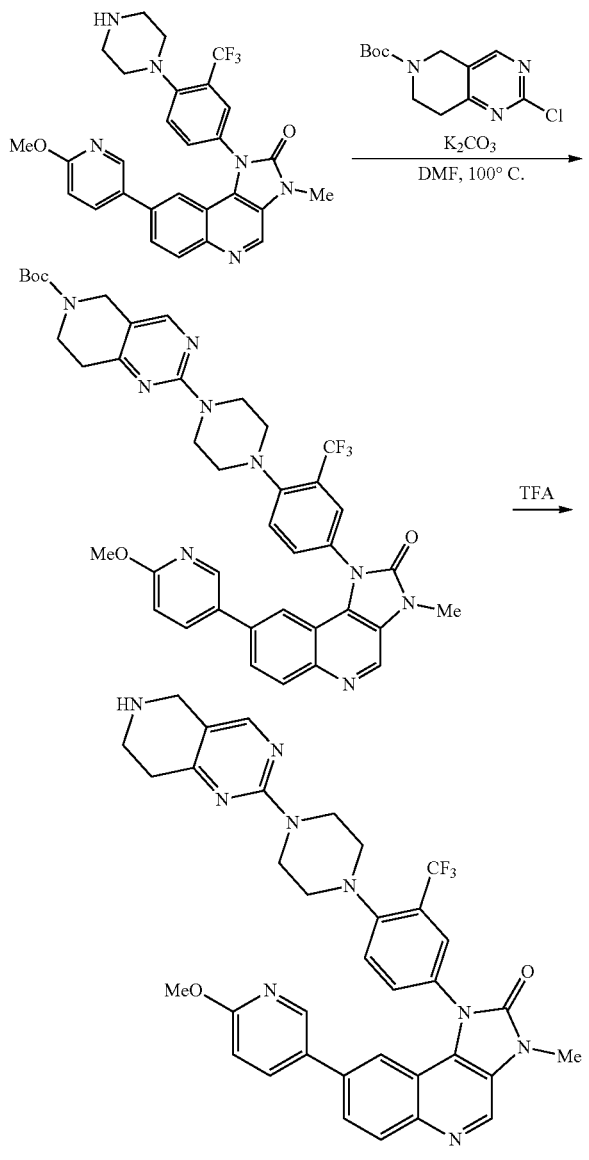

Step 1: Synthesis of tert-butyl 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)-7,8-dihydropyrido[4,3-d]pyrimidine-6(5H)-carboxylate To a mixture of 8-(6-methoxypyridin-3-yl)-3-methyl-1-(4-(piperazin-1-yl)-3-(trifluoromethyl)phenyl)-1H-imidazo[4,5-c]quinolin-2(3H)-one (0.3 g, 561.24 µmol, 1.0 equiv) and tert-butyl 2-chloro-7,8-dihydropyrido[4,3-d]pyrimidine-6(5H)-carboxylate (151.38 mg, 561.24 µmol, 1.0 equiv) in DMF (5 mL) was added $K_2CO_3$ (193.92 mg, 1.40 mmol, 2.5 equiv). The mixture was stirred at 100° C. for 14 h, at which point $H_2O$ (20 mL) was added. The aqueous layer was extracted with EtOAc (3×40 mL) and the combined organic layers were concentrated under reduced pressure. The crude material was purified by column chromatography (30/1 to 15/1 DCM/MeOH) to give the product (0.30 g, 69.6% yield) as a light-yellow solid. LCMS (ESI) m/z: [M+H] calcd for $C_{40}H_{40}F_3N_9O_4$: 768.33; found 768.5.

Step 2: Synthesis of 8-(6-methoxypyridin-3-yl)-3-methyl-1-(4-(4-(5,6,7,8-tetrahydropyrido[4,3-d]pyrimidin-2-yl)piperazin-1-yl)-3-(trifluoromethyl)phenyl)-1H-imidazo[4,5-c]quinolin-2(3H)-one A solution of tert-butyl 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)-7,8-dihydropyrido[4,3-d]pyrimidine-6(5H)-carboxylate (0.8 g, 1.04 mmol, 1.0 equiv) in TFA (8 mL) was stirred at room temperature for 2 h. The solvent was concentrated under reduced pressure and the residue was dissolved in MeCN (5 mL), then the solution was added dropwise to MTBE (150 mL). The precipitate was filtered and the solid was dried under reduced pressure to give the product (600 mg, 70.6% yield) as a yellow solid. LCMS (ESI) m/z: [M+H] calcd for $C_{35}H_{32}F_3N_9O_2$: 668.27; found 668.3.

Monomer AC. 5-(4-amino-1-(piperidin-4-ylmethyl)-1H-pyrazolo[3,4-d]pyrimidin-3-yl)benzo[d]oxazol-2-amine trifluoroacetic acid salt

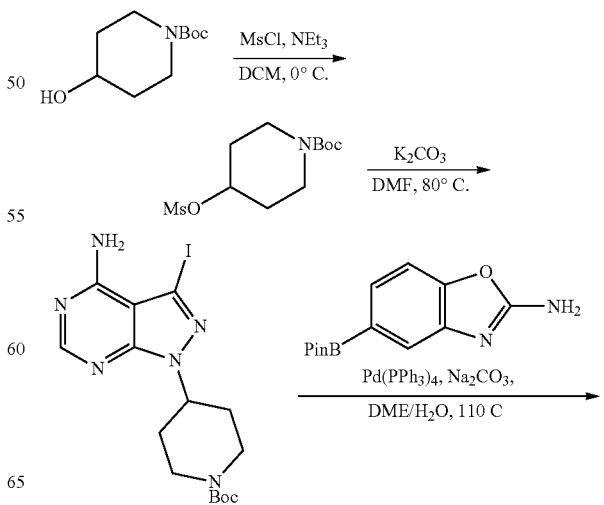

-continued

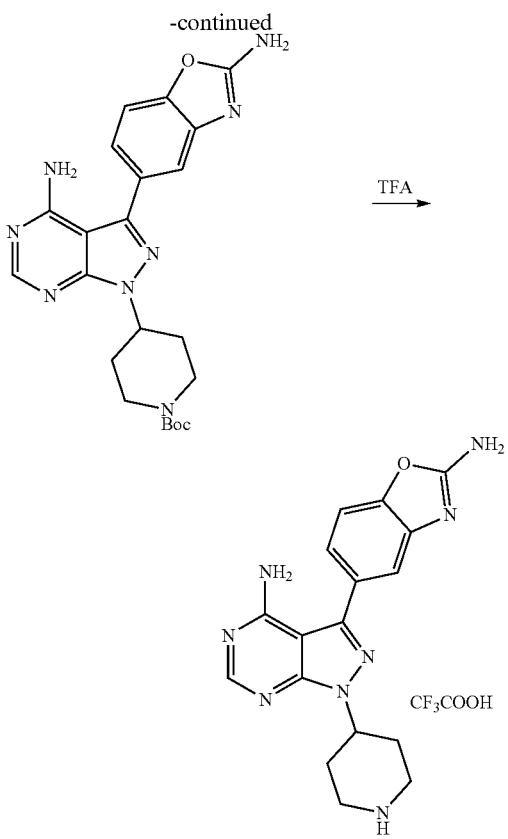

Step 1: Synthesis of tert-butyl 4-((methylsulfonyl)oxy)piperidine-1-carboxylate To a solution of tert-butyl 4-hydroxypiperidine-1-carboxylate (4 g, 19.87 mmol, 1.0 equiv) and Et$_3$N (3.87 mL, 27.82 mmol, 1.4 equiv) in DCM (40 mL) was added MsCl (2.15 mL, 27.82 mmol, 1.4 equiv) at 0° C. Then the reaction mixture was stirred at room temperature for 1 h. H$_2$O (50 mL) was added and the aqueous phase was extracted with DCM (3×50 mL). The combined organic phase was washed with brine, dried with anhydrous Na$_2$SO$_4$, filtered and concentrated under reduced pressure to give the product (5.62 g, 101% crude yield) as a yellow solid which was used directly in the next step.

Step 2: Synthesis of tert-butyl 4-(4-amino-3-iodo-1H-pyrazolo[3,4-d]pyrimidin-1-yl)piperidine-1-carboxylate To a suspension of 3-iodo-1H-pyrazolo[3,4-d]pyrimidin-4-amine (5 g, 19.16 mmol, 1.0 equiv) and tert-butyl 4-((methylsulfonyl)oxy)piperidine-1-carboxylate (5.62 g, 20.11 mmol, 1.05 equiv) in DMF (100 mL) was added K$_2$CO$_3$ (5.29 g, 38.31 mmol, 2.0 equiv). The mixture was stirred at 80° C. for 12 h. The reaction mixture was then added to H$_2$O (400 mL) at 0° C. The resulting precipitate was filtered to give the product (5.0 g, 58.8% yield) as a yellow solid. LCMS (ESI) m/z: [M+H] calcd for C$_{15}$H$_{21}$IN$_6$O$_2$: 445.09; found 445.1.

Step 3: Synthesis of tert-butyl 4-(4-amino-3-(2-aminobenzo[d]oxazol-5-yl)-1H-pyrazolo[3,4-d]pyrimidin-1-yl)piperidine-1-carboxylate To a suspension of tert-butyl 4-(4-amino-3-iodo-1H-pyrazolo[3,4-d]pyrimidin-1-yl)piperidine-1-carboxylate (5 g, 11.25 mmol, 1.0 equiv), 5-(4,4,5,5-tetramethyl-1,3,2-dioxaborolan-2-yl)benzo[d]oxazol-2-amine (3.51 g, 13.51 mmol, 1.2 equiv) and Na$_2$CO$_3$ (5.96 g, 56.27 mmol, 5.0 equiv) in H$_2$O (50 mL) and DME (100 mL) was added Pd(PPh$_3$)$_4$ (1.30 g, 1.13 mmol, 0.1 equiv) at room temperature under N$_2$. The mixture was stirred at 110° C. for 3 h. The reaction mixture was then cooled to room temperature and filtered. The filtrate was partitioned between EtOAc (100 mL) and H$_2$O (100 mL) and then the aqueous layer was separated and extracted with EtOAc (3×100 mL). The combined organic layer was washed with brine (20 mL) and dried over anhydrous Na$_2$SO$_4$, filtered, and concentrated under reduced pressure. The residue was triturated with EtOAc (30 mL) and filtered to give the product (3.6 g, 71.0% yield) as a yellow solid. LCMS (ESI) m/z: [M+H] calcd for C$_{22}$H$_{26}$N$_8$O$_3$: 451.22; found 451.3.

Step 4: Synthesis of 5-(4-amino-1-(piperidin-4-yl)-1H-pyrazolo[3,4-d]pyrimidin-3-yl)benzo[d]oxazol-2-amine trifluoroacetic acid salt A solution of tert-butyl 4-(4-amino-3-(2-aminobenzo[d]oxazol-5-yl)-1H-pyrazolo[3,4-d]pyrimidin-1-yl)piperidine-1-carboxylate (1.4 g, 3.11 mmol, 1.0 equiv) in TFA (10 mL) was stirred at room temperature for 30 min. The reaction solution was concentrated under reduced pressure and the crude solid was dissolved in MeCN (20 mL). The solution was added dropwise to MTBE (100 mL) and the resulting solid was filtered to give the product (1.6 g, 85.8% yield) as a yellow solid. LCMS (ESI) m/z: [M+H] calcd for C$_{17}$H$_{18}$N$_8$O$_3$: 351.17; found 351.1.

Monomer AD. 1-(piperidin-4-yl)-3-(1H-pyrrolo[2,3-b]pyridin-5-yl)-1H-pyrazolo[3,4-d]pyrimidin-4-amine trifluoroacetic acid salt

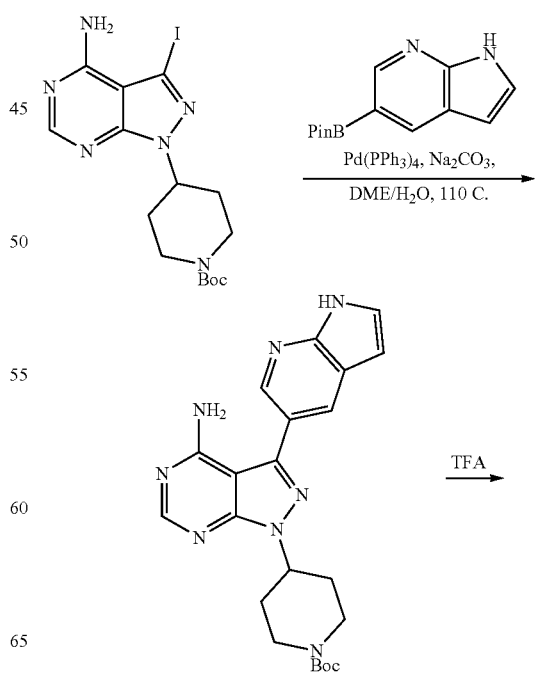

-continued

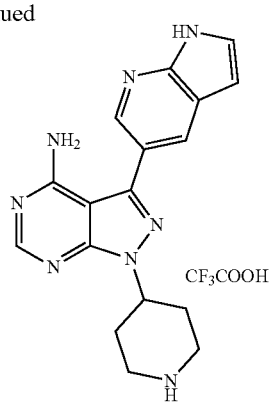

Step 1: Synthesis of tert-butyl 4-(4-amino-3-(1H-pyrrolo[2,3-b]pyridin-5-yl)-1H-pyrazolo[3,4-d]pyrimidin-1-yl)piperidine-1-carboxylate To a suspension of 5-(4,4,5-trimethyl-1,3,2-dioxaborolan-2-yl)-1H-pyrrolo[2,3-b]pyridine (857.12 mg, 3.51 mmol, 1.2 equiv), tert-butyl 4-(4-amino-3-iodo-1H-pyrazolo[3,4-d]pyrimidin-1-yl)piperidine-1-carboxylate (1.3 g, 2.93 mmol, 1.0 equiv) and $Na_2CO_3$ (1.55 g, 14.63 mmol, 5.0 equiv) in DME (20 mL) and $H_2O$ (10 mL) was added $Pd(PPh_3)_4$ (338.13 mg, 292.62 μmol, 0.1 equiv) at room temperature under $N_2$. The mixture was stirred at 110° C. for 3 h. The reaction mixture was then cooled to room temperature and filtered. The filtrate was partitioned between EtOAc (50 mL) and $H_2O$ (50 mL) and the aqueous layer was separated and extracted with EtOAc (3×50 mL). The combined organic layer were washed with brine, dried over anhydrous $Na_2SO_4$, filtered, and concentrated under reduced pressure. The residue was triturated with EtOAc (10 mL), filtered, the solid cake was dried under reduced pressure to give the product (1.0 g, 78.7% yield) as a yellow solid.

Step 2: Synthesis of 1-(piperidin-4-yl)-3-(1H-pyrrolo[2,3-b]pyridin-5-yl)-1H-pyrazolo[3,4-d]pyrimidin-4-amine trifluoroacetic acid salt A solution of tert-butyl 4-(4-amino-3-(1H-pyrrolo[2,3-b]pyridin-5-yl)-1H-pyrazolo[3,4-d]pyrimidin-1-yl)piperidine-1-carboxylate (1.5 g, 3.45 mmol, 1.0 equiv) in TFA (10 mL) was stirred at room temperature for 30 min. The reaction solution was concentrated under reduced pressure and the crude residue was dissolved in MeCN (20 mL). The solution was added dropwise to MTBE (100 mL) and the resulting solid was filtered to give the product (1.19 g, 74.2% yield) as a light yellow solid. LCMS (ESI) m/z: [M+H] calcd for $C_{17}H_{18}N_8$: 335.18; found 335.1.

Monomer AE. (4-((2-aminoethyl)sulfonyl)-2-methylphenyl)(7-(6-aminopyridin-3-yl)-2,3-dihydrobenzo[f][1,4]oxazepin-4(5H)-yl)methanone

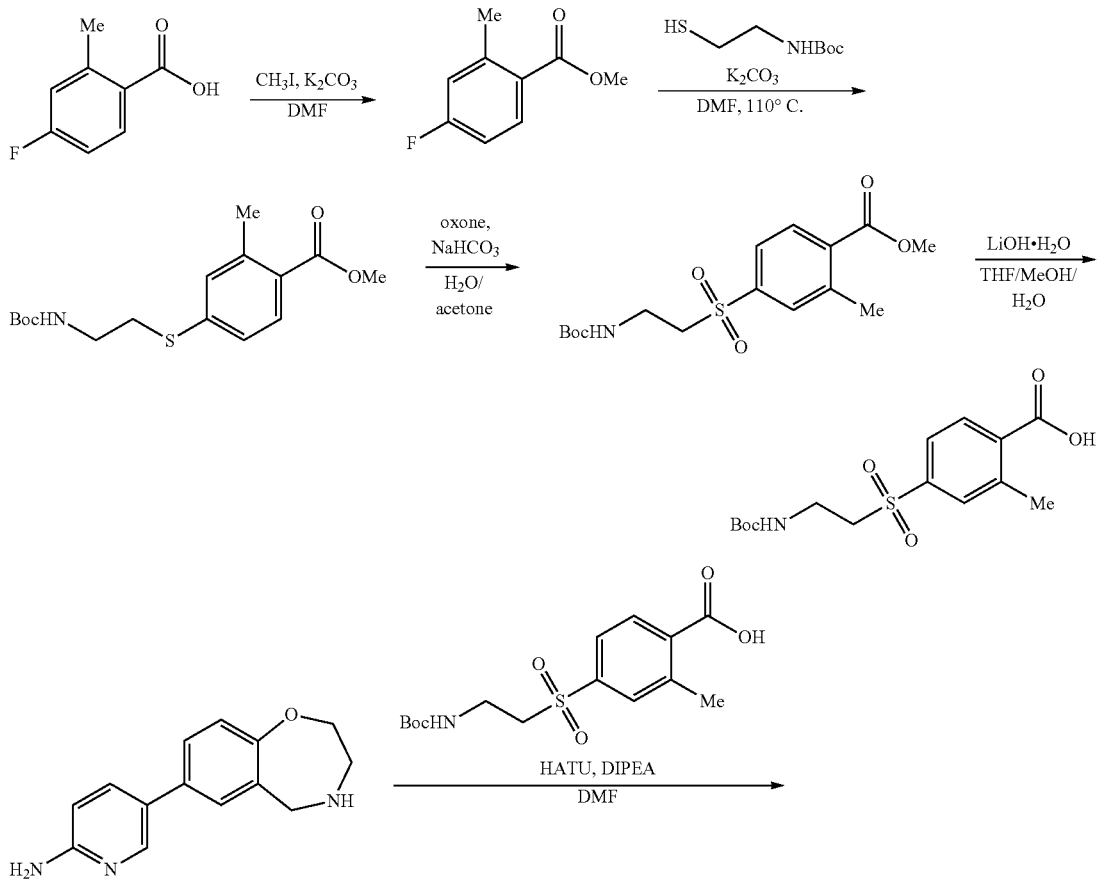

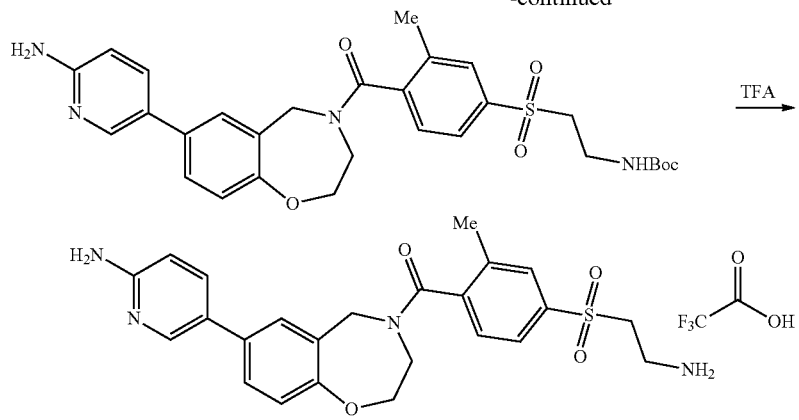

-continued

Step 1: Synthesis of methyl 4-fluoro-2-methylbenzoate

To a solution of 4-fluoro-2-methylbenzoic acid (86 g, 557.94 mmol, 1.0 equiv) in DMF (900 mL) was added $K_2CO_3$ (231.33 g, 1.67 mol, 3.0 equiv) and iodomethane (79.19 g, 557.94 mmol, 34.73 mL, 1.0 equiv). The mixture was stirred at room temperature for 1 h. The solution of methyl 4-fluoro-2-methylbenzoate in DMF (900 mL) was used directly in the next step.

Step 2: Synthesis of methyl 4-((2-((tert-butoxycarbonyl)amino)ethyl)thio)-2-methylbenzoate To a solution of methyl 4-fluoro-2-methylbenzoate (93.8 g, 557.94 mmol, 1.0 equiv) in DMF (900 mL) was added tert-butyl (2-mercaptoethyl)carbamate (98.91 g, 557.97 mmol, 1.0 equiv) and $K_2CO_3$ (154.23 g, 1.12 mol, 2.0 equiv). The reaction was stirred at 110° C. for 12 h, at which point the mixture was cooled to room temperature and added to $H_2O$ (1000 mL). The aqueous layer was then extracted with EtOAc (3×600 mL) and the combined organic layers were washed with brine, dried, and concentrated under reduced pressure. Purification by silica gel chromatography (0→25% EtOAc/petroleum ether) afforded the desired product as a colorless oil (144 g, 79% yield).

Step 3: Synthesis of methyl 4-((2-((tert-butoxycarbonyl)amino)ethyl)sulfonyl)-2-methylbenzoate To two separate batches containing a solution of methyl 4-((2-((tert-butoxycarbonyl)amino)ethyl)thio)-2-methylbenzoate (72 g, 221.25 mmol, 1.0 equiv), NaOH (2 M, 110.6 mL, 1.0 equiv), and $NaHCO_3$ (55.76 g, 663.75 mmol, 3.0 equiv) in acetone (750 mL) was added potassium peroxymonosulfate (284.28 g, 462.41 mmol, 2.1 equiv). The mixture was stirred for 12 h at room temperature, at which point the two batches were combined and then the mixture was acidified to pH 5 by addition of 1N HCl. The aqueous layer was extracted with EtOAc (3×1500 mL) and the combined organic phases were washed with brine (2×500 mL), dried, and concentrated under reduced pressure. Purification by silica gel chromatography (0→25% EtOAc/petroleum ether) afforded the desired product as a white solid (120 g, 76% yield).

Step 4: Synthesis of 4-((2-((tert-butoxycarbonyl)amino)ethyl)sulfonyl)-2-methylbenzoic acid To a solution of methyl 4-((2-((tert-butoxycarbonyl)amino)ethyl)sulfonyl)-2-methylbenzoate (35 g, 97.92 mmol, 1.0 equiv) in THF (200 mL), MeOH (100 mL) and $H_2O$ (100 mL) was added $LiOH.H_2O$ (12.33 g, 293.77 mmol, 3.0 equiv) at room temperature. The reaction mixture was stirred at 40° C. for 1 h. The mixture was then concentrated under reduced pressure to remove THF and MeOH. The aqueous phase was neutralized with 0.5N HCl and the resulting precipitate was isolated by filtration. The solid cake was washed with $H_2O$ (3×20 mL) to afford the desired product as a white solid (25 g, 74% yield).

Step 5: Synthesis of tert-butyl (2-((4-(7-(6-aminopyridin-3-yl)-2,3,4,5-tetrahydrobenzo[f][1,4]oxazepine-4-carbonyl)-3-methylphenyl)sulfonyl)ethyl)carbamate To a solution of 4-((2-((tert-butoxycarbonyl)amino)ethyl)sulfonyl)-2-methylbenzoic acid (9.7 g, 28.25 mmol, 1.0 equiv) and 5-(2,3,4,5-tetrahydrobenzo[f][1,4]oxazepin-7-yl)pyridin-2-amine (8.88 g, 28.25 mmol, 1.0 equiv, 2HCl) in DMF (120 mL) was added HATU (16.11 g, 42.37 mmol, 1.5 equiv) and DIPEA (18.25 g, 141.24 mmol, 24.60 mL, 5.0 equiv). The reaction was stirred at room temperature for 1 h, at which point the reaction mixture was poured into $H_2O$ (1000 mL). The mixture was stirred for 5 min and the resulting precipitate was collected by filtration to give the crude product. The crude product was triturated with EtOAc (100 mL), filtered, and the solid cake was dried under reduced pressure to afford the desired product as a white solid (14 g, 87% yield).

Step 6: Synthesis of (4-((2-aminoethyl)sulfonyl)-2-methylphenyl)(7-(6-aminopyridin-3-yl)-2,3-dihydrobenzo[f][1,4]oxazepin-4(5H)-yl)methanone A solution tert-butyl (2-((4-(7-(6-aminopyridin-3-yl)-2,3,4,5-tetrahydrobenzo[f][1,4] oxazepine-4-carbonyl)-3-methylphenyl)sulfonyl)ethyl)carbamate (19 g, 33.53 mmol, 1.0 equiv) in TFA (100 mL) was stirred at room temperature for 30 min. The solution was then concentrated under reduced pressure. The residue was triturated with MeCN (30 mL) and then dripped into MTBE (600 mL) and stirred for 20 min. The suspension was filtered and the resulting solid was dissolved in MeCN (30 mL) and concentrated under reduced pressure to afford the desired product as a light yellow solid (24 g, TFA salt). LCMS (ESI) m/z: [M+H] calcd for $C_{24}H_{26}N_4O_4S$:467.18; found 467.1.

427

Monomer AF. 5-(4-amino-1-((5,6,7,8-tetrahydro-pyrido[4,3-d]pyrimidin-2-yl)methyl)-1H-pyrazolo[3,4-d]pyrimidin-3-yl)benzo[d]oxazol-2-amine

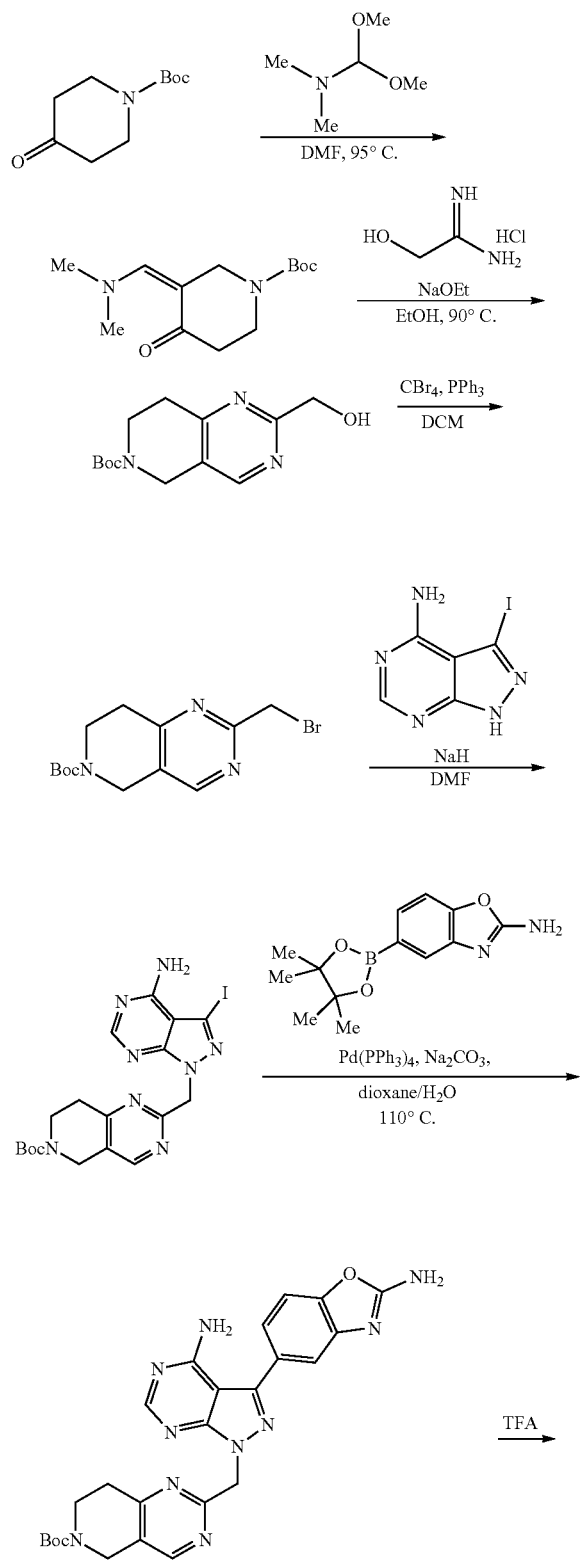

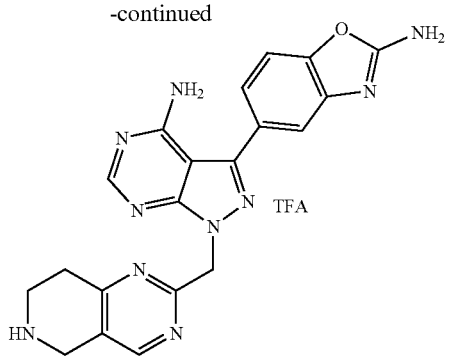

Step 1: Synthesis of (Z)-tert-butyl 3-((dimethyl-amino)methylene)-4-oxopiperidine-1-carboxylate A solution of tert-butyl 4-oxopiperidine-1-carboxylate (15 g, 75.28 mmol, 1.0 equiv) and 1,1-dimethoxy-N,N-dimethylmethanamine (11.00 mL, 82.81 mmol, 1.1 equiv) in DMF (105 mL) was stirred at 95° C. for 12 h. The reaction mixture was then concentrated under reduced pressure and the resulting residue was dissolved in EtOAc (30 mL) and washed with brine (3×30 mL). The aqueous phase was extracted with EtOAc (50 mL), and the combined organic phases were dried and concentrated under reduced pressure to afford the desired product as a yellow solid (10.1 g, 53% yield).

Step 2: Synthesis of tert-butyl 2-(hydroxymethyl)-7,8-dihydropyrido[4,3-d]pyrimidine-6(5H)-carboxylate To a solution of NaOEt (1.98 g, 29.10 mmol, 1.0 equiv) in EtOH (70 mL) was added (Z)-tert-butyl 3-((dimethylamino)methylene)-4-oxopiperidine-1-carboxylate (7.4 g, 29.10 mmol, 1.0 equiv) and 2-hydroxyacetimidamide hydrochloride (3.54 g, 32.01 mmol, 1.1 equiv). The reaction mixture was heated to 90° C. for 12 h, at which point the mixture was cooled to room temperature and concentrated under reduced pressure. The residue was partitioned with EtOAc (40 mL) and washed with sat. NaHCO$_3$(40 mL). The aqueous phase was extracted with EtOAc (3×20 mL) and the combined organic phases were washed with brine (2×50 mL), dried, and concentrated under reduced pressure. Purification by silica gel chromatography (25% EtOAc/petroleum ether) afforded the desired product as a yellow solid (7.24 g, 94% yield).

Step 3: Synthesis of tert-butyl 2-(bromomethyl)-7,8-dihydropyrido[4,3-d]pyrimidine-6(5H)-carboxylate To a solution of tert-butyl 2-(hydroxymethyl)-7,8-dihydropyrido[4,3-d]pyrimidine-6(5H)-carboxylate (6.24 g, 23.52 mmol, 1.0 equiv) and PPh$_3$ (12.34 g, 47.04 mmol, 2.0 equiv) in DCM (140 mL) was added CBr$_4$ (14.82 g, 44.69 mmol, 1.9 equiv). The mixture was stirred at room temperature for 3 h, at which point mixture was concentrated under reduced pressure. The residue was partitioned between EtOAc (20 mL) and H$_2$O (20 mL), the aqueous phase was extracted with EtOAc (3×20 mL). The combined organic phases were washed with brine (2×50 mL), dried, and concentrated under reduced pressure. Purification by silica gel chromatography (14% EtOAc/petroleum ether) afforded the desired product as a yellow solid (3.6 g, 47% yield).

Step 4: Synthesis of tert-butyl 2-((4-amino-3-iodo-1H-pyrazolo[3,4-d]pyrimidin-1-yl)methyl)-7,8-dihydropyrido[4,3-d]pyrimidine-6(5H)-carboxylate To a solution of 3-iodo-1H-pyrazolo[3,4-d]pyrimidin-4-amine (1.59 g, 6.09 mmol, 1.0 equiv) in DMF (15 mL) was added NaH (243.73 mg, 6.09 mmol, 60 wt. %, 1.0 equiv) at 0° C. The suspension was stirred for 30 min and then tert-butyl 2-(bromomethyl)-7,8-dihydropyrido[4,3-d]pyrimidine-6(5H)-carboxylate (2.2 g, 6.70 mmol, 1.1 equiv) was added. The reaction mixture was warmed to room temperature and stirred for 3 h. The mixture was poured into H₂O at 0° C. and the precipitate was collected by filtration to afford the desired product as a brown solid (2.5 g, 66% yield).

Step 5: Synthesis of tert-butyl 2-((4-amino-3-(2-aminobenzo[d]oxazol-5-yl)-1H-pyrazolo[3,4-d]pyrimidin-1-yl)methyl)-7,8-dihydropyrido[4,3-d]pyrimidine-6(5H)-carboxylate To a solution of tert-butyl 2-((4-amino-3-iodo-1H-pyrazolo[3,4-d]pyrimidin-1-yl)methyl)-7,8-dihydropyrido[4,3-d]pyrimidine-6(5H)-carboxylate (4.55 g, 8.95 mmol, 1.0 equiv), 5-(4,4,5,5-tetramethyl-1,3,2-dioxaborolan-2-yl)benzo[d]oxazol-2-amine (2.79 g, 10.74 mmol, 1.2 equiv) and Na₂CO₃ (4.74 g, 44.76 mmol, 5.0 equiv) in dioxane (70 mL) and H₂O (35 mL) was added Pd(PPh₃)₄ (1.03 g, 895.11 µmol, 0.1 equiv). The reaction mixture was heated to 110° C. for 3 h, at which point the mixture was cooled to room temperature and poured into H₂O at 0° C. The precipitate was filtered, and the solid cake was dried under reduced pressure. The crude product was washed with EtOAc (50 mL) to afford the desired product as light yellow solid (3.14 g, 68% yield).

Step 6: Synthesis of 5-(4-amino-1-((5,6,7,8-tetrahydropyrido[4,3-d]pyrimidin-2-yl)methyl)-1H-pyrazolo[3,4-d]pyrimidin-3-yl)benzo[d]oxazol-2-amine A solution of tert-butyl 2-((4-amino-3-(2-aminobenzo[d]oxazol-5-yl)-1H-pyrazolo[3,4-d]pyrimidin-1-yl)methyl)-7,8-dihydropyrido[4,3-d]pyrimidine-6(5H)-carboxylate (3.14 g, 6.10 mmol, 1.0 equiv) in TFA (20 mL) was stirred at room temperature for 30 min. The mixture was concentrated under reduced pressure and the resulting residue was added dissolved in MeCN (7 mL) and added to MTBE (700 mL). The precipitate was collected by filtration to afford the desired product as a brown solid (4.25 g, 92% yield, 3 TFA). LCMS (ESI) m/z: [M+H] calcd for $C_{20}H_{18}N_{10}O$: 415.18; found 415.1.

Monomer AG. 5-(4-amino-1-((2-((2-aminoethyl)sulfonyl)-1,2,3,4-tetrahydroisoquinolin-6-yl)methyl)-1H-pyrazolo[3,4-d]pyrimidin-3-yl)benzo[d]oxazol-2-amine

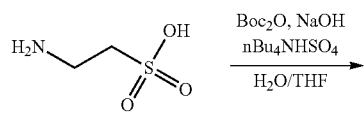

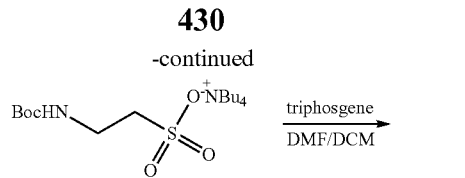

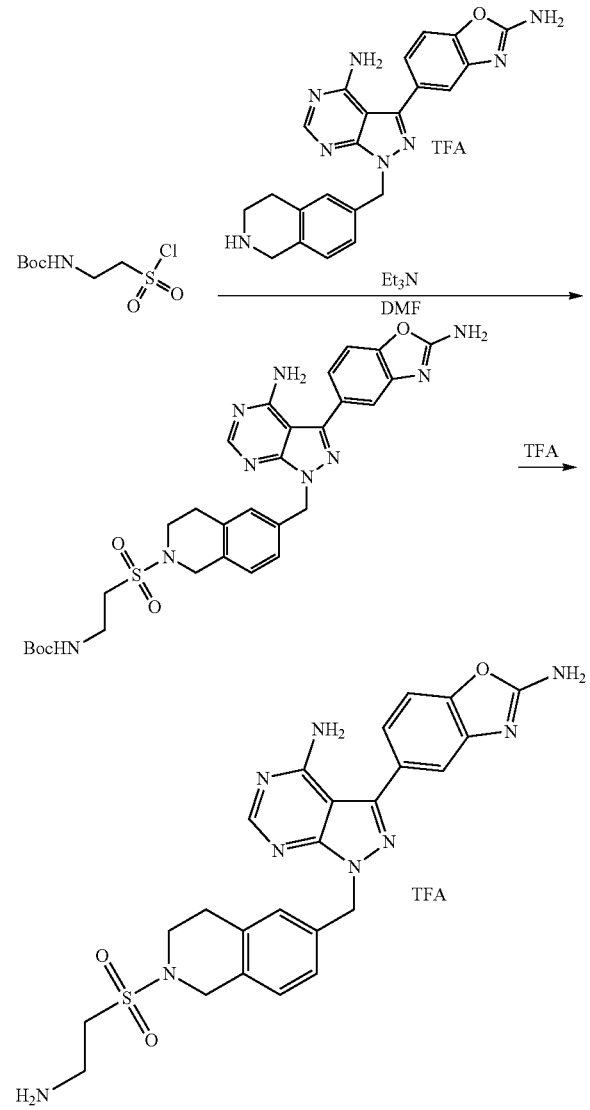

Step 1: Synthesis of N-Boc taurine tetrabutylammonium salt

To a solution of 2-aminoethanesulfonic acid (10.00 mL, 79.91 mmol, 1.0 equiv) in THF (60 mL) and aqueous NaOH (2 M, 40 mL, 1.0 equiv) was added Boc₂O (18.31 g, 83.90 mmol, 1.05 equiv). The mixture was stirred at room temperature for 15 h, at which point the mixture was extracted with EtOAc (10 mL). The aqueous phase was diluted with H₂O (450 mL), treated with LiOH·H₂O (3.35 g, 79.83 mmol, 1.0 equiv) and nBu₄NHSO₄ (27.13 g 79.90 mmol, 1.0 equiv) and stirred for 30 min. This mixture was extracted with DCM (3×80 mL), and the combined organic phases were dried and concentrated under reduced pressure to afford the desired product as a colorless oil (34.26 g, 91% yield).

Step 2: Synthesis of tert-butyl (2-(chlorosulfonyl)ethyl)carbamate

To a solution of N-Boc taurine tetrabutylammonium salt (4.7 g, 10.05 mmol, 1.0 equiv) in DCM (42 mL) was added DMF (77.32 1.00 mmol, 0.1 equiv) followed by a solution of triphosgene (0.5 M, 8.04 mL, 0.4 equiv) in DCM at 0° C. The mixture was warmed to room temperature and stirred for 30 min. The solution of tert-butyl (2-(chlorosulfonyl)ethyl)carbamate (2.45 g, crude) in DCM was used directly in the next step.

Step 3: Synthesis of tert-butyl (2-((6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)sulfonyl)ethyl)carbamate To a solution of 5-(4-amino-1-((1,2,3,4-tetrahydroisoquinolin-6-yl)methyl)-1H-pyrazolo[3,4-d]pyrimidin-3-yl)benzo[d]oxazol-2-amine (6.04 g, 9.44 mmol, 1.0 equiv, 2TFA) in DMF (40 mL) was added Et$_3$N (7.88 mL, 56.63 mmol, 6.0 equiv). A solution of tert-butyl (2-(chlorosulfonyl)ethyl)carbamate in DCM (42 mL) at 0° C. was added. The mixture was warmed to room temperature and stirred 16 h. The reaction mixture was concentrated under reduced pressure to remove DCM and the resulting solution was purified by reverse phase chromatography (15→45% MeCN/H$_2$O) to afford the desired product as a white solid (5.8 g, 83% yield, TFA). LCMS (ESI) m/z: [M+H] calcd for C$_{29}$H$_{33}$N$_9$O$_5$S: 620.24; found 620.3.

Step 4: Synthesis of 5-(4-amino-1-((2-((2-aminoethyl)sulfonyl)-1,2,3,4-tetrahydroisoquinolin-6-yl)methyl)-1H-pyrazolo[3,4-d]pyrimidin-3-yl)benzo[d]oxazol-2-amine A solution of tert-butyl (2-((6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)sulfonyl)ethyl)carbamate (5.8 g, 9.36 mmol, 1.0 equiv) in TFA (48 mL) was stirred at room temperature for 0.5 h, at which point the reaction mixture was concentrated under reduced pressure. The crude product dissolved in MeCN (30 mL) and was added dropwise into MTBE (200 mL). The mixture was stirred for 5 min and filtered, the filter cake was dried under reduced pressure to afford the desired product as a yellow solid (3.6 g, 62% yield, 2.2TFA). LCMS (ESI) m/z: [M+H] calcd for C$_{24}$H$_{25}$N$_9$O$_3$S: 520.19; found 520.1.

Monomer AIL tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate

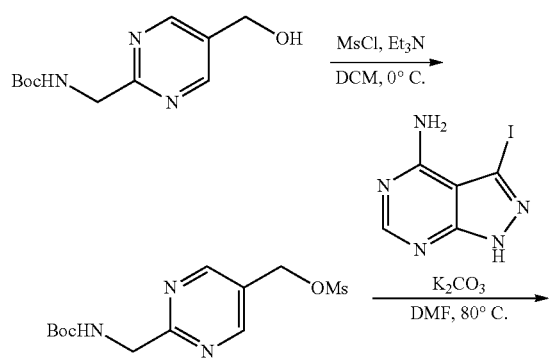

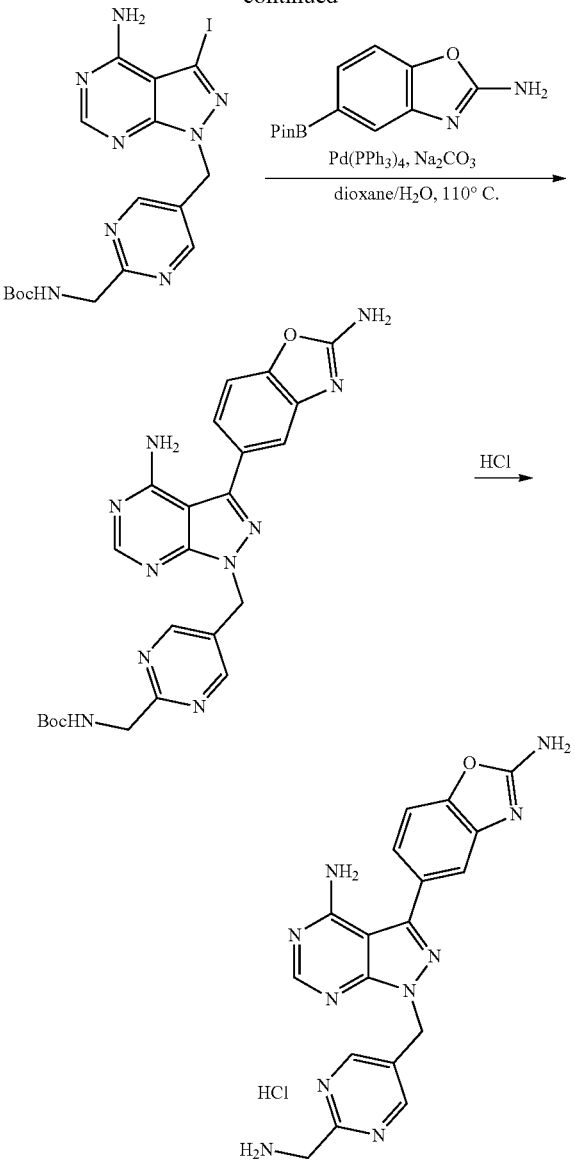

Step 1: Synthesis of (2-(((tert-butoxycarbonyl)amino)methyl)pyrimidin-5-yl)methyl methanesulfonate To a solution of tert-butyl ((5-(hydroxymethyl)pyrimidin-2-yl)methyl)carbamate (4.2 g, 17.55 mmol, 1.0 equiv) in DCM (42 mL) at 0° C. was added Et$_3$N (7.33 mL, 52.66 mmol, 3.0 equiv) followed by MsCl (2.41 g, 21.06 mmol, 1.63 mL, 1.2 equiv). The mixture was stirred at 0° C. for 10 min, and then H$_2$O (15 mL) was added. The reaction mixture was extracted with DCM (5×10 mL) and the combined organic phases were washed with brine (5 mL), dried, filtered, and concentrated under reduced pressure to afford the desired product (5.5 g, 98.7% yield) as a colorless solid.

Step 2: Synthesis of tert-butyl ((5-((4-amino-3-iodo-1H-pyrazolo[3,4-d]pyrimidin-1-yl)methyl)pyrimidin-2-yl)methyl)carbamate To a solution of (2-(((tert-butoxycarbonyl)amino)methyl)pyrimidin-5-yl)methyl methanesulfonate (5.47 g, 17.24 mmol, 1.2 equiv) and 3-iodo-1H-pyrazolo[3,4-d] pyrimidin-4-amine (3.75 g, 14.37 mmol, 1.0 equiv) in DMF (55 mL) at room temperature was added K₂CO₃ (5.96 g, 43.10 mmol, 3 equiv). The mixture was stirred at 80° C. for 5 h, at which point H₂O (100 mL) and brine (20 mL) were poured into the reaction mixture. The solution was extracted with EtOAc (10×30 mL) and the combined organic phases were dried, filtered, and concentrated under reduced pressure. Purification by silica gel chromatography (0→30% EtOAc/MeOH) afforded the desired product (2 g, 28.9% yield) as a yellow solid.

Step 3: Synthesis of tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate To a solution of tert-butyl ((5-((4-amino-3-iodo-1H-pyrazolo[3,4-d]pyrimidin-1-yl)methyl)pyrimidin-2-yl)methyl)carbamate (2 g, 4.15 mmol, 1.0 equiv), 5-(4,4,5,5-tetramethyl-1,3,2-dioxaborolan-2-yl)-1,3-benzoxazol-2-amine (1.13 g, 4.35 mmol, 1.05 equiv) and Na₂CO₃ (688.39 mg, 8.29 mmol, 2.0 equiv) in dioxane (20 mL) and H₂O (10 mL) was added Pd(PPh₃)₄ (479.21 mg, 414.70 μmol, 0.1 equiv). The mixture was stirred at 110° C. for 1 h, at which time the mixture was cooled to room temperature, filtered, and the solid cake washed with MeOH (3×10 mL). The filtrate was concentrated under reduced pressure to remove MeOH and then added dropwise into H₂O (50 mL). The resulting suspension was filtered, and the filter cake was washed with H₂O (3×10 mL). The solid cake was stirred in MeOH (20 mL) for 30 min. The resulting suspension was filtered, and the filter cake washed with MeOH (3×8 mL). The filter cake was dried under reduced pressure to afford the desired product (1.03 g, 48.9% yield) as a white solid. LCMS (ESI) m/z: [M+H] calcd for C₂₃H₂₄N₁₀O₃: 489.21; found 489.2.

Step 4: Synthesis of 5-(4-amino-1-{[2-(aminomethyl)pyrimidin-5-yl]methyl}-1H-pyrazolo[3,4-d]pyrimidin-3-yl)-1,3-benzoxazol-2-amine To tert-butyl ((5-((4-amino-3-(2-aminobenzo[d]oxazol-5-yl)-1H-pyrazolo[3,4-d]pyrimidin-1-yl)methyl)pyrimidin-2-yl)methyl)carbamate (100 mg, 0.205 mmol, 1.0 equiv) was added con. HCl (850 10.2 mmol, 50 equiv). The reaction was stirred for 1 h and was then poured into acetone (3 mL). The resulting precipitate was filtered, washed with acetone, and dried under reduced pressure to afford the desired product (80 mg, 92% yield) as a brown solid. LCMS (ESI) m/z: [M+H] calcd for C₁₄H₁₆N₁₀O: 389.16; found 389.0.

Monomer AI. 5-(4-(dimethylamino)-1-((1,2,3,4-tetrahydroisoquinolin-6-yl)methyl)-1H-pyrazolo[3,4-d]pyrimidin-3-yl)benzo[d]oxazol-2-amine trifluoroacetic acid salt

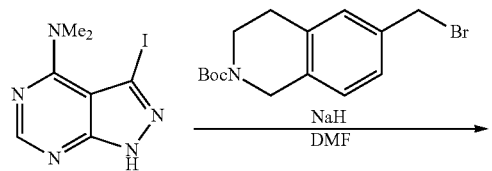

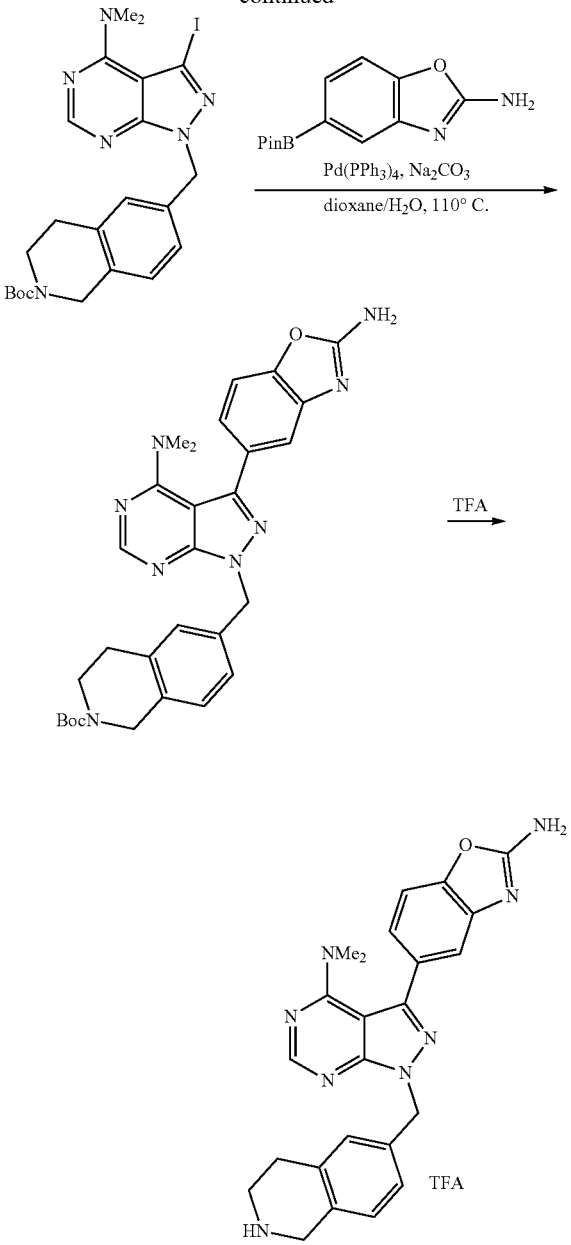

Step 1: Synthesis of tert-butyl 6-((4-(dimethylamino)-3-iodo-1H-pyrazolo[3,4-d]pyrimidin-1-yl)methyl)-3,4-dihydroisoquinoline-2(1H)-carboxylate To a solution of 3-iodo-N,N-dimethyl-1H-pyrazolo[3,4-d]pyrimidin-4-amine (3.6 g, 12.45 mmol, 1.0 equiv) in DMF (36 mL) at 0° C. was added NaH (523.00 mg, 13.08 mmol, 60 wt. %, 1.05 equiv). The mixture was stirred at 0° C. for 30 min. To the reaction mixture was then added a solution of tert-butyl 6-(bromomethyl)-3,4-dihydroisoquinoline-2(1H)-carboxylate (4.47 g, 13.70 mmol, 1.1 equiv) in DMF (18 mL) at 0° C. The mixture was stirred at room temperature for 2 h. The reaction mixture was then added to cold H₂O (200 mL) and stirred for 30 min. The resulting precipitate was collected by filtration to afford the desired product (6 g, 71.9% yield) as a white solid.

Step 2: Synthesis of tert-butyl 6-((3-(2-aminobenzo[d]oxazol-5-yl)-4-(dimethylamino)-1H-pyrazolo[3,4-d]pyrimidin-1-yl)methyl)-3,4-dihydroisoquinoline-2(1H)-carboxylate To a solution of tert-butyl 6-((4-(dimethylamino)-3-iodo-1H-pyrazolo[3,4-d]pyrimidin-1-yl)methyl)-3,4-dihydroisoquinoline-2(1H)-carboxylate (2 g, 2.96 mmol, 1.0 equiv) and 5-(4,4,5,5-tetramethyl-1,3,2-dioxaborolan-2-yl)benzo[d]oxazol-2-amine (922.81 mg, 3.55 mmol, 1.2 equiv) in dioxane (24 mL) and H$_2$O (12 mL) was added Na$_2$CO$_3$ (1.57 g, 14.78 mmol, 5.0 equiv) and Pd(PPh$_3$)$_4$ (341.66 mg, 295.66 μmol, 0.1 equiv). The mixture was stirred at 110° C. for 12 h. The reaction mixture was then poured into cold H$_2$O (200 mL) and stirred for 30 min. The resulting precipitate was collected by filtration. Purification by silica gel chromatography (5→100% petroleum ether/EtOAc) afforded the desired product (1.2 g, 72.3% yield) as a yellow solid.

Step 3: Synthesis of 5-(4-(dimethylamino)-1-((1,2,3,4-tetrahydroisoquinolin-6-yl)methyl)-1H-pyrazolo[3,4-d]pyrimidin-3-yl)benzo[d]oxazol-2-amine A solution of tert-butyl 6-((3-(2-aminobenzo[d]oxazol-5-yl)-4-(dimethylamino)-1H-pyrazolo[3,4-d]pyrimidin-1-yl)methyl)-3,4-dihydroisoquinoline-2(1H)-carboxylate (1.7 g, 3.14 mmol, 1.0 equiv) in TFA (10 mL) was stirred at room temperature for 30 min. The reaction mixture was then concentrated under reduced pressure. The residue was added to MeCN (10 mL) and the solution was added dropwise into MTBE (200 mL). The resulting solid was dissolved in MeCN (30 mL) and the solution was concentrated under reduced pressure to afford the desired product (1.67 g, 92.9% yield,) as a yellow solid. LCMS (ESI) m/z: [M+H] calcd for C$_{24}$H$_{24}$N$_8$O: 441.22; found 441.2.

Monomer AJ. 4-amino-5-(2-aminobenzo[d]oxazol-5-yl)-5H-pyrimido[5,4-b]indole-7-carboxylic acid

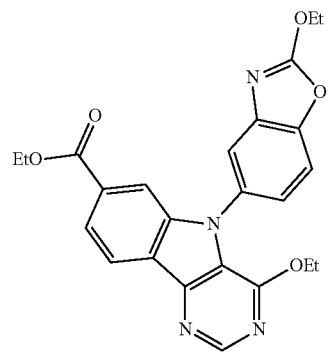

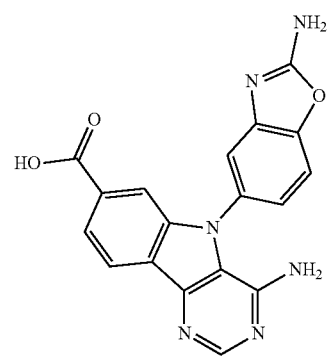

This monomer can be prepared from 7-methyl-5H-pyrimido[5,4-b]indol-4-ol by benzylic oxidation to the carboxylic acid, conversion to the ethyl ester, followed by O-ethylation with triethyloxonium tetrafluoroborate. Palladium-mediated arylation followed by ester hydrolysis and final ammonia-olysis provides the monomer.

Monomer AK. 4-amino-5-(2-aminobenzo[d]oxazol-5-yl)-5H-pyrimido[5,4-b]indole-8-carboxylic acid

 1) KMnO$_4$
2) HCl, EtOH
3) Et$_3$O$^+$BF$_4$$^-$

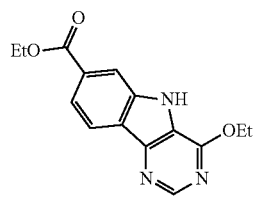 Pd(PPh$_3$)$_4$, binap, NaOtBu

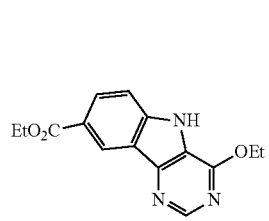 1) KMnO$_4$
2) HCl, EtOH
3) Et$_3$O$^+$BF$_4$$^-$

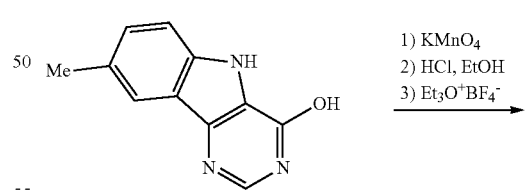 Pd(PPh$_3$)$_4$, binap, NaOtBu

437

-continued

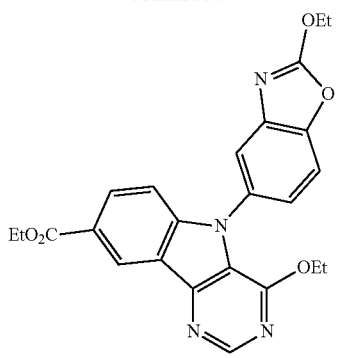

5) LiOH
6) NH₃, sealed tube ↓

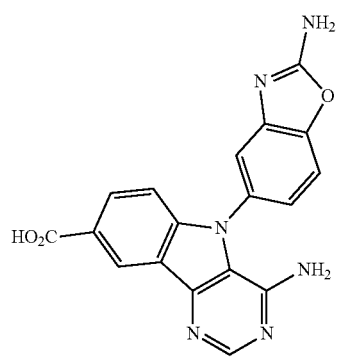

This monomer can be prepared following a similar route as that to prepare the previous monomer, but using the isomeric starting material from 8-methyl-5H-pyrimido[5,4-b]indol-4-ol. Benzylic oxidation to the carboxylic acid, conversion to the ethyl ester, followed by O-ethylation with triethyloxonium tetrafluoroborate and palladium-mediated arylation, followed by ester hydrolysis and final ammonia-olysis provides the monomer.

Monomer AL. 3-(2,4-bis((S)-3-methylmorpholino)-4a,8a-dihydropyrido[2,3-d]pyrimidin-7-yl)benzoic acid

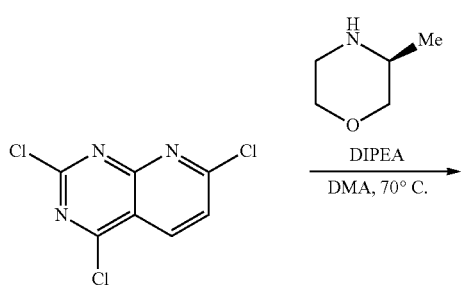

438

-continued

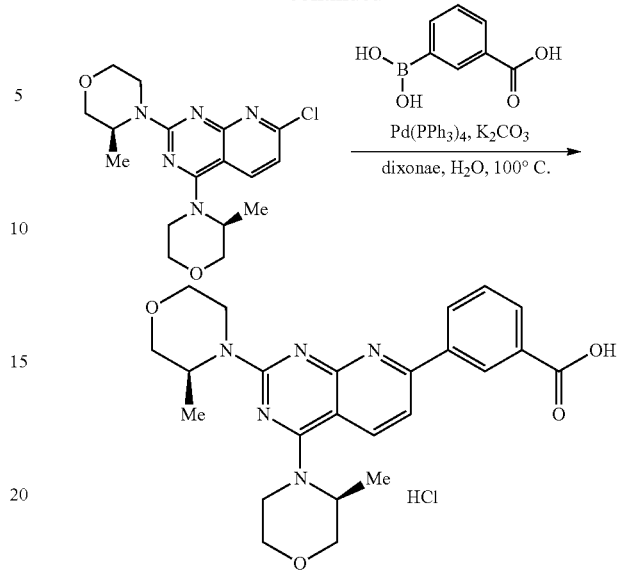

Step 1: Synthesis of (3S)-4-[7-chloro-2-[(3S)-3-methylmorpholin-4-yl]pyrido[2,3-d] pyrimidin-4-yl] 3-methyl-morpholine To a solution of 2,4,7-trichloropyrido[2,3-d]pyrimidine (4.0 g, 17.06 mmol, 1.0 equiv) in DMA (10 mL) was added (3S)-3-methylmorpholine (4.31 g, 42.65 mmol, 2.5 equiv) and DIPEA (5.51 g, 42.65 mmol, 7.43 mL, 2.5 equiv). The reaction solution was heated to 70° C. for 48 h. The reaction suspension was cooled to room temperature, poured into cold H₂O (50 mL) to precipitate out a solid. The solid was filtered and the filter cake was rinsed with H₂O, and dried under reduced pressure to give the crude product, which was purified by column chromatography on silica gel (0→100% petroleum ether/EtOAc) to give (3S)-4-[7-chloro-2-[(3S)-3-methylmorpholin-4-yl]pyrido[2,3-d] pyrimidin-4-yl]3-methyl-morpholine (3.5 g, 56.4% yield) as a yellow solid. LCMS (ESI) m/z: [M+H] calcd for $C_{17}H_{22}CN_5O_2$: 364.15; found 364.2.

Step 2: Synthesis of 3-[2,4-bis[(3S)-3-methylmorpholin-4-yl]pyrido[2,3-d]pyrimidin-7-yl]benzoic acid To a solution of (3S)-4-[7-chloro-2-[(3S)-3-methylmorpholin-4-yl]pyrido[2,3-d]pyrimidin-4-yl]-3-methyl-morpholine (2 g, 5.50 mmol, 1.0 equiv) and 3-boronobenzoic acid (1.09 g, 6.60 mmol, 1.2 equiv) in 1,4-dioxane (40 mL) was added a solution of K₂CO₃ (911.65 mg, 6.60 mmol, 1.2 equiv) in H₂O (4 mL), followed by Pd(PPh₃)₄ (317.60 mg, 274.85 μmol, 0.05 equiv). The solution was degassed for 10 min and refilled with N₂, then the reaction mixture was heated to 100° C. under N₂ for 5 h. The reaction was cooled to room temperature and filtered. The filtrate was acidified by HCl (2N) to pH 3, and the aqueous layer was washed with EtOAc (3×20 mL). Then, the aqueous phase was concentrated under reduced pressure to give a residue, which was purified by column chromatography on silica gel (50%-100% petroleum ether/EtOAc) to give 3-[2,4-bis[(3S)-3-methylmorpholin-4-yl]pyrido[2,3-d]pyrimidin-7-yl]benzoic acid hydrochloride (2.5 g, 89.9% yield) as a yellow solid. LCMS (ESI) m/z: [M+H] calcd for $C_{24}H_{27}N_5O_4$: 450.21; found 450.2.

Reference for preparation of this monomer: Menear, K.; Smith, G. C. M.; Malagu, K.; Duggan, H. M. E.; Martin, N. M. B.; Leroux, F. G. M. 2012. Pyrido-, pyrazo- and pyrimido-pyrimidine derivatives as mTOR inhibitors. U.S. Pat. No. 8,101,602. Kudos Pharmaceuticals, Ltd, which is incorporated by reference in its entirety.

Monomer AM. (1r,4r)-4-[4-amino-5-(7-methoxy-1H-indol-2-yl)imidazo[4,3-f][1,2,4]triazin-7-yl]cyclohexane-1-carboxylic acid

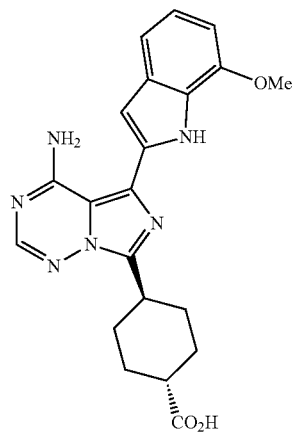 [SMILES: COc1cccc2cc(-c3nc([C@H]4CC[C@H](C(=O)O)CC4)n4ncnc(N)c34)[nH]c12]

This monomer, also known as OSI-027 (CAS #=936890-98-1), is a commercially available compound. At the time this application was prepared, it was available for purchase from several vendors.

Monomer AN. 2-(4-(4-(8-(6-methoxypyridin-3-yl)-3-methyl-2-oxo-2,3-dihydro-1H-imidazo[4,5-c]quinolin-1-yl)-2-(trifluoromethyl)phenyl)piperazin-1-yl)pyrimidine-5-carboxylic acid

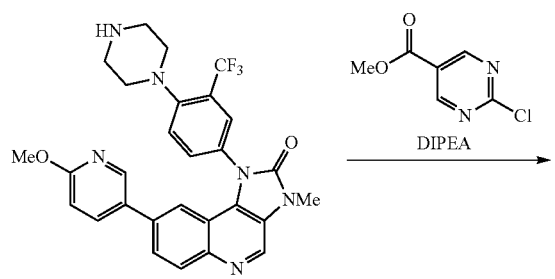

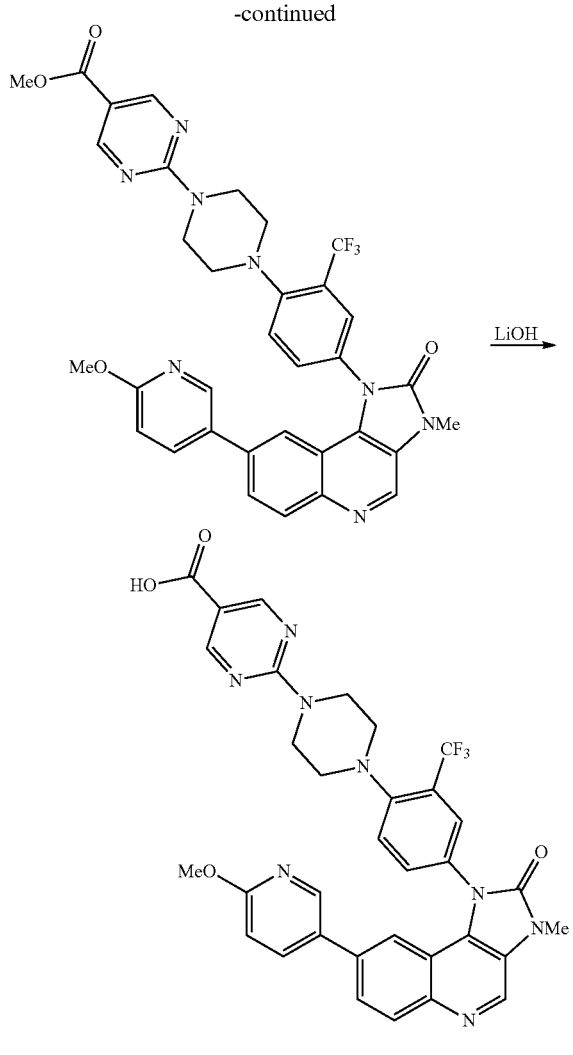

Preparation of this monomer proceeds by reaction of BGT226 with methyl 2-chloropyrimidine-5-carboxylate, followed by ester hydrolysis, to give the titled Monomer.

Monomer AO. 4-amino-5-{1H-pyrrolo[2,3-b]pyridin-5-yl}-5H-pyrimido[5,4-b]indole-8-carboxylic acid

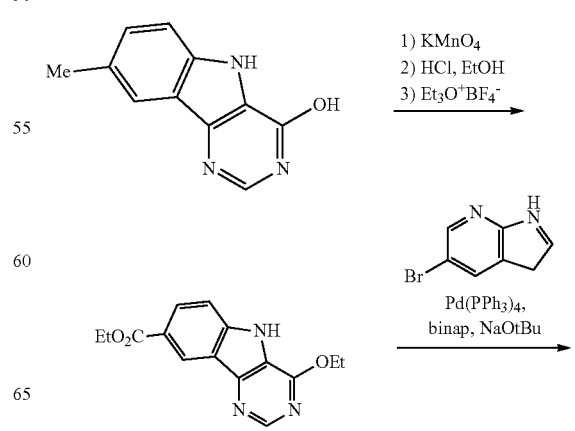

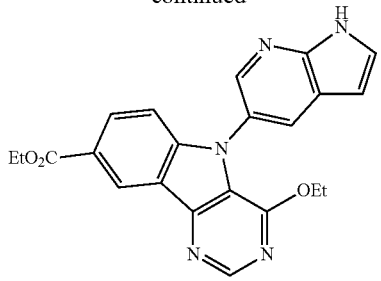

5) LiOH
6) NH₃, sealed tube

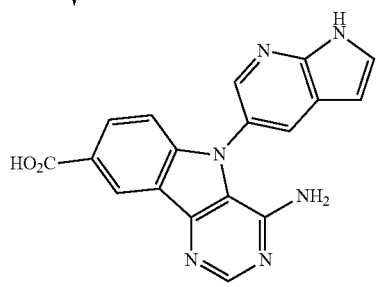

This monomer can be prepared from 7-methyl-5H-pyrimido[5,4-b]indol-4-ol by benzylic oxidation to the carboxylic acid, conversion to the ethyl ester, followed by O-ethylation with triethyloxonium tetrafluoroborate. Palladium-mediated arylation followed by ester hydrolysis and final ammonia-olysis provides the monomer.

Preparation of Pre- and Post-Linkers

Building Block A. tert-butyl N-[(tert-butoxy)carbonyl]-N-{[2-(piperazin-1-yl)pyrimidin-5-yl]methyl}carbamate

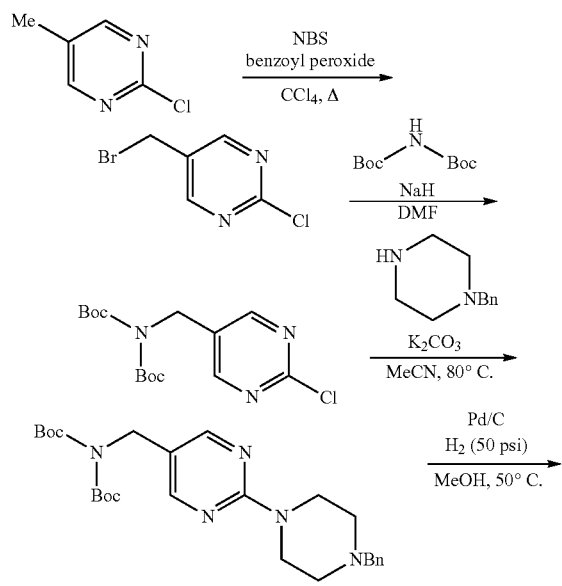

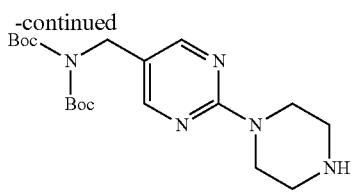

Step 1: Synthesis of 5-(bromomethyl)-2-chloropyrimidine

To a solution of 2-chloro-5-methylpyrimidine (92 g, 715.62 mmol, 1.0 equiv) in CCl₄ (1000 mL) was added NBS (178.31 g, 1.00 mol, 1.4 equiv) and benzoyl peroxide (3.47 g, 14.31 mmol, 0.02 equiv). The mixture was stirred at 76° C. for 18 h. The reaction mixture was then cooled to room temperature and concentrated under reduced pressure. The reaction mixture was filtered and the solid cake was washed with DCM (150 mL). The resulting solution was concentrated under reduced pressure to give the crude product. The residue was purified by silica gel chromatography (1/0 to 0/1 petroleum ether/EtOAc) to give the product (70.8 g, 47.7% crude yield) as a yellow oil, which was used directly for the next step. LCMS (ESI) m/z: [M+H] calcd for C₅H₄BrClN₂: 206.93; found 206.9.

Step 2: Synthesis of tert-butyl N-tert-butoxycarbonyl-N-((2-piperazin-1-ylpyrimidin-5-yl)methyl)carbamate To a solution of tert-butyl N-tert-butoxycarbonylcarbamate (36.89 g, 169.79 mmol, 0.74 equiv) in DMF (750 mL) was added NaH (6.88 g, 172.09 mmol, 60 wt. %, 0.75 equiv) at 0° C. The mixture was stirred at 0° C. for 30 min. Then, 5-(bromomethyl)-2-chloropyrimidine (47.6 g, 229.45 mmol, 1.0 equiv) was added at 0° C. The reaction mixture was stirred at room temperature for 15.5 h. The mixture was then poured into H₂O (1600 mL) and the aqueous phase was extracted with EtOAc (3×300 mL). The combined organic phase was washed with brine (2×200 mL), dried with anhydrous Na₂SO₄, filtered and concentrated under reduced pressure. The residue was purified by silica gel chromatography (1/0 to 0/1 petroleum ether/EtOAc) to give the product (70 g, crude) as a yellow solid, which was used in the next step directly.

Step 3: Synthesis of tert-butyl N-tert-butoxycarbonyl-N-[(2-piperazin-1-ylpyrimidin-5-yl)methyl]carbamate To a solution of 1-benzylpiperazine (30.44 g, 122.16 mmol, 1.0 equiv, 2HCl) in MeCN (550 mL) was added tert-butyl N-tert-butoxycarbonyl-N-((2-chloropyrimidin-5-yl)methyl)carbamate (42 g, 122.16 mmol, 1.0 equiv) and K₂CO₃ (84.42 g, 610.81 mmol, 5.0 equiv). The mixture was stirred at 80° C. for 61 h. The reaction mixture was then diluted with EtOAc (150 mL) and the mixture was filtered. The resulting solution was concentrated under reduced pressure to give the crude product. The residue was purified by silica gel chromatography (1/0 to 0/1 petroleum ether/EtOAc) to give the product (45 g, 74% yield) as a white solid.

Step 4: Synthesis of tert-butyl N-tert-butoxycarbonyl-N-[(2-piperazin-1-ylpyrimidin-5-yl)methyl]carbamate To a solution of tert-butyl N-[[2-(4-benzylpiperazin-1-yl)pyrimidin-5-yl]methyl]-N-tert-butoxycarbonyl-carbamate (24 g, 49.63 mmol, 1.0 equiv) in MeOH (600 mL) was added Pd/C (24 g, 47.56 mmol, 10 wt. %, 1.0 equiv) under argon. The mixture was degassed under reduced pressure and purged with $H_2$ three times. The mixture was stirred under $H_2$ (50 psi) at 50° C. for 19 h. The reaction mixture was cooled to room temperature, filtered, and the filter cake was washed with MeOH (500 mL). The resulting solution was concentrated under reduced pressure. The residue was purified by silica gel chromatography (1/0 to 0/1 EtOAc/MeOH) to give the product (25.5 g, 68% yield) as a white solid.

Building block B. 2-(4-(5-(((Cert-butoxycarbonyl)amino)methyl)pyrimidin-2-yl)piperazin-1-yl)pyrimidine-5-carboxylic acid

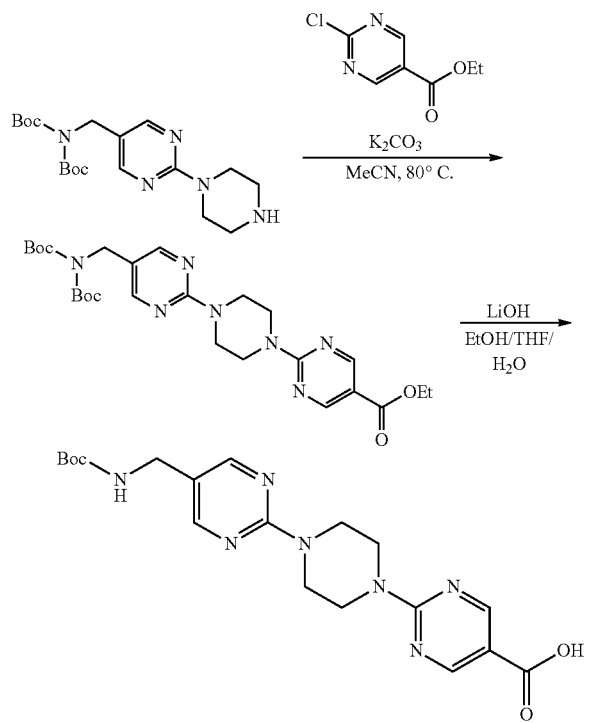

Step 1: Synthesis of ethyl 2-(4-(5-((bis(tert-butoxycarbonyl)amino)methyl)pyrimidin-2-yl)piperazin-1-yl)pyrimidine-5-carboxylate To a solution of ethyl 2-chloropyrimidine-5-carboxylate (2.37 g, 12.71 mmol, 1.0 equiv) and tert-butyl N-tert-butoxycarbonyl-N-((2-piperazin-1-ylpyrimidin-5-yl)methyl)carbamate (5 g, 12.71 mmol, 1.0 equiv) in MeCN (80 mL) was added $K_2CO_3$ (5.27 g, 38.12 mmol, 3.0 equiv). The mixture was stirred at 80° C. for 16 h. The reaction mixture was then poured into $H_2O$ (200 mL) and the suspension was filtered. The filtrate was washed with $H_2O$ (80 mL) and dried under reduced pressure to give the product (6.1 g, 87% yield) as a white solid.

Step 2: Synthesis of 2-(4-(5-(((tert-butoxycarbonyl)amino)methyl)pyrimidin-2-yl)piperazin-1-yl)pyrimidine-5-carboxylic acid To a solution of ethyl 2-(4-(5-((bis(tert-butoxycarbonyl)amino)methyl)pyrimidin-2-yl)piperazin-1-yl)pyrimidine-5-carboxylate (5 g, 9.20 mmol, 1.0 equiv) in $H_2O$ (50 mL), EtOH (15 mL) and THF (50 mL) was added LiOH.$H_2O$ (1.54 g, 36.79 mmol, 4.0 equiv). The reaction mixture was stirred at 55° C. for 16 h. The mixture was then concentrated to remove THF and EtOH and then the mixture was diluted with $H_2O$ (55 mL) and was acidified (pH=3) with aqueous HCl (1 N). The mixture was filtered and the filter cake was washed with $H_2O$ (36 mL). The filter cake was dried under reduced pressure to give the product (2.7 g, 69.3%) as a white solid. LCMS (ESI) m/z: [M+H] calcd for $C_{19}H_{25}N_7O_4$: 416.21; found 416.1.

Building block C. tert-butyl 2-(piperazin-1-yl)-7,8-dihydropyrido[4,3-d]pyrimidine-6(5H)-carboxylate

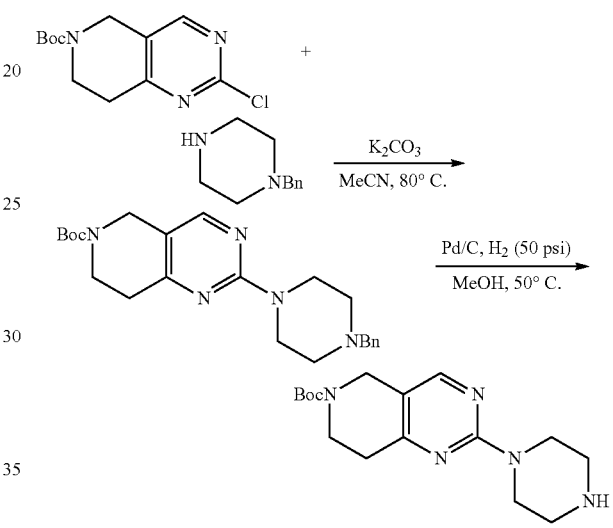

Step 1: Synthesis of tert-butyl 2-(4-benzylpiperazin-1-yl)-7,8-dihydropyrido[4,3-d]pyrimidine-6(5H)-carboxylate To a solution of tert-butyl 2-chloro-7,8-dihydropyrido[4,3-d]pyrimidine-6(5H)-carboxylate (15 g, 55.61 mmol, 1.0 equiv) in MeCN (150 mL) was added 1-benzylpiperazine (11.76 g, 66.73 mmol, 1.2 equiv) and $K_2CO_3$ (46.12 g, 333.67 mmol, 6.0 equiv). The mixture was stirred at 80° C. for 27 h. The reaction mixture was diluted with EtOAc (200 mL), filtered and concentrated under reduced pressure. The crude product was purified by silica gel chromatography (1/0 to 0/1 petroleum ether/EtOAc) to give the product (20.2 g, 80% yield) as a white solid. LCMS (ESI) m/z: [M+H] calcd for $C_{23}H_{31}N_5O_2$: 410.26; found 410.1.

Step 2: Synthesis of tert-butyl 2-(piperazin-1-yl)-7,8-dihydropyrido[4,3-d]pyrimidine-6(5H)-carboxylate To a solution of tert-butyl 2-(4-benzylpiperazin-1-yl)-7,8-dihydropyrido[4,3-d]pyrimidine-6(5H)-carboxylate (8 g, 19.53 mmol, 1.0 equiv) in MeOH (200 mL) was added Pd/C (8 g, 19.53 mmol, 10 wt. %, 1.0 equiv) under argon. The mixture was degassed and purged with $H_2$ three times. The mixture was stirred under $H_2$ (50 psi) at 50° C. for 19 h. The reaction mixture was cooled to room temperature, filtered through a pad of Celite and the filter cake was washed with MeOH (150 mL). The resulting solution was concentrated under reduced pressure and the crude product was washed with petroleum ether (60 mL) to give the product (9.25 g, 72% yield) as a white solid. LCMS (ESI) m/z: [M+H] calcd for $C_{16}H_{25}N_5O_2$: 320.21; found 320.2.

Building block D. 2-(4-(6-(tert-butoxycarbonyl)-5,6,7,8-tetrahydropyrido[4,3-d]pyrimidin-2-yl)piperazin-1-yl)pyrimidine-5-carboxylic acid

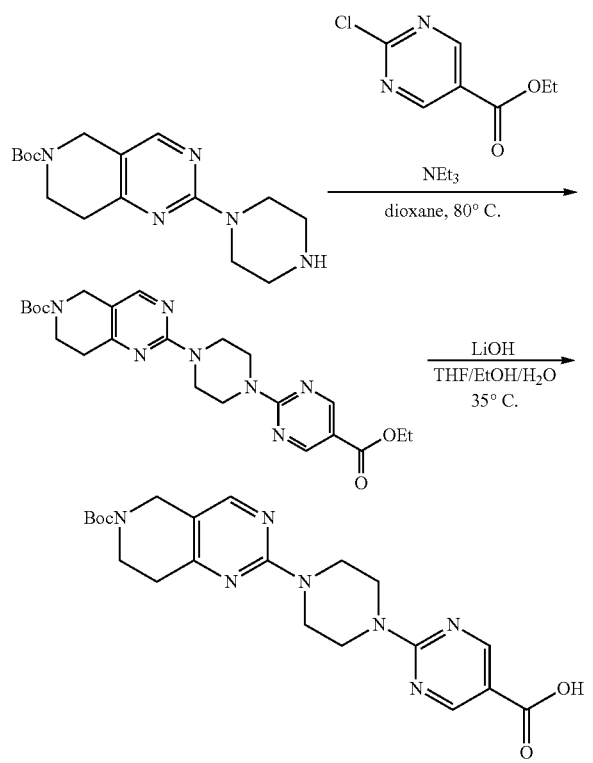

Step 1: Synthesis of tert-butyl 2-(4-(5-(ethoxycarbonyl)pyrimidin-2-yl)piperazin-1-yl)-7,8-dihydropyrido[4,3-d]pyrimidine-6(5H)-carboxylate To a solution of ethyl 2-chloropyrimidine-5-carboxylate (4.09 g, 21.92 mmol, 1.0 equiv) in dioxane (80 mL) was added tert-butyl 2-(piperazin-1-yl)-7,8-dihydropyrido[4,3-d]pyrimidine-6(5H)-carboxylate (7 g, 21.92 mmol, 1.0 equiv) and $Et_3N$ (9.15 mL, 65.75 mmol, 3.0 equiv). The mixture was stirred at 90° C. for 64 h. The solution was poured into $H_2O$ (200 mL) and then the mixture was filtered and the filter cake was washed with $H_2O$ (100 mL) followed by petroleum ether (60 mL). The filter cake was dried under reduced pressure to give the product (10.1 g, 92% yield) as a brown solid. LCMS (ESI) m/z: [M+H] calcd for $C_{23}H_{31}N_7O_4$: 470.25; found 470.4.

Step 2: Synthesis of 2-(4-(6-(tert-butoxycarbonyl)-5,6,7,8-tetrahydropyrido[4,3-d]pyrimidin-2-yl)piperazin-1-yl)pyrimidine-5-carboxylic acid To a solution of tert-butyl 2-(4-(5-(ethoxycarbonyl)pyrimidin-2-yl)piperazin-1-yl)-7,8-dihydropyrido[4,3-d]pyrimidine-6(5H)-carboxylate (6.0 g, 12.78 mmol, 1.0 equiv) in THF (40 mL), EtOH (20 mL) and $H_2O$ (40 mL) was added $LiOH·H_2O$ (1.07 g, 25.56 mmol, 2.0 equiv). The reaction mixture was stirred at 35° C. for 15 h. The mixture was then concentrated under reduced pressure to remove THF and EtOH. The mixture was then diluted with $H_2O$ (500 mL) and was adjusted to pH 3 with aqueous HCl (1 N). The mixture was filtered and the filter cake was washed with $H_2O$ (80 mL) followed by petroleum ether (80 mL). The filter cake was dried under reduced pressure to give the product (3.8 g, 65% yield) as a white solid. LCMS (ESI) m/z: [M+H] calcd for $C_{21}H_{27}N_7O_4$: 442.22; found 442.3.

Building block E. tert-butyl methyl((2-(piperazin-1-yl)pyrimidin-5-yl)methyl)carbamate

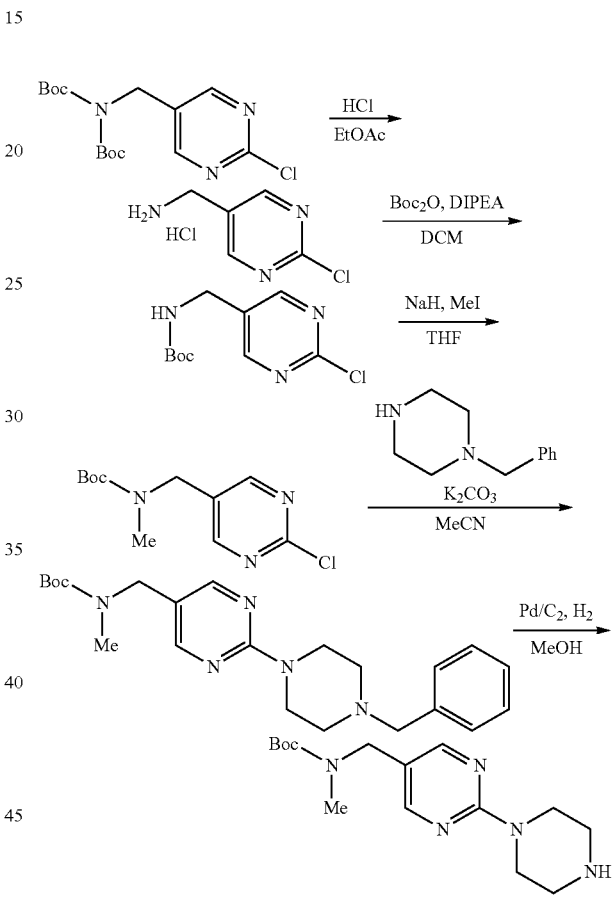

Step 1: Synthesis of (2-chloropyrimidin-5-yl)methanamine

To a solution of tert-butyl N-tert-butoxycarbonyl-N-((2-chloropyrimidin-5-yl)methyl)carbamate (28 g, 81.44 mmol, 1.0 equiv) in EtOAc (30 mL) was added HCl in EtOAc (260 mL). The reaction mixture was stirred at room temperature for 5 h. The reaction mixture was filtered and the filter cake was washed with EtOAc (100 mL). The solid cake was dried under reduced pressure to give the product (14.3 g, 96.6% yield) as a white solid.

Step 2: Synthesis of tert-butyl ((2-chloropyrimidin-5-yl)methyl)carbamate

To a solution of (2-chloropyrimidin-5-yl)methanamine (13 g, 72.21 mmol, 1.0 equiv, HCl) in DCM (130 mL) was added DIPEA (20.41 mL, 144.42 mmol, 1.8 equiv) and Boc₂O (16.59 mL, 72.21 mmol, 1.0 equiv), then the mixture was stirred at room temperature for 3 h. The reaction mixture was added to H₂O (100 mL) and then the aqueous layer was separated and extracted with DCM (2×100 mL). Then combined organic phase was washed with sat. NH₄Cl (2×200 mL) and brine (2×200 mL), dried with anhydrous Na₂SO₄, filtered and concentrated under reduced pressure. The residue was purified by silica gel chromatography (1/0 to 1/1 petroleum ether/EtOAc) to give the product (12 g, 68.2% yield) as a white solid.

Step 3: Synthesis of tert-butyl ((2-chloropyrimidin-5-yl)methyl)(methyl)carbamate To a solution of tert-butyl ((2-chloropyrimidin-5-yl)methyl)carbamate (11 g, 45.14 mmol, 1.0 equiv) and MeI (14.05 mL, 225.70 mmol, 5.0 equiv) in THF (150 mL) was added NaH (1.99 g, 49.65 mmol, 60 wt. %, 1.1 equiv) at 0° C. The mixture was stirred at 0° C. for 3 h and then the reaction was quenched with H₂O (100 mL). The aqueous phase was extracted with EtOAc (3×150 mL) and the combined organic phase was washed with brine (50 mL), dried with anhydrous Na₂SO₄, filtered and concentrated under reduced pressure. The residue was purified by silica gel chromatography (1/0 to 3/1 petroleum ether/EtOAc) to give the product (9 g, 77.4% yield) as a white solid.

Step 4: Synthesis of tert-butyl ((2-(4-benzylpiperazin-1-yl)pyrimidin-5-yl)methyl)(methyl)carbamate To a solution of tert-butyl ((2-chloropyrimidin-5-yl)methyl)(methyl)carbamate (9 g, 34.92 mmol, 1.0 equiv) in MeCN (90 mL) was added 1-benzylpiperazine (8.70 g, 34.92 mmol, 1.0 equiv, 2HCl), and K₂CO₃ (24.13 g, 174.61 mmol, 5.0 equiv). The reaction mixture was stirred at 80° C. for 20 h. The mixture was then filtered and concentrated under reduced pressure. The residue was purified by silica gel chromatography (1/0 to 1/1 petroleum ether/EtOAc) to give the product (12 g, 86.4% yield) as a yellow oil.

Step 5: Synthesis of tert-butyl methyl((2-(piperazin-1-yl)pyrimidin-5-yl)methyl)carbamate To a solution of tert-butyl ((2-(4-benzylpiperazin-1-yl)pyrimidin-5-yl)methyl)(methyl)carbamate (12 g, 30.19 mmol, 1.0 equiv) in MeOH (120 mL) was added Pd/C (2 g, 10 wt. %). The suspension was degassed and purged with H₂ and then the mixture was stirred under H₂ (15 psi) at room temperature for 3 h. The reaction mixture was filtered through Celite and the filtrate was concentrated under reduced pressure. The residue was purified by silica gel chromatography 1/0 to 1/1 petroleum ether/EtOAc) to give semi-pure material (9 g) as a yellow oil. Petroleum ether was added to the residue and the solution was stirred at −60° C. until solid appeared. The suspension was filtered and the filtrate was concentrated under reduced pressure to give the product (4.07 g, 55.6% yield) as a yellow oil. LCMS (ESI) m/z: [M+H] calcd for C₁₅H₂₅N₅O₂: 308.21; found 308.1.

Building block F. 2-(4-(5-(Wert-butoxycarbonyl)(methyl)amino)methyl) pyrimidin-2-yl)piperazin-1-yl)pyrimidine-5-carboxylic acid

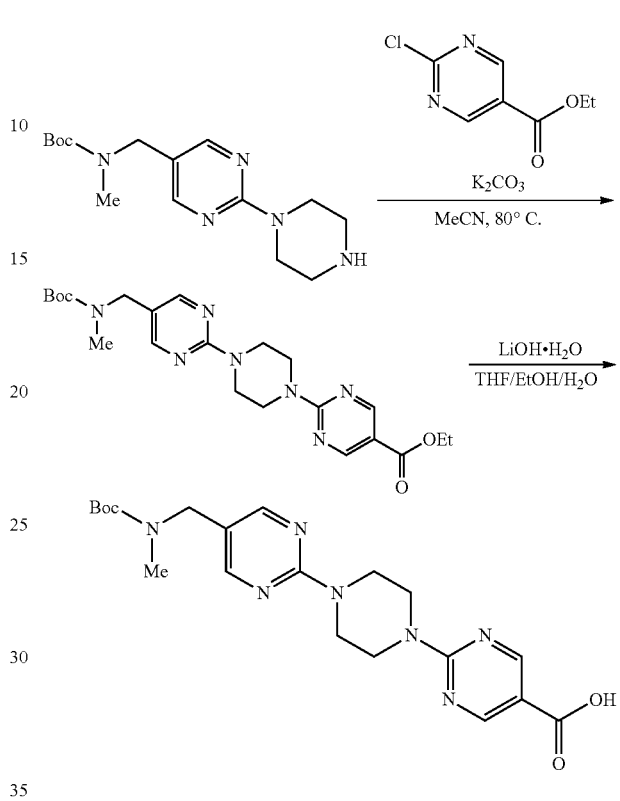

Step 1: Synthesis of ethyl 2-(4-(5-(((tert-butoxycarbonyl)(methyl)amino)methyl) pyrimidin-2-yl)piperazin-1-yl)pyrimidine-5-carboxylate To a mixture of tert-butyl methyl((2-(piperazin-1-yl)pyrimidin-5-yl)methyl)carbamate (4.3 g, 13.99 mmol, 1.0 equiv) and ethyl 2-chloropyrimidine-5-carboxylate (2.87 g, 15.39 mmol, 1.1 equiv) in MeCN (20 mL) was added K₂CO₃ (3.87 g, 27.98 mmol, 2.0 equiv). The mixture was stirred at 80° C. for 12 h. The reaction mixture then cooled to room temperature and was filtered. The filtrate was concentrated under reduced pressure and the crude product was purified by silica gel chromatography (1/0 to 1/1 petroleum ether/EtOAc) to give the product (4.7 g, 71.3% yield) as a white solid.

Step 2: Synthesis of 2-(4-(5-(((tert-butoxycarbonyl)(methyl)amino)methyl) pyrimidin-2-yl)piperazin-1-yl)pyrimidine-5-carboxylic acid To a solution of ethyl 2-(4-(5-(((tert-butoxycarbonyl)(methyl)amino)methyl)pyrimidin-2-yl)piperazin-1-yl)pyrimidine-5-carboxylate (6 g, 13.11 mmol, 1.0 equiv) in THF (100 mL), EtOH (30 mL), and H₂O (30 mL) was added LiOH·H₂O (1.10 g, 26.23 mmol, 2.0 equiv). The mixture was stirred at room temperature for 16 h. The mixture was then concentrated under reduced pressure to remove THF and EtOH and then neutralized by the addition of 1N HCl. The resulting precipitate was collected by filtration to give the product (5.11 g, 90.1% yield) as a white solid. LCMS (ESI) m/z: [M+H] calcd for $C_{20}H_{27}N_7O_4$: 430.22; found 430.2.

Building block G. tert-butyl N-tert-butoxycarbonyl-$N_4$(2-(2-((tert-butyl(diphenyl)silyl)oxymethyl)piperazin-1-yl)pyrimidin-5-yl)methyl)carbamate

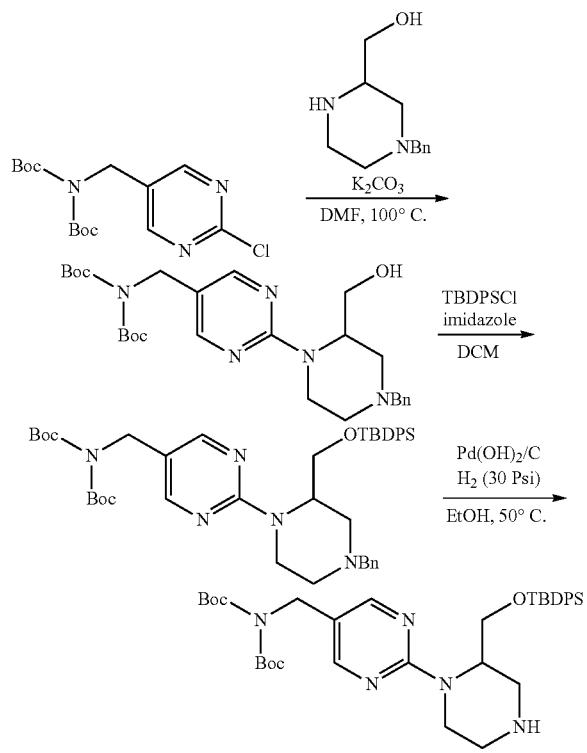

Step 1: Synthesis of tert-butyl N-((2-(4-benzyl-2-(hydroxymethyl)piperazin-1-yl)pyrimidin-5-yl)methyl)-N-tert-butoxycarbonyl-carbamate To a solution of tert-butyl N-tert-butoxycarbonyl-N-((2-chloropyrimidin-5-yl)methyl)carbamate (18.33 g, 53.32 mmol, 1.1 equiv) and (4-benzylpiperazin-2-yl)methanol (10 g, 48.48 mmol, 1.0 equiv) in DMF (100 mL) was added $K_2CO_3$ (13.40 g, 96.95 mmol, 2.0 equiv). The mixture was stirred at 100° C. for 12 h. The reaction mixture was then cooled to room temperature and $H_2O$ (100 mL) was added. The aqueous layer was extracted with EtOAc (2×150 mL) and the combined organic layer was washed with brine (20 mL), dried with $Na_2SO_4$, filtered and the filtrate was concentrated under reduced pressure to give the product (7.3 g, 29.3% yield) as a yellow oil. LCMS (ESI) m/z: [M+H] calcd for $C_{27}H_{39}N_5O_5$: 514.31; found 514.5.

Step 2: Synthesis of tert-butyl N-((2-(4-benzyl-2-((tert-butyl(diphenyl)silyl)oxymethyl)piperazin-1-yl)pyrimidin-5-yl)methyl)-N-tert-butoxycarbonyl-carbamate To a solution of tert-butyl N-((2-(4-benzyl-2-(hydroxymethyl)piperazin-1-yl)pyrimidin-5-yl)methyl)-N-tert-butoxycarbonyl-carbamate (2.3 g, 4.48 mmol, 1.0 equiv) in DCM (30 mL) was added imidazole (609.69 mg, 8.96 mmol, 2.0 equiv) and TBDPSCl (1.73 mL, 6.72 mmol, 1.5 equiv). The reaction mixture was stirred at room temperature for 2 h. The mixture was then washed with $H_2O$ (100 mL) and the aqueous phase extracted with EtOAc (2×60 mL). The combined organic phase was washed with brine (20 mL), dried with $Na_2SO_4$, filtered and concentrated under reduced pressure. The residue was purified by silica gel chromatography (20/1 to 3/1 petroleum ether/EtOAc) to give the product (4 g, 59.4% yield) as a yellow oil. LCMS (ESI) m/z: [M+H] calcd for $C_{43}H_{57}N_5O_5Si$: 752.42; found 752.4.

Step 3: Synthesis of tert-butyl N-tert-butoxycarbonyl-N-((2-(2-((tert-butyl(diphenyl)silyl)oxymethyl) piperazin-1-yl)pyrimidin-5-yl)methyl)carbamate To a solution of tert-butyl N-((2-(4-benzyl-2-((tert-butyl (diphenyl)silyl)oxymethyl)piperazin-1-yl)pyrimidin-5-yl) methyl)-N-tert-butoxycarbonyl-carbamate (3.3 g, 4.39 mmol, 1.0 equiv) in EtOH (10 mL) was added $Pd(OH)_2/C$ (1 g, 10 wt. %). The mixture was heated to 50° C. under $H_2$ (30 psi) for 30 h. The mixture was then cooled to room temperature, filtered through Celite, and concentrated under reduced pressure. The residue was purified by silica gel chromatography (20/1 to 3/1 EtOAc/EtOH) to give the product (1.44 g, 45.6% yield) as a yellow solid. LCMS (ESI) m/z: [M+H] calcd for $C_{36}H_{51}N_5O_5Si$: 662.38; found 662.3.

Building block H. 2-(4-(5-(((Cert-butoxycarbonyl) amino)methyl)pyrimidin-2-yl)-3-(hydroxymethyl) piperazin-1-yl)pyrimidine-5-carboxylic acid

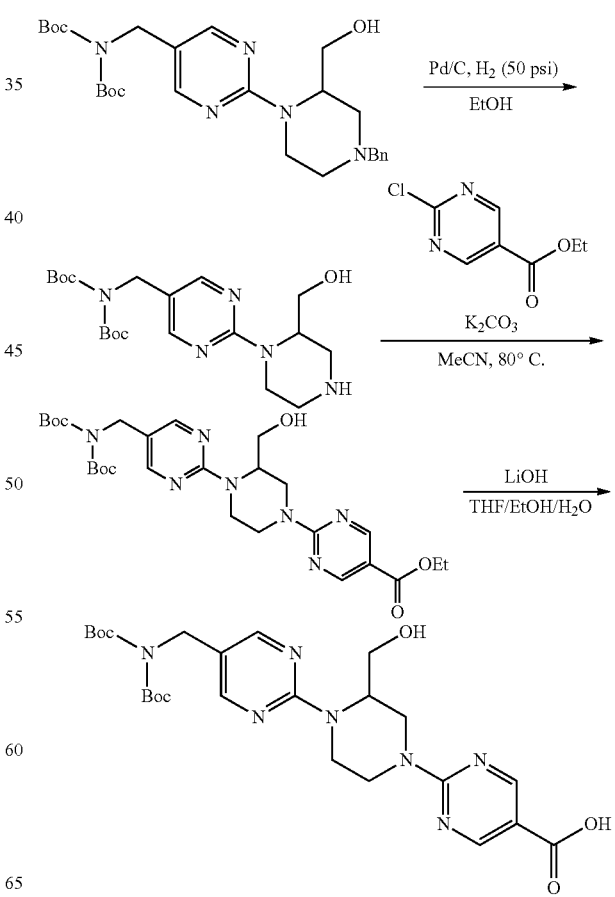

Step 1: Synthesis of tert-butyl N-tert-butoxycarbonyl-N-((2-(2-(hydroxymethyl)piperazin-1-yl)pyrimidin-5-yl)methyl)carbamate To a solution of tert-butyl N-((2-(4-benzyl-2-(hydroxymethyl)piperazin-1-yl)pyrimidin-5-yl)methyl)-N-tert-butoxycarbonyl-carbamate (3 g, 5.84 mmol, 1.0 equiv) in EtOH (40 mL) was added Pd/C (2 g, 10 wt. %). The suspension was degassed and purged with H$_2$, then stirred under H$_2$ (50 psi) at 30° C. for 16 h. The reaction mixture was cooled to room temperature and filtered through Celite and then concentrated under reduced pressure to give the product (1.6 g, crude) as a yellow oil. LCMS (ESI) m/z: [M+H] calcd for C$_{20}$H$_{33}$N$_5$O$_5$: 424.26; found 424.3.

Step 2: Synthesis of ethyl 2-(4-(5-((bis(tert-butoxycarbonyl)amino)methyl)pyrimidin-2-yl)-3-(hydroxymethyl)piperazin-1-yl)pyrimidine-5-carboxylate To a solution of tert-butyl N-tert-butoxycarbonyl-N-((2-(2-(hydroxymethyl)piperazin-1-yl)pyrimidin-5-yl)methyl)carbamate (1.4 g, 3.31 mmol, 1.0 equiv) in MeCN (20 mL) was added K$_2$CO$_3$ (2.28 g, 16.53 mmol, 5.0 equiv) and ethyl 2-chloropyrimidine-5-carboxylate (616.84 mg, 3.31 mmol, 1.0 equiv). The solution was stirred at 80° C. for 4 h. The mixture was cooled to room temperature and poured into H$_2$O (30 mL). The aqueous layer was extracted with EtOAc (2×30 mL) and the combined organic layer was washed with brine (20 mL), dried with Na$_2$SO$_4$, filtered and concentrated under reduced pressure. The mixture was purified by silica gel chromatography (20/1 to 3/1 petroleum ether/EtOAc) to give the product (1.6 g, 66.7% yield) as a light yellow solid. LCMS (ESI) m/z: [M+H] calcd for C$_{27}$H$_{39}$N$_7$O$_7$: 574.30; found 574.4.

Step 3: Synthesis of 2-(4-(5-(((tert-butoxycarbonyl)amino)methyl)pyrimidin-2-yl)-3-(hydroxymethyl)piperazin-1-yl)pyrimidine-5-carboxylic acid To a solution of ethyl 2-(4-(5-((bis(tert-butoxycarbonyl)amino)methyl)pyrimidin-2-yl)-3-(hydroxymethyl)piperazin-1-yl)pyrimidine-5-carboxylate (1.4 g, 2.44 mmol, 1.0 equiv) in THF (6 mL) and EtOH (6 mL) at 0° C. was added a solution of LiOH.H$_2$O (512.07 mg, 12.20 mmol, 5.0 equiv) in H$_2$O (3 mL). The reaction mixture was warmed to room temperature and stirred for 2 h. The mixture was then concentrated under reduced pressure to remove THF and EtOH. The aqueous phase was adjusted to pH 3 with 0.1M HCl and the resulting suspension was filtered. The solid cake was dried under reduced pressure to give the product (613.14 mg, 55.6% yield) as a white solid. LCMS (ESI) m/z: [M+H] calcd for C$_{20}$H$_{27}$N$_7$O$_5$: 446.22; found 446.2.

Building block I. tert-butyl N-[(tert-butoxy)carbonyl]-N-({2-[(3R)-3-(hydroxymethyl)piperazin-1-yl]pyrimidin-5-yl}methyl)carbamate

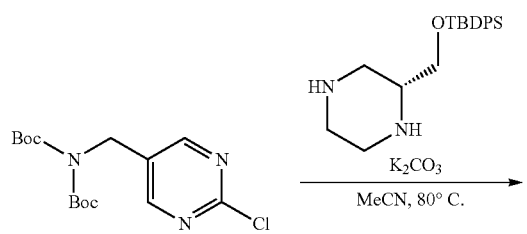

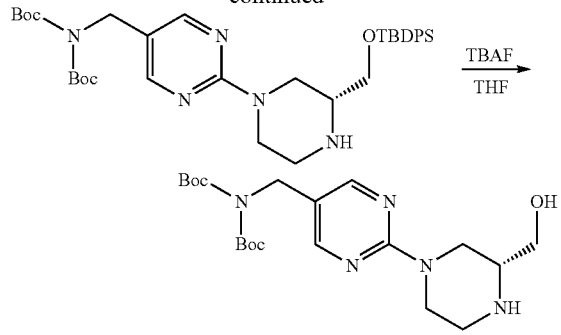

Step 1: Synthesis of (R)-tert-butyl-N-tert-butoxycarbonyl-((2-(3-(((tert-butyldiphenylsilyl)-oxy)methyl)piperazin-1-yl)pyrimidin-5-yl)methyl)carbamate To a solution of tert-butyl-N-tert-butoxycarbonyl-((2-chloropyrimidin-5-yl)methyl)carbamate (24.24 g, 70.51 mmol, 1.0 equiv) in MeCN (300 mL) was added (R)-2-(((tert-butyldiphenylsilyl)oxy)methyl)piperazine (25 g, 70.51 mmol, 1.0 equiv) and K$_2$CO$_3$ (29.24 g, 211.53 mmol, 3.0 equiv). The mixture was stirred at 80° C. for 16 h. The reaction mixture was then cooled to room temperature, diluted with EtOAc (200 mL), filtered and the filtrate was concentrated under reduced pressure. Purification by silica gel chromatography (0→100% EtOAc/petroleum ether) afforded the desired product (46.5 g, 94% yield) as a white solid.

Step 2: Synthesis of tert-butyl N-[(tert-butoxy)carbonyl]-N-({2-[(3R)-3-(hydroxymethyl)piperazin-1-yl]pyrimidin-5-yl}methyl)carbamate To a solution of (R)-tert-butyl-N-tert-butoxycarbonyl-((2-(3-(((tert-butyldiphenylsilyl)oxy)methyl)piperazin-1-yl)pyrimidin-5-yl)methyl)carbamate (12 g, 18.13 mmol, 1.0 equiv) in THF (120 mL) was added TBAF (1 M, 23.93 mL, 1.3 equiv). The mixture was stirred at room temperature for 2 h. The reaction mixture was then poured into H$_2$O (300 mL) and the aqueous phase was extracted with EtOAc (3×80 mL). The combined organic phases were combined, washed with brine (80 mL), dried, filtered and the filtrate was concentrated under reduced pressure. Purification by silica gel chromatography (0→20% MeOH/DCM) afforded the desired product (5 g, 64% yield) as a yellow solid.

Building block J. 2-{4-[5-({[(tert-butoxy)carbonyl]amino}methyl)pyrimidin-2-yl]piperazin-1-yl}pyrimidine-5-carboxylic acid

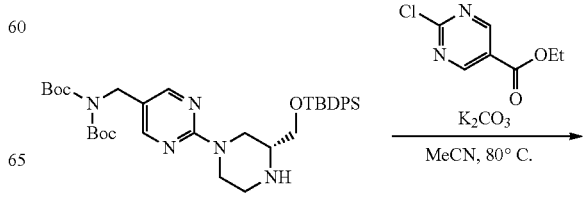

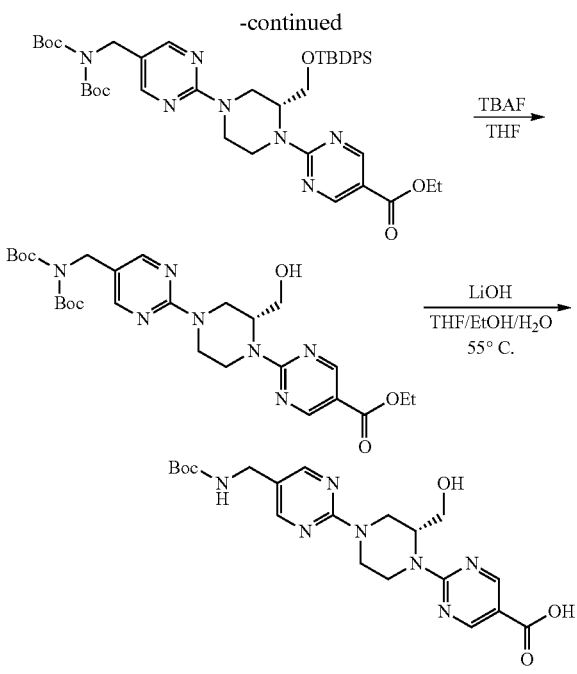

Step 1: Synthesis of (R)-ethyl 2-(4-(5-(((di-tert-butoxycarbonyl)amino)methyl)pyrimidin-2-yl)-2-(((tert-butyldiphenylsilyl)oxy)methyl)piperazin-1-yl)pyrimidine-5-carboxylate To a solution of (R)-tert-butyl-N-tert-butoxycarbonyl-N-((2-(3-(((tert-butyldiphenylsilyl)oxy)methyl)piperazin-1-yl)pyrimidin-5-yl)methyl)carbamate (31.5 g, 45.21 mmol, 1.0 equiv) in MeCN (350 mL) was added ethyl 2-chloropyrimidine-5-carboxylate (8.44 g, 45.21 mmol, 1.0 equiv) and $K_2CO_3$ (18.75 g, 135.63 mmol, 3.0 equiv). The mixture was stirred at 80° C. for 16 h. The reaction mixture was then cooled to room temperature, diluted with EtOAc (150 mL), and filtered to remove inorganic salts. The filtrate was then concentrated under reduced pressure. Purification by silica gel chromatography (0→100% EtOAc/petroleum ether) afforded the desired product (33.5 g, 89% yield).

Step 2: Synthesis of (R)-ethyl 2-(4-(5-(((di-tert-butoxycarbonyl)amino)methyl)pyrimidin-2-yl)-2-(hydroxymethyl)piperazin-1-yl)pyrimidine-5-carboxylate To a solution of (R)-ethyl 2-(4-(5-(((di-tert-butoxycarbonyl)amino)methyl)pyrimidin-2-yl)-2-(((tert-butyldiphenylsilyl)oxy)methyl)piperazin-1-yl)pyrimidine-5-carboxylate (36.5 g, 44.95 mmol, 1.0 equiv) in THF (300 mL) was added TBAF (1 M, 59.33 mL, 1.32 equiv). The mixture was stirred at room temperature for 6 h, at which point the reaction mixture was poured into $H_2O$ (500 mL). The aqueous phase was separated and extracted with EtOAc (3×150 mL) and the combined organic layers were washed with brine (150 mL), dried, filtered, and the filtrate was concentrated under reduced pressure. Purification by silica gel chromatography (0→100% EtOAc/petroleum ether) afforded the desired product (17 g, 64% yield) as a yellow oil.

Step 3: Synthesis of (R)-2-(4-(5-(((tert-butoxycarbonyl)amino)methyl)pyrimidin-2-yl)-2-(hydroxymethyl)piperazin-1-yl)pyrimidine-5-carboxylic acid To a solution of (R)-ethyl 2-(4-(5-(((di-tert-butoxycarbonyl)amino)methyl)pyrimidin-2-yl)-2-(hydroxymethyl)piperazin-1-yl)pyrimidine-5-carboxylate (17 g, 29.64 mmol, 1.0 equiv) in $H_2O$ (160 mL), EtOH (80 mL) and THF (160 mL) was added $LiOH·H_2O$ (4.97 g, 118.54 mmol, 4.0 equiv). The reaction mixture was stirred at 55° C. for 16 h. To the mixture was then added $LiOH·H_2O$ (1.01 g, 24.00 mmol, 0.81 equiv) and the reaction mixture was stirred at 55° C. for an additional 9 h. The mixture was cooled to room temperature, diluted with $H_2O$ (150 mL), and concentrated under reduced pressure to remove THF and EtOH. The mixture was acidified (pH=5) with 1 N HCl, filtered, and the filter cake washed with $H_2O$ (2×30 mL). The filter cake was dried under reduced pressure to afford the desired product (9.2 g, 67% yield) as a white solid. LCMS (ESI) m/z: [M+H] calcd for $C_{20}H_{27}N_7O_5$: 446.22; found 446.1.

Building block K. tert-butyl N-[(tert-butoxy)carbonyl]-N-({2-[(3S)-3-(hydroxymethyl)piperazin-1-yl]pyrimidin-5-yl}methyl)carbamate

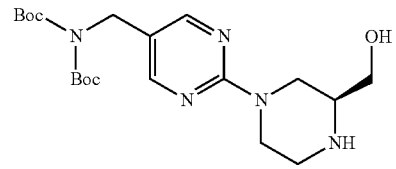 [SMILES: CC(C)(C)OC(=O)N(Cc1cnc(N2CCN[C@H](CO)C2)nc1)C(=O)OC(C)(C)C]

This building block is prepared by a process similar to that for Building block I by utilizing [(2S)-piperazin-2-yl]methanol.

Building block L. 2-[(2S)-4-[5-({[(tert-butoxy)carbonyl]amino}methyl)pyrimidin-2-yl]-2-(hydroxymethyl)piperazin-1-yl]pyrimidine-5-carboxylic acid

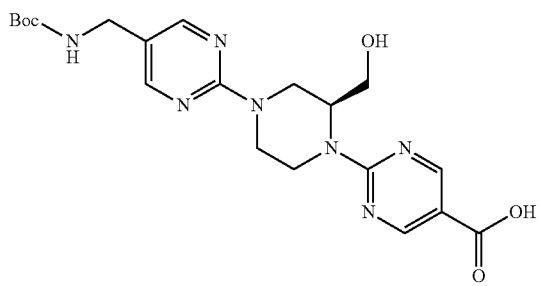 [SMILES: CC(C)(C)OC(=O)NCc1cnc(N2CCN(c3ncc(C(=O)O)cn3)[C@H](CO)C2)nc1]

This building block is prepared from Building block K by a process similar to that for Building block J.

Building block M. tert-butyl 2-[(3R)-3-(hydroxymethyl)piperazin-1-yl]-5H,6H,7H,8H-pyrido[4,3-d]pyrimidine-6-carboxylate

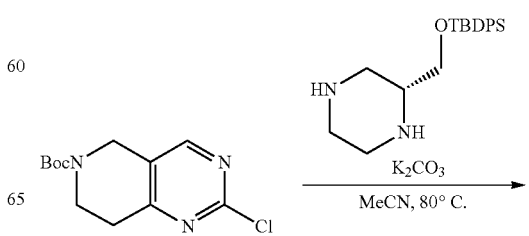

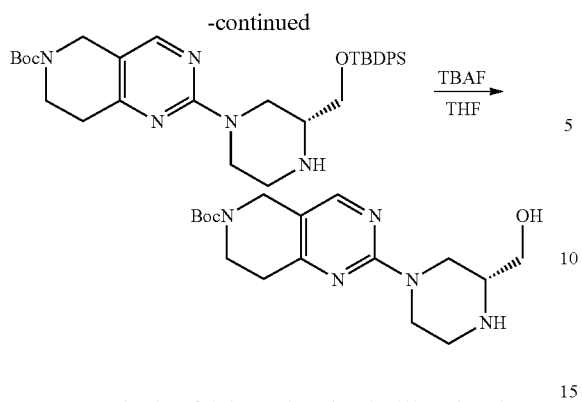

Step 1: Synthesis of (R)-tert-butyl 2-(3-(((tert-butyl-diphenylsilyl)oxy)-methyl)piperazin-1-yl)-'7,8-dihydropyrido[4,3-d]pyrimidine-6(5H)-carboxylate To a solution of (R)-2-(((tert-butyldiphenylsilyl)oxy) methyl)piperazine (25 g, 70.51 mmol, 1.0 equiv) in MeCN (250 mL) was added $K_2CO_3$ (29.24 g, 211.53 mmol, 3.0 equiv) and tert-butyl 2-chloro-7,8-dihydropyrido[4,3-d]pyrimidine-6(5H)-carboxylate (17.12 g, 63.46 mmol, 0.9 equiv). The mixture was stirred at 80° C. for 17 h. The reaction mixture was then cooled to room temperature, filtered, and the filtrated was concentrated under reduced pressure. Purification by silica gel chromatography (0→100% EtOAc/petroleum ether) afforded the desired product (31 g, 73.5% yield) as a white solid. LCMS (ESI) m/z: [M+H] calcd for $C_{33}H_{45}N_5O_3Si$: 588.34; found 588.2.

Step 2: Synthesis of (R)-tert-butyl 2-(3-(hydroxymethyl)piperazin-1-yl)-7,8-dihydropyrido[4,3-d]pyrimidine-6(5H)-carboxylate To a mixture of (R)-tert-butyl 2-(3-(((tert-butyldiphenyl-silyl)oxy)methyl)piperazin-1-yl)-7,8-dihydropyrido[4,3-d] pyrimidine-6(5H)-carboxylate (12 g, 20.41 mmol, 1.0 equiv) in THF (120 mL) was added TBAF (1.0 M, 24.50 mL, 1.2 equiv). The mixture was stirred at room temperature for 5 h. The mixture was poured into $H_2O$ (100 mL), and the aqueous phase was extracted with EtOAc (2×100 mL). The combined organic phases were washed with brine (100 mL), dried, filtered, and the filtrate was concentrated under reduced pressure. Purification by silica gel chromatography (0→10% MeOH/DCM) afforded the desired product (6 g, 84.1% yield) as a white solid. LCMS (ESI) m/z: [M+H] calcd for $C_{17}H_{27}N_5O_3$: 350.22; found 350.2.

Building block N. 2-[(2R)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

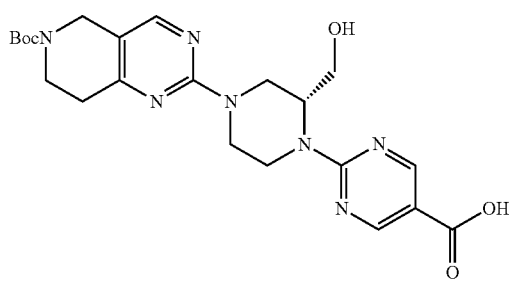 [SMILES: CC(C)(C)OC(=O)N1CCc2nc(N3CCN(c4ncc(C(=O)O)cn4)[C@@H](CO)C3)ncc2C1]

This building block is prepared from Building block M by a process similar to that for Building block J.

Building block O. tert-butyl 2-[(3S)-3-(hydroxymethyl)piperazin-1-yl]-5H,6H,7H,8H-pyrido[4,3-d] pyrimidine-6-carboxylate

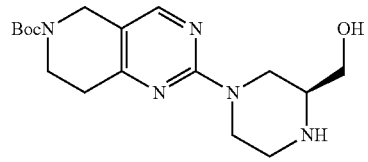 [SMILES: CC(C)(C)OC(=O)N1CCc2nc(N3CCN[C@H](CO)C3)ncc2C1]

This building block is prepared by a process similar to that for Building block I by utilizing tert-butyl 2-chloro-7,8-dihydropyrido[4,3-d]pyrimidine-6(5H)-carboxylate and [(2S)-piperazin-2-yl]methanol.

Building block P. 2-[(2S)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

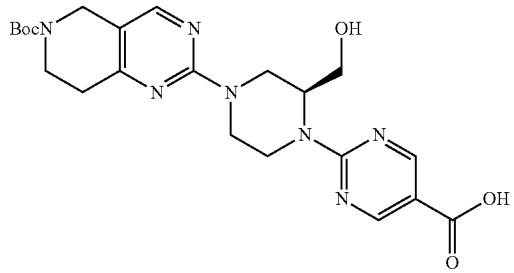 [SMILES: CC(C)(C)OC(=O)N1CCc2nc(N3CCN(c4ncc(C(=O)O)cn4)[C@H](CO)C3)ncc2C1]

This building block is prepared from Building block O by a process similar to that for Building block J.

Building block Q. tert-butyl N-[(tert-butoxy)carbonyl]-N-({2-[(3S)-3-[(dimethylamino)methyl]piperazin-1-yl]pyrimidin-5-yl}methyl)carbamate

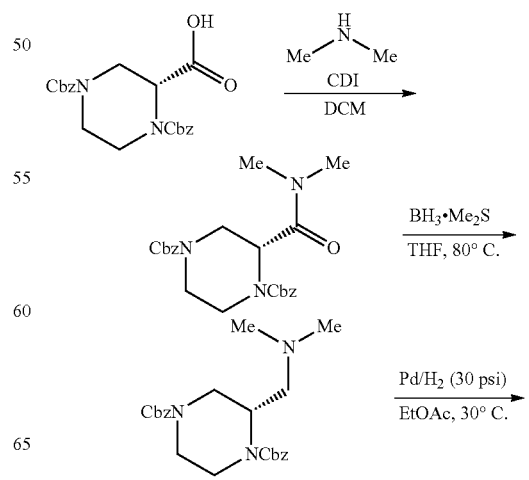

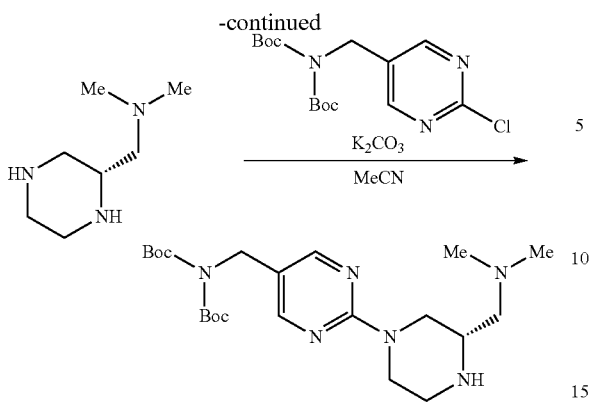

Step 1: Synthesis of (R)-dibenzyl 2-(dimethylcarbamoyl)piperazine-1,4-dicarboxylate To a solution of CDI (12.21 g, 75.30 mmol, 1.2 equiv) in DCM (300 mL) at 0° C. was added (R)-1,4-bis((benzyloxy)carbonyl)piperazine-2-carboxylic acid (25 g, 62.75 mmol, 1.0 equiv). The mixture was stirred at 0° C. for 0.5 h, at which time dimethylamine (8.51 mL, 92.87 mmol, 1.5 equiv, HCl) was added. The reaction mixture was warmed to room temperature and stirred for 12 h. The reaction mixture was then added to H$_2$O (200 mL), and the aqueous layer was separated and extracted with DCM (2×200 mL). The combined organic phases were washed with brine (2×50 mL), dried, filtered, and the filtrate was concentrated under reduced pressure. Purification by silica gel chromatography (50→100% EtOAc/petroleum ether) afforded the desired product (23.5 g, 88.0% yield) as a yellow oil.

Step 2: Synthesis of (S)-dibenzyl 2-((dimethylamino)methyl)piperazine-1,4-dicarboxylate To a solution of (R)-dibenzyl 2-(dimethylcarbamoyl)piperazine-1,4-dicarboxylate (28 g, 65.81 mmol, 1.0 equiv) in THF (300 mL) at 0° C. was added BH$_3$.Me$_2$S (10 M, 13.16 mL, 2.0 equiv). The reaction mixture was then stirred at 80° C. for 3 h. The reaction mixture was cooled to room temperature and then MeOH (50 mL) was added. After stirring for an additional 1 h the mixture was concentrated under reduced pressure. Purification by silica gel chromatography (50→100% EtOAc/petroleum ether) afforded the desired product (18 g, 66.5% yield) as a yellow oil.

Step 3: Synthesis of (R)-N,N-dimethyl-1-(piperazin-2-yl)methanamine

To a solution of (S)-dibenzyl 2-((dimethylamino)methyl)piperazine-1,4-dicarboxylate (18 g, 43.74 mmol, 1.0 equiv) in EtOAc (200 mL) was added Pd/C (1.5 g, 10 wt. %). The suspension was degassed under reduced pressure and purged with H$_2$ three times. The suspension was stirred under H$_2$ (30 psi) at 30° C. for 5 h. The reaction mixture was then filtered through celite and the filtrate was concentrated under reduced pressure to afford the desired product (6 g, 95.8% yield) as a yellow solid.

Step 4: Synthesis of tert-butyl N-tert-butoxycarbonyl-N-((2-((3S)-3-((dimethylamino)methyl)piperazin-1-yl)pyrimidin-5-yl)methyl)carbamate To a solution of (R)-N,N-dimethyl-1-(piperazin-2-yl)methanamine (2.8 g, 19.55 mmol, 1.0 equiv) in MeCN (40 mL) was added tert-butyl N-tert-butoxycarbonyl-N-((2-chloropyrimidin-5-yl)methyl)carbamate (6.72 g, 19.55 mmol, 1.0 equiv) and K$_2$CO$_3$ (5.40 g, 39.10 mmol, 2.0 equiv). The mixture was stirred at 80° C. for 24 h. The mixture was then cooled to room temperature, filtered, and the filter cake washed with EtOAc (3×10 mL). The filtrate was then concentrated under reduced pressure. Purification by silica gel chromatography (0→100% MeOH/EtOAc) afforded the desired product (5.3 g, 57.8% yield) as a yellow oil. LCMS (ESI) m/z: [M+H] calcd for C$_{22}$H$_{38}$N$_6$O$_4$: 451.31; found 451.2.

Building block R. 2-[(2S)-4-[5-({[(tert-butoxy)carbonyl]amino}methyl)pyrimidin-2-yl]-2-[(dimethylamino)methyl]piperazin-1-yl]pyrimidine-5-carboxylic acid

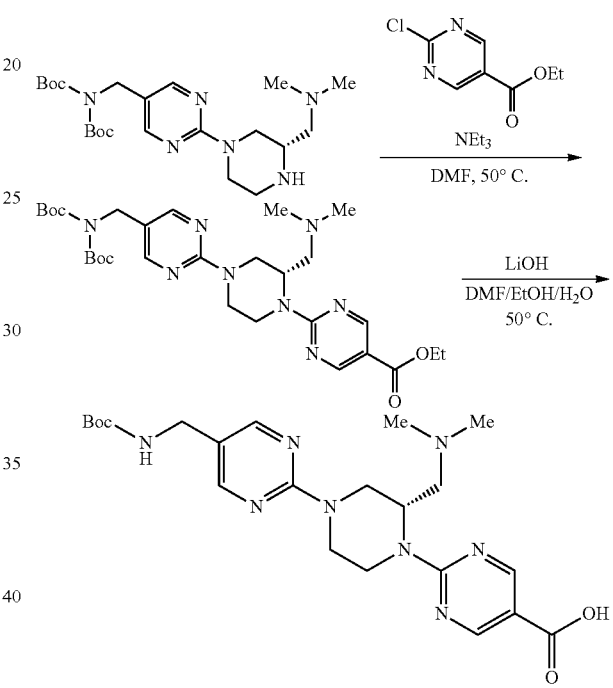

Step 1: Synthesis of (9-ethyl 2-(4-(5-(((bi-tert-butoxycarbonyl)amino)methyl) pyrimidin-2-yl)-2-((dimethylamino)methyl)piperazin-1-yl)pyrimidine-5-carboxylate To a solution of (S)-tert-butyl-N-tert-butoxycarbonyl ((2-(3-((dimethylamino)methyl) piperazin-1-yl)pyrimidin-5-yl)methyl)carbamate (3.26 g, 7.24 mmol, 1.0 equiv) in DMF (30 mL) was added Et$_3$N (3.02 mL, 21.71 mmol, 3.0 equiv) and ethyl 2-chloropyrimidine-5-carboxylate (1.47 g, 7.86 mmol, 1.1 equiv). The mixture was stirred at 50° C. for 3 h and then concentrated under reduced pressure to afford the desired product (4.35 g, crude) as a solution in DMF (30 mL), which was used directly in the next step. LCMS (ESI) m/z: [M+H] calcd for C$_{29}$H$_{44}$N$_8$O$_6$: 601.35; found 601.5.

Step 2: Synthesis of (S)-2-(4-(5-(((tert-butoxycarbonyl)amino)methyl)-pyrimidin-2-yl)-2-((dimethylamino)methyl)piperazin-1-yl)pyrimidine-5-carboxylic acid To a solution of (S)-ethyl 2-(4-(5-(((bi-tert-butoxycarbonyl)amino)methyl)-pyrimidin-2-yl)-2-((dimethylamino)

methyl)piperazin-1-yl)pyrimidine-5-carboxylate (4.35 g, 7.24 mmol, 1.0 equiv) in DMF (30 mL) was added DMF (50 mL), EtOH (30 mL), and H$_2$O (30 mL). To the solution was then added LiOH.H$_2$O (3 g, 71.50 mmol, 9.9 equiv) at 50° C. The reaction was stirred at 50° C. for 36 h. The mixture was then cooled to room temperature, neutralized with 0.5 N HCl, and concentrated under reduced pressure. Purification by reverse phase chromatography (2→30% MeCN/H$_2$O) afforded the desired product (1.15 g, 34% yield) as a white solid. LCMS (ESI) m/z: [M+H] calcd for C$_{22}$H$_{32}$N$_8$O$_4$: 473.26; found 473.3.

Building block S. tert-butyl N-[(tert-butoxy)carbonyl]-N-({2-[(3R)-3-[(dimethylamino)methyl]piperazin-1-yl]pyrimidin-5-yl}methyl)carbamate

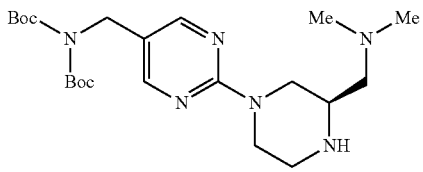 [SMILES: CN(C)C[C@@H]1CN(c2ncc(CN(C(=O)OC(C)(C)C)C(=O)OC(C)(C)C)cn2)CCN1]

This building block is prepared by a process similar to that for Building block I by utilizing dimethyl({[(2S)-piperazin-2-yl]methyl})amine.

Building block T. 2-[(2R)-4-[5-({[(tert-butoxy)carbonyl]amino}methyl)pyrimidin-2-yl]-2-[(dimethylamino)methyl]piperazin-1-yl]pyrimidine-5-carboxylic acid

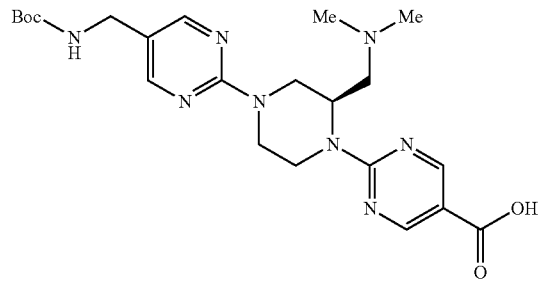 [SMILES: CN(C)C[C@@H]1CN(c2ncc(CNC(=O)OC(C)(C)C)cn2)CCN1c1ncc(C(=O)O)cn1]

This building block is prepared from Building block S by a process similar to that for Building block J.

Building block U. tert-butyl 2-[(3S)-3-[(dimethylamino)methyl]piperazin-1-yl]-5H,6H,7H,8H-pyrido[4,3-d]pyrimidine-6-carboxylate

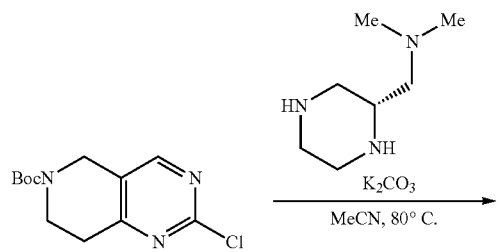

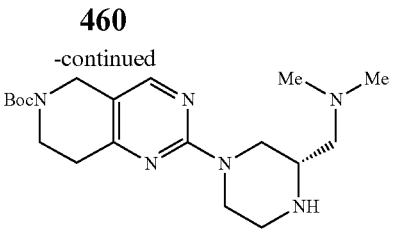

To a solution of tert-butyl 2-chloro-7,8-dihydropyrido[4,3-d]pyrimidine-6(5H)-carboxylate (4.80 g, 17.80 mmol, 1.4 equiv) in MeCN (45 mL) was added K$_2$CO$_3$ (10.42 g, 75.40 mmol, 3.0 equiv) and (R)-N,N-dimethyl-1-(piperazin-2-yl)methanamine (3.6 g, 25.13 mmol, 1.0 equiv). The mixture was stirred at 80° C. for 8 h. The mixture was then cooled to room temperature, filtered, and the filter cake was washed with EtOAc (50 mL). To the organic phase was added H$_2$O (50 mL) and the aqueous phase was extracted with EtOAc (3×50 mL). The combined organic phases were washed with brine (5 mL), dried, filtered and concentrated under reduced pressure. Purification by silica gel chromatography (8→67% EtOAc/petroleum ether) afforded the desired product (6.5 g, 63.5% yield) as a yellow oil.

Building block V. 2-[(2S)-4-{6-[(tert-butoxy)carbonyl]-5H,6H,7H,8H-pyrido[4,3-d]pyrimidin-2-yl}-2-[(dimethylamino)methyl]piperazin-1-yl]pyrimidine-5-carboxylic acid

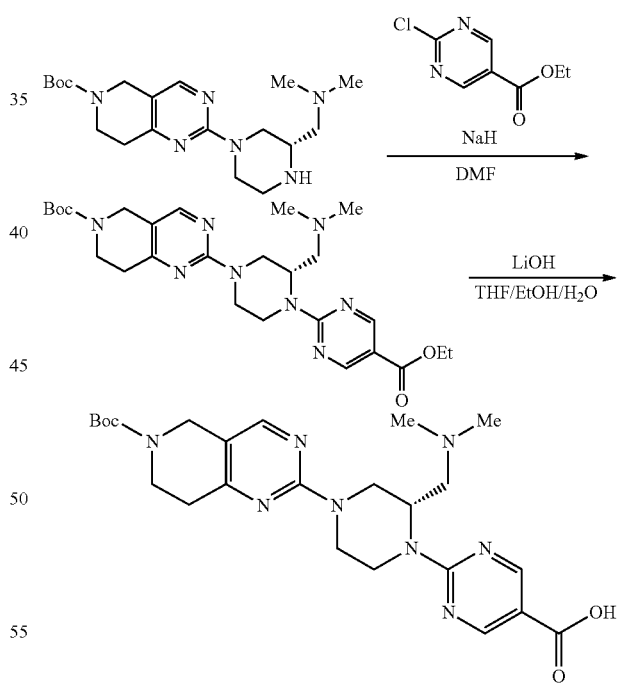

Step 1: Synthesis of (S)-tert-butyl 2-(3-((dimethylamino)methyl)-4-(5-(ethoxycarbonyl)pyrimidin-2-yl)piperazin-1-yl)-7,8-dihydropyrido[4,3-d]pyrimidine-6(5H)-carboxylate To a solution of (S)-tert-butyl 2-(3-((dimethylamino)methyl)piperazin-1-yl)-7,8-dihydropyrido[4,3-d]pyrimidine-6(5H)-carboxylate (3 g, 7.97 mmol, 1.0 equiv) in DMF (70 mL) at 0° C. was added NaH (382.44 mg, 9.56 mmol, 60 wt. %, 1.2 equiv). The suspension was stirred at 0° C. for 0.5 h, then ethyl 2-chloropyrimidine-5-carboxylate (1.49 g, 7.97 mmol, 1 equiv) in DMF (50 mL) was added, dropwise. The mixture was warmed to room temperature and stirred for 5 h. The mixture was then cooled to 0° C. and poured into H$_2$O (360 mL). The suspension was filtered, and the filter cake washed with H$_2$O (30 mL) and dried under reduced pressure. Purification by silica gel chromatography (6%→33% EtOAc/petroleum ether) afforded the desired product (1.8 g, 39.6% yield) as a brown oil.

Step 2: Synthesis of (S)-2-(4-(6-(tert-butoxycarbonyl)-5,6,7,8-tetrahydropyrido[4,3-d]pyrimidin-2-yl)-2-((dimethylamino)methyl)piperazin-1-yl)pyrimidine-5-carboxylic acid To a solution of (S)-tert-butyl 2-(3-((dimethylamino)methyl)-4-(5-(ethoxycarbonyl)pyrimidin-2-yl)piperazin-1-yl)-7,8-dihydropyrido[4,3-d]pyrimidine-6(5H)-carboxylate (1.1 g, 2.09 mmol, 1.0 equiv) in THF (5 mL), EtOH (2.5 mL), and H$_2$O (2.5 mL) was added LiOH.H$_2$O (175.30 mg, 4.18 mmol, 2.0 equiv). The mixture was stirred at room temperature for 2 h, at which point the pH was adjusted to 7 by the addition of 1 N HCl at 0° C. The mixture was concentrated under reduced pressure to remove THF and MeOH. The resulting suspension was filtered, and the filter cake was washed with H$_2$O (5 mL) and dried under reduced pressure to afford the desired product (680 mg, 65.3% yield) as a white solid. LCMS (ESI) m/z: [M+H] calcd for C$_{24}$H$_{34}$N$_8$O$_4$: 499.28; found 499.2.

Building block W. tert-butyl 2-[(3R)-3-[(dimethylamino)methyl]piperazin-1-yl]-5H,6H,7H,8H-pyrido[4,3-d]pyrimidine-6-carboxylate

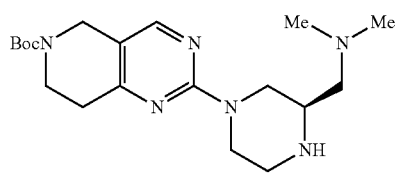 [SMILES: CN(C)C[C@@H]1CN(c2ncc3c(n2)CCN(C(=O)OC(C)(C)C)C3)CCN1]

This building block is prepared by a process similar to that for Building block I by utilizing tert-butyl 2-chloro-7,8-dihydropyrido[4,3-d]pyrimidine-6(5H)-carboxylate and dimethyl({[(2S)-piperazin-2-yl]methyl})amine.

Building block X. 2-[(2R)-4-{6-[(tert-butoxy)carbonyl]-5H,6H,7H,8H-pyrido[4,3-d] pyrimidin-2-yl}-2-[(dimethylamino)methyl]piperazin-1-yl]pyrimidine-5-carboxylic acid

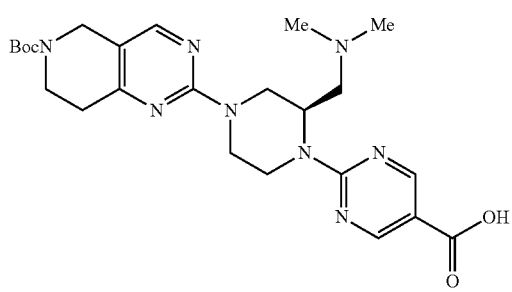 [SMILES: CN(C)C[C@@H]1CN(c2ncc3c(n2)CCN(C(=O)OC(C)(C)C)C3)CCN1c1ncc(C(=O)O)cn1]

This building block is prepared from Building block W by a process similar to that for Building block J.

Building block Y. tert-butyl (2R)-4-{6-[(tert-butoxy)carbonyl]-5H,6H,7H,8H-pyrido[4,3-d]pyrimidin-2-yl}piperazine-2-carboxylate

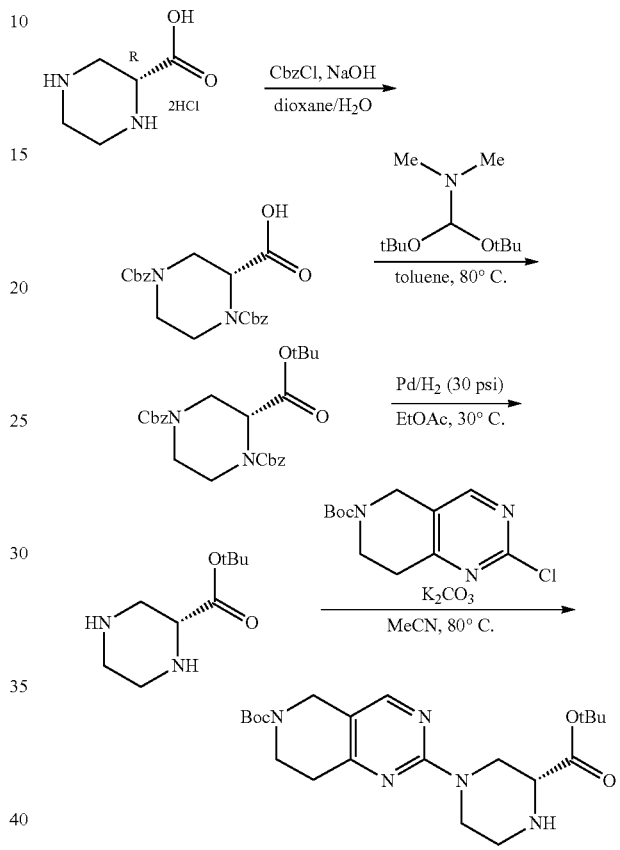

Step 1: Synthesis of (R)-1,4-bis((benzyloxy)carbonyl)piperazine-2-carboxylic acid To a solution of (R)-piperazine-2-carboxylic acid (70 g, 344.71 mmol, 1.0 equiv, 2HCl) in dioxane (1120 mL) and H$_2$O (700 mL) was added 50% aq. NaOH until the solution was pH=11. Benzyl chloroformate (156.82 mL, 1.10 mol, 3.2 equiv) was added and the reaction mixture was stirred at room temperature for 12 h. To the solution was then added H$_2$O (1200 mL) and the aqueous layer was washed with MTBE (3×800 mL). The aqueous layer was adjusted to pH=2 with concentrated HCl (12N) and extracted with EtOAc (2×1000 mL). The combined organic extracts were dried, filtered and the filtrate was concentrated under reduced pressure to afford the desired product (137 g, 99.8% yield) as a yellow solid. LCMS (ESI) m/z: [M+H] calcd for C$_{21}$H$_{22}$N$_2$O$_6$: 399.16; found 399.2.

Step 2: Synthesis of (R)-1,4-dibenzyl 2-tert-butyl piperazine-1,2,4-tricarboxylate To a solution of (R)-1,4-bis((benzyloxy)carbonyl)piperazine-2-carboxylic acid (50 g, 125.50 mmol, 1.0 equiv) in toluene (500 mL) at 80° C. was added 1,1-di-tert-butoxy- N,N-dimethylmethanamine (57.17 mL, 238.45 mmol, 1.9 equiv). The solution was stirred at 80° C. for 2 h, at which point the reaction mixture was cooled to room temperature and partitioned between EtOAc (300 mL) and H$_2$O (500 mL). The aqueous layer was extracted with EtOAc (2×500 mL) and the combined organic layers were dried, filtered and the filtrate was concentrated under reduced pressure. Purification by silica gel chromatography (0%-25% EtOAc/petroleum ether) afforded the desired product (35 g, 61.2% yield) as a white solid. LCMS (ESI) m/z: [M+Na] calcd for C$_{25}$H$_{30}$N$_2$O$_6$: 477.20; found 477.1.

Step 3: Synthesis of (R)-tert-butyl piperazine-2-carboxylate

To a solution of (R)-1,4-dibenzyl 2-tert-butyl piperazine-1,2,4-tricarboxylate (35 g, 77.01 mmol, 1.0 equiv) in EtOAc (350 mL) was added Pd/C (10 g, 10 wt. %). The suspension was degassed under reduced pressure and purged with H$_2$ three times. The mixture was stirred under H$_2$ (30 psi) at 30° C. for 4 h. The reaction mixture was then filtered through celite, the residue was washed with MeOH (5×200 mL), and the filtrate was concentrated under reduced pressure to afford the desired product (14 g, 79.6% yield) as yellow oil. LCMS (ESI) m/z: [M+H] calcd for C$_9$H$_{18}$N$_2$O$_2$: 187.15; found 187.1.

Step 4: Synthesis of (R)-tert-butyl 2-(3-(tert-butoxycarbonyl)piperazin-1-yl)-7,8-dihydropyrido[4,3-d]pyrimidine-6(5H)-carboxylate To a solution of tert-butyl (2R)-piperazine-2-carboxylate (12 g, 64.43 mmol, 1.0 equiv) in MeCN (200 mL) was added K$_2$CO$_3$ (17.81 g, 128.86 mmol, 2.0 equiv) and tert-butyl 2-chloro-7,8-dihydropyrido[4,3-d]pyrimidine-6(5H)-carboxylate (17.38 g, 64.43 mmol, 1.0 equiv). The reaction mixture was heated to 80° C. and stirred for 12 h. The reaction mixture was then cooled to room temperature and filtered, the residue was washed with EtOAc (3×150 mL), and the filtrate was concentrated under reduced pressure. Purification by silica gel chromatography (0%→100% EtOAc/petroleum ether) afforded the desired product (19 g, 69.2% yield) as a yellow solid. LCMS (ESI) m/z: [M+H] calcd for C$_{21}$H$_{33}$N$_5$O$_4$: 420.26; found 420.2.

Building block Z. 4-amino-2-[(2R)-2-[(tert-butoxy)carbonyl]-4-{6-[(tert-butoxy)carbonyl]-5H,6H,7H,8H-pyrido[4,3-d]pyrimidin-2-yl}piperazin-1-yl]pyrimidine-5-carboxylic acid

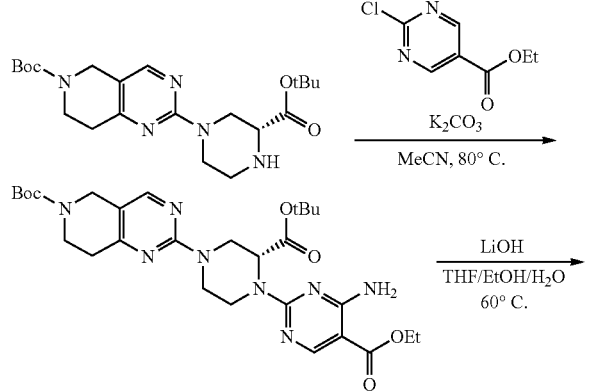

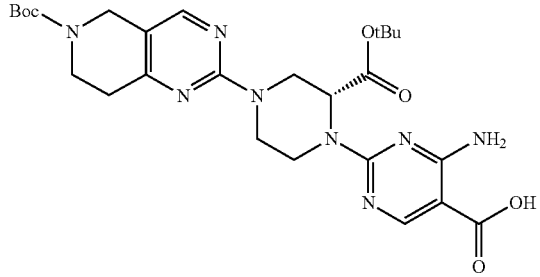

Step 1: Synthesis of (R)-tert-butyl 2-(4-(4-amino-5-(ethoxycarbonyl)pyrimidin-2-yl)-3-(tert-butoxycarbonyl)piperazin-1-yl)-7,8-dihydropyrido[4,3-d]pyrimidine-6(5H)-carboxylate To a stirred solution of (R)-tert-butyl 2-(3-(tert-butoxycarbonyl)piperazin-1-yl)-7,8-dihydropyrido[4,3-d]pyrimidine-6(5H)-carboxylate (12 g, 28.60 mmol, 1.0 equiv) in MeCN (150 mL) was added K$_2$CO$_3$ (7.91 g, 57.20 mmol, 2.0 equiv) and ethyl 4-amino-2-chloropyrimidine-5-carboxylate (6.92 g, 34.32 mmol, 1.2 equiv). The reaction mixture was stirred at 80° C. for 12 h, at which point the reaction mixture was filtered and the filtrate was concentrated under reduced pressure. Purification by silica gel chromatography (0%→17% EtOAc/petroleum ether) afforded the desired product (16 g, 91.6% yield) as a yellow solid. LCMS (ESI) m/z: [M+H] calcd for C$_{28}$H$_{40}$N$_8$O$_6$: 585.32; found 585.1.

Step 2: Synthesis of (R)-4-amino-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid To two separate batches run in parallel each containing a solution of (R)-tert-butyl 2-(4-(4-amino-5-(ethoxycarbonyl)pyrimidin-2-yl)-3-(tert-butoxycarbonyl)piperazin-1-yl)-7,8-dihydropyrido[4,3-d]pyrimidine-6(5H)-carboxylate (7 g, 11.97 mmol, 1.0 equiv) in THF (70 mL), EtOH (35 mL) and H$_2$O (35 mL) was added LiOH.H$_2$O (2.01 g, 47.89 mmol, 4.0 equiv). The mixtures were stirred at 60° C. for 3 h, at which point the two reaction mixtures were combined, and were adjusted to pH=7 with 1 N HCl. The mixture was concentrated under reduced pressure to remove THF and EtOH, filtered, and the residue was dried under reduced pressure. The residue was stirred in MTBE (100 mL) for 10 min, filtered, and the residue was dried under reduced pressure to afford the desired product (8.02 g, 55.1% yield) as a white solid. LCMS (ESI) m/z: [M+H] calcd for C$_{26}$H$_{36}$N$_8$O$_6$: 557.29; found 557.3.

Building block AA. tert-butyl (2S)-4-{6-[(tert-butoxy)carbonyl]-5H,6H,7H,8H-pyrido[4,3-d]pyrimidin-2-yl}piperazine-2-carboxylate

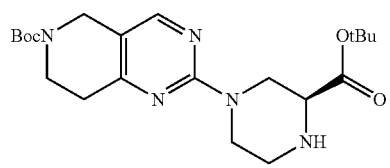 [SMILES: CC(C)(C)OC(=O)[C@@H]1CN(c2ncc3c(n2)CCN(C(=O)OC(C)(C)C)C3)CCN1]

This building block is prepared by a process similar to that for Building block I by utilizing tert-butyl 2-chloro-7,8-dihydropyrido[4,3-d]pyrimidine-6(5H)-carboxylate and tert-butyl (2S)-piperazine-2-carboxylate.

Building block AB. 4-amino-2-[(2S)-2-[(tert-butoxy)carbonyl]-4-{6-[(tert-butoxy)carbonyl]-5H,6H,7H,8H-pyrido[4,3-d] pyrimidin-2-yl}piperazin-1-yl]pyrimidine-5-carboxylic acid

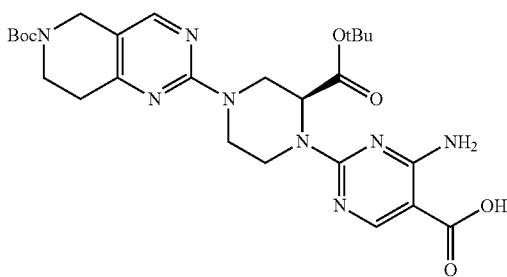 [SMILES: CC(C)(C)OC(=O)[C@@H]1CN(c2ncc3c(n2)CCN(C(=O)OC(C)(C)C)C3)CCN1c1ncc(C(=O)O)c(N)n1]

This building block is prepared from Building block AA by a process similar to that for Building block J by utilizing ethyl 4-amino-2-chloropyrimidine-5-carboxylate.

Building block AC. 4-amino-2-(4-{6-[(tert-butoxy)carbonyl]-5H,6H,7H,8H-pyrido[4,3-d]pyrimidin-2-yl}piperazin-1-yl)pyrimidine-5-carboxylic acid

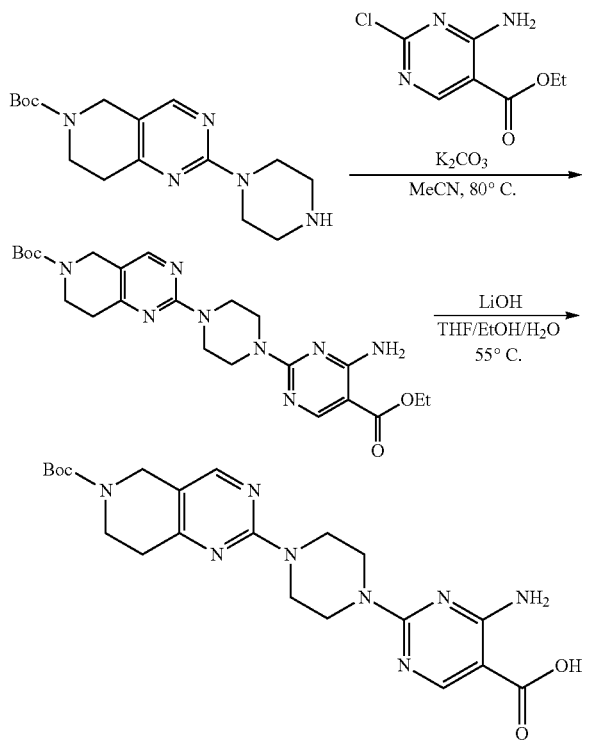

Step 1: Synthesis of tert-butyl 2-(4-(4-amino-5-(ethoxycarbonyl)pyrimidin-2-yl)piperazin-1-yl)-7,8-dihydropyrido[4,3-d]pyrimidine-6(5H)-carboxylate To a solution of tert-butyl 2-(piperazin-1-yl)-7,8-dihydropyrido[4,3-d]pyrimidine-6(5H)-carboxylate (8.3 g, 25.99 mmol, 1.0 equiv) and ethyl 4-amino-2-chloropyrimidine-5-carboxylate (5.24 g, 25.99 mmol, 1.0 equiv) in MeCN (100 mL) was added to $K_2CO_3$ (7.18 g, 51.97 mmol, 2.0 equiv). The reaction was stirred at 80° C. for 12 h. The reaction was then cooled to room temperature, DCM (100 mL) was added, and the reaction mixture was stirred for 30 min. The suspension was filtered, and the filter cake was washed with DCM (6×100 mL). The filtrate was concentrated under reduced pressure and the residue was triturated with EtOAc (30 mL), filtered and then the filter cake was dried under reduced pressure to afford the desired product (8.7 g, 65.9% yield) as light yellow solid.

Step 2: Synthesis of 4-amino-2-(4-(6-(tert-butoxycarbonyl)-5,6,7,8-tetrahydropyrido[4,3-d]pyrimidin-2-yl)piperazin-1-yl)pyrimidine-5-carboxylic acid To a solution of tert-butyl 2-(4-(4-amino-5-(ethoxycarbonyl)pyrimidin-2-yl)piperazin-1-yl)-7,8-dihydropyrido[4,3-d]pyrimidine-6(5H)-carboxylate (8.7 g, 17.95 mmol, 1.0 equiv) in THF (120 mL), EtOH (60 mL), and $H_2O$ (60 mL) was added $LiOH.H_2O$ (1.51 g, 35.91 mmol, 2.0 equiv). The mixture was stirred at 55° C. for 12 h. The reaction mixture was then concentrated under reduced pressure to remove EtOH and THF, and the reaction mixture was adjusted to pH=6 by the addition of 1 N HCl. The precipitate was filtered, and the filter cake was washed with $H_2O$ (3×50 mL) and then dried under reduced pressure to afford the desired product (7.3 g, 89.1% yield) as light yellow solid. LCMS (ESI) m/z: [M+H] calcd for $C_{21}H_{28}N_8O_4$: 457.23; found 457.2.

Building block AD. 4-amino-2-{4-[5-({[(tert-butoxy)carbonyl]amino}methyl)pyrimidin-2-yl]piperazin-1-yl}pyrimidine-5-carboxylic acid

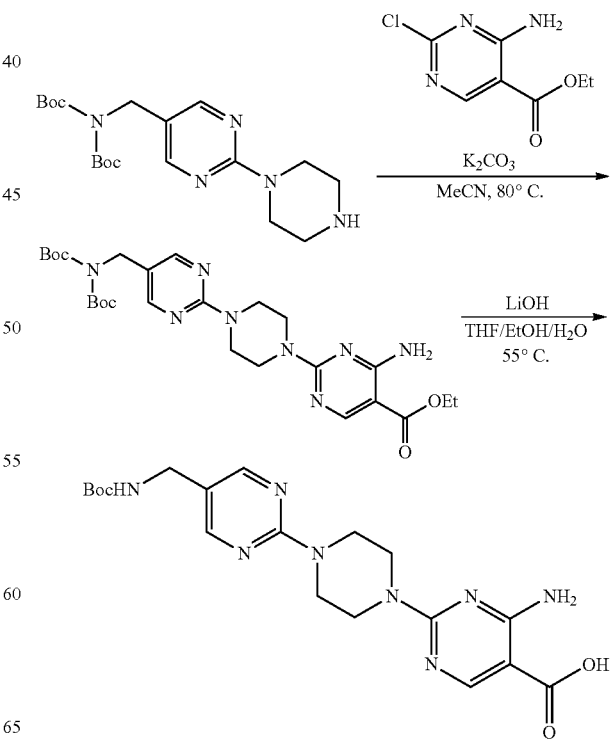

Step 1: Synthesis of ethyl 4-amino-2-(4-(5-(((di-tert-butoxycarbonyl)amino)methyl)pyrimidin-2-yl)piperazin-1-yl)pyrimidine-5-carboxylate To a solution of tert-butyl-N-tert-butoxycarbonyl-N-((2-(piperazin-1-yl)pyrimidin-5-yl)methyl)carbamate (8.3 g, 21.09 mmol, 1.0 equiv) in MeCN (100 mL) was added ethyl 4-amino-2-chloropyrimidine-5-carboxylate (4.04 g, 20.04 mmol, 0.95 equiv) and $K_2CO_3$ (8.75 g, 63.28 mmol, 3.0 equiv). The mixture was stirred at 80° C. for 3 h. The reaction was then cooled to room temperature, DCM (150 mL) was added, and the reaction mixture was stirred for 30 min. The suspension was filtered, the filter cake was washed with DCM (3×100 mL), and the filtrate was concentrated under reduced pressure. Purification by silica gel chromatography (0%→100% EtOAc/petroleum ether) afforded the desired product (8.35 g, 67% yield) as a white solid.

Step 2: Synthesis of 4-amino-2-(4-(5-(((tert-butoxycarbonyl)amino)methyl)pyrimidin-2-yl)piperazin-1-yl)pyrimidine-5-carboxylic acid To a solution of ethyl 4-amino-2-(4-(5-(((di-tert-butoxycarbonyl)amino)methyl)pyrimidin-2-yl)piperazin-1-yl)pyrimidine-5-carboxylate (8.3 g, 14.86 mmol, 1.0 equiv) in $H_2O$ (70 mL), EtOH (36 mL) and THF (80 mL) was added $LiOH \cdot H_2O$ (2.49 g, 59.43 mmol, 4.0 equiv). The reaction mixture was stirred at 55° C. for 16 h. The mixture was then concentrated under reduced pressure to remove THF and EtOH. The mixture was diluted with $H_2O$ (55 mL) and was adjusted to pH=6 by the addition of 1 N HCl. The mixture was filtered, and the filter cake was washed with $H_2O$ (2×20 mL). The solid cake was dried under reduced pressure to afford the desired product (5.5 g, 84% yield) as a white solid. LCMS (ESI) m/z: [M+H] calcd for $C_{19}H_{26}N_8O_4$: 431.22; found 431.4.

Building block AE. 4-amino-2-[(2R)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid

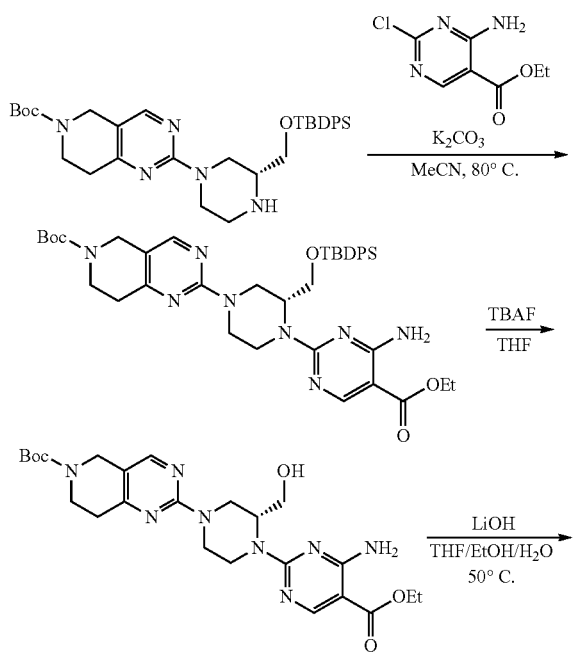

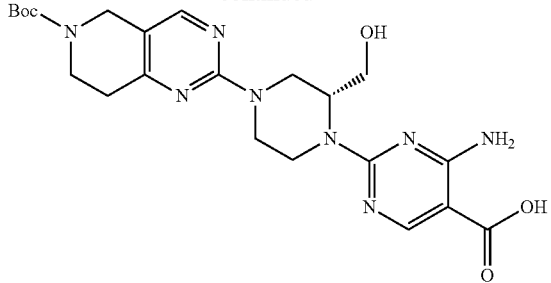

Step 1: Synthesis of (R)-tert-butyl 2-(4-(4-amino-5-(ethoxycarbonyl)pyrimidin-2-yl)-3-(((tert-butyldiphenyl silyl)oxy)methyl)piperazin-1-yl)-7,8-dihydropyrido[4,3-d]pyrimidine-6(5H)-carboxylate To a solution of (R)-tert-butyl 2-(3-(((tert-butyldiphenylsilyl)oxy)methyl) piperazin-1-yl)-7,8-dihydropyrido[4,3-d]pyrimidine-6(5H)-carboxylate (17.2 g, 29.26 mmol, 1.0 equiv) in MeCN (200 mL) was added $K_2CO_3$ (12.13 g, 87.78 mmol, 3.0 equiv) and ethyl 4-amino-2-chloropyrimidine-5-carboxylate (6.37 g, 31.60 mmol, 1.08 equiv). The mixture was stirred at 80° C. for 18 h. The reaction mixture was then cooled to room temperature, filtered and the filtrate was concentrated under reduced pressure. Purification by silica gel chromatography (0%→33% EtOAc/petroleum ether) afforded the desired product (20.3 g, 90.6% yield) as a white solid. LCMS (ESI) m/z: [M+H] calcd for $C_{40}H_{52}N_8O_5Si$: 753.39; found 753.4.

Step 2: Synthesis of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid To a solution of (R)-tert-butyl 2-(4-(4-amino-5-(ethoxycarbonyl)pyrimidin-2-yl)-3-(((tert-butyldiphenylsilyl)oxy)methyl)piperazin-1-yl)-7,8-dihydropyrido[4,3-d]pyrimidine-6(5H)-carboxylate (20.3 g, 26.96 mmol, 1.0 equiv) in THF (200 mL) was added TBAF (1.0 M, 50.75 mL, 1.9 equiv). The reaction mixture was stirred at room temperature for 5 h. The mixture was then poured into $H_2O$ (200 mL) and the aqueous phase was extracted with EtOAc (2×150 mL). The combined organic phases were washed with brine (2×100 mL), dried, filtered and concentrated under reduced pressure. Purification by silica gel chromatography (0%→20% EtOAc/petroleum ether) afforded the desired product (12 g, 85.7% yield) as a white solid. LCMS (ESI) m/z: [M+H] calcd for $C_{24}H_{34}N_8O_5$: 515.28; found 515.4.

Step 3: Synthesis of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid To a solution of (R)-4-amino-2-(4-(6-(tert-butoxycarbonyl)-5,6,7,8-tetrahydropyrido[4,3-d]pyrimidin-2-yl)-2-(hydroxymethyl)piperazin-1-yl)pyrimidine-5-carboxylic acid (12 g, 23.32 mmol, 1.0 equiv) in THF (100 mL), EtOH (30 mL), and $H_2O$ (30 mL) was added $LiOH \cdot H_2O$ (5.87 g, 139.92 mmol, 6.0 equiv). The mixture was stirred at 50° C. for 22 h. The mixture was then concentrated under reduced pressure to remove THF and EtOH. The aqueous phase was neutralized with 1 N HCl and the resulting precipitate was Building block AF. 4-amino-2-[(2S)-4-{6-[(tert-butoxy)carbonyl]-5H,6H,7H,8H-pyrido[4,3-d]pyrimidin-2-yl}-2-(hydroxymethyl)piperazin-1-yl]pyrimidine-5-carboxylic acid filtered. The filter cake was washed with H₂O (50 mL) and dried under reduced pressure. The filtrate was extracted with DCM (8×60 mL) and the combined organic phases were washed with brine (2×50 mL), dried, filtered, and concentrated under reduced pressure. The resulting residue was combined with the initial filter cake and the solid was dissolved in DCM (150 mL) and concentrated under reduced pressure to afford the desired product (9.76 g, 85.2% yield) as a white solid. LCMS (ESI) m/z: [M+H] calcd for $C_{22}H_{30}N_8O_5$: 487.24; found 487.2.

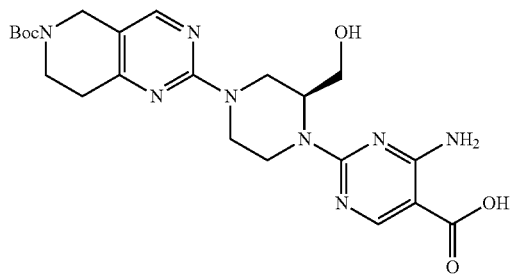 [SMILES: CC(C)(C)OC(=O)N1CCc2nc(N3CCN(c4ncc(C(=O)O)c(N)n4)[C@H](CO)C3)ncc2C1]

This building block is prepared from Building block O by a process similar to that for Building block J by utilizing ethyl 4-amino-2-chloropyrimidine-5-carboxylate.

Building block AG. 2-((2-(4-(5-((di-(tert-butoxycarbonyl)amino)methyl)pyrimidin-2-yl)piperazin-1-yl)-2-oxoethyl)(methyl)amino)acetic acid

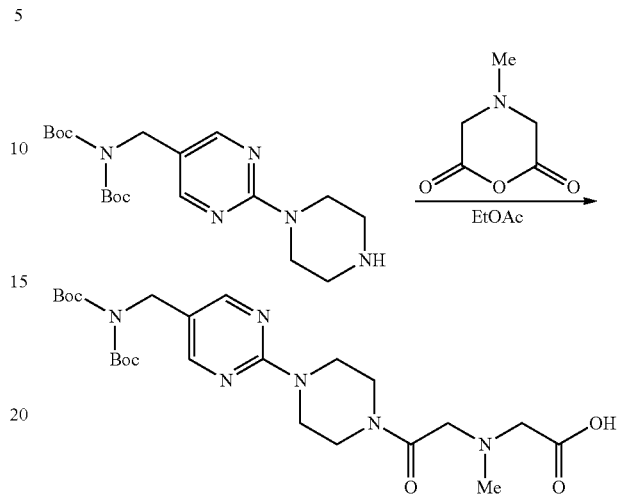

To a solution of tert-butyl N-tert-butoxycarbonyl-N-((2-piperazin-1-ylpyrimidin-5-yl)methyl)carbamate (4.88 g, 12.39 mmol, 1.0 equiv) in EtOAc (40 mL) was added 4-methylmorpholine-2,6-dione (1.6 g, 12.39 mmol, 1.0 equiv). The reaction was stirred at room temperature for 2 h then reaction mixture was concentrated under reduced pressure to give the crude product. The residue was triturated with EtOAc (15 mL) and filtered to give the product (5.65 g, 87.2% yield) as a white solid. LCMS (ESI) m/z: [M+H] calcd for $C_{24}H_{39}N_6O_7$: 523.28; found 523.3.

Building block AR tert-butyl N-tert-butoxycarbonyl-N-((2-(4-(3-(2-piperazin-1-ylethoxy)propanoyl)piperazin-1-yl)pyrimidin-5-yl)methyl)carbamate

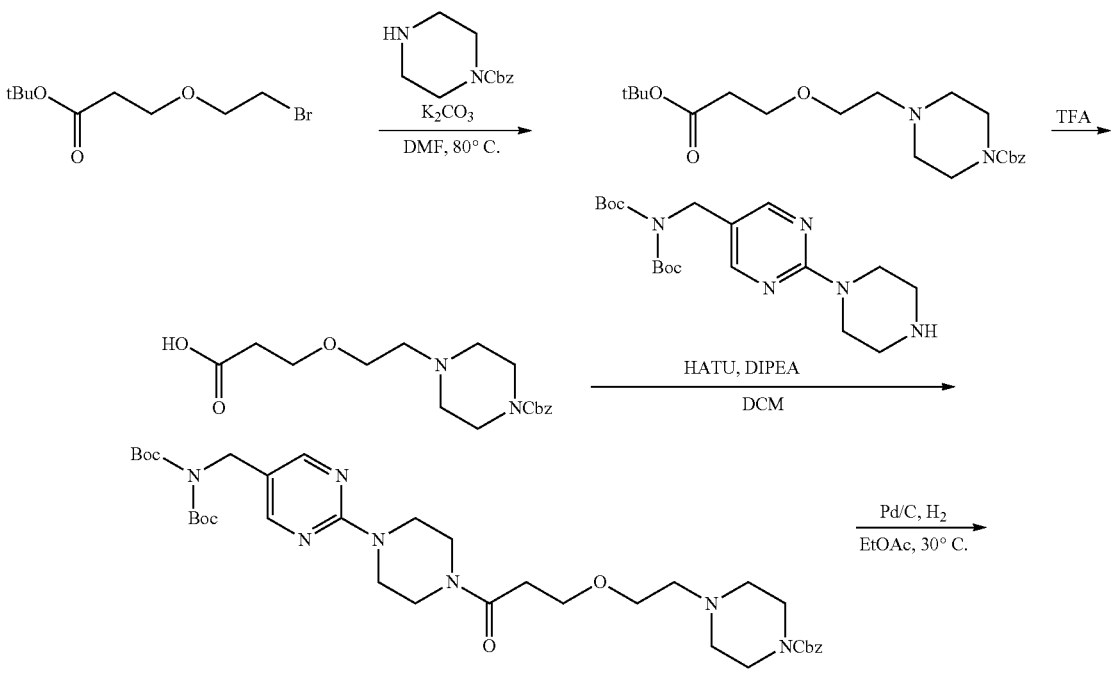

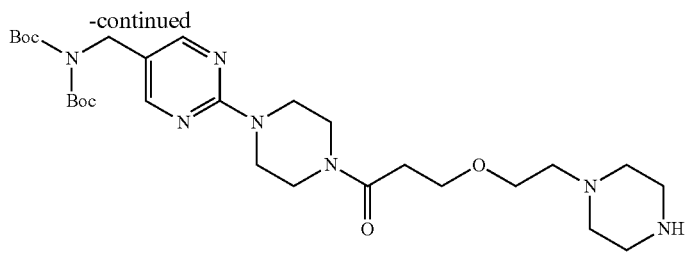

Step 1: Synthesis of benzyl 4-(2-(3-(tert-butoxy)-3-oxopropoxy)ethyl)piperazine-1-carboxylate To a solution of tert-butyl 3-(2-bromoethoxy)propanoate (35 g, 138.27 mmol, 1.0 equiv) and benzyl piperazine-1-carboxylate (31.14 mL, 138.27 mmol, 1.0 equiv, HCl) in MeCN (420 mL) was added K$_2$CO$_3$ (57.33 g, 414.80 mmol, 3.0 equiv). The reaction was stirred at 80° C. for 20 h. The reaction mixture was cooled to room temperature and the suspension was filtered. The filter cake was washed with EtOAc (3×50 mL) and the combined filtrates were concentrated under reduced pressure to give the crude product. The residue was purified by silica gel chromatography (5/1 to 0/1 petroleum ether/EtOAc) to give the product (46 g, 84.8% yield) as a yellow oil.

Step 2: Synthesis of 3-(2-(4-((benzyloxy)carbonyl)piperazin-1-yl)ethoxy)propanoic acid A solution of benzyl 4-(2-(3-(tert-butoxy)-3-oxopropoxy)ethyl)piperazine-1-carboxylate (21 g, 53.50 mmol, 1.0 equiv) in TFA (160 mL) was stirred at room temperature for 2 h and then concentrated under reduced pressure. The residue was purified by silica gel chromatography (1/0 to 4/1 EtOAc/MeOH) to give the product (20.4 g, 84.7% yield, TFA) as a yellow oil. LCMS (ESI) m/z: [M+H] calcd for C$_{17}$H$_{24}$N$_2$O$_5$: 337.18; found 337.1.

Step 3: Synthesis of benzyl 4-(2-(3-(4-(5-(((di-tert-butoxycarbonyl)amino)methyl)pyrimidin-2-yl)piperazin-1-yl)-3-oxopropoxy)ethyl)piperazine-1-carboxylate To a solution of 3-(2-(4-((benzyloxy)carbonyl)piperazin-1-yl)ethoxy)propanoic acid (20.2 g, 44.85 mmol, 1.0 equiv, TFA) in DCM (500 mL) was added HATU (25.58 g, 67.27 mmol, 1.5 equiv) and DIPEA (17.39 g, 134.55 mmol, 23.44 mL, 3.0 equiv). The reaction was stirred at room temperature for 30 min, and then tert-butyl N-tert-butoxycarbonyl-N-((2-piperazin-1-ylpyrimidin-5-yl)methyl)carbamate (14.12 g, 35.88 mmol, 0.8 equiv) was added. The reaction mixture was stirred at for 2 h and then quenched with sat. NH$_4$Cl (500 mL). The aqueous phase was extracted with DCM (3×300 mL) and the combined organic phase was washed with brine (30 mL), dried with anhydrous Na$_2$SO$_4$, filtered and concentrated under reduced pressure to give crude product. The residue was purified by silica gel chromatography (0/1 petroleum ether/EtOAc to 10/1 DCM/MeOH) to give the product (29 g, 90.8% yield) as a yellow oil. LCMS (ESI) m/z: [M+H] calcd for C$_{36}$H$_{53}$N$_7$O$_8$: 712.41; found 712.4.

Step 4: Synthesis of tert-butyl N-tert-butoxycarbonyl-N-((2-(4-(3-(2-piperazin-1-ylethoxy)propanoyl)piperazin-1-yl)pyrimidin-5-yl)methyl)carbamate To a solution of 4-(2-(3-(4-(5-(((di-tert-butoxycarbonyl)amino)methyl)pyrimidin-2-yl)piperazin-1-yl)-3-oxopropoxy)ethyl)piperazine-1-carboxylate (5 g, 7.02 mmol, 1.0 equiv) in EtOAc (150 mL) was added Pd/C (2 g, 10 wt. %). The suspension was degassed and purged with H$_2$ and then stirred under H$_2$ (30 psi) at 30° C. for 3 h. The suspension was then cooled to room temperature and filtered through Celite. The filter cake was washed with MeOH (15×100 mL) and the combined filtrates were concentrated under reduced pressure to give the product (12 g, 89.9% yield) as a light yellow oil. LCMS (ESI) m/z: [M+H] calcd for C$_{28}$H$_{47}$N$_7$O$_6$: 578.37; found 578.5.

Building block AI. ethyl 2-(piperazin-1-yl)pyrimidine-5-carboxylate

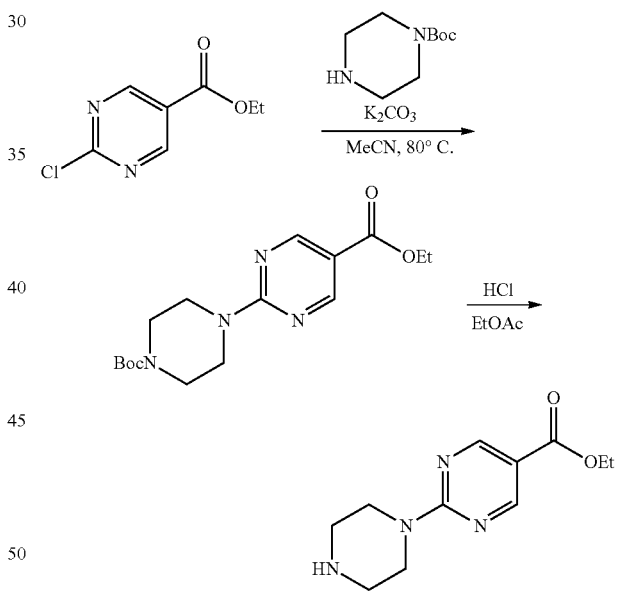

Step 1: Synthesis of ethyl 2-(4-(tert-butoxycarbonyl)piperazin-1-yl)pyrimidine-5-carboxylate To a solution of tert-butyl piperazine-1-carboxylate (11.94 g, 53.59 mmol, 1.0 equiv, HCl) and ethyl 2-chloropyrimidine-5-carboxylate (10 g, 53.59 mmol, 1.0 equiv) in MeCN (100 mL) was added K$_2$CO$_3$ (7.41 g, 53.59 mmol, 1.0 equiv). The mixture was stirred at 80° C. for 17 h and then poured into H$_2$O (200 mL). The mixture was filtered and the filter cake was washed with H$_2$O (80 mL) and dried under reduced pressure to give the product (15.76 g, 82% yield) as a white solid.

Step 2: Synthesis of ethyl 2-(piperazin-1-yl)pyrimidine-5-carboxylate

To a solution of ethyl 2-(4-(tert-butoxycarbonyl)piperazin-1-yl)pyrimidine-5-carboxylate (15.7 g, 46.67 mmol, 1.0 equiv) in EtOAc (150 mL) was added HCl/EtOAc (150 mL) at 0° C. The resulting mixture was stirred at room temperature for 9 h. The reaction mixture was filtered and the filter cake was washed with EtOAc (100 mL). The solid was dried under reduced pressure to give the product (12.55 g, 96% yield, HCl) as a white solid. LCMS (ESI) m/z: [M+H] calcd for $C_{11}H_{16}N_4O_2$: 237.14; found 237.3.

Building block AJ. 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylic acid

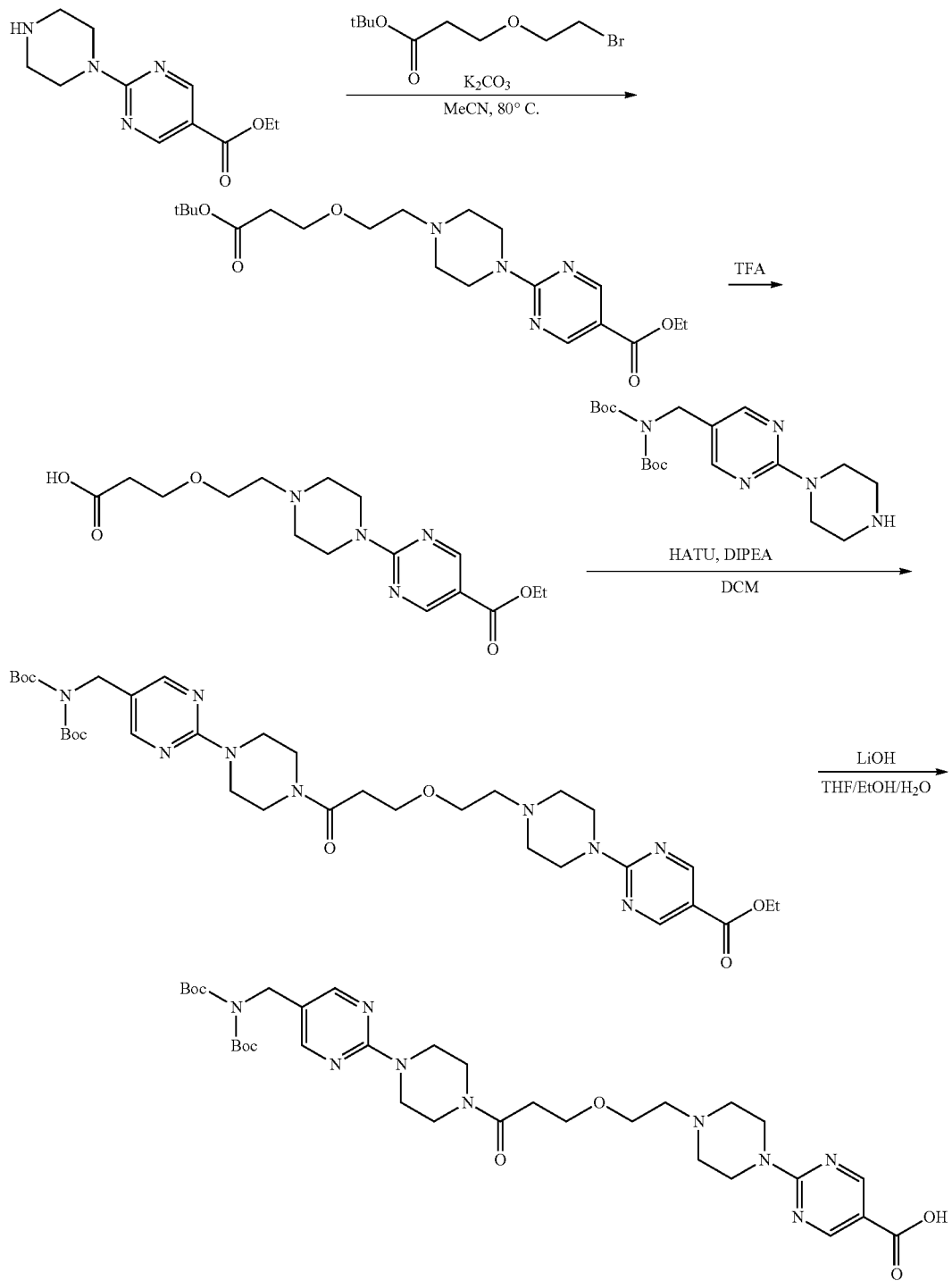

Step 1: Synthesis of ethyl 2-(4-(2-(3-(tert-butoxy)-3-oxopropoxy)ethyl)piperazin-1-yl)pyrimidine-5-carboxylate To a solution of ethyl 2-piperazin-1-ylpyrimidine-5-carboxylate (17.92 g, 75.85 mmol, 1.2 equiv) and tert-butyl 3-(2-bromoethoxy)propanoate (16 g, 63.21 mmol, 1.0 equiv) in MeCN (200 mL) was added $K_2CO_3$ (17.47 g, 126.42 mmol, 2.0 equiv). The reaction was stirred at 80° C. for 12 h and then the reaction mixture was filtered, and the filtrate was concentrated under reduced pressure. The crude product was suspended in petroleum ether (200 mL) and stirred for 20 min at 0° C. and then filtered. The solid was dried under reduced pressure to give the product (19.4 g, 75.1% yield) as a yellow solid.

Step 2: Synthesis of 3-(2-(4-(5-(ethoxycarbonyl)pyrimidin-2-yl)piperazin-1-yl)ethoxy)propanoic acid A solution of ethyl 2-(4-(2-(3-(tert-butoxy)-3-oxopropoxy)ethyl)piperazin-1-yl)pyrimidine-5-carboxylate (19.4 g, 47.49 mmol, 1.0 equiv) in TFA (200 mL) was stirred at room temperature for 30 min. The reaction mixture was then concentrated under reduced pressure and the residue purified by silica gel chromatography (50/1 to 1/1 EtOAc/MeOH) to give the product (18 g, 81.3% yield) as a yellow oil.

Step 3: Synthesis of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate To a solution of 3-(2-(4-(5-(ethoxycarbonyl)pyrimidin-2-yl)piperazin-1-yl)ethoxy)propanoic acid (13 g, 27.87 mmol, 1.0 equiv,) in DCM (200 mL) was added HATU (15.90 g, 41.81 mmol, 1.5 equiv) and DIPEA (19.42 mL, 111.49 mmol, 4.0 equiv). The reaction was then stirred at room temperature for 30 min and then tert-butyl N-tert-butoxycarbonyl-N-[(2-piperazin-1-ylpyrimidin-5-yl)methyl]carbamate (10.97 g, 27.87 mmol, 1.0 equiv) was added. The mixture was stirred at for 2 h and then poured into a sat. $NH_4Cl$ solution (200 mL). The aqueous phase was extracted with DCM (2×200 mL) and the combined organic phase was washed with brine (2×20 mL), dried with anhydrous $Na_2SO_4$, filtered and concentrated under reduced pressure. The residue was purified by silica gel chromatography (100/1 to 9/1 EtOAc/MeOH) to give the product (17 g, 79% yield) as yellow oil.

Step 4: Synthesis of 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylic acid To a solution of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate (11 g, 15.11 mmol, 1.0 equiv) in THF (40 mL), EtOH (10 mL), and $H_2O$ (20 mL) was added $LiOH.H_2O$ (1.27 g, 30.23 mmol, 2.0 equiv). The mixture was then stirred at 35° C. for 1.5 h. The reaction mixture was extracted with EtOAc (30 mL) and the aqueous phase was adjusted to pH=7 by addition of HCl (1 N). The mixture was then concentrated under reduced pressure. The crude product was purified by reversed-phase chromatography (20/1 to 3/1 $H_2O$/MeCN) to give the product (6.1 g, 67.3% yield) as a white solid. LCMS (ESI) m/z: [M+H] calcd for $C_{33}H_{49}N_9O_8$: 700.38; found 700.4.

Building block AK. 2-(4-(2-(3-(4-(5-(((Cert-butoxycarbonyl)amino)methyl)pyrimidin-2-yl)piperazin-1-yl)-3-oxopropoxy)ethyl)piperazin-1-yl)pyrimidine-5-carboxylic acid

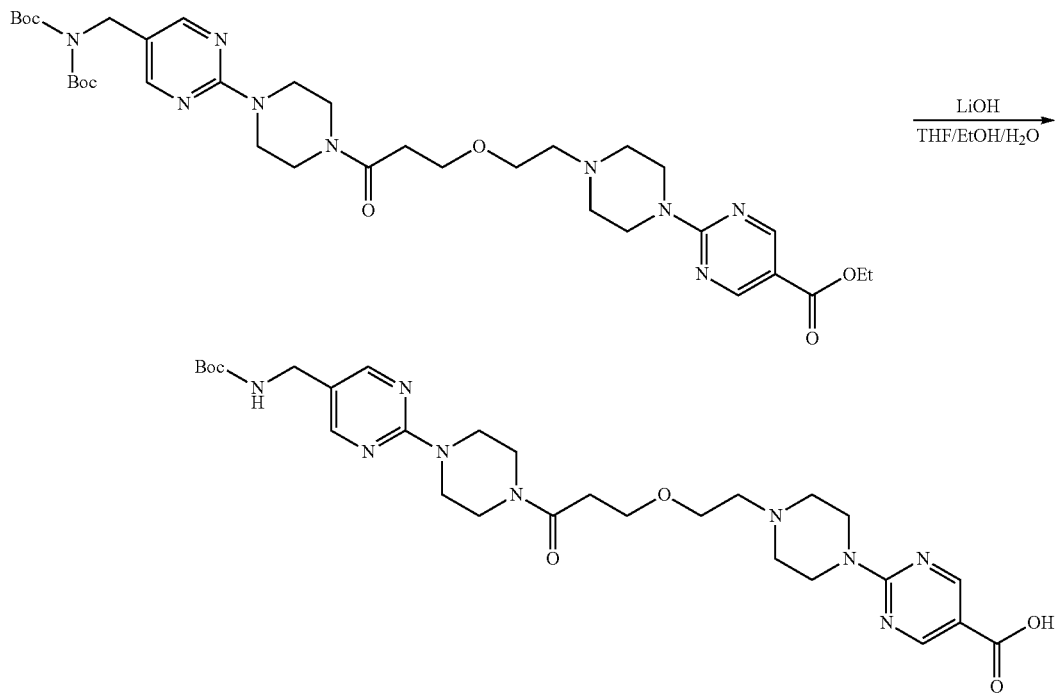

A solution of ethyl 2-(4-(2-(3-(4-(5-(((di-tert-butoxycarbonyl)amino)methyl)pyrimidin-2-yl)piperazin-1-yl)-3-oxopropoxy)ethyl)piperazin-1-yl)pyrimidine-5-carboxylate (5.4 g, 7.42 mmol, 1.0 equiv) in THF (40 mL), EtOH (10 mL), and H$_2$O (10 mL) was added LiOH.H$_2$O (933.92 mg, 22.26 mmol, 3.0 equiv). The mixture was then stirred at 30° C. for 12 h. The reaction mixture was then extracted with EtOAc (2×50 mL) and the aqueous phase was adjusted to pH=7 by addition of HCl (1 N). The solution was then concentrated under reduced pressure. The crude product was purified by reversed-phase chromatography (20/1 to 3/1 H$_2$O/MeCN) to give the product (1.01 g, 22.5% yield) as a white solid. LCMS (ESI) m/z: [M+H] calcd for C$_{28}$H$_{41}$N$_9$O$_6$: 600.33; found 600.2.

Building block AL. 4-{4-[2-(3-{4-[5-({[(tert-butoxy)carbonyl]amino}methyl)pyrimidin-2-yl]piperazin-1-yl}-3-oxopropoxy)ethyl]piperazin-1-yl}-4-oxobutanoic acid

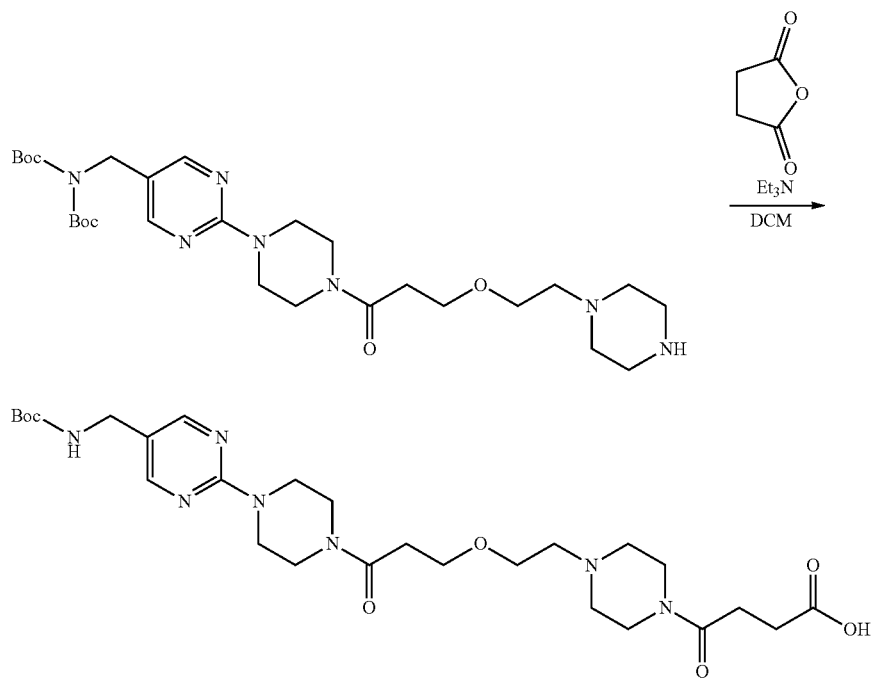

To a solution of tert-butyl N-tert-butoxycarbonyl-N-((2-(4-(3-(2-piperazin-1-ylethoxy)propanoyl)piperazin-1-yl)pyrimidin-5-yl)methyl)carbamate (1.0 equiv) in DCM is added succinic anhydride (1.2 equiv) and Et$_3$N (2.0 equiv). The reaction is stirred at room temperature until consumption of starting material, as determined by LCMS analysis. The reaction mixture is then concentrated under reduced pressure to give the crude product. The residue is purified by silica gel chromatography to afford the product.

Building block AM. 2-(4-(4-(4-(5-((((Cert-butoxycarbonyl)amino)methyl)pyrimidin-2-yl)piperazin-1-yl)-4-oxobutyl)piperazin-1-yl)pyrimidine-5-carboxylic acid

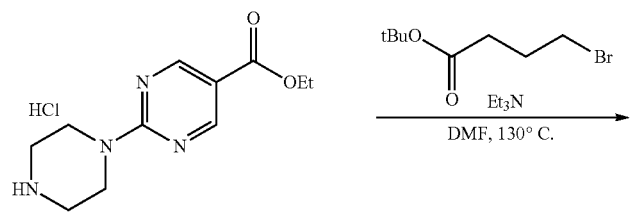

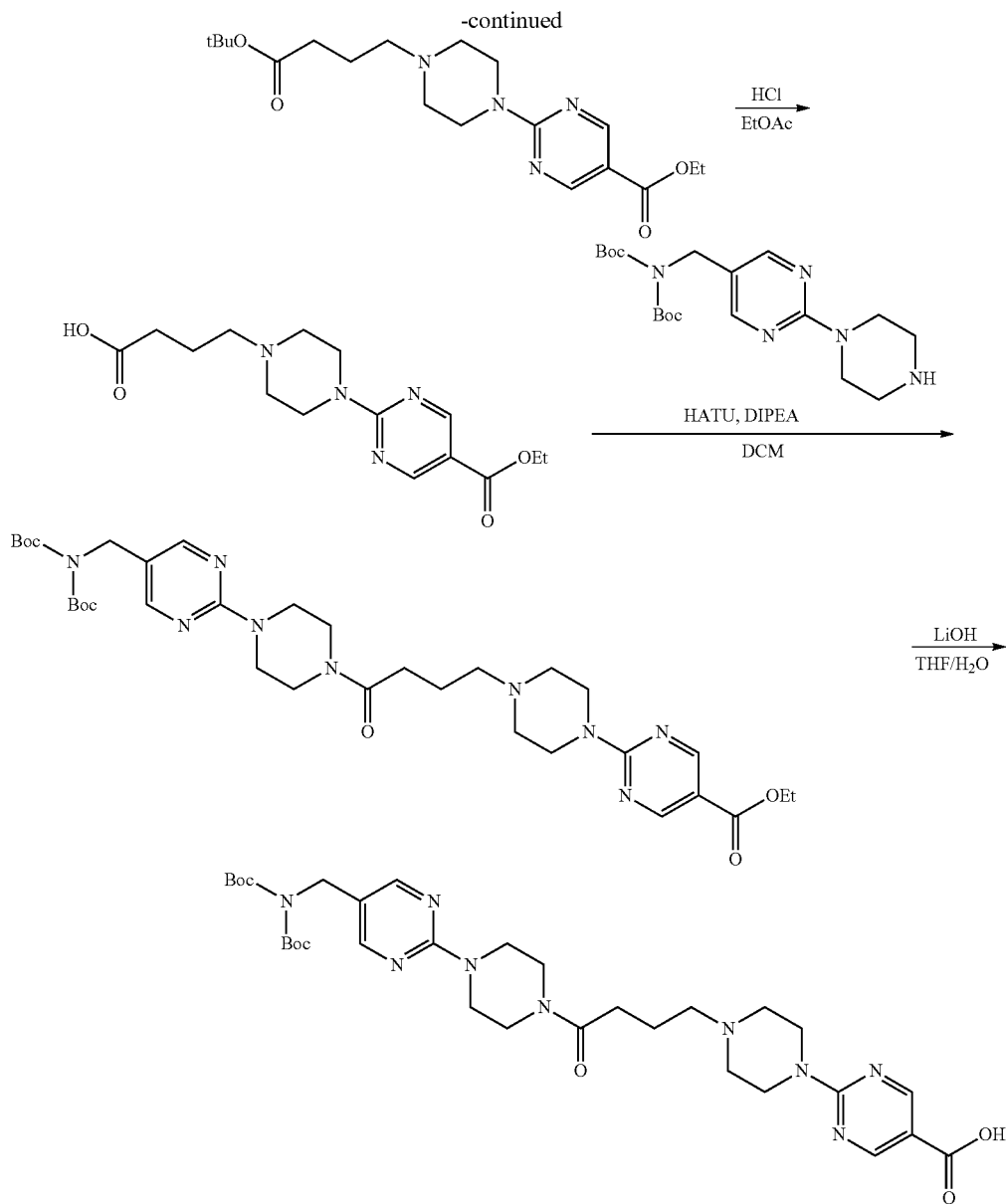

Step 1: Synthesis of ethyl 2-(4-(4-(tert-butoxy)-4-oxobutyl)piperazin-1-yl)pyrimidine-5-carboxylate To a solution of ethyl 2-(piperazin-1-yl)pyrimidine-5-carboxylate hydrochloride (10 g, 36.67 mmol, 1.0 equiv, HCl) and tert-butyl 4-bromobutanoate (8.18 g, 36.67 mmol, 1.0 equiv) in DMF (100 mL) was added $Et_3N$ (15.31 mL, 110.00 mmol, 3.0 equiv). The mixture was stirred at 130° C. for 14 h. The mixture was then poured into $H_2O$ (400 mL) and the solution was extracted with EtOAc (3×150 mL). The combined organic layer was washed with brine (200 mL), dried over $Na_2SO_4$ and concentrated under reduced pressure. The residue was purified by silica gel chromatography (5/1 to 1/1 petroleum ether/EtOAc) to give the product (9.5 g, 68.5% yield) as a yellow solid. LCMS (ESI) m/z: [M+H] calcd for $C_{19}H_{30}N_4O_4$: 379.24; found 379.2, 380.2.

Step 2: Synthesis of 4-(4-(5-(ethoxycarbonyl)pyrimidin-2-yl)piperazin-1-yl)butanoic acid hydrochloride To a solution of ethyl 2-(4-(4-(tert-butoxy)-4-oxobutyl)piperazin-1-yl)pyrimidine-5-carboxylate (9.5 g, 25.10 mmol, 1.0 equiv) in EtOAc (100 mL) was added HCl/EtOAc (500 mL). The mixture was stirred at room temperature for 10 h and then the solution was concentrated under reduced pressure to give the product (9.6 g, 96.8% yield, 2HCl) as a white solid. LCMS (ESI) m/z: [M+H] calcd for $C_{15}H_{22}N_4O_4$: 323.17; found 323.2.

Step 3: Synthesis of ethyl 2-(4-(4-(4-(5-((((di-tert-butoxycarbonyl)amino)methyl)pyrimidin-2-yl)piperazin-1-yl)-4-oxobutyl)piperazin-1-yl)pyrimidine-5-carboxylic acid To a solution of 4-(4-(5-(ethoxycarbonyl)pyrimidin-2-yl)piperazin-1-yl)butanoic acid hydrochloride (5 g, 15.51 mmol, 1.0 equiv) and tert-butyl N-tert-butoxycarbonyl-N-((2-piperazin-1-ylpyrimidin-5-yl)methyl)carbamate (6.10 g, 15.51 mmol, 1.0 equiv) in DMF (150 mL) was added DIPEA (8.11 mL, 46.53 mmol, 3.0 equiv) and HATU (7.08 g, 18.61 mmol, 1.2 equiv). The mixture was stirred at room temperature for 3 h and then the solution was poured into $H_2O$ (600 mL). The aqueous layer was extracted with EtOAc (3×200 mL) and then the combined organic layer was washed with brine (100 mL), dried with $Na_2SO_4$ and concentrated under reduced pressure. The residue was purified by silica gel chromatography (50/1 to 15/1 DCM/MeOH) to give the product (6.3 g, 58.2% yield) as a yellow solid. LCMS (ESI) m/z: [M+H] calcd for $C_{34}H_{51}N_9O_7$: 698.40; found 698.6.

Step 4: Synthesis of 2-(4-(4-(4-(5-(((tert-butoxycarbonyl)amino)methyl)pyrimidin-2-yl)piperazin-1-yl)-4-oxobutyl)piperazin-1-yl)pyrimidine-5-carboxylic acid To a solution of ethyl 2-(4-(4-(4-(5-((bis(tert-butoxycarbonyl)amino)methyl)pyrimidin-2-yl)piperazin-1-yl)-4-oxobutyl)piperazin-1-yl)pyrimidine-5-carboxylate (4.5 g, 6.45 mmol, 1.0 equiv) in EtOH (7 mL) and THF (28 mL) was added a solution of $LiOH·H_2O$ (541.17 mg, 12.90 mmol, 2.0 equiv) in $H_2O$ (7 mL). The mixture was stirred at 30° C. for 8 h, then additional $LiOH·H_2O$ (541 mg, 12.90 mmol, 2.0 equiv) was added. After stirring for an additional 8 h at 30° C., the solution was concentrated under reduced pressure. $H_2O$ (20 mL) was added and solution was adjusted to pH 3 with 1N HCl. The suspension was filtered and the solid dried under reduced pressure to give the product (3.2 g, 79.1% yield) as a white solid. LCMS (ESI) m/z: [M+H] calcd for $C_{27}H_{39}N_9O_5$: 570.32; found 570.3.

Building Block AN. 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid

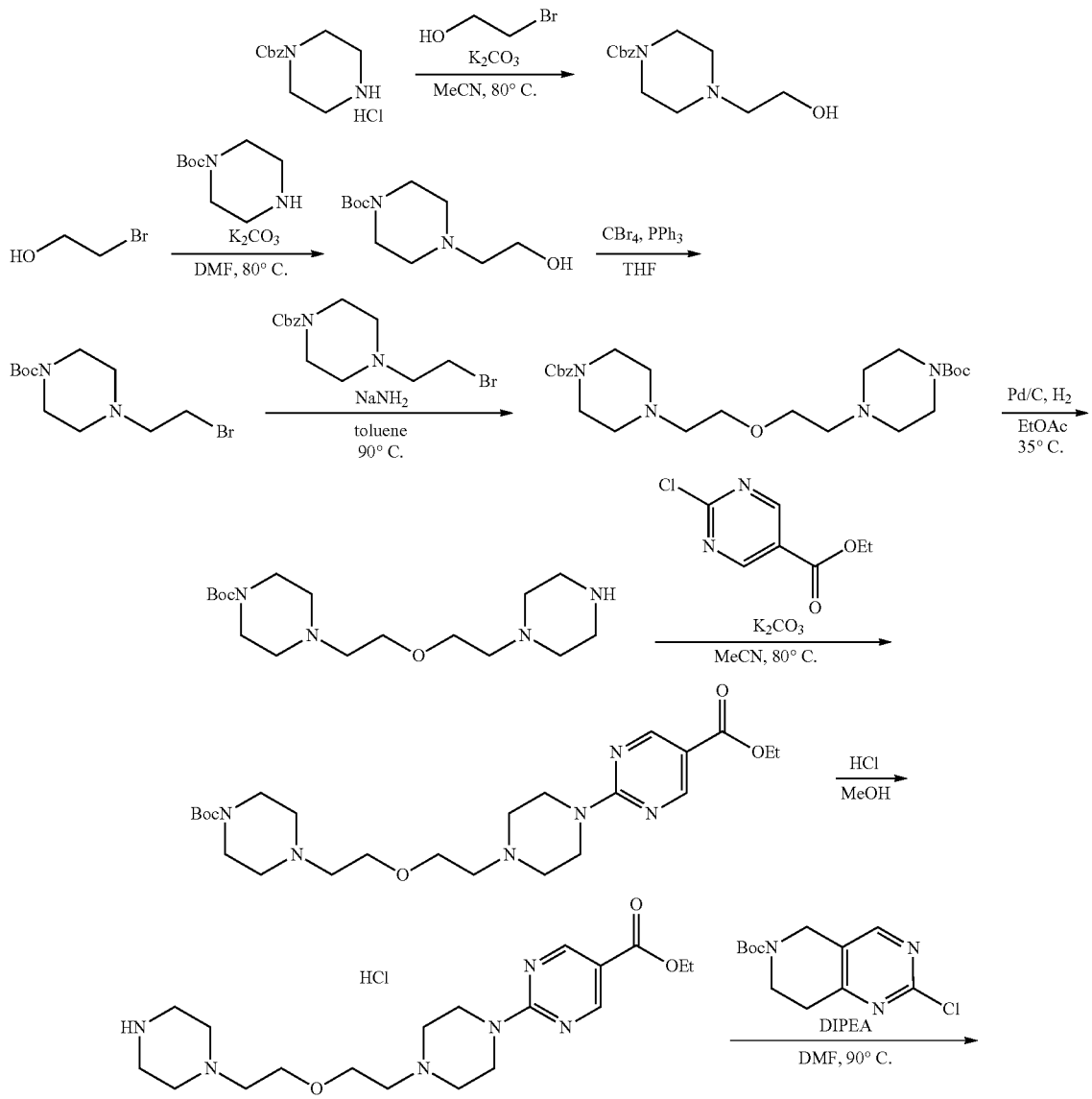

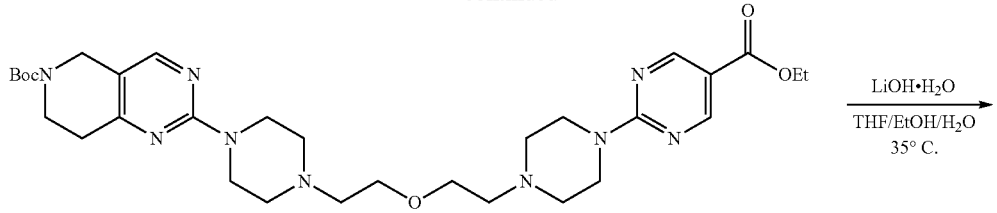

Step 1: Synthesis of benzyl 4-(2-hydroxyethyl)piperazine-1-carboxylate

To a solution of benzyl piperazine-1-carboxylate hydrochloride (41.09 g, 160.04 mmol, 1.0 equiv, HCl) in MeCN (200 mL) was added K$_2$CO$_3$ (66.36 g, 480.13 mmol, 3.0 equiv) and 2-bromoethanol (20 g, 160.04 mmol, 1.0 equiv). The reaction mixture was stirred at 80° C. for 16 h, at which point it was cooled to room temperature and filtered. The filter cake was washed with EtOAc (100 mL) and the filtrate then washed with H$_2$O (100 mL). The aqueous phase was extracted with EtOAc (3×50 mL) and the combined organic phases were washed with brine (50 mL), dried, and concentrated under reduced pressure. Purification by silica gel chromatography (5→25% MeOH/EtOAc) afforded the desired product as a yellow solid (20 g, 47% yield). LCMS (ESI) m/z: [M+H] calcd for C$_{14}$H$_{20}$N$_2$O$_3$: 265.16; found 264.9.

Step 2: Synthesis of tert-butyl 4-(2-hydroxyethyl)piperazine-1-carboxylate

To a solution of tert-butyl piperazine-1-carboxylate (198.72 g, 1.07 mol, 1.0 equiv) in MeCN (1500 mL) was added 2-bromoethanol (240 g, 1.92 mol, 1.8 equiv) and K$_2$CO$_3$ (221.19 g, 1.60 mol, 1.5 equiv). The reaction mixture was stirred at 80° C. for 16 h, at which point the mixture was cooled to room temperature, filtered, and the filtrate was concentrated under reduced pressure. Purification by silica gel chromatography (0→14% MeOH/EtOAc) afforded the desired product as a white solid (146 g, 59% yield).

Step 3: Synthesis of tert-butyl 4-(2-bromoethyl)piperazine-1-carboxylate

To a solution of tert-butyl 4-(2-hydroxyethyl)piperazine-1-carboxylate (45 g, 195.39 mmol, 1.0 equiv) in THF (600 mL) was added triphenylphosphine (97.38 g, 371.25 mmol, 1.9 equiv) and CBr$_4$ (116.64 g, 351.71 mmol, 1.8 equiv). The mixture was stirred at room temperature for 3 h. Two separate batches were combined, and the reaction mixture was filtered, and the filtrate concentrated under reduced pressure. Purification by silica gel chromatography (1→25% EtOAc/petroleum ether) afforded the desired product as a light-yellow solid (31 g, 27% yield).

Step 4: Synthesis of benzyl 4-(2-(2-(4-(tert-butoxycarbonyl)piperazin-1-yl)ethoxy)ethyl)piperazine-1-carboxylate To a solution of benzyl 4-(2-hydroxyethyl)piperazine-1-carboxylate (18 g, 68.10 mmol, 1.0 equiv) in toluene (200 mL) was added NaNH$_2$ (26.57 g, 680.99 mmol, 10.0 equiv). tert-Butyl 4-(2-bromoethyl)piperazine-1-carboxylate (25 g, 85.27 mmol, 1.25 equiv) was added and the mixture was heated to 90° C. for 18 h. The mixture was cooled to room temperature and poured into H$_2$O (700 mL) at 0° C. The aqueous phase was extracted with EtOAc (3×240 mL) and the combined organic phases were washed successively with H$_2$O (350 mL) and sat. brine (2×200 mL), dried, filtered, and concentrated under reduced pressure. Purification by silica gel chromatography (0→12% MeOH/EtOAc) afforded the desired product as a light-yellow oil (20 g, 62% yield).

Step 5: Synthesis of tert-butyl 4-(2-(2-(piperazin-1-yl)ethoxy)ethyl)piperazine-1-carboxylate To a solution of benzyl 4-(2-(2-(4-(tert-butoxycarbonyl)piperazin-1-yl)ethoxy)ethyl)piperazine-1-carboxylate (20 g, 41.96 mmol, 1.0 equiv) in EtOAc (180 mL) was added Pd/C (8 g, 10 wt. %). The suspension was degassed under reduced pressure and purged with H$_2$ three times. The mixture was stirred under H$_2$ (30 psi) at 35° C. for 12 h. The reaction mixture was then filtered, and the filtrate was concentrated under reduced pressure. Purification by silica gel chromatography (0→100% MeOH/EtOAc) afforded the desired product as a colorless oil (10.8 g, 75% yield).

Step 6: Synthesis of ethyl 2-(4-(2-(2-(4-(tert-butoxycarbonyl)piperazin-1-yl)ethoxy)-ethyl)piperazin-1-yl)pyrimidine-5-carboxylate To a solution of tert-butyl 4-(2-(2-(piperazin-1-yl)ethoxy)ethyl)piperazine-1-carboxylate (10.8 g, 31.54 mmol, 1.0 equiv) in MeCN (100 mL) was added K$_2$CO$_3$ (13.08 g, 94.61 mmol, 3.0 equiv) and ethyl 2-chloropyrimidine-5-carboxylate (5.88 g, 31.54 mmol, 1.0 equiv). The mixture was stirred at 80° C. for 12 h, at which point the reaction was cooled to room temperature, filtered, and the filtrate concentrated under reduced pressure. Purification by silica gel chromatography (0→9% MeOH/DCM) afforded the desired product as a white solid (13.6 g, 85% yield).

Step 7: Synthesis of 2-(4-(2-(2-(4-(6-(tert-butoxycarbonyl)-5,6,7,8-tetrahydropyrido-[4,3-d]pyrimidin-2-yl)piperazin-1-yl)ethoxy)ethyl)piperazin-1-yl)pyrimidine-5-carboxylic acid To a solution of ethyl 2-(4-(2-(2-(4-(tert-butoxycarbonyl)piperazin-1-yl)ethoxy)ethyl)piperazin-1-yl)pyrimidine-5-carboxylate (13.6 g, 27.61 mmol, 1.0 equiv) in MeOH (50 mL) was added a solution of HCl in MeOH (4 M, 150 mL, 21.7 equiv). The reaction was stirred at room temperature for 4 h, at which point the mixture was concentrated under reduced pressure to afford the crude desired product as a white solid (13.8 g, 4HCl) that was taken directly onto the next step. LCMS (ESI) m/z: [M+H] calcd for $C_{19}H_{32}N_6O_3$: 393.26; found 393.3.

Step 8: Synthesis of tert-butyl 2-(4-(2-(2-(4-(5-(ethoxycarbonyl)pyrimidin-2-yl)-piperazin-1-yl)ethoxy)ethyl)piperazin-1-yl)-7,8-dihydropyrido[4,3-d]pyrimidine-6(5H)-carboxylate To a stirred solution of 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid (10.2 g, 18.95 mmol, 1.0 equiv, 4HCl) and DIPEA (16.50 mL, 94.74 mmol, 5.0 equiv) in DMF (100 mL) was added tert-butyl 2-chloro-7,8-dihydropyrido[4,3-d]pyrimidine-6(5H)-carboxylate (5.11 g, 18.95 mmol, 1.0 equiv). The reaction mixture was stirred at 90° C. for 12 h. The reaction mixture was then cooled to room temperature and added to EtOAc (200 mL) and H₂O (400 mL). The aqueous phase was extracted with EtOAc (2×100 mL) and the combined organic phases were washed with aqueous NH₄Cl (4×100 mL), brine (2×100 mL), dried, filtered and concentrated under reduced pressure. Purification by silica gel chromatography (0→9% MeOH/DCM) afforded the desired product as a white solid (5.4 g, 45% yield). LCMS (ESI) m/z: [M+H] calcd for $C_{31}H_{47}N_9O_5$: 626.38; found 626.3.

Step 9: Synthesis of 2-(4-(2-(2-(4-(6-(tert-butoxycarbonyl)-5,6,7,8-tetrahydropyrido[4,3-d]pyrimidin-2-yl)piperazin-1-yl)ethoxy)ethyl)piperazin-1-yl)pyrimidine-5-carboxylic acid To a solution of tert-butyl 2-(4-(2-(2-(4-(5-(ethoxycarbonyl)pyrimidin-2-yl)piperazin-1-yl)ethoxy)ethyl)piperazin-1-yl)-'7,8-dihydropyrido[4,3-d]pyrimidine-6(5H)-carboxylate (5.4 g, 8.63 mmol, 1.0 equiv) in THF (50 mL), EtOH (20 mL), and H₂O (20 mL) was added LiOH.H₂O (1.09 g, 25.89 mmol, 3.0 equiv). The reaction mixture was stirred at 35° C. for 12 h, at which point the mixture was concentrated under reduced pressure to remove THF and EtOH. The aqueous phase was neutralized to pH=7 with 0.5N HCl and concentrated under reduced pressure. Purification by reverse phase chromatography afforded the desired product as a white solid (4.72 g, 92% yield). LCMS (ESI) m/z: [M+H] calcd for $C_{29}H_{43}N_9O_5$: 598.35; found 598.3.

Building block AO. 1'-[(tert-butoxy)carbonyl]-[1,4'-bipiperidine]-4-carboxylic acid

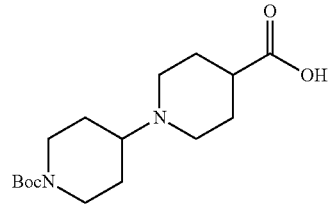 [SMILES: CC(C)(C)OC(=O)N1CCC(N2CCC(C(=O)O)CC2)CC1]

At the time of this application this building block was commercially available (CAS #201810-59-5).

Building block AP. 2-((2-(piperazin-1-yl)pyrimidin-5-yl)methyl)isoindoline-1,3-dione hydrochloride salt

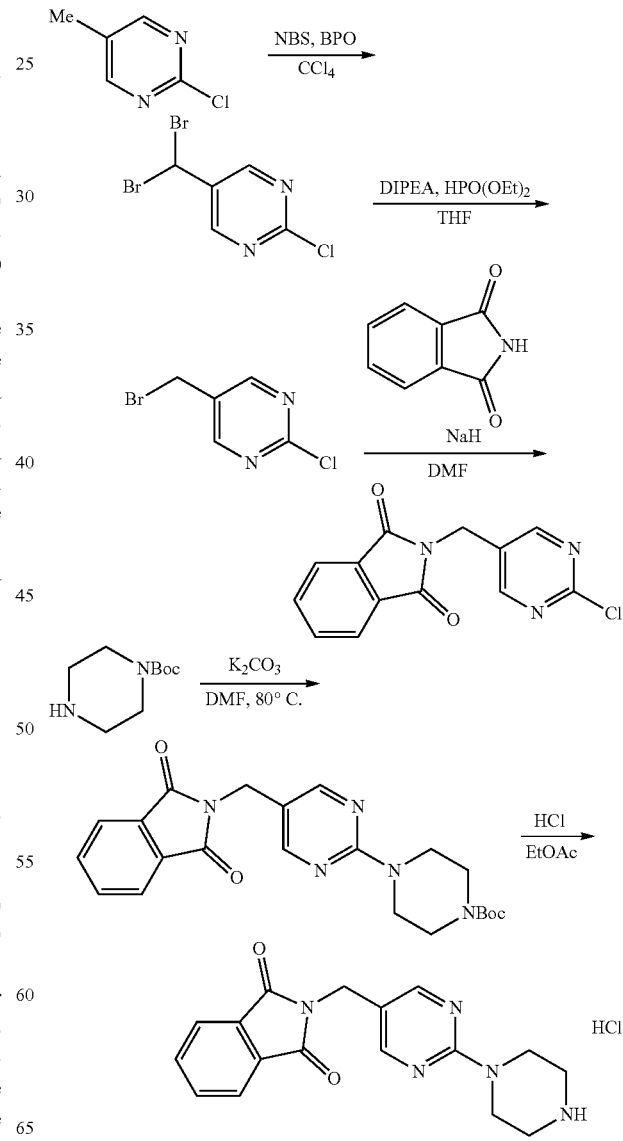

Step 1: Synthesis of 2-chloro-5-(dibromomethyl)pyrimidine

To a solution of 2-chloro-5-methylpyrimidine (100 g, 777.85 mmol, 1.0 equiv) in CCl$_4$ (1200 mL) was added NBS (304.58 g, 1.71 mol, 2.2 equiv) and AIBN (51.09 g, 311.14 mmol, 0.4 equiv). The mixture was stirred at 80° C. for 16 h. The reaction solution was then cooled to room temperature, filtered, and the filtrate was poured into H$_2$O (1500 mL). The solution was diluted with DCM (3×250 mL) and the organic layer washed with brine (300 mL), dried with anhydrous Na$_2$SO$_4$, filtered and concentrated under reduced pressure to give the crude product as a brown oil, which was used directly in the next step.

Step 2: Synthesis of 5-(bromomethyl)-2-chloropyrimidine

To a solution of 2-chloro-5-(dibromomethyl)pyrimidine (229 g, 799.72 mmol, 1.0 equiv) in THF (600 mL) was added DIPEA (111.44 mL, 639.77 mmol, 0.8 equiv) and 1-ethoxyphosphonoyloxyethane (82.57 mL, 639.77 mmol, 0.8 equiv). The mixture was stirred at room temperature for 19 h. The mixture was then poured into H$_2$O (1200 mL) and the aqueous phase was extracted with EtOAc (3×300 mL). The combined organic phase was washed with brine (300 mL), dried with anhydrous Na$_2$SO$_4$, filtered and concentrated under reduced pressure. The residue was purified by silica gel chromatography (1/0 to 0/1 petroleum ether/EtOAc) to give the product as a brown oil, which was used directly for the next step.

Step 3: Synthesis of 2-((2-chloropyrimidin-5-yl)methyl)isoindoline-1,3-dione To a mixture of isoindoline-1,3-dione (15 g, 101.95 mmol, 1.0 equiv) in DMF (126 mL) was added NaH (4.89 g, 122.34 mmol, 60 wt. %, 1.2 equiv) at 0° C. The mixture was stirred at 0° C. for 30 min, then a solution of 5-(bromomethyl)-2-chloropyrimidine (30.21 g, 101.95 mmol, 1.0 equiv) in DMF (24 mL) was added dropwise to the above mixture at room temperature. The mixture was stirred at room temperature for 2 h and was then cooled to 0° C. and quenched with sat. NH$_4$Cl (600 mL). The suspension was filtered and the solid dried under reduced pressure to give the crude product (27.4 g, 98.2% yield) as a grey solid, which was used directly in the next step. LCMS (ESI) m/z: [M+H] calcd for C$_{13}$H$_8$ClN$_3$O$_2$: 274.04; found 274.0.

Step 4: Synthesis of tert-butyl 4-(5-((1,3-dioxoisoindolin-2-yl)methyl)pyrimidin-2-yl)piperazine-1-carboxylate To a solution of 2-((2-chloropyrimidin-5-yl)methyl)isoindoline-1,3-dione (27 g, 98.66 mmol, 1.0 equiv) and tert-butyl piperazine-1-carboxylate (20.21 g, 108.52 mmol, 1.1 equiv) in DMF (270 mL) was added K$_2$CO$_3$ (34.09 g, 246.64 mmol, 2.5 equiv). The mixture was stirred at 80° C. for 3 h and then the reaction was cooled to room temperature and poured into H$_2$O (1200 mL). The suspension was filtered and the solid was dried under reduced pressure to give the crude product (35.58 g, 85.2% yield) as a white solid, which was used directly in the next step.

Step 5: Synthesis of 2-((2-(piperazin-1-yl)pyrimidin-5-yl)methyl)isoindoline-1,3-dione A solution of tert-butyl 4-(5-((1,3-dioxoisoindolin-2-yl)methyl)pyrimidin-2-yl)piperazine-1-carboxylate (15 g, 35.42 mmol, 1 equiv) in HCl/EtOAc (150 mL) was stirred at room temperature for 2 h. The mixture was filtered and then the filter cake was washed with EtOAc (20 mL) and dried under reduced pressure to give the product (42.53 g, 92.5% yield) as a white solid.

Building block AQ. 2-[(2-{4-[2-(3-{4-[5-({bis[(tert-butoxy)carbonyl]amino}methyl)pyrimidin-2-yl]piperazin-1-yl}-3-oxopropoxy)ethyl]piperazin-1-yl}-2-oxoethyl)(methyl)amino]acetic acid

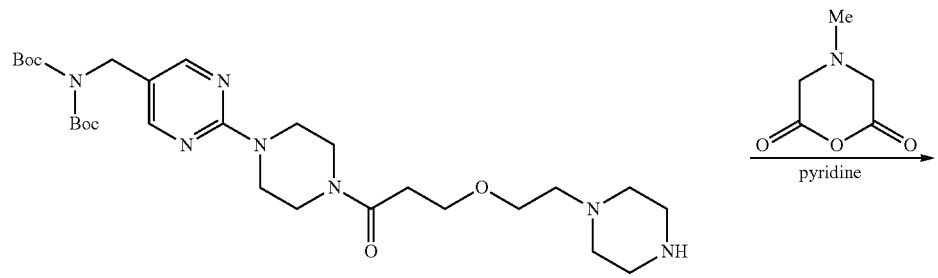

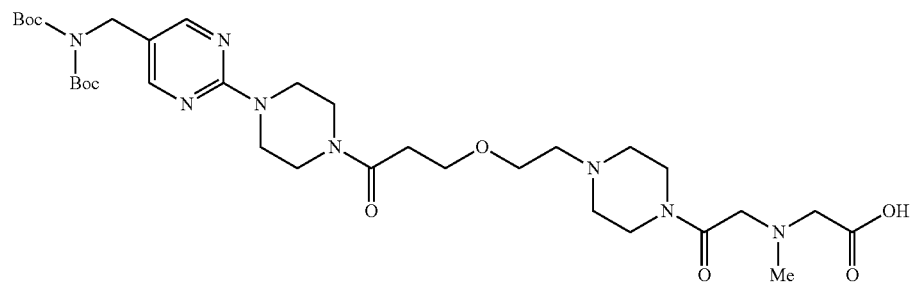

To a solution of tert-butyl N-[(tert-butoxy)carbonyl]-N-{[2-(4-{3-[2-(piperazin-1-yl)ethoxy]propanoyl}piperazin-1-yl)pyrimidin-5-yl]methyl}carbamate (300 mg, 519 μmol, 1.0 equiv) in pyridine (8 mL) at 0° C. was added 4-methylmorpholine-2,6-dione (80.3 mg, 622 μmol, 1.2 equiv). The reaction mixture was stirred at 0° C. for 1 h and then warmed to room temperature and stirred for an additional 12 h. The solvent was concentrated under reduced pressure and the solid was partitioned between DCM and H$_2$O. The organic layer was separated, dried over MgSO$_4$ and the solvent was concentrated under reduced pressure to give the product (23.0 mg, 6.28% yield). LCMS (ESI) m/z: [M+H] calcd for C$_{33}$H$_{54}$N$_8$O$_9$: 707.41; found 707.4.

Building Block AR. 2-(4-(2-(3-(4-(6-(tert-butoxycarbonyl)-5,6,7,8-tetrahydropyrido[4,3-d] pyrimidin-2-yl)piperazin-1-yl)-3-oxopropoxy)ethyl)piperazin-1-yl)pyrimidine-5-carboxylic acid Step 1: Synthesis of tert-butyl 2-(4-(3-(2-(4-(5-(ethoxycarbonyl)pyrimidin-2-yl)piperazin-1-yl)ethoxy)propanoyl)piperazin-1-yl)-7,8-dihydropyrido[4,3-d]pyrimidine-6(5H)-carboxylate To a solution of 3-(2-(4-(5-(ethoxycarbonyl)pyrimidin-2-yl)piperazin-1-yl)ethoxy) propanoic acid (6 g, 12.86 mmol, 1.0 equiv, TFA) in DMF (55 mL) was added HATU (6.36 g, 16.72 mmol, 1.3 equiv) and DIPEA (11.20 mL, 64.32 mmol, 5.0 equiv). After 0.5 h, tert-butyl 2-(piperazin-1-yl)-7,8-dihydropyrido[4,3-d]pyrimidine-6(5H)-carboxylate (4.11 g, 12.86 mmol, 1.0 equiv) was added. The mixture was stirred for 3 h, at which point it was filtered and the solid cake was dried under reduced pressure to afford the desired product as a white solid (7.5 g, 89% yield). LCMS (ESI) m/z: [M+H] calcd for C$_{32}$H$_{47}$N$_9$O$_6$: 654.37; found 654.4.

Step 2: Synthesis of 2-(4-(2-(3-(4-(6-(tert-butoxycarbonyl)-5,6,7,8-tetrahydropyrido[4,3-d]pyrimidin-2-yl)piperazin-1-yl)-3-oxopropoxy)ethyl)piperazin-1-yl)pyrimidine-5-carboxylic acid To a solution of tert-butyl 2-(4-(3-(2-(4-(5-(ethoxycarbonyl)pyrimidin-2-yl)piperazin-1-yl)ethoxy)propanoyl)piperazin-1-yl)-7,8-dihydropyrido[4,3-d]pyrimidine-6(5H)-carboxylate (7.2 g, 11.01 mmol, 1.0 equiv) in THF (72 mL), EtOH (36 mL) and H$_2$O (36 mL) was added LiOH.H$_2$O (1.85 g, 44.05 mmol, 4.0 equiv). The reaction mixture was stirred at room temperature for 2.5 h, at which point the mixture was filtered and the filtrate was concentrated under reduced pressure to remove THF and EtOH. The aqueous phase was neutralized to pH=7 with 1N HCl, and then concentrated under reduced pressure. Purification by reverse phase chromatography (30% MeCN/H$_2$O) afforded the desired product as a white solid (3.85 g, 54% yield). LCMS (ESI) m/z: [M+H] calcd for C$_{30}$H$_{43}$N$_9$O$_6$: 626.34; found 626.3.

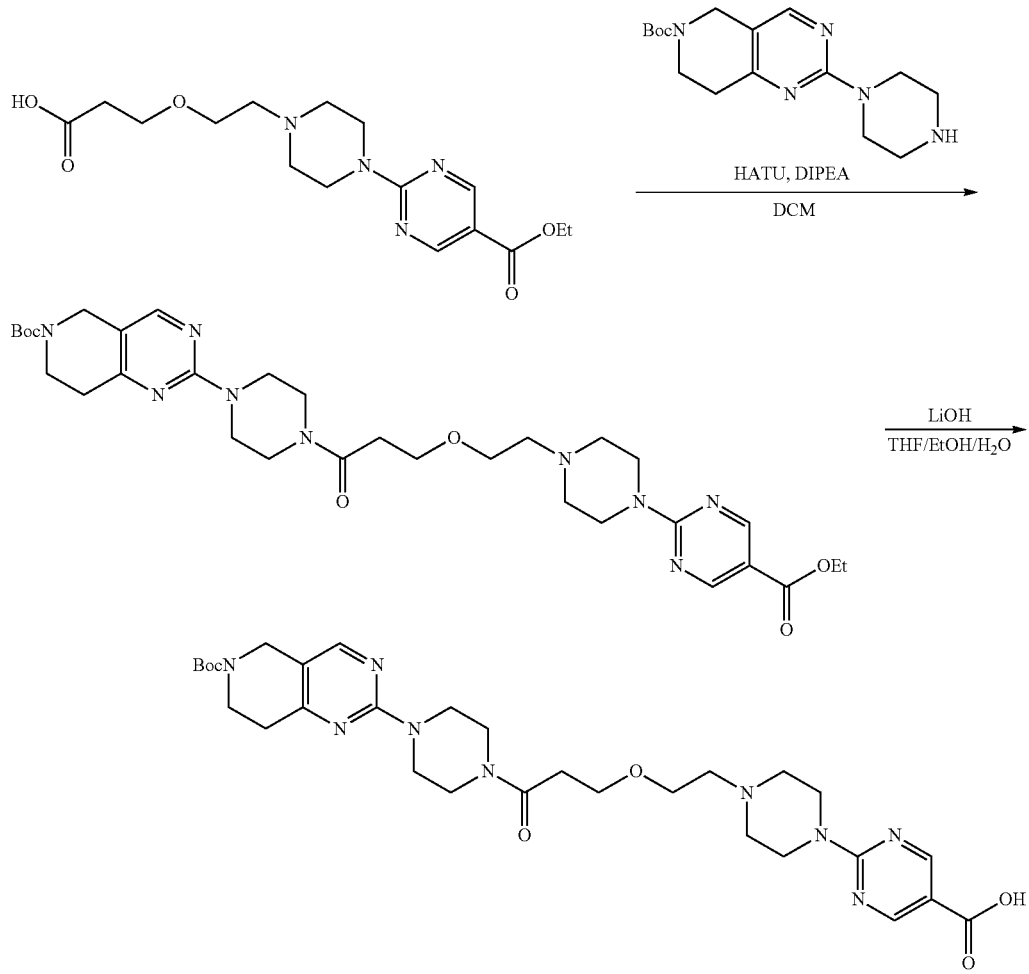

Building Block AS. 2-(4-(2-(2-(3-(4-(5-((di-tert-butoxycarbonylamino)methyl)pyrimidin-2-yl)piperazin-1-yl)-3-oxo-propoxy)ethoxy)ethyl)piperazin-1-yl)pyrimidine-5-carboxylic acid

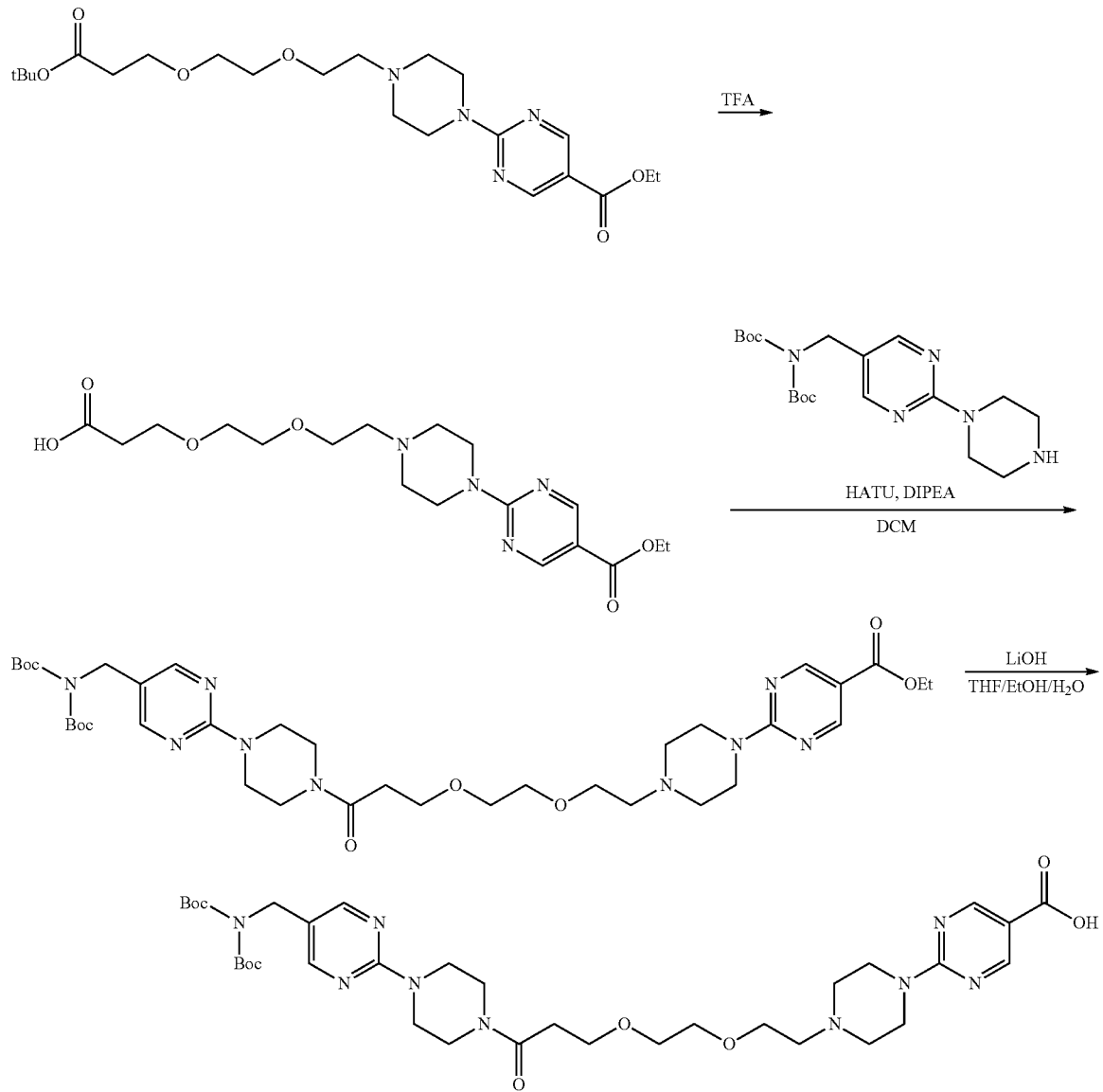

Step 1: Synthesis of 3-(2-(2-(4-(5-(ethoxycarbonyl)pyrimidin-2-yl)piperazin-1yl)ethoxy)ethoxy)propanoic acid A solution of ethyl 2-(4-(2-(2-(3-(tert-butoxy)-3-oxopropoxy)ethoxy)ethyl)piperazin-1-yl)pyrimidine-5-carboxylate (4 g, 8.84 mmol, 1.0 equiv) in TFA (12.29 mL, 166.00 mmol, 18.8 equiv) was stirred at room temperature for 3 h. The reaction mixture was concentrated under reduced pressure. Purification by silica gel chromatography (0→20% MeOH/EtOAc) afforded the desired product as a brown oil (4.35 g, 95% yield, TFA salt).

Step 2: Synthesis of ethyl 2-(4-(2-(2-(3-(4-(5-((bis(tert-butoxycarbonyl)amino)methyl)pyrimidin-2-yl)piperazin-1-yl)-3-oxopropoxy)ethoxy)ethyl)piperazin-1-yl)pyrimidine-5-carboxylate To a solution of 3-(2-(2-(4-(5-ethoxycarbonylpyrimidin-2-yl)piperazin-1-yl)ethoxy)ethoxy)propanoic acid (3.8 g, 7.44 mmol, 1.0 equiv, TFA) in DCM (30 mL) was added HATU (4.25 g, 11.17 mmol, 1.5 equiv) and DIPEA (6.48 mL, 37.22 mmol, 5.0 equiv). The reaction was stirred at room temperature for 30 min, and then tert-butyl N-tert-butoxycarbonyl-N-((2-piperazin-1ylpyrimidin-5-yl)methyl)carbamate (2.93 g, 7.44 mmol, 1.0 equiv) was added. The mixture was stirred at room temperature for 3.5 h, at which Step 3: Synthesis of 2-(4-(2-(2-(3-(4-(5-((di-tert-butoxycarbonylamino)methyl)pyrimidin-2-yl)piperazin-1-yl)-3-oxo-propoxy)ethoxy)ethyl)piperazin-1-yl)pyrimidine-5-carboxylic acid To a solution of ethyl 2-(4-(2-(2-(3-(4-(5-((bis(tert-butoxycarbonyl)amino)methyl)pyrimidin-2-yl)piperazin-1-yl)-3-oxo-propoxy)ethoxy)ethyl)piperazin-1-yl)pyrimidine-5-carboxylate (1.4 g, 1.81 mmol, 1.0 equiv) in THF (28 mL), EtOH (14 mL) and $H_2O$ (14 mL) was added $LiOH \cdot H_2O$ (304.44 mg, 7.25 mmol, 4.0 equiv). The mixture was stirred at 40° C. for 30 min, at which point the reaction mixture was concentrated under reduced pressure. Purification by reverse phase chromatography (10→40% MeCN/$H_2O$) afforded the desired product as a yellow solid (500 mg, 43% yield).

Building block AT. 2-{4-[2-(2-{4-[5-({[(tert-butoxy)carbonyl]amino}methyl)pyrimidin-2-yl]piperazin-1-yl}ethoxy)ethyl]piperazin-1-yl}pyrimidine-5-carboxylic acid mixture was stirred at 80° C. for 12 h. The mixture was then cooled to room temperature and poured into $H_2O$ (300 mL). The aqueous phase was extracted with EtOAc (3×80 mL). The combined organic phases were washed with sat. $NH_4Cl$ (4×80 mL) and brine (150 mL), dried, filtered and the filtrate was concentrated under reduced pressure. Purification by silica gel chromatography (0%-17% MeOH/EtOAc) afforded the desired product (7.7 g, 81.1% yield) as a light yellow oil. LCMS (ESI) m/z: [M+Na] calcd for $C_{34}H_{53}N_9O_7$: 722.40; found 722.4.

Step 2: Synthesis of 2-(4-(2-(2-(4-(5-(((tert-butoxycarbonyl)amino)methyl)pyrimidin-2-yl)piperazin-1-yl)ethoxy)ethyl)piperazin-1-yl)pyrimidine-5-carboxylic acid To a solution of ethyl 2-(4-(2-(2-(4-(5-(((di-tert-butoxycarbonyl)amino)methyl)pyrimidin-2-yl)piperazin-1-yl)ethoxy)ethyl)piperazin-1-yl)pyrimidine-5-carboxylate (7.7

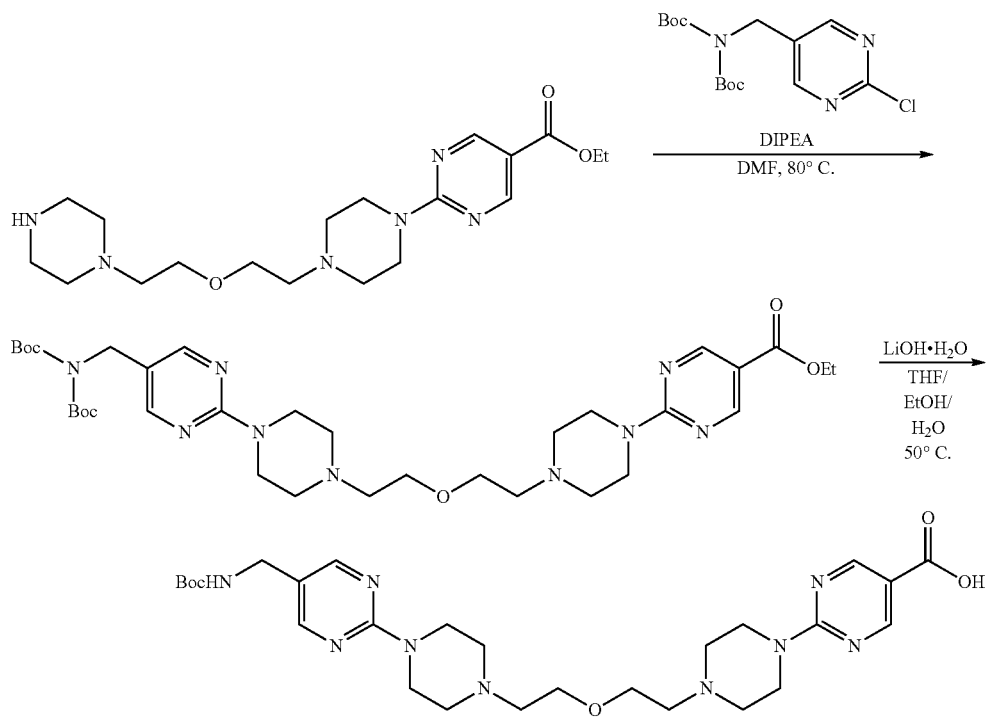

Step 1: Synthesis of ethyl 2-(4-(2-(2-(4-(5-(((di-tert-butoxycarbonyl)amino)methyl)pyrimidin-2-yl)piperazin-1-yl)ethoxy)ethyl)piperazin-1-yl)pyrimidine-5-carboxylate To a solution of ethyl 2-(4-(2-(2-(piperazin-1-yl)ethoxy)ethyl)piperazin-1-yl)pyrimidine-5-carboxylate hydrochloride (7.3 g, 13.56 mmol, 1.0 equiv, 4HCl) in DMF (75 mL) was added DIPEA (14.17 mL, 81.36 mmol, 6.0 equiv) and tert-butyl-N-tert-butoxycarbonyl-N-[(2-chloropyrimidin-5-yl)methyl]carbamate (5.59 g, 16.27 mmol, 1.2 equiv). The g, 11.00 mmol, 1.0 equiv) in THF (80 mL), EtOH (20 mL), and $H_2O$ (40 mL) was added $LiOH \cdot H_2O$ (2.31 g, 55.01 mmol, 5.0 equiv). The mixture was stirred at 50° C. for 26 h. The mixture was then concentrated under reduced pressure to remove THF and EtOH. The aqueous phase was neutralized with 0.5 N HCl, and concentrated under reduced pressure. Purification by reverse phase chromatography afforded the desired product (4.67 g, 74.3% yield) as a white solid. LCMS (ESI) m/z: [M−H] calcd for $C_{27}H_{41}N_9O_5$: 570.31; found 570.3.

Building block AU. (R)-tert-butyl 4-(5-(((tert-butoxycarbonyl-N-tert-butoxycarbonyl)amino)methyl)pyrimidin-2-yl)piperazine-2-carboxylate

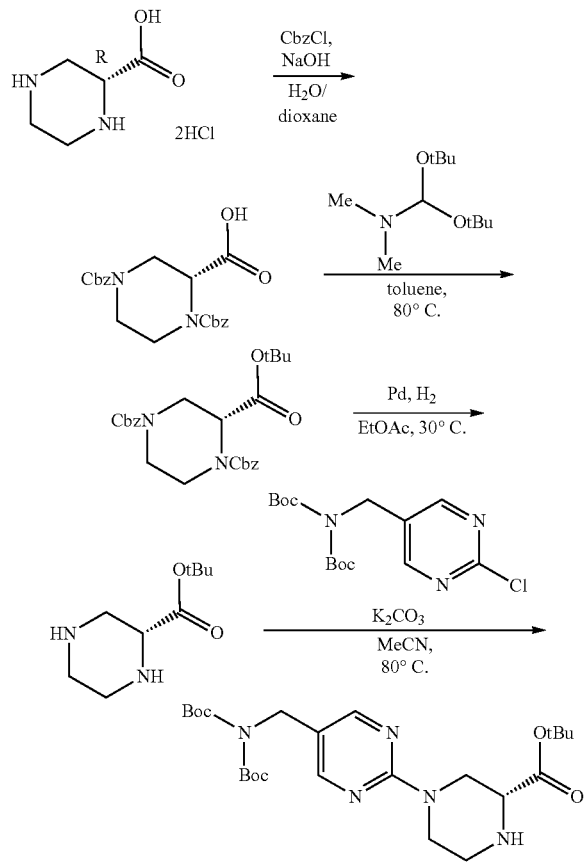

Step 1: Synthesis of (R)-1,4-bis((benzyloxy)carbonyl)piperazine-2-carboxylic acid To two separate batches containing a solution (2R)-piperazine-2-carboxylic acid (70 g, 344.71 mmol, 1 equiv, 2HCl) in $H_2O$ (700 mL) and dioxane (1120 mL) was added 50% aq. NaOH until pH=11. Benzyl chloroformate (156.82 mL, 1.10 mol, 3.2 equiv) was added and the reaction was stirred at room temperature for 12 h. The two reaction mixtures were combined and $H_2O$ (1200 mL) was added. The aqueous layer was extracted with MTBE (3×1000 mL), adjusted to pH=2 with con. HCl, and then extracted with EtOAc (2×1000 mL). The combined organic phases were dried, filtered, and concentrated under reduced pressure to afford the desired product (280 g, 86% yield). LCMS (ESI) m/z: [M+H] calcd for $C_{21}H_{22}N_2O_6$: 399.16; found 399.0.

Step 2: Synthesis of (R)-1,4-dibenzyl 2-tert-butyl piperazine-1,2,4-tricarboxylate To a solution of (R)-1,4-bis((benzyloxy)carbonyl)piperazine-2-carboxylic acid (70 g, 175.70 mmol, 1.0 equiv) in toluene (700 mL) at 80° C. was added 1,1-di-tert-butoxy-N,N-dimethylmethanamine (80.04 mL, 333.83 mmol, 1.9 equiv). The reaction was stirred at 80° C. for 2 h, at which point it was cooled to room temperature and partitioned between EtOAc (300 mL) and $H_2O$ (500 mL). The aqueous layer was extracted with EtOAc (2×500 mL) and the combined organic layers were dried, filtered, and concentrated under reduced pressure. Purification by silica gel chromatography (0→25 EtOAc/petroleum ether) afforded the desired product as a white solid (50 g, 57% yield). LCMS (ESI) m/z: [M+Na] calcd for $C_{25}H_{30}N_2O_6$: 477.20; found 476.9.

Step 3: Synthesis of (R)-tert-butyl piperazine-2-carboxylate

To a solution of (R)-1,4-dibenzyl 2-tert-butyl piperazine-1,2,4-tricarboxylate (50 g, 110.01 mmol, 1 equiv) in EtOAc (20 mL) was added Pd/C (15 g, 10 wt. %). The suspension was degassed under reduced pressure and purged with $H_2$ three times. The suspension was stirred under $H_2$ (30 psi) at 30° C. for 4 h. The reaction mixture was then filtered, the residue was washed with MeOH (5×200 mL), and the filtrate concentrated under reduced pressure to afford the desired product as a yellow oil (17 g, 81% yield). LCMS (ESI) m/z: [M+H] calcd for $C_9H_{18}N_2O_2$: 187.15; found 187.1.

Step 4: Synthesis of (R)-tert-butyl 4-(5-(((tert-butoxycarbonyl-N-tert-butoxycarbonyl)amino)methyl)pyrimidin-2-yl)piperazine-2-carboxylate To a suspension of (R)-tert-butyl piperazine-2-carboxylate (8 g, 23.27 mmol, 1.0 equiv) and tert-butyl-N-tert-butoxycarbonyl ((2-chloropyrimidin-5-yl)methyl)carbamate (5.20 g, 27.92 mmol, 1.2 equiv) in MeCN (100 mL) was added $K_2CO_3$ (6.43 g, 46.54 mmol, 2.0 equiv). The reaction mixture was heated to 80° C. for 12 h, at which point it was cooled to room temperature, filtered, and the filtrate was concentrated under reduced pressure. Purification by silica gel chromatography (0→100% EtOAc/petroleum ether) afforded the desired product as a yellow solid (9.2 g, 73% yield). LCMS (ESI) m/z: [M+H] calcd for $C_{24}H_{39}N_5O_6$: 494.30; found 494.1.

Building block AV. (S)-tert-butyl 4-(5-(((tert-butoxycarbonyl-N-tert-butoxycarbonyl)amino)methyl)pyrimidin-2-yl)piperazine-2-carboxylate

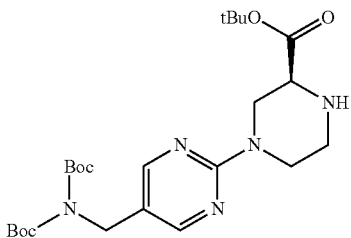

This building block is prepared by a process similar to that for Building block AU by utilizing (2S)-piperazine-2-carboxylic acid.

Building block AW. (R)-2-(4-(2-(3-(2-(tert-butoxy-carbonyl)-4-(5-(((cert-butoxycarbonyl-N-tert-bu-toxycarbonyl)amino)methyl)pyrimidin-2-yl)piper-azin-1-yl)-3-oxopropoxy)ethyl)piperazin-1-yl)pyrimidine-5-carboxylic acid

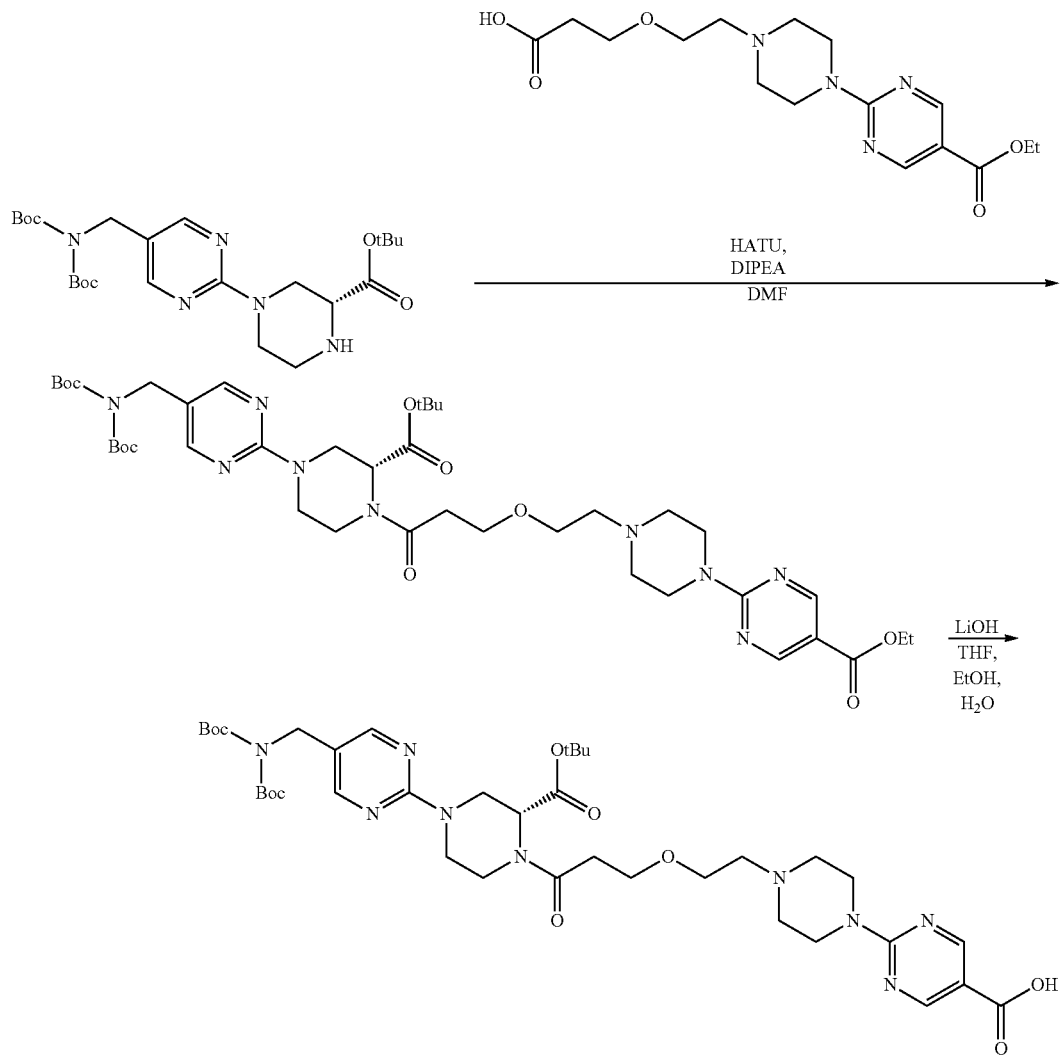

Step 1: Synthesis of (R)-ethyl 2-(4-(2-(3-(2-(tert-butoxycarbonyl)-4-(5-(((tert-butoxycarbonyl-N-tert-butoxycarbonyl)amino)methyl)pyrimidin-2-yl)piper-azin-1-yl)-3-oxopropoxy)ethyl)piperazin-1-yl)pyrimidine-5-carboxylate To a solution of (R)-tert-butyl 4-(5-(((tert-butoxycarbo-nyl-N-tert-butoxycarbonyl)amino)methyl)pyrimidin-2-yl)piperazine-2-carboxylate (5.3 g, 11.36 mmol, 1.0 equiv, TFA) in DCM (80 mL) was added HATU (6.48 g, 17.05 mmol, 1.5 equiv) and DIPEA (7.92 mL, 45.45 mmol, 4.0 equiv). The reaction was stirred at room temperature for 30 min and then tert-butyl (2R)-4-(5-((bis(tert-butoxycarbonyl)amino)methyl)pyrimidin-2-yl)piperazine-2-carboxylate (5.61 g, 11.36 mmol, 1.0 equiv) was added. The mixture was stirred for 1 h, at which point sat. NH₄Cl (80 mL) was added. The organic phase was washed with sat. NH₄Cl (5×80 mL), dried, filtered, and concentrated under reduced pressure. Purification by silica gel chromatography (0→9% MeOH/EtOAc) afforded the desired product as a yellow solid (8.4 g, 85% yield).

Step 2: Synthesis of (R)-2-(4-(2-(3-(2-(tert-butoxy-carbonyl)-4-(5-(((tert-butoxycarbonyl-N-tert-butoxy-carbonyl)amino)methyl)pyrimidin-2-yl)piperazin-1-yl)-3-oxopropoxy)ethyl)piperazin-1-yl)pyrimidine-5-carboxylic acid To two separate batches containing a solution a solution of (R)-ethyl 2-(4-(2-(3-(2-(tert-butoxycarbonyl)-4-(5-(((tert-butoxycarbonyl-N-tert-butoxycarbonyl)amino)methyl)py-rimidin-2-yl)piperazin-1-yl)-3-oxopropoxy)ethyl)piperazin-1-yl)pyrimidine-5-carboxylate (3.4 g, 4.11 mmol, 1.0 equiv)

in THF (16 mL), EtOH (8 mL) and H₂O (8 mL) was added LiOH.H₂O (344.61 mg, 8.21 mmol, 2.0 equiv). The mixture was stirred at room temperature for 2 h. The two reaction mixtures were then combined and were adjusted to pH=7 with 11\T HCl. The solution was concentrated under reduced pressure to remove THF and EtOH. The solution was then filtered, and the resulting solid was purified by reverse phase chromatography to afford the desired product as a white solid (4 g, 59% yield). LCMS (ESI) m/z: [M+H] calcd for $C_{38}H_{57}N_9O_{10}$: 800.43; found 800.3.

Building block AX. (S)-2-(4-(2-(3-(2-(tert-butoxycarbonyl)-4-(5-(((cert-butoxycarbonyl-N-tert-butoxycarbonyl)amino)methyl)pyrimidin-2-yl)piperazin-1-yl)-3-oxopropoxy)ethyl)piperazin-1-yl)pyrimidine-5-carboxylic acid

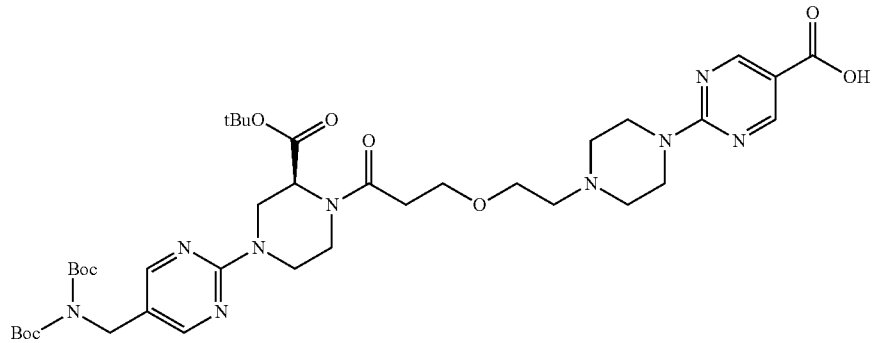 [SMILES: CC(C)(C)OC(=O)[C@@H]1CN(c2ncc(CN(C(=O)OC(C)(C)C)C(=O)OC(C)(C)C)cn2)CCN1C(=O)CCOCCN1CCN(c2ncc(C(=O)O)cn2)CC1]

This building block is prepared from Building block AV by a process similar to that for Building block AW.

Building block AY. 1'-(2-(3-(4-(5-(((Cert-butoxycarbonyl)amino)methyl)pyrimidin-2-yl) piperazin-1-yl)-3-oxopropoxy)ethyl)-[1,4'-bipiperidine]-4-carboxylic acid.

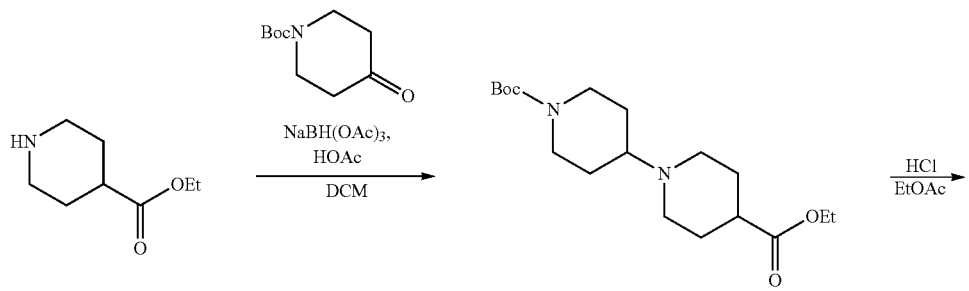

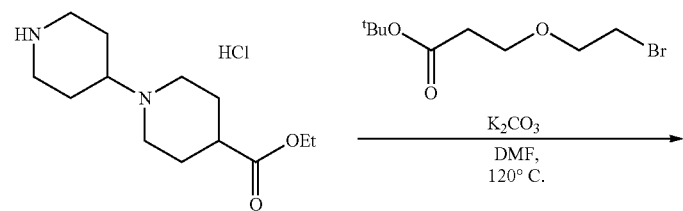

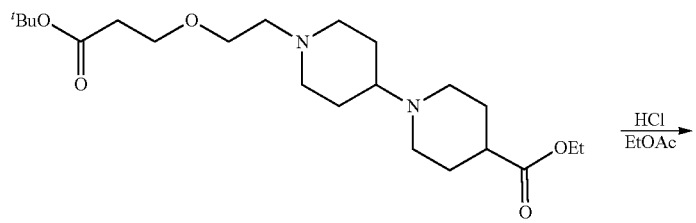

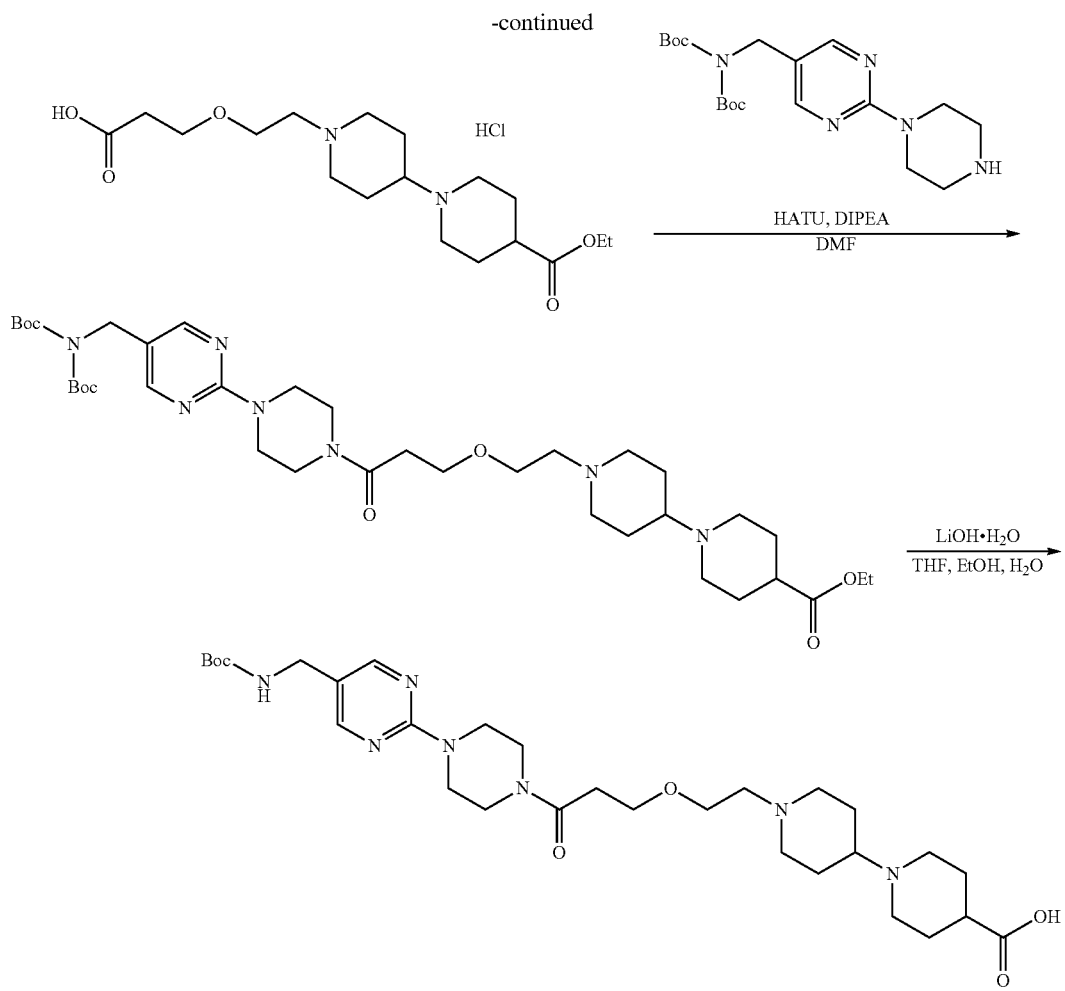

Step 1: Synthesis of 1'-tert-butyl 4-ethyl [1,4'-bipiperidine]-1',4-dicarboxylate To a solution of ethyl piperidine-4-carboxylate (30 g, 150.57 mmol, 1.0 equiv) and tert-butyl 4-oxopiperidine-1-carboxylate (23.67 g, 150.57 mmol, 1.0 equiv) in DCM (300 mL) was added HOAc (6.00 mL, 104.95 mmol, 0.7 equiv). The mixture was stirred at room temperature for 30 min, then NaBH(OAc)$_3$ (63.82 g, 301.13 mmol, 2.0 equiv) was added. The mixture was stirred for 16 h, at which point H$_2$O (50 mL) was added. The aqueous phase was extracted with DCM (3×15 mL) and the combined organic phases were washed with brine (10 mL), dried, filtered, and concentrated under reduced pressure. Purification by silica gel chromatography (8→100 MeOH/EtOAc) afforded the desired product as a yellow oil (30 g, 59% yield).

Step 2: Synthesis of ethyl [1,4'-bipiperidine]-4-carboxylate

To a solution of HCl in EtOAc (200 mL) was added 1'-tert-butyl 4-ethyl [1,4'-bipiperidine]-1',4-dicarboxylate (20 g, 58.74 mmol, 1.0 equiv). The mixture was stirred at room temperature for 3 h. The mixture was then concentrated under reduced pressure to afford the desired crude product as a white solid (15 g, HCl salt).

Step 3: Synthesis of ethyl 1'-(2-(3-(tert-butoxy)-3-oxopropoxy)ethyl)-[1,4'-bipiperidine]-4-carboxylate To a solution of tert-butyl 3-(2-bromoethoxy)propanoate (6.46 g, 25.54 mmol, 1.0 equiv) in DMF (240 mL) was added K$_2$CO$_3$ (10.59 g, 76.61 mmol, 3.0 equiv) and ethyl [1,4'-bipiperidine]-4-carboxylate (8 g, 25.54 mmol, 1.0 equiv, 2HCl). The mixture was stirred at 120° C. for 12 h, at which point the reaction was cooled to room temperature, filtered, the filter cake washed with H$_2$O (20 mL), and the filtrate was concentrated under reduced pressure. Purification by silica gel chromatography (0→11% MeOH/EtOAc) afforded the desired product as a yellow oil (6.6 g, 63% yield).

Step 4: Synthesis of 3-(2-(4-(ethoxycarbonyl)-[1,4'-bipiperidin]-1'-yl)ethoxy)propanoic acid To the solution of HCl in EtOAc (70 mL) was added ethyl 1'-(2-(3-(tert-butoxy)-3-oxopropoxy) ethyl)-[1,4'-bipiperidine]-4-carboxylate (6.6 g, 16.00 mmol, 1.0 equiv). The mixture was stirred at room temperature for 3 h, at which point the reaction was concentrated under reduced pressure to afford the desired product as a white solid (6.5 g, 95% yield, 2HCl).

Step 5: Synthesis of ethyl 1'-(2-(3-(4-(5-(((N,N-di-tert-butoxycarbonyl)amino)methyl)pyrimidin-2-yl)piperazin-1-yl)-3-oxopropoxy)ethyl)-[1,4'-bipiperidine]-4-carboxylate To a solution of tert-butyl-tert-butoxycarbonyl((2-(piperazin-1-yl)pyrimidin-5-yl)methyl)carbamate (2.49 g, 6.33 mmol, 1.5 equiv) in DMF (40 mL) was added DIPEA (9.74 mL, 55.89 mmol, 6.0 equiv) and HATU (5.31 g, 13.97 mmol, 1.5 equiv). The mixture was stirred at room temperature for 30 min, and then 3-(2-(4-(ethoxycarbonyl)-[1,4'-bipiperidin]-1'-yl)ethoxy) propanoic acid (4 g, 9.32 mmol, 1.0 equiv, 2HCl) was added. The mixture was stirred at for 1.5 h, at which point H$_2$O (5 mL) and EtOAc (20 mL) were added. The aqueous phase was extracted with EtOAc (3×10 mL) and the combined organic phases were washed with brine (5 mL), dried, filtered and concentrated under reduced pressure. Purification by reverse phase chromatography afforded the desired product as a brown oil (1.6 g, 23% yield). LCMS (ESI) m/z: [M+H] calcd for C$_{37}$H$_{61}$N$_7$O$_8$: 732.47; found 732.6.

Step 6: Synthesis of 1'-(2-(3-(4-(5-(((tert-butoxycarbonyl)amino)methyl)pyrimidin-2-yl)piperazin-1-yl)-3-oxopropoxy)ethyl)-[1,4'-bipiperidine]-4-carboxylic acid To a solution of ethyl 1'-(2-(3-(4-(5-(((N,N-di-tert-butoxycarbonyl)amino)methyl)pyrimidin-2-yl)piperazin-1-yl)-3-oxopropoxy)ethyl)-[1,4'-bipiperidine]-4-carboxylate (1.4 g, 1.91 mmol, 1.0 equiv) in THF (7.5 mL), EtOH (3.8 mL), and H$_2$O (3.8 mL) was added LiOH.H$_2$O (321.07 mg, 7.65 mmol, 4.0 equiv). The mixture was stirred at room temperature for 2 h, at which point the mixture was concentrated under reduced pressure. Purification by reverse phase chromatography (5→38% MeCN/H$_2$O) afforded the desired product as a yellow solid (325 mg, 22% yield). LCMS (ESI) m/z: [M+H] calcd for C$_{30}$H$_{49}$N$_7$O$_6$: 604.38; found 604.3.

Building block AZ. 1-(4-{2-[2-(2-{[(benzyloxy)carbonyl]amino}ethoxy)ethoxy]ethyl}piperazin-1-yl)-3,6,9,12-tetraoxapentadecan-15-oic acid

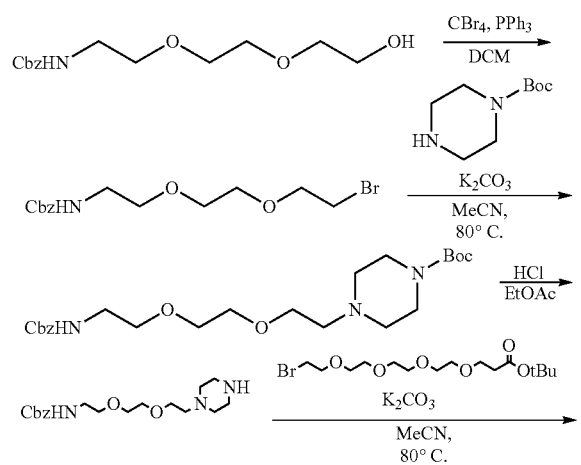

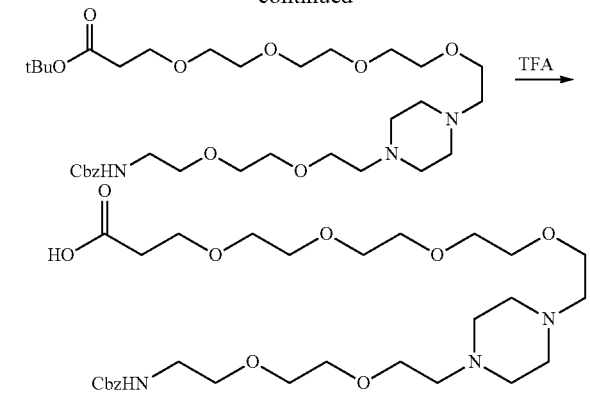

Step 1: Synthesis of benzyl (2-(2-(2-bromoethoxy)ethoxy)ethyl)carbamate

To a solution of benzyl (2-(2-(2-hydroxyethoxy)ethoxy)ethyl)carbamate (10 g, 35.30 mmol, 1.0 equiv) in DCM (300 mL) at 0° C. was added PPh$_3$ (13.79 g, 52.59 mmol, 1.49 equiv) and CBr$_4$ (17.44 g, 52.59 mmol, 1.49 equiv). Then the mixture was warmed to room temperature and stirred for 12 h. The reaction mixture was then filtered, and the filtrate was concentrated under reduced pressure. Purification by silica gel chromatography (1%→25% EtOAc/petroleum ether) afforded the desired product (10.8 g, 88.4% yield) as yellow oil.

Step 2: Synthesis of tert-butyl 4-(3-oxo-1-phenyl-2,7,10-trioxa-4-azadodecan-12-yl)piperazine-1-carboxylate To a solution of benzyl (2-(2-(2-bromoethoxy)ethoxy)ethyl)carbamate (10.8 g, 31.19 mmol, 1.0 equiv) and tert-butyl piperazine-1-carboxylate (5.81 g, 31.19 mmol, 1.0 equiv) in MeCN (100 mL) was added K$_2$CO$_3$ (4.31 g, 31.19 mmol, 1.0 equiv). The mixture was stirred at 80° C. for 1 h. The reaction mixture was then filtered, and the filtrate was concentrated under reduced pressure. Purification by silica gel chromatography (0%→50% MeOH/EtOAc) afforded the desired product (13.1 g, 93.0% yield) as yellow oil.

Step 3: Synthesis of benzyl (2-(2-(2-(piperazin-1-yl)ethoxy)ethoxy)ethyl)carbamate A solution of tert-butyl 4-(3-oxo-1-phenyl-2,7,10-trioxa-4-azadodecan-12-yl)piperazine-1-carboxylate (5.64 g, 12.49 mmol, 1.0 equiv) in HCl/EtOAc (50 mL, 4 M) was stirred at room temperature for 1 h. The reaction mixture was then concentrated under reduced pressure to afford the desired product (5.23 g, crude, HCl salt) as yellow oil.

Step 4: Synthesis of tert-butyl 1-(4-(3-oxo-1-phenyl-2,7,10-trioxa-4-azadodecan-12-yl)piperazin-1-yl)-3,6,9,12-tetraoxapentadecan-15-oate A solution of benzyl (2-(2-(2-(piperazin-1-yl)ethoxy)ethoxy)ethyl)carbamate (13.3 g, 31.34 mmol, 1.0 equiv, 2HCl) and tert-butyl 1-bromo-3,6,9,12-tetraoxapentadecan-15-oate in MeCN (150 mL) was added K$_2$CO$_3$ (21.66 g, 156.71 mmol, 5.0 equiv). The mixture was stirred at 80° C. for 12 h. The reaction mixture was then filtered, and the filtrate was concentrated under reduced pressure. Purification by silica gel chromatography (1%→17% MeOH/DCM) afforded the desired product (5.4 g, 26.3% yield) as a yellow oil.

Step 5: Synthesis of 1-(4-(3-oxo-1-phenyl-2,7,10-trioxa-4-azadodecan-12-yl)piperazin-1-yl)-3,6,9,12-tetraoxapentadecan-15-oic acid A solution of tert-butyl 1-(4-(3-oxo-1-phenyl-2,7,10-trioxa-4-azadodecan-12-yl)piperazin-1-yl)-3,6,9,12-tetraoxapentadecan-15-oate (2.4 g, 3.66 mmol, 1.0 equiv) in TFA (20 mL) was stirred at room temperature for 30 min. The reaction mixture was then concentrated under reduced pressure to afford the desired product (3.03 g, TFA salt) as yellow oil.

Building Block BA. (R)-2-(2-(tert-butoxycarbonyl)-4-(6-(tert-butoxycarbonyl)-5,6,7,8-tetrahydropyrido[4,3-d] pyrimidin-2-yl)piperazin-1-yl)pyrimidine-5-carboxylic acid

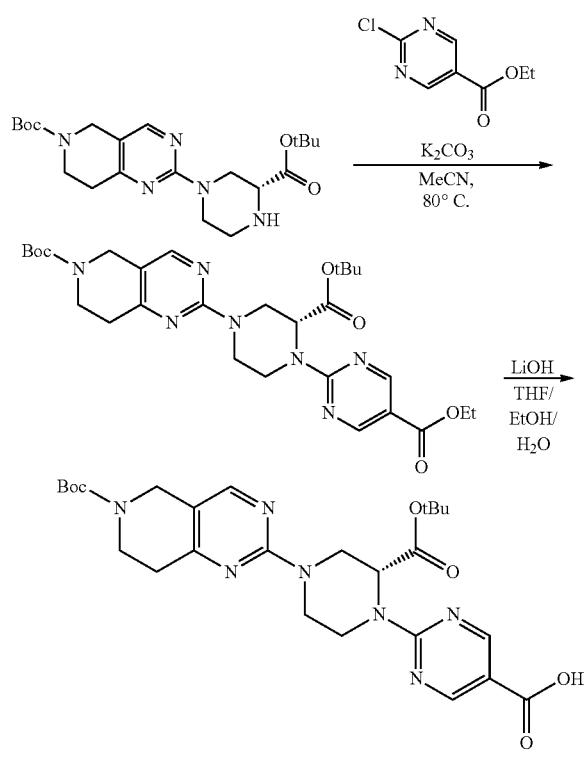

Step 1: Synthesis of (R)-tert-butyl 2-(3-(tert-butoxycarbonyl)-4-(5-(ethoxycarbonyl)pyrimidin-2-yl)piperazin-1-yl)-7,8-dihydropyrido [4,3-d]pyrimidine-6(5H)-carboxylate To two separate batches run in parallel each containing a solution of (R)-tert-butyl 2-(3-(tert-butoxycarbonyl)piperazin-1-yl)-7,8-dihydropyrido[4,3-d]pyrimidine-6(5H)-carboxylate (6 g, 14.30 mmol, 1.0 equiv) and K$_2$CO$_3$ (3.95 g, 28.60 mmol, 2.0 equiv) in MeCN (80 mL) was added ethyl 2-chloropyrimidine-5-carboxylate (3.20 g, 17.16 mmol, 1.2 equiv). The reaction mixtures were stirred at 80° C. for 12 h. The two reactions mixtures were combined and filtered, the residue was washed with EtOAc (3×50 mL), and the filtrate was concentrated under reduced pressure. Purification by silica gel chromatography (0%→17% MeOH/EtOAc) afforded the desired product (15 g, 91.5% yield) as a yellow solid. LCMS (ESI) m/z: [M+H] calcd for C$_{24}$H$_{39}$N$_7$O$_6$: 570.31; found 570.1.

Step 2: Synthesis of (R)-2-(2-(tert-butoxycarbonyl)-4-(6-(tert-butoxycarbonyl)-5,6,7,8-tetrahydropyrido[4,3-d]pyrimidin-2-yl)piperazin-1-yl)pyrimidine-5-carboxylic acid To a solution of (R)-tert-butyl 2-(3-(tert-butoxycarbonyl)-4-(5-(ethoxycarbonyl)pyrimidin-2-yl)piperazin-1-yl)-7,8-dihydropyrido[4,3-d]pyrimidine-6(5H)-carboxylate (15 g, 26.33 mmol, 1.0 equiv) in THF (80 mL), EtOH (40 mL) and H$_2$O (40 mL) was added LiOH.H$_2$O (2.21 g, 52.66 mmol, 2.0 equiv). The mixture was stirred at room temperature for 6 h. The reaction mixture was then adjusted to pH=6 with 1 N HCl. The resulting suspension was filtered, and the solid cake was dried under reduced pressure to afford the desired product (10.87 g, 75.9% yield) as a white solid. LCMS (ESI) m/z: [M+H] calcd for C$_{26}$H$_{35}$N$_7$O$_6$: 542.27; found 542.1.

Building Block BB. (S)-2-(2-(tert-butoxycarbonyl)-4-(6-(tert-butoxycarbonyl)-5,6,7,8-tetrahydropyrido[4,3-d] pyrimidin-2-yl)piperazin-1-yl)pyrimidine-5-carboxylic acid

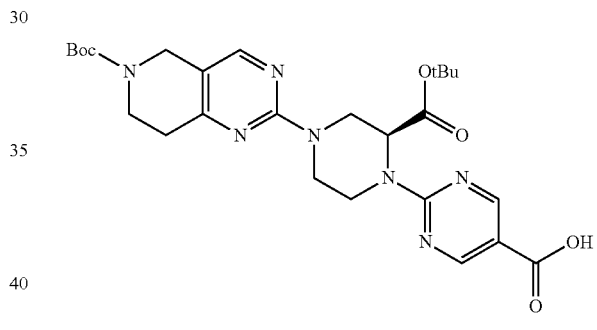

This building block is prepared from Building block AA by a process similar to that for Building block BA.

Building Block BC. 2-[(2R)-2-[(tert-butoxy)carbonyl]-4-[5-({[(tert-butoxy)carbonyl]amino}methyl)pyrimidin-2-yl]piperazin-1-yl]pyrimidine-5-carboxylic acid

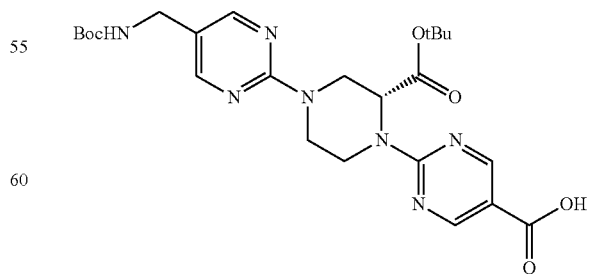

This building block is prepared from Building block AU by a process similar to that for Building block BA.

Building Block BD. 2-[(2S)-2-[(tert-butoxy)carbonyl]-4-[5-({[(tert-butoxy)carbonyl]amino}methyl)pyrimidin-2-yl]piperazin-1-yl] pyrimidine-5-carboxylic acid

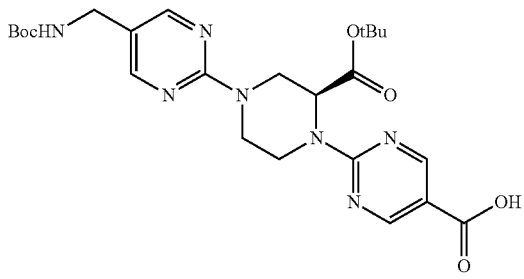 [SMILES: CC(C)(C)OC(=O)NCc1cnc(N2CCN(c3ncc(C(=O)O)cn3)[C@H](C(=O)OC(C)(C)C)C2)nc1]

This building block is prepared from Building block AV by a process similar to that for Building block BA.

Building block BE. 15-(6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)-1-((1S,4S)-5-(2-(2-(2-aminoethoxy)ethoxy)ethyl)-2,5-diazabicyclo[2.2.1]heptan-2-yl)-3,6,9,12-tetraoxapentadecan-15-one Step 1: Synthesis of (1S,4S)-tert-butyl 5-(3-oxo-1-phenyl-2,7,10-trioxa-4-azadodecan-12-yl)-2,5-diazabicyclo[2.2.1]heptane-2-carboxylate To a solution of (1S,4S)-tert-butyl 2,5-diazabicyclo[2.2.1]heptane-2-carboxylate (2.85 g, 14.37 mmol, 1.0 equiv) in MeCN (50 mL) was added K$_2$CO$_3$ (3.97 g, 28.75 mmol, 2.0 equiv) and benzyl (2-(2-(2-bromoethoxy)ethoxy)ethyl)carbamate (4.98 g, 14.37 mmol, 1.0 equiv). The mixture was stirred at 80° C. for 24 h. The reaction mixture was then filtered, and the filtrate was concentrated under reduced pressure. Purification by silica gel chromatography (0→10% MeOH/EtOAc) afforded the desired product (6.2 g, 93.0% yield) as colorless oil. LCMS (ESI) m/z: [M+H] calcd for C$_{24}$H$_{37}$N$_3$O$_6$: 464.27; found 464.2.

Step 2: Synthesis of benzyl (2-(2-(2-((1S,4S)-2,5-diazabicyclo[2.2.1]heptan-2-yl)ethoxy)ethoxy)ethyl) carbamate To a solution of (1S,4S)-tert-butyl 5-(3-oxo-1-phenyl-2,7,10-tri oxa-4-azadodecan-12-yl)-2,5-diazabicyclo[2.2.1]heptane-2-carboxylate (6.2 g, 13.37 mmol, 1.0 equiv) in DCM (60 mL) was added TFA (20.7 mL, 279.12 mmol, 20.9 equiv). The reaction was stirred for 2 h, at which point the mixture was concentrated under reduced pressure at 45° C. to afford the desired crude product (10.5 g, 4TFA) as light brown oil, which was used the next step directly. LCMS (ESI) m/z: [M+H] calcd for C$_{19}$H$_{29}$N$_3$O$_4$: 364.22; found 364.2.

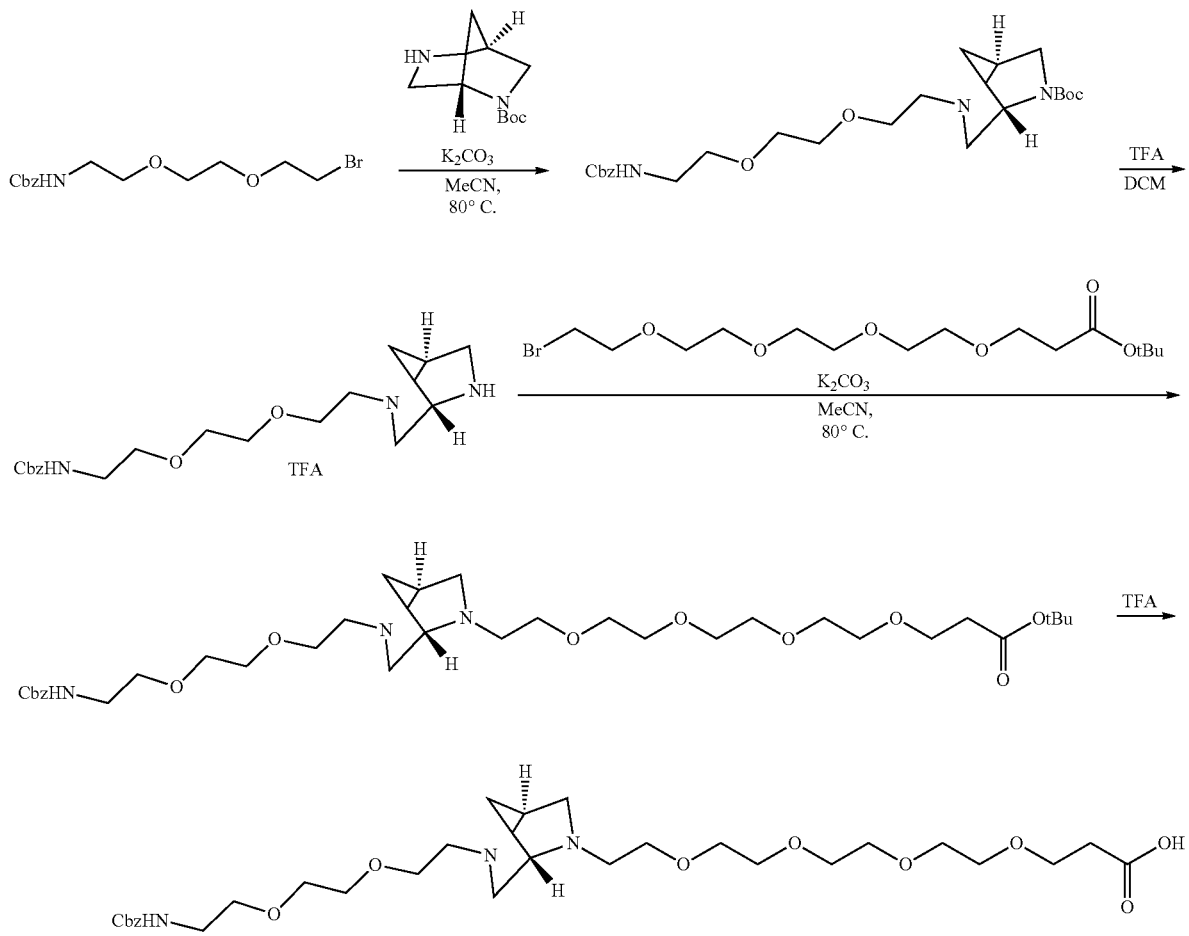

Step 3: Synthesis of tert-butyl 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oate To a solution of benzyl (2-(2-(2-((1S,4S)-2,5-diazabicyclo[2.2.1]heptan-2-yl)ethoxy) ethoxy)ethyl)carbamate (5 g, 6.10 mmol, 1.0 equiv, 4TFA) in MeCN (80 mL) was added $K_2CO_3$ (5.06 g, 36.61 mmol, 6.0 equiv) and tert-butyl 1-bromo-3,6,9,12-tetraoxapentadecan-15-oate (2.35 g, 6.10 mmol, 1.0 equiv). The reaction mixture was stirred at 80° C. for 12 h. The reaction mixture was then filtered, and the filtrate was concentrated under reduced pressure. Purification by silica gel chromatography (0→15% MeOH/EtOAc) afforded the desired product (5.2 g, 92.8% yield) as light yellow oil. LCMS (ESI) m/z: [M+H] calcd for $C_{34}H_{57}N_3O_{10}$: 668.4; found 668.4.

Step 4: Synthesis of 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oic acid A solution of tert-butyl 1-((1S,4S)-5-(3-oxo-1-phenyl-2,7,10-trioxa-4-azadodecan-12-yl)-2,5-diazabicyclo[2.2.1]heptan-2-yl)-3,6,9,12-tetraoxapentadecan-15-oate (5.2 g, 5.66 mmol, 1.0 equiv) in TFA (47.3 mL, 638.27 mmol, 112.75 equiv) was stirred at room temperature for 30 min. The mixture was then concentrated under reduced pressure at 45° C. Purification by reverse phase chromatography (2→35% MeCN/$H_2O$ (0.05% $NH_4OH$)) afforded the desired product (1.88 g, 54.3% yield) as light brown oil. LCMS (ESI) m/z: [M+H] calcd for $C_{30}H_{49}N_3O_{10}$: 612.34; found 612.3.

Building block BF. 21-(6-((4-amino-3-(2-aminobenzo[d]oxazol-5-yl)-1H-pyrazolo[3,4-d]pyrimidin-1-yl)methyl)-3,4-dihydroisoquinolin-2(1H)-yl)-1-(piperazin-1-yl)-3,6,9,12,15,18-hexaoxahenicosan-21-one Step 1: Synthesis of benzyl 4-(23,23-dimethyl-21-oxo-3,6,9,12,15,18,22-heptaoxatetracosyl) piperazine-1-carboxylate To a solution of tert-butyl 1-bromo-3,6,9,12,15,18-hexaoxahenicosan-21-oate (5 g, 10.56 mmol, 1.0 equiv) and benzyl piperazine-1-carboxylate (2.62 mL, 11.62 mmol, 1.1 equiv, HCl) in MeCN (50 mL) was added $K_2CO_3$ (4.38 g, 31.69 mmol, 3.0 equiv). The reaction mixture was stirred at 80° C. for 10 h. The mixture was then filtered, the solid cake washed with EtOAc (3×3 mL), and the filtrate concentrated under reduced pressure. Purification by silica gel chromatography (0→10% MeOH/EtOAc) afforded the desired product (4 g, 61.8% yield) as a red liquid.

Step 2: Synthesis of 1-(4-((benzyloxy)carbonyl)piperazin-1-yl)-3,6,9,12,15,18-hexaoxahenicosan-1-oic acid To a solution of benzyl 4-(23,23-dimethyl-21-oxo-3,6,9,12,15,18,22-heptaoxatetracosyl)piperazine-1-carboxylate (1.8 g, 2.94 mmol, 1.0 equiv) in DCM (10 mL) was added TFA (10 mL). The solution was stirred for 0.5 h. The solution was then concentrated under reduced pressure. To the residue was added DCM (30 mL) and then the solution was concentrated under reduced pressure to afford the desired product (1.6 g, 2.87 mmol, TFA) as a red liquid.

Preparation of Rapamycin Monomers

Monomer 1. 32(R)-hydroxy 26-aminooxyacetic acid rapamycin

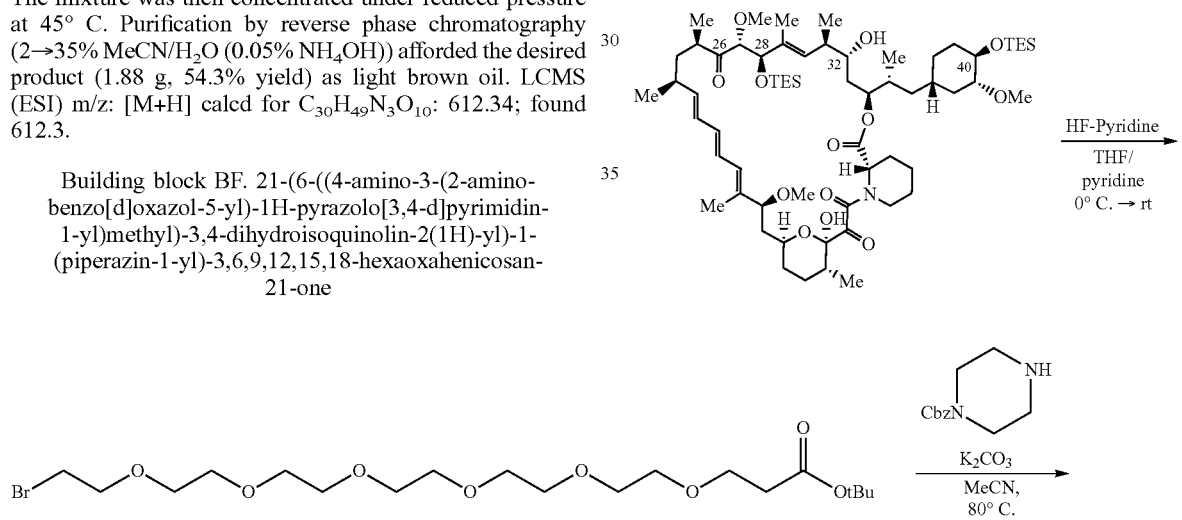

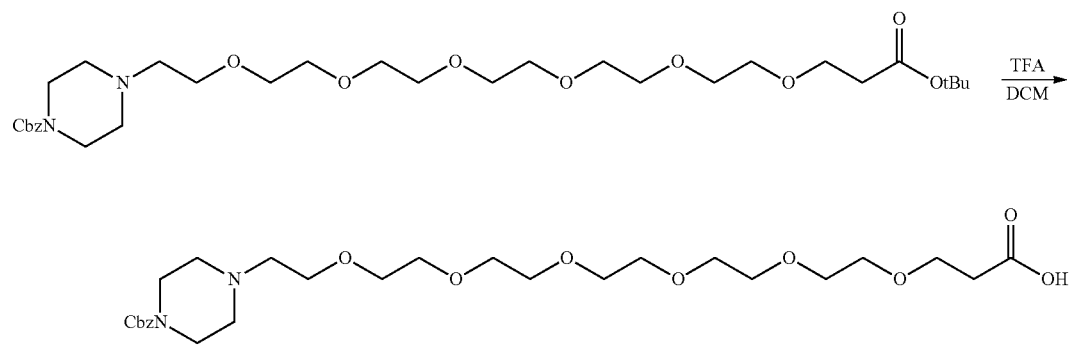

-continued

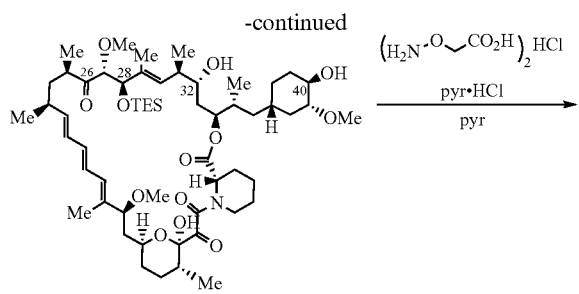

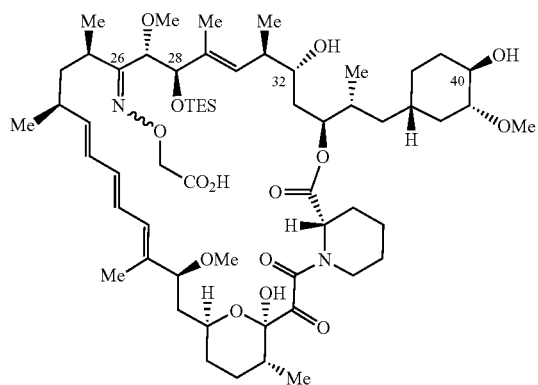

Step 1: Synthesis of 32(R)-hydroxy rapamycin

A solution of 32(R)-hydroxy-28,40-bistriethylsilyl rapamycin (3.64 g, 3.18 mmol, 1 equiv) in THF (41.8 mL) was treated with pyridine (20.8 mL, 258 mmol, 81 equiv) and the reaction mixture was cooled to 0° C. The solution was treated dropwise with 70% HF-pyridine (4.60 mL, 159 mmol, 50 equiv) and the reaction mixture was stirred at 0° C. for 20 min followed by warming to room temperature. After 5 h, the reaction mixture was cooled back to 0° C. and carefully added to ice cold sat. NaHCO$_3$ solution (400 mL). The mixture was extracted with EtOAc (2×100 mL) and the organic phases were washed with 75 mL portions of H$_2$O, sat. NaHCO$_3$ solution and brine. The organic solution was dried over Na$_2$SO$_4$, filtered and concentrated to yield a light yellow oil that produced a stiff foam under reduced pressure. The crude material was purified by silica gel chromatography (20→40% acetone/hex) to yield the desired product as a white amorphous solid (1.66 g, 57% yield). LCMS (ESI) m/z: [M+Na] calcd for C$_{51}$H$_{81}$NO$_{13}$: 938.56; found 938.7; m/z: [M−H] calcd for C$_{51}$H$_{81}$NO$_{13}$: 914.56; found 914.7.

Step 2: Synthesis of 32(R)-hydroxy 26-aminooxyacetic acid rapamycin

To a dry reaction flask was added 32(R)-hydroxy rapamycin (3.39 g, 3.70 mmol, 1.0 equiv) and carboxymethoxylamine hemihydrochloride (1.62 g, 7.40 mmol, 2.0 equiv), followed by pyridine (18 mL) at room temperature. Pyridine hydrochloride (2.99 g, 25.9 mmol, 7.0 equiv) was added and then the reaction mixture was heated to 50° C. After 1.5 days, the solvent was removed under reduced pressure and the semisolid material was purified by reverse phase chromatography (15→90% MeCN/H$_2$O, no TFA) to afford the product, a mixture of E/Z oxime isomers, as a white powder (1.51 g, 41% yield). LCMS (ESI) m/z: [M+Na] calcd for C$_{53}$H$_{84}$N$_2$O$_{15}$: 1011.58; found 1011.6.

Monomer 2. 32(R)-methoxy 26-aminooxyacetic acid rapamycin

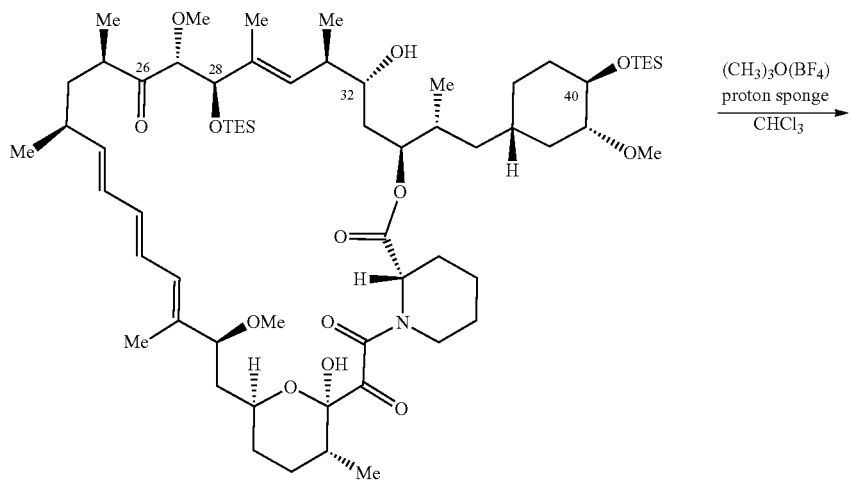

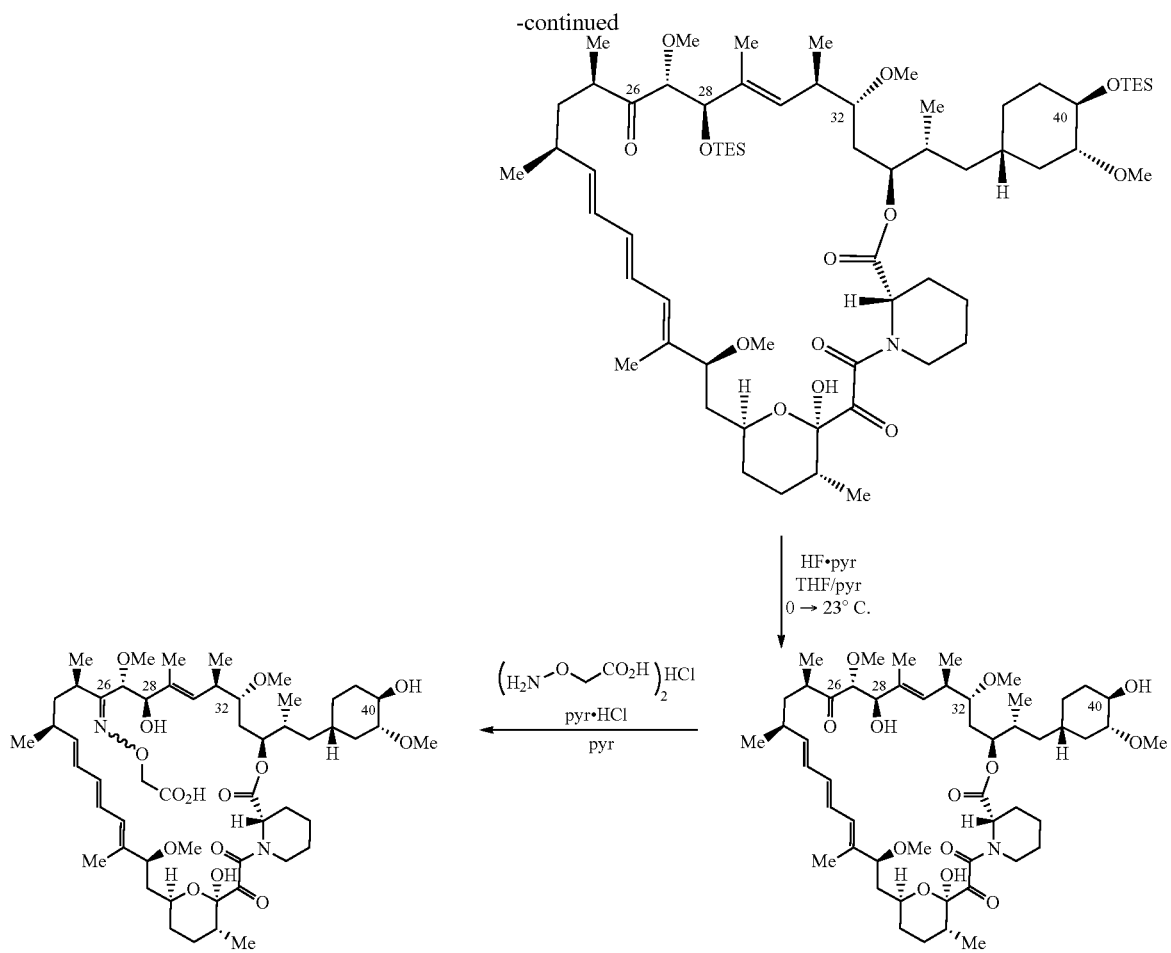

Step 1: Synthesis of 32(R)-methoxy-28,40-bistriethylsilyl rapamycin

To a stirred solution of 32(R)-hydroxy-28,40-bistriethylsilyl rapamycin (3.83 g, 3.34 mmol, 1.0 equiv) in chloroform (95.8 mL) was added Proton Sponge® (7.17 g, 33.5 mmol, 10.0 equiv) along with freshly dried 4 A molecular sieves (4 g). The solution was stirred for 1 h prior to the addition of trimethyloxonium tetrafluoroborate (4.95 g, 33.5 mmol, 10.0 equiv, dried by heating under reduced pressure at 50° C. for 1 h before use) at room temperature. The reaction mixture was stirred for 18 h, and then the reaction mixture was diluted with DCM and filtered through Celite. The filtrate was washed sequentially with aqueous 1 M HCl (2×), sat. aqueous NaHCO$_3$ solution, then dried and concentrated under reduced pressure. Purification by silica gel chromatography (10→20% EtOAc/hexanes) afforded the desired product as a yellow oil that was contaminated with 3 wt. % Proton Sponge. The residue was taken up in MTBE and washed with aqueous 1 M HCl, sat. aqueous NaHCO$_3$ solution, dried, and then concentrated under reduced pressure to furnish a yellow foam (3.15 g, 81.2% yield). LCMS (ESI) m/z: [M−TES+H$_2$O] calcd for C$_{64}$H$_{111}$NO$_{13}$Si$_2$: 1061.68; found 1061.9.

Step 2: Synthesis of 32(R)-methoxy rapamycin

To a stirred solution of 32(R)-methoxy-28,40-bistriethylsilyl rapamycin (1.11 g, 0.958 mmol, 1.0 equiv) in THF (12.6 mL) and pyridine (6.30 mL) in a plastic vial was added 70% HF-pyridine (2.22 mL, 76.6 mmol, 80.0 equiv) dropwise at 0° C. The reaction mixture was stirred at 0° C. for 20 min before being warmed to room temperature for 3 h. The reaction mixture was cooled to 0° C. and poured slowly into ice cold sat. aqueous NaHCO$_3$ solution (50 mL). The aqueous layer was extracted with EtOAc (3×) and the combined organics were washed with sat. aqueous NaHCO$_3$ solution, brine, dried, and concentrated under reduced pressure. The yellow residue was dissolved in MeOH (5 mL) and added dropwise to H$_2$O (50 mL) to produce a white precipitate. After stirring for 15 min the slurry was filtered on a medium porosity funnel and the cake washed with H$_2$O (2×). The solids were then dissolved in MeCN (50 mL) and lyophilized overnight to provide the product as a white solid (780 mg, 87% yield). LCMS (ESI) m/z: [M+Na] calcd for C$_{52}$H$_{83}$NO$_{13}$: 952.58; found 952.4.

Step 3: Synthesis of 32(R)-methoxy 26-aminooxyacetic acid rapamycin

To a dry reaction flask was added 32(R)-methoxy rapamycin (118 mg, 0.127 mmol, 1.0 equiv) and carboxymethoxylamine hemihydrochloride (137 mg, 0.634 mmol, 5.0 equiv), followed by pyridine (0.59 mL) at room temperature. Pyridine hydrochloride (0.103 g, 0.888 mmol, 7.0 equiv) was added and then the reaction mixture was heated to 50° C. After 1.5 days, the reaction mixture was cooled to room temperature and added dropwise into H$_2$O (25 mL) followed

515 by cooling the mixture to 0° C. The precipitated solid was filtered, washed with H₂O twice and dried to afford the product, a mixture of E/Z oxime isomers, as a white powder (99 mg, 77% yield). LCMS (ESI) m/z: [M−H] calcd for $C_{54}H_{86}N_2O_{15}$: 1001.59; found 1001.7.

Monomers 3. 32(R)-ethoxy 26-aminooxyacetic acid rapamycin

516

Step 1: Synthesis of 32(R)-ethoxy-28,40-bistriethylsilyl rapamycin

A solution of 32(R)-hydroxyhydroxy-28,40-bistriethylsilyl rapamycin (773 mg, 0.675 mmol, 1.0 equiv) in chloroform (19 mL) was treated with N,N,N',N'-tetramethyl-1,8-naphthalenediamine (1.85 g, 8.63 mmol, 12.8 equiv) along with freshly dried 4A molecular sieves. The mixture was stirred for 1 h at room temperature and treated with trieth-

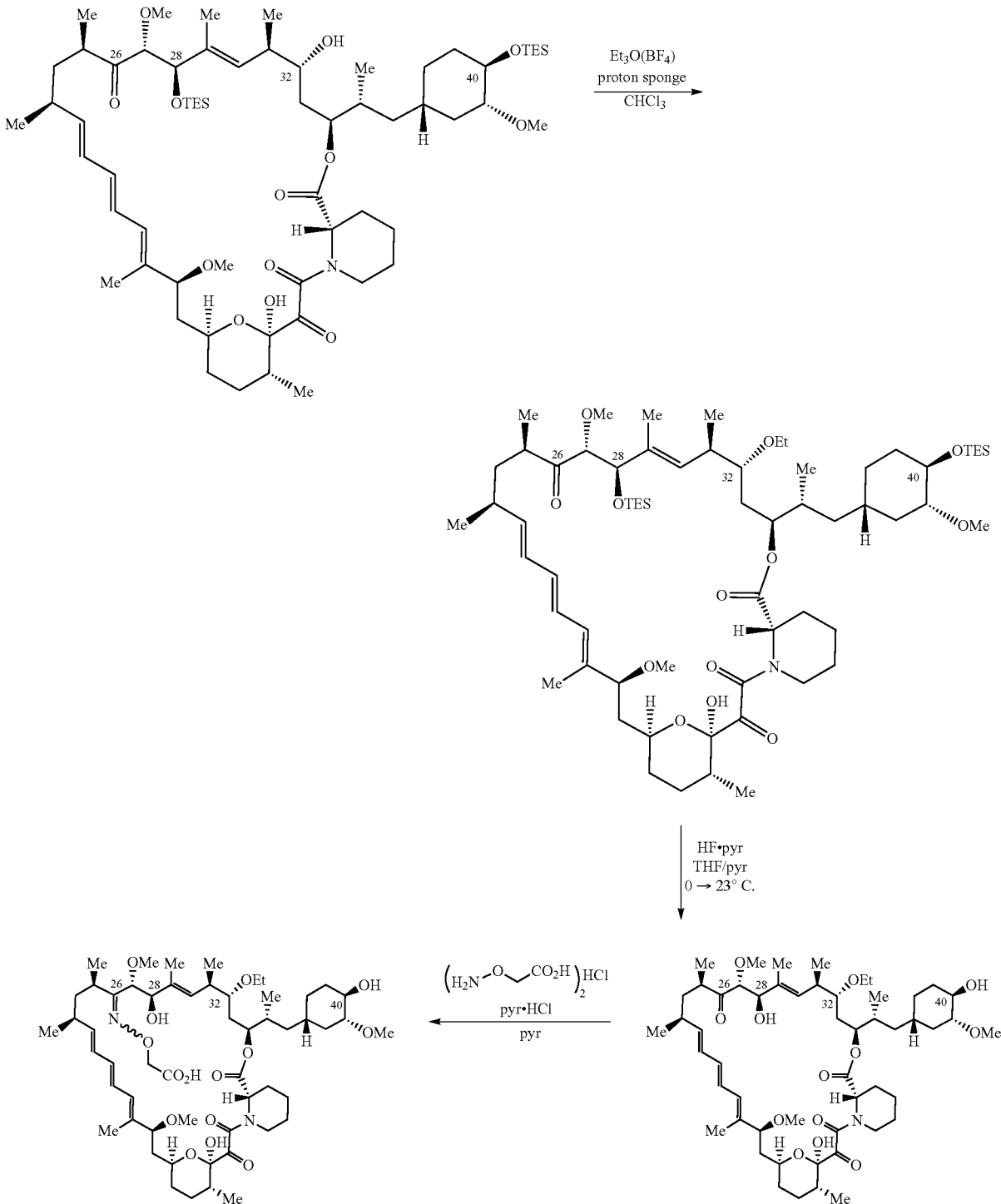

yloxonium tetrafluoroborate (1.51 g, 7.95 mmol, 11.8 equiv) in one portion at room temperature. The reaction mixture was stirred for 3 h, at which point the reaction mixture was diluted with DCM and filtered through Celite, washing the filter pad with additional DCM. The combined filtrates were washed twice with 1M HCl, once with saturated NaHCO$_3$ solution, and dried over Na$_2$SO$_4$. The solution was filtered and concentrated to a residue. The crude residue was treated with MTBE and filtered to remove polar insoluble material. The filtrate was concentrated and purified by silica gel chromatography (5→25% EtOAc/hex) to afford the product as a foam (516 mg, 65% yield). LCMS (ESI) m/z: [M+Na] calcd for C$_{65}$H$_{113}$NO$_{13}$Si$_2$ 1194.77; found 1194.6.

Step 2: Synthesis of 32(R)-ethoxy rapamycin

To a solution of 32(R)-ethoxy-28,40-bistriethylsilyl rapamycin (131 mg, 0.112 mmol, 1.0 equiv) in THF (1.3 mL) at 0° C. was added pyridine (271 μL, 3.35 mmol, 3.4 equiv) followed by 70% HF-pyridine (51 μL, 1.8 mmol, 1.8 equiv). The reaction flask was capped and stored in the fridge for 3 days, at which point the reaction mixture was poured into cold saturated NaHCO$_3$(20 mL). The aqueous layer extracted with EtOAc (3×20 mL) and the combined organic layers were washed with 1M HCl (2×20 mL), saturated NaHCO$_3$ solution (20 mL), and brine. The solution was dried over Na$_2$SO$_4$, filtered, and concentrated. The residue was taken up in MeOH (1.5 mL) and added dropwise to H$_2$O (20 mL). The solids were filtered and washed with additional H$_2$O to provide the product (53 mg, 51% yield) as a white powder. LCMS (ESI) m/z: [M+Na] calcd for C$_{53}$H$_{85}$NO$_{13}$: 966.59; found 966.5.

Step 3: Synthesis of 32(R)-ethoxy 26-aminooxyacetic acid rapamycin

To a dry reaction flask is added 32(R)-ethoxy rapamycin (1.0 equiv) and carboxymethoxylamine hemihydrochloride (5.0 equiv), followed by pyridine at room temperature. Pyridine hydrochloride (7.0 equiv) is added and then the reaction mixture is heated to 50° C. After 1.5 days, the reaction mixture is cooled to room temperature and added dropwise into H$_2$O followed by cooling the mixture to 0° C. The precipitated solid is filtered, washed with H$_2$O twice and dried to afford the product, a mixture of E/Z oxime isomers.

Monomer 4. 32(R)-hydroxy 26-(3-aminooxybenzoic acid) rapamycin

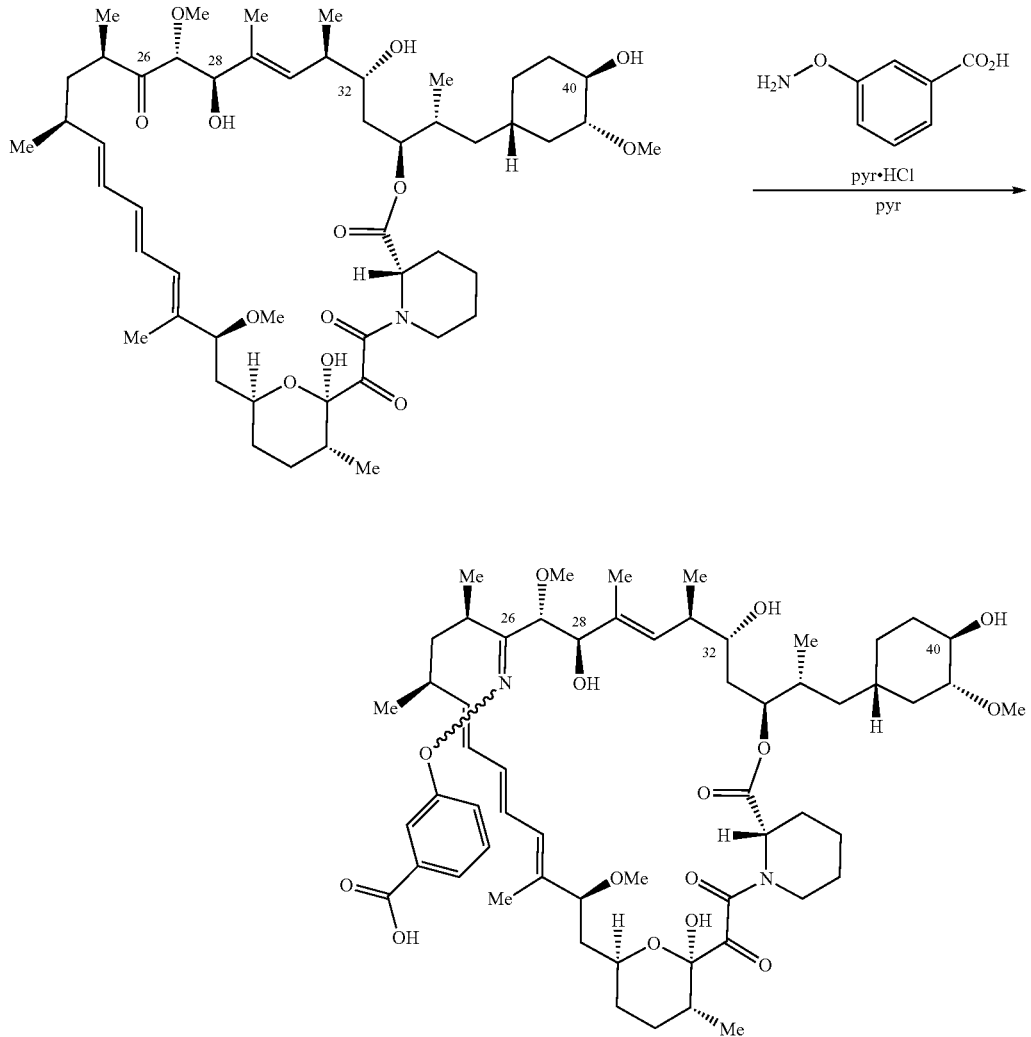

To a solution of 32(R)-hydroxy rapamycin (0.500 g, 0.546 mmol, 1.0 equiv) and 3-(aminooxy)benzoic acid (0.207 g, 1.35 mmol, 2.5 equiv) in pyridine (2.6 mL) was added pyridine hydrochloride (0.442 g, 3.82 mmol, 7.0 equiv). The reaction mixture heated to 50° C. After 43 h, additional 3-(aminooxy)benzoic acid (0.103 g, 0.67 mmol, 1.2 equiv) and 4 M HCl in dioxane (0.136 mL, 0.54 mmol, 1.0 equiv) was added. After 24 h, the reaction was cooled to room temperature and the solution was partitioned between EtOAc and 1M HCl. The aqueous layer was extracted with EtOAc and the combined organic layers were washed with 2M HCl, $H_2O$, and brine, dried with $Na_2SO_4$ and concentrated under reduced pressure. The crude product was purified by silica gel chromatography (15→50% acetone/DCM then 5% MeOH/DCM) to provide the semi-pure product. Repurification by preparative plate silica gel chromatography (50% acetone/DCM) provided the product (0.089 g, 16% yield) as a white foam. LCMS (ESI) m/z: [M+Na] calcd for $C_{58}H_{86}N_2O_{15}$: 1073.59; found 1073.5.

Monomer 5. 32(R)-hydroxy
26-(2-aminooxy-2-methylpropanoic acid) rapamycin

To a solution of 32(R)-hydroxy rapamycin (0.500 g, 0.546 mmol, 1.0 equiv) and 2-(aminooxy)-2-methylpropanoic acid hydrochloride (0.340 g, 2.18 mmol, 4.0 equiv) in pyridine (2.6 mL) was added pyridine hydrochloride (0.504 g, 4.36 mmol, 8.0 equiv). The reaction mixture was heated to 50° C. for 64 h. The reaction mixture was then cooled to room temperature and was partitioned between EtOAc and 2N HCl. The aqueous layer was extracted with EtOAc and then the combined organic layers were washed with 2N HCl, $H_2O$, and brine, dried with $Na_2SO_4$ and concentrated under reduced pressure. The residue was purified by silica gel chromatography (20→50% acetone/DCM) to provide semi-pure product (0.275 g). Trituration with 50% $Et_2O$/hexane (40 mL) afforded the purified product (0.127 g, 23% yield) as a white solid. LCMS (ESI) m/z: [M+Na] calcd for $C_{55}H_{88}N_2O_{15}$: 1039.61; found 1039.6.

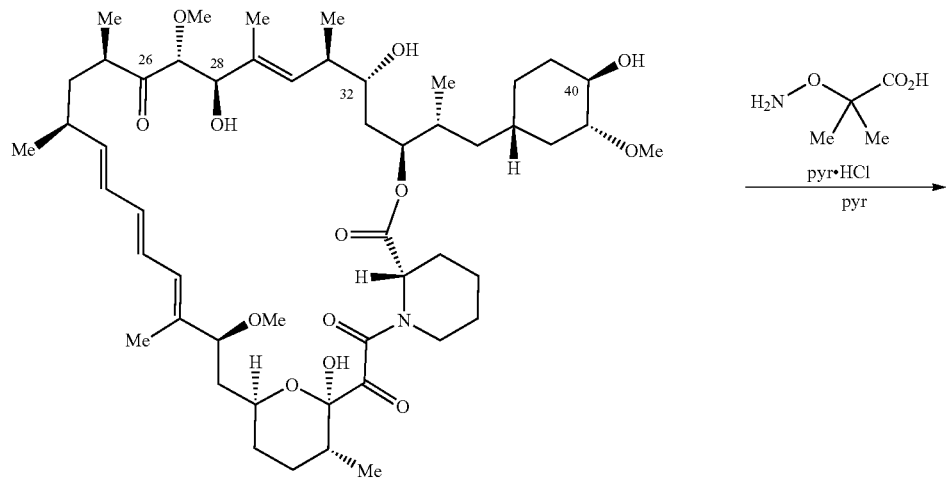

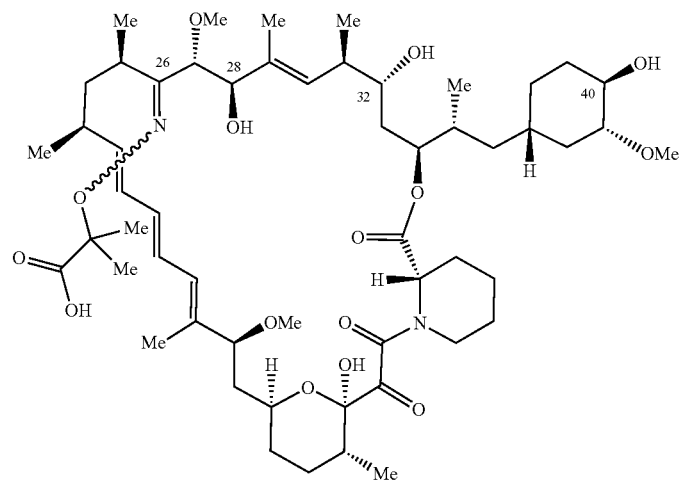

Monomer 6. 26-aminooxyacetic acid rapamycin
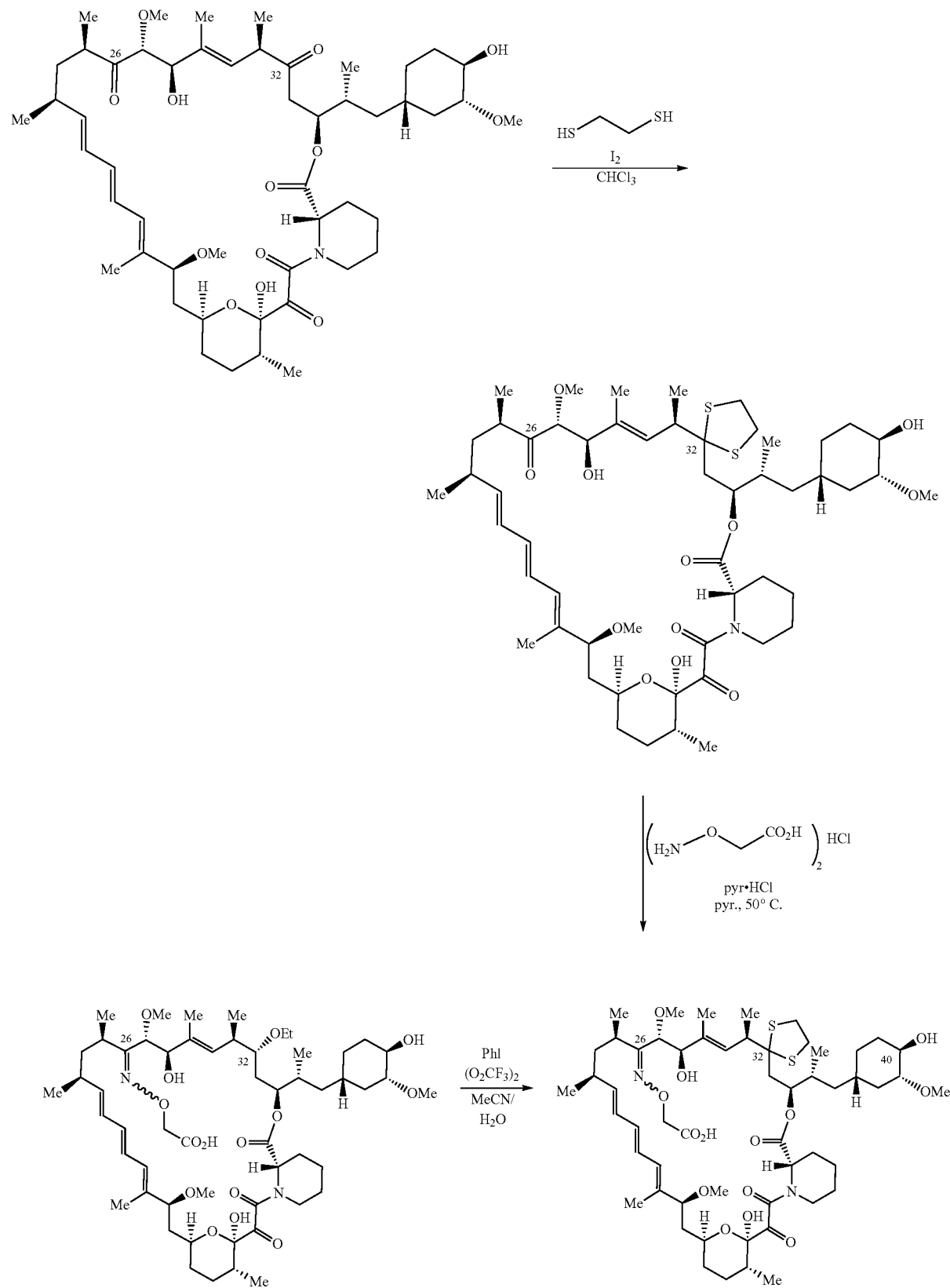

Step 1: Synthesis of 32-(1,3-dithiolane) rapamycin

To a solution of rapamycin (1.0 equiv) in chloroform is added 1,2-ethanedithiol (1.1 equiv) followed by iodine (0.1 equiv). The solution is stirred at room temperature until consumption of rapamycin, as determined by LCMS analysis. After aqueous workup, the crude material is purified by silica gel chromatography to provide the product.

Step 2: Synthesis of 32-(1,3-dithiolane) 26-aminooxyacetic acid rapamycin

To a dry reaction flask is added 32-(1,3-dithiolane) rapamycin (1.0 equiv) and carboxymethoxylamine hemihydrochloride (5.0 equiv), followed by pyridine at room temperature. Pyridine hydrochloride (7.0 equiv) is added and then the reaction mixture is heated to 50° C. After 1.5 days, the reaction mixture is cooled to room temperature and added dropwise into H$_2$O followed by cooling the mixture to 0° C. The precipitated solid is filtered, washed with H$_2$O twice and dried to afford the product, a mixture of E/Z oxime isomers.

Step 3: Synthesis of 26-aminooxyacetic acid rapamycin

To a solution of 32-(1,3-dithiolane) 26-aminooxyacetic acid rapamycin in MeCN and H$_2$O at room temperature is added [bis(trifluoroacetoxy)iodo]benzene. The solution is stirred at room temperature until consumption of starting material, as determined by LCMS analysis. After aqueous workup, the crude material is purified by silica gel chromatography to provide the product.

Monomer 7. 32-deoxy 26-aminooxyacetic acid rapamycin

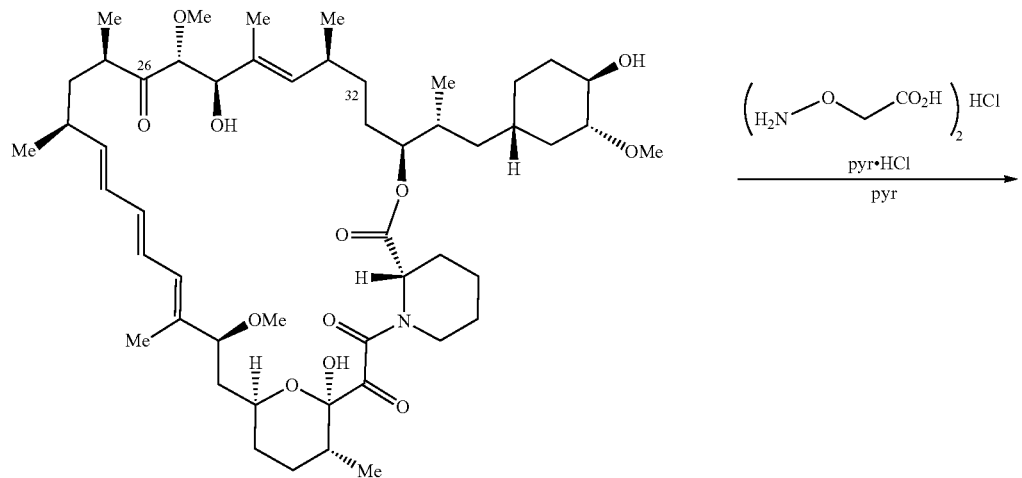

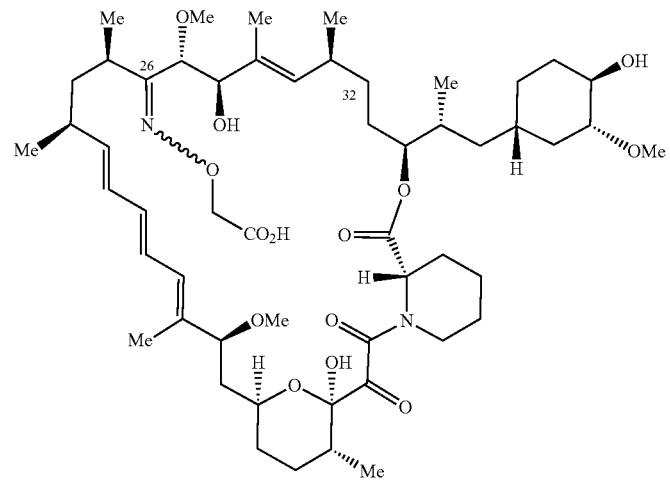

To a solution of 32-deoxy rapamycin (880 mg, 0.978 mmol, 1.0 equiv) and carboxymethoxylamine hemihydrochloride (430 mg, 2.0 mmol) in pyridine (10.4 mL) was added pyridine hydrochloride (791.7 mg, 6.851 mmol, 7.0 equiv) and then the reaction mixture was heated to 50° C. After 67 h, the reaction mixture was cooled to room temperature and added to H$_2$O (100 mL). The aqueous layer was extracted EtOAc (2×100 mL) and the combined organic layers were washed with H$_2$O (50 mL), dried, filtered, and concentrated under reduced pressure. Purification by reverse phase chromatography (15→100% MeCN/H$_2$O) afforded the desired product (190 mg, 20%) as a colorless fluffy solid. LCMS (ESI) m/z: [M+Na] calcd for C$_{53}$H$_{84}$N$_2$O$_{14}$: 995.58; found 995.7; [M−H] calcd for C$_{53}$H$_{84}$N$_2$O$_{14}$: 971.58; found 972.0.

Monomer 8. 32(R)-methoxy 26-aminooxyacetic acid 40(R)-[[(3-(4-methyl-1-piperazinyl)propyl] carbamate] rapamycin

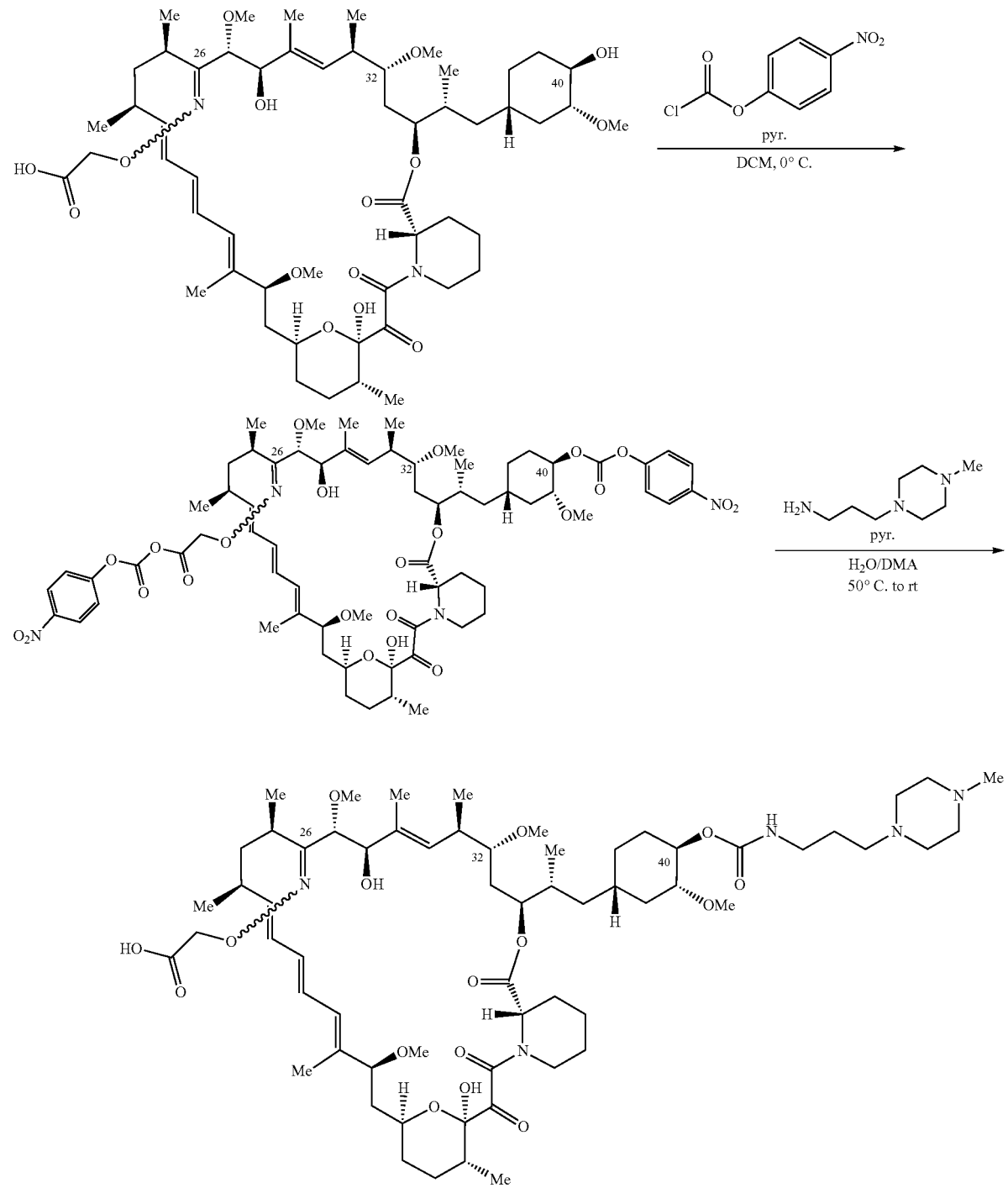

Step 1: Synthesis of 32(R)-methoxy 26-(2-{[(4-nitrophenoxy)carbonyl]oxy}-2-oxoethoxy)imino 40(R)-(4-nitrophenyl)carbonate rapamycin To a solution of 32(R)-methoxy 26-aminooxyacetic acid rapamycin (300 mg, 0.299 mmol, 1.0 equiv) in DCM (10.6 mL) was added 4 A molecular sieves (300 mg). The suspension was stirred for 1 h and then pyridine (239 2.98 mmol, 10.0 equiv) was added. The reaction was cooled to 0° C. and then O-(4-nitrophenyl)chloroformate (153 mg, 0.897 mmol, 3.0 equiv) was added. The reaction warmed to room temperature and stirred for 2 h, at which point the solvent was removed under reduced pressure to provide a crude white solid that was taken directly onto the next step. LCMS (ESI) m/z: [M+H] calcd for $C_{68}H_{92}N_4O_{23}$: 1333.63; found 1333.6.

Step 2: Synthesis of 32(R)-methoxy 26-aminooxyacetic acid 40(R)-[[(3-(4-methyl-1-piperazinyl)propyl]carbamate] rapamycin To a solution of 32(R)-methoxy 26-(2-{[(4-nitrophenoxy)carbonyl]oxy}-2-oxoethoxy)imino 40(R)-(4-nitrophenyl)carbonate rapamycin (0.270 g, 0.2024 mmol, 1.0 equiv) in DMA (1.0 mL) was added pyridine (161 2.02 mmol, 10.0 equiv) and $H_2O$ (1.09 mL, 60.7 mmol, 300 equiv). The reaction stirred at 50° C. for 8 h, at which point the reaction was cooled to room temperature and stirred for an additional 12 h. To the reaction mixture was then added 3-(4-methylpiperazin-1-yl)propan-1-amine (63.6 mg, 0.4048 mmol, 2.0 equiv) and the reaction stirred for 1 h, at which point the mixture was purified by reverse phase chromatography (10→100% MeCN/$H_2O$) to afford the desired product as a white solid (17.0 mg, 7% yield). LCMS (ESI) [M+H] calcd for $C_{63}H_{103}N_5O_{16}$: 1186.75; found 1186.8.

General Procedures and Specific Examples

General Procedure 1: Coupling of a carboxylic acid and an amine followed by N-Boc deprotection

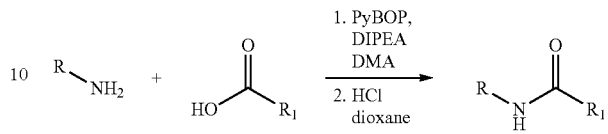

Step 1

To a 0.1 M solution of carboxylic acid (1.0 equiv) in DMA was added an amine (1.2 equiv), DIPEA (4.0 equiv) and PyBOP (1.3 equiv). The reaction was allowed to stir until consumption of the carboxylic acid, as indicated by LCMS. The reaction mixture was then purified by silica gel chromatography to afford the product.

Step 2

To a 0.03 M solution of N-Boc protected amine (1.0 equiv) in dioxane was added HCl (4 M in dioxane, 10 equiv). The reaction was allowed to stir until consumption of the N-Boc protected amine, as indicated by LCMS. The reaction was then concentrated under reduced pressure, and the resulting oil was azeotroped with DCM to afford the product.

Intermediate A1-1. 1-amino-N-{4-[4-amino-3-(2-amino-1,3-benzoxazol-5-yl)-1H-2$\lambda^4$-pyrazolo[3,4-d]pyrimidin-2-yl]butyl}-3,6,9,12,15,18,21,24-octaoxa-heptacosan-27-amide hydrochloride

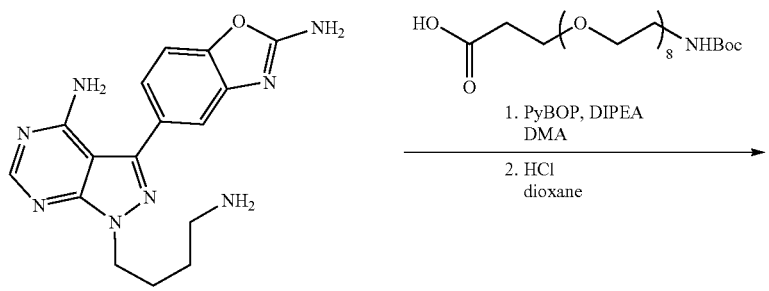

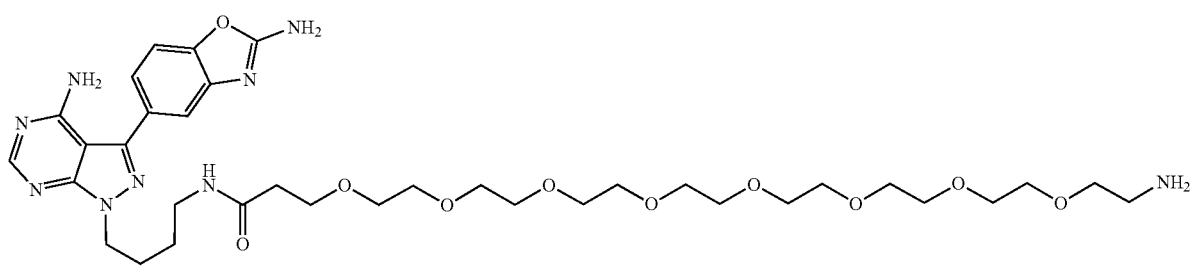

Step 1: Synthesis of tert-butyl N-[26-({4-[4-amino-3-(2-amino-1,3-benzoxazol-5-yl)-1H-2$\lambda^4$-pyrazolo[3,4-d]pyrimidin-2-yl]butyl}carbamoyl)-3,6,9,12,15,18,21,24-octaoxahexacosan-1-yl]carbamate To a solution of 1-{[(tert-butoxy)carbonyl]amino}-3,6,9,12,15,18,21,24-octaoxaheptacosan-27-oic acid (250 mg, 0.4615 mmol, 1.0 equiv) and 5-(4-amino-1-(4-aminobutyl)-1H-pyrazolo[3,4-d]pyrimidin-3-yl)benzo[d]-oxazol-2-amine trifluoroacetic acid salt (375 mg, 0.8307 mmol, 1.8 equiv) in DMA (4.61 mL) was added DIPEA (239 1.38 mmol, 3.0 equiv) followed by PyBOP (312 mg, 0.599 mmol, 1.3 equiv). The homogenous reaction mixture was stirred at room temperature. After 3 h, the crude reaction solution was purified by preparative HPLC (10→99% MeCN/H$_2$O) to provide the product (127 mg, 31% yield) as a pink solid. LCMS (ESI) m/z: [M+H] calcd for C$_{40}$H$_{63}$N$_9$O$_{12}$: 862.47; found 862.3.

Step 2: Synthesis of 1-amino-N-{4-[4-amino-3-(2-amino-1,3-benzoxazol-5-yl)-1H-2$\lambda^4$-pyrazolo[3,4-d]pyrimidin-2-yl]butyl}-3,6,9,12,15,18,21,24-octaoxaheptacosan-27-amide hydrochloride To solution of tert-butyl N-[26-({4-[4-amino-1,3-benzoxazol-5-yl)-1H-2$\lambda^4$-pyrazolo[3,4-d]pyrimidin-2-yl]butyl}carbamoyl)-3,6,9,12,15,18,21,24-octaoxahexacosan-1-yl]carbamate (124 mg, 0.1436 mmol, 1.0 equiv) in dioxane (2 mL) was added 4N HCl in dioxane (2 mL). The heterogeneous solution was vigorously stirred for 2 h, at which point the reaction mixture was concentrated under reduced pressure. The product was dissolved in H$_2$O and lyophilized to afford the product (132 mg, 115%) as a light pink gum. LCMS (ESI) m/z: [M+H] calcd for C$_{35}$H$_{55}$N$_9$O$_{10}$: 762.42; found 762.3.

Following General Procedure 1, but using the appropriate amine-containing active site inhibitor in Table 2 and PEG carboxylic acid, the Intermediates A1 in Table 5 were prepared:

TABLE 5
Additional amines prepared
| Structure | Molecular Formula | Calculated MW | Observed MW |
|---|---|---|---|
| 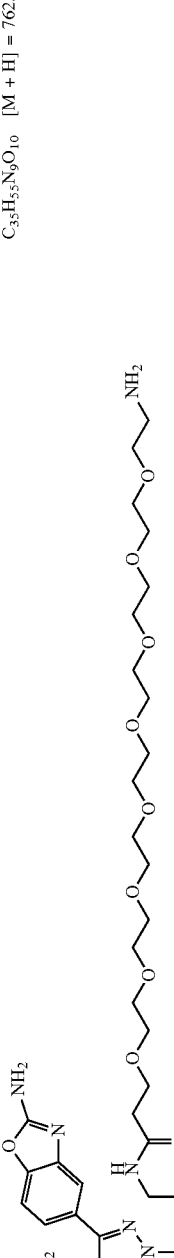 Intermediate A1-1 | C35H55N9O10 | [M + H] = 762.42 | [M + H] = 762.3 |
| 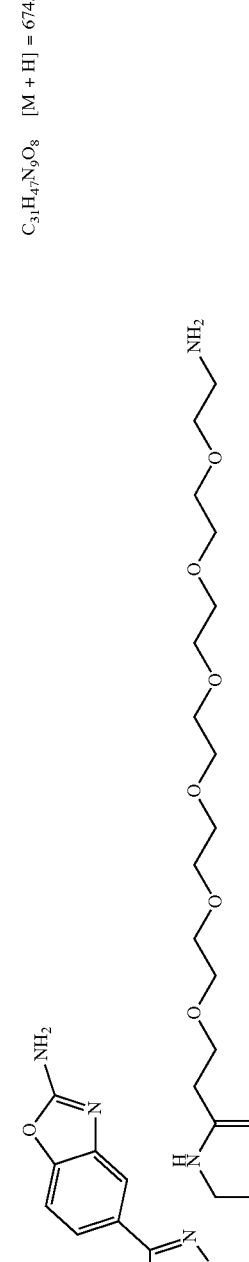 Intermediate A1-2 | C31H47N9O8 | [M + H] = 674.36 | [M + H] = 674.3 |
| 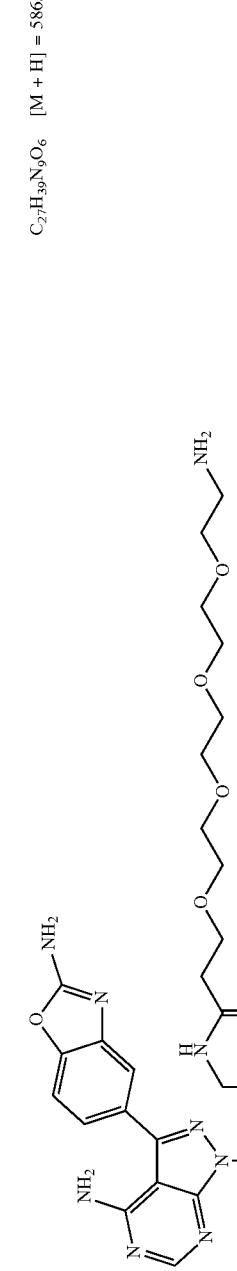 Intermediate A1-3 | C27H39N9O6 | [M + H] = 586.31 | [M + H] = 586.6 |

TABLE 5-continued

Additional amines prepared

| Structure | Molecular Formula | Calculated MW | Observed MW |
|---|---|---|---|
| Intermediate A1-4 | C₂₅H₃₅N₉O₅ | [M + H] = 542.29 | [M + H] = 542.3 |
| Intermediate A1-5 | C₂₃H₃₁N₉O₄ | [M + H] = 498.26 | [M + H] = 498.2 |
| Intermediate A1-6 | C₂₁H₂₇N₉O₃ | [M + H] = 454.23 | [M + H] = 454.1 |

TABLE 5-continued

Additional amines prepared

| Structure | Molecular Formula | Calculated MW | Observed MW |
|---|---|---|---|
| Intermediate A1-7 | $C_{41}H_{57}N_9O_{10}$ | $[M + H] = 836.43$ | $[M + H] = 836.3$ |
| Intermediate A1-8 | $C_{37}H_{49}N_9O_8$ | $[M + H] = 748.38$ | $[M + H] = 748.2$ |
| Intermediate A1-9 | $C_{33}H_{41}N_9O_6$ | $[M + H] = 660.33$ | $[M + H] = 660.2$ |

TABLE 5-continued
Additional amines prepared
| Structure | Molecular Formula | Calculated MW | Observed MW |
|---|---|---|---|
| 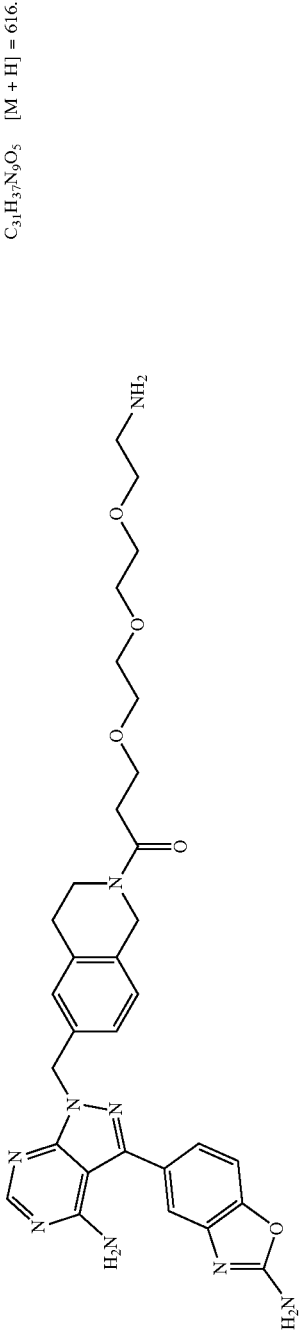 | $C_{31}H_{37}N_9O_5$ | [M + H] = 616.30 | [M + H] = 616.3 |
| 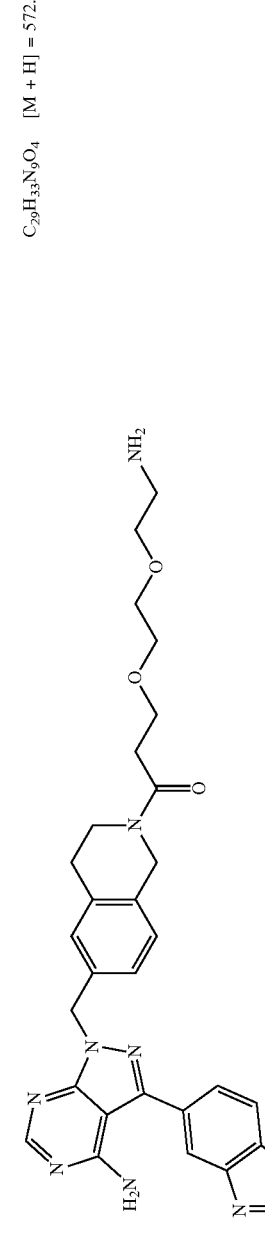 Intermediate A1-10 | $C_{29}H_{33}N_9O_4$ | [M + H] = 572.28 | [M + H] = 572.3 |
| 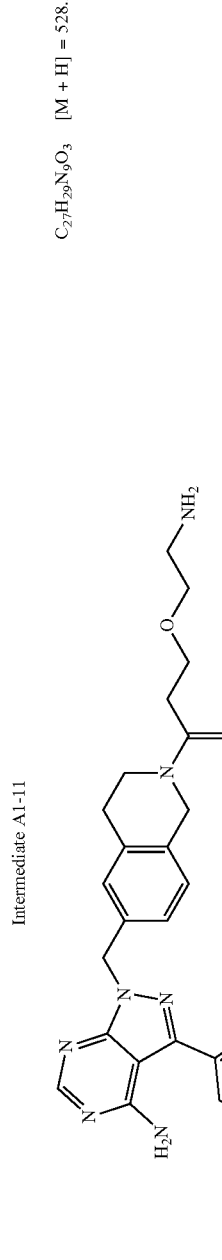 Intermediate A1-11 | $C_{27}H_{29}N_9O_3$ | [M + H] = 528.25 | [M + H] = 528.2 |

TABLE 5-continued
Additional amines prepared
| Structure | Molecular Formula | Calculated MW | Observed MW |
|---|---|---|---|
| Intermediate A1-12 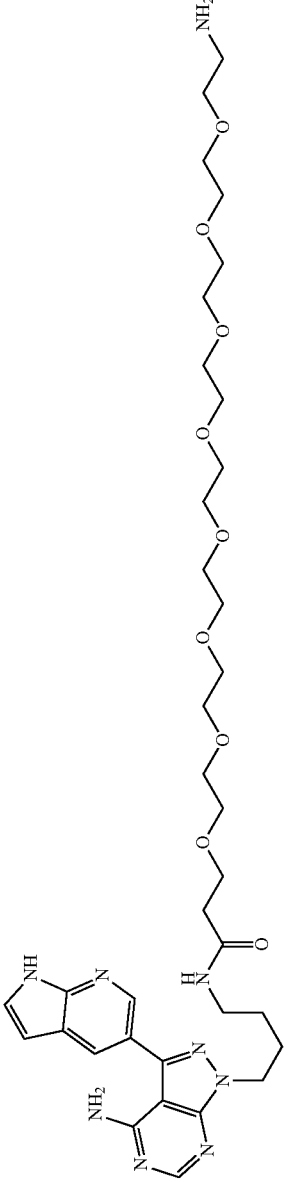 | $C_{35}H_{55}N_9O_9$ | [M + H] = 746.42 | [M + H] = 746.4 |
| Intermediate A1-13 | | | |
| Intermediate A1-14 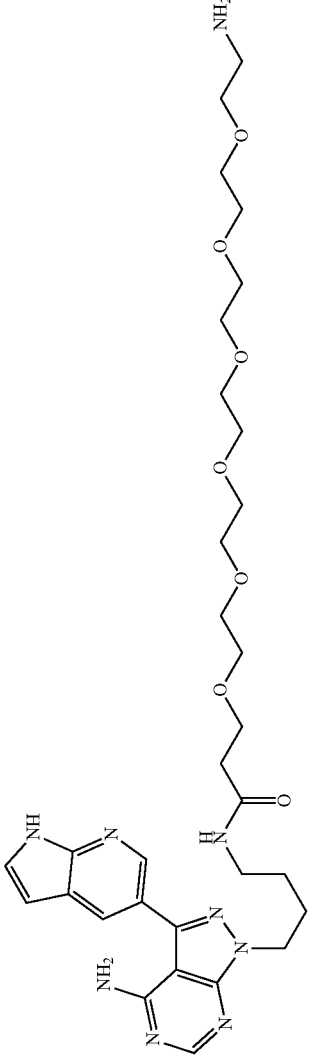 | $C_{31}H_{47}N_9O_7$ | [M + H] = 658.37 | [M + H] = 658.3 |

TABLE 5-continued
Additional amines prepared
| Structure | Molecular Formula | Calculated MW | Observed MW |
|---|---|---|---|
| 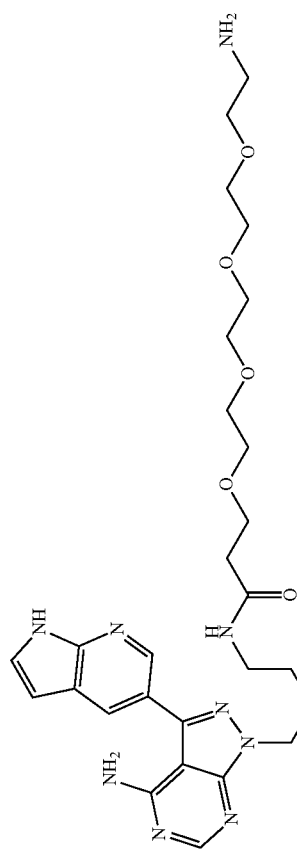 Intermediate A1-15 | $C_{27}H_{39}N_9O_5$ | $[M + H] = 570.32$ | $[M + H] = 570.2$ |
| 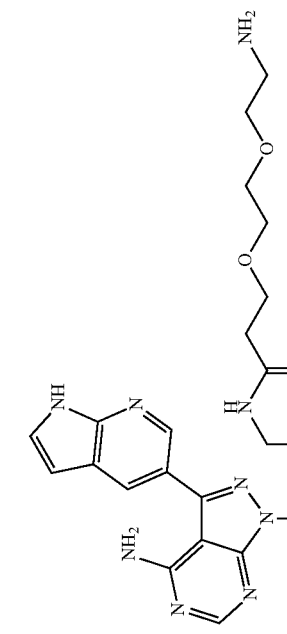 Intermediate A1-16 | $C_{23}H_{31}N_9O_3$ | $[M + H] = 482.26$ | $[M + H] = 482.3$ |

TABLE 5-continued

Additional amines prepared

| Structure | Molecular Formula | Calculated MW | Observed MW |
|---|---|---|---|
| Intermediate A1-17 | C₂₁H₂₇N₉O₂ | [M + H] = 438.24 | [M + H] = 438.4 |
| Intermediate A1-18 | C₄₉H₇₃N₉O₁₃ | [M + H] = 996.54 | [M + H] = 996.4 |
| Intermediate A1-19 | C₄₅H₆₅N₉O₁₁ | [M + H] = 908.49 | [M + H] = 908.3 |

TABLE 5-continued

Additional amines prepared

| Structure | Molecular Formula | Calculated MW | Observed MW |
|---|---|---|---|
| Intermediate A1-20 | $C_{41}H_{57}N_9O_9$ | [M + H] = 820.44 | [M + H] = 820.3 |
| Intermediate A1-21 | $C_{37}H_{49}N_9O_7$ | [M + H] = 732.39 | [M + H] = 732.3 |
| Intermediate A1-22 | $C_{35}H_{45}N_9O_6$ | [M + H] = 688.36 | [M + H] = 688.3 |

TABLE 5-continued

Additional amines prepared

| Structure | Molecular Formula | Calculated MW | Observed MW |
|---|---|---|---|
| Intermediate A1-23 | C₃₃H₄₁N₉O₅ | [M + H] = 644.33 | [M + H] = 644.3 |
| Intermediate A1-24 | C₃₁H₃₇N₉O₄ | [M + H] = 600.31 | [M + H] = 600.4 |
| Intermediate A1-25 | C₃₆H₅₅N₉O₁₀ | [M + H] = 774.42 | [M + H] = 774.7 |

TABLE 5-continued

Additional amines prepared

| Structure | Molecular Formula | Calculated MW | Observed MW |
|---|---|---|---|
| Intermediate A1-26 | $C_{32}H_{47}N_9O_8$ | [M + H] = 686.36 | [M + H] = 686.4 |
| Intermediate A1-27 | $C_{40}H_{63}N_9O_{11}$ | [M + H] = 846.47 | [M + H] = 846.8 |
| Intermediate A1-28 | $C_{43}H_{54}F_3N_7O_9$ | [M + H] = 870.40 | [M + H] = 870.4 |

TABLE 5-continued
Additional amines prepared
| Structure | Molecular Formula | Calculated MW | Observed MW |
|---|---|---|---|
| 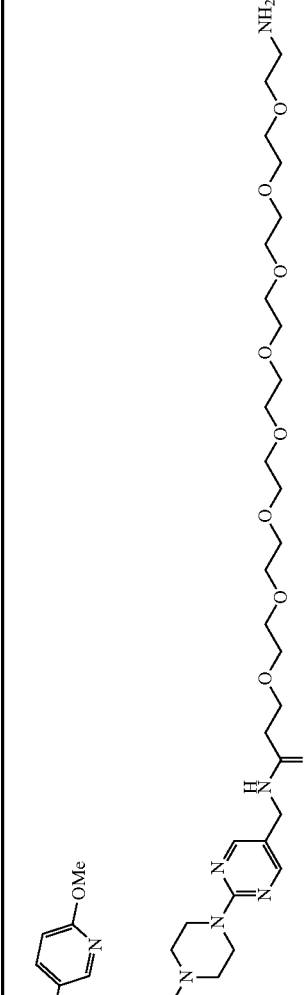 Intermediate A1-29 | $C_{52}H_{67}F_3N_{10}O_{11}$ | $[M + H] = 1065.50$ | $[M + H] = 1065.4$ |
|  Intermediate A1-30 | $C_{48}H_{59}F_3N_{10}O_9$ | $[M + H] = 977.45$ | $[M + H] = 977.4$ |

TABLE 5-continued

Additional amines prepared

| Structure | Molecular Formula | Calculated MW | Observed MW |
|---|---|---|---|
| Intermediate A1-31 | C₃₉H₅₇F₃N₁₂O₁₂ | [M + H] = 853.43 | [M + H] = 853.4 |
| Intermediate A1-32 | C₄₀H₅₅N₉O₁₀ | [M + H] = 822.42 | [M + H] = 822.2 |
| Intermediate A1-33 | C₃₉H₅₅N₉O₁₀ | [M + H] = 810.42 | [M + H] = 810.3 |

TABLE 5-continued

Additional amines prepared

| Structure | Molecular Formula | Calculated MW | Observed MW |
|---|---|---|---|
| Intermediate A1-34 | $C_{43}H_{63}N_5O_{13}S$ | $[M + H] = 890.42$ | $[M + H] = 890.3$ |
| Intermediate A1-35 | $C_{39}H_{54}FN_5O_{11}S$ | $[M + H] = 820.36$ | $[M + H] = 820.3$ |
| Intermediate A1-36 | $C_{43}H_{62}FN_5O_{13}S$ | $[M + H] = 908.41$ | $[M + H] = 908.3$ |

TABLE 5-continued

Additional amines prepared

| Structure | Molecular Formula | Calculated MW | Observed MW |
|---|---|---|---|
| Intermediate A1-37 | $C_{47}H_{62}F_3N_7O_{11}$ | [M + H] = 958.46 | [M + H] = 958.3 |
| Intermediate A1-38 | $C_{34}H_{43}N_9O_6$ | [M + H] = 674.34 | [M + H] = 674.3 |
| Intermediate A1-39 | $C_{41}H_{64}N_8O_{11}$ | [M + H] = 845.48 | [M + H] = 845.3 |

TABLE 5-continued

Additional amines prepared

| Structure | Molecular Formula | Calculated MW | Observed MW |
|---|---|---|---|
| Intermediate A1-40 | $C_{37}H_{56}N_8O_9$ | [M + H] = 757.43 | [M + H] = 757.3 |
| Intermediate A1-41 | $C_{27}H_{36}N_8O_4$ | [M + H] = 537.29 | [M + H] = 537.2 |
| Intermediate A1-42 | $C_{37}H_{53}N_{11}O_{10}$ | [M + H] = 812.41 | [M + H] = 812.3 |

TABLE 5-continued

Additional amines prepared

| Structure | Molecular Formula | Calculated MW | Observed MW |
|---|---|---|---|
| Intermediate A1-43 | $C_{36}H_{56}N_8O_{10}$ | [M + H] = 761.42 | [M + H] = 761.3 |
| Intermediate A1-44 | $C_{43}H_{61}N_9O_{10}$ | [M + H] = 864.46 | [M + H] = 864.4 |
| Intermediate A1-45 | $C_{43}H_{62}N_{10}O_{12}S$ | [M + H] = 943.44 | [M + H] = 943.3 |

TABLE 5-continued

Additional amines prepared

| Structure | Molecular Formula | Calculated MW | Observed MW |
|---|---|---|---|
| Intermediate A1-46 | $C_{39}H_{55}N_{11}O_{10}$ | [M + H] = 838.42 | [M + H] = 838.3 |

Following General Procedure 1, but using the appropriate Intermediate A1 in Table 5 and PEG carboxylic acid, the Intermediates A2 in Table 6 were prepared:

TABLE 6

Additional amines prepared

| Structure | Molecular Formula | Calculated MW | Observed MW |
|---|---|---|---|
| 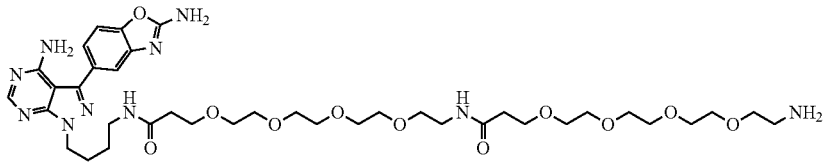 [SMILES: NCCOCCOCCOCCOCCC(=O)NCCOCCOCCOCCOCCC(=O)NCCCCn1nc(-c2ccc3oc(N)nc3c2)c2c(N)ncnc21]<br>Intermediate A2-1 | $C_{38}H_{60}N_{10}O_{11}$ | [M + H] = 833.45 | [M + H] = 833.8 |
| 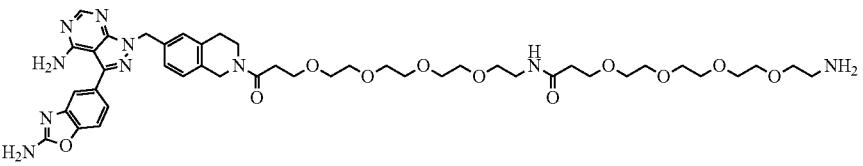 [SMILES: NCCOCCOCCOCCOCCC(=O)NCCOCCOCCOCCOCCC(=O)N1CCc2cc(Cn3nc(-c4ccc5oc(N)nc5c4)c4c(N)ncnc43)ccc2C1]<br>Intermediate A2-2 | $C_{44}H_{62}N_{10}O_{11}$ | [M + H] = 907.47 | [M + H] = 908.0 |
| 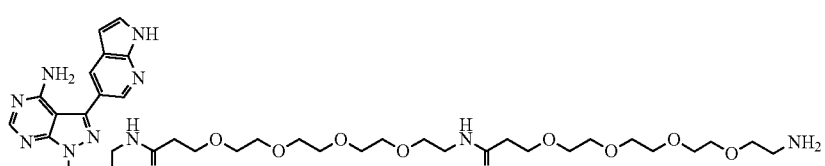<br>Intermediate A2-3 | $C_{38}H_{60}N_{10}O_{10}$ | [M + H] = 817.46 | [M + H] = 817.4 |
| 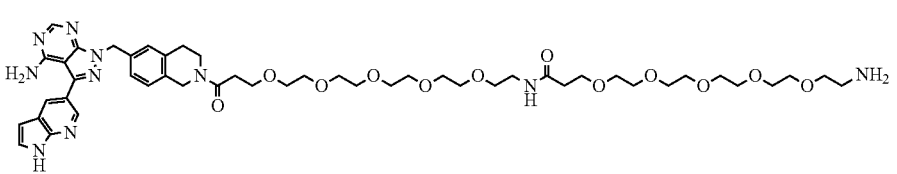 [SMILES: NCCOCCOCCOCCOCCOCCC(=O)NCCOCCOCCOCCOCCOCCC(=O)N1CCc2cc(Cn3nc(-c4cnc5[nH]ccc5c4)c4c(N)ncnc43)ccc2C1]<br>Intermediate A2-4 | $C_{48}H_{70}N_{10}O_{12}$ | [M + H] = 979.53 | [M + H] = 979.9 |
| 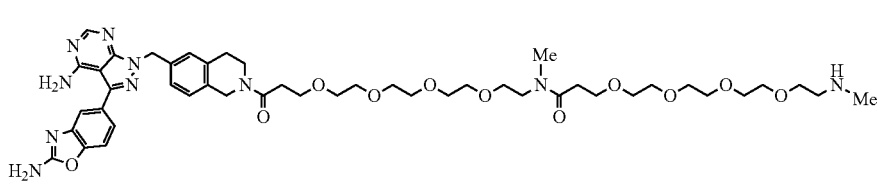 [SMILES: CNCCOCCOCCOCCOCCC(=O)N(C)CCOCCOCCOCCOCCC(=O)N1CCc2cc(Cn3nc(-c4ccc5oc(N)nc5c4)c4c(N)ncnc43)ccc2C1]<br>Intermediate A2-5 | $C_{46}H_{66}N_{10}O_{11}$ | [M + H] = 935.50 | [M + H] = 935.3 |
| 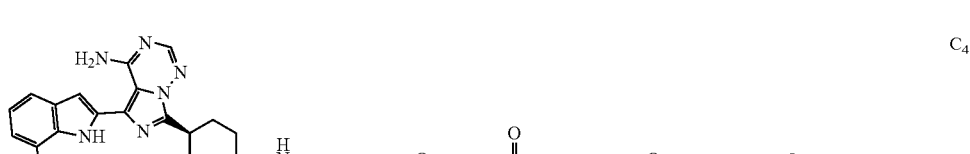<br>Intermediate A2-6 | $C_{40}H_{61}N_{9}O_{10}$ | [M + H] = 828.46 | [M + H] = 828.3 |

General Procedure 2: Coupling of a carboxylic acid containing rapamycin monomer and an active site inhibitor containing intermediate having a primary or secondary amine

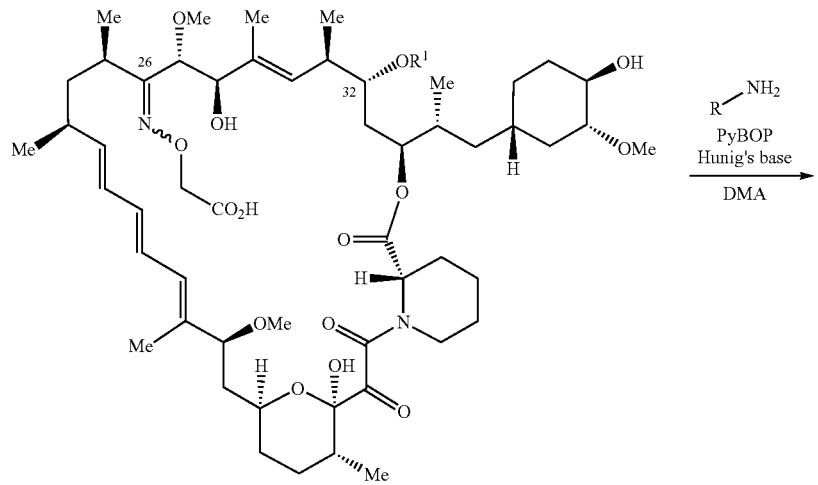

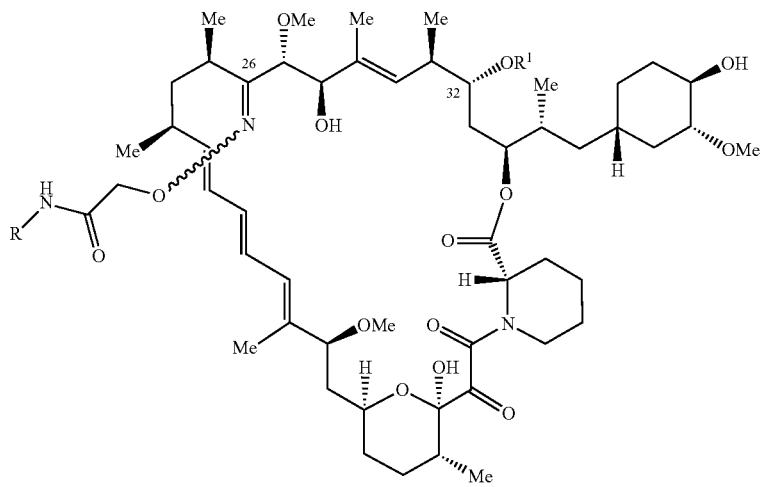

To a 0.05 M solution of rapamycin carboxylic acid monomer (1.0 equiv) and active site inhibitor containing intermediate (1.5 equiv) in DMA was added DIPEA (5.0 equiv) followed by PyBOP (1.8 equiv). The resulting homogenous solution was stirred at room temperature under nitrogen. Upon completion as determined by LCMS analysis, the crude reaction mixture was purified by preparative HPLC to provide the product.

Example 1: Synthesis of Series 1 bivalent rapamycin compound

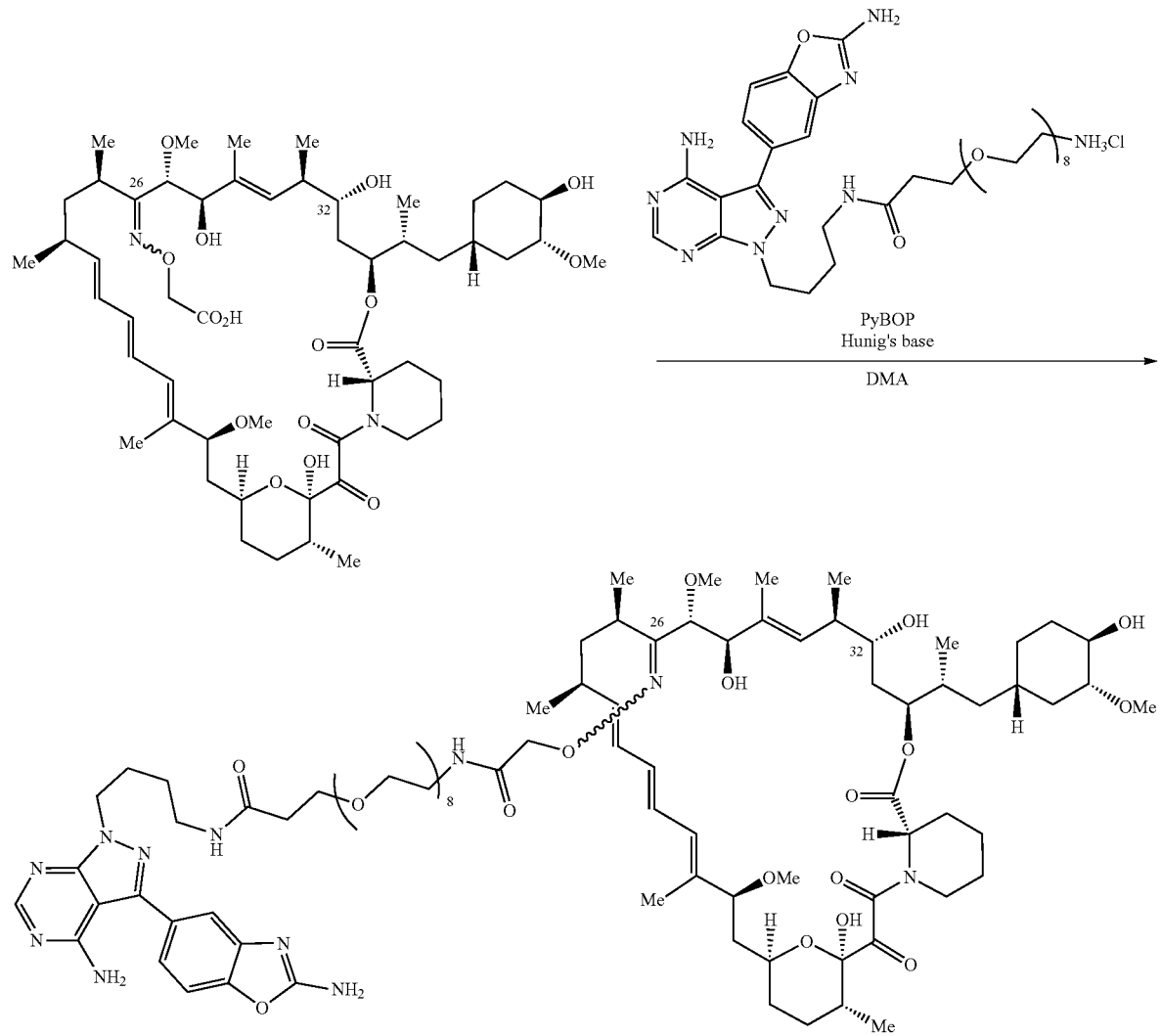

To a solution of 32(R)-hydroxy 26-aminooxyacetic acid rapamycin (28 mg, 28.30 1.0 equiv) and 1-amino-N-{4-[4-amino-3-(2-amino-1,3-benzoxazol-5-yl)-1H-pyrazolo[3,4-d]pyrimidin-1-yl]butyl}-3,6,9,12,15,18,21,24-octaoxahep-tacosan-27-amide hydrochloride (33.8 mg, 42.33 μmol, 1.5 equiv) in DMA (566 μL) was added DIPEA (24.5 μL, 141.5 μmol, 5.0 equiv) followed by PyBOP (26.5 mg, 50.94 μmol, 1.8 equiv). The resulting homogenous solution was stirred at room temperature. After 5 h, the crude reaction mixture was purified by preparative HPLC (40→99% MeCN/H$_2$O) to provide the product (21 mg, 42% yield), as a fluffy white solid. LCMS (ESI) m/z: [M+H] calcd for $C_{88}H_{137}N_{11}O_{24}$: 1732.99; found 1732.9.

Following General Procedure 2, but using the appropriate rapamycin carboxylic acid monomer in Table 1 and Intermediates A1 and A2 from Tables 5 and 6, the Series 1 bivalent analogs in Table 7 were synthesized:

TABLE 7
Series 1 Bivalent Compounds:
| Structure | Molecular Formula | Calculated MW | Observed MW |
|---|---|---|---|
| 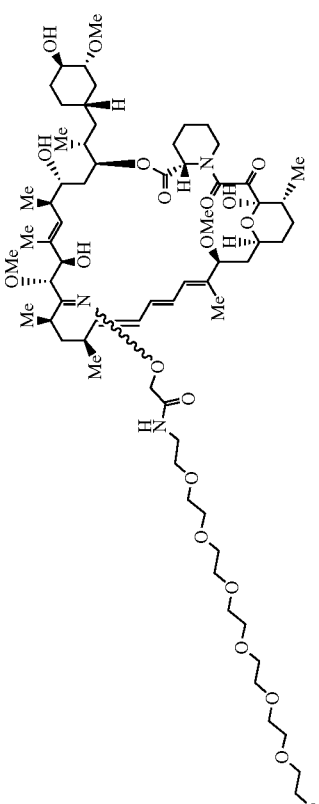 Example 1 | C$_{88}$H$_{137}$N$_{11}$O$_{24}$ | [M + H] = 1732.99 | [M + H] = 1732.9 |

TABLE 7-continued
Series 1 Bivalent Compounds:
| Structure | Molecular Formula | Calculated MW | Observed MW |
|---|---|---|---|
| 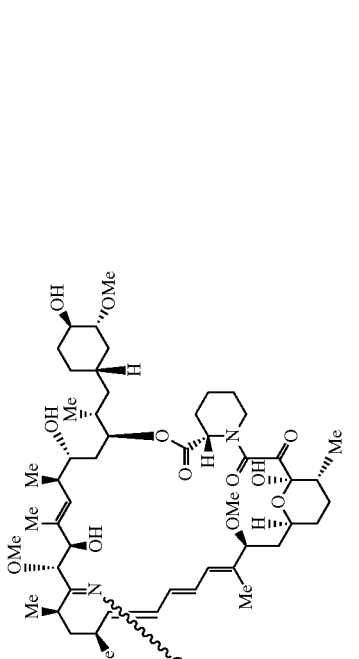 Example 2 | $C_{84}H_{129}N_{11}O_{22}$ | $[M + H] = 1644.94$ | $[M + H] = 1644.8$ |
| 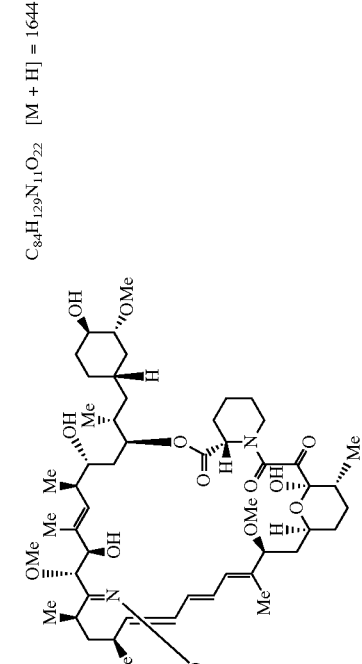 Example 3 | $C_{84}H_{129}N_{11}O_{22}$ | $[M + H] = 1644.94$ | $[M + H] = 1644.9$ |

TABLE 7-continued
Series 1 Bivalent Compounds:
| Structure | Molecular Formula | Calculated MW | Observed MW |
|---|---|---|---|
| 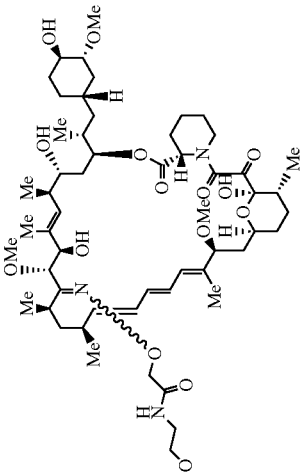<br>Example 4 | $C_{94}H_{139}N_{11}O_{24}$ | $[M+H] = 1807.01$ | $[M+H] = 1806.9$ |
| 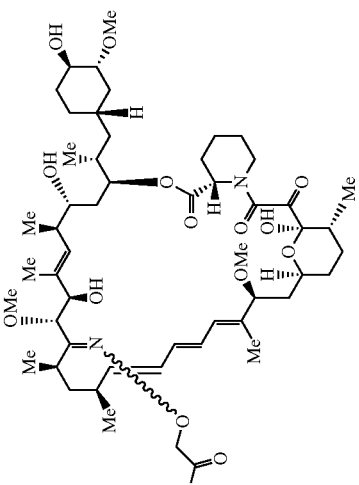<br>Example 5 | $C_{90}H_{131}N_{11}O_{22}$ | $[M+H] = 1718.95$ | $[M+H] = 1719.0$ |

TABLE 7-continued
Series 1 Bivalent Compounds:
| Structure | Molecular Formula | Calculated MW | Observed MW |
|---|---|---|---|
| 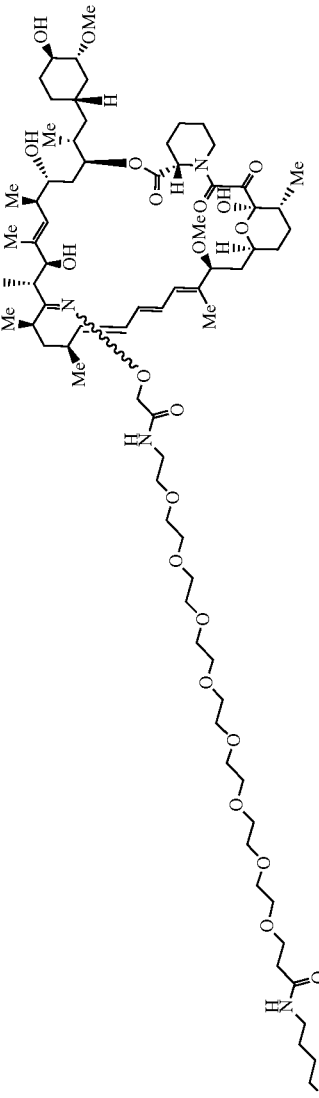 | $C_{88}H_{137}N_{11}O_{23}$ | $[M + H] = 1717.00$ | $[M + H] = 1716.8$ |
Example 6

TABLE 7-continued
Series 1 Bivalent Compounds:
| Structure | Molecular Formula | Calculated MW | Observed MW |
|---|---|---|---|
| 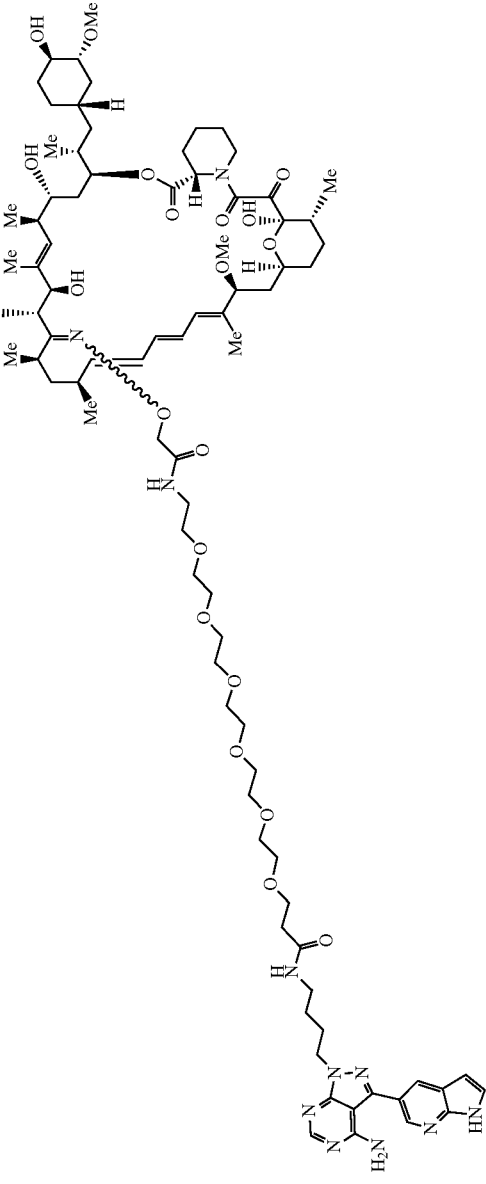 Example 7 | $C_{84}H_{129}N_{11}O_{21}$ | $[M + H] = 1628.94$ | $[M + H] = 1628.8$ |

TABLE 7-continued

Series 1 Bivalent Compounds:

| Structure | Molecular Formula | Calculated MW | Observed MW |
|---|---|---|---|
| Example 8 | $C_{89}H_{139}N_{11}O_{23}$ | [M + H] = 1731.01 | [M + H] = 1730.9 |
| Example 9 | $C_{94}H_{139}N_{11}O_{23}$ | [M + H] = 1791.01 | [M + H] = 1790.9 |

TABLE 7-continued

Series 1 Bivalent Compounds:

| Structure | Molecular Formula | Calculated MW | Observed MW |
|---|---|---|---|
| Example 10 | $C_{90}H_{131}N_{11}O_{21}$ | [M + H] = 1702.96 | [M + H] = 1703.0 |
| Example 11 | $C_{95}H_{141}N_{11}O_{23}$ | [M + H] = 1805.03 | [M + H] = 1804.9 |

TABLE 7-continued

Series 1 Bivalent Compounds:

| Structure | Molecular Formula | Calculated MW | Observed MW |
|---|---|---|---|
| Example 12 | $C_{85}H_{129}N_{11}O_{22}$ | [M + H] = 1656.94 | [M + H] = 1656.9 |
| Example 13 | $C_{96}H_{136}F_3N_9O_{23}$ | [M + H] = 1840.98 | [M + H] = 1841.0 |

TABLE 7-continued

Series 1 Bivalent Compounds:

| Structure | Molecular Formula | Calculated MW | Observed MW |
|---|---|---|---|
| Example 14 | $C_{101}H_{141}F_3N_{12}O_{23}$ | $[M+H] = 1948.03$ | $[M+H] = 1947.9$ |
| Example 45 | $C_{96}H_{145}N_7O_{27}S$ | $[M+H] = 1861.00$ | $[M+H] = 1860.8$ |

TABLE 7-continued

Series 1 Bivalent Compounds:

| Structure | Molecular Formula | Calculated MW | Observed MW |
|---|---|---|---|
| Example 46 | $C_{96}H_{144}FN_7O_{27}S$ | [M + H] = 1878.99 | [M + H] = 1878.7 |
| Example 47 | $C_{92}H_{136}FN_7O_{25}S$ | [M + H] = 1790.94 | [M + H] = 1791.0 |

TABLE 7-continued

Series 1 Bivalent Compounds:

| Structure | Molecular Formula | Calculated MW | Observed MW |
|---|---|---|---|
| Example 48 | $C_{92}H_{135}N_{11}O_{22}$ | [M + H] = 1746.99 | [M + H] = 1747.0 |
| Example 67 | $C_{94}H_{138}N_{11}O_{23}$ | [M + H] = 1790.00 | [M + H] = 1789.7 |

General Procedure 3: Coupling of a halide containing PEG ester and an amine containing pre-linker followed by ester deprotection

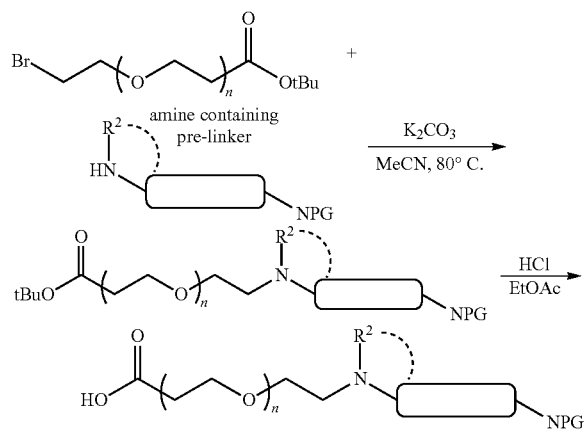

Step 1

To a 0.1 M solution of amine containing pre-linker (1.0 equiv) in MeCN was added $K_2CO_3$ (2.0 equiv) followed by halide containing PEG ester (1.0 equiv). The reaction was stirred at 80° C. until consumption of amine containing pre-linker, as indicated by LCMS analysis. The reaction was then purified by silica gel chromatography to afford the product.

Step 2

To a 0.1 M solution of PEG tert-butyl ester (1.0 equiv) in EtOAc was added a solution of HCl in EtOAc. The resulting suspension was stirred at room temperature until consumption of the PEG ester, as indicated by LCMS analysis. The reaction was then concentrated under reduced pressure to afford the product.

Intermediate B1-1. 1-(4-(5-((1,3-dioxoisoindolin-2-yl)methyl)pyrimidin-2-yl)piperazin-1-yl)-3,6,9,12-tetraoxapentadecan-15-oic acid

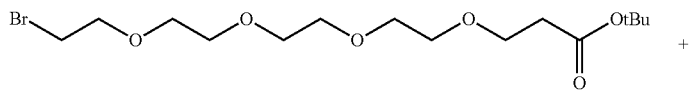

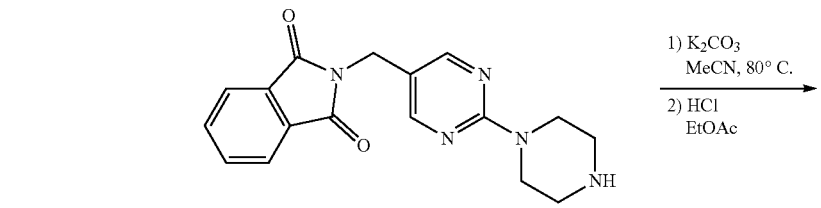

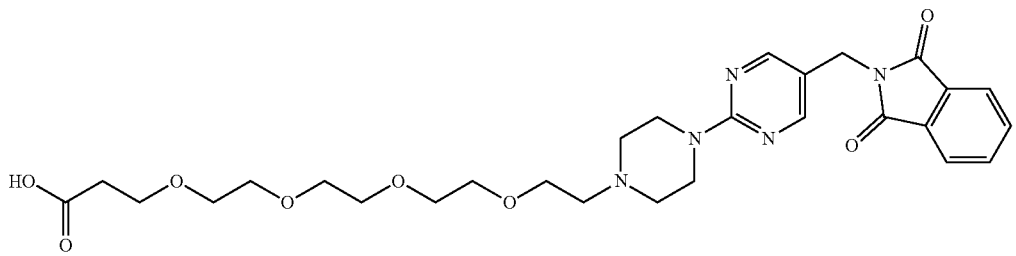 [SMILES: O=C(O)CCOCCOCCOCCOCCN1CCN(c2ncc(CN3C(=O)c4ccccc4C3=O)cn2)CC1]

Step 1: Synthesis of tert-butyl 1-(4-(5-((1,3-dioxoisoindolin-2-yl)methyl)pyrimidin-2-yl)piperazin-1-yl)-3,6,9,12-tetraoxapentadecan-15-oate To a mixture of 2-((2-(piperazin-1-yl)pyrimidin-5-yl)methyl)isoindoline-1,3-dione (7.97 g, 24.66 mmol, 1.0 equiv) in MeCN (200 mL) was added $K_2CO_3$ (6.82 g, 49.31 mmol, 2.0 equiv) followed by tert-butyl 1-bromo-3,6,9,12-tetraoxapentadecan-15-oate (9.5 g, 24.66 mmol, 1.0 equiv). The reaction mixture was heated to 85° C. and stirred for 15 h. The mixture was then cooled to room temperature and filtered. The filtrate was concentrated under reduced pressure and the residue purified by silica gel chromatography (0→20% EtOAc/MeOH) to give the product (11.5 g, 74.3% yield) as a light yellow liquid.

Step 2: Synthesis of 1-(4-(5-((1,3-dioxoisoindolin-2-yl)methyl)pyrimidin-2-yl)piperazin-1-yl)-3,6,9,12-tetraoxapentadecan-15-oic acid To a solution of tert-butyl 1-(4-(5-((1,3-dioxoisoindolin-2-yl)methyl)pyrimidin-2-yl)piperazin-1-yl)-3,6,9,12-tetraoxapentadecan-15-oate (3.5 g, 5.58 mmol, 1.0 equiv) in EtOAc (50 mL) was added a solution of HCl in EtOAc (500 mL). The mixture was stirred at room temperature for 3 h. The mixture was then concentrated under reduced pressure to give the product (5.3 g, 78.2% yield, HCl) as a white solid. LCMS (ESI) m/z: [M+H] calcd for $C_{28}H_{37}N_5O_8$: 572.27; found 572.4.

Following General Procedure 3, but using the appropriate halide containing PEG and amine containing pre-linkers in Table 4, the Intermediates B1 in Table 8 were prepared:

General Procedure 4: Coupling of a PEG carboxylic acid and an amine containing active site inhibitor followed by amine deprotection

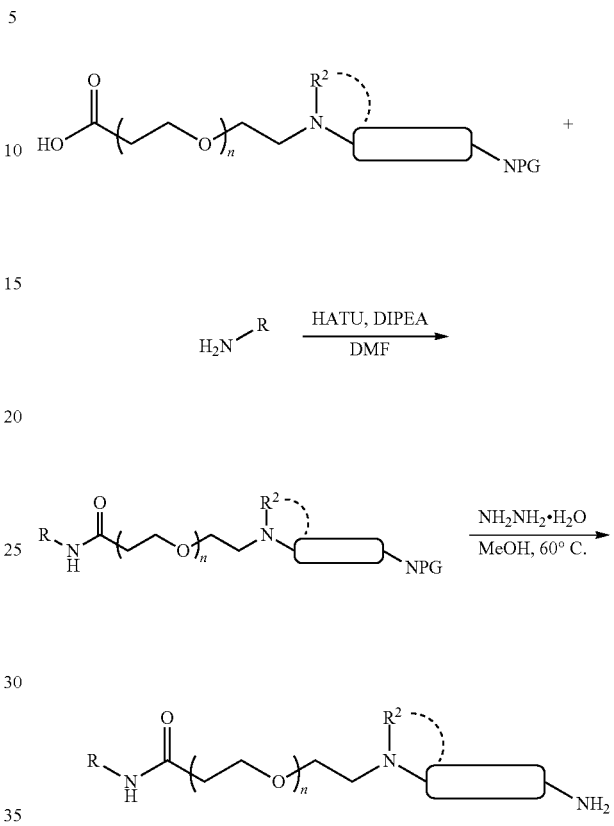

Step 1

To a 0.15 M solution of PEG carboxylic acid (1.0 equiv) in DMF was added HATU (1.3 equiv) and DIPEA (5.0 equiv). After stirring for 30 min, the amine containing active site inhibitor (1.2 equiv) was added. The reaction was stirred at room temperature until consumption of PEG carboxylic acid, as indicated by LCMS. The reaction was then purified by reverse phase chromatography to afford the product.

TABLE 8

| Additional protected amines prepared | | | |
|---|---|---|---|
| Structure | Molecular Formula | Calculated MW | Observed MW |
| <br>Intermediate B1-1 | $C_{28}H_{37}N_5O_8$ | [M + H] = 572.27 | [M + H] = 572.4 |

Step 2

To a 0.1 M solution of phthalimide protected amine (1.0 equiv) in MeOH at 0° C. was added NH$_2$NH$_2$.H$_2$O (4.0 equiv). The resulting mixture was stirred at 60° C. until consumption of the phthalimide protected amine, as indicated by LCMS analysis. The reaction was then purified by reverse phase chromatography to afford the product.

Intermediate B2-1. N-(4-(4-amino-3-(2-aminobenzo[d]oxazol-5-yl)-1H-pyrazolo[3,4-d] pyrimidin-1-yl)butyl)-1-(4-(5-(aminomethyl)pyrimidin-2-yl)piperazin-1-yl)-3,6,9,12-tetraoxapentadecan-15-amide

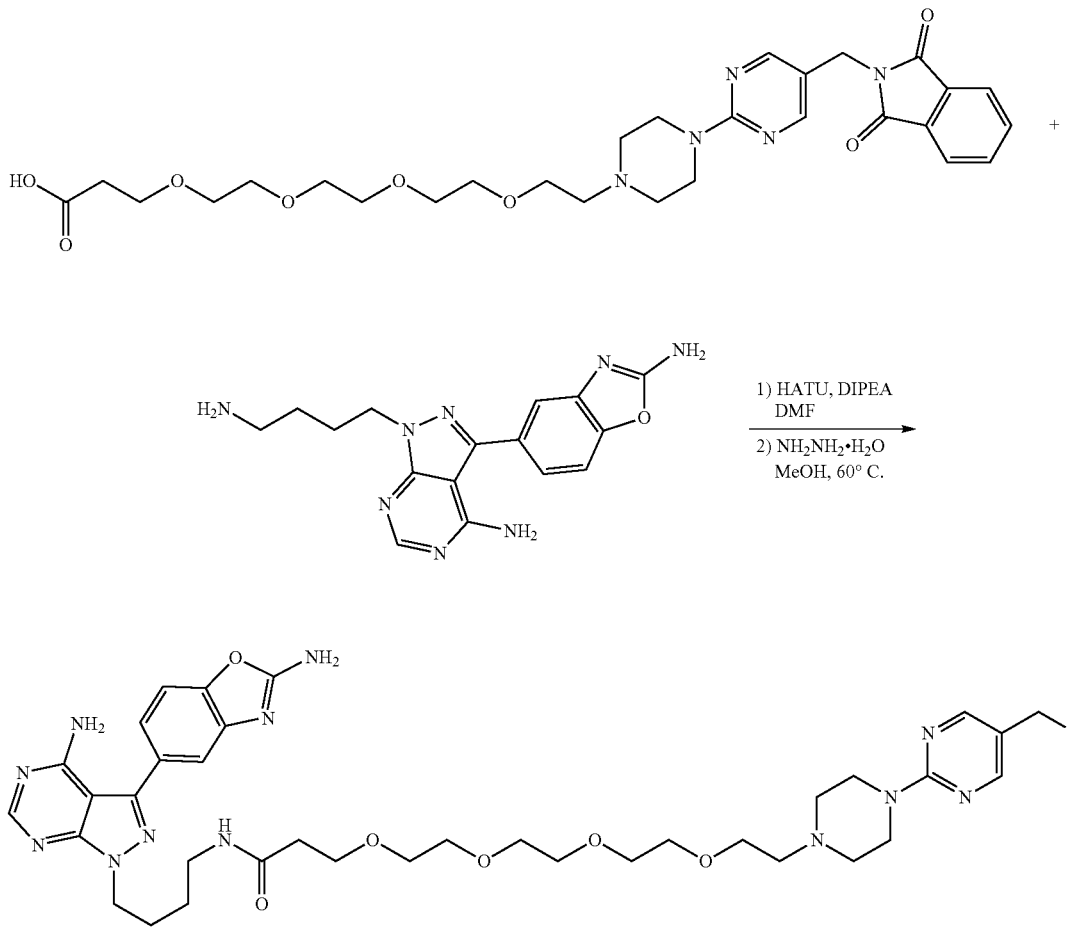

Step 1: Synthesis of N-(4-(4-amino-3-(2-aminobenzo[d]oxazol-5-yl)-1H-pyrazolo[3,4-d]pyrimidin-1-yl)butyl)-1-(4-(5-(((1,3-dioxoisoindolin-2-yl)methyl)pyrimidin-2-yl)piperazin-1-yl)-3,6,9,12-tetraoxapentadecan-15-amide To a mixture of 1-(4-(5-(((1,3-dioxoisoindolin-2-yl)methyl)pyrimidin-2-yl)piperazin-1-yl)-3,6,9,12-tetraoxapentadecan-15-oic acid (3 g, 4.93 mmol, 1.0 equiv, HCl) in DMF (30 mL) was added HATU (12.11 μL, 6.41 mmol, 1.3 equiv) and DIPEA (4.30 mL, 24.67 mmol, 5.0 equiv). After 30 min, 5-(4-amino-1-(4-aminobutyl)-1H-pyrazolo[3,4-d]pyrimidin-3-yl)benzo[d]oxazol-2-amine (4.03 g, 5.92 mmol, 1.2 equiv, 3TFA) was added. The mixture was stirred at room temperature for 3 h. The reaction mixture was then purified by prep-HPLC (MeCN/H$_2$O) to give the product (5.4 g, 81.2% yield) as a light red solid. LCMS (ESI) m/z: [M+2H]/2 calcd for C$_{44}$H$_{53}$N$_{13}$O$_8$: 446.71; found 447.0.

Step 2: Synthesis of N-(4-(4-amino-3-(2-aminobenzo[d]oxazol-5-yl)-1H-pyrazolo[3,4-d]pyrimidin-1-yl)butyl)-1-(4-(5-(aminomethyl)pyrimidin-2-yl)piperazin-1-yl)-3,6,9,12-tetraoxapentadecan-15-amide To a mixture of N-(4-(4-amino-3-(2-aminobenzo[d]oxazol-5-yl)-1H-pyrazolo[3,4-d]pyrimidin-1-yl)butyl)-1-(4-(5-(((1,3-dioxoisoindolin-2-yl)methyl)pyrimidin-2-yl)piperazin-1-yl)-3,6,9,12-tetraoxapentadecan-15-amide (4 g, 2.97 mmol, 1.0 equiv, 4TFA) in MeOH (25 mL) at 0° C. was added NH$_2$NH$_2$.H$_2$O (588.63 μL, 11.87 mmol, 4.0 equiv). The mixture was stirred at 60° C. for 2 h. The mixture was then cooled to room temperature and filtered, and the filter cake was washed with MeOH (5 mL). The filtrate was concentrated under reduced pressure and the residue was purified by prep-HPLC (MeCN/H$_2$O) to give the product (700 mg, 24.5% yield) as a white solid. LCMS (ESI) m/z: [M+2H]/2 calcd for C$_{36}$H$_{51}$N$_{13}$O$_6$: 381.71; found 381.8.

Following General Procedure 4, but using the appropriate Intermediate B1 in Table 8 and amine containing active site inhibitors in Table 2, the Intermediates B2 in Table 9 were prepared:

TABLE 9

Additional amines prepared

| Structure | Molecular Formula | Calculated MW | Observed MW |
|---|---|---|---|
| Intermediate B2-1 | $C_{36}H_{51}N_{13}O_6$ | [M + 2H]/2 = 381.71 | [M + 2H]/2 = 381.8 |
| Intermediate B2-2 | $C_{42}H_{53}N_{13}O_6$ | [M + H] = 836.43 | [M + H] = 836.4 |
| Intermediate B2-3 | $C_{36}H_{51}N_{13}O_5$ | [M + 2H]/2 = 373.72 | [M + 2H]/2 = 737.7 |

General Procedure 5: Coupling of a halide containing PEG carboxylic acid and an amine containing active site inhibitor

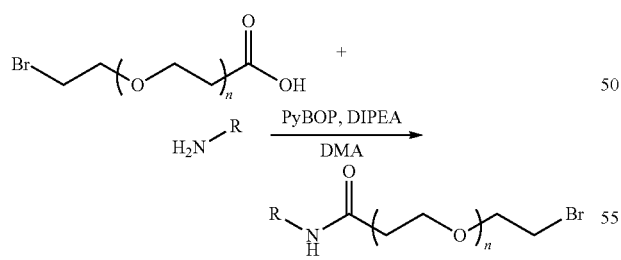

To a 0.1 M solution of amine containing active site inhibitor (1.0 equiv) and PEG containing carboxylic acid (1.2 equiv) in DMA was added DIPEA (4.0 equiv) followed by PyBOP (1.3 equiv). The reaction was stirred until consumption of amine containing active site inhibitor, as indicated by LCMS. The reaction was then purified by reverse phase HPLC to afford the product.

Intermediate B3-1. 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-bromo-3,6,9,12,15-pentaoxaoctadecan-18-one

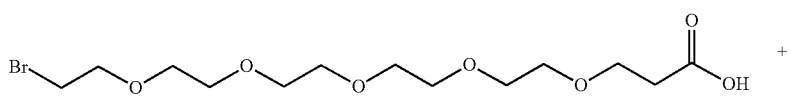

-continued

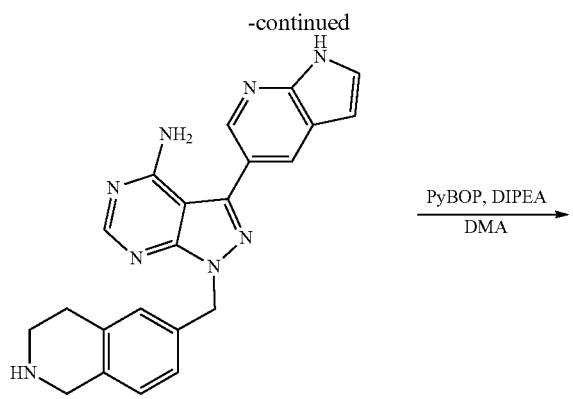

PyBOP, DIPEA
———————→
DMA

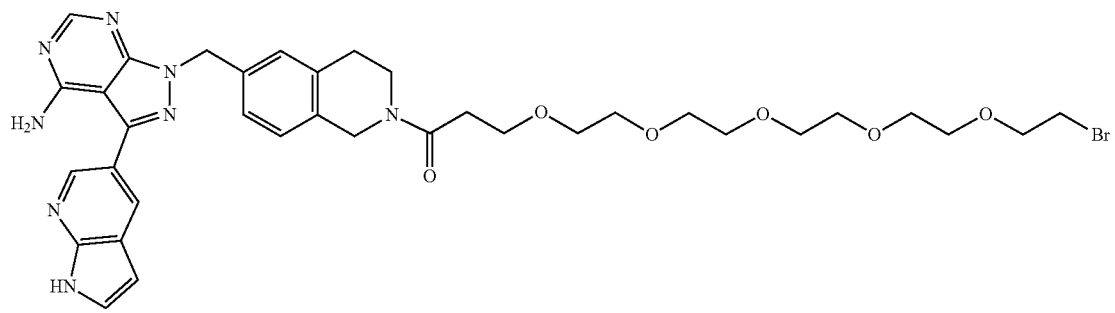

To a solution of 1-bromo-3,6,9,12,15-pentaoxaoctadecan-18-oic acid (105 mg, 282 μmol, 1.2 equiv) and 3-{1H-pyrrolo[2,3-b]pyridin-5-yl}-1-[(1,2,3,4-tetrahydroisoquinolin-6-yl)methyl]-1H-pyrazolo[3,4-d]pyrimidin-4-amine (120 mg, 235 μmol, 1.0 equiv) in DMA (2.34 mL) was added DIPEA (163 μL, 940 μmol, 4.0 equiv) followed by PyBOP (158 mg, 305 μmol, 1.3 equiv). The resulting solution was stirred at room temperature for 3 h then purified by reverse phase HPLC (10→98% MeCN+0.1% formic acid/H$_2$O+0.1% formic acid) to afford the product (82.7 mg, 47% yield). LCMS (ESI) m/z: [M+H] calcd for C$_{35}$H$_{43}$BrN$_8$O$_6$: 751.26; found 751.2.

Following General Procedure 5, but using the appropriate halide containing PEG carboxylic acid and amine containing active site inhibitors in Table 2, the Intermediates B3 in Table 10 were prepared:

TABLE 10

Additional PEG halides prepared

| Structure | Molecular Formula | Calculated MW | Observed MW |
|---|---|---|---|
| Intermediate B3-1 | C$_{35}$H$_{43}$BrN$_8$O$_6$ | [M + H] = 751.26 | [M + H] = 751.2 |

TABLE 10-continued

Additional PEG halides prepared

| Structure | Molecular Formula | Calculated MW | Observed MW |
|---|---|---|---|
| 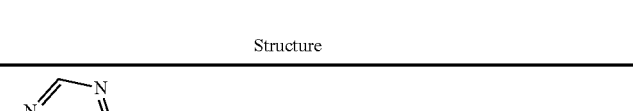  Intermediate B3-2 | $C_{27}H_{27}BrN_8O_3$ | [M + H] = 591.15 | [M + H] = 591.2 |

General Procedure 6: Displacement of a PEG halide with an amine containing post linker and deprotection of the amine

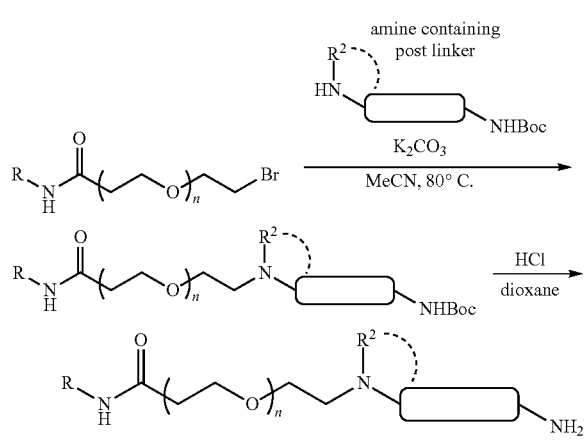

Step 1

To a 0.1 M solution of halide containing PEG (1.0 equiv) in MeCN was added $K_2CO_3$ (3.0 equiv) followed by amine containing post linker (1.2 equiv). The resulting suspension was heated to 80° C. and stirred until consumption of the PEG halide, as indicated by LCMS analysis. The reaction was cooled to room temperature and then purified by silica gel chromatography to afford the product.

Step 2

To a 0.07 M solution of N-Boc protected amine (1.0 equiv) in dioxane was added HCl (4 M in dioxane, 10.0 equiv). The reaction was stirred until consumption of N-Boc protected amine, as indicated by LCMS analysis. The reaction was then concentrated under reduced pressure to afford the product.

Intermediate B2-4. 18-{6-1(4-amino-3-{1H-pyrrolo[2,3-[3]pyridin-5-yl}-1H-pyrazolo[3,4-d]pyrimidin-1-yl)methyl]-1,2,3,4-tetrahydroisoquinolin-2-yl}-1-(4-{5H,6H,7H,8H-pyrido[4,3-d]pyrimidin-2-yl}piperazin-1-yl)-3,6,9,12,15-pentaoxaoctadecan-18-one

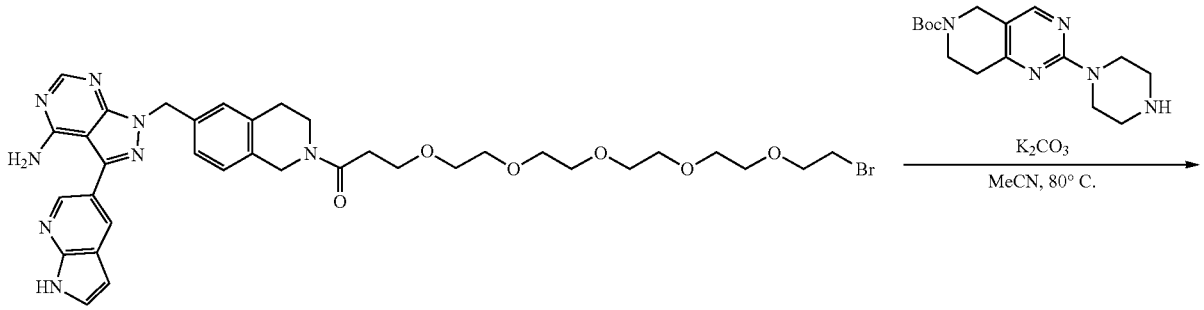

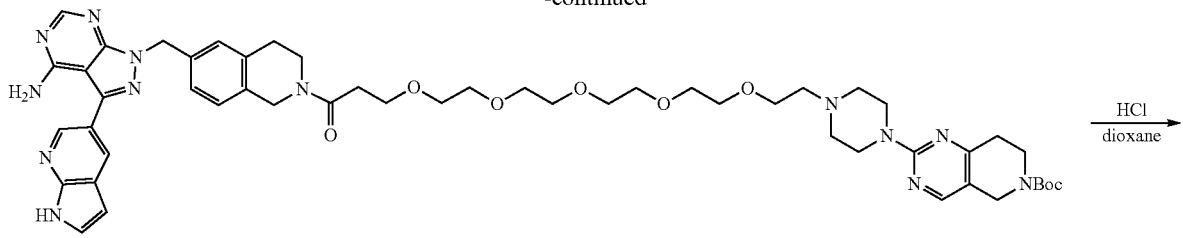

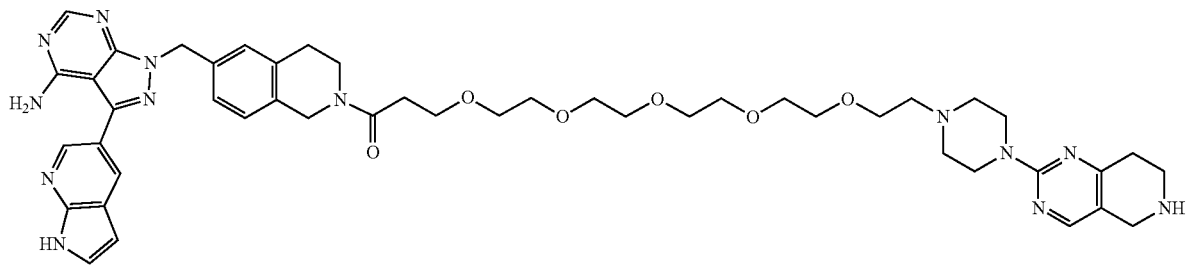

Step 1: Synthesis of tert-butyl 2-[4-(18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-18-oxo-3,6,9,12,15-pentaoxaoctadecan-1-yl)piperazin-1-yl]-5H, 6H,7H, 8H-pyrido[4,3-d]pyrimidine-6-carboxylate To a suspension of 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-bromo-3,6,9,12,15-pentaoxaoctadecan-18-one (82.7 mg, 110 µmol, 1.0 equiv) in MeCN (1.09 mL) was added K$_2$CO$_3$ (45.6 mg, 330 µmol, 3.0 equiv) followed by tert-butyl 2-(piperazin-1-yl)-5H,6H,7H,8H-pyrido[4,3-d]pyrimidine-6-carboxylate (42.1 mg, 132 µmol, 1.2 equiv). The resulting suspension was heated to 80° C. for 8 h, then purified by silica gel chromatography (0→20% MeOH/DCM) to afford the product (75.1 mg, 70% yield). LCMS (ESI) m/z: [M+H] calcd for C$_{51}$H$_{67}$N$_{13}$O$_8$: 990.53; found 990.5.

Step 2: Synthesis of 18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-1-(4-{5H,6H,7H, 8H-pyrido[4,3-d]pyrimidin-2-yl}piperazin-1-yl)-3,6,9,12,15-pentaoxaoctadecan-18-one To a solution of tert-butyl 2-[4-(18-{6-[(4-amino-3-{1H-pyrrolo[2,3-b]pyridin-5-yl}-1H-pyrazolo[3,4-d]pyrimidin-1-yl)methyl]-1,2,3,4-tetrahydroisoquinolin-2-yl}-18-oxo-3,6,9,12,15-pentaoxaoctadecan-1-yl)piperazin-1-yl]-5H,6H,7H,8H-pyrido[4,3-d]pyrimidine-6-carboxylate (75.1 mg, 75.8 µmol, 1.0 equiv) in dioxane (1 mL) was added HCl (4 M in dioxane, 472 µL, 1.89 mmol, 10.0 equiv). The solution was stirred at room temperature for 45 min, then concentrated under reduced pressure to afford the product. LCMS (ESI) m/z: [M+Na] calcd for C$_{46}$H$_{59}$N$_{13}$O$_6$: 912.46; found 912.5.

Following General Procedure 6, but using the appropriate PEG carboxylic acid and amine containing active site inhibitors in Table 2, the Intermediates B2 in Table 11 were prepared:

TABLE 11

Additional amines prepared

| Structure | Molecular Formula | Calculated MW | Observed MW |
|---|---|---|---|
| Intermediate B2-4 | C$_{46}$H$_{59}$N$_{13}$O$_6$ | [M + H] = 890.48 | [M + H] = 890.5 |

Following General Procedure 1, but using the appropriate carboxylic acid PEG tert-butyl ester and amine containing active site inhibitors in Table 2, the Intermediates B4 in Table 12 were prepared:

TABLE 12

Additional amines prepared

| Structure | Molecular Formula | Calculated MW | Observed MW |
|---|---|---|---|
| Intermediate B4-1 | $C_{28}H_{38}N_8O_8$ | [M + H] = 615.29 | [M + H] = 615.1 |

Following General Procedure 1, but using the appropriate Intermediates B4 in Table 12 and amine containing pre-linkers in Table 4, the Intermediates B2 in Table 13 were prepared:

TABLE 13

Additional amines prepared

| Structure | Molecular Formula | Calculated MW | Observed MW |
|---|---|---|---|
| Intermediate B2-5 | $C_{39}H_{53}N_{13}O_7$ | [M + H] = 816.43 | [M + H] = 816.4 |

Following General Procedure 1, but using the appropriate Intermediates A1 and amine containing pre-linkers in Table 4, the Intermediates B2 in Table 14 were prepared:

TABLE 14

Additional amines prepared

| Structure | Molecular Formula | Calculated MW | Observed MW |
|---|---|---|---|
| Intermediate B2-6 | $C_{41}H_{52}N_{16}O_6$ | [M + H] = 865.44 | [M + H] = 865.2 |

TABLE 14-continued

Additional amines prepared

| Structure | Molecular Formula | Calculated MW | Observed MW |
|---|---|---|---|
| Intermediate B2-7 | $C_{39}H_{48}N_{16}O_5$ | [M + H] = 821.41 | [M + H] = 821.2 |
| Intermediate B2-8 | $C_{37}H_{44}N_{16}O_4$ | [M + H] = 777.38 | [M + H] = 777.3 |
| Intermediate B2-9 | $C_{49}H_{58}N_{16}O_7$ | [M + H] = 983.48 | [M + H] = 983.4 |
| Intermediate B2-10 | $C_{43}H_{46}N_{16}O_4$ | [M + H] = 851.40 | [M + H] = 851.4 |
| Intermediate B2-11 | $C_{43}H_{56}N_{16}O_6$ | [M + H] = 893.47 | [M + H] = 893.3 |
| Intermediate B2-12 | $C_{49}H_{58}N_{16}O_6$ | [M + H] = 989.46 | [M + H] = 989.4 |

TABLE 14-continued

Additional amines prepared

| Structure | Molecular Formula | Calculated MW | Observed MW |
|---|---|---|---|
| Intermediate B2-13 | C₄₇H₅₄N₁₆O₅ | [M + H] = 923.46 | [M + H] = 923.4 |
| Intermediate B2-14 | C₃₉H₅₀N₁₆O₆ | [M + H] = 839.42 | [M + H] = 839.3 |
| Intermediate B2-15 | C₄₇H₅₆N₁₆O₇ | [M + H] = 957.46 | [M + H] = 957.7 |
| Intermediate B2-16 | C₄₅H₅₂N₁₆O₆ | [M + H] = 935.42 | [M + H] = 935.3 |
| Intermediate B2-17 | C₄₃H₄₈N₁₆O₅ | [M + H] = 891.39 | [M + H] = 891.4 |
| Intermediate B2-18 | C₄₁H₅₄N₁₆O₆ | [M + H] = 867.45 | [M + H] = 867.3 |

TABLE 14-continued
Additional amines prepared
| Structure | Molecular Formula | Calculated MW | Observed MW |
|---|---|---|---|
| 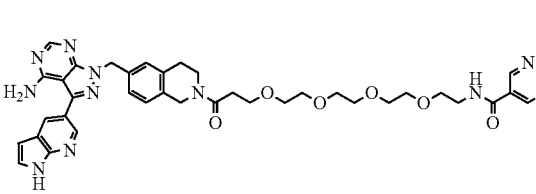<br>Intermediate B2-19 | $C_{47}H_{56}N_{16}O_6$ | [M + H] = 941.47 | [M + H] = 941.2 |
| 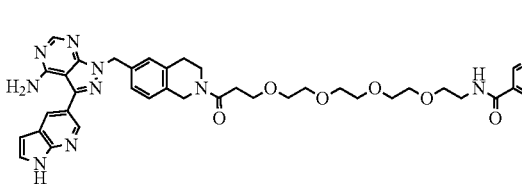<br>Intermediate B2-20 | $C_{48}H_{58}N_{16}O_6$ | [M + H] = 955.48 | [M + H] = 955.2 |
| 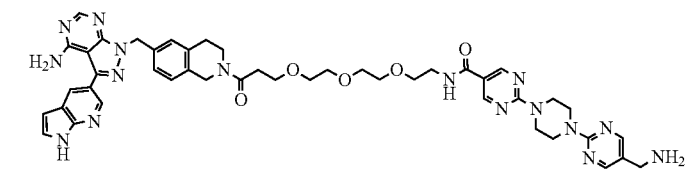 [SMILES: NCc1cnc(N2CCN(c3ncc(C(=O)NCCOCCOCCOCCC(=O)N4CCc5cc(Cn6nc(-c7cnc8[nH]ccc8c7)c7c(N)ncnc76)ccc5C4)cn3)CC2)nc1]<br>Intermediate B2-21 | $C_{45}H_{52}N_{16}O_5$ | [M + H] = 897.44 | [M + H] = 897.3 |
| 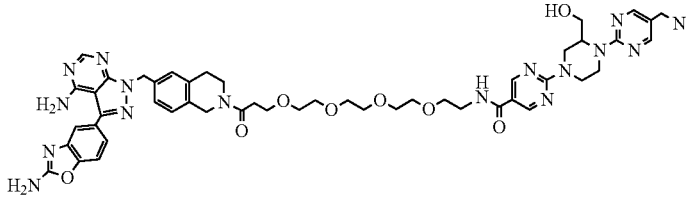<br>Intermediate B2-22 | $C_{48}H_{58}N_{16}O_8$ | [M + H] = 987.47 | [M + H] = 987.42 |
| 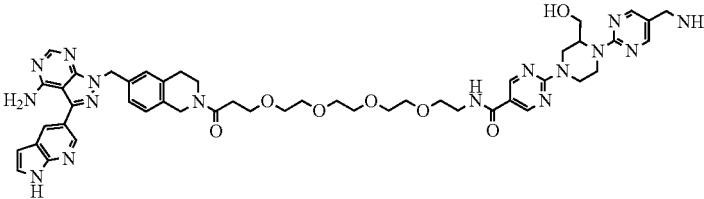 [SMILES: NCc1cnc(N2CCN(c3ncc(C(=O)NCCOCCOCCOCCOCCC(=O)N4CCc5cc(Cn6nc(-c7cnc8[nH]ccc8c7)c7c(N)ncnc76)ccc5C4)cn3)CC2CO)nc1]<br>Intermediate B2-23 | $C_{48}H_{58}N_{16}O_7$ | [M + H] = 971.48 | [M + H] = 971.31 |
| 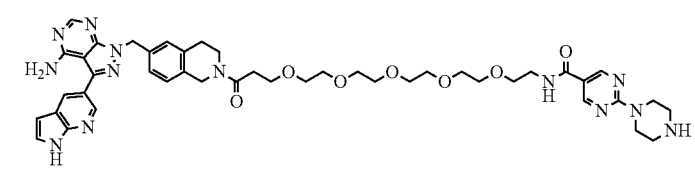 [SMILES: Nc1ncnc2c1c(-c1cnc3[nH]ccc3c1)nn2Cc1ccc2c(c1)CCN(C(=O)CCOCCOCCOCCOCCOCCNC(=O)c1cnc(N3CCNCC3)nc1)C2]<br>Intermediate B2-24 | $C_{44}H_{55}N_{13}O_7$ | [M + H] = 878.44 | [M + H] = 878.5 |

TABLE 14-continued

Additional amines prepared

| Structure | Molecular Formula | Calculated MW | Observed MW |
|---|---|---|---|
| Intermediate B2-25 | C₃₇H₅₁N₁₅O₆ | [M + H] = 802.42 | [M + H] = 802.4 |
| Intermediate B2-26 | C₄₃H₅₃N₁₅O₆ | [M + H] = 876.44 | [M + H] = 876.4 |
| Intermediate B2-27 | C₃₇H₅₁N₁₅O₅ | [M + H] = 786.43 | [M + H] = 786.5 |
| Intermediate B2-28 | C₅₀H₅₈N₁₆O₉ | [M + H] = 1027.47 | [M + H] = 1027.1 |
| Intermediate B2-29 | C₃₅H₄₃N₁₇O₄ | [M + H] = 766.38 | [M + H] = 766.3 |
| Intermediate B2-30 | C₄₁H₄₅N₁₇O₄ | [M + H] = 840.39 | [M + H] = 840.4 |

TABLE 14-continued

Additional amines prepared

| Structure | Molecular Formula | Calculated MW | Observed MW |
|---|---|---|---|
| Intermediate B2-31 | C₄₇H₅₇N₁₇O₇ | [M + H] = 972.47 | [M + H] = 972.5 |
| Intermediate B2-32 | C₄₈H₅₉N₁₇O₇ | [M + H] = 986.49 | [M + H] = 986.4 |
| Intermediate B2-33 | C₄₇H₅₇N₁₇O₆ | [M + H] = 956.48 | [M + H] = 956.3 |
| Intermediate B2-34 | C₄₉H₅₉N₁₇O₆ | [M + H] = 982.49 | [M + H] = 982.2 |
| Intermediate B2-35 | C₄₄H₆₁N₁₁O₉ | [M + H] = 888.48 | [M + H] = 888.3 |
| Intermediate B2-36 | C₄₄H₅₁N₁₇O₄ | [M + H] = 882.44 | [M + H] = 882.4 |

TABLE 14-continued

Additional amines prepared

| Structure | Molecular Formula | Calculated MW | Observed MW |
|---|---|---|---|
| Intermediate B2-37 | $C_{43}H_{52}N_{14}O_4$ | [M + H] = 829.44 | [M + H] = 829.3 |
| Intermediate B2-38 | $C_{41}H_{56}N_{10}O_8$ | [M + H] = 817.44 | [M + H] = 817.2 |
| Intermediate B2-39 | $C_{43}H_{59}N_{11}O_9$ | [M + H] = 874.46 | [M + H] = 874.3 |

Following General Procedure 2, but using the appropriate rapamycin carboxylic acid monomer in Table 1 and Intermediates B2 from Tables 9, 11, and 13 and 14, the Series 2 bivalent analogs in Table 15 were synthesized:

TABLE 15
Series 2 Bivalent Compounds:
| Structure | Molecular Formula | Calculated MW | Observed MW |
|---|---|---|---|
| 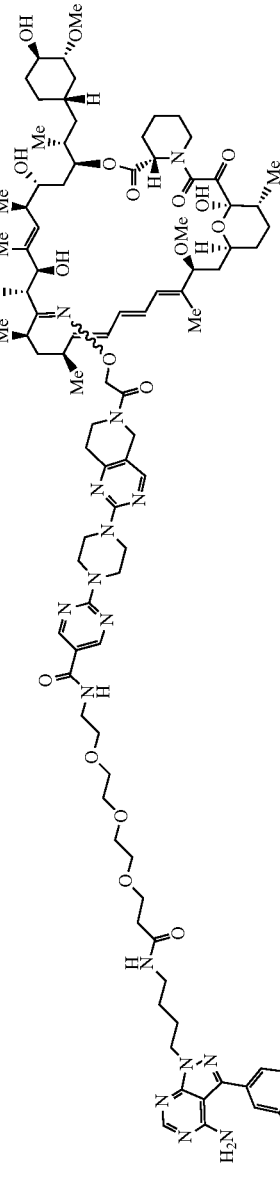 Example 15 | $C_{94}H_{134}N_{18}O_{20}$ | [M + H] = 1836.01 | [M + H] = 1836.3 |
| 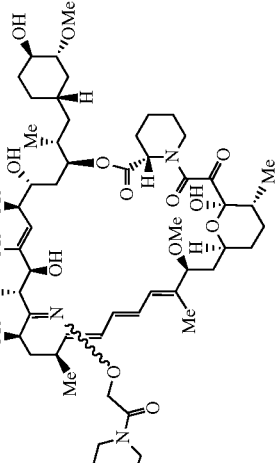 Example 16 | $C_{92}H_{130}N_{18}O_{19}$ | [M + H] = 1791.98 | [M + H] = 1792.1 |

TABLE 15-continued
Series 2 Bivalent Compounds:
| Structure | Molecular Formula | Calculated MW | Observed MW |
|---|---|---|---|
| Example 17 | $C_{90}H_{126}N_{18}O_{18}$ | [M + H] = 1747.96 | [M + H] = 1748.2 |
| Example 18 | $C_{96}H_{128}N_{18}O_{18}$ | [M + H] = 1821.97 | [M + H] = 1821.7 |
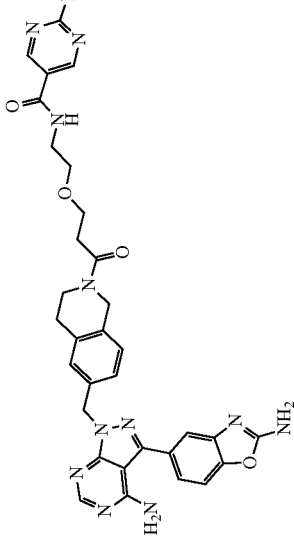

TABLE 15-continued

Series 2 Bivalent Compounds:

| Structure | Molecular Formula | Calculated MW | Observed MW |
|---|---|---|---|
| Example 19 | $C_{100}H_{136}N_{18}O_{19}$ | $[M + H] = 1894.03$ | $[M + H] = 1894.0$ |
| Example 20 | $C_{92}H_{132}N_{18}O_{20}$ | $[M + H] = 1809.99$ | $[M + H] = 1809.6$ |

TABLE 15-continued

Series 2 Bivalent Compounds:

| Structure | Molecular Formula | Calculated MW | Observed MW |
|---|---|---|---|
| Example 21 | $C_{98}H_{134}N_{18}O_{19}$ | $[M + H] = 1868.02$ | $[M + H] = 1867.9$ |
| Example 22 | $C_{90}H_{133}N_{17}O_{19}$ | $[M + H] = 1757.00$ | $[M + H] = 1756.8$ |

TABLE 15-continued
Series 2 Bivalent Compounds:
| Structure | Molecular Formula | Calculated MW | Observed MW |
|---|---|---|---|
| 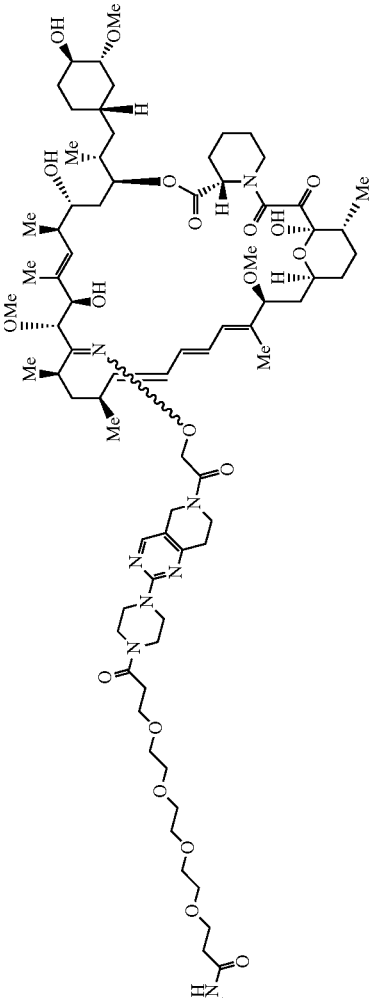 Example 23 | $C_{92}H_{135}N_{15}O_{21}$ | $[M + H] = 1787.00$ | $[M + H] = 1787.0$ |
| 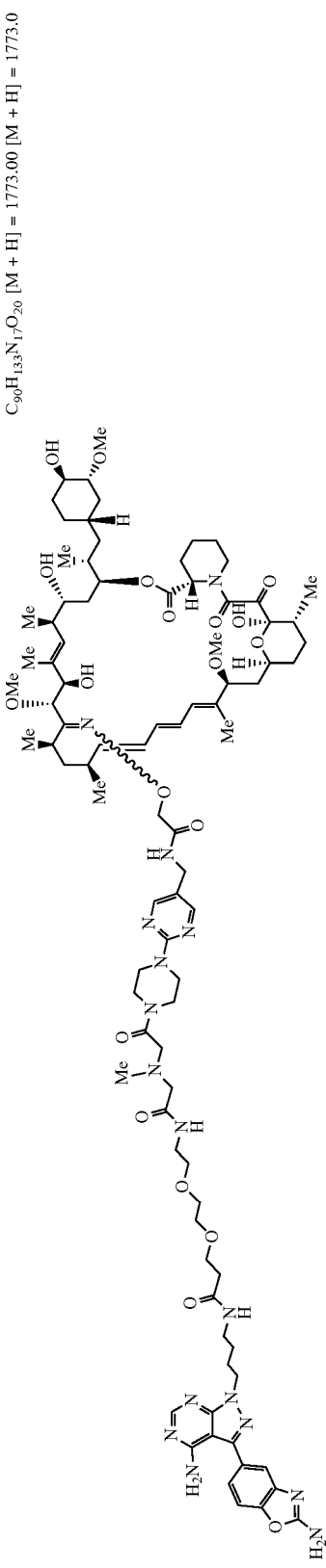 Example 24 | $C_{90}H_{133}N_{17}O_{20}$ | $[M + H] = 1773.00$ | $[M + H] = 1773.0$ |

TABLE 15-continued
Series 2 Bivalent Compounds:
| Structure | Molecular Formula | Calculated MW | Observed MW |
|---|---|---|---|
| 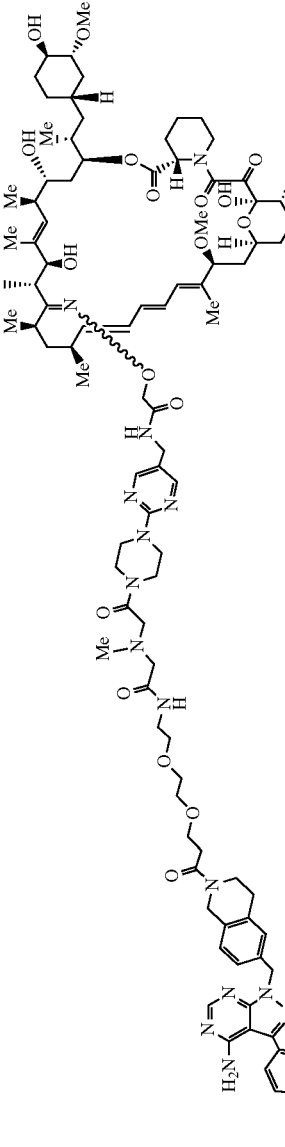 Example 25 | $C_{96}H_{135}N_{17}O_{20}$ | $[M+H] = 1847.02$ | $[M+H] = 1847.0$ |
| 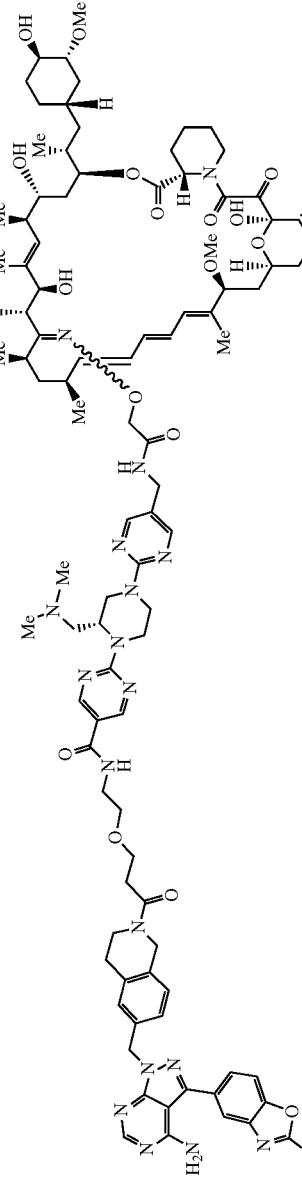 Example 49 | $C_{97}H_{133}N_{19}O_{18}$ | $[M+H] = 1853.02$ | $[M+H] = 1852.9$ |

TABLE 15-continued
Series 2 Bivalent Compounds:
| Structure | Molecular Formula | Calculated MW | Observed MW |
|---|---|---|---|
| Example 50 | $C_{94}H_{127}N_{19}O_{18}$ | $[M + H] = 1810.97$ | $[M + H] = 1811.1$ |
| Example 51 | $C_{88}H_{125}N_{19}O_{18}$ | $[M + H] = 1736.95$ | $[M + H] = 1737.0$ |
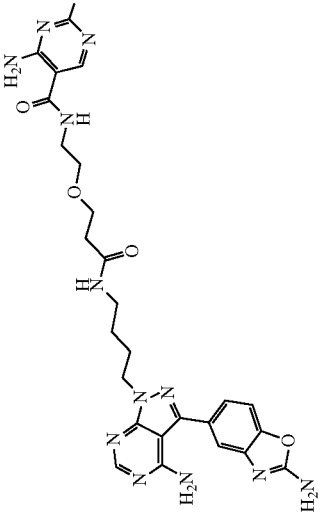

TABLE 15-continued

Series 2 Bivalent Compounds:

| Structure | Molecular Formula | Calculated MW | Observed MW |
|---|---|---|---|
| Example 52 | $C_{96}H_{134}N_{16}O_{18}$ | $[M + H] = 1800.01$ | $[M + H] = 1800.1$ |
| Example 68 | $C_{97}H_{143}N_{13}O_{23}$ | $[M + H] = 1859.05$ | $[M + H] = 1859.0$ |

Following General Procedure 1, but using the appropriate amine containing active site inhibitors in Table 2 and amine containing pre-linkers in Table 4, the Intermediates C1 in Table 16 were prepared:

TABLE 16

Additional amines prepared

| Structure | Molecular Formula | Calculated MW | Observed MW |
| --- | --- | --- | --- |
| Intermediate C1-1 | $C_{36}H_{35}N_{15}O_2$ | [M + H] = 710.32 | [M + H] = 710.2 |
| Intermediate C1-2 | $C_{30}H_{33}N_{15}O$ | [M + H] = 620.31 | [M + H] = 620.2 |
| Intermediate C1-3 | $C_{38}H_{37}N_{15}O_2$ | [M + H] = 736.34 | [M + H] = 736.2 |

TABLE 16-continued
Additional amines prepared
| Structure | Molecular Formula | Calculated MW | Observed MW |
|---|---|---|---|
| 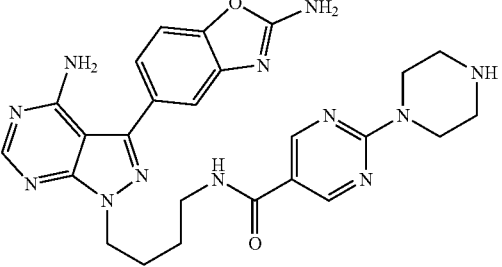<br>Intermediate C1-4 | $C_{25}H_{28}N_{12}O_2$ | [M + H] = 529.26 | [M + H] = 529.5 |
| 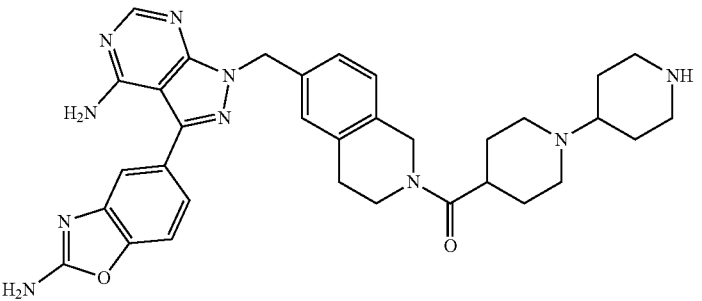 [SMILES: Nc1nc2cc(-c3nn(Cc4ccc5c(c4)CCN(C(=O)C4CCN(C6CCNCC6)CC4)C5)c4ncnc(N)c34)ccc2o1]<br>Intermediate C1-5 | $C_{33}H_{38}N_{10}O_2$ | [M + H] = 607.33 | [M + H] = 607.3 |
| 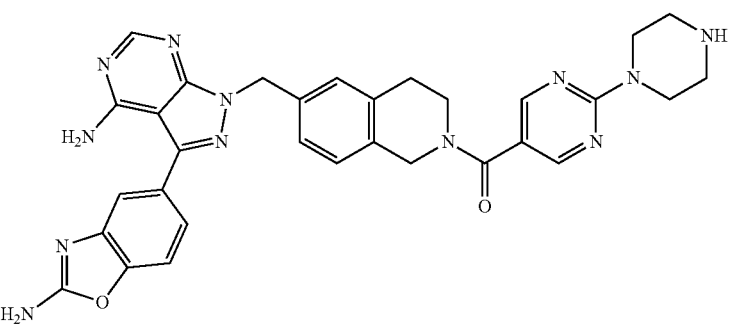 [SMILES: Nc1nc2cc(-c3nn(Cc4ccc5c(c4)CCN(C(=O)c4cnc(N6CCNCC6)nc4)C5)c4ncnc(N)c34)ccc2o1]<br>Intermediate C1-6 | $C_{31}H_{30}N_{12}O_2$ | [M + H] = 603.27 | [M + H] = 603.3 |
| 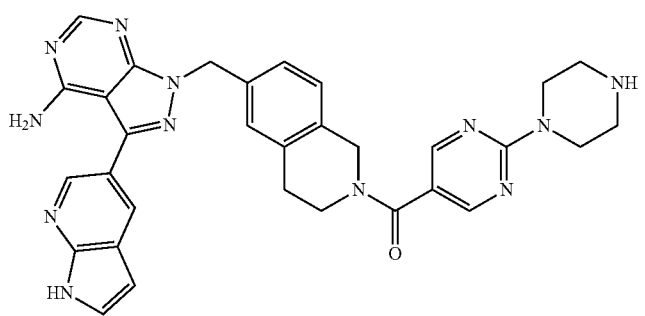 [SMILES: Nc1ncnc2c1c(-c1cnc3[nH]ccc3c1)nn2Cc1ccc2c(c1)CCN(C(=O)c1cnc(N3CCNCC3)nc1)C2]<br>Intermediate C1-7 | $C_{31}H_{30}N_{12}O$ | [M + H] = 587.28 | [M + H] = 587.3 |

TABLE 16-continued
Additional amines prepared
| Structure | Molecular Formula | Calculated MW | Observed MW |
|---|---|---|---|
| 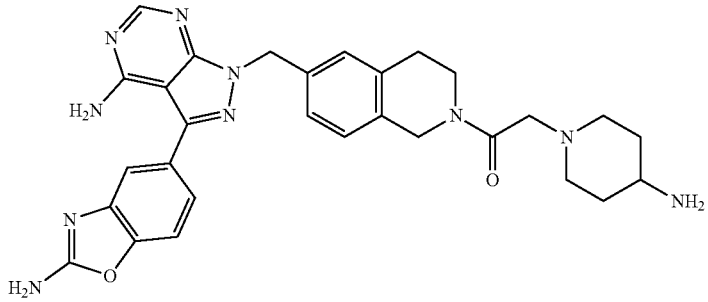 [SMILES: Nc1nc2cc(-c3nn(Cc4ccc5c(c4)CCN(C(=O)CN4CCC(N)CC4)C5)c4ncnc(N)c34)ccc2o1]<br>Intermediate C1-8 | $C_{29}H_{32}N_{10}O_2$ | [M + H] = 553.28 | [M + H] = |
Following General Procedure 1, but using the PEG carboxylic acids and Intermediates C1 in Table 16, the Intermediates C2 in Table 17 were prepared:

TABLE 17
Additional amines prepared
| Structure | Molecular Formula | Calculated MW | Observed MW |
|---|---|---|---|
| 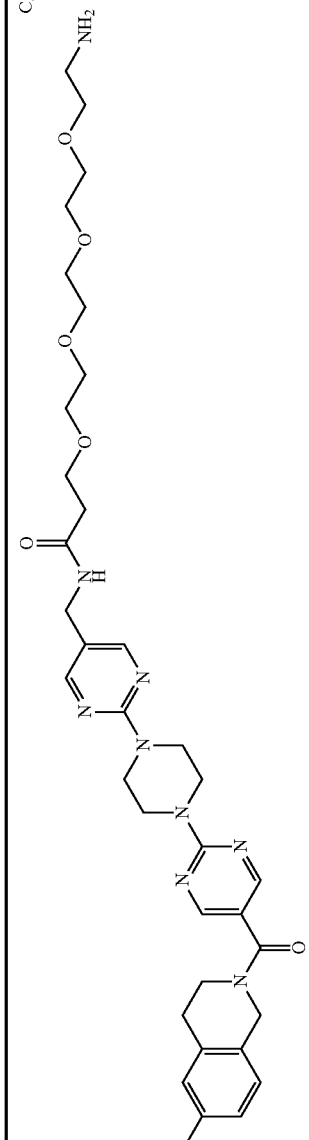<br>Intermediate C2-1 | $C_{47}H_{56}N_{16}O_7$ | $[M+H] = 957.46$ | $[M+H] = 957.7$ |
| 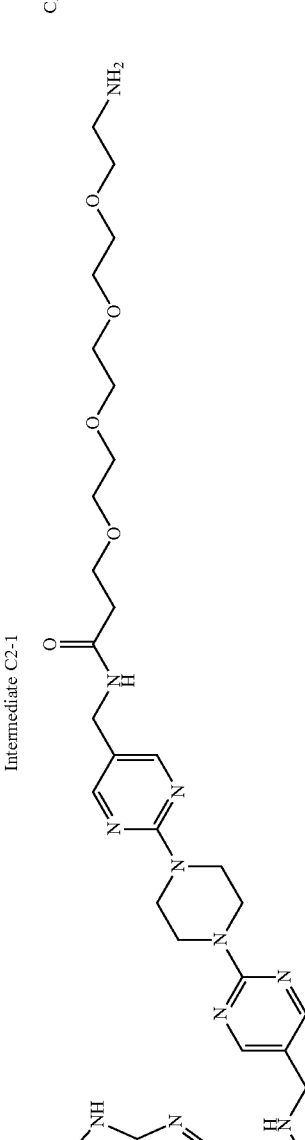<br>Intermediate C2-2 | $C_{41}H_{54}N_{16}O_6$ | $[M+H] = 867.45$ | $[M+H] = 867.2$ |

TABLE 17-continued
Additional amines prepared
| Structure | Molecular Formula | Calculated MW | Observed MW |
|---|---|---|---|
| 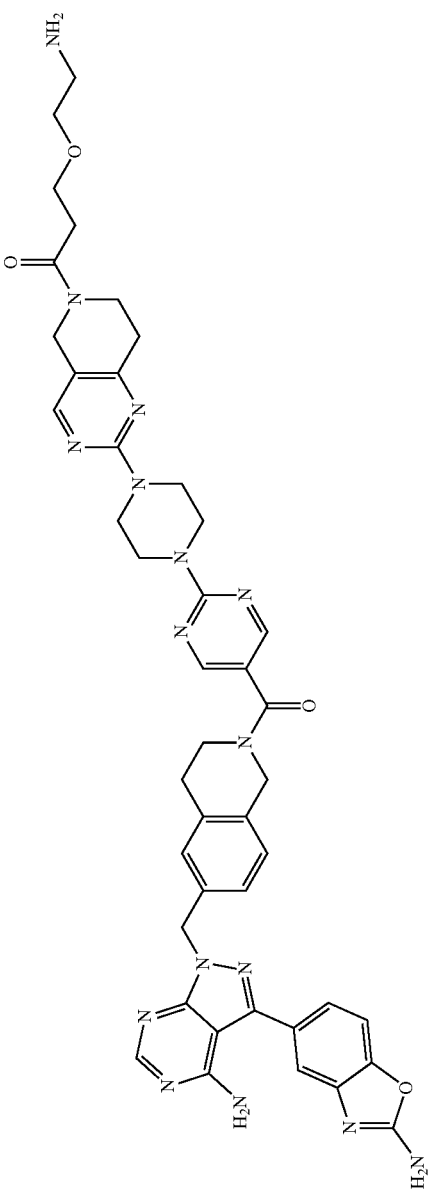 Intermediate C2-3 | $C_{43}H_{46}N_{16}O_4$ | $[M+H] = 851.40$ | $[M+H] = 851.2$ |
| 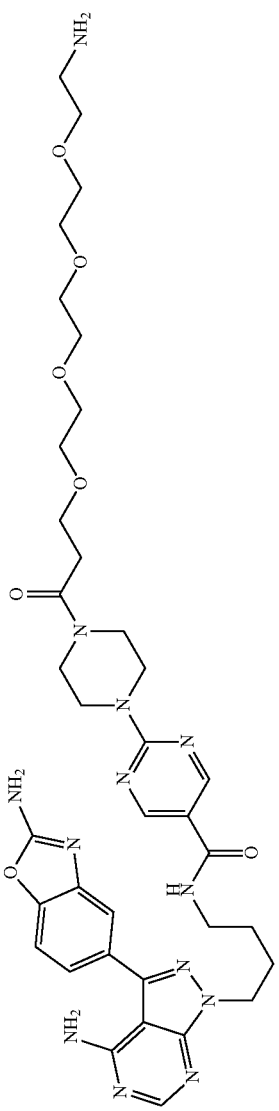 Intermediate C2-4 | $C_{36}H_{49}N_{13}O_7$ | $[M+H] = 776.40$ | $[M+H] = 776.3$ |

TABLE 17-continued

Additional amines prepared

| Structure | Molecular Formula | Calculated MW | Observed MW |
|---|---|---|---|
| Intermediate C2-5 | $C_{30}H_{37}N_{13}O_4$ | [M + H] = 644.32 | [M + H] = 644.3 |
| Intermediate C2-6 | $C_{48}H_{67}N_{11}O_9$ | [M + H] = 942.52 | [M + H] = 943.2 |
| Intermediate C2-7 | $C_{44}H_{61}N_{11}O_9$ | [M + H] = 888.48 | [M + H] = 888.3 |

Following General Procedure 2, but using the appropriate rapamycin carboxylic acid monomer in Table 1 and Intermediates C2 from Table 17, the Series 3 bivalent analogs in Table 18 were synthesized:

TABLE 18
Series 3 Bivalent Compounds
| Structure | Molecular Formula | Calculated MW | Observed MW |
|---|---|---|---|
| 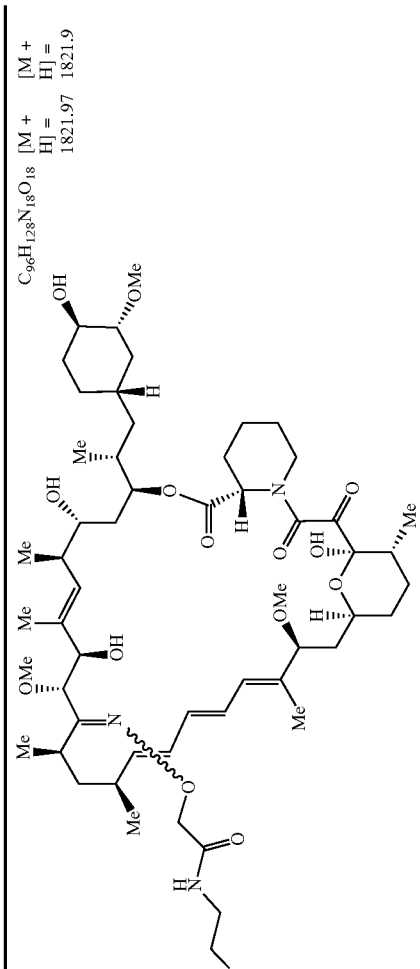 Example 26 | $C_{96}H_{128}N_{18}O_{18}$ | $[M+H] = 1821.97$ | $[M+H] = 1821.9$ |

TABLE 18-continued
Series 3 Bivalent Compounds
| Structure | Molecular Formula | Calculated MW | Observed MW |
|---|---|---|---|
| Example 27 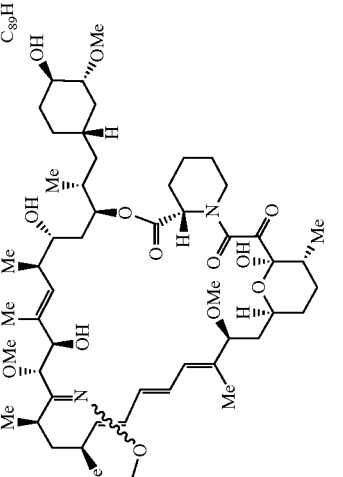 | $C_{89}H_{131}N_{15}O_{21}$ | $[M+H] = 1746.97$ | $[M+H] = 1746.9$ |
| Example 28 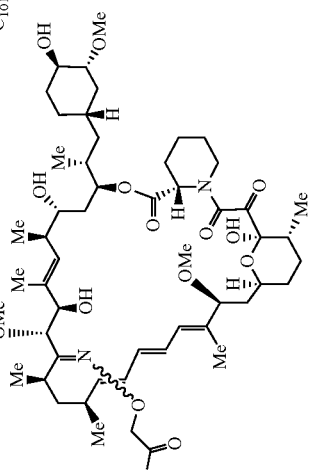 | $C_{101}H_{149}N_{13}O_{23}$ | $[M+H] = 1913.10$ | $[M+H] = 1913.0$ |

TABLE 18-continued

Series 3 Bivalent Compounds

| Structure | Molecular Formula | Calculated MW | Observed MW |
|---|---|---|---|
| Example 69 | $C_{97}H_{143}N_{13}O_{23}$ | $[M+H] = 1859.05$ | $[M+H] = 1858.9$ |

Following General Procedure 1, but using the appropriate Intermediates C2 in Table 17 and amine containing pre-linkers in Table 4, the Intermediates D1 in Table 19 were prepared:

TABLE 19

Additional amines prepared

| Structure | Molecular Formula | Calculated MW | Observed MW |
|---|---|---|---|
| 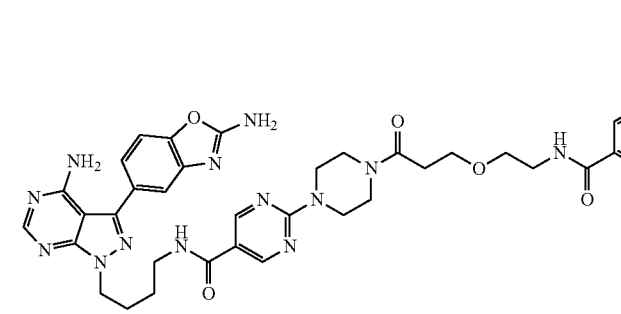<br>Intermediate D1-1 | $C_{44}H_{52}N_{20}O_5$ | [M + H] = 941.45 | [M + H] = 941.5 |

Following General Procedure 1, but using the appropriate amine containing active site inhibitors in Table 2 and amine containing pre-linkers in Table 4, the Intermediates D1 in Table 20 were prepared:

TABLE 20
Additional amines prepared
| Structure | Molecular Formula | Calculated MW | Observed MW |
|---|---|---|---|
| 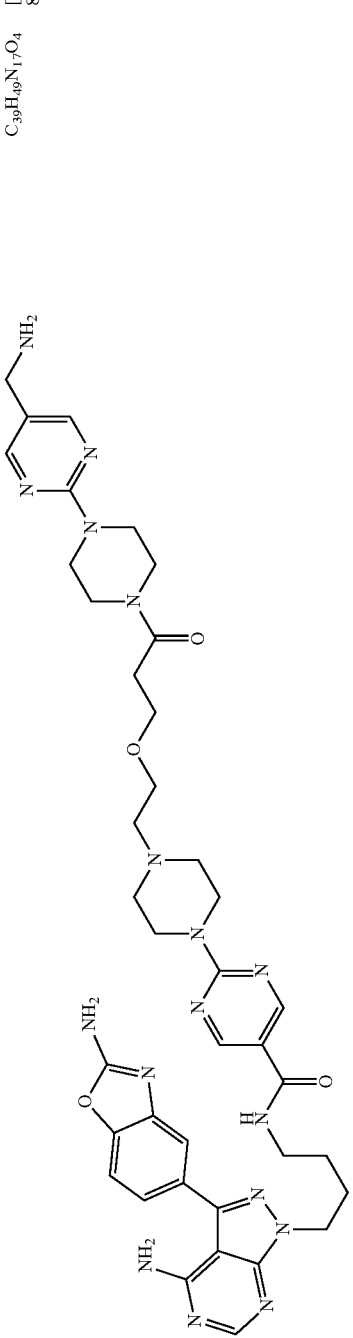<br>Intermediate D1-2 | C₃₉H₄₉N₁₇O₄ | [M + H] = 820.43 | [M + H] = 820.4 |
| 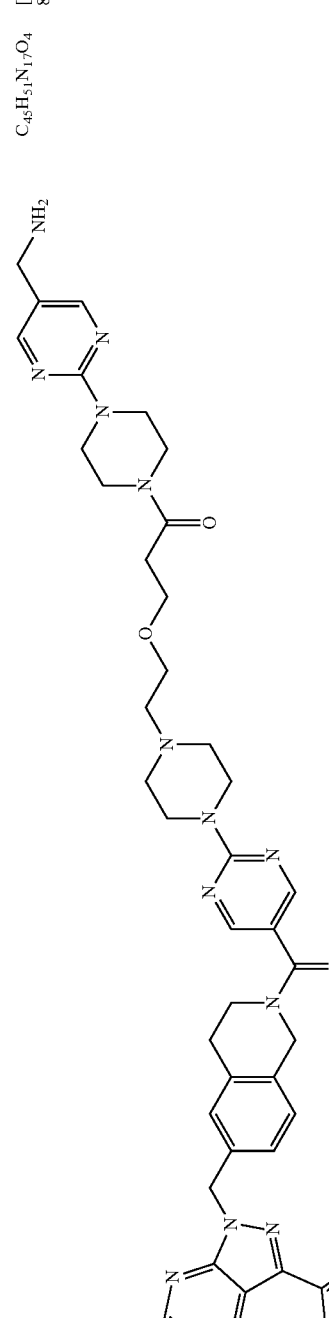<br>Intermediate D1-3 | C₄₅H₅₁N₁₇O₄ | [M + H] = 894.44 | [M + H] = 894.4 |

TABLE 20-continued
Additional amines prepared
| Structure | Molecular Formula | Calculated MW | Observed MW |
|---|---|---|---|
| 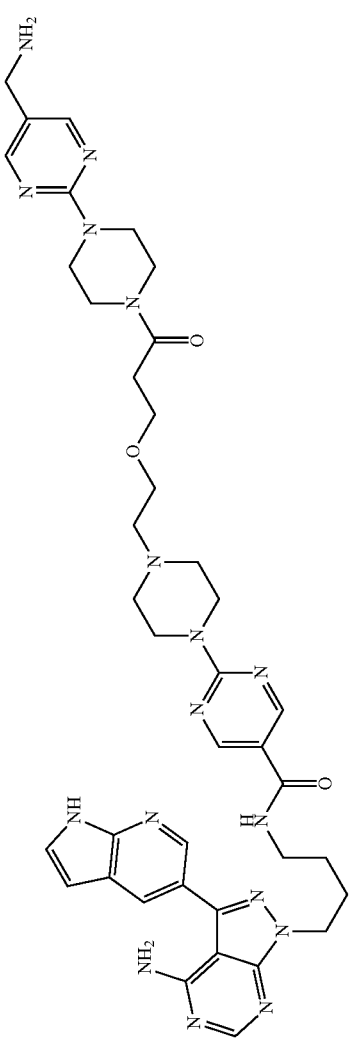<br>Intermediate D1-4 | $C_{39}H_{49}N_{17}O_3$ | $[M+H] = 804.43$ | $[M+H] = 804.4$ |
| 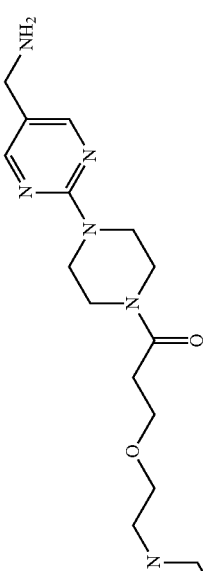<br>Intermediate D1-5 | $C_{45}H_{51}N_{17}O_3$ | $[M+H] = 878.45$ | $[M+H] = 878.4$ |

TABLE 20-continued

Additional amines prepared

| Structure | Molecular Formula | Calculated MW | Observed MW |
|---|---|---|---|
| Intermediate D1-6 | C$_{40}$H$_{49}$N$_{17}$O$_4$ | [M + H] = 832.43 | [M + H] = 832.4 |
| Intermediate D1-7 | C$_{58}$H$_{63}$F$_3$N$_{18}$O$_5$ | [M + H] = 1149.53 | [M + H] = 1149.4 |

TABLE 20-continued

Additional amines prepared

| Structure | Molecular Formula | Calculated MW | Observed MW |
|---|---|---|---|
| Intermediate D1-8 | C$_{45}$H$_{56}$N$_{16}$O$_{5}$ | [M + H] = 901.47 | [M + H] = 901.4 |
| Intermediate D1-9 | C$_{38}$H$_{51}$N$_{15}$O$_{4}$ | [M + H] = 782.43 | [M + H] = 782.4 |

TABLE 20-continued

Additional amines prepared

| Structure | Molecular Formula | Calculated MW | Observed MW |
|---|---|---|---|
| Intermediate D1-10 | $C_{47}H_{53}N_{17}O_4$ | [M + H] = 920.46 | [M + H] = 920.4 |
| Intermediate D1-11 | $C_{47}H_{56}FN_{13}O_7S$ | [M + H] = 966.42 | [M + H] = 966.3 |

TABLE 20-continued

Additional amines prepared

| Structure | Molecular Formula | Calculated MW | Observed MW |
|---|---|---|---|
| Intermediate D1-12 | $C_{47}H_{57}N_{13}O_7S$ | [M + H] = 948.43 | [M + H] = 948.4 |
| Intermediate D1-13 | $C_{47}H_{55}N_{17}O_4$ | [M + H] = 922.47 | [M + H] = 922.4 |

TABLE 20-continued

Additional amines prepared

| Structure | Molecular Formula | Calculated MW | Observed MW |
|---|---|---|---|
| Intermediate D1-14 | C₄₇H₅₃N₁₇O₃ | [M + H] = 904.46 | [M + H] = 904.4 |
| Intermediate D1-15 | C₄₄H₅₁N₁₇O₃ | [M + H] = 866.45 | [M + H] = 866.3 |

TABLE 20-continued

Additional amines prepared

| Structure | Molecular Formula | Calculated MW | Observed MW |
|---|---|---|---|
| Intermediate D1-16 | $C_{46}H_{53}N_{17}O_3$ | [M + H] = 892.46 | [M + H] = 892.3 |
| Intermediate D1-17 | $C_{44}H_{51}N_{17}O_2$ | [M + H] = 850.45 | [M + H] = 850.3 |

TABLE 20-continued

Additional amines prepared

| Structure | Molecular Formula | Calculated MW | Observed MW |
|---|---|---|---|
| Intermediate D1-18 | C₄₆H₅₃N₁₇O₂ | [M + H] = 876.47 | [M + H] = 876.3 |
| Intermediate D1-19 | C₄₄H₅₃N₁₅O₅ | [M + H] = 872.45 | [M + H] = 872.3 |

TABLE 20-continued
Additional amines prepared
| Structure | Molecular Formula | Calculated MW | Observed MW |
|---|---|---|---|
| 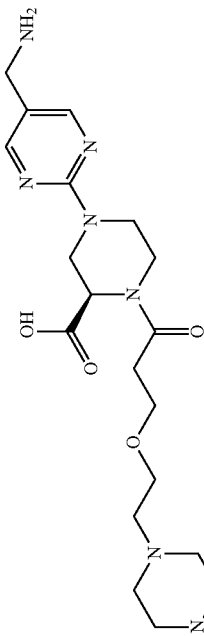 Intermediate D1-20 | C<sub>46</sub>H<sub>51</sub>N<sub>17</sub>O<sub>6</sub> | [M + H] = 938.61 | [M + H] = 938.3 |
| 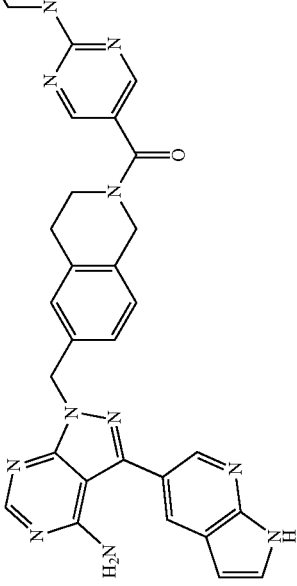 Intermediate D1-21 | C<sub>46</sub>H<sub>51</sub>N<sub>17</sub>O<sub>5</sub> | [M + H] = 922.44 | [M + H] = 922.3 |

TABLE 20-continued
Additional amines prepared
| Structure | Molecular Formula | Calculated MW | Observed MW |
|---|---|---|---|
| 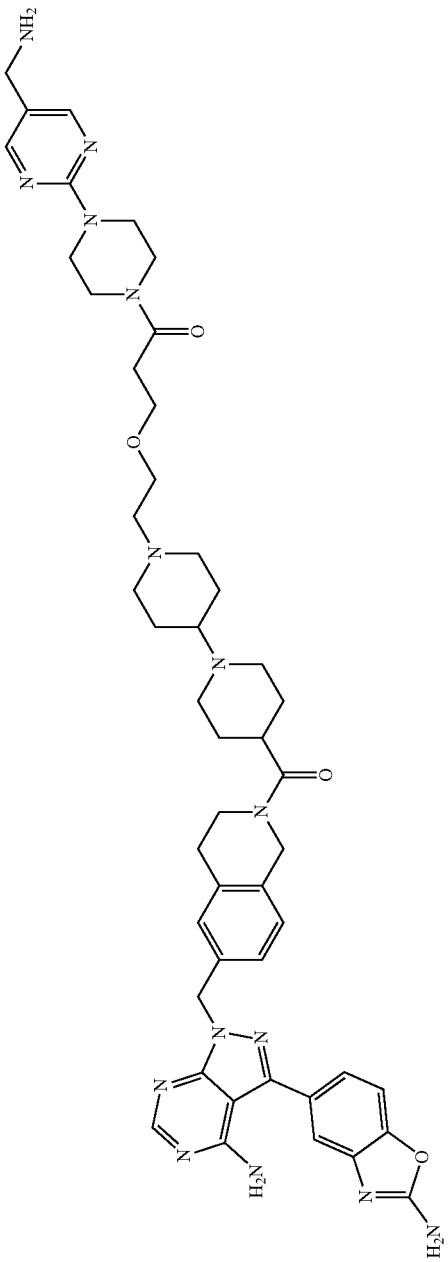<br>Intermediate D1-22 | $C_{47}H_{59}N_{15}O_4$ | [M + H] = 898.50 | [M + H] = 898.4 |

Following General Procedure 2, but using the appropriate rapamycin carboxylic acid monomer in Table 1 and Intermediates D1 from Tables 19 and 20, the Series 4 bivalent analogs in Table 21 were synthesized:

TABLE 21
Series 4 Bivalent Compounds
| Structure | Molecular Formula | Calculated MW | Observed MW |
|---|---|---|---|
| Example 29 | $C_{92}H_{131}N_{19}O_{18}$ | [M + H] = 1791.00 | [M + H] = 1791.9 |
| Example 30 | $C_{98}H_{133}N_{19}O_{18}$ | [M + H] = 1865.02 | [M + H] = 1864.9 |
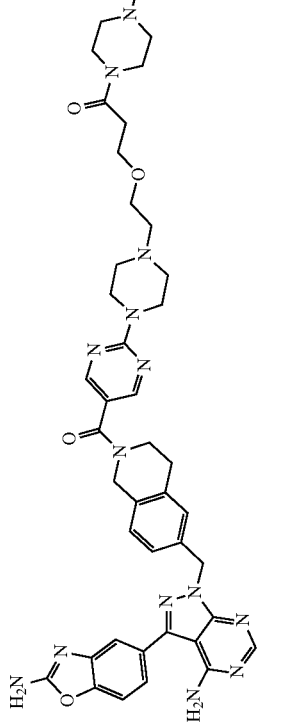

TABLE 21-continued
Series 4 Bivalent Compounds
| Structure | Molecular Formula | Calculated MW | Observed MW |
|---|---|---|---|
| 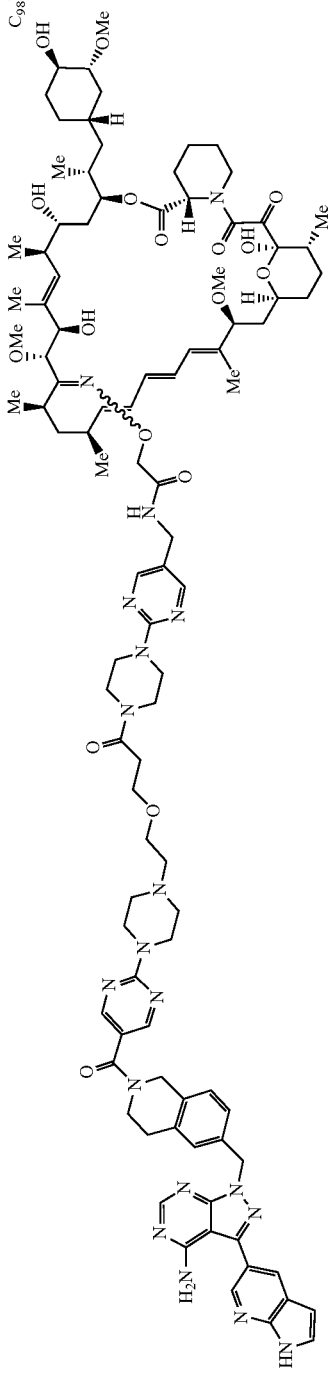 Example 31 | C₉₈H₁₃₃N₁₉O₁₇ | [M + H] = 1849.02 | [M + H] = 1849.0 |
| 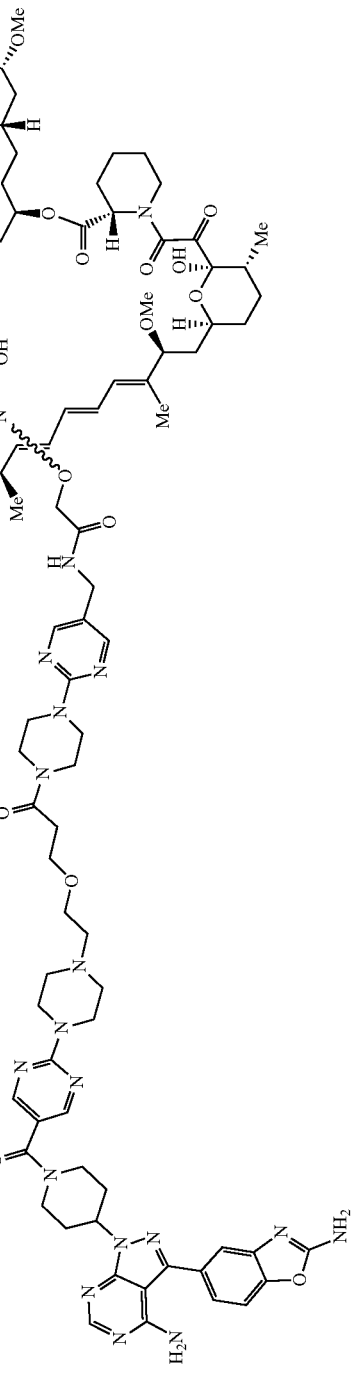 Example 32 | C₉₃H₁₃₁N₁₉O₁₈ | [M + H] = 1802.20 | [M + H] = 1803.0 |

TABLE 21-continued

Series 4 Bivalent Compounds

| Structure | Molecular Formula | Calculated MW | Observed MW |
|---|---|---|---|
| Example 33 | $C_{111}H_{145}F_3N_{20}O_{19}$ | [M + 2H]/2 = 1060.55 | [M + 2H]/2 = 1061.0 |
| Example 34 | $C_{99}H_{135}N_{19}O_{18}$ | [M + H] = 1879.29 | [M + H] = 1879.1 |

TABLE 21-continued
Series 4 Bivalent Compounds
| Structure | Molecular Formula | Calculated MW | Observed MW |
|---|---|---|---|
| 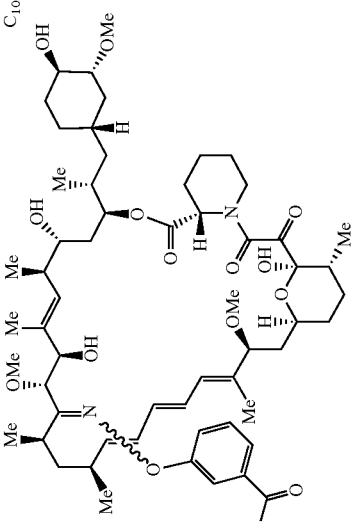 Example 35 | $C_{103}H_{135}N_{19}O_{18}$ | [M + H] = 1927.03 | [M + H] = 1927.0 |
| 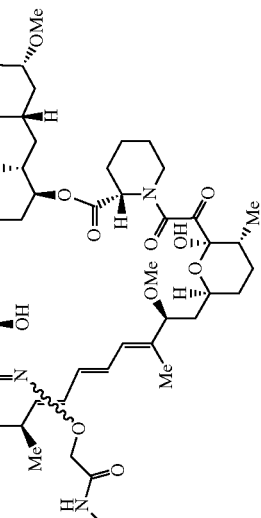 Example 36 | $C_{98}H_{138}N_{18}O_{19}$ | [M + H] = 1872.05 | [M + H] = 1871.9 |

TABLE 21-continued
Series 4 Bivalent Compounds
| Structure | Molecular Formula | Calculated MW | Observed MW |
|---|---|---|---|
| 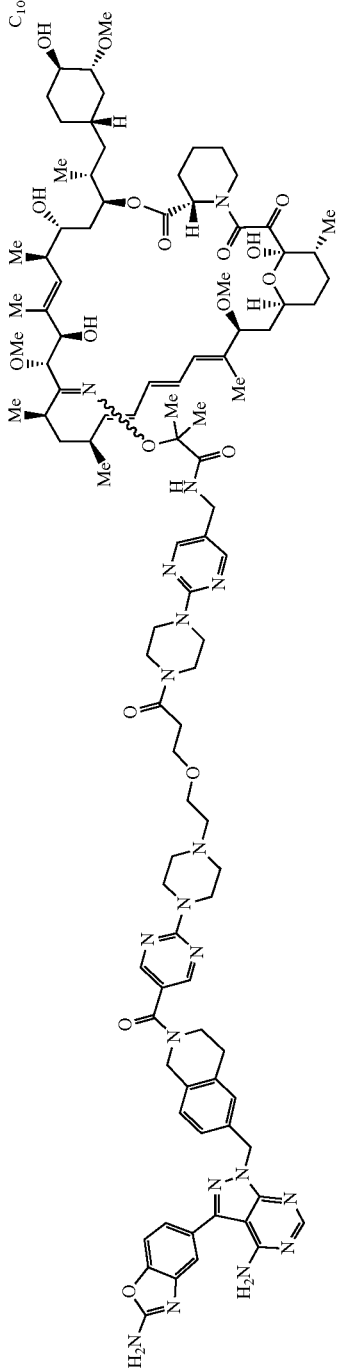 Example 38 | $C_{100}H_{137}N_{19}O_{18}$ | $[M+H] = 1893.05$ | $[M+H] = 1893.1$ |
| 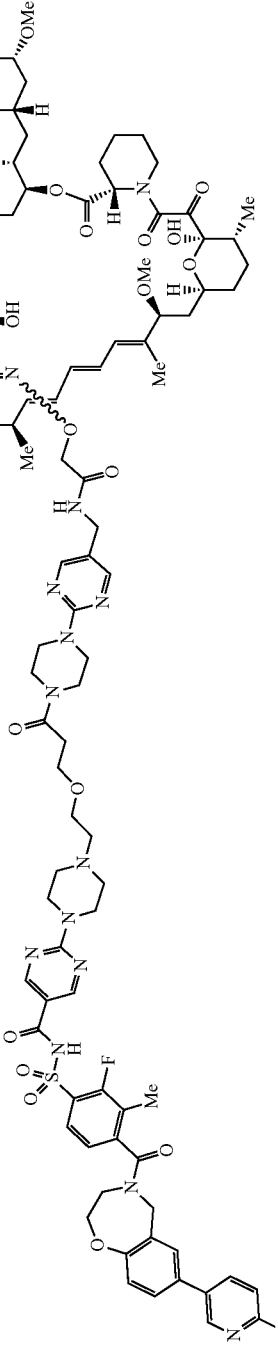 Example 53 | $C_{100}H_{138}FN_{15}O_{21}S$ | $[M+H] = 1937.00$ | $[M+H] = 1937.0$ |

TABLE 21-continued

Series 4 Bivalent Compounds

| Structure | Molecular Formula | Calculated MW | Observed MW |
|---|---|---|---|
| Example 54 | $C_{108}H_{152}N_{22}O_{19}$ | [M + 2H]/2 = 1031.59 | [M + 2H]/2 = 1032.1 |
| Example 55 | $C_{99}H_{133}N_{19}O_{20}$ | [M + H] = 1909.01 | [M + H] = 1909.0 |

TABLE 21-continued

Series 4 Bivalent Compounds

| Structure | Molecular Formula | Calculated MW | Observed MW |
|---|---|---|---|
| Example 56 | $C_{100}H_{135}N_{19}O_{20}$ | $[M + H] = 1923.02$ | $[M + H] = 1923.1$ |
| Example 57 | $C_{100}H_{135}N_{19}O_{18}$ | $[M + H] = 1891.03$ | $[M + H] = 1891.1$ |

TABLE 21-continued

Series 4 Bivalent Compounds

| Structure | Molecular Formula | Calculated MW | Observed MW |
|---|---|---|---|
| Example 58 | $C_{101}H_{137}N_{19}O_{18}$ | [M + H] = 1905.05 | [M + H] = 1905.1 |
| Example 59 | $C_{97}H_{133}N_{19}O_{17}$ | [M + H] = 1837.02 | [M + H] = 1837.1 |

TABLE 21-continued

Series 4 Bivalent Compounds

| Structure | Molecular Formula | Calculated MW | Observed MW |
|---|---|---|---|
| Example 60 | C₉₈H₁₃₅N₁₉O₁₇ | [M + H] = 1851.04 | [M + H] = 1851.0 |

TABLE 21-continued

Series 4 Bivalent Compounds

| Structure | Molecular Formula | Calculated MW | Observed MW |
|---|---|---|---|
| Example 61 | C$_{99}$H$_{135}$N$_{19}$O$_{17}$ | [M + H] = 1863.04 | [M + H] = 1863.0 |

TABLE 21-continued
Series 4 Bivalent Compounds
| Structure | Molecular Formula | Calculated MW | Observed MW |
|---|---|---|---|
| 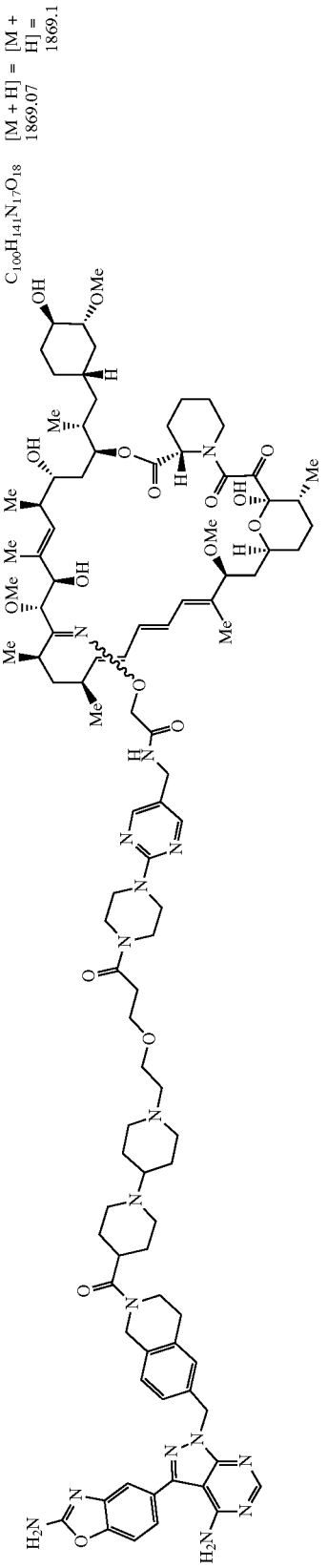 Example 62 | $C_{100}H_{137}N_{19}O_{17}$ | $[M+H] = 1877.05$ | $[M+H] = 1877.0$ |
| Example 63 | $C_{100}H_{141}N_{17}O_{18}$ | $[M+H] = 1869.07$ | $[M+H] = 1869.1$ |

TABLE 21-continued

Series 4 Bivalent Compounds

| Structure | Molecular Formula | Calculated MW | Observed MW |
|---|---|---|---|
| Example 64 | C₁₀₁H₁₄₃N₁₇O₁₈ | [M + H] = 1883.09 | [M + H] = 1883.1 |

Following General Procedure 1, but using the appropriate Intermediates C1 in Table 16 and amine containing pre-linkers in Table 4, the Intermediates E1 in Table 22 were prepared:

TABLE 22

Additional amines prepared

| Structure | Molecular Formula | Calculated MW | Observed MW |
|---|---|---|---|
| Intermediate E1-1 | $C_{39}H_{43}N_{19}O_3$ | [M + H] = 826.39 | [M + H] = 826.5 |
| Intermediate E1-2 | $C_{45}H_{45}N_{19}O_3$ | [M + H] = 900.41 | [M + H] = 900.2 |
| Intermediate E1-3 | $C_{45}H_{45}N_{19}O_2$ | [M + H] = 884.41 | [M + H] = 884.4 |
| Intermediate E1-4 | $C_{47}H_{47}N_{19}O_3$ | [M + H] = 926.42 | [M + H] = 926.6 |

TABLE 22-continued

Additional amines prepared

| Structure | Molecular Formula | Calculated MW | Observed MW |
|---|---|---|---|
| Intermediate E1-5 | C₄₇H₄₇N₁₉O₂ | [M + H] = 910.43 | [M + H] = 910.2 |
| Intermediate E1-6 | C₃₈H₄₇N₁₇O₃ | [M + H] = 790.41 | [M + H] = 790.4 |
| Intermediate E1-7 | C₄₄H₄₉N₁₇O₃ | [M + H] = 864.43 | [M + H] = 864.3 |
| Intermediate E1-8 | C₃₉H₄₇N₁₇O₃ | [M + H] = 802.41 | [M + H] = 802.3 |

Following General Procedure 2, but using the appropriate rapamycin carboxylic acid monomer in Table 1 and Intermediates E1 from Table 22, the Series 5 bivalent analogs in Table 23 were synthesized:

TABLE 23
Series 5 Bivalent Compounds:
| Structure | Molecular Formula | Calculated MW | Observed MW |
|---|---|---|---|
| Example 37 | $C_{91}H_{129}N_{19}O_{17}$ | [M + H] = 1760.99 | [M + H] = 1761.0 |
| Example 65 | $C_{97}H_{131}N_{19}O_{17}$ | [M + H] = 1835.00 | [M + H] = 1834.9 |
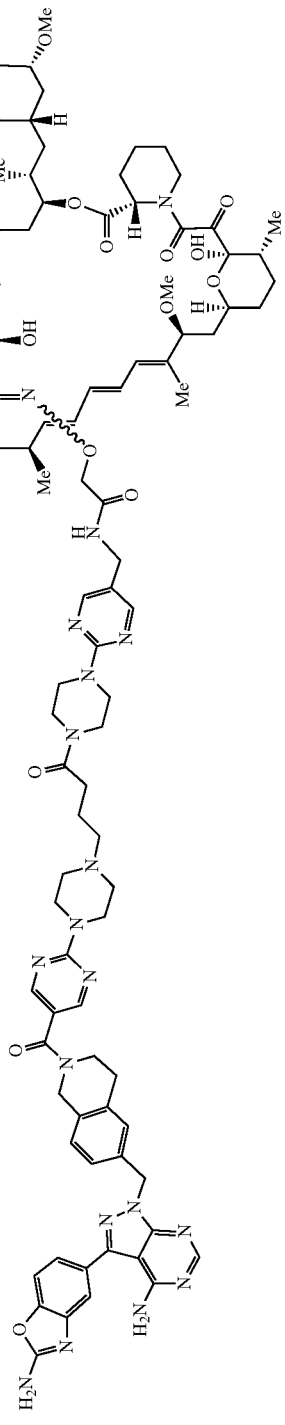

TABLE 23-continued
Series 5 Bivalent Compounds:
| Structure | Molecular Formula | Calculated MW | Observed MW |
|---|---|---|---|
| 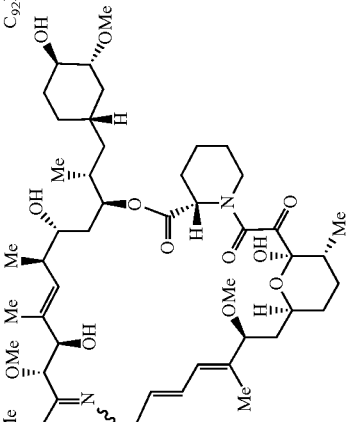 Example 66 | $C_{92}H_{129}N_{19}O_{17}$ | [M + H] = 1772.99 | [M + H] = 1773.0 |

TABLE 24
Additional amines prepared
| Structure | Molecular Formula | Calculated MW | Observed MW |
|---|---|---|---|
| 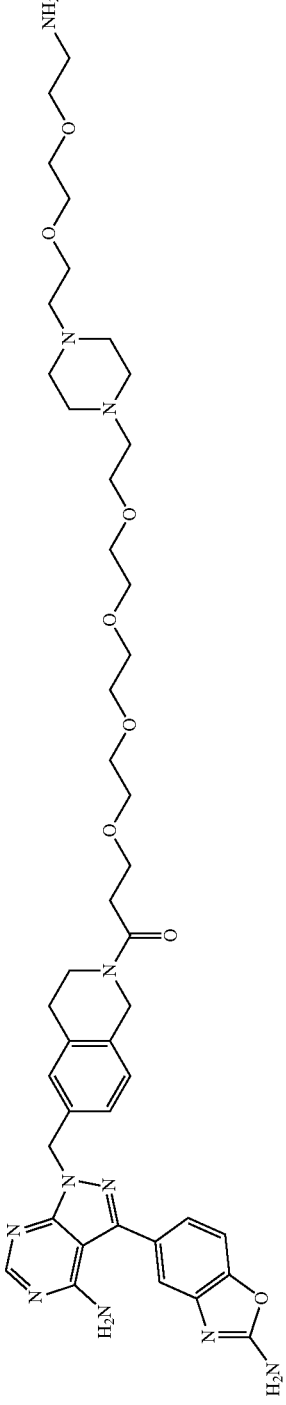<br>Intermediate F1-1 | $C_{43}H_{61}N_{11}O_8$ | $[M+H] = 860.48$ | $[M+H] = 860.4$ |
| 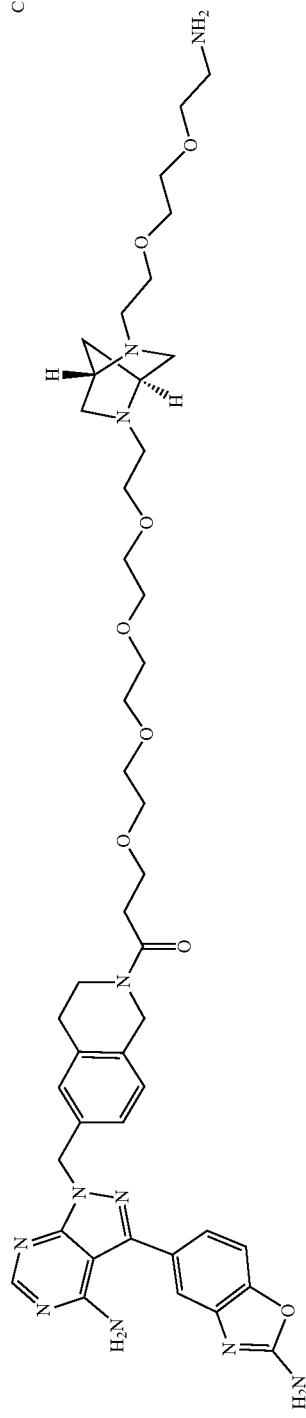<br>Intermediate F1-2 | $C_{44}H_{61}N_{11}O_8$ | $[M+H] = 872.48$ | $[M+H] = 872.2$ |

Following General Procedure 2, but using the appropriate rapamycin carboxylic acid monomer in Table 1 and Intermediates F1 from Table 24, the Series 6 bivalent analogs in Table 25 were synthesized:

TABLE 25
Series 6 Bivalent Compounds:
| Structure | Molecular Formula | Calculated MW | Observed MW |
|---|---|---|---|
| 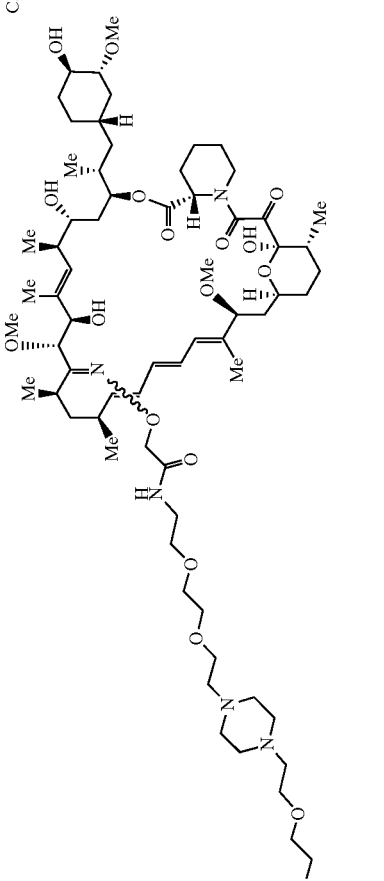 Example 70 | $C_{96}H_{143}N_{13}O_{22}$ | $[M+H] = 1831.06$ | $[M+H] = 1830.9$ |

Following General Procedure 1, but using the appropriate Intermediates A1 in Table 5 and amine containing pre-linkers in Table 4, the Intermediates G1 in Table 26 were prepared:

TABLE 26

Additional amines prepared

| Structure | Molecular Formula | Calculated MW | Observed MW |
|---|---|---|---|
| Intermediate G1-1 | C₄₄H₅₈N₁₈O₆ | [M + H] = 935.49 | [M + H] = 935.5 |
| Intermediate G1-2 | C₅₀H₆₀N₁₈O₆ | [M + H] = 1009.50 | [M + H] = 1009.5 |

TABLE 26-continued
Additional amines prepared
| Structure | Molecular Formula | Calculated MW | Observed MW |
|---|---|---|---|
| 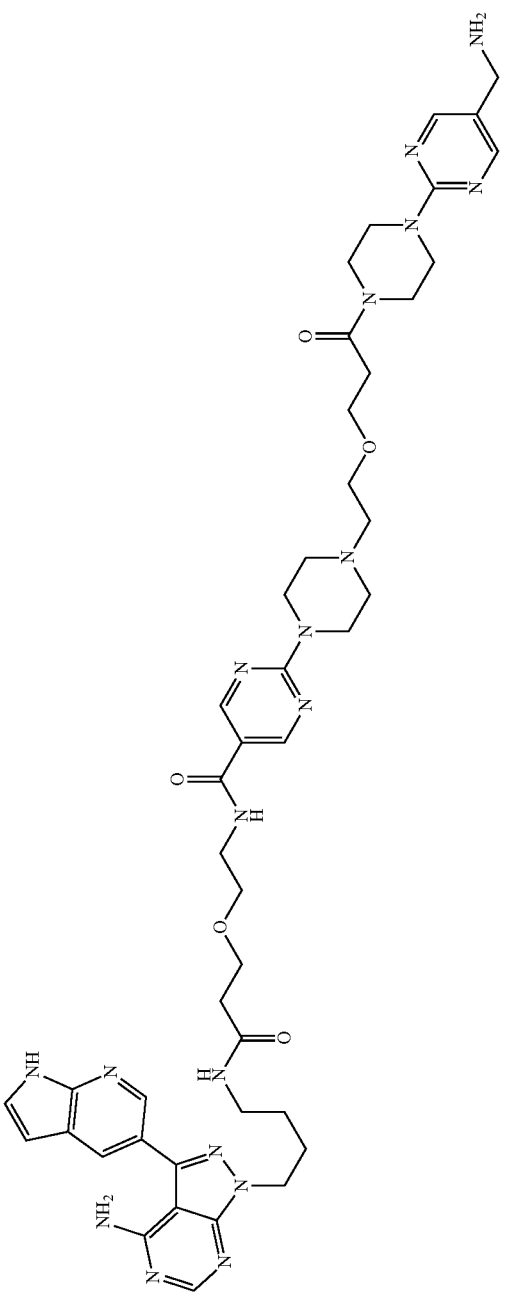<br>Intermediate G1-3 | $C_{44}H_{58}N_{18}O_5$ | [M + H] = 919.49 | [M + H] = 919.5 |

Following General Procedure 6, but using the appropriate Intermediates B3 in Table 10 and amine containing pre-linkers in Table 4, the Intermediates G1 in Table 27 were prepared:

TABLE 27

Additional amines prepared

| Structure | Molecular Formula | Calculated MW | Observed MW |
|---|---|---|---|
| 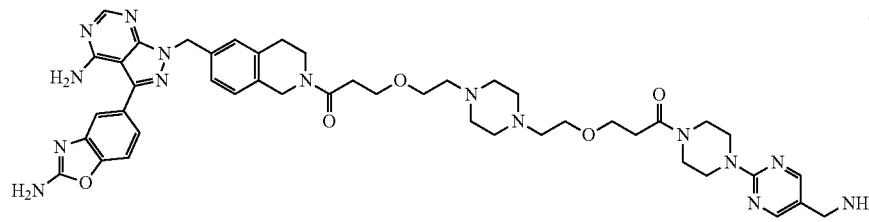 [SMILES: NCc1cnc(N2CCN(C(=O)CCOCCN3CCN(CCOCCC(=O)N4CCc5cc(Cn6nc(-c7ccc8oc(N)nc8c7)c7c(N)ncnc76)ccc5C4)CC3)CC2)nc1]<br>Intermediate G1-4 | $C_{45}H_{57}N_{15}O_5$ | [M + H] = 888.48 | [M + H] = 888.4 |

Following General Procedure 2, but using the appropriate rapamycin carboxylic acid monomer in Table 1 and Intermediates G1 from Tables 26 and 27, the Series 7 bivalent analogs in Table 28 were synthesized:

TABLE 28

Series 7 Bivalent Compounds

| Structure | Molecular Formula | Calculated MW | Observed MW |
|---|---|---|---|
| Example 39 | $C_{103}H_{142}N_{20}O_{20}$ | $[M+H] = 1980.08$ | $[M+H] = 1980.1$ |
| Example 40 | $C_{98}H_{139}N_{17}O_{19}$ | $[M+H] = 1859.05$ | $[M+H] = 1858.9$ |

TABLE 28-continued

Series 7 Bivalent Compounds

| Structure | Molecular Formula | Calculated MW | Observed MW |
|---|---|---|---|
| Example 41 | $C_{97}H_{140}N_{20}O_{20}$ | $[M+H] = 1906.07$ | $[M+H] = 1906.0$ |

Following General Procedure 1, but using the appropriate Intermediates D1 in Tables 19 and 20 and PEG carboxylic acids, the Intermediates H1 in Table 29 were prepared:

TABLE 29

Additional amines prepared

| Structure | Molecular Formula | Calculated MW | Observed MW |
|---|---|---|---|
| Intermediate H1-1 | C₄₄H₅₈N₁₈O₆ | [M + H] = 935.49 | [M + H] = 935.5 |
| Intermediate H1-2 | C₅₀H₆₀N₁₈O₆ | [M + 2H]/2 = 505.23 | [M + H]/2 = 505.4 |

TABLE 29-continued

Additional amines prepared

| Structure | Molecular Formula | Calculated MW | Observed MW |
|---|---|---|---|
| Intermediate H1-3 | C₄₄H₅₈N₁₈O₅ | [M + 2H]/2 = 460.25 | [M + H]/2 = 460.3 |

Following General Procedure 2, but using the appropriate rapamycin carboxylic acid monomer in Table 1 and Intermediates H1 from Table 29, the Series 8 bivalent analogs in Table 30 were synthesized:

TABLE 30
Series 8 Bivalent Compounds:
| Structure | Molecular Formula | Calculated MW | Observed MW |
|---|---|---|---|
| 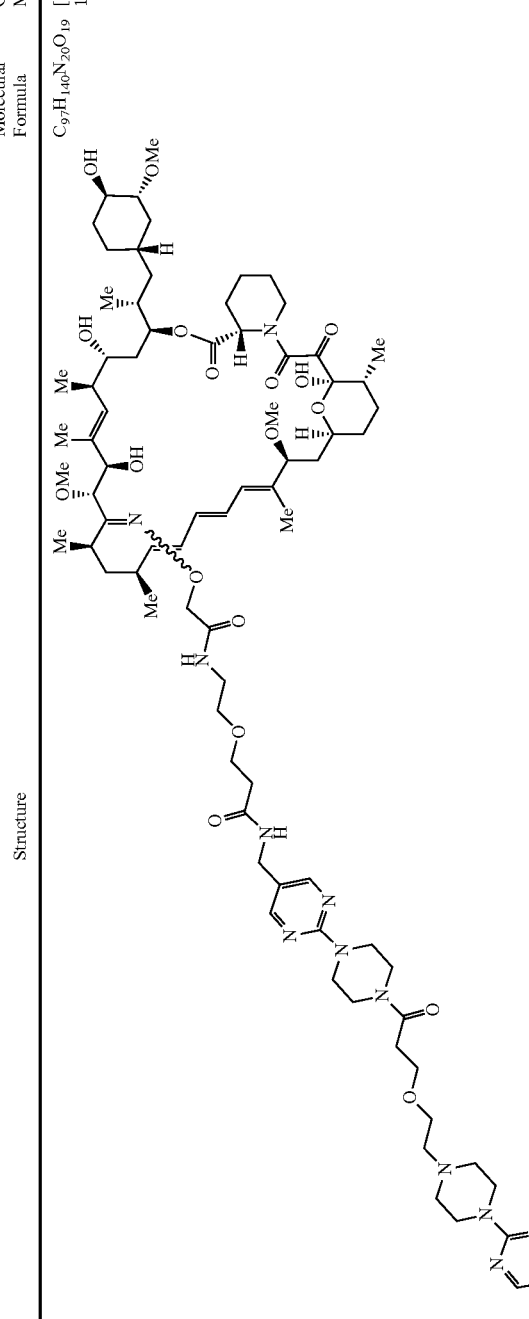 Example 42 | $C_{97}H_{140}N_{20}O_{19}$ | [M + H] = 1890.07 | [M + H] = 1890.0 |

TABLE 30-continued
Series 8 Bivalent Compounds:
| Structure | Molecular Formula | Calculated MW | Observed MW |
|---|---|---|---|
| 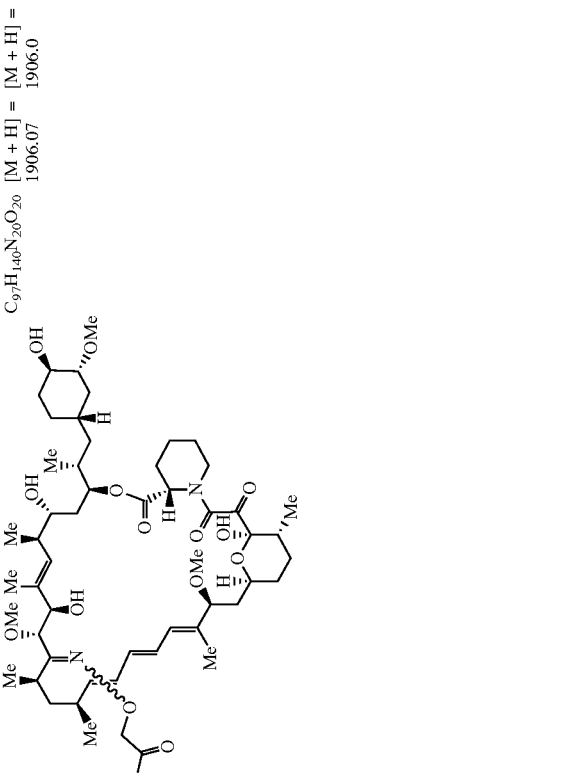<br>Example 43 | $C_{97}H_{140}N_{20}O_{20}$ | $[M+H] = 1906.07$ | $[M+H] = 1906.0$ |

TABLE 30-continued

Series 8 Bivalent Compounds:

| Structure | Molecular Formula | Calculated MW | Observed MW |
|---|---|---|---|
| Example 44 | $C_{103}H_{142}N_{20}O_{20}$ | $[M + H] = 1980.08$ | $[M + H] = 1980.1$ |

Biological Examples

Cell Based AlphaLISA Assays For Determining IC50 For Inhibition of P-Akt (S473), P-4E-BP1 (T37/46), and P-P70S6K (T389) in MDA-MB-468 Cells mTOR Kinase Cellular Assay To measure functional activity of mTORC1 and mTORC2 in cells the phosphorylation of 4EBP1 (Thr37/46) and P70S6K (Thr389), and AKT1/2/3 (Ser473) was monitored using AlphaLisa SureFire Ultra Kits (Perkin Elmer). MDA-MB-468 cells (ATCC® HTB-132) are cultured in 96-well tissue culture plates and treated with compounds in the disclosure at concentrations varying from 0.017-1,000 nM for two to four hours at 37° C. Incubations are terminated by removal of the assay buffer and addition of lysis buffer provided with the assay kit. Samples are processed according to the manufacturer's instructions. The Alpha signal from the respective phosphoproteins is measured in duplicate using a microplate reader (Envision, Perkin-Elmer or Spectramax M5, Molecular Devices). Inhibitor concentration response curves are analyzed using normalized $IC_{50}$ regression curve fitting with control based normalization.

As an example, measured $IC_{50}$ values for selected compounds are reported below:

| Example | p-P70S6K-(T389) | p-4E-BP1-(T37/46) | p-AKT1/2/3-(S473) |
|---|---|---|---|
| MLN-128 | ++ | ++ | ++ |
| Rapamycin | +++ | − | − |
| 1 | ++ | ++ | + |
| 2 | +++ | ++ | + |
| 3 | +++ | ++ | + |
| 4 | +++ | ++ | + |
| 5 | +++ | +++ | + |
| 6 | ++ | ++ | − |
| 7 | +++ | ++ | − |
| 8 | +++ | ++ | − |
| 9 | ++ | ++ | − |
| 10 | +++ | ++ | − |
| 11 | ++ | ++ | − |
| 12 | +++ | +++ | + |
| 13 | +++ | +++ | ++ |
| 14 | +++ | ++ | + |
| 15 | ++ | ++ | + |
| 16 | ++ | ++ | − |
| 17 | ++ | ++ | − |
| 18 | ++ | ++ | − |
| 19 | ++ | ++ | − |
| 20 | ++ | ++ | − |
| 21 | ++ | ++ | − |
| 22 | ++ | + | − |
| 23 | ++ | ++ | + |
| 24 | ++ | + | + |
| 25 | ++ | + | − |
| 26 | ++ | ++ | − |
| 27 | ++ | ++ | + |
| 28 | ++ | ++ | + |
| 29 | ++ | ++ | + |
| 30 | +++ | ++ | − |
| 31 | +++ | ++ | − |
| 32 | +++ | ++ | ++ |
| 33 | + | − | − |
| 34 | ++ | ++ | − |
| 35 | + | − | − |
| 36 | ++ | + | − |
| 37 | +++ | ++ | ++ |
| 39 | ++ | ++ | − |
| 40 | ++ | ++ | − |
| 42 | ++ | ++ | − |
| 43 | +++ | ++ | + |
| 44 | +++ | ++ | + |
| 45 | ++ | ++ | − |
| 46 | ++ | ++ | − |
| 47 | ++ | + | − |
| 48 | + | ++ | − |
| 49 | ++ | ++ | − |
| 50 | + | − | − |
| 51 | + | − | − |
| 52 | ++ | ++ | − |
| 53 | +++ | ++ | − |
| 54 | ++ | ++ | − |
| 55 | +++ | ++ | − |
| 56 | +++ | ++ | ++ |
| 57 | +++ | ++ | − |
| 58 | ++ | ++ | − |
| 59 | +++ | ++ | − |
| 60 | ++ | ++ | − |
| 61 | ++ | ++ | − |
| 62 | ++ | − | − |
| 63 | +++ | ++ | − |
| 64 | +++ | ++ | − |
| 65 | ++ | ++ | − |
| 66 | ++ | − | − |
| 67 | +++ | +++ | + |
| 68 | ++ | ++ | + |
| 69 | ++ | ++ | − |
| 70 | ++ | ++ | + |

Note:
pIC50 (p-P70S6K-(T389))
≥9  +++
9 > pIC50 ≥ 8  ++
8 > pIC50 ≥ 6  +
<6  − pIC50 (p-4E-BP1-(T37/46) or p-AKT1/2/3-(S473))
≥8.5  +++
8.5 > pIC50 ≥ 7.5  ++
7.5 > pIC50 ≥ 6.0  +
<6  −

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A compound of Formula Ia:

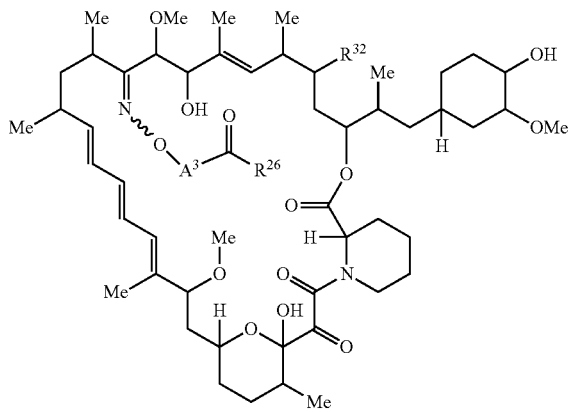

(Ia)

or a pharmaceutically acceptable salt, stereoisomer, tautomer, or oxepane isomer thereof, wherein:

$R^{32}$ is H, =O, —$OR^3$, or —$N_3$;

$A^3$ is —[$C(R^3)_2$]n—, ($C_6$-$C_{10}$)arylene, cycloalkylene, heteroarylene, or heterocyclylene;

$R^{26}$ is -$A^1$-$L^1$-$A^2$-B; -$A^1$-$A^2$-B; or -$L^2$-$A^1$-$L^1$-$A^2$-$L^3$-B;

$A^1$ and $A^2$ are independently absent or are independently selected from

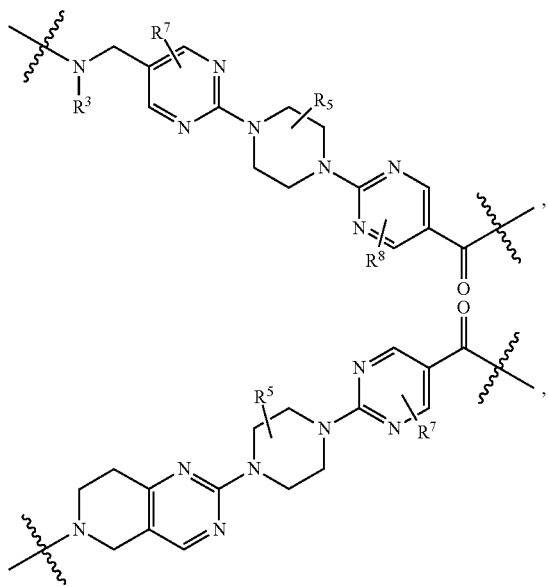

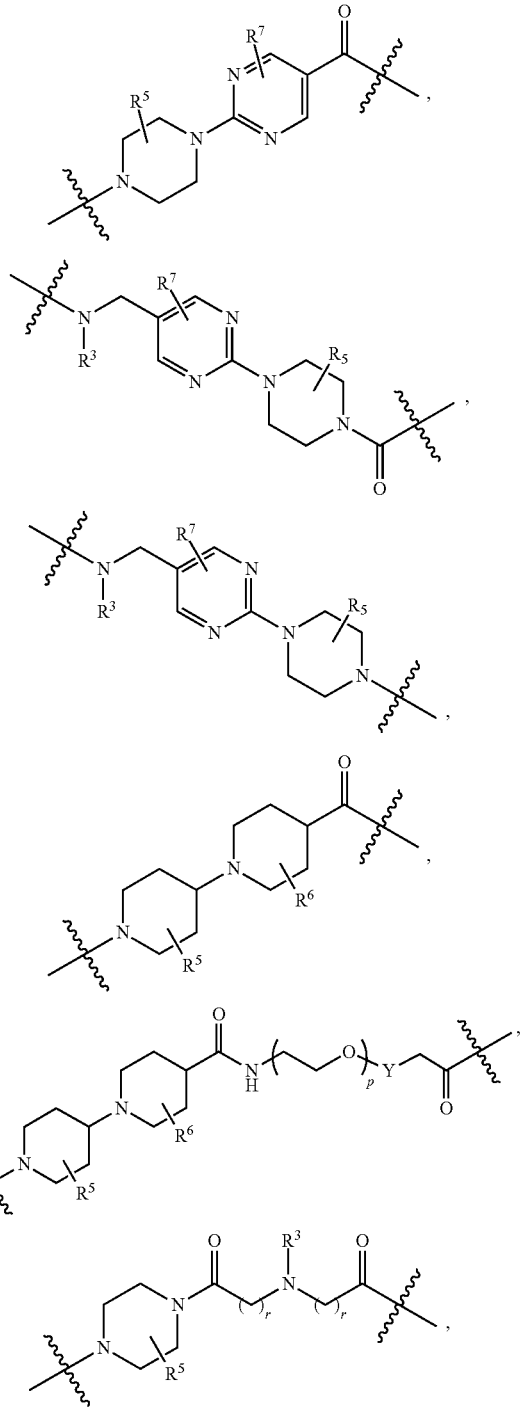

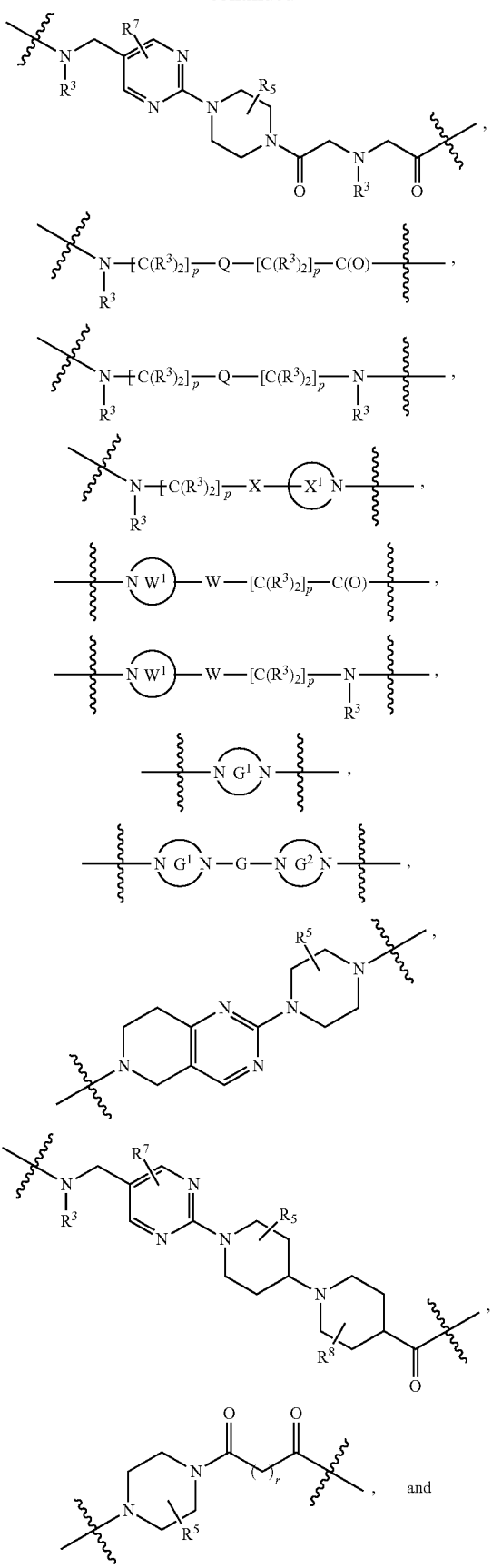

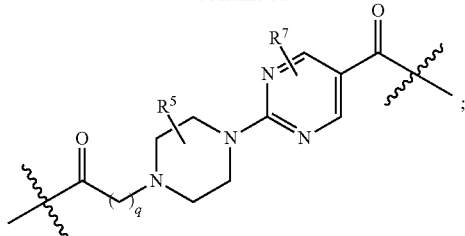

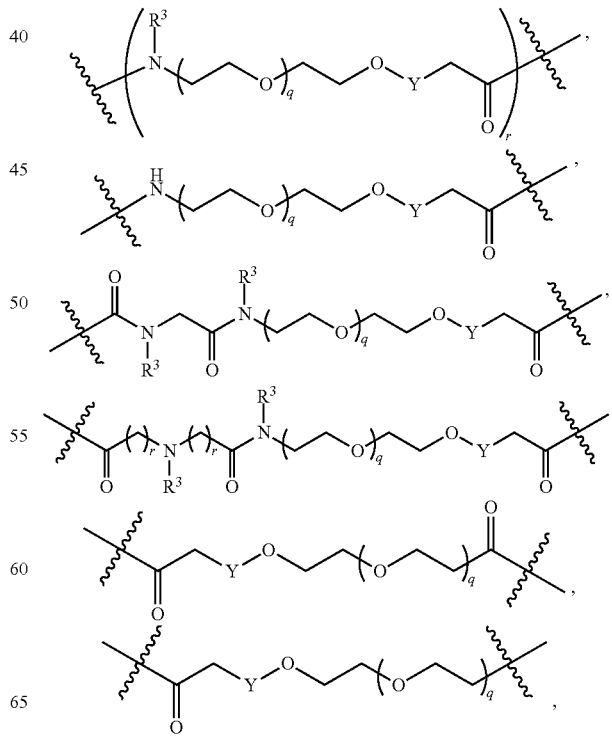

wherein the bond on the left side of $A^1$, as drawn, is bound to —C(=O)— or $L^2$; and wherein the bond on the right side of the $A^2$ moiety, as drawn, is bound to B or $L^3$;

each Q is independently 1 to 3 rings selected from arylene, cycloalkylene, heteroarylene, and heterocyclylene;

each X is independently absent or 1 to 2 rings selected from arylene, cycloalkylene, heteroarylene, and heterocyclylene;

each $X^1$ is independently a heteroarylene or heterocyclylene ring;

each W is independently absent or 1 to 2 rings selected from arylene, cycloalkylene, heteroarylene, and heterocyclylene;

each $W^1$ is independently a heteroarylene or heterocyclylene ring;

each G is independently absent or a ring selected from arylene, cycloalkylene, heteroarylene, and heterocyclylene;

each $G^1$ and $G^2$ are independently heteroarylene or heterocyclylene ring;

each $L^1$ is independently selected from

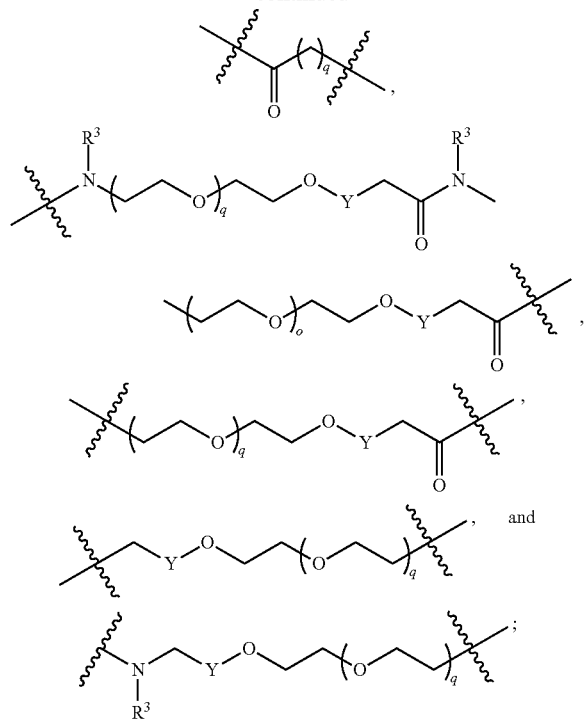
$L^2$ and $L^3$ are independently absent or are independently selected from
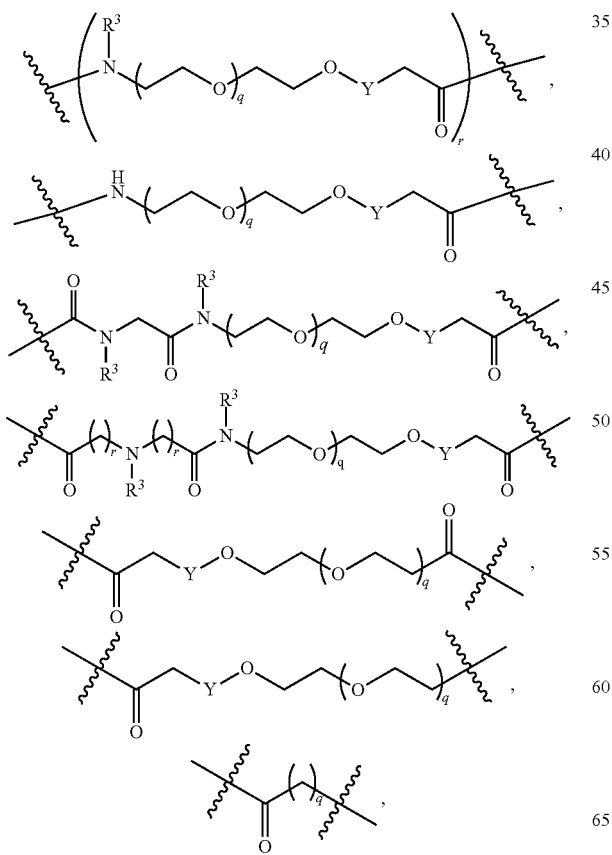
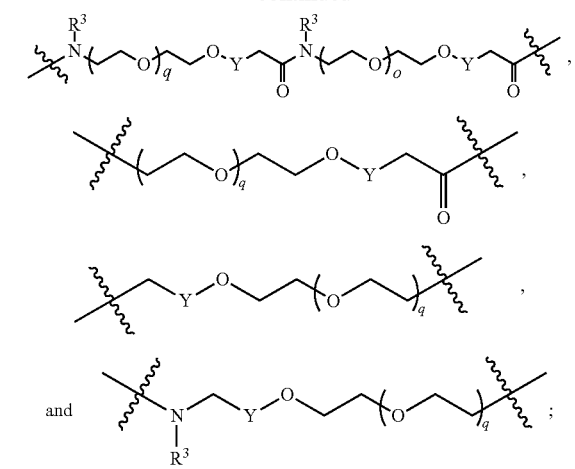
and
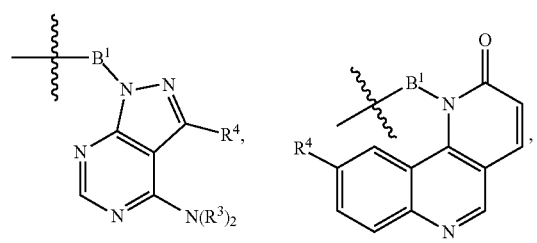
each B is independently selected from
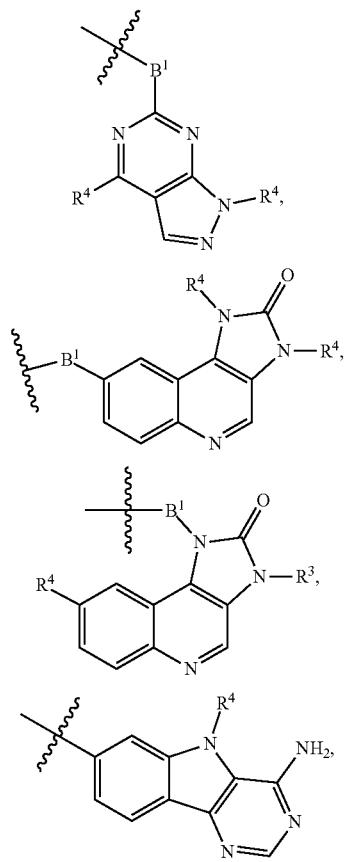

-continued

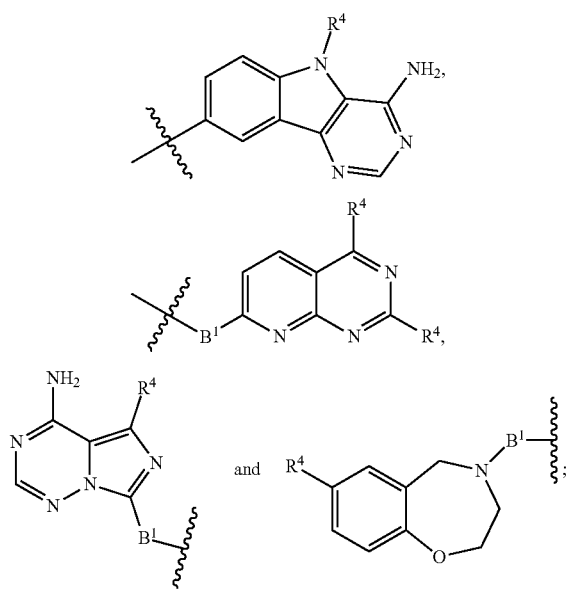

each B¹ is independently selected from

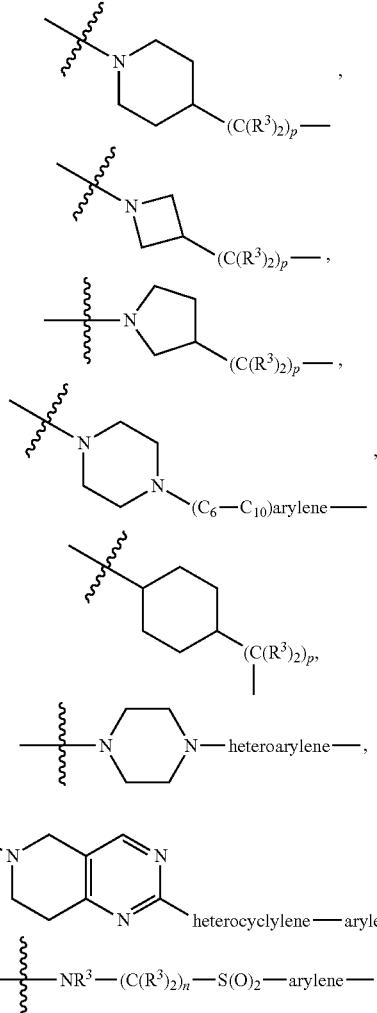

-continued

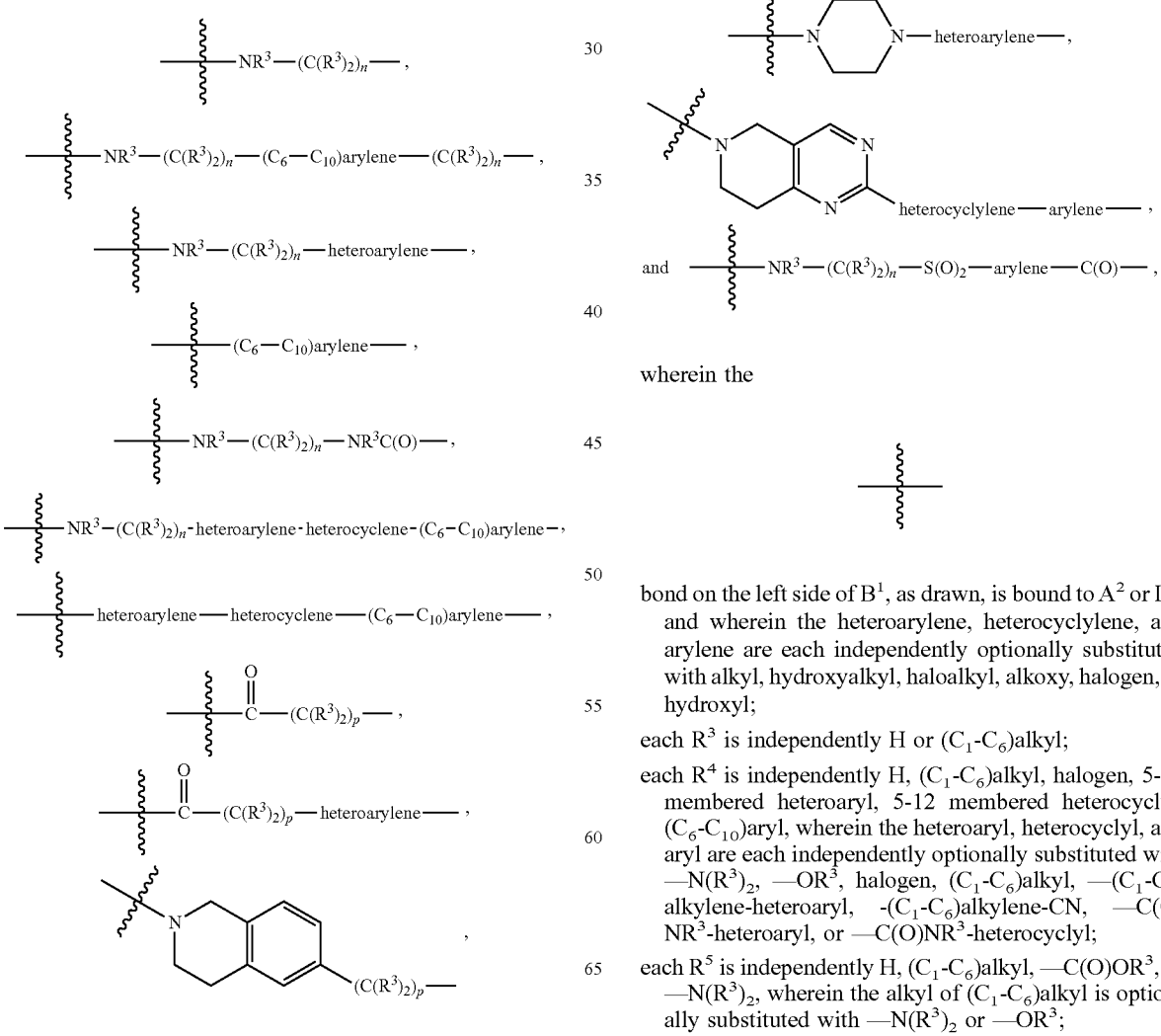

bond on the left side of B¹, as drawn, is bound to A² or L¹; and wherein the heteroarylene, heterocyclylene, and arylene are each independently optionally substituted with alkyl, hydroxyalkyl, haloalkyl, alkoxy, halogen, or hydroxyl;

each $R^3$ is independently H or $(C_1\text{-}C_6)$alkyl;

each $R^4$ is independently H, $(C_1\text{-}C_6)$alkyl, halogen, 5-12 membered heteroaryl, 5-12 membered heterocyclyl, $(C_6\text{-}C_{10})$aryl, wherein the heteroaryl, heterocyclyl, and aryl are each independently optionally substituted with —N(R³)₂, —OR³, halogen, $(C_1\text{-}C_6)$alkyl, —$(C_1\text{-}C_6)$alkylene-heteroaryl, -$(C_1\text{-}C_6)$alkylene-CN, —C(O)NR³-heteroaryl, or —C(O)NR³-heterocyclyl;

each $R^5$ is independently H, $(C_1\text{-}C_6)$alkyl, —C(O)OR³, or —N(R³)₂, wherein the alkyl of $(C_1\text{-}C_6)$alkyl is optionally substituted with —N(R³)₂ or —OR³;

each $R^6$ is independently H, $(C_1$-$C_6)$alkyl, —C(O)O$R^3$, or —N($R^3$)$_2$, wherein the alkyl of $(C_1$-$C_6)$alkyl is optionally substituted with —N($R^3$)$_2$ or —O$R^3$;

each $R^7$ is independently H, $(C_1$-$C_6)$alkyl, —C(O)O$R^3$, or —N($R^3$)$_2$, wherein the alkyl of $(C_1$-$C_6)$alkyl is optionally substituted with —N($R^3$)$_2$ or —O$R^3$;

each $R^8$ is independently H, $(C_1$-$C_6)$alkyl, —C(O)O$R^3$, or —N($R^3$)$_2$, wherein the alkyl of $(C_1$-$C_6)$alkyl is optionally substituted with —N($R^3$)$_2$ or —O$R^3$;

each Y is independently C($R^3$)$_2$ or a bond;

each n is independently an integer from one to 12;

each o is independently an integer from zero to 30;

each p is independently an integer from zero to 12;

each q is independently an integer from zero to 30; and each r is independently an integer from one to 6.

2. The compound of claim 1, or a pharmaceutically acceptable salt, stereoisomer, tautomer, or oxepane isomer thereof, wherein $R^{32}$ is =O or —O$R^3$.

3. The compound of claim 1, or a pharmaceutically acceptable salt, stereoisomer, tautomer, or oxepane isomer thereof, wherein $A^3$ is —[C($R^3$)$_2$]— or —$(C_6$-$C_{10})$arylene—.

4. The compound of claim 1, or a pharmaceutically acceptable salt, stereoisomer, tautomer, or oxepane isomer thereof, wherein $R^{26}$ is -$A^1$-$L^1$-$A^2$-B, wherein $A^1$ and $A^2$ are absent;

-$A^1$-$L^1$-$A^2$-B, wherein $A^2$ is absent;

-$A^1$-$L^1$-$A^2$-B, wherein $A^1$ is absent;

-$A^1$-$L^1$-$A^2$-B;

-$A^1$-$A^2$-B; or

-$L^2$-$A^1$-$L^1$-$A^2$-$L^3$-B.

5. The compound of claim 1, selected from the group consisting of:

783 784
Example 1
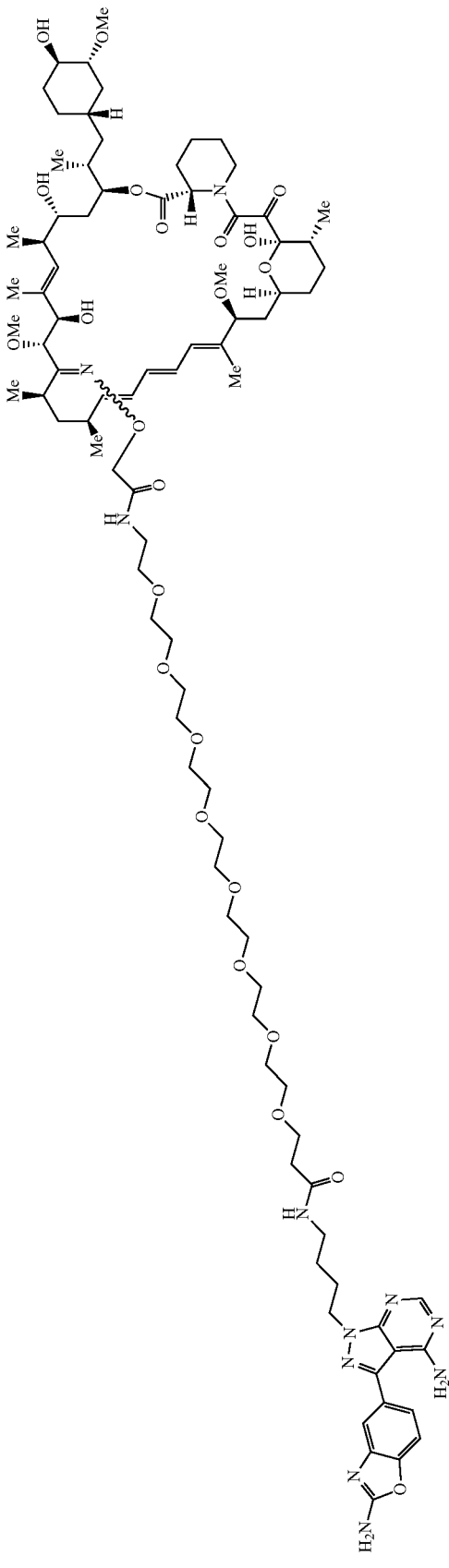
Example 2
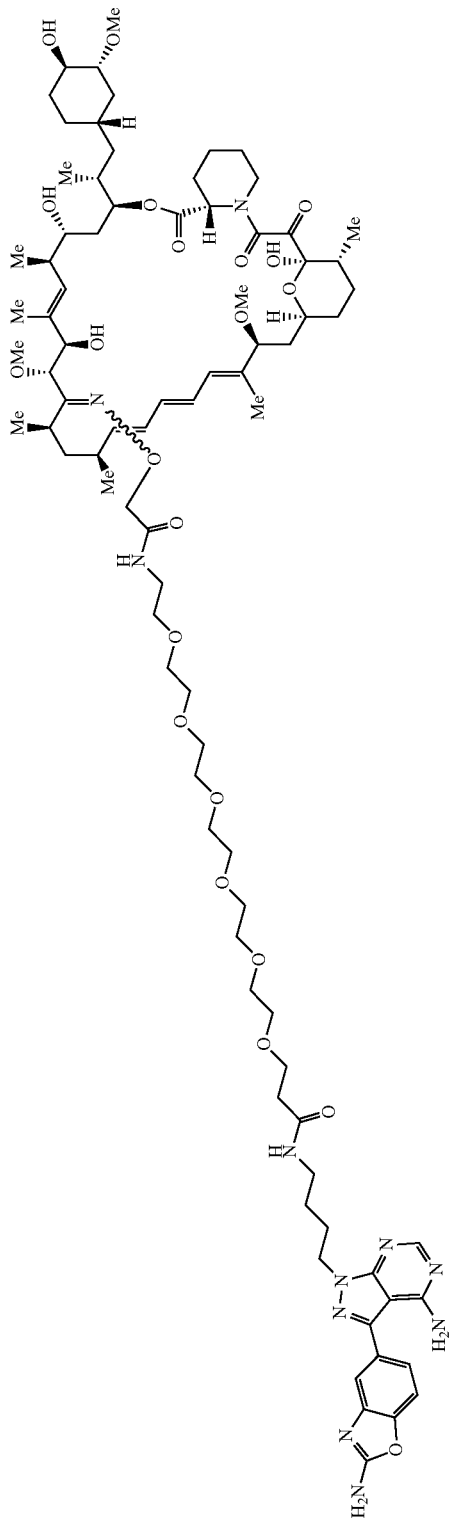

Example 3
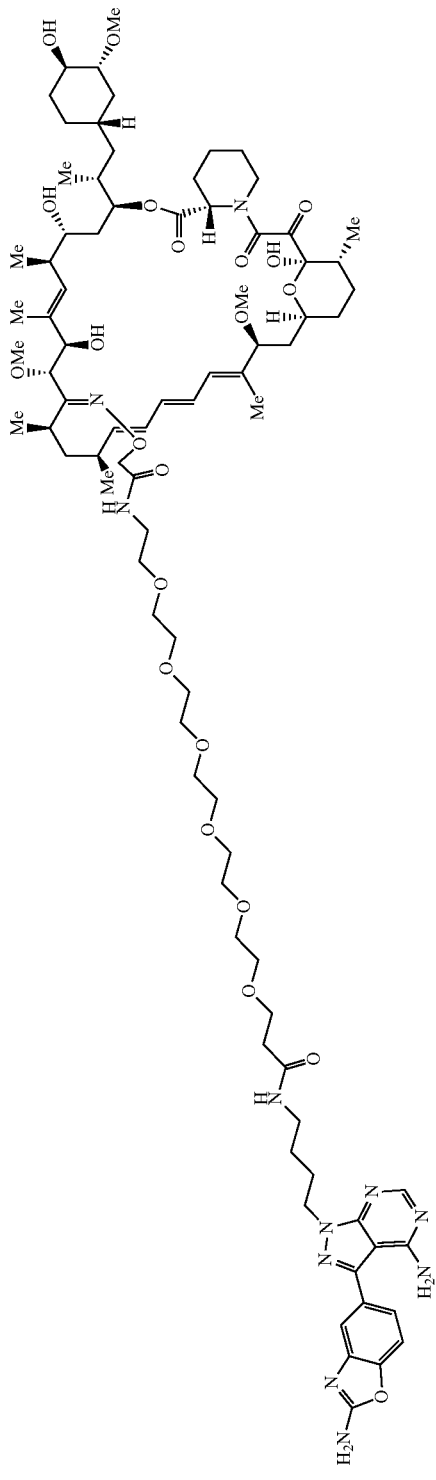
Example 4
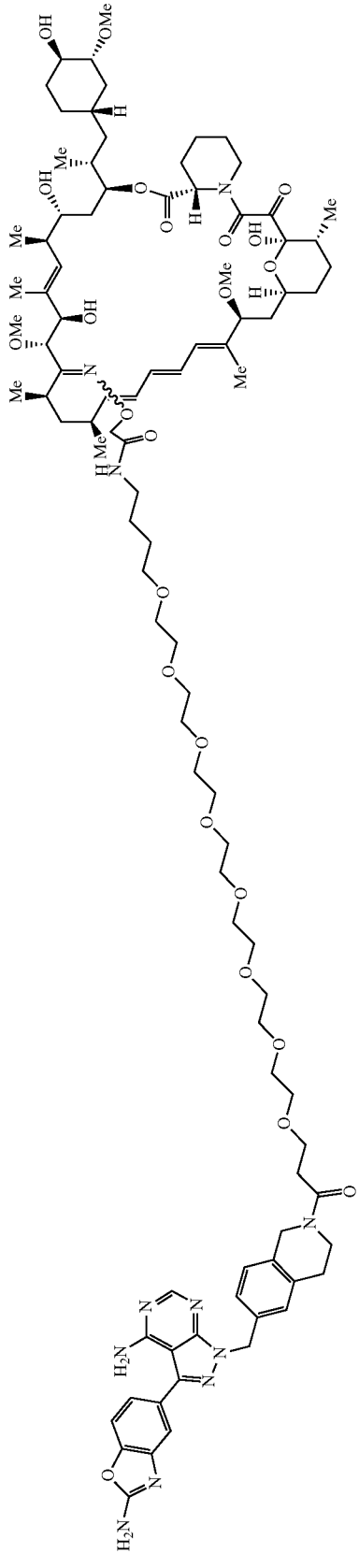

-continued
| Example 5 | Example 6 |
|---|---|
| 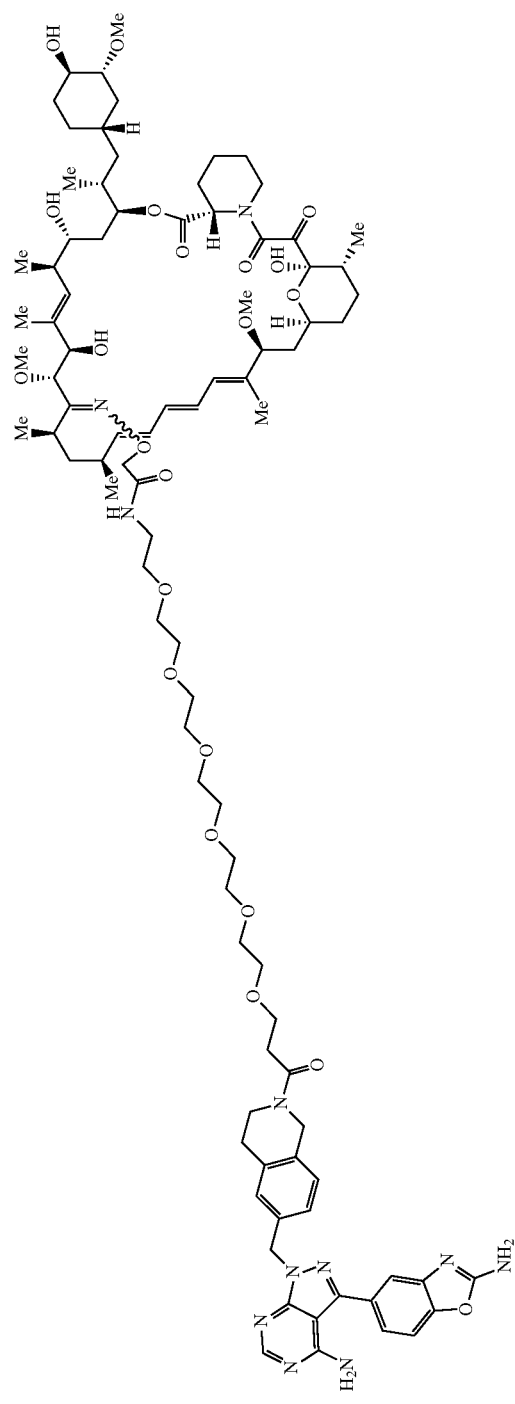 | 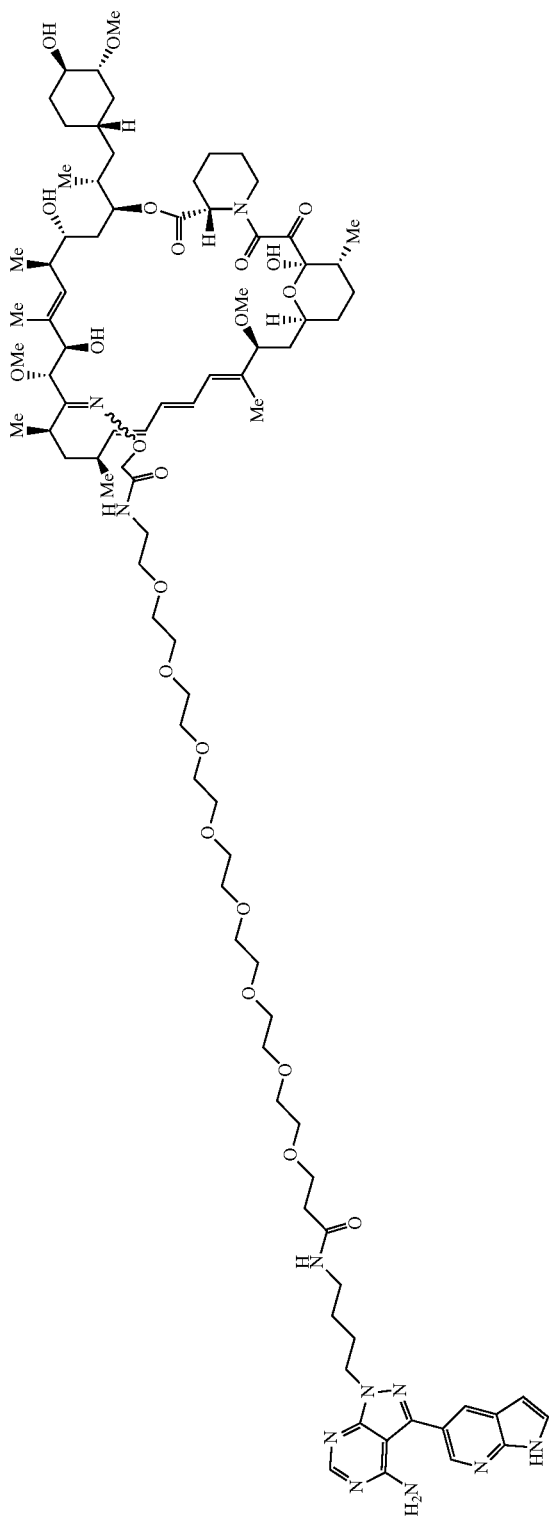 |

Example 7
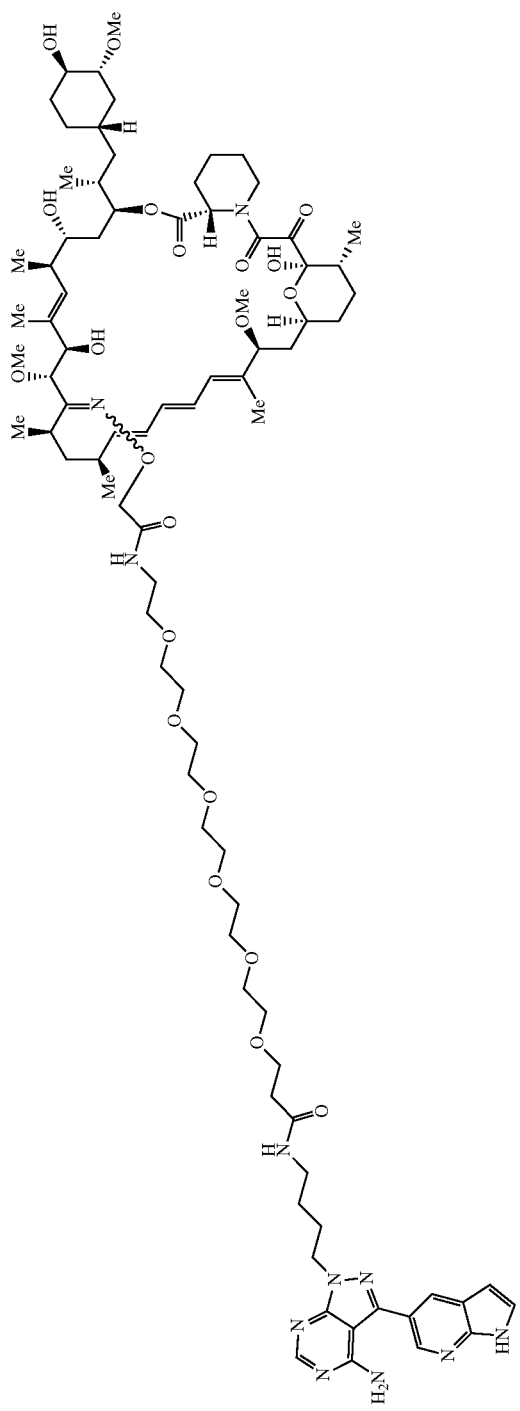
Example 8
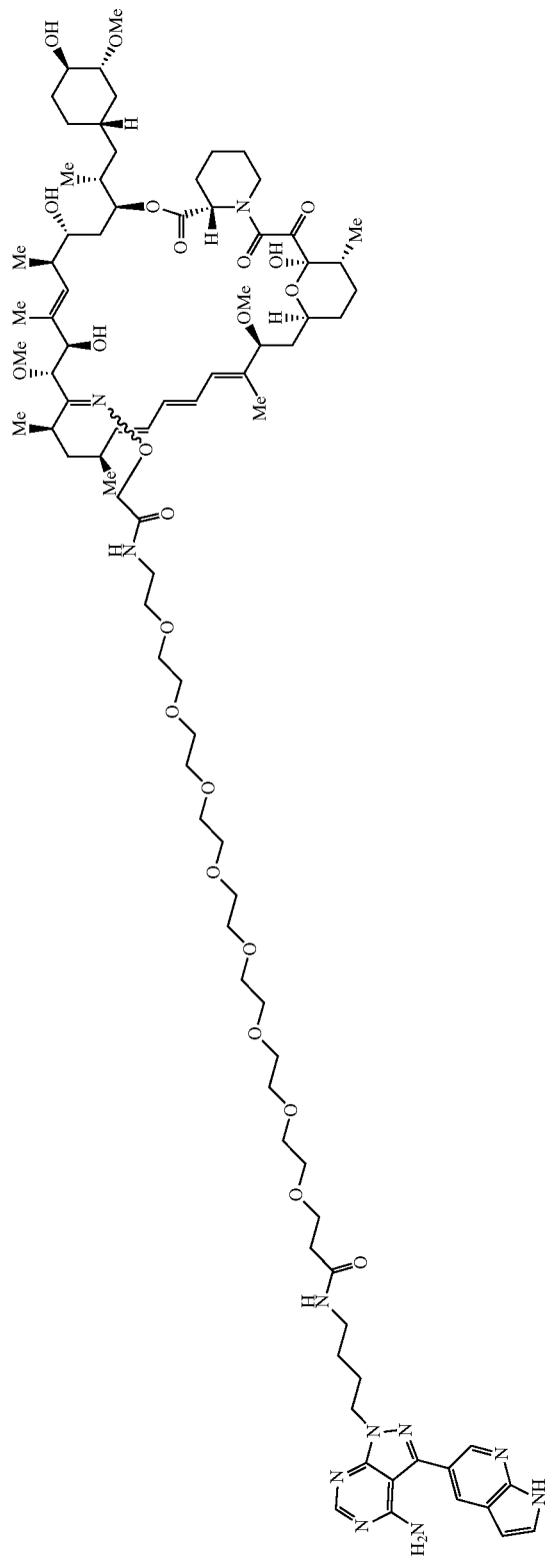

791
Example 9
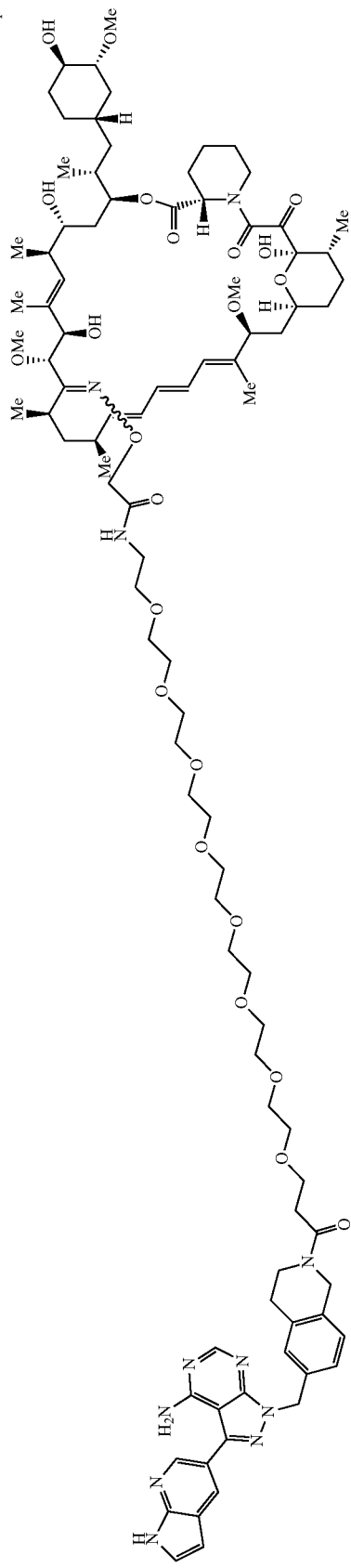
-continued
792
Example 10
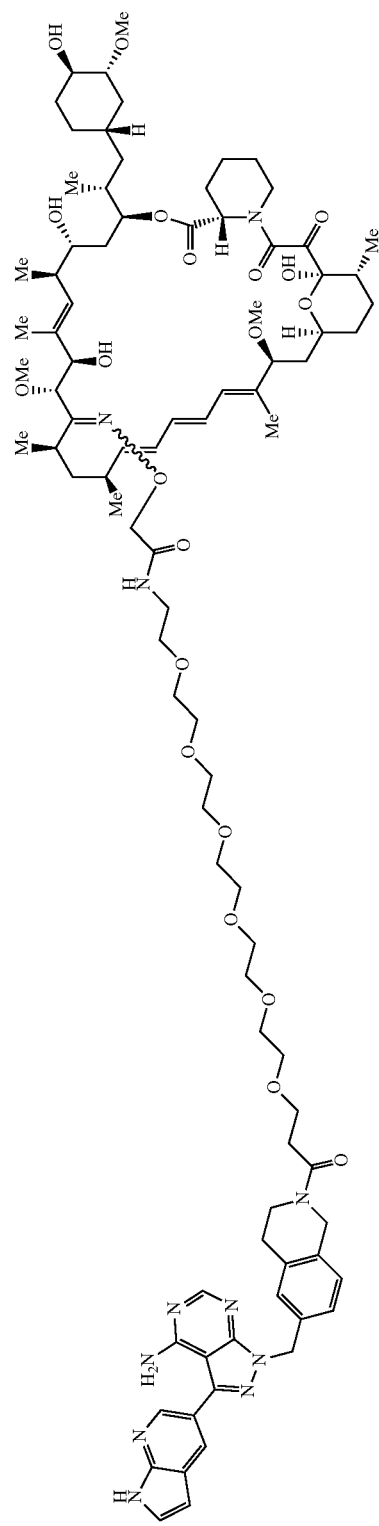

793
Example 11
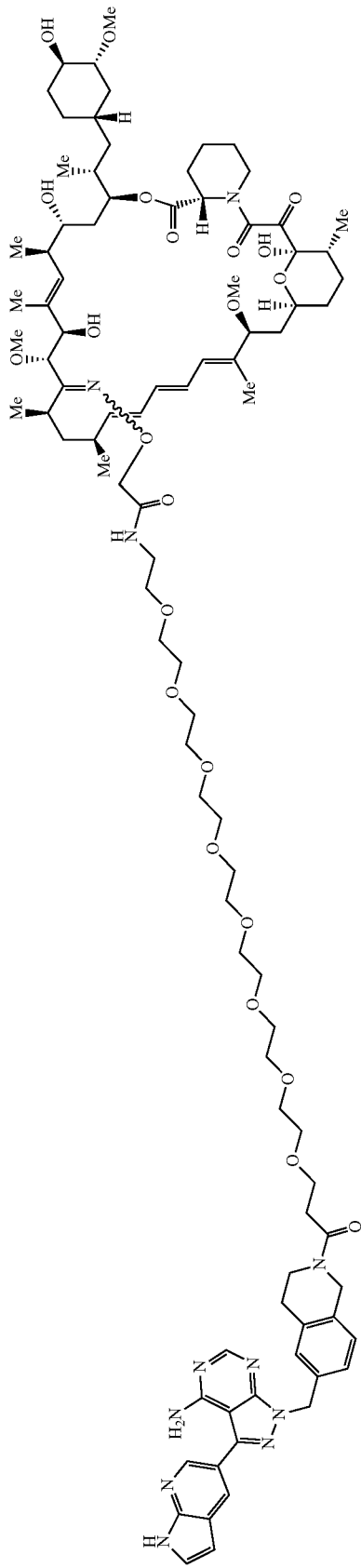
-continued
794
Example 12
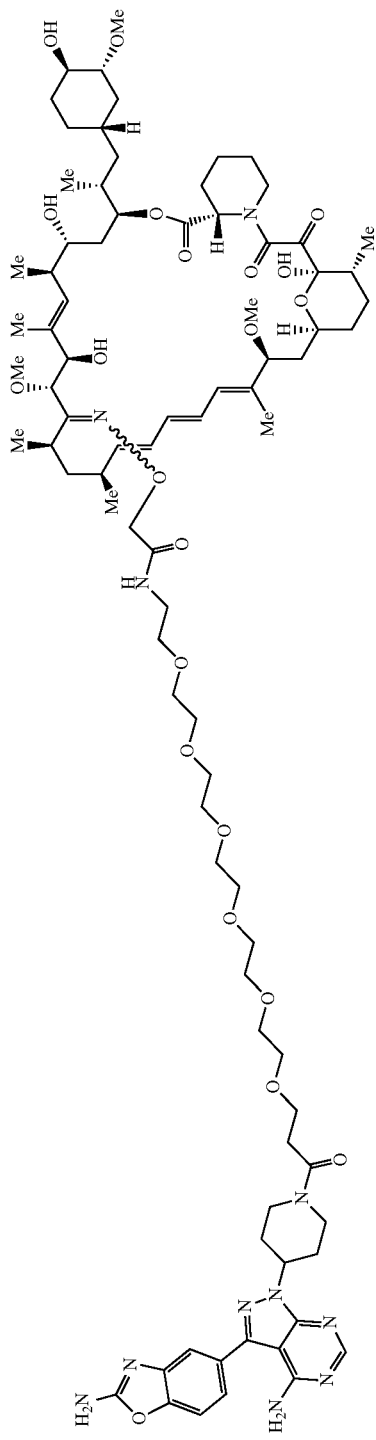

Example 13
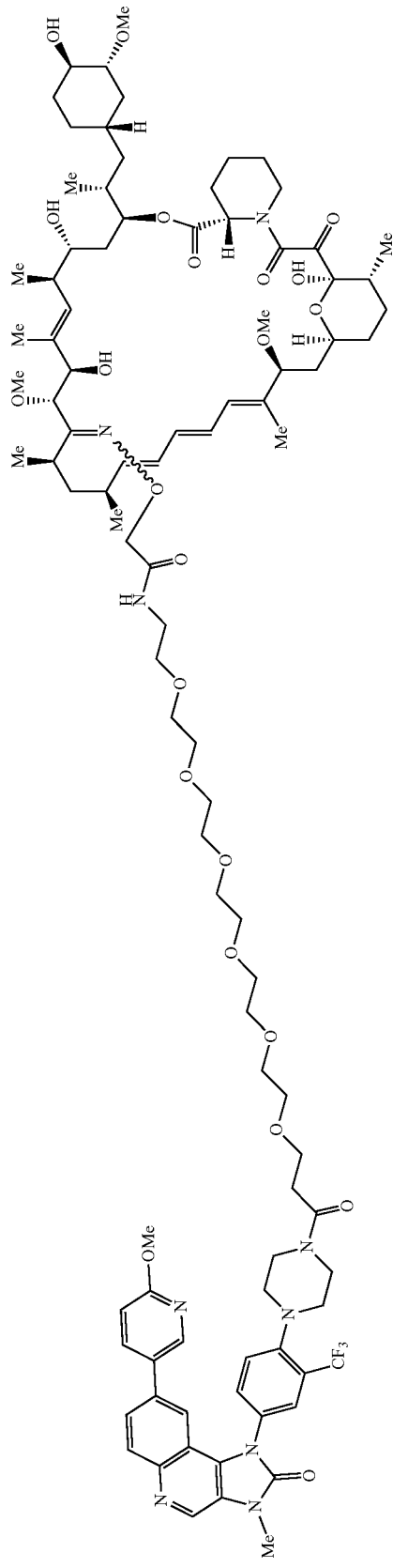
Example 14
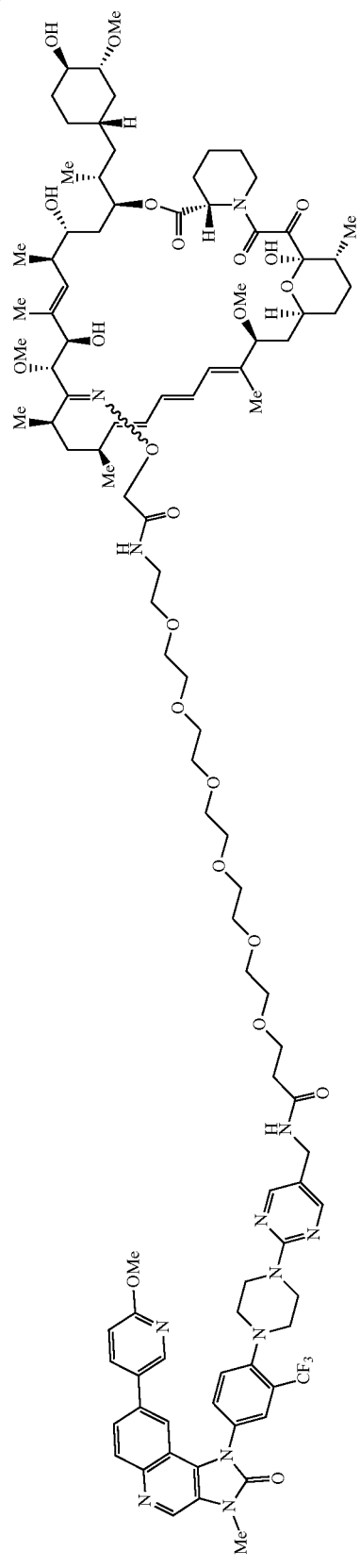

Example 15
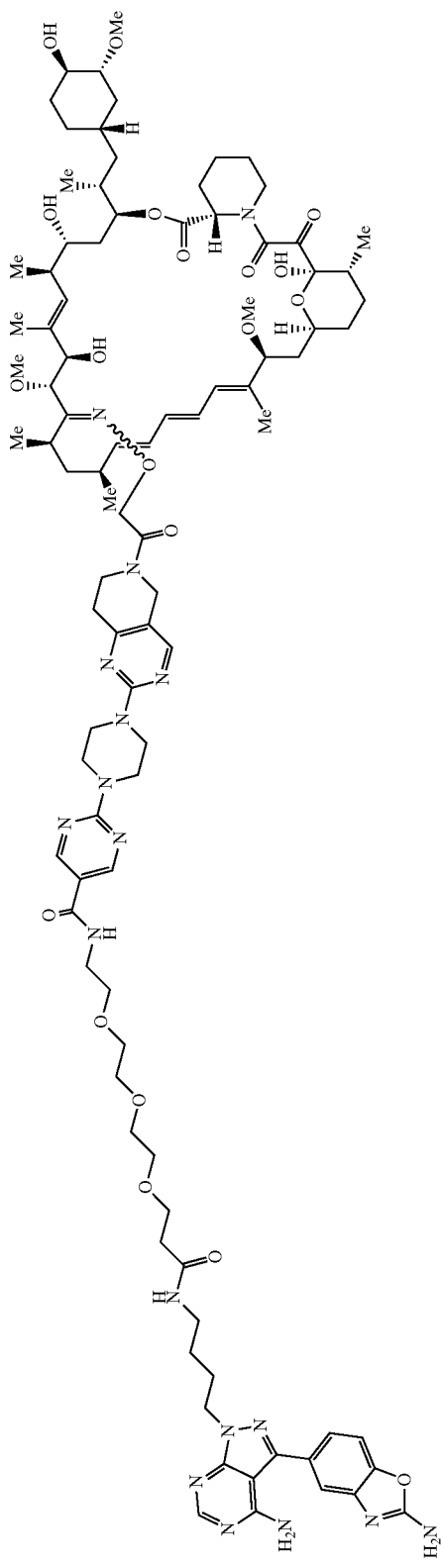
Example 16
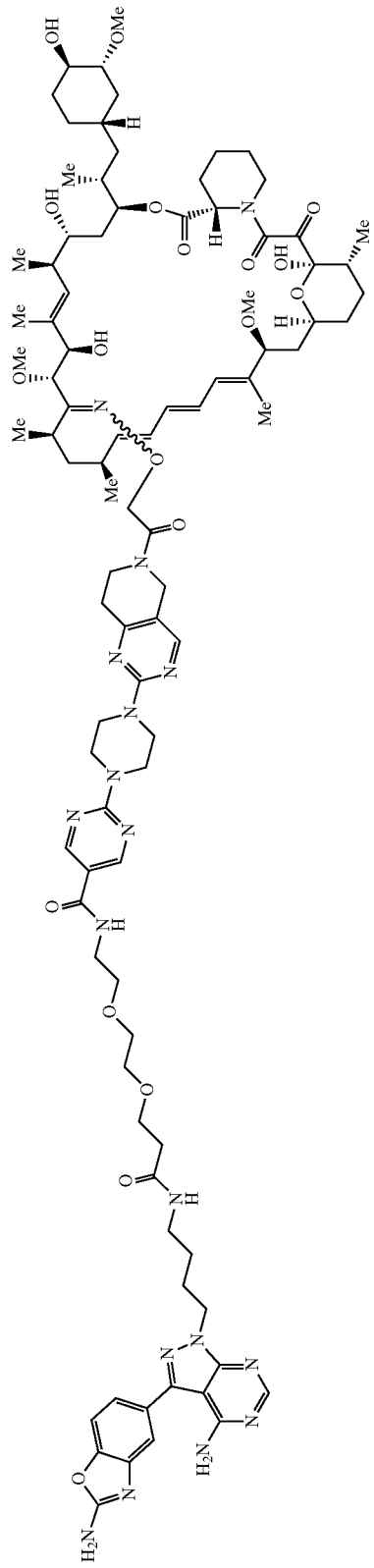

-continued
| Example 17 | Example 18 |
|---|---|
| 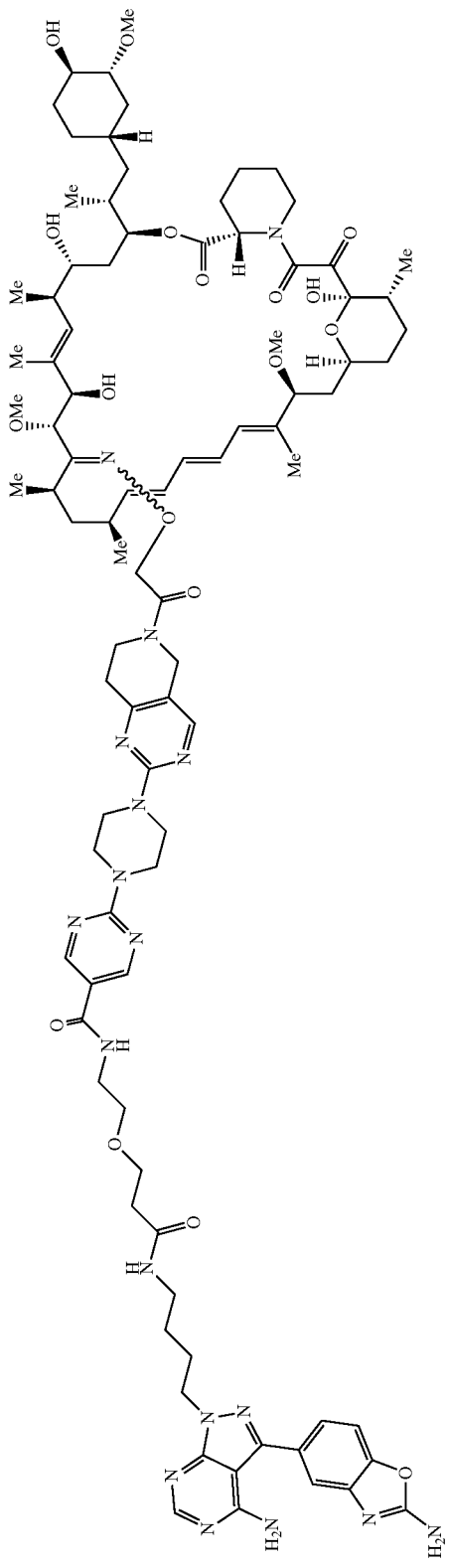 | 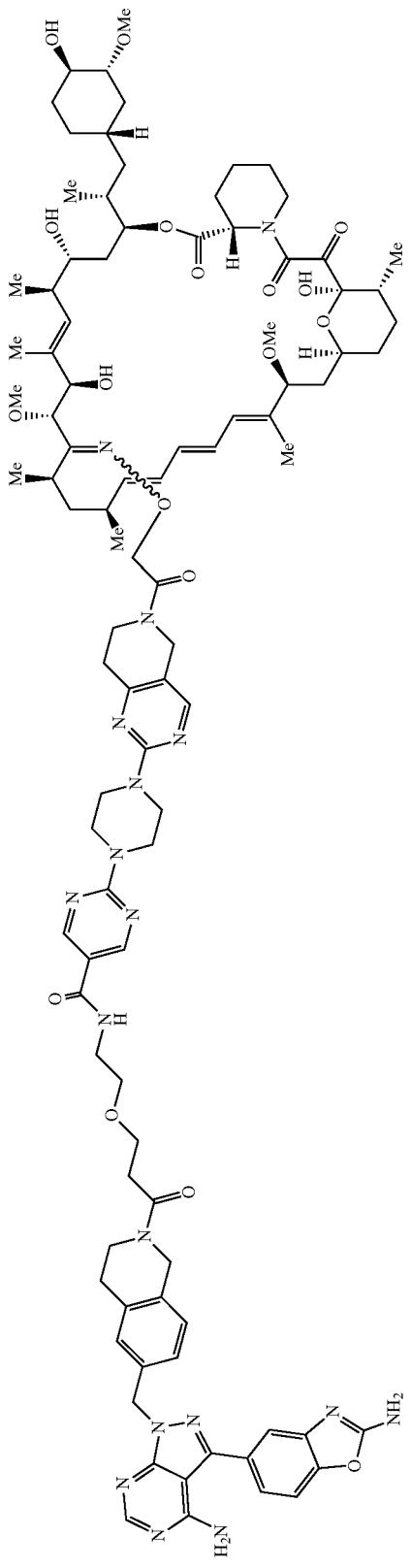 |
| 799 | 800 |

801 Example 19
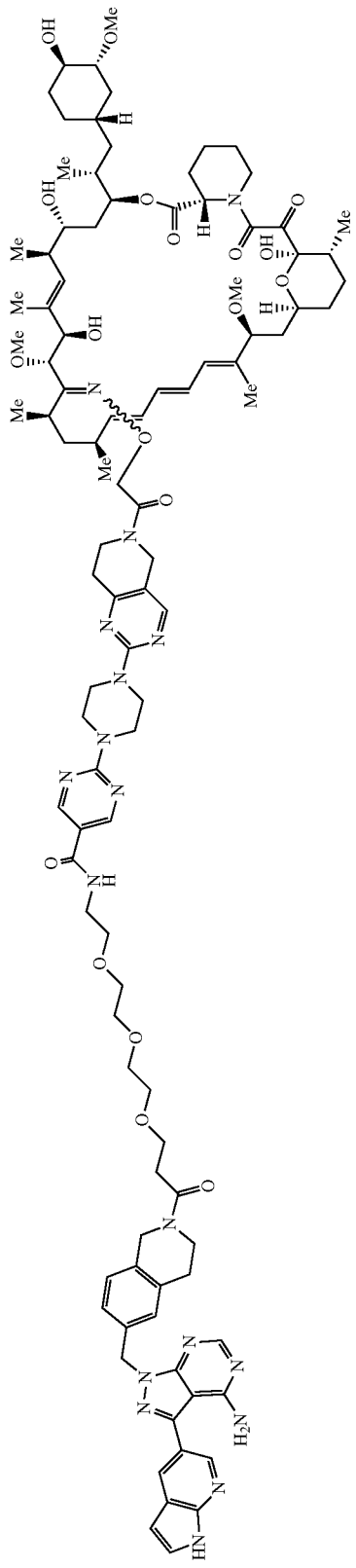
802 Example 20
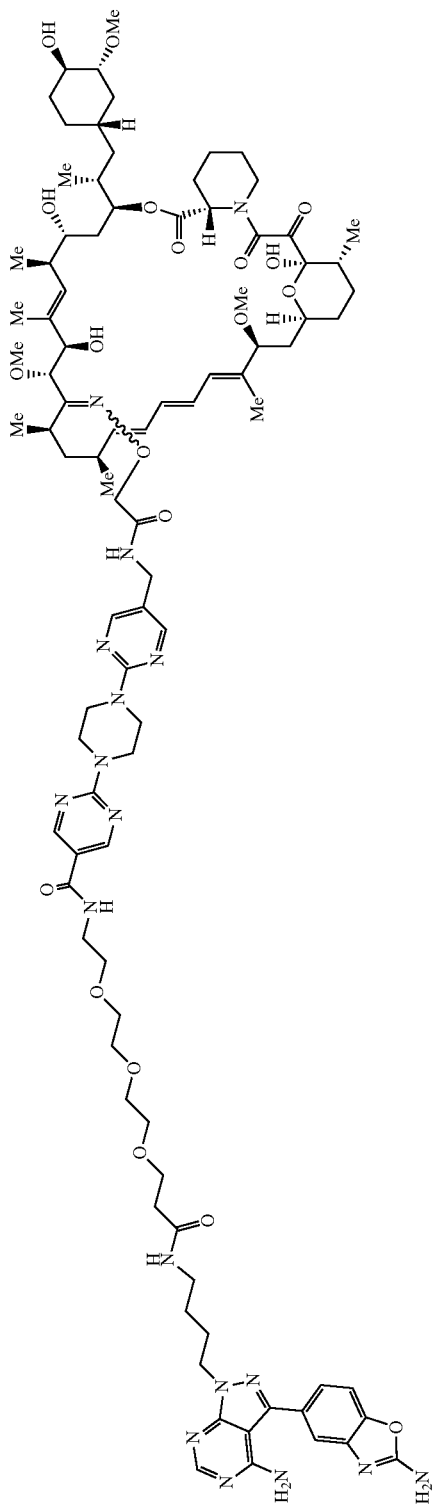

-continued
Example 21
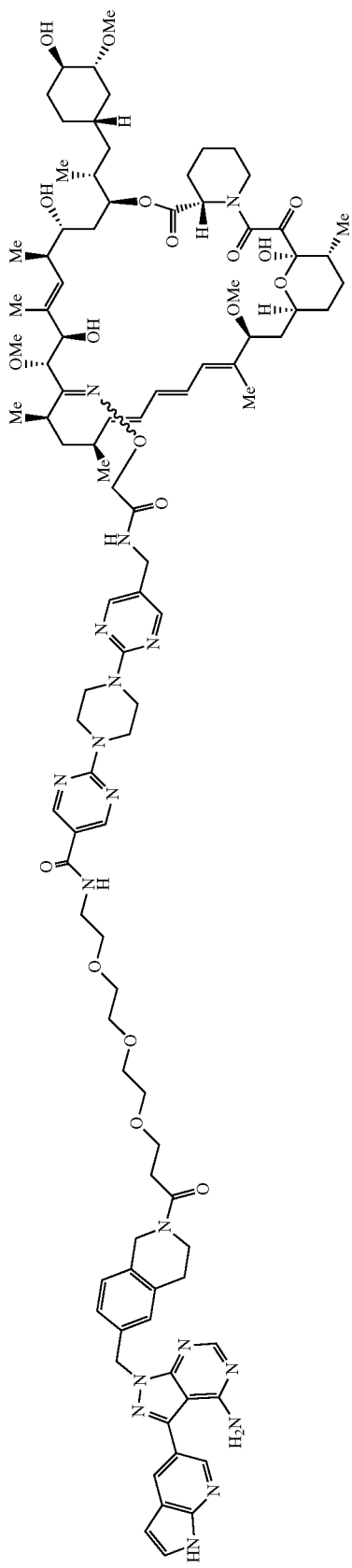
Example 22
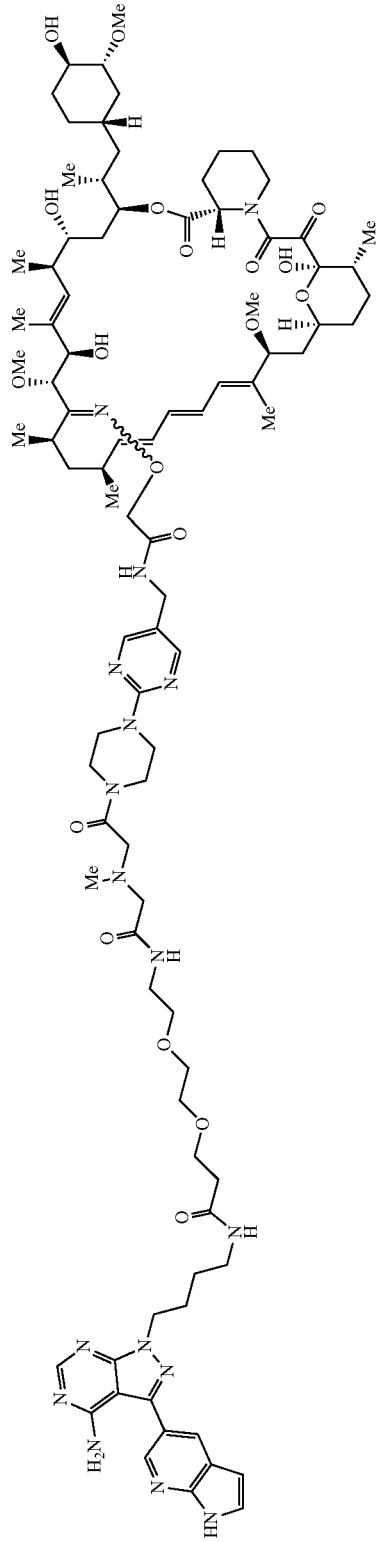

Example 23
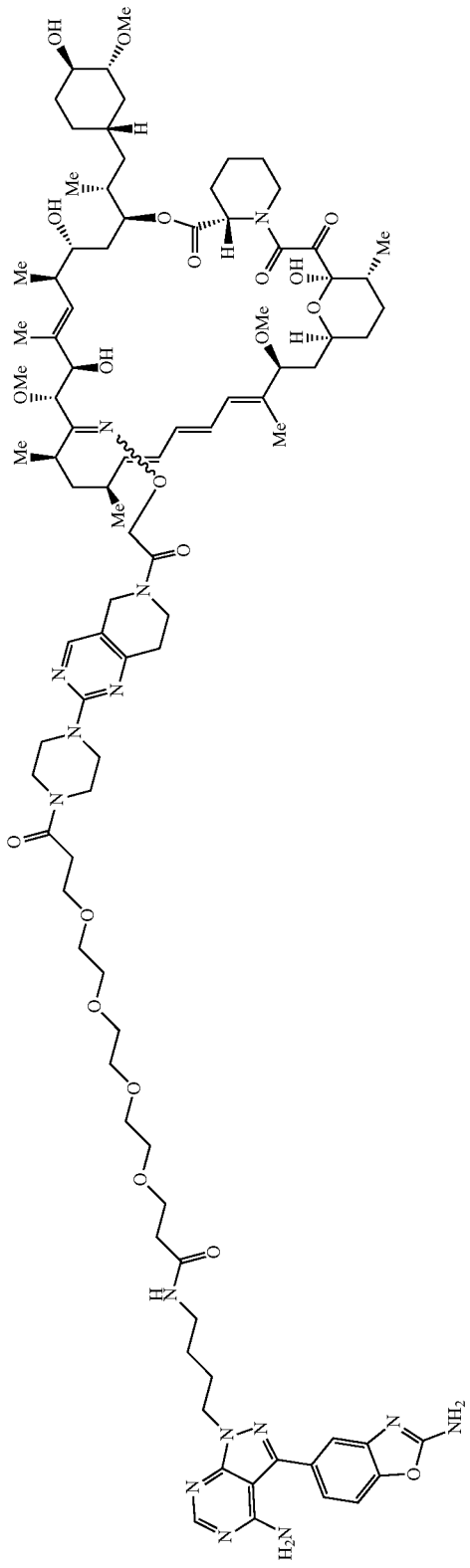
Example 24
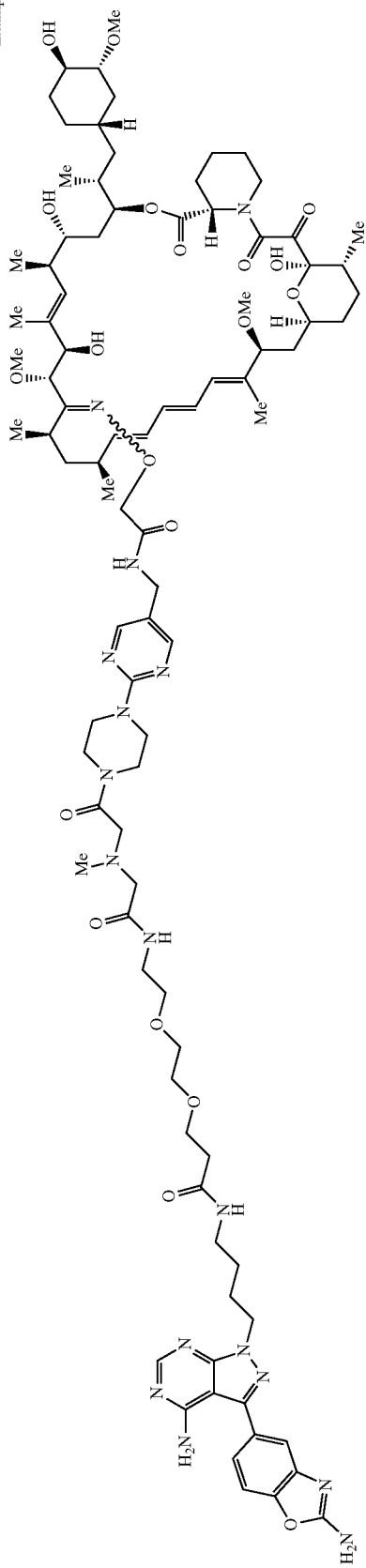

-continued
Example 25
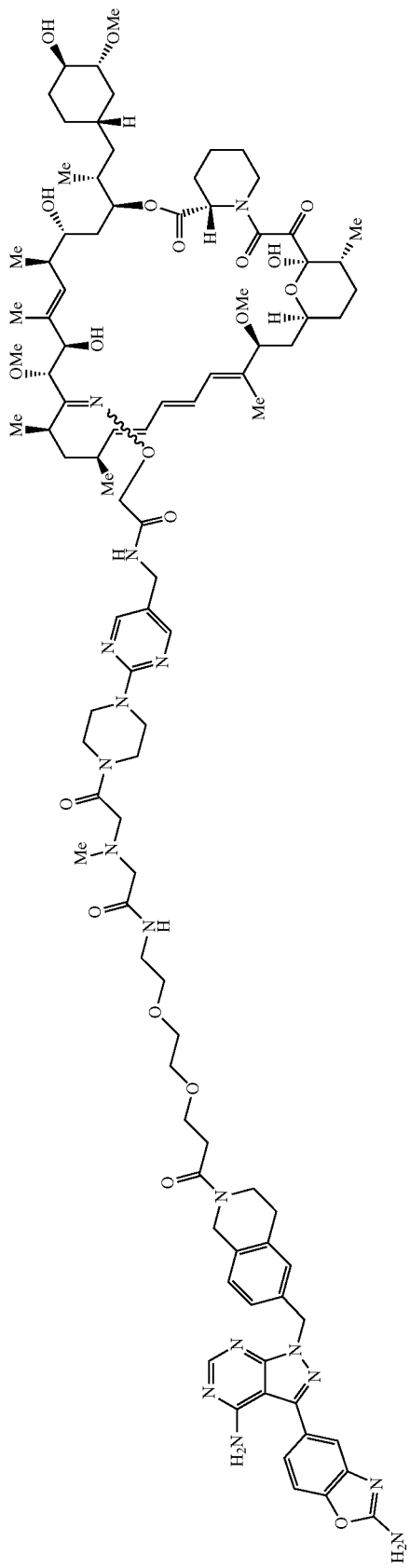
807
Example 26
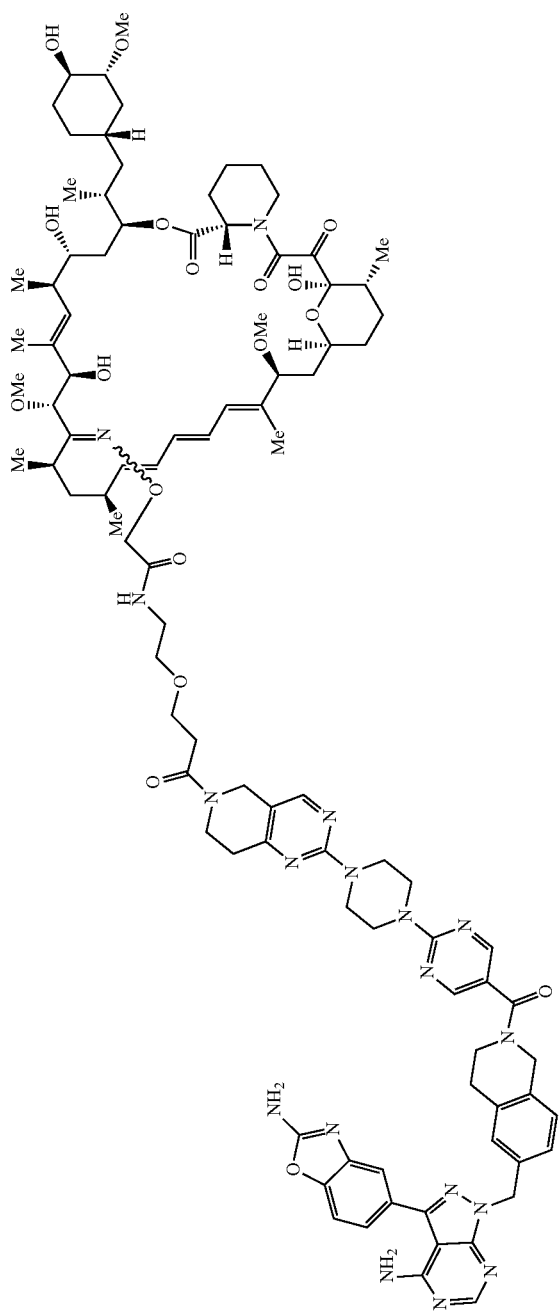
808

Example 27 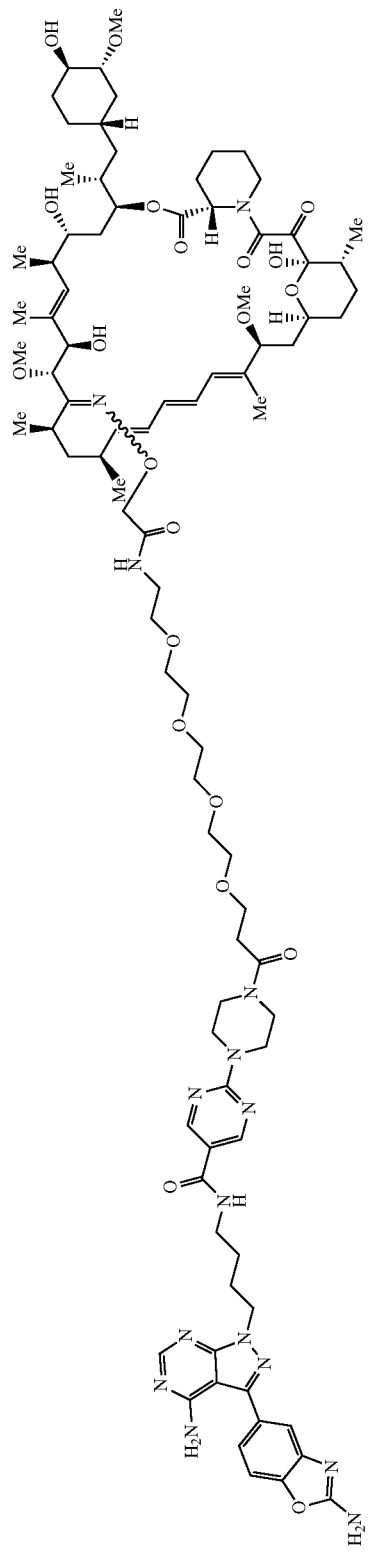
Example 28 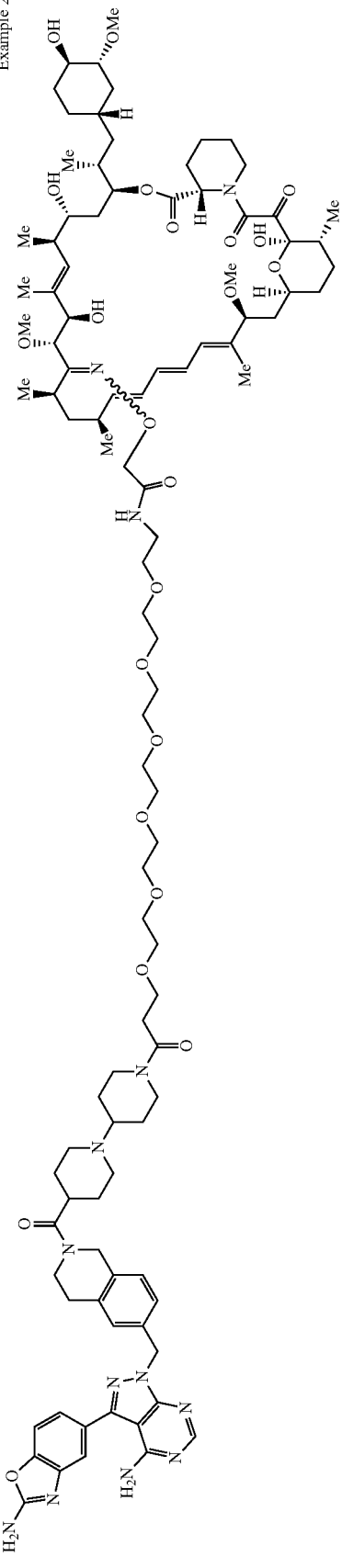

-continued
Example 29
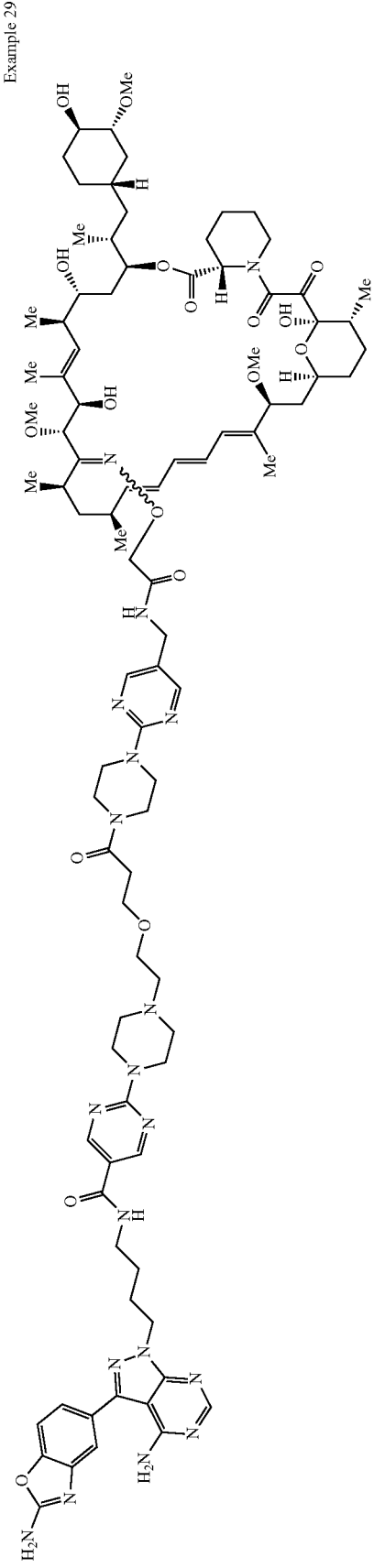
Example 30
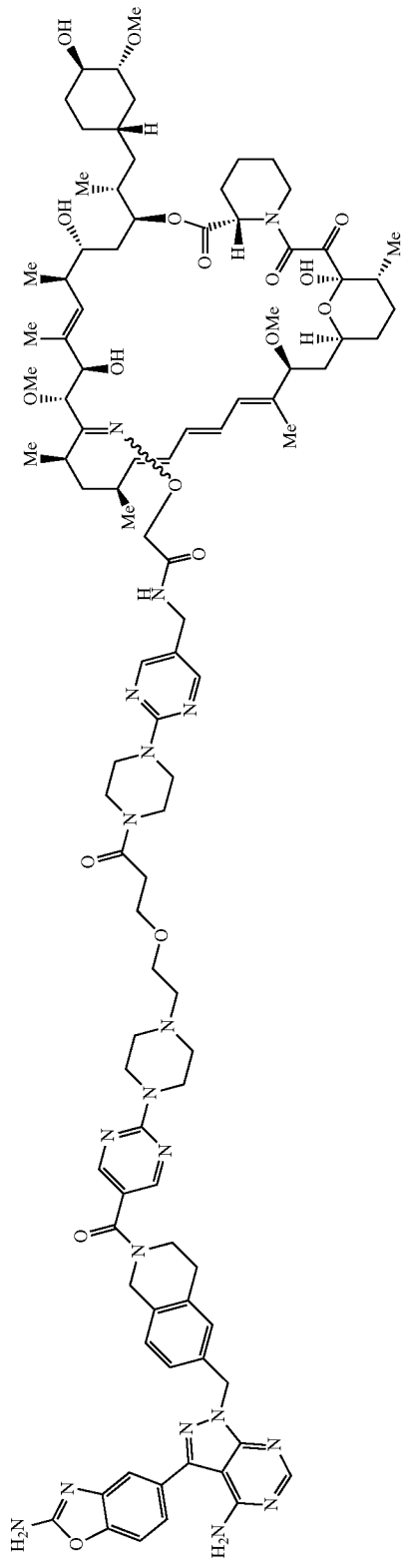

813 814
Example 31 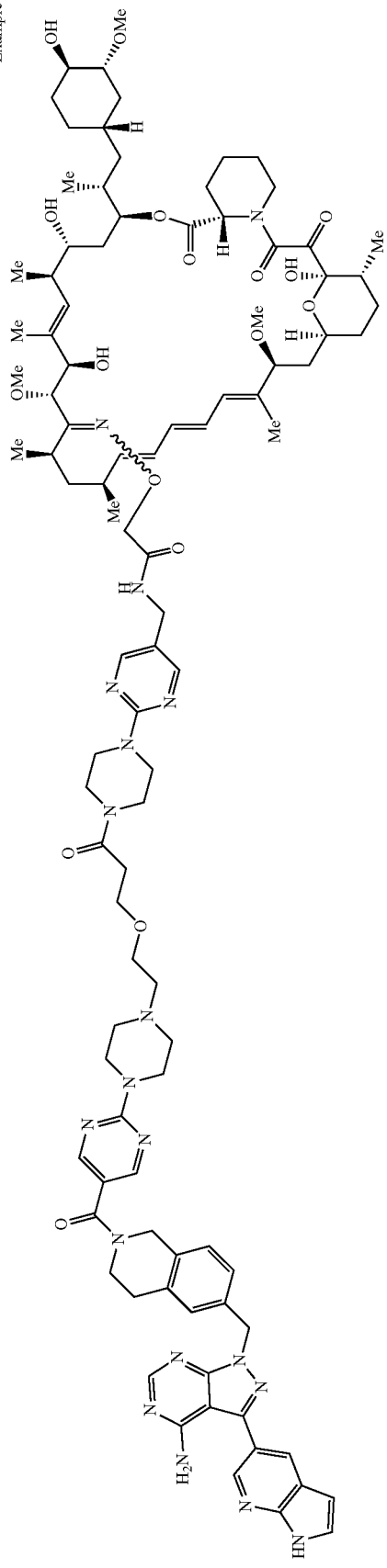
-continued
Example 32 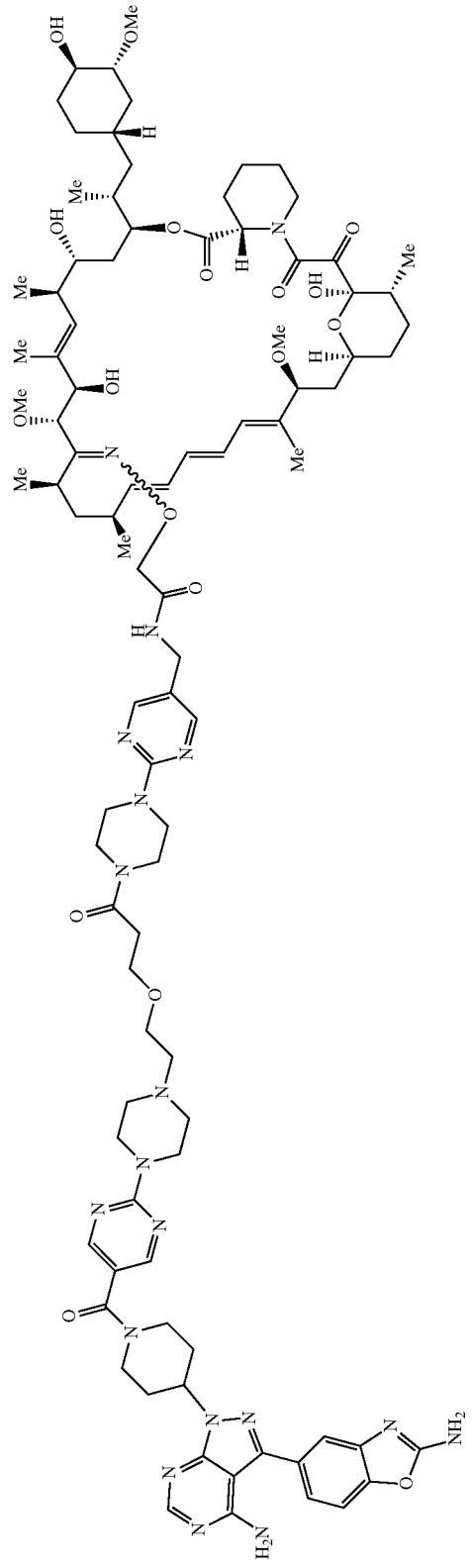

815 Example 33
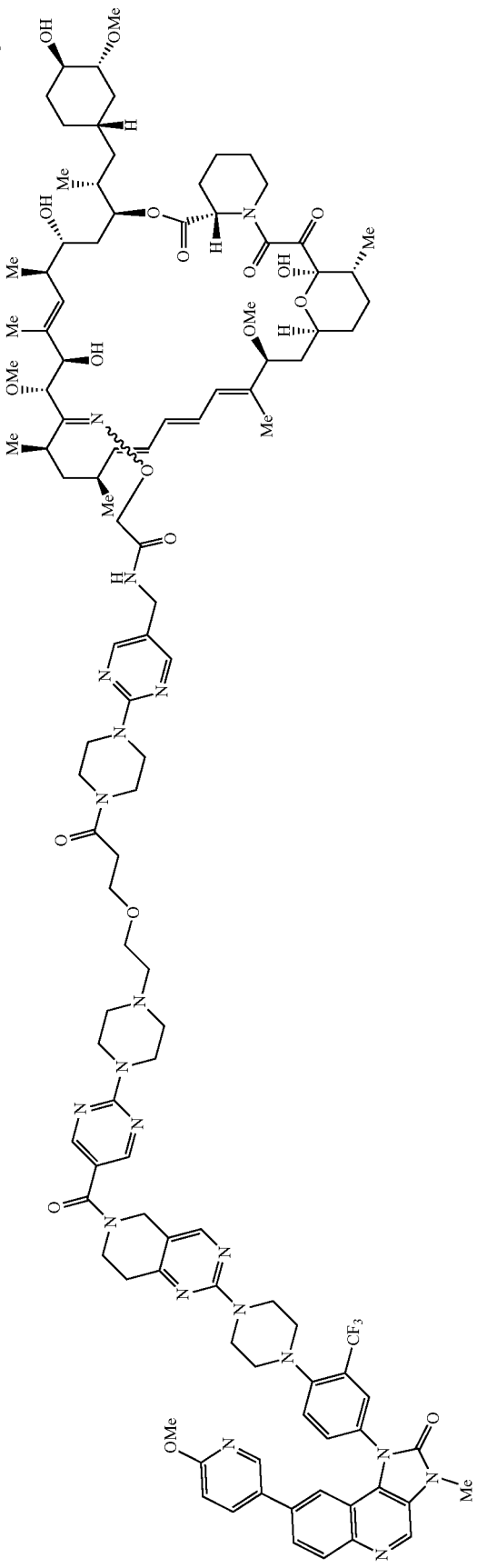
816 Example 34
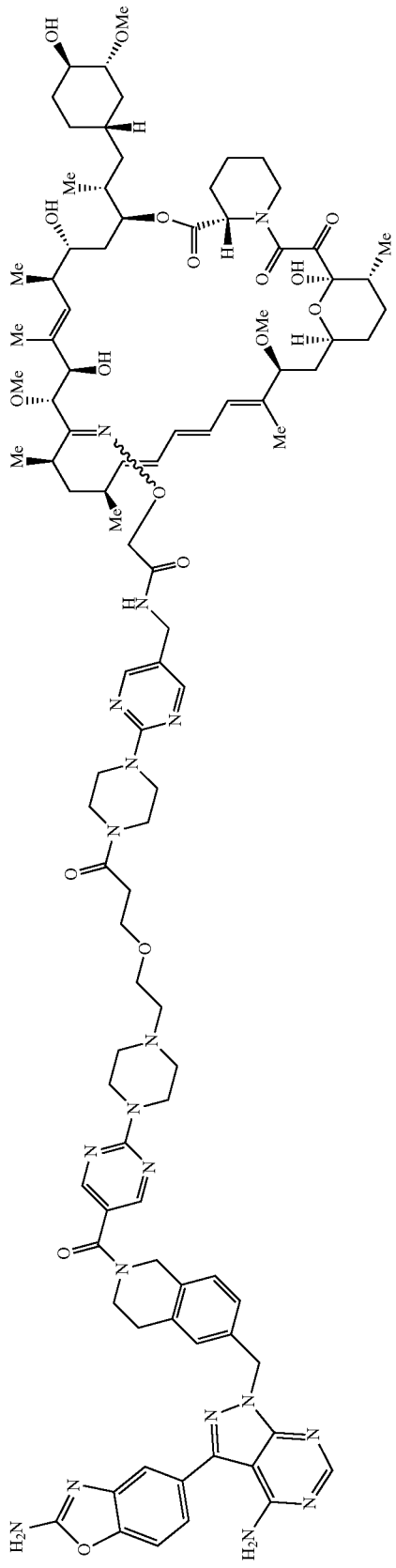

817
818
Example 35
Example 36
-continued
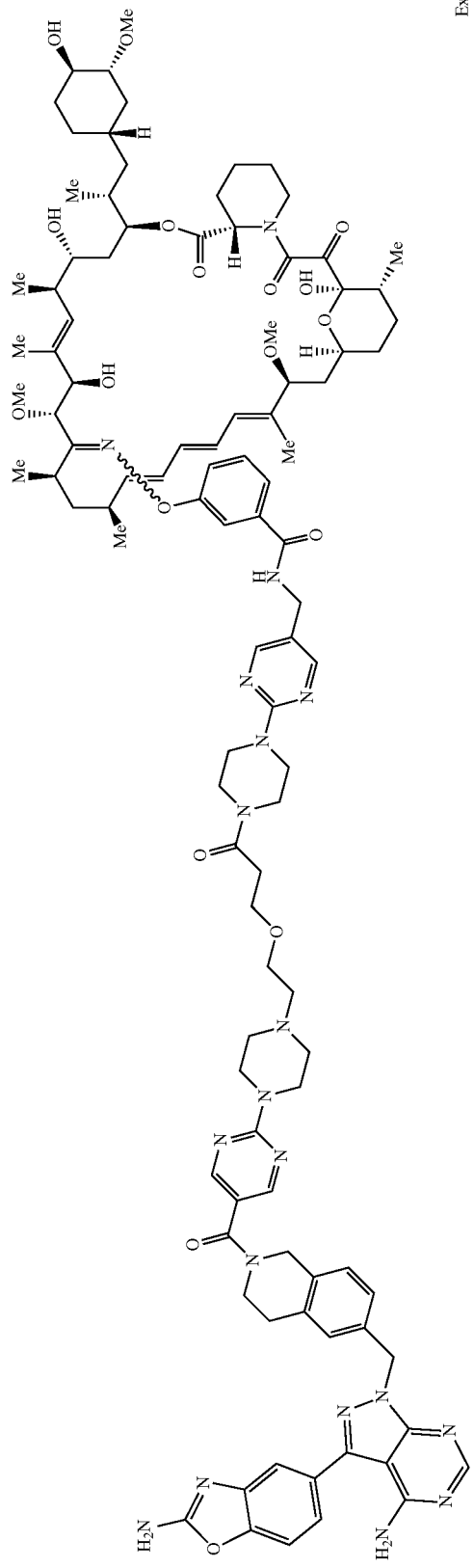
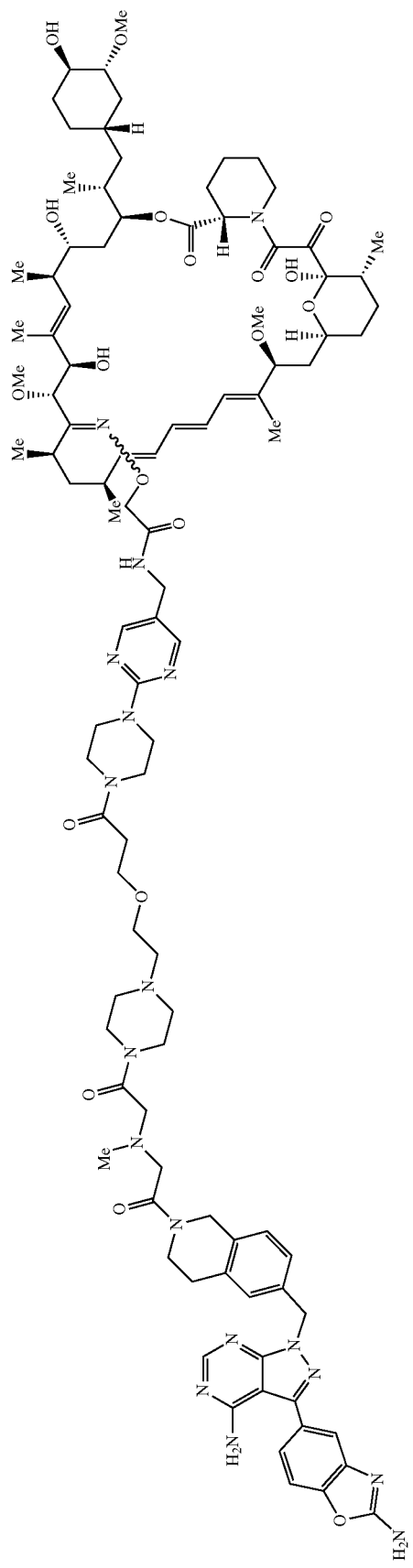

819
820
Example 37 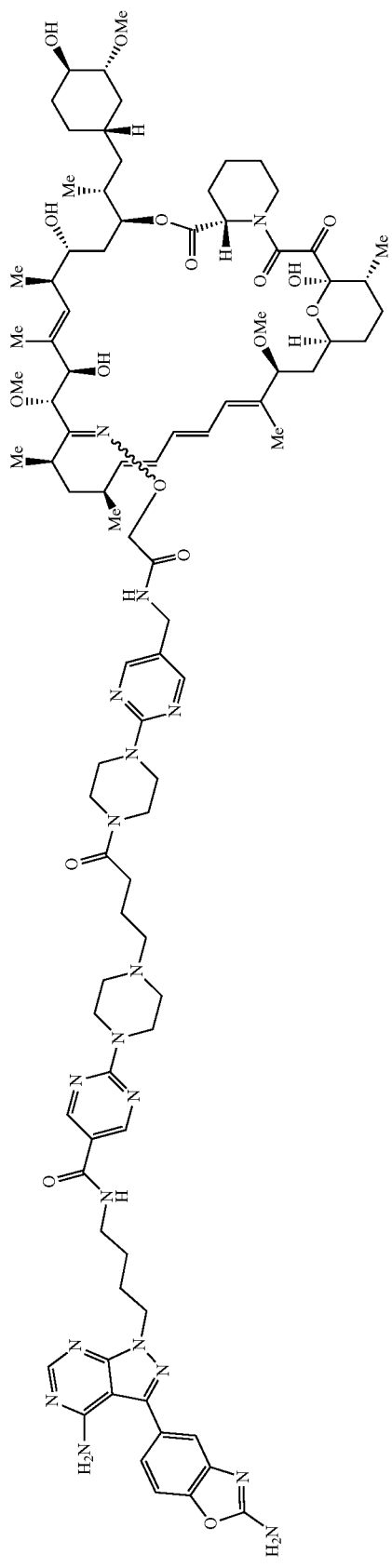
-continued
Example 38 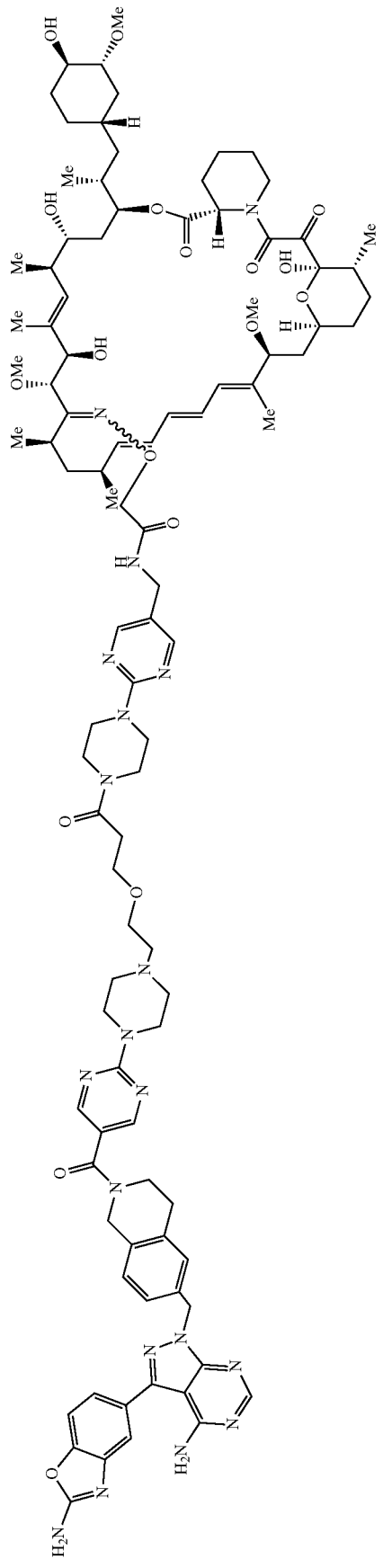

821
Example 39
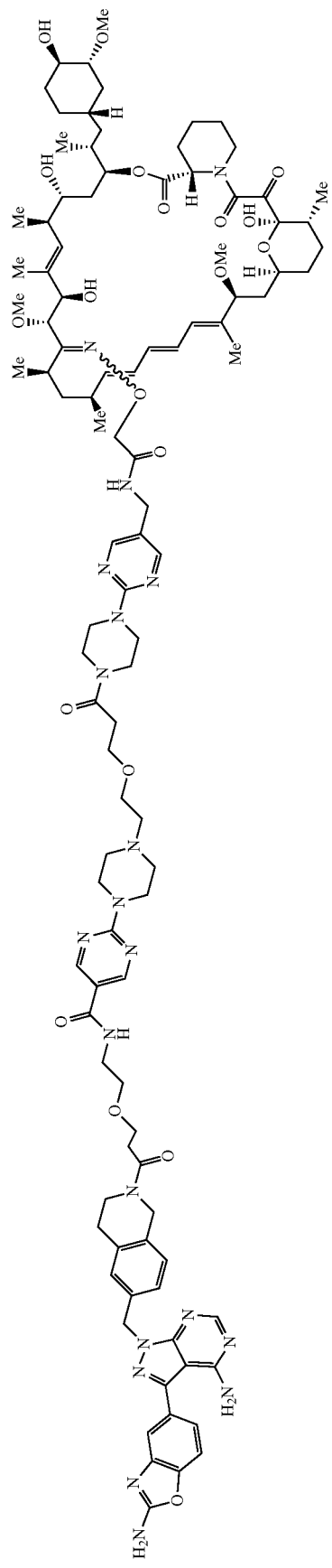
-continued
822
Example 40
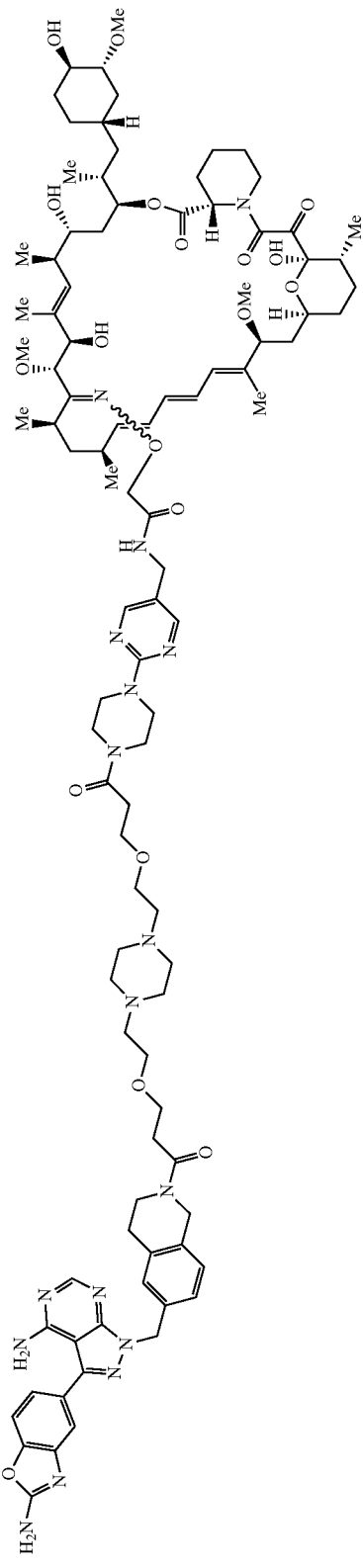

823
Example 41
-continued
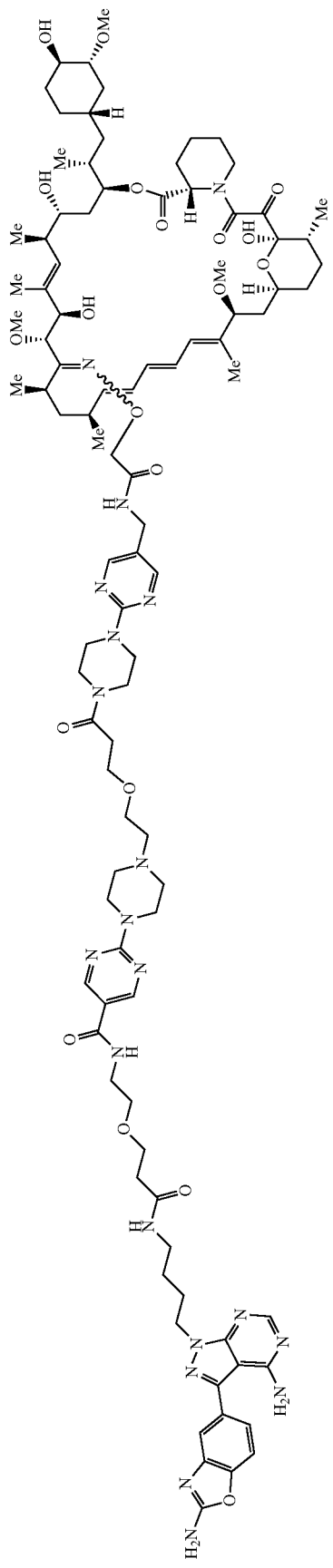
824
Example 42
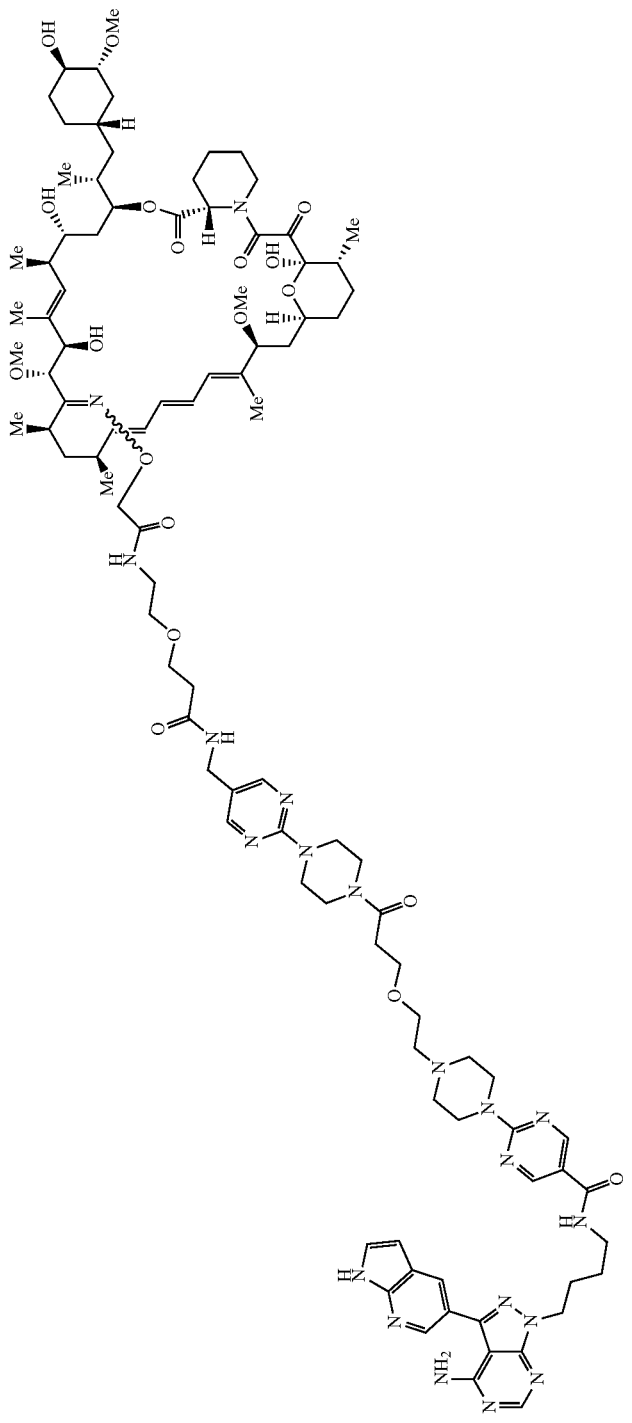

Example 43
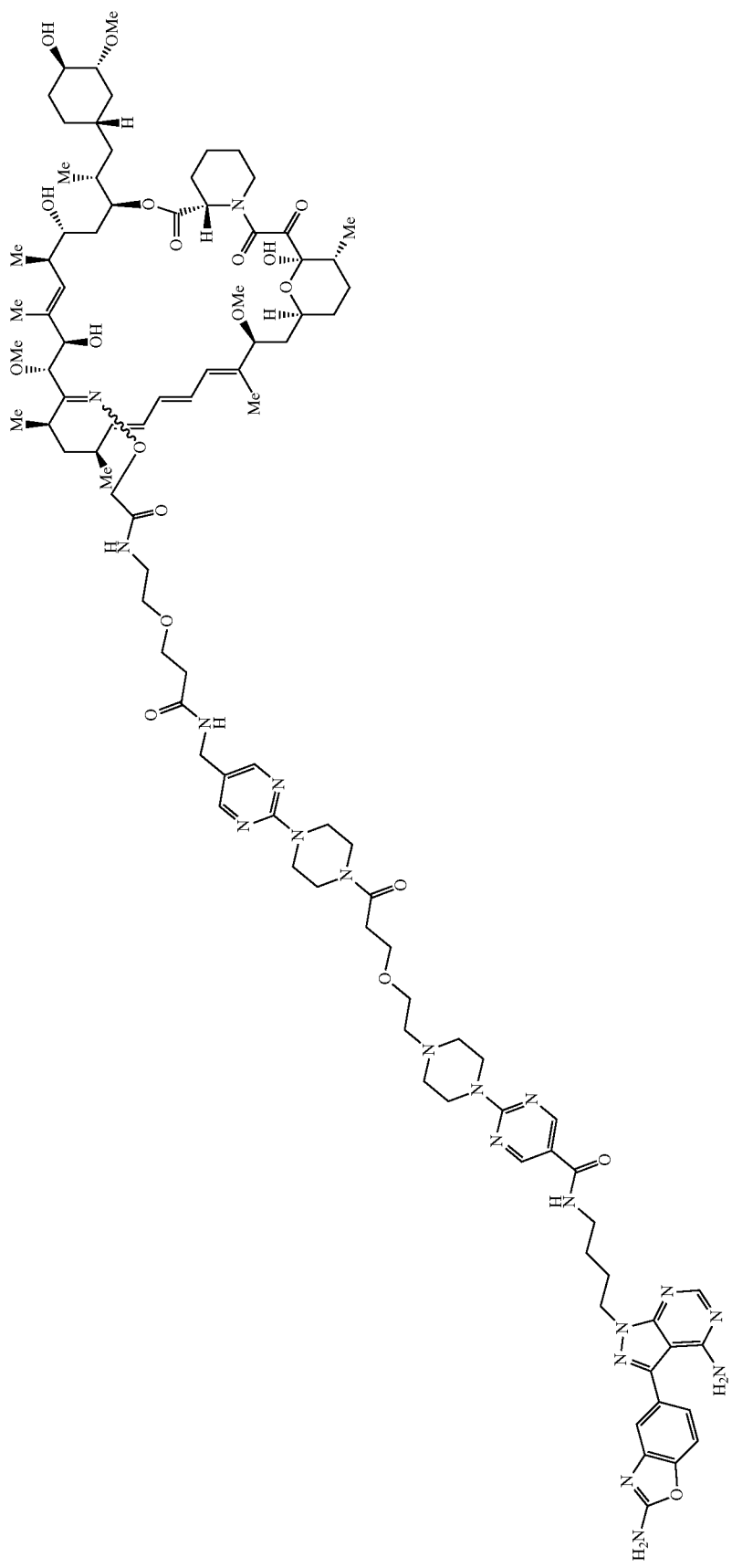

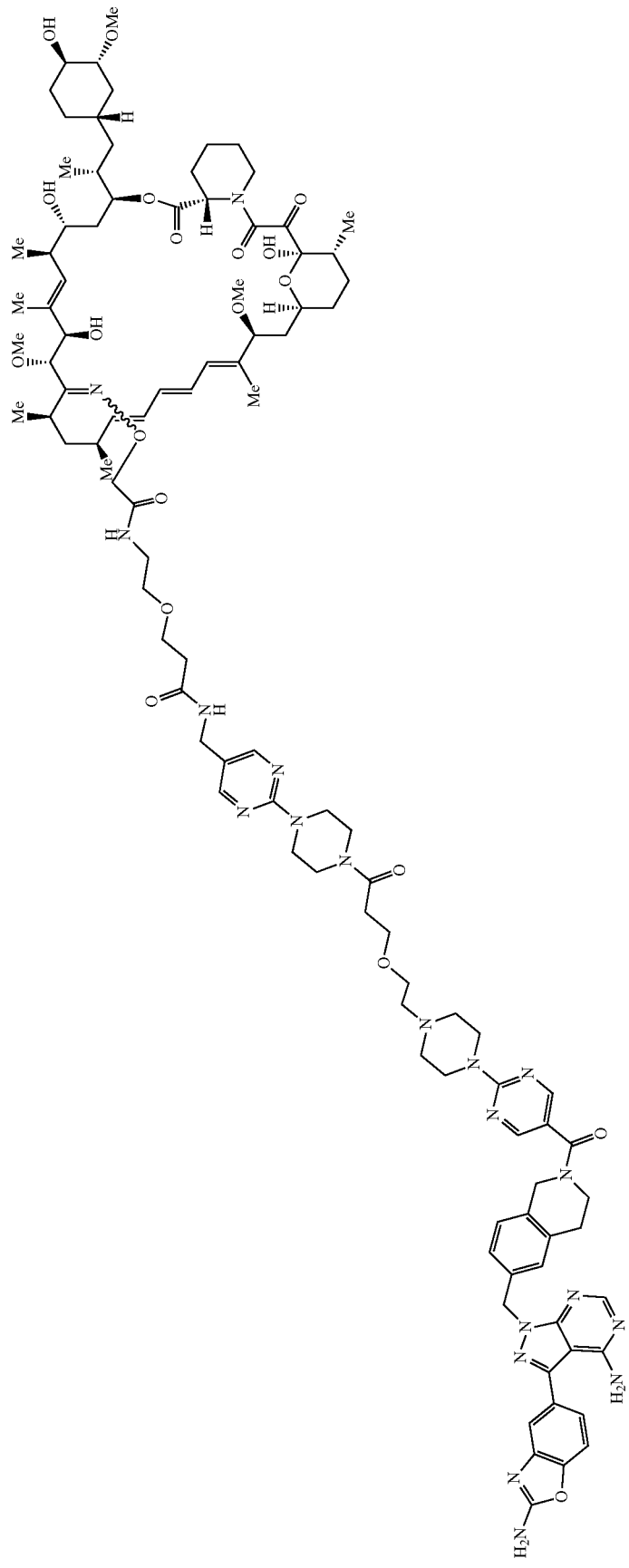
Example 44 or a pharmaceutically acceptable salt, stereoisomer, tautomer, or oxepane isomer thereof.

6. The compound of claim 1, selected from the group consisting of:

831 832
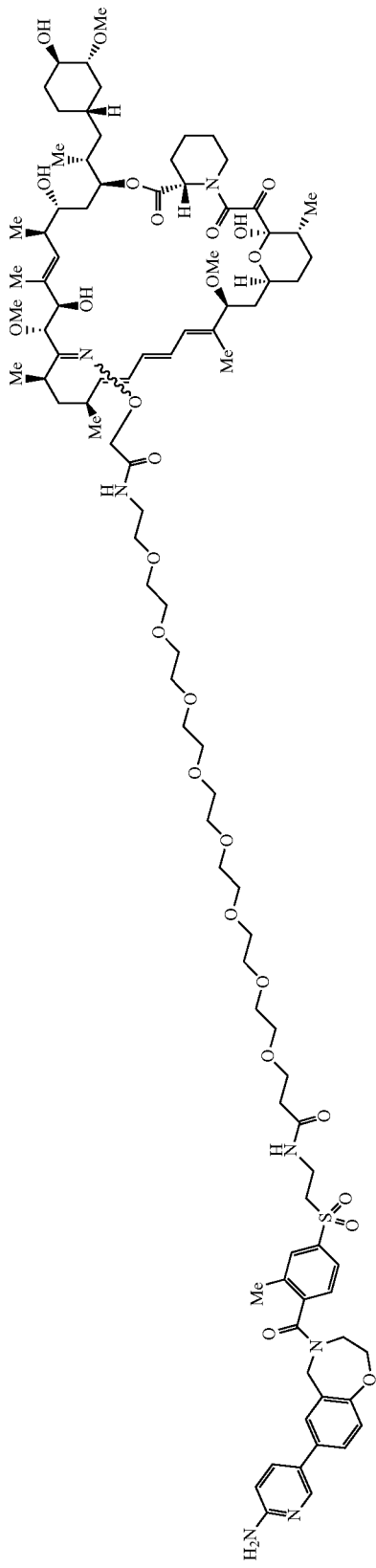
Example 45
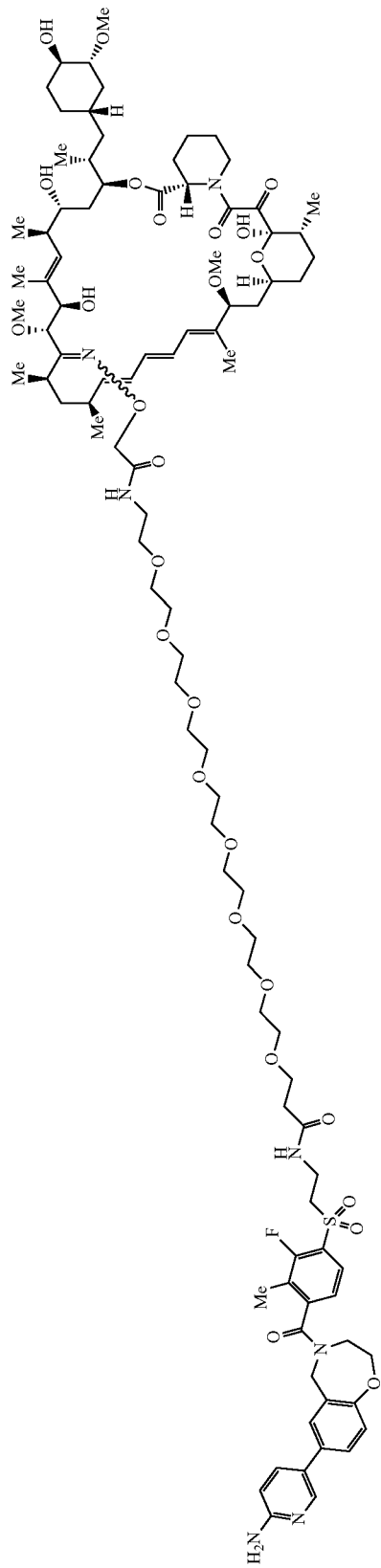
Example 46

833 Example 47
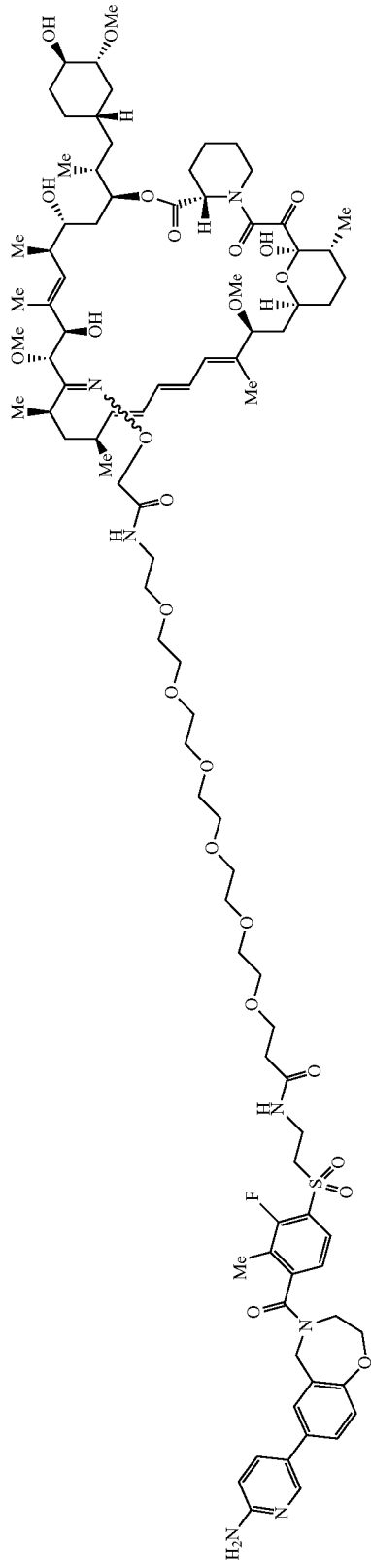
834 Example 48
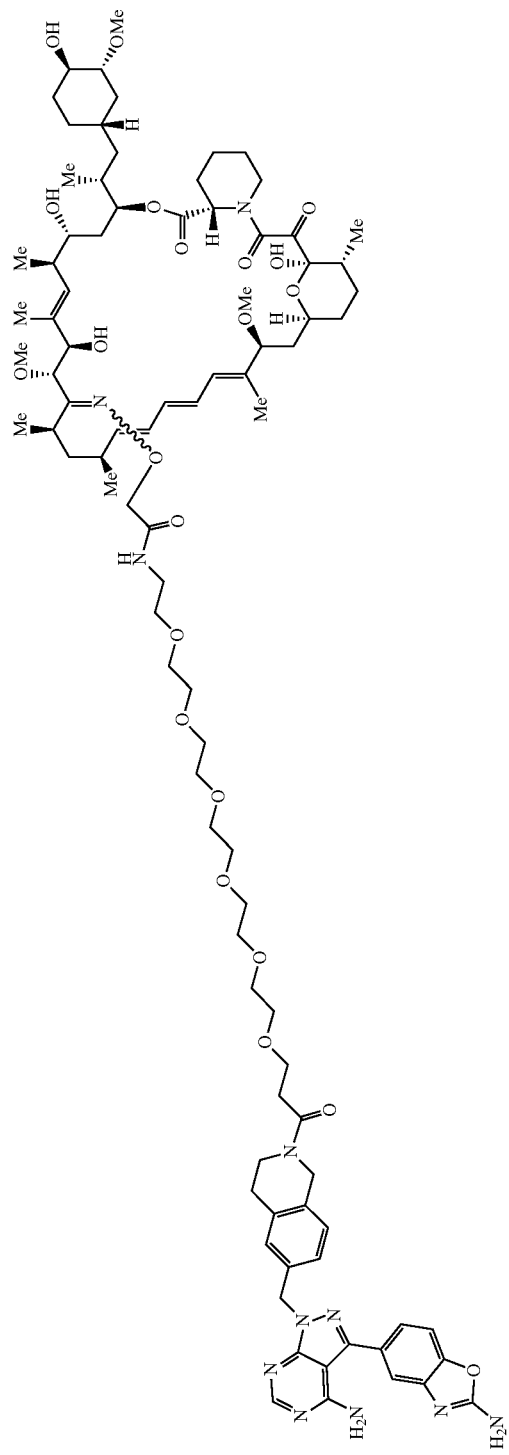

835 836
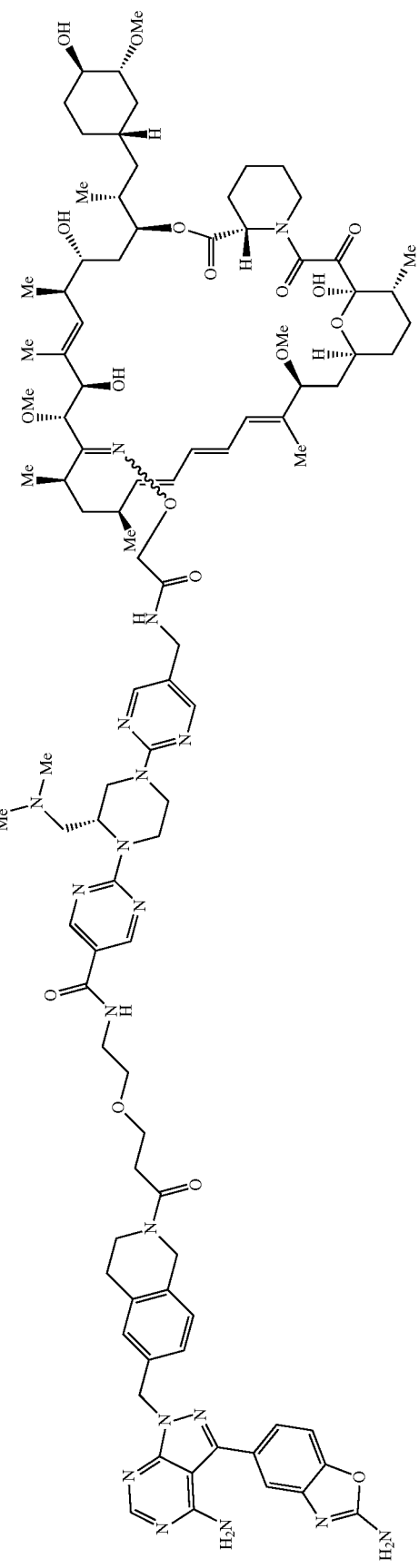
Example 49
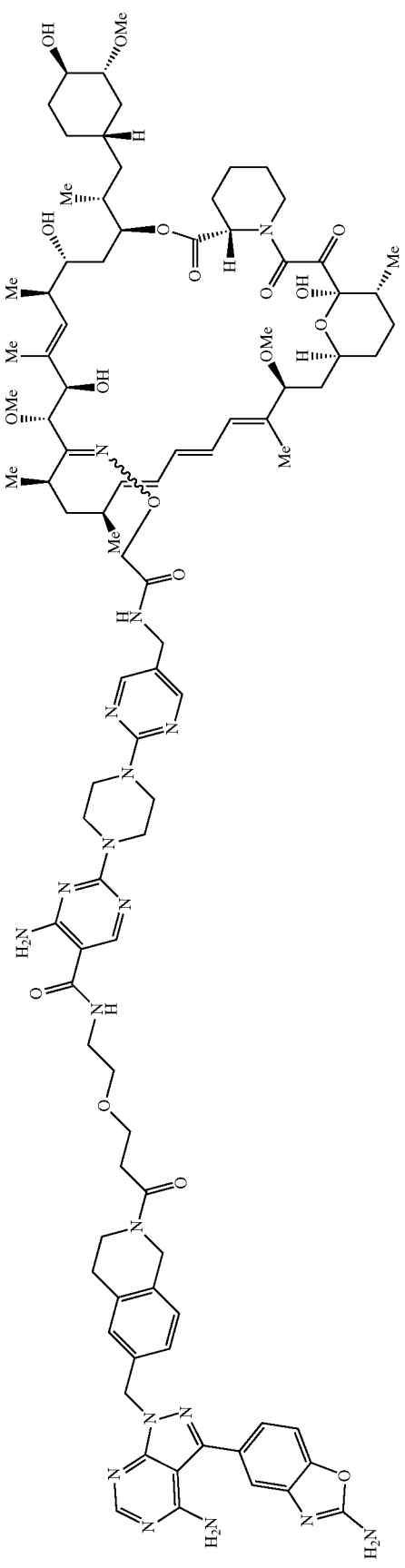
Example 50

837
Example 51
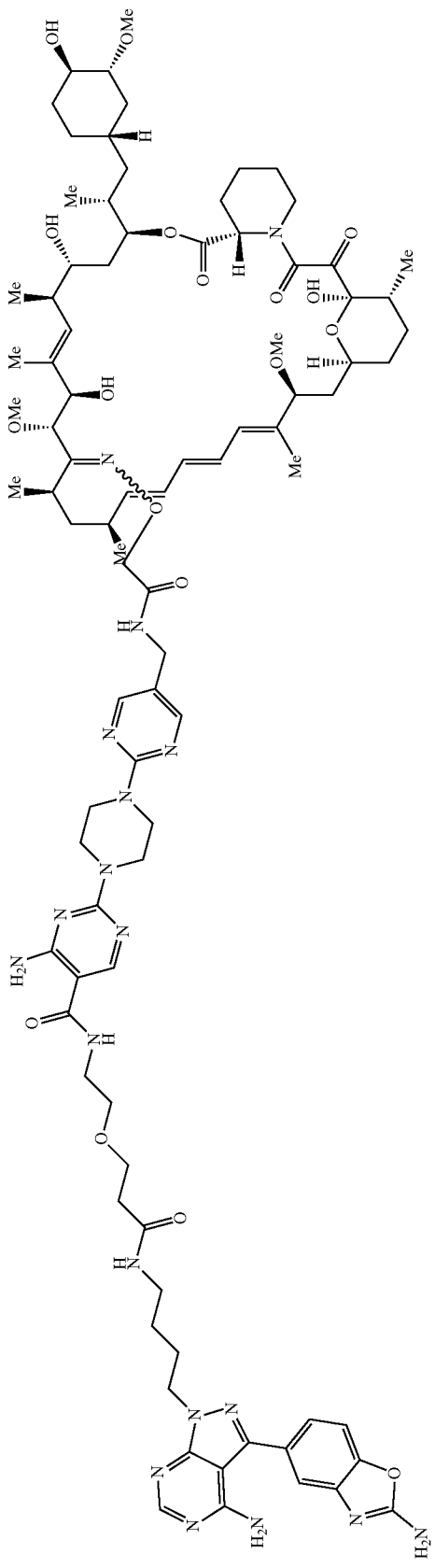
838
Example 52
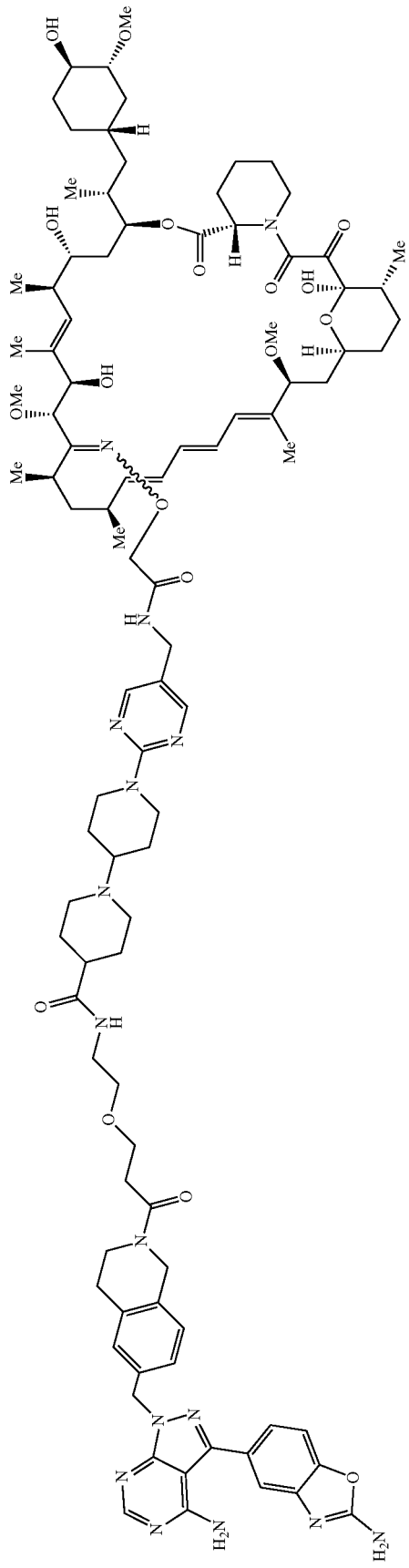

Example 53
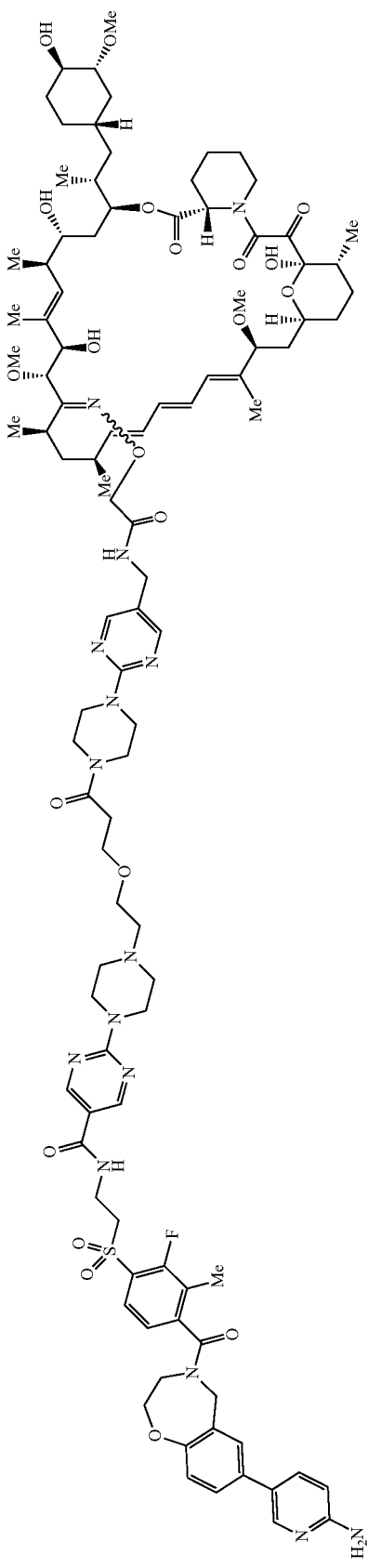
Example 54
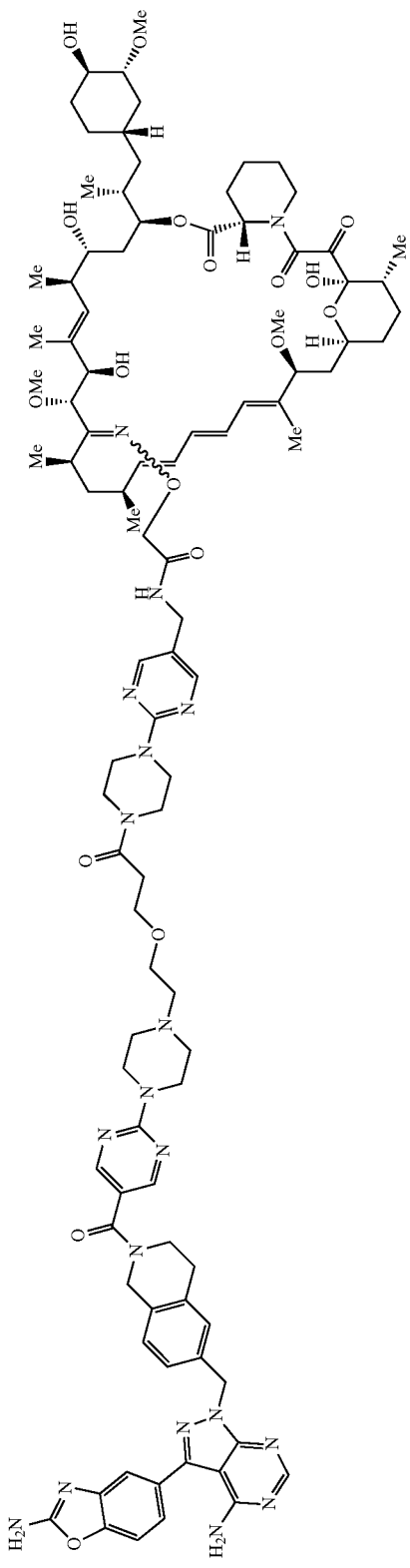

841
Example 55
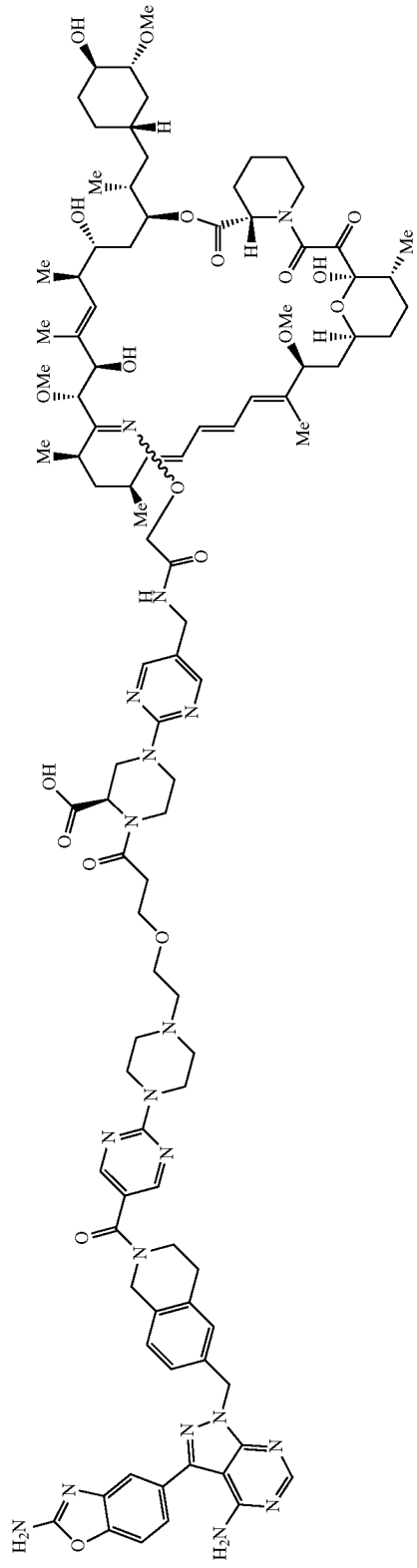
842
Example 56
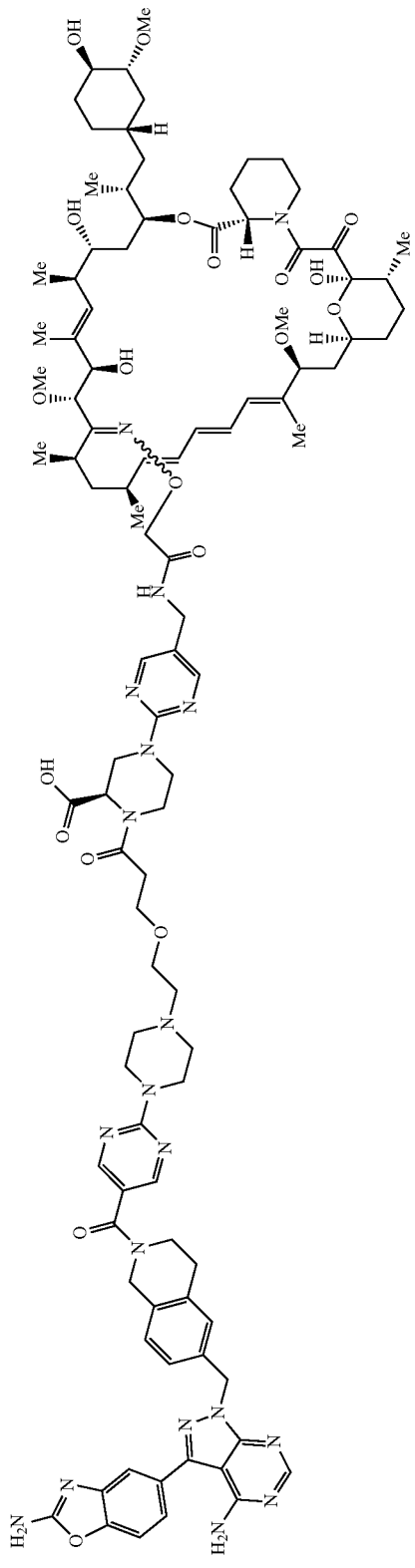

Example 57
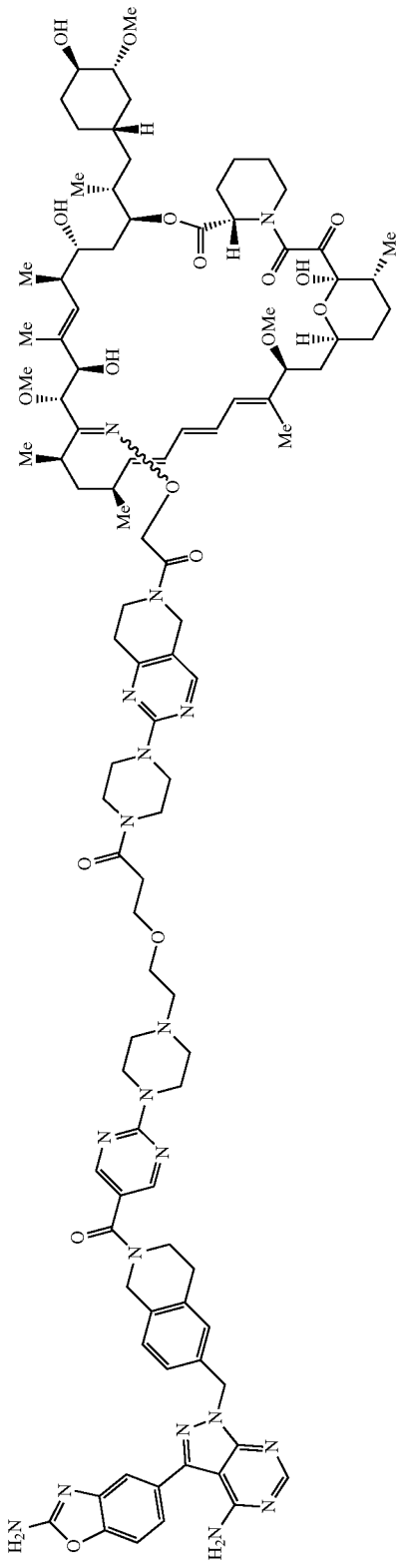
Example 58
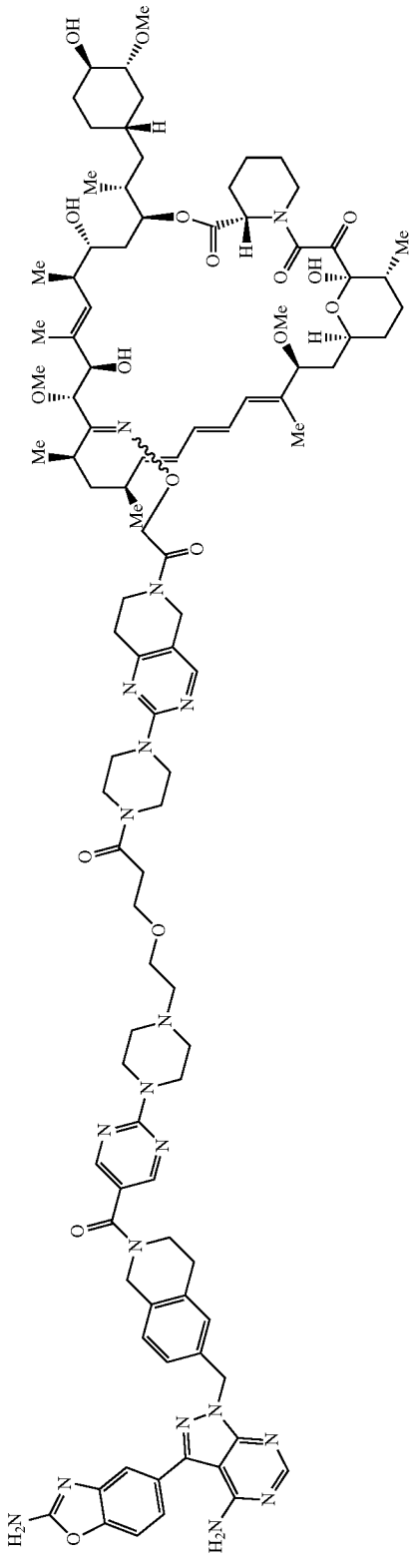

845 846
Example 59 Example 60
-continued
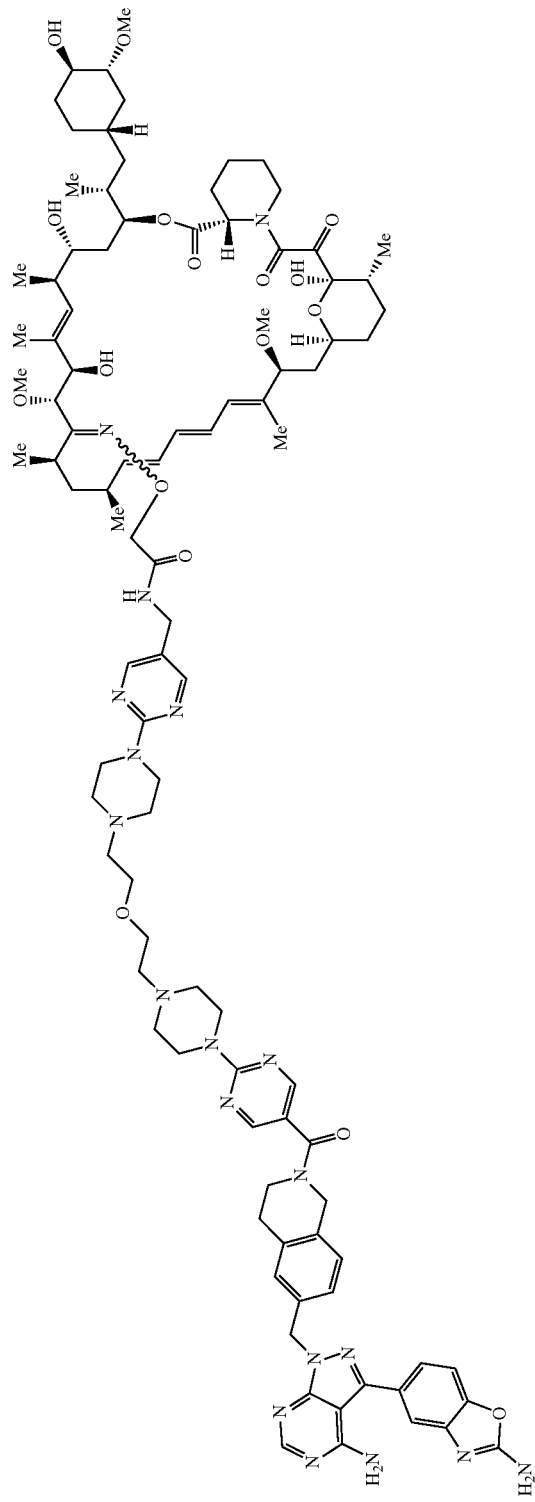
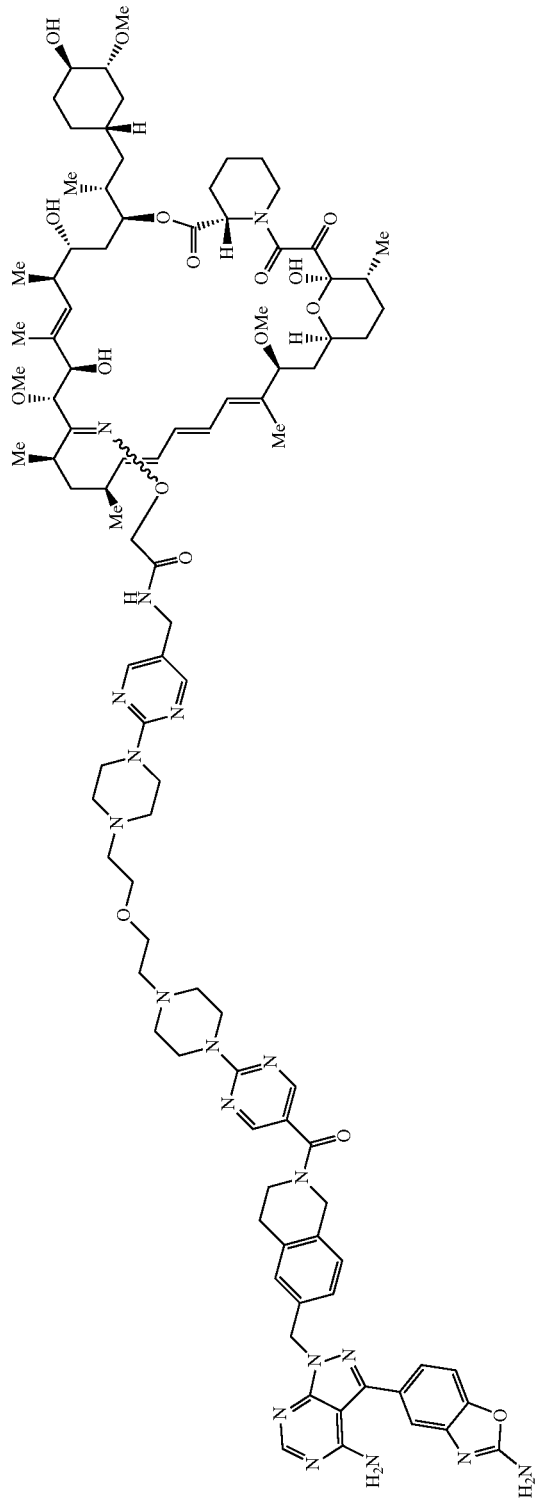

-continued
| 847 | 848 |
|---|---|
| Example 61 | Example 62 |
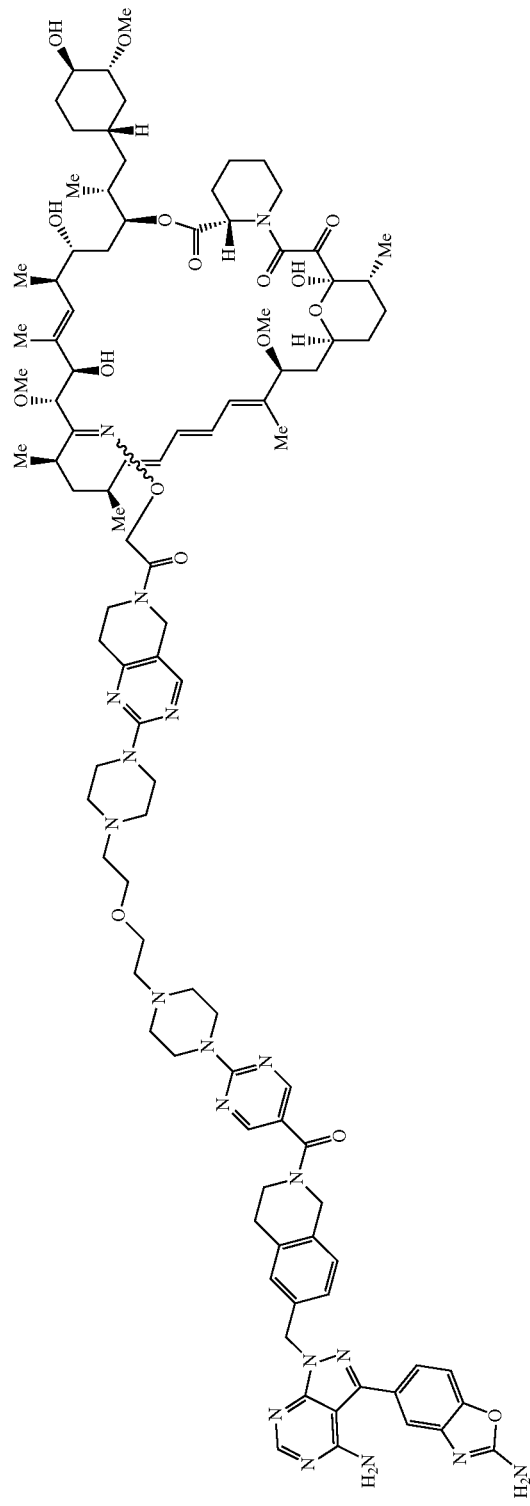
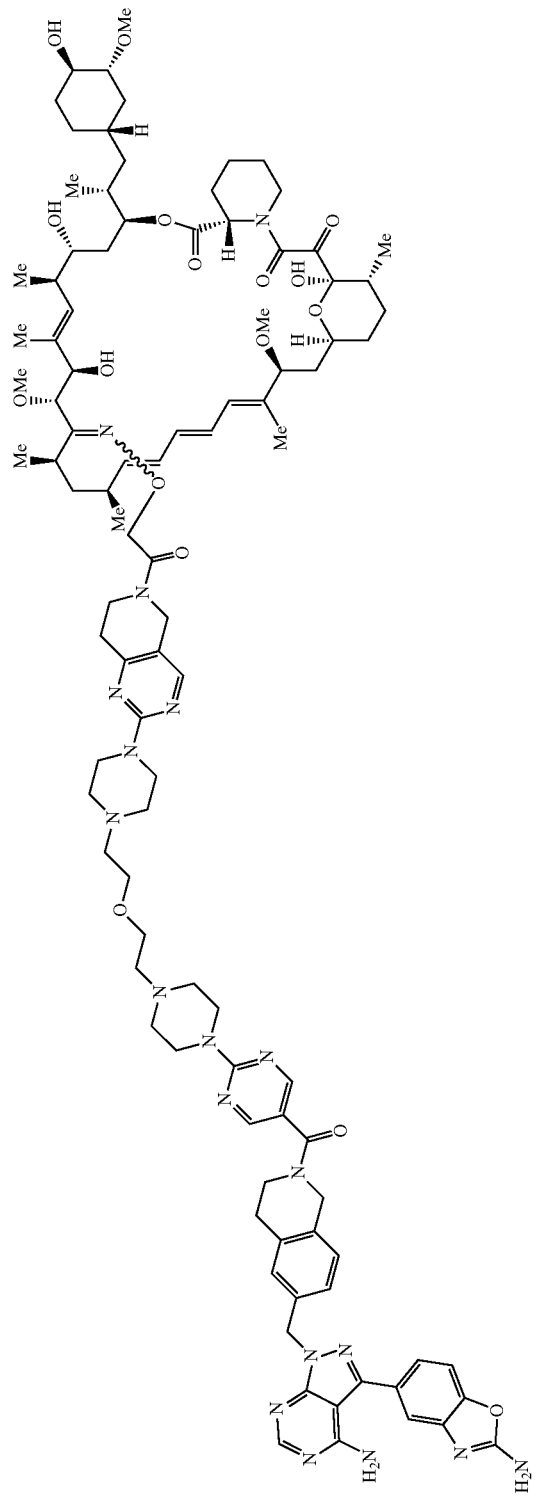

Example 63
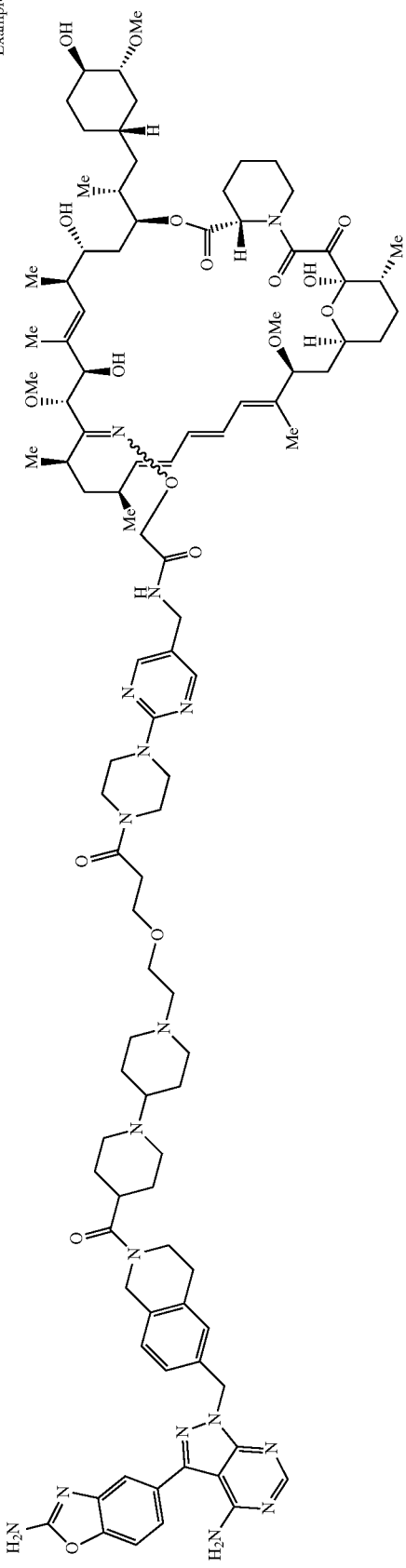
Example 64
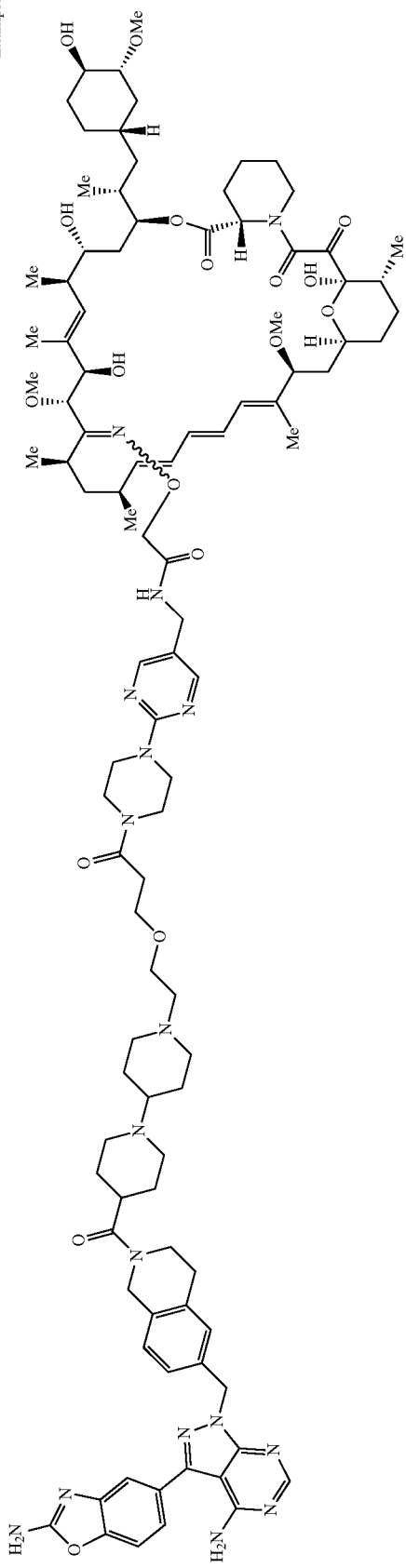

851
852
Example 65
Example 66
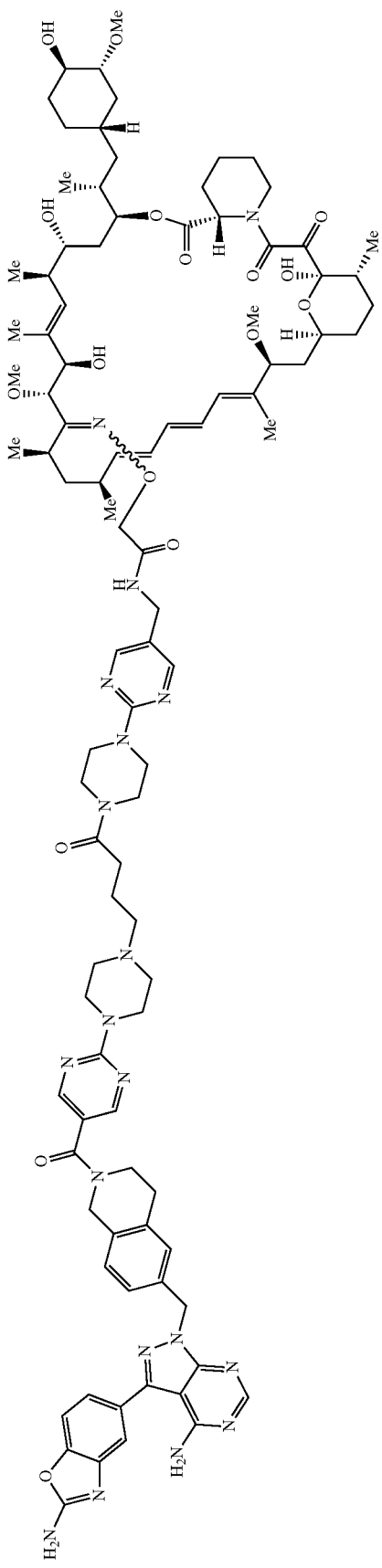
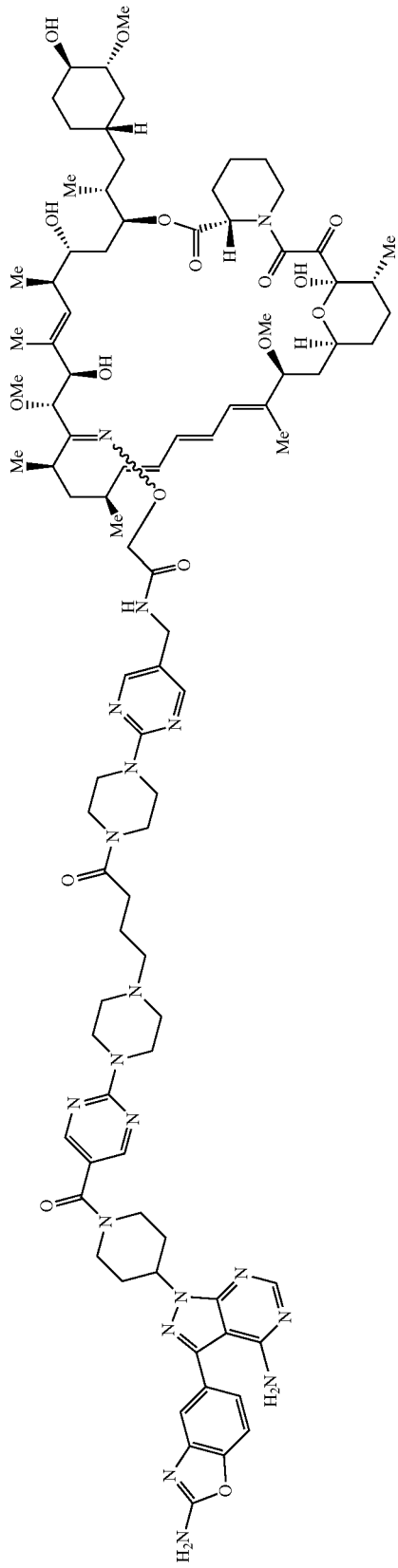

or a pharmaceutically acceptable salt, stereoisomer, tautomer, or oxepane isomer thereof.

7. The compound of claim 1, selected from the group consisting of:

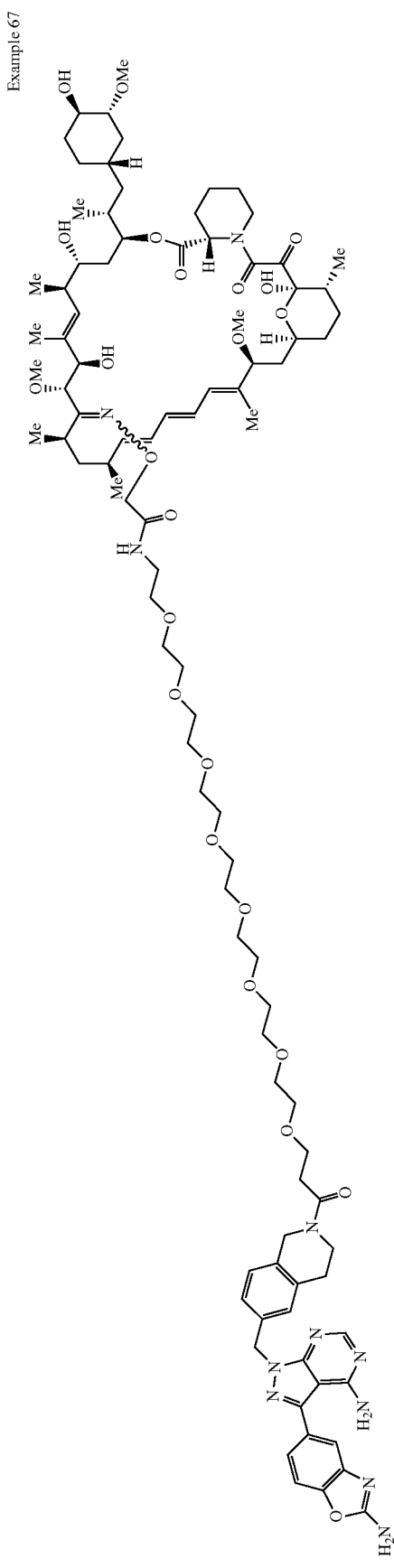
855
Example 67
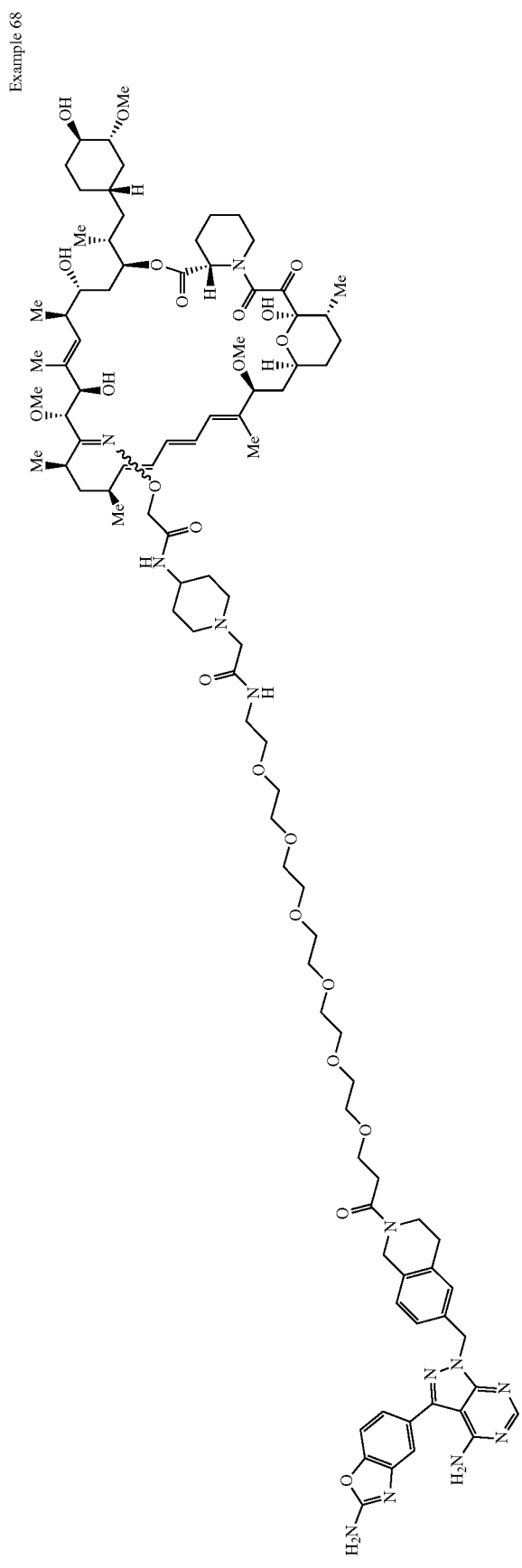
856
Example 68

Example 69
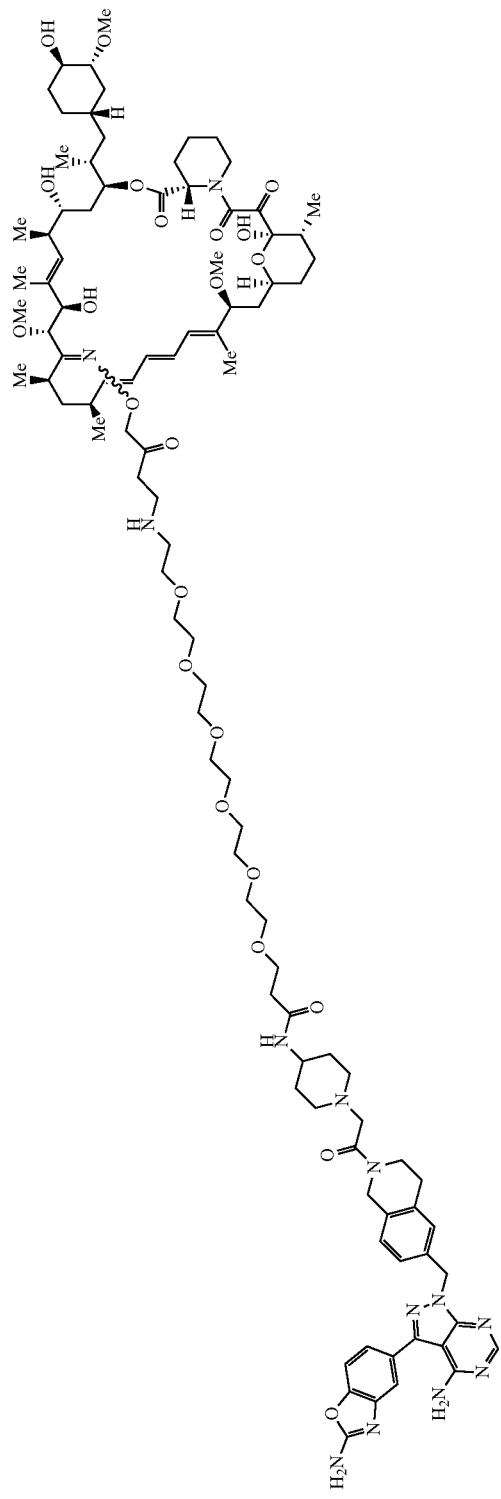
Example 70
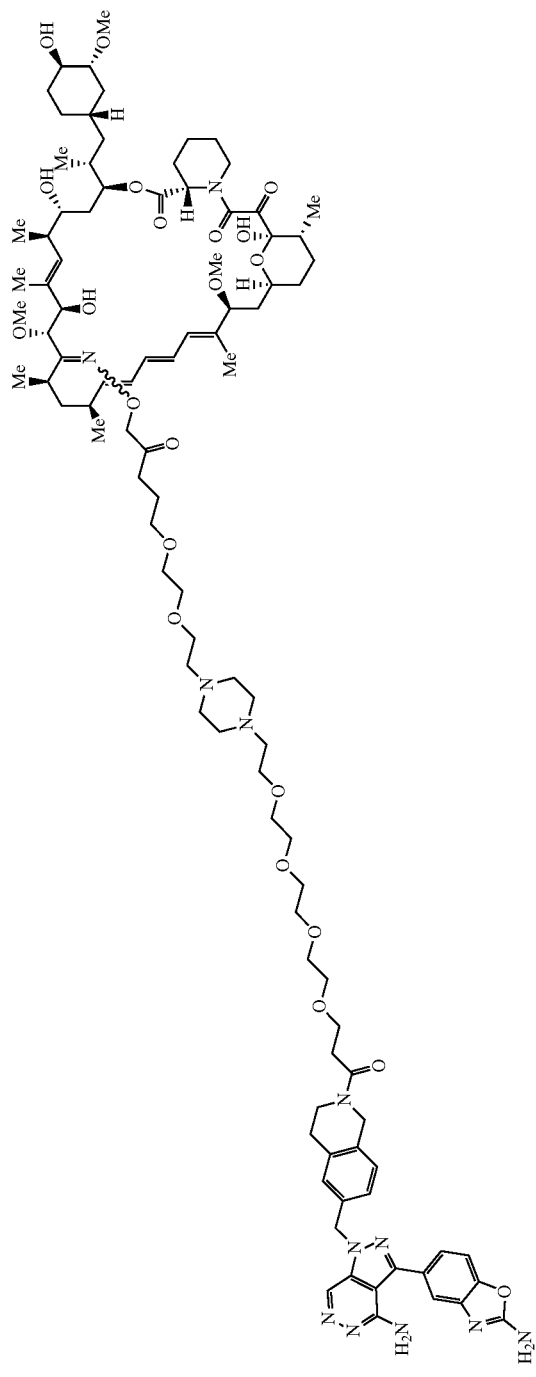

or a pharmaceutically acceptable salt, stereoisomer, tautomer, or oxepane isomer thereof.

8. A pharmaceutical composition comprising a compound of claim 1, or a pharmaceutically acceptable salt, stereoisomer, tautomer, or oxepane isomer thereof, and at least one of a pharmaceutically acceptable carrier, diluent, or excipient.

* * * * *